US011752206B2

(12) United States Patent
Ciaramella et al.

(10) Patent No.: US 11,752,206 B2
(45) **Date of Patent: *Sep. 12, 2023**

(54) HERPES SIMPLEX VIRUS VACCINE

(71) Applicant: ModernaTX, Inc., Cambridge, MA (US)

(72) Inventors: Giuseppe Ciaramella, Sudbury, MA (US); Shinu John, Somerville, MA (US); Andrew J. Bett, Lansdale, PA (US); Danilo R. Casimiro, Harleysville, PA (US); Dai Wang, Blue Bell, PA (US); Lan Zhang, Chalfont, PA (US)

(73) Assignee: ModernaTX, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/494,130

(22) PCT Filed: Mar. 15, 2018

(86) PCT No.: PCT/US2018/022622

§ 371 (c)(1),
(2) Date: Sep. 13, 2019

(87) PCT Pub. No.: WO2018/170256

PCT Pub. Date: Sep. 20, 2018

(65) Prior Publication Data

US 2020/0129615 A1 Apr. 30, 2020

Related U.S. Application Data

(60) Provisional application No. 62/471,786, filed on Mar. 15, 2017.

(51) Int. Cl.

| | |
|---|---|
| ***A61K 39/245*** | (2006.01) |
| ***A61P 31/22*** | (2006.01) |
| ***A61K 9/00*** | (2006.01) |
| ***A61K 9/51*** | (2006.01) |
| ***A61K 39/39*** | (2006.01) |
| ***C07K 14/005*** | (2006.01) |
| ***C12N 7/00*** | (2006.01) |
| ***A61K 47/69*** | (2017.01) |
| ***A61K 39/00*** | (2006.01) |

(52) U.S. Cl.

CPC .......... *A61K 39/245* (2013.01); *A61K 9/0019* (2013.01); *A61K 9/5123* (2013.01); *A61K 9/5146* (2013.01); *A61K 39/39* (2013.01); *A61K 47/6929* (2017.08); *A61P 31/22* (2018.01); *C07K 14/005* (2013.01); *C12N 7/00* (2013.01); *A61K 2039/53* (2013.01); *A61K 2039/54* (2013.01); *A61K 2039/545* (2013.01); *A61K 2039/55516* (2013.01); *A61K 2039/70* (2013.01); *C07K 2319/02* (2013.01); *C07K 2319/40* (2013.01); *C12N 2710/16622* (2013.01); *C12N 2710/16634* (2013.01)

(58) Field of Classification Search

CPC .. A61K 39/245; A61K 9/0019; A61K 9/5123; A61K 9/5146; A61K 39/39; A61K 47/6929; A61K 2039/53; A61K 2039/54; A61K 2039/545; A61K 2039/55516; A61K 2039/70; A61K 9/51; A61K 39/12; A61P 31/22; C07K 14/005; C07K 2319/02; C07K 2319/40; C12N 7/00; C12N 2710/16622; C12N 2710/16634; Y02A 50/30

See application file for complete search history.

(56) References Cited

U.S. PATENT DOCUMENTS

| | | | |
|---|---|---|---|
| 5,750,114 | A | 5/1998 | Burke et al. |
| 5,955,088 | A | 9/1999 | Ghiasi et al. |
| 6,500,419 | B1 | 12/2002 | Hone et al. |
| 6,514,948 | B1 | 2/2003 | Raz et al. |
| 6,610,044 | B2 | 8/2003 | Mathiesen |
| 7,001,890 | B1 | 2/2006 | Wagner et al. |
| 8,569,256 | B2 | 10/2013 | Heyes et al. |
| 8,609,142 | B2 | 12/2013 | Troiano et al. |
| 8,613,954 | B2 | 12/2013 | Zale et al. |
| 8,617,608 | B2 | 12/2013 | Zale et al. |
| 8,710,200 | B2 | 4/2014 | Schrum et al. |
| 8,734,832 | B2 | 5/2014 | O'Hagan et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,877,206 | B2 | 11/2014 | Chen et al. |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

Chen S, et. al. J Control Release. Aug. 10, 2016;235:236-244. Epub May 26, 2016. "Introduction" pp. 236-237.*

(Continued)

*Primary Examiner* — Rachel B Gill

(74) *Attorney, Agent, or Firm* — Wolf, Greenfield & Sacks, P.C.

(57) ABSTRACT

Herpes simplex virus (HSV) ribonucleic acid (RNA) vaccines, as well as methods of using the vaccines and compositions comprising the vaccines. In a preferred embodiment, the vaccine is formulated as a lipid nanoparticle comprising at least one cationic lipid.

9 Claims, No Drawings

Specification includes a Sequence Listing.

(56) References Cited

U.S. PATENT DOCUMENTS 8,980,864 B2 3/2015 Hoge et al.
8,999,380 B2 4/2015 Bancel et al.
9,149,543 B2 10/2015 Hecker et al.
9,221,891 B2 12/2015 Bancel et al.
9,283,287 B2 3/2016 Bancel et al.
9,303,079 B2 4/2016 Bancel et al.
9,464,124 B2 10/2016 Bancel et al.
9,512,456 B2 12/2016 Wang et al.
9,533,047 B2 1/2017 de Fougerolles et al.
9,572,896 B2 2/2017 Bancel et al.
9,597,380 B2 3/2017 Chakraborty et al.
9,669,089 B2 * 6/2017 Thess ...................... A61P 33/00
9,868,691 B2 1/2018 Benenato et al.
9,868,692 B2 * 1/2018 Benenato .............. C07C 227/16
9,872,900 B2 1/2018 Ciaramella et al.
10,022,435 B2 * 7/2018 Ciaramella .......... A61K 9/5146
10,023,626 B2 7/2018 Bolen et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,232,055 B2 3/2019 Kariko et al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,442,756 B2 * 10/2019 Benenato ................ A61P 37/04
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge
10,653,767 B2 5/2020 Ciaramella et al.
10,695,419 B2 6/2020 Ciaramella et al.
10,709,779 B2 * 7/2020 Ciaramella ............ A61K 39/39
10,857,105 B2 12/2020 Benenato et al.
10,925,958 B2 2/2021 Ciaramella
11,027,025 B2 6/2021 Hoge et al.
11,045,540 B2 6/2021 Ciaramella
11,103,578 B2 8/2021 Ciaramella et al.
11,351,242 B1 6/2022 Lori et al.
11,384,352 B2 7/2022 Miracco
11,406,703 B2 8/2022 Kramarczyk et al.
11,464,848 B2 10/2022 Ciaramella et al.
2001/0001066 A1 5/2001 Cezayirli et al.
2002/0147167 A1 10/2002 Armstrong et al.
2003/0032615 A1 2/2003 Feigner et al.
2004/0132683 A1 7/2004 Felgner et al.
2005/0032730 A1 2/2005 Von Der Mulbe et al.
2005/0059624 A1 3/2005 Hoerr et al.
2005/0170508 A1 8/2005 Huang et al.
2005/0250723 A1 11/2005 Hoerr et al.
2006/0172003 A1 8/2006 Meers et al.
2006/0172966 A1 8/2006 Lipford et al.
2007/0280929 A1 12/2007 Hoerr et al.
2009/0098162 A1 4/2009 Freiman et al.
2009/0148467 A1 6/2009 Friedman et al.
2010/0130588 A1 * 5/2010 Yaworski ........... C12N 15/1137
514/44 A
2010/0189729 A1 7/2010 Hoerr et al.
2010/0203076 A1 8/2010 Fotin-Mleczek et al.
2010/0239608 A1 9/2010 Von Der Mulbe et al.
2010/0249208 A1 9/2010 Hecker et al.
2010/0303851 A1 12/2010 Hoerr et al.
2011/0117125 A1 * 5/2011 Hope ................. A61K 31/7088
424/204.1
2011/0250225 A1 10/2011 Fotin-Mleczek et al.
2011/0269950 A1 11/2011 Von Der Mulbe et al.
2011/0311472 A1 12/2011 Hoerr et al.
2012/0101148 A1 4/2012 Aking et al.
2012/0189700 A1 7/2012 Aguilar et al.
2012/0258046 A1 10/2012 Mutske
2012/0328655 A1 * 12/2012 Dubensky, Jr. ......... A61P 33/00
424/274.1
2013/0028925 A1 1/2013 Friedman et al.
2013/0102034 A1 4/2013 Schrum et al.
2013/0121988 A1 5/2013 Hoerr et al.
2013/0142818 A1 6/2013 Baumhof et al.
2013/0171234 A1 7/2013 Fairman et al.
2013/0171241 A1 7/2013 Geall
2013/0183355 A1 7/2013 Jain et al.
2013/0189351 A1 7/2013 Geall
2013/0195867 A1 8/2013 Hoerr et al.
2013/0195968 A1 8/2013 Geall et al.
2013/0195969 A1 8/2013 Geall et al.
2013/0202684 A1 8/2013 Geall et al.
2013/0236533 A1 9/2013 Von Andrian et al.
2013/0236974 A1 9/2013 De Fougerolles
2013/0245103 A1 9/2013 de Fougerolles et al.
2013/0245107 A1 9/2013 de Fougerolles et al.
2013/0259923 A1 10/2013 Bancel et al.
2013/0266640 A1 10/2013 De Fougerolles et al.
2013/0295043 A1 11/2013 Kallen et al.
2013/0336998 A1 12/2013 Kallen et al.
2014/0065228 A1 3/2014 Yarowoski et al.
2014/0127247 A1 5/2014 Dubensky et al.
2014/0134201 A1 5/2014 Tureci et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0271829 A1 * 9/2014 Lilja ...................... A61K 39/25
424/450
2014/0308304 A1 10/2014 Manoharan et al.
2014/0378538 A1 12/2014 Bancel
2015/0051268 A1 2/2015 Bancel et al.
2015/0056253 A1 2/2015 Bancel et al.
2015/0064242 A1 3/2015 Heyes et al.
2015/0141499 A1 5/2015 Bancel et al.
2015/0307542 A1 10/2015 Roy et al.
2015/0315541 A1 11/2015 Bancel et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0130308 A1 5/2016 Weiner et al.
2016/0243221 A1 8/2016 Hoge et al.
2016/0317647 A1 11/2016 Ciaramella et al.
2017/0043037 A1 2/2017 Kariko et al.
2017/0202979 A1 7/2017 Chakraborty et al.
2017/0204152 A1 7/2017 Nelson et al.
2017/0210698 A1 * 7/2017 Benenato .............. C07C 233/72
2017/0130255 A1 10/2017 Wang et al.
2017/0340724 A1 * 11/2017 Ciaramella ............ A61K 39/12
2017/0340725 A1 * 11/2017 Ciaramella ............ C07K 16/10
2018/0000953 A1 1/2018 Almarsson et al.
2018/0002393 A1 1/2018 Bancel et al.
2018/0028645 A1 * 2/2018 Ciaramella ............ A61K 39/39
2018/0028664 A1 2/2018 Besin et al.
2018/0147298 A1 * 5/2018 Besin ................... A61K 47/543
2018/0214537 A1 8/2018 Mutzke et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271795 A1 * 9/2018 Martini ..................... A61P 3/00
2018/0271970 A1 9/2018 Ciaramella et al.
2018/0273977 A1 9/2018 Mousavi et al.
2018/0274009 A1 9/2018 Marquardt et al.
2018/0280496 A1 10/2018 Ciaramella et al.
2018/0289792 A1 * 10/2018 Ciaramella .......... A61K 39/118
2018/0296663 A1 10/2018 Hipp et al.
2018/0303925 A1 * 10/2018 Weissman .............. C12N 15/11
2018/0303929 A1 * 10/2018 Ciaramella .......... A61K 39/245
2018/0311336 A1 11/2018 Ciaramella et al.
2018/0311343 A1 * 11/2018 Huang ................... A61K 39/12
2018/0312549 A1 11/2018 Ciaramella
2018/0318409 A1 * 11/2018 Valiante ............... A61K 9/5123
2018/0363019 A1 12/2018 Hoge
2018/0369374 A1 * 12/2018 Frederick ........... C07K 14/5434
2018/0371047 A1 * 12/2018 Ticho ..................... C07K 16/26
2019/0002890 A1 1/2019 Martini et al.
2019/0008938 A1 1/2019 Ciaramella et al.
2019/0008948 A1 * 1/2019 Ciaramella .............. C12N 7/00

(56) References Cited

U.S. PATENT DOCUMENTS

| | | | | |
|---|---|---|---|---|
| 2019/0015501 | A1* | 1/2019 | Ciaramella | A61K 39/155 |
| 2019/0085368 | A1 | 3/2019 | Bancel et al. | |
| 2019/0099481 | A1 | 4/2019 | Ciaramella et al. | |
| 2019/0167811 | A1* | 6/2019 | Benenato | A61K 47/28 |
| 2019/0175517 | A1* | 6/2019 | Martini | A61K 9/5146 |
| 2019/0175727 | A1* | 6/2019 | Huang | A61K 9/5123 |
| 2019/0192646 | A1 | 6/2019 | Cohen et al. | |
| 2019/0192653 | A1 | 6/2019 | Hoge et al. | |
| 2019/0274968 | A1* | 9/2019 | Weissman | A61K 9/5123 |
| 2019/0275170 | A1* | 9/2019 | Benenato | A61K 9/51 |
| 2019/0298657 | A1* | 10/2019 | Martini | A61K 9/0019 |
| 2019/0298658 | A1 | 10/2019 | Benenato | |
| 2019/0300906 | A1* | 10/2019 | Martini | A61K 9/51 |
| 2019/0314292 | A1 | 10/2019 | Benenato et al. | |
| 2019/0314493 | A1 | 10/2019 | Ciaramella et al. | |
| 2019/0336452 | A1 | 11/2019 | Brader | |
| 2019/0336595 | A1* | 11/2019 | Ciaramella | A61K 39/12 |
| 2019/0351040 | A1* | 11/2019 | Valiante | A61K 45/06 |
| 2019/0382774 | A1* | 12/2019 | Hoge | C12N 15/85 |
| 2019/0390181 | A1* | 12/2019 | Benenato | A61K 47/14 |
| 2020/0030432 | A1 | 1/2020 | Ciaramella et al. | |
| 2020/0032274 | A1 | 1/2020 | Mauger et al. | |
| 2020/0038499 | A1 | 2/2020 | Narayanan et al. | |
| 2020/0054737 | A1* | 2/2020 | Ciaramella | A61K 39/12 |
| 2020/0069599 | A1* | 3/2020 | Smith | A61K 48/0075 |
| 2020/0069793 | A1 | 3/2020 | Ciaramella | |
| 2020/0069794 | A1 | 3/2020 | Ciaramella et al. | |
| 2020/0071689 | A1 | 3/2020 | Miracco | |
| 2020/0085916 | A1* | 3/2020 | Martini | A61P 7/08 |
| 2020/0109420 | A1 | 4/2020 | Brito et al. | |
| 2020/0129608 | A1 | 4/2020 | Ciaramella et al. | |
| 2020/0129615 | A1 | 4/2020 | Ciaramella et al. | |
| 2020/0163878 | A1* | 5/2020 | Baumhof | C07C 255/24 |
| 2020/0239869 | A1 | 7/2020 | Issa et al. | |
| 2020/0254086 | A1 | 8/2020 | Hoge et al. | |
| 2020/0282047 | A1 | 9/2020 | Ciaramella et al. | |
| 2020/0306191 | A1 | 10/2020 | Schariter et al. | |
| 2020/0338190 | A1* | 10/2020 | Ciaramella | A61P 31/22 |
| 2020/0368162 | A1 | 11/2020 | Martini | |
| 2021/0046173 | A1 | 2/2021 | Ciaramella et al. | |
| 2021/0163919 | A1 | 6/2021 | Issa et al. | |
| 2021/0187097 | A1 | 6/2021 | Ciaramella et al. | |
| 2021/0206818 | A1 | 7/2021 | Huang et al. | |
| 2021/0217484 | A1 | 7/2021 | Giessel et al. | |
| 2021/0228707 | A1 | 7/2021 | Mektar et al. | |
| 2021/0268086 | A1 | 9/2021 | Zhong et al. | |
| 2021/0309976 | A1 | 10/2021 | Dousis et al. | |
| 2022/0031631 | A1 | 2/2022 | Almarsson et al. | |
| 2022/0047518 | A1 | 2/2022 | Hennessy et al. | |
| 2022/0054653 | A1 | 2/2022 | Martini et al. | |
| 2022/0062175 | A1 | 3/2022 | Smith et al. | |
| 2022/0125899 | A1 | 4/2022 | Ashburn et al. | |
| 2022/0145381 | A1 | 5/2022 | Elich et al. | |
| 2022/0236253 | A1 | 7/2022 | Hopson | |
| 2022/0241399 | A1 | 8/2022 | Lusso et al. | |

FOREIGN PATENT DOCUMENTS

| | | | | |
|---|---|---|---|---|
| CA | 2473135 | A1 | 6/2003 | |
| EP | 1083232 | B1 | 2/2005 | |
| EP | 1301614 | B1 | 11/2006 | |
| EP | 1383556 | B1 | 10/2007 | |
| EP | 1905844 | A2 | 2/2008 | |
| EP | 1026253 | B2 | 12/2012 | |
| EP | 2188379 | B1 | 1/2013 | |
| WO | WO 1990/011092 | A1 | 10/1990 | |
| WO | WO 1991/007425 | A1 | 5/1991 | |
| WO | WO 1993/015749 | A1 | 8/1993 | |
| WO | WO 1995/027069 | A1 | 3/1995 | |
| WO | WO 1998/020016 | A1 | 5/1998 | |
| WO | WO 1999/052503 | A2 | 10/1999 | |
| WO | WO 2000/063364 | A2 | 10/2000 | |
| WO | WO 2001/021810 | A1 | 3/2001 | |
| WO | WO 2001/093836 | A2 | 12/2001 | |
| WO | WO 2004/058166 | A2 | 7/2004 | |
| WO | WO 2005/007689 | A1 | 1/2005 | |
| WO | WO 2008/011609 | A1 | 1/2008 | |
| WO | WO 2008/014979 | A3 | 2/2008 | |
| WO | WO 2008/052770 | A2 | 5/2008 | |
| WO | WO 2008/083949 | A2 | 7/2008 | |
| WO | WO 2010/037408 | A1 | 4/2010 | |
| WO | WO 2010/042877 | A1 | 4/2010 | |
| WO | WO 2010/054406 | A1 | 5/2010 | |
| WO | WO 2010/088927 | A1 | 8/2010 | |
| WO | WO 2010/115046 | A2 | 10/2010 | |
| WO | WO 2011/005799 | A2 | 1/2011 | |
| WO | WO 2011/106607 | A | 2/2011 | |
| WO | WO 2011/069529 | A1 | 6/2011 | |
| WO | WO 2011/069586 | A1 | 6/2011 | |
| WO | WO 2011/144358 | A1 | 11/2011 | |
| WO | WO 2012/006369 | A2 | 1/2012 | |
| WO | WO 2012/006380 | A2 | 1/2012 | |
| WO | WO 2012/019630 | A1 | 2/2012 | |
| WO | WO 2012/019780 | A1 | 2/2012 | |
| WO | WO 2012/051211 | A1 | 4/2012 | |
| WO | WO 2012/075040 | A2 | 6/2012 | |
| WO | WO 2012/089225 | A1 | 7/2012 | |
| WO | WO 2012/113513 | A1 | 8/2012 | |
| WO | WO 2012/116714 | A1 | 9/2012 | |
| WO | WO 2012/116715 | A1 | 9/2012 | |
| WO | WO 2012/116810 | A1 | 9/2012 | |
| WO | WO 2012/116811 | A1 | 9/2012 | |
| WO | WO 2013/006837 | A1 | 1/2013 | |
| WO | WO 2013/006838 | A1 | 1/2013 | |
| WO | WO 2013/006842 | A2 | 1/2013 | |
| WO | WO 2013/030778 | A2 | 3/2013 | |
| WO | WO 2013/052167 | A2 | 4/2013 | |
| WO | WO 2013/055905 | A1 | 4/2013 | |
| WO | WO 2013/056132 | A2 | 4/2013 | |
| WO | WO 2013/059496 | A1 | 4/2013 | |
| WO | WO-2013086373 | A1 * | 6/2013 | C12N 15/111 |
| WO | WO 2013/109604 | A1 | 7/2013 | |
| WO | WO 2013/113502 | A1 | 8/2013 | |
| WO | WO 2013/174409 | A1 | 11/2013 | |
| WO | WO 2014/071963 | A1 | 5/2014 | |
| WO | WO 2014/072061 | A1 | 5/2014 | |
| WO | WO 2014/089239 | A1 | 6/2014 | |
| WO | WO 2014/127917 | A1 | 8/2014 | |
| WO | WO 2014/152027 | A1 | 9/2014 | |
| WO | WO 2014/160243 | A1 | 10/2014 | |
| WO | WO 2015/005253 | A1 | 1/2015 | |
| WO | WO 2015/013551 | A1 | 1/2015 | |
| WO | WO 2015/024667 | A1 | 2/2015 | |
| WO | WO 2015/024668 | A2 | 2/2015 | |
| WO | WO 2015/164674 | A1 | 4/2015 | |
| WO | WO 2015/189425 | A1 | 12/2015 | |
| WO | WO-2015199952 | A1 * | 12/2015 | C12Y 304/21022 |
| WO | WO 2016/057912 | A1 | 4/2016 | |
| WO | WO 2016/164762 | A1 | 10/2016 | |
| WO | WO 2016/176330 | A1 | 11/2016 | |
| WO | WO 2016/201377 | A1 | 12/2016 | |
| WO | WO 2016/203025 | A1 | 12/2016 | |
| WO | WO 2017/011773 | A2 | 1/2017 | |
| WO | WO 2017/015457 | A1 | 1/2017 | |
| WO | WO 2017/020026 | A1 | 2/2017 | |
| WO | WO 2017/062513 | A1 | 4/2017 | |
| WO | WO 2017/066789 | A1 | 4/2017 | |
| WO | WO 2017/070601 | A1 | 4/2017 | |
| WO | WO 2017/070618 | A1 | 4/2017 | |
| WO | WO 2017/070620 | A1 | 4/2017 | |
| WO | WO 2017/070623 | A1 | 4/2017 | |
| WO | WO 2017/075531 | A1 | 5/2017 | |
| WO | WO 2017/127750 | A1 | 7/2017 | |
| WO | WO-2017127750 | A1 * | 7/2017 | C12N 15/113 |
| WO | WO 2017/201333 | A1 | 11/2017 | |
| WO | WO 2017/201340 | A1 | 11/2017 | |
| WO | WO 2017/201342 | A1 | 11/2017 | |
| WO | WO 2017/201347 | A1 | 11/2017 | |
| WO | WO 2017/201349 | A1 | 11/2017 | |
| WO | WO 2016/091391 | A1 | 2/2018 | |
| WO | WO 2018/053209 | A1 | 3/2018 | |
| WO | WO 2018/075980 | A1 | 4/2018 | |
| WO | WO 2018/081459 | A1 | 5/2018 | |
| WO | WO 2018/089851 | A1 | 5/2018 | |

(56) References Cited

FOREIGN PATENT DOCUMENTS

| | | | | |
|---|---|---|---|---|
| WO | WO 2018/107088 A1 | 6/2018 | | |
| WO | WO 2018/111967 A1 | 6/2018 | | |
| WO | WO 2018/140733 A1 | 8/2018 | | |
| WO | WO 2018/144082 A1 | 8/2018 | | |
| WO | WO 2018/144778 A1 | 8/2018 | | |
| WO | WO 2018/151816 A1 | 8/2018 | | |
| WO | WO 2018/157009 A1 | 8/2018 | | |
| WO | WO-2018157009 A1 * | 8/2018 | ......... | A61K 31/7115 |
| WO | WO 2018/170245 A1 | 9/2018 | | |
| WO | WO 2018/170256 A1 | 9/2018 | | |
| WO | WO 2018/170260 A1 | 9/2018 | | |
| WO | WO 2018/170270 A1 | 9/2018 | | |
| WO | WO 2018/170347 A1 | 9/2018 | | |
| WO | WO 2018/175783 A1 | 9/2018 | | |
| WO | WO 2018/187590 A2 | 10/2018 | | |
| WO | WO 2018/200737 A1 | 11/2018 | | |
| WO | WO 2018/232355 A1 | 12/2018 | | |
| WO | WO 2018/232357 A1 | 12/2018 | | |
| WO | WO 2019/036670 A1 | 2/2019 | | |
| WO | WO 2019/036682 A1 | 2/2019 | | |
| WO | WO 2019/036683 A1 | 2/2019 | | |
| WO | WO 2019/036685 A1 | 2/2019 | | |
| WO | WO 2019/055807 A1 | 3/2019 | | |
| WO | WO 2019/103993 A1 | 5/2019 | | |
| WO | WO 2019/148101 A1 | 8/2019 | | |
| WO | WO 2020/006242 A1 | 1/2020 | | |
| WO | WO 2020/056370 A1 | 3/2020 | | |
| WO | WO 2020/061284 A1 | 3/2020 | | |
| WO | WO 2020/061295 A1 | 3/2020 | | |
| WO | WO 2020/061367 A1 | 3/2020 | | |
| WO | WO-2020061367 A1 * | 3/2020 | ........... | C07C 335/08 |
| WO | WO 2020/097291 A1 | 5/2020 | | |
| WO | WO 2020/172239 A1 | 8/2020 | | |
| WO | WO 2020/185811 A1 | 9/2020 | | |
| WO | WO 2020/190750 A1 | 9/2020 | | |
| WO | WO 2020/243561 A1 | 12/2020 | | |
| WO | WO 2021/030533 A1 | 2/2021 | | |
| WO | WO 2021/050864 A1 | 3/2021 | | |
| WO | WO 2021/055811 A1 | 3/2021 | | |
| WO | WO 2021/155243 A1 | 8/2021 | | |
| WO | WO 2021/159040 A2 | 8/2021 | | |
| WO | WO 2021/159130 A2 | 8/2021 | | |
| WO | WO 2021/211343 A1 | 10/2021 | | |
| WO | WO 2021/222304 A1 | 11/2021 | | |
| WO | WO 2021/231929 A1 | 11/2021 | | |
| WO | WO 2021/231963 A1 | 11/2021 | | |
| WO | WO 2021/237084 A1 | 11/2021 | | |
| WO | WO 2021/247817 A1 | 12/2021 | | |
| WO | WO 2022/067010 A1 | 3/2022 | | |
| WO | WO 2022/150717 A1 | 7/2022 | | |
| WO | WO 2022/155524 A1 | 7/2022 | | |
| WO | WO 2022/155530 A1 | 7/2022 | | |
| WO | WO 2022/187698 A1 | 9/2022 | | |
| WO | WO 2022/204491 A1 | 9/2022 | | |
| WO | WO 2022/212191 A1 | 10/2022 | | |
| WO | WO 2022/212442 A1 | 10/2022 | | |
| WO | WO 2022/212711 A2 | 10/2022 | | |
| WO | WO 2022/221335 A1 | 10/2022 | | |
| WO | WO 2022/221336 A1 | 10/2022 | | |
| WO | WO 2022/221359 A1 | 10/2022 | | |
| WO | WO 2022/221440 A1 | 10/2022 | | |

OTHER PUBLICATIONS

Xue HY, et. al. Curr Pharm Des. 2015;21(22):3140-7.*

Hassett KJ, et. al. Mol Ther Nucleic Acids. Apr. 15, 2019;15:1-11. Epub Feb. 7, 2019.*

Poveda C, et al. Vaccines (Basel). Sep. 2, 2019;7(4):131.*

Durbin AF, et. al. mBio. Sep. 20, 2016;7(5):e00833-16.*

John S, et. al. Vaccine. Mar. 14, 2018;36(12):1689-1699. Epub Feb. 15, 2018.*

Dropulic LK, Cohen JI. The challenge of developing a herpes simplex virus 2 vaccine. Expert Rev Vaccines. Dec. 2012;11 (12):1429-40.*

Whitley R, Baines J. Clinical management of herpes simplex virus infections: past, present, and future. F1000Res. Oct. 31, 2018;7: F1000 Faculty Rev-1726.*

Johnston C, Gottlieb SL, Wald A. Status of vaccine research and development of vaccines for herpes simplex virus. Vaccine. Jun. 3, 2016;34(26):2948-2952. Epub Mar. 11, 2016. (Year: 2016).*

Cairns TM, Huang ZY, Gallagher JR, Lin Y, Lou H, Whitbeck JC, Wald A, Cohen GH, Eisenberg RJ. Patient-Specific Neutralizing Antibody Responses to Herpes Simplex Virus Are Attributed to Epitopes on gD, gB, or Both and Can Be Type Specific. J Virol. Sep. 2015;89(18):9213-31. Epub Jun. 24, 2015. (Year: 2015).*

Schmidt-Chanasit J. Glycoprotein B [Human alphaherpesvirus 2]. GenBank: ADG45159.1. Dep. Jun. 24, 2010. (Year: 2010).*

Swain MA, et al. RecName: Full=Envelope glycoprotein C; Flags: Precursor. UniProtKB/Swiss-Prot: P06475.1. Dep. May 1, 1992. (Year: 1992).*

Davison, AJ. envelope glycoprotein D [Human alphaherpesvirus 2]. NCBI Reference Sequence: YP_009137218.1. Dep. May 16, 2016 . (Year: 2016).*

Dutton JL, Li B, Woo WP, Marshak JO, Xu Y, Huang ML, Dong L, Frazer IH, Koelle DM. A novel DNA vaccine technology conveying protection against a lethal herpes simplex viral challenge in mice. PLoS One. Oct. 3, 2013;8(10):e76407. (Year: 2013).*

Awasthi S, Hook LM, Shaw CE, Pahar B, Stagray JA, Liu D, Veazey RS, Friedman HM. An HSV-2 Trivalent Vaccine Is Immunogenic in Rhesus Macaques and Highly Efficacious in Guinea Pigs. PLoS Pathog. Jan. 19, 2017;13(1):e1006141. (Year: 2017 ).*

International Search Report and Written Opinion for Application No. PCT/US2018/022622 dated Jul. 3, 2018.

Awasthi et al., A paradigm shift: vaccine-induced antibodies as an immune correlate of protection against herpes simplex virus type 1 genital herpes. J Infect Dis. Mar. 2014;209(6):813-5. doi: 10.1093/infdis/jit658. Epub Nov. 27, 2013.

Bahl et al., Preclinical and Clinical Demonstration of Immunogenicity by mRNA Vaccines against H10N8 and H7N9 Influenza Viruses, Mol Ther. Jun. 7, 2017;25(6):1316-1327. doi: 10.1016/j.ymthe.2017.03.035. Epub Apr. 27, 2017.

Bowie et al., Deciphering the message in protein sequences: tolerance to amino acid substitutions. Science. Mar. 16, 1990;247(4948):1306-10.

Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.

Chen et al., Human monoclonal antibodies targeting the haemagglutinin glycoprotein can neutralize H7N9 influenza virus. Nat Commun. Mar. 30, 2015;6:6714. doi: 10.1038/ncomms7714.

Cheng et al., Multifunctional triblock copolymers for intracellular messenger RNA delivery. Biomaterials. Oct. 2012; 33(28): 6868-6876.

Cu et al., Enhanced Delivery and Potency of Self-Amplifying mRNA Vaccines by Electroporation in Situ, Vaccines, 2013, 1, 367-383. Abstract Only.

Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.

Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Ernsting et al., Factors controlling the pharmacokinetics, biodistribtion and intratumoral penetration of nanoparticles. J Control Release. Dec. 28, 2013;172(3):782-94. doi: 10.1016/j.jconrel.2013.09.013. Epub Sep. 25, 2013.

Ewert et al., Cationic liposome-nucleic acid complexes for gene delivery and silencing: pathways and mechanisms for plasmid DNA and siRNA. Top Curr Chem. 2010:296:191-226.

(56) References Cited

OTHER PUBLICATIONS

Fleeton et al., Self-replicative RNA vaccines elicit protection against influenza A virus, respiratory syncytial virus, and a tickborae encephalitis virus. J Infect Dis. May 1, 2001;183(9):1395-8. Epub Mar. 30, 2001.
Gaskell et al., Feline herpesvirus. Vet Res. Mar.-Apr. 2007;38(2):337-54. Epub Feb. 13, 2007.
Geall et al., Nonviral delivery of self-amplifying RNA vaccines. Proc Natl Acad Sci U S A. Sep. 4, 2012;109(36):14604.9. doi:10.1073/pnas.1209367109. Epub Aug. 20, 2012.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Gorander et al., Secreted portion of glycoprotein g of herpes simplex virus type 2 is a novel antigen for type-discriminating serology. J Clin Microbiol. Aug. 2003;41(8):3681-6.
Holtkamp et al., Modification of antigen-encoding RNA increases stability, translational efficacy, and T-cell stimulatory capacity of dendritic cells. Blood. Dec. 15, 2006;108(13):4009-17.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kuhn et al., mRNA as a versatile tool for exogenous protein expression. Current Gene Therapy. Oct. 2012; 12 (5): 347-361.
Kussie et al., A single engineered amino acid substitution changes antibody fine specificity. J Immunol. Jan. 1, 1994;152(1):146-52.
Leitner et al., DNA and RNA-based vaccines: principles, progress and prospects. Vaccine. Dec. 10, 1999;18 (9-10):765-77.
Leroueil et al., Wide varieties of cationic nanoparticles induce defects in supported lipid bilayers. Nano Lett. Feb. 2008;8(2):420-4. doi: 10.1021/n10722929. Epub Jan. 25, 2008.
Lian et al., Trends and developments in liposome drug delivery systems. J Pharm Sci. Jun. 2001;90(6):667-80.
Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.
Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.
Liu et al., Human herpesviras 2 strain 16293 glycoprotein D (US6) gene, complete cds. GenBank: AY779754. Encodes AAW23134. Apr. 14, 2009.
Lohith, In vivo imaging of mRNA based vaccine antigen in non-human primates using PET reporter mRNA-probe combination, Molecular Imaging and Biology, Dec. 2017, vol. 19, No. 1 Supplement, p. S703.
Lorenzi et al., Intranasal vaccination with messenger RNA as a new approach in gene therapy: Use against tuberculosis. BMC Biotechnol. Oct. 2010; 10(77): 1-11.
Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97bld2/MacLachlan_mRNA_Conf_2013.pdf. Last accessed Dec. 22, 2016.
Madden et al. Svstemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Martinon et al., Induction of virus-specific cytotoxic T lymphocytes in vivo by liposome-entrapped mRNA. EurJ Immunol. Jul. 1993;23(7):1719-22.
Mckenzie et al., Nucleic acid vaccines: tasks and tactics. Immunol Res. 2001 ;24(3):225-44.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mol Ther. Apr. 2000;2(2):176-81.
Mockey et al., mRNA-based cancer vaccine: prevention of B16 melanoma progression and metastasis bv systemic injection of MART1 mRNA histidylated lipopolyplexes. Cancer Gene, Ther. Sep. 2007;14(9):802-14. Epub Jun. 22, 2007.
Perche et al., Enhancement of dendritic cells transfection in vivo and of vaccination against B16F10 melanoma with mannosylated histidylated lipopolyplexes loaded with tumor antigen messenger RNA. Nanomedicine. Aug. 2011;7(4):445-53. doi: 10.1016/j.nano.2010.12.010. Epub Jan. 8, 2011.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Pollard et al., Type I IFN counteracts the induction of antigen-specific immune responses by lipid-based delivery of mRNA vaccines. Mol Ther. Jan. 2013; 21 (1): 251-259.
Rodriguez et al., Delivery of recombinant vaccines against bovine herpesvirus type 1 gD and Babesia bovis MSA-2c to mice using liposomes derived from egg yolk lipids. Vet J. Jun. 2013;196(3):550-1. doi: 10.1016/j.tvjl.2012.10.036. Epub Nov. 24, 2012.
Rouse et al., Induction in vitro of primary cytotoxic T-lymphocvte responses with DNA encoding herpes simplex virus proteins. J Virol. Sep. 1994;68(9):5685-9.
Schirrmacher et al., Intra-pinna ant-tumor vaccination with self-replicating infectious RNA or with DNA encoding a model tumor antigen and a cytokine. Gene Ther. Jul. 2000;7(13):1137-47.
Schott et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Sciortino et al., RNAs extracted from herpes simplex virus 1 virions: apparent selectivity of viral but not cellular RNAs packaged in virions. J Virol. Sep. 2001;75(17):8105-16.
Small et al., Viruses—from pathogens to vaccine carriers.Curr Opin Virol. Oct. 2011;1(4):241-5. doi: 10.1016/j.coviro.2011.07.009.
Stanberry et al., Glycoprotein-D-adjuvant vaccine to prevent genital herpes. N Engl J Med. Nov. 21, 2002;347(21):1652-61.
Szebeni et al.. Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the, development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Thess et al.. Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Vassilev et al., Microparticle-mediated RNA immunization against bovine viral diarrhea virus. Vaccine. Feb. 28, 2001;19(15-16):Sep. 2012.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

(56) References Cited

OTHER PUBLICATIONS

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Whitley et al., Clinical management of herpes simplex virus infections: past, present, and future. Version 1. F1000Res. 2018; 7: F1000 Faculty Rev-1726.

Winkler et al., Changing the antigen binding specificity by single point mutations of an anti-p24 (HIV-1) antibody. J Immunol. Oct. 15, 2000;165(8):4505-14.

Wong et al., An mRNA vaccine for influenza. Nat Biotechnol. Dec. 2012;30(12):1202-4. doi: 10.1038/nbt.2439.

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.

Ying et al., Cancer therapy using a self-replicating RNA. vaccine. Nat Med. Jul. 1999;5(7):823-7.

U.S. Appl. No. 90/014,395, filed Oct. 24, 2019, Ciaramella et al.

U.S. Appl. No. 16/880,829, filed May 21, 2020, Ciaramella et al.

U.S. Appl. No. 16/348,943, filed May 10, 2019, Ciaramella.

U.S. Appl. No. 16/608,451, filed Oct. 25, 2019, Ciaramella et al.

Adamiak, et al. glycoprotein E [Human alphaherpesvirus 2]. GenBank: ABU45436.1. Pub. Nov. 29, 2007. 1 page.

Awasthi et al., Immunization With a Vaccine Combining Herpes Simplex Virus 2 (HSV-2) Glycoprotein C (gC) and gD Subunits Improves the Protection of Dorsal Root Ganglia in Mice and Reduces the Frequency of Recurrent Vaginal Shedding of HSV-2 DNA in Guinea Pigs Compared to Immunization With gD Alone. J Virol. Oct. 2011;85(20):10472-86. doi: 10.1128/JVI.00849-11. Epub Aug. 3, 2011.

Cunnigham, The herpes zoster subunit vaccine. Expert Opin Biol Ther. 2016;16(2):265-71. doi: 10.1517/14712598.2016.1134481. PMID: 26865048.

Davison, envelope glycoprotein D [Human alphaherpesvirus 2]. NCBI Reference Sequence: YP 009137218.1. May 12, 2015. 3 pages.

Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.

Hodgman et al. RecName: Full=Envelope glycoprotein I; Short=gl; Flags: Precursor. UniProtKB/Swiss-Prot: P06764.1. Rev. Jan. 10, 2015. 1 page.

Kalantari-Dehagi et al., Discovery of Potential Diagnostic and Vaccine Antigens in Herpes Simplex Virus 1 and 2 by Proteome-Wide Antibody Profiling. J Virol. Apr. 2012;86(8):4328-39. doi: 10.1128/JVI.05194-11. Epub Feb. 8, 2012.

Morello et al., Immunization With Herpes Simplex Virus 2 (HSV-2) Genes Plus Inactivated HSV-2 Is Highly Protective Against Acute and Recurrent HSV-2 Disease. J Virol. Apr. 2011;85(7):3461-72. doi: 10.1128/JVI.02521-10. Epub Jan. 26, 2011.

Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.

Petro et al., Herpes simplex type 2 virus deleted in glycoprotein D protects against vaginal, skin and neural disease. Elife. Mar. 10, 2015;4:e06054. doi: 10.7554/eLife.06054.

Reichmuth et al., mRNA Vaccine Delivery Using Lipid Nanoparticles. Ther Deliv. 2016;7(5):319-34. doi: 10.4155/tde-2016-0006.

Schmidt-Chanasit, glycoprotein B [Human alphaherpesvirus 2]. Gen Bank: ADG45118.1. Jun. 24, 2010. 2 pages.

Shah et al., Shingrix for Herpes Zoster: A Review. Skin Therapy Lett. Jul. 2019;24(4):5-7.

Swain et al. RecName: Full=Envelope glycoprotein C; Flags: Precursor UniProtKB/Swiss-Prot: P06475.1. Rev. Jan. 7, 2015. 3 pages.

Zhao et al., Chapter Two: Lipid Nanoparticles for Gene Delivery. Book: Advances in Genetics. Elsevier, 2014. 24 pages.

U.S. Appl. No. 16/036,318, filed Jul. 16, 2018, Ciaramella et al.

U.S. Appl. No. 16/144,394, filed Sep. 27, 2018, Ciaramella et al.

U.S. Appl. No. 17/204,801, filed Mar. 17, 2021, Ciaramella et al.

U.S. Appl. No. 15/748,773, filed Jan. 30, 2018, Ciaramella et al.

U.S. Appl. No. 15/753,293, filed Feb. 17, 2018, Smith.

U.S. Appl. No. 15/748,782, filed Jan. 30, 2018, Mousavi et al.

U.S. Appl. No. 15/767,587, filed Apr. 11, 2018, Ciaramella.

U.S. Appl. No. 16/833,409, filed Mar. 27, 2020, Ciaramella.

U.S. Appl. No. 15/767,600, filed Apr. 11, 2018, Ciaramella et al.

U.S. Appl. No. 15/769,710, filed Apr. 19, 2018, Ciaramella et al.

U.S. Appl. No. 15/767,609, filed Apr. 11, 2018, Ciaramella et al.

U.S. Appl. No. 15/767,613, filed Apr. 11, 2018, Ciaramella et al.

U.S. Appl. No. 15/767,618, filed Apr. 11, 2018, Ciaramella et al.

U.S. Appl. No. 16/853,973, filed Apr. 21, 2020, Ciaramella et al.

U.S. Appl. No. 16/850,519, filed Apr. 16, 2020, Ciaramella et al.

U.S. Appl. No. 15/746,286, filed Jan. 19, 2018, Ciaramella et al.

U.S. Appl. No. 16/897,859, filed Jun. 10, 2020, Ciaramella et al.

U.S. Appl. No. 16/898,268, filed Jun. 10, 2020, Ciaramella et al.

U.S. Appl. No. 16/599,661, filed Oct. 11, 2019, Besin et al.

U.S. Appl. No. 16/333,330, filed Mar. 14, 2019, Hoge et al.

U.S. Appl. No. 16/864,566, filed May 1, 2020, Ciaramella et al.

U.S. Appl. No. 16/897,734, filed Jun. 10, 2020, Ciaramella et al.

U.S. Appl. No. 16/468,838, filed Jun. 12, 2019, Miracco.

U.S. Appl. No. 16/001,765, filed Jun. 6, 2018, Marquardt et al.

U.S. Appl. No. 17/127,949, filed Dec. 18, 2020, Ciaramella.

U.S. Appl. No. 16/467,142, filed Jun. 6, 2019, Ciaramella et al.

U.S. Appl. No. 16/603,111, filed Oct. 4, 2019, Brito et al.

U.S. Appl. No. 16/482,844, filed Aug. 1, 2019, Valiante et al.

U.S. Appl. No. 16/496,135, filed Sep. 20, 2019, Narayanan et al.

U.S. Appl. No. 16/483,012, filed Aug. 1, 2019, Mauger et al.

U.S. Appl. No. 16/657,122, filed Oct. 18, 2019, Rabideau et al.

U.S. Appl. No. 16/362,366, filed Mar. 22, 2019, Ciaramella.

U.S. Appl. No. 16/493,986, filed Sep. 13, 2019, Ciaramella et al.

U.S. Appl. No. 16/494,103, filed Sep. 13, 2019, Ciaramella et al.

U.S. Appl. No. 16/494,162, filed Sep. 13, 2019, Ciaramella.

U.S. Appl. No. 17/245,973, filed Apr. 30, 2021, Ciaramella.

U.S. Appl. No. 16/494,988, filed Sep. 17, 2019, Ciaramella et al.

U.S. Appl. No. 17/155.592, filed Jan. 22, 2021, Ciaramella et al.

U.S. Appl. No. 16/639,265, filed Feb. 14, 2020, Issa et al.

U.S. Appl. No. 16/639,305, filed Feb. 14, 2020, Issa et al.

U.S. Appl. No. 16/765,285, filed May 19, 2020 Ciaramella et al.

U.S. Appl. No. 16/302,607, filed Nov. 16, 2018, Benenato et al.

U.S. Appl. No. 16/623,069, filed Dec. 16, 2019, Hoge et al.

U.S. Appl. No. 16/639,403, filed Feb. 14, 2020, Hoge et al.

U.S. Appl. No. 16/848,318, filed Apr. 14, 2020, Ciaramella et al.

U.S. Appl. No. 16/965,589, filed Jul. 28, 2020, Ciaramella et al.

U.S. Appl. No. 17/255,949, filed Dec. 23, 2020, Zhong et al.

U.S. Appl. No. 17/277,423, filed Mar. 18, 2021, Almarsson et al.

U.S. Appl. No. 17/277,452, filed Mar. 18, 2021, Hennessy et al.

U.S. Appl. No. 17/276,112, filed Mar. 12, 2021, Martini et al.

U.S. Appl. No. 17/291,947, filed May 6, 2021, Ashburn et al.

U.S. Appl. No. 16/788,182, filed Feb. 11, 2020, Panther et al.

U.S. Appl. No. 16/794,318, filed Feb. 19, 2020, Mauger et al.

U.S. Appl. No. 17/145,164, filed Jan. 8, 2021, Giessel et al.

U.S. Appl. No. 17/000,201, filed Aug. 21, 2020, Stewart-Jones et al.

U.S. Appl. No. 17/000,215, filed Aug. 21, 2020, Stewart-Jones et al.

Egan et al., An HSV-2 nucleoside-modified mRNA genital herpes vaccine containing glycoproteins gC, gD, and gE protects mice against HSV-1 genital lesions and latent infection. PLoS Pathog. Jul. 27, 2020;16(7):e1008795.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Mccallister et al., Prospects and perspectives for development of a vaccine against herpes simplex virus infections. Expert Rev Vaccines. Nov. 2014; 13(11 ): 1349-60. Epub Jul. 31, 2014. (Year: 2014).

Natuk et al., Recombinant vesicular stomatitis virus vectors expressing herpes simplex virus type 2 gD elicit robust CD4+ Th1 immune responses and are protective in mouse and guinea pig models of vaginal challenge. J Viral. May 2006;80(9):4447-57.

(56) References Cited

OTHER PUBLICATIONS

Pardi et al., mRNA vaccines—a new era in vaccinology. Nat Rev Drug Discov. Apr. 2018;17(4):261-279. doi: 10.1038/nrd.2017.243. Epub Jan. 12, 2018.
Schlake et al., Developing mRNA-vaccine technologies. RNA Biol. Nov. 2012;9(11):1319-30. doi: 10.4161/rna.22269. Epub Oct. 12, 2012.
Zhao et al., Nanoparticle vaccines. Vaccine. Jan. 9, 2014;32(3):327-37. doi: 10.1016/j.vaccine.2013.11.069. Epub Dec. 2, 2013.
Kohl et al., Limited antibody-dependent cellular cytotoxicity antibody response induced by a herpes simplex virus type 2 subunit vaccine. J Infect Dis. Jan. 2000;181(1):335-9. doi: 10.1086/315208.
Mcallister et al., Prospects and perspectives for development of a vaccine against herpes simplex virus infections. Expert Rev Vaccines. Nov. 2014;13(11):1349-60. doi: 10.1586/14760584.2014.932694. Epub Jul. 31, 2014.

* cited by examiner

HERPES SIMPLEX VIRUS VACCINE

RELATED APPLICATIONS

This application is a national stage filing under 35 U.S.C. § 371 of international application number PCT/US2018/022622, filed Mar. 15, 2018, which was published under PCT Article 21(2) in English and claims the benefit under 35 U.S.C. § 119(e) of U.S. provisional application No. 62/471,786, filed Mar. 15, 2017, which is incorporated by reference herein in its entirety.

BACKGROUND

Herpes simplex viruses (HSV) are double-stranded linear DNA viruses in the Herpesviridae family. Two members of the herpes simplex virus family infect humans—known as HSV-1 and HSV-2. Symptoms of HSV infection include the formation of blisters in the skin or mucous membranes of the mouth, lips, and/or genitals. HSV is a neuroinvasive virus that can cause sporadic recurring episodes of viral reactivation in infected individuals. HSV is transmitted by contact with an infected area of the skin during a period of viral activation.

Deoxyribonucleic acid (DNA) vaccination is one technique used to stimulate humoral and cellular immune responses to foreign antigens, such as HSV antigens. The direct injection of genetically engineered DNA (e.g., naked plasmid DNA) into a living host results in a small number of its cells directly producing an antigen, resulting in a protective immunological response. With this technique, however, come potential problems, including the possibility of insertional mutagenesis, which could lead to the activation of oncogenes or the inhibition of tumor suppressor genes.

SUMMARY

Provided herein are ribonucleic acid (RNA) vaccines that build on the knowledge that modified RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The RNA (e.g., mRNA) vaccines of the present disclosure may be used to induce a balanced immune response against herpes simplex virus (HSV), comprising both cellular and humoral immunity, without risking the possibility of insertional mutagenesis, for example.

The RNA (e.g., mRNA) vaccines may be utilized in various settings depending on the prevalence of the infection or the degree or level of unmet medical need. The RNA vaccines may be utilized to treat and/or prevent a HSV of various genotypes, strains, and isolates. The RNA vaccines have superior properties in that they produce much larger antibody titers and produce responses earlier than commercially available anti-viral therapeutic treatments. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines which are manufactured ex vivo and may trigger unwanted cellular responses, the RNA vaccines are presented to the cellular system in a more native fashion.

Some embodiments of the present disclosure provide herpes simplex virus (HSV) vaccines that include at least one ribonucleic acid (RNA) polynucleotide having an open reading frame encoding at least one HSV antigenic polypeptide (including immunogenic fragments thereof, e.g., immunogenic fragments capable of inducing an immune response to HSV).

Some embodiments of the present disclosure provide herpes simplex virus (HSV) vaccines that include (i) at least one ribonucleic acid (RNA) polynucleotide having an open reading frame encoding at least one HSV antigenic polypeptide (including immunogenic fragments thereof, e.g., immunogenic fragments capable of inducing an immune response to HSV) and (ii) a pharmaceutically-acceptable carrier.

In some embodiments, at least one antigenic polypeptide is HSV (HSV-1 or HSV-2) glycoprotein B, HSV (HSV-1 or HSV-2) glycoprotein C, HSV (HSV-1 or HSV-2) glycoprotein D, HSV (HSV-1 or HSV-2) glycoprotein E, HSV (HSV-1 or HSV-2) glycoprotein I. In some embodiments, at least one antigenic polypeptide has at least 95%, at least 96%, at least 97%, at least 98% or at least 99% identity to HSV (HSV-1 or HSV-2) glycoprotein B, HSV (HSV-1 or HSV-2) glycoprotein C, HSV (HSV-1 or HSV-2) glycoprotein D, HSV (HSV-1 or HSV-2) glycoprotein E, HSV (HSV-1 or HSV-2) glycoprotein I or HSV (HSV-1 or HSV-2) ICP4 protein.

In some embodiments, at least one antigen polypeptide is a non-glycogenic polypeptide, for example, but not limited to, HSV (HSV-1 or HSV-2) ICP4 protein, HSV (HSV-1 or HSV-2) ICP0 protein.

In some embodiments, at least one antigenic polypeptide has at least 95%, at least 96%, at least 97%, at least 98% or at least 99% identity to HSV (HSV-1 or HSV-2) glycoprotein B, HSV (HSV-1 or HSV-2) glycoprotein C, HSV (HSV-1 or HSV-2) glycoprotein D, HSV (HSV-1 or HSV-2) glycoprotein E, HSV (HSV-1 or HSV-2) glycoprotein I or HSV (HSV-1 or HSV-2) ICP4 protein.

In some embodiments, at least one antigenic polypeptide is HSV (HSV-1 or HSV-2) glycoprotein C, HSV (HSV-1 or HSV-2) glycoprotein D, a combination of HSV (HSV-1 or HSV-2) glycoprotein C and HSV (HSV-1 or HSV-2) glycoprotein D.

In some embodiments, a HSV vaccine includes at least one RNA polynucleotide having an open reading frame encoding HSV (HSV-1 or HSV-2) glycoprotein D, formulated with aluminum hydroxide and a 3-O-deacylated form of monophosphoryl lipid A (MPL). In some embodiments, the HSV vaccine is formulated for intramuscular injection.

In some embodiments, at least one RNA polynucleotide encodes an antigenic polypeptide having greater than 90% identity to an amino acid sequence of any one of SEQ ID NO: 24-53 or 66-67 (e.g., in Table 2 or 3) and having membrane fusion activity. In some embodiments, at least one RNA polynucleotide encodes an antigenic polypeptide having greater than 95% identity to an amino acid sequence of any one of SEQ ID NO: 24-53 or 66-67 (e.g., in Table 2 or 3) and having membrane fusion activity. In some embodiments, at least one RNA polynucleotide encodes an antigenic polypeptide having greater than 96% identity to an amino acid sequence of any one of SEQ ID NO: 24-53 or 66-67 (e.g., in Table 2 or 3) and having membrane fusion activity. In some embodiments, at least one RNA polynucleotide encodes an antigenic polypeptide having greater than 97% identity to an amino acid sequence of any one of SEQ ID NO: 24-53 or 66-67 (e.g., in Table 2 or 3) and having membrane fusion activity. In some embodiments, at least one RNA polynucleotide encodes an antigenic polypeptide having greater than 98% identity to an amino acid sequence of any one of SEQ ID NO: 24-53 or 66-67 (e.g., in Table 2 or 3) and having membrane fusion activity. In some embodiments, at least one RNA polynucleotide encodes an antigenic polypeptide having greater than 99% identity to an amino acid sequence of any one of SEQ ID NO: 24-53 or 66-67 (e.g., in Table 2 or 3) and having membrane fusion activity. In some embodiments, at least one RNA polynucleotide encodes an antigenic polypeptide having 95-99% identity to an amino acid sequence of any one of SEQ ID NO: 24-53 or 66-67 (e.g., in Table 2 or 3) and having membrane fusion activity.

In some embodiments, at least one RNA polynucleotide encodes an antigenic polypeptide having an amino acid sequence of any one of SEQ ID NO: 24-53 or 66-67 (e.g., in Table 2 or 3) and is codon optimized mRNA.

In some embodiments, at least one mRNA polynucleotide encodes an antigenic polypeptide having an amino acid sequence of any one of SEQ ID NO: 24-53 or 66-67 (e.g., in Table 2 or 3) and has less than 80% identity to wild-type mRNA sequence. In some embodiments, at least one mRNA polynucleotide encodes an antigenic polypeptide having an amino acid sequence of any one of SEQ ID NO: 24-53 or 66-67 (e.g., in Table 2 or 3) and has less than 75%, 85% or 95% identity to wild-type mRNA sequence. In some embodiments, at least one mRNA polynucleotide encodes an antigenic polypeptide having an amino acid sequence of any one of SEQ ID NO: 24-53 or 66-67 (e.g., in Table 2 or 3) and has 50-80%, 60-80%, 40-80%, 30-80%, 70-80%, 75-80% or 78-80% identity to wild-type mRNA sequence. In some embodiments, at least one mRNA polynucleotide encodes an antigenic polypeptide having an amino acid sequence of any one of SEQ ID NO: 24-53 or 66-67 (e.g., in Table 2 or 3) and has 40-85%, 50-85%, 60-85%, 30-85%, 70-85%, 75-85%, or 80-85% identity to wild-type mRNA sequence. In some embodiments, at least one mRNA polynucleotide encodes an antigenic polypeptide having an amino acid sequence of any one of SEQ ID NO: 24-53 or 66-67 (e.g., in Table 2 or 3) and has 40-90%, 50-90%, 60-90%, 30-90%, 70-90%, 75-90%, 80-90%, or 85-90% identity to wild-type mRNA sequence.

In some embodiments, at least one RNA polynucleotide is encoded by a nucleic acid having greater than 90% identity to a nucleic acid sequence of any one of SEQ ID NO: 1-23 or 54-64 (e.g., in Table 1 or 3). In some embodiments, at least one RNA polynucleotide is encoded by a nucleic acid having greater than 95% identity to a nucleic acid sequence of any one of SEQ ID NO: 1-23 or 54-64 (e.g., in Table 1 or 3). In some embodiments, at least one RNA polynucleotide is encoded by a nucleic acid having greater than 96% identity to a nucleic acid sequence of any one of SEQ ID NO: 1-23 or 54-64 (e.g., in Table 1 or 3). In some embodiments, at least one RNA polynucleotide is encoded by a nucleic acid having greater than 97% identity to a nucleic acid sequence of any one of SEQ ID NO: 1-23 or 54-64 (e.g., in Table 1 or 3). In some embodiments, at least one RNA polynucleotide is encoded by a nucleic acid having greater than 98% identity to a nucleic acid sequence of any one of SEQ ID NO: 1-23 or 54-64 (e.g., in Table 1 or 3). In some embodiments, at least one RNA polynucleotide is encoded by a nucleic acid having greater than 99% identity to a nucleic acid sequence of any one of SEQ ID NO: 1-23 or 54-64 (e.g., in Table 1 or 3). In some embodiments, at least one RNA polynucleotide is encoded by a nucleic acid having 95-99% identity to a nucleic acid sequence of any one of SEQ ID NO: 1-23 or 54-64 (e.g., in Table 1 or 3).

In some embodiments, at least one mRNA polynucleotide is encoded by a nucleic acid having a sequence of any one of SEQ ID NO: 1-23 or 54-64 (e.g., in Table 1 or 3) and has less than 80% identity to wild-type mRNA sequence. In some embodiments, at least one mRNA polynucleotide is encoded by a nucleic acid having a sequence of any one of SEQ ID NO: 1-23 or 54-64 (e.g., in Table 1 or 3) and has less than 75%, 85% or 95% identity to a wild-type mRNA sequence. In some embodiments, at least one mRNA polynucleotide is encoded by a nucleic acid having a sequence of any one of SEQ ID NO: 1-23 or 54-64 (e.g., in Table 1 or 3) and has less than 50-80%, 60-80%, 40-80%, 30-80%, 70-80%, 75-80% or 78-80% identity to wild-type mRNA sequence. In some embodiments, at least one mRNA polynucleotide is encoded by a nucleic acid having a sequence of any one of SEQ ID NO: 1-23 or 54-64 (e.g., in Table 1 or 3) and has less than 40-85%, 50-85%, 60-85%, 30-85%, 70-85%, 75-85%, or 80-85% identity to wild-type mRNA sequence. In some embodiments, at least one mRNA polynucleotide is encoded by a nucleic acid having a sequence of any one of SEQ ID NO: 1-23 or 54-64 (e.g., in Table 1 or 3) and has less than 40-90%, 50-90%, 60-90%, 30-90%, 70-90%, 75-90%, 80-90%, or 85-90% identity to wild-type mRNA sequence.

In some embodiments, at least one RNA polynucleotide comprises a nucleic acid having greater than 90% identity to a nucleic acid sequence of any one of SEQ ID NO: 90-124. In some embodiments, at least one RNA polynucleotide comprises a nucleic acid having greater than 95% identity to a nucleic acid sequence of any one of SEQ ID NO: 90-124. In some embodiments, at least one RNA polynucleotide comprises a nucleic acid having greater than 96% identity to a nucleic acid sequence of any one of SEQ ID NO: 90-124. In some embodiments, at least one RNA polynucleotide comprises a nucleic acid having greater than 97% identity to a nucleic acid sequence of any one of SEQ ID NO: 90-124. In some embodiments, at least one RNA polynucleotide comprises a nucleic acid having greater than 98% identity to a nucleic acid sequence of any one of SEQ ID NO: 90-124. In some embodiments, at least one RNA polynucleotide comprises a nucleic acid having greater than 99% identity to a nucleic acid sequence of any one of SEQ ID NO: 90-124. In some embodiments, at least one RNA polynucleotide comprises a nucleic acid having 95-99% identity to a nucleic acid sequence of any one of SEQ ID NO: 90-124.

In some embodiments, at least one mRNA polynucleotide comprises a nucleic acid having a sequence of any one of SEQ ID NO: 90-124 and has less than 80% identity to wild-type mRNA sequence. In some embodiments, at least one mRNA polynucleotide comprises a nucleic acid having a sequence of any one of SEQ ID NO: 90-124 and has less than 75%, 85% or 95% identity to a wild-type mRNA sequence. In some embodiments, at least one mRNA polynucleotide comprises a nucleic acid having a sequence of any one of SEQ ID NO: 90-124 and has less than 50-80%, 60-80%, 40-80%, 30-80%, 70-80%, 75-80% or 78-80% identity to wild-type mRNA sequence. In some embodiments, at least one mRNA polynucleotide comprises a nucleic acid having a sequence of any one of SEQ ID NO: 90-124 and has less than 40-85%, 50-85%, 60-85%, 30-85%, 70-85%, 75-85%, or 80-85% identity to wild-type mRNA sequence. In some embodiments, at least one mRNA polynucleotide comprises a nucleic acid having a sequence of any one of SEQ ID NO: 90-124 and has less than 40-90%, 50-90%, 60-90%, 30-90%, 70-90%, 75-90%, 80-90%, or 85-90% identity to wild-type mRNA sequence.

Table 3 provides National Center for Biotechnology Information (NCBI) accession numbers of interest. It should be understood that the phrase "an amino acid sequence of Table 3" refers to an amino acid sequence identified by one or more NCBI accession numbers listed in Table 3. Each of the nucleic acid sequences, amino acid sequences, and variants having greater than 95% identity to each of the nucleic acid sequences and amino acid sequences encompassed by the Accession Numbers of Table 3 are included within the constructs of the present disclosure.

In some embodiments, at least one mRNA polynucleotide encodes an antigenic polypeptide having an amino acid sequence of any one of SEQ ID NO: 24-53 or 66-67 (e.g., in Table 2 or 3) and has greater than 80% identity to wild-type mRNA sequence, but does not include wild-type mRNA sequence.

In some embodiments, at least one RNA polynucleotide encodes an antigenic polypeptide that attaches to cell receptors.

In some embodiments, at least one RNA polynucleotide encodes an antigenic polypeptide that causes fusion of viral and cellular membranes.

In some embodiments, at least one RNA polynucleotide encodes an antigenic polypeptide that is responsible for binding of the HSV to a cell being infected.

In some embodiments, the vaccines further comprise an adjuvant.

Some embodiments of the present disclosure provide a herpes simplex virus (HSV) vaccine that includes at least one ribonucleic acid (RNA) polynucleotide having an open reading frame encoding at least one HSV antigenic polypeptide.

In some embodiments, the HSV vaccine includes at least one RNA polynucleotide having an open reading frame encoding at least one HSV antigenic polypeptide having at least one modification.

In some embodiments, the HSV vaccine includes at least one RNA polynucleotide having an open reading frame encoding at least one HSV antigenic polypeptide having at least one modification, at least one 5' terminal cap, and is formulated within a lipid nanoparticle.

In some embodiments, a 5' terminal cap is 7mG(5')ppp (5')NlmpNp.

In some embodiments, at least one chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

In some embodiments, a lipid nanoparticle comprises a cationic lipid, a PEG-modified lipid, a sterol, and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z, 15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the cationic lipid is

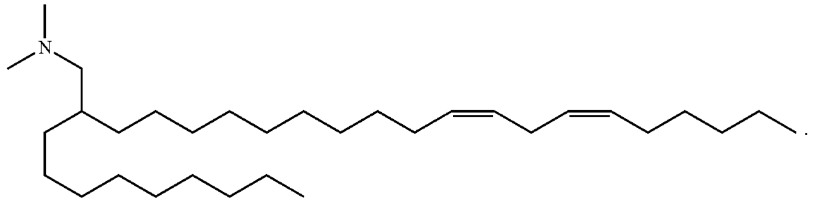 [SMILES: CCCCC/C=C\C/C=C\CCCCCCCCCC(CCCCCCCCC)CN(C)C]

In some embodiments, the cationic lipid is

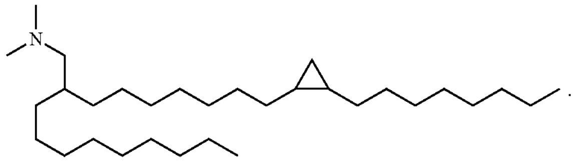 [SMILES: CCCCCCCCCC(CCCCCCCC1CC1CCCCCCCC)CN(C)C]

In some embodiments, the cationic lipid is selected from compounds of Formula (I):

(I)

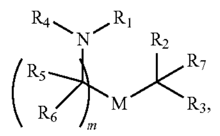

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or isomers thereof.

In some embodiments, a subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)R, —C(O)N(R)OR, and —C(=N$R_9$)N$(R)_2$, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or isomers thereof.

In some embodiments, a subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is —$(CH_2)_n$Q or —$(CH_2)_n$CHQR, where Q is —N$(R)_2$, and n is selected from 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or isomers thereof.

In some embodiments, a subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of —$(CH_2)_n$Q, —$(CH_2)_n$CHQR, —CHQR, and —CQ$(R)_2$, where Q is —N$(R)_2$, and n is selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or isomers thereof.

In some embodiments, a subset of compounds of Formula (I) includes those of Formula (IA):

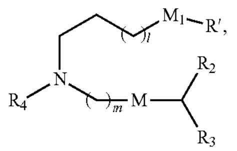

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, —N(R)C(O)R, —N(R)S$(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

Some embodiments of the present disclosure provide a herpes simplex virus (HSV) vaccine that includes at least one ribonucleic acid (RNA) polynucleotide having an open reading frame encoding at least one HSV antigenic polypeptide, wherein at least 80% of the uracil in the open reading frame have a chemical modification, optionally wherein the HSV vaccine is formulated in a lipid nanoparticle.

In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame have a N1-methyl pseudouridine in the 5-position of the uracil.

Some embodiments of the present disclosure provide methods of inducing an antigen specific immune response in a subject, comprising administering to the subject a HSV vaccine in an amount effective to produce an antigen specific immune response.

In some embodiments, an antigen specific immune response comprises a T cell response or a B cell response.

In some embodiments, a method of producing an antigen specific immune response involves a single administration of the HSV vaccine. In some embodiments, a method further includes administering to the subject a booster dose of the HSV vaccine. A booster vaccine according to this invention may comprise any HSV vaccine disclosed herein.

In some embodiments, a HSV vaccine is administered to the subject by intradermal or intramuscular injection.

Also provided herein are HSV vaccines for use in a method of inducing an antigen specific immune response in a subject, the method comprising administering the HSV vaccine to the subject in an amount effective to produce an antigen specific immune response in the subject.

Further provided herein are uses of HSV vaccines in the manufacture of a medicament for use in a method of inducing an antigen specific immune response in a subject, the method comprising administering the HSV vaccine to the subject in an amount effective to produce an antigen specific immune response.

In some embodiments, an anti-HSV antigenic polypeptide antibody titer produced in the subject is increased by at least 1 log relative to a control. In some embodiments, the anti-HSV antigenic polypeptide antibody titer produced in the subject is increased by 1-3 log relative to a control.

In some embodiments, the anti-HSV antigenic polypeptide antibody titer produced in the subject is increased at least 2 times relative to a control. In some embodiments, the anti-HSV antigenic polypeptide antibody titer produced in the subject is increased at least 5 times relative to a control. In some embodiments, the anti-HSV antigenic polypeptide antibody titer produced in the subject is increased at least 10 times relative to a control. In some embodiments, the anti-HSV antigenic polypeptide antibody titer produced in the subject is increased 2-10 times relative to a control.

In some embodiments, the control is an anti-HSV antigenic polypeptide antibody titer produced in a subject who has not been administered HSV vaccine. In some embodiments, the control is an anti-HSV antigenic polypeptide antibody titer produced in a subject who has been administered a live attenuated or inactivated HSV vaccine. In some embodiments, the control is an anti-HSV antigenic polypeptide antibody titer produced in a subject who has been administered a recombinant or purified HSV protein vaccine. In some embodiments, the control is an anti-HSV antigenic polypeptide antibody titer produced in a subject who has been administered an HSV virus-like particle (VLP) vaccine.

In some embodiments, the effective amount is a dose equivalent to at least a 2-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a dose equivalent to at least a 4-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a dose equivalent to at least a 10-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a dose equivalent to at least a 100-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a dose equivalent to at least a 1000-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a dose equivalent to a 2-fold to 1000-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a total dose of 25 μg to 1000 μg, or 50 μg to 1000 μg, or 25 to 200 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

Other aspects of the present disclosure provide methods of inducing an antigen specific immune response in a subject, the method comprising administering to a subject the HSV RNA (e.g., mRNA) vaccine described herein in an effective amount to produce an antigen specific immune response in a subject.

In some embodiments, an antigen specific immune response comprises (an increase in) antigenic polypeptide antibody production. In some embodiments, an anti-HSV antigenic polypeptide antibody titer produced in the subject is increased by at least 1 log relative to a control. In some embodiments, an anti-HSV antigenic polypeptide antibody titer produced in the subject is increased by 1 log to 3 log relative to a control.

In some embodiments, the anti-HSV antigenic polypeptide antibody titer produced in the subject is increased at least 2 times relative to a control. In some embodiments, the anti-HSV antigenic polypeptide antibody titer produced in the subject is increased at least 5 times relative to a control. In some embodiments, the anti-HSV antigenic polypeptide antibody titer produced in the subject is increased at least 10 times relative to a control. In some embodiments, the anti-HSV antigenic polypeptide antibody titer produced in the subject is increased 2 times to 10 times relative to a control.

In some embodiments, the control is an anti-HSV antigenic polypeptide antibody titer produced in a subject who has not been administered HSV vaccine. In some embodiments, the control is an anti-HSV antigenic polypeptide antibody titer produced in a subject who has been administered a live attenuated or inactivated HSV vaccine. In some embodiments, the control is an anti-HSV antigenic polypeptide antibody titer produced in a subject who has been administered a recombinant or purified HSV protein vaccine. In some embodiments, the control is an anti-HSV antigenic polypeptide antibody titer produced in a subject who has been administered a HSV VLP vaccine.

In some embodiments, the effective amount administered to a subject is a dose (of HSV RNA, e.g., mRNA, vaccine) equivalent to at least a 2-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant HSV protein vaccine, a live attenuated HSV vaccine, or a HSV VLP vaccine.

In some embodiments, the effective amount administered to a subject is a dose (of HSV RNA, e.g., mRNA, vaccine) equivalent to at least a 4-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount administered to a subject is a dose (of HSV RNA, e.g., mRNA, vaccine) equivalent to at least a 10-fold reduction in the standard of care dose of a recombinant HSV protein vaccine, and wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount is a dose (of HSV RNA, e.g., mRNA, vaccine) administered to a subject equivalent to at least a 100-fold reduction in the standard of care dose of a recombinant HSV protein vaccine, wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount administered to a subject is a dose (of HSV RNA, e.g., mRNA, vaccine) equivalent to at least a 1000-fold reduction in the standard of care dose of a recombinant HSV protein vaccine, and wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount administered to a subject is a dose (of HSV RNA, e.g., mRNA, vaccine) equivalent to a 2-fold to 1000-fold reduction in the standard of care dose of a recombinant HSV protein vaccine, and wherein an anti-HSV antigenic polypeptide antibody titer produced in the subject is equivalent to an anti-HSV antigenic polypeptide antibody titer produced in a control subject administered the standard of care dose of a recombinant or purified HSV protein vaccine, a live attenuated or inactivated HSV vaccine, or a HSV VLP vaccine.

In some embodiments, the effective amount administered to a subject is a total dose (of HSV RNA, e.g., mRNA, vaccine) of 50 μg to 1000 μg. In some embodiments, the effective amount is a total dose of 50 μg, 100 μg, 200 μg, 400 μg, 800 μg, or 1000 μg. In some embodiments, the effective amount is a dose of 25 μg administered to the subject a total of two times. In some embodiments, the effective amount is a dose of 50 μg administered to the subject a total of two times. In some embodiments, the effective amount is a dose of 100 μg administered to the subject a total of two times. In some embodiments, the effective amount is a dose of 200 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the efficacy (or effectiveness) of the HSV RNA (e.g., mRNA) vaccine against HSV is greater than 60%.

Vaccine efficacy may be assessed using standard analyses (see, e.g., Weinberg et al., *J Infect Dis.* 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100;\text{ and}$$

$$\text{Efficacy}=(1-\text{RR})\times 100.$$

Likewise, vaccine effectiveness may be assessed using standard analyses (see, e.g., Weinberg et al., *J Infect Dis.* 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, the efficacy (or effectiveness) of the HSV RNA (e.g., mRNA) vaccine against HSV is greater than 65%. In some embodiments, the efficacy (or effectiveness) of the vaccine against HSV is greater than 70%. In some embodiments, the efficacy (or effectiveness) of the vaccine against HSV is greater than 75%. In some embodiments, the efficacy (or effectiveness) of the vaccine against HSV is greater than 80%. In some embodiments, the efficacy (or effectiveness) of the vaccine against HSV is greater than 85%. In some embodiments, the efficacy (or effectiveness) of the vaccine against HSV is greater than 90%.

In some embodiments, the vaccine immunizes the subject against HSV up to 1 year (e.g. for a single HSV season). In some embodiments, the vaccine immunizes the subject against HSV for up to 2 years. In some embodiments, the vaccine immunizes the subject against HSV for more than 2 years. In some embodiments, the vaccine immunizes the subject against HSV for more than 3 years. In some embodiments, the vaccine immunizes the subject against HSV for more than 4 years. In some embodiments, the vaccine immunizes the subject against HSV for 5-10 years.

In some embodiments, the subject has been exposed to HSV, is infected with (has) HSV, or is at risk of infection by HSV.

In some embodiments, the subject is immunocompromised (has an impaired immune system, e.g., has an immune disorder or autoimmune disorder).

In some embodiments, the subject is a subject about 10 years old, about 20 years old, or older (e.g., about 10, 11, 12, 13, 14, 15, 16, 17, 18, 19, or 20 years old).

In some embodiments, the subject is an adult between the ages of about 20 years and about 50 years (e.g., about 20, 25, 30, 35, 40, 45 or 50 years old).

Some aspects of the present disclosure provide herpes simplex virus (HSV) RNA (e.g., mRNA) vaccines containing a signal peptide linked to a HSV antigenic polypeptide. Thus, in some embodiments, the HSV RNA (e.g., mRNA) vaccines contain at least one ribonucleic acid (RNA) polynucleotide having an open reading frame encoding a signal peptide linked to a HSV antigenic peptide. Also provided herein are nucleic acids encoding the HSV RNA (e.g., mRNA) vaccines disclosed herein.

In some embodiments, the signal peptide is a IgE signal peptide. In some embodiments, the signal peptide is an IgE HC (Ig heavy chain epsilon-1) signal peptide. In some embodiments, the signal peptide has the sequence MDWTWILFLVAAATRVHS (SEQ ID NO: 78). In some embodiments, the signal peptide is an IgGK signal peptide. In some embodiments, the signal peptide has the sequence METPAQLLFLLLLWLPDTTG (SEQ ID NO: 79). In some embodiments, the signal peptide is selected from: a Japanese encephalitis PRM signal sequence (MLGSNSGQRVVFTILLLLVAPAYS; SEQ ID NO: 80), VSVg protein signal sequence (MKCLLYLAFLFIGVNCA; SEQ ID NO: 81), and Japanese encephalitis JEV signal sequence (MWLVSLAIVTACAGA; SEQ ID NO: 82).

In some embodiments, an effective amount of an HSV RNA (e.g., mRNA) vaccine (e.g., a single dose of the HSV vaccine) results in a 2-fold to 200-fold (e.g., about 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 180-, 190- or 200-fold) increase in serum neutralizing antibodies against HSV, relative to a control. In some embodiments, a single dose of the HSV RNA (e.g., mRNA) vaccine results in an about 5-fold, 50-fold, or 150-fold increase in serum neutralizing antibodies against HSV, relative to a control. In some embodiments, a single dose of the HSV RNA (e.g., mRNA) vaccine results in an about 2-fold to 10 fold, or an about 40 to 60 fold increase in serum neutralizing antibodies against HSV, relative to a control.

In some embodiments, the serum neutralizing antibodies are against HSV A and/or HSV B.

In some embodiments, the HSV vaccine is formulated in a MC3 lipid nanoparticle or a L-608 lipid nanoparticle.

In some embodiments, the methods further comprise administering a booster dose of the HSV RNA (e.g., mRNA) vaccine. In some embodiments, the methods further comprise administering a second booster dose of the HSV vaccine.

In some embodiments, efficacy of RNA vaccines RNA (e.g., mRNA) can be significantly enhanced when combined with a flagellin adjuvant, in particular, when one or more antigen-encoding mRNAs is combined with an mRNA encoding flagellin.

RNA (e.g., mRNA) vaccines combined with the flagellin adjuvant (e.g., mRNA-encoded flagellin adjuvant) have superior properties in that they may produce much larger antibody titers and produce responses earlier than commercially available vaccine formulations. While not wishing to be bound by theory, it is believed that the RNA vaccines, for example, as mRNA polynucleotides, are better designed to produce the appropriate protein conformation upon translation, for both the antigen and the adjuvant, as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Some embodiments of the present disclosure provide RNA (e.g., mRNA) vaccines that include at least one RNA (e.g., mRNA) polynucleotide having an open reading frame encoding at least one antigenic polypeptide (including immunogenic fragments thereof, e.g., immunogenic fragments capable of inducing an immune response to HSV) and at least one RNA (e.g., mRNA polynucleotide) having an open reading frame encoding a flagellin adjuvant.

In some embodiments, at least one flagellin polypeptide (e.g., encoded flagellin polypeptide) is a flagellin protein. In some embodiments, at least one flagellin polypeptide (e.g., encoded flagellin polypeptide) is an immunogenic flagellin fragment. In some embodiments, at least one flagellin polypeptide and at least one antigenic polypeptide are encoded by a single RNA (e.g., mRNA) polynucleotide. In other embodiments, at least one flagellin polypeptide and at least one antigenic polypeptide are each encoded by a different RNA polynucleotide.

In some embodiments, at least one flagellin polypeptide has at least 80%, at least 85%, at least 90%, or at least 95% identity to a flagellin polypeptide having a sequence of SEQ ID NO: 89, 125, or 126.

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first virus antigenic polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no chemical modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 ug and 400 ug of one or more RNA polynucleotides having an open reading frame comprising at least one chemical modification or optionally no chemical modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a virus strain in an individual or population of individuals comprising administering to said individual or population an antigenic memory booster nucleic acid vaccine comprising (a) at least one RNA polynucleotide, said polynucleotide comprising at least one chemical modification or optionally no chemical modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 ug/kg and 400 ug/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no modified nucleotides (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Both chemically modified and unmodified RNA vaccines are useful in the invention. Surprisingly, in contrast to prior art reports that it was preferable to use chemically unmodified mRNA formulated in a carrier for the production of vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding an virus antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding an virus antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a virus antigenic polypeptide in an effective amount to vaccinate the subject.

In some aspects the invention is a method of vaccinating a subject with a combination vaccine including at least two nucleic acid sequences encoding antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

The RNA polynucleotide is one of SEQ ID NO: 1-23, 54-64, and 90-124 and includes at least one chemical modification. In other embodiments the RNA polynucleotide is one of SEQ ID NO: 1-23, 54-64, and 90-124 and does not include any nucleotide modifications, or is unmodified. In yet other embodiments the at least one RNA polynucleotide encodes an antigenic protein of any of SEQ ID NO: 24-53 and 66-67 and includes at least one chemical modification.

In other embodiments the RNA polynucleotide encodes an antigenic protein of any of SEQ ID NO: 24-53 and 66-67 and does not include any nucleotide modifications, or is unmodified.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose).

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

The details of various embodiments of the invention are set forth in the description below. Other features, objects, and advantages of the invention will be apparent from the description and the drawings, and from the claims.

DETAILED DESCRIPTION

Embodiments of the present disclosure provide RNA (e.g., mRNA) vaccines that include polynucleotide encoding a herpes simplex virus (HSV) antigen. HSV is a double-stranded, linear DNA virus in the Herpesviridae. Two members of the herpes simplex virus family infect humans—known as HSV-1 and HSV-2. Symptoms of HSV infection include the formation of blisters in the skin or mucous membranes of the mouth, lips and/or genitals. HSV is a neuroinvasive virus that can cause sporadic recurring episodes of viral reactivation in infected individuals. HSV is transmitted by contact with an infected area of the skin during a period of viral activation. HSV most commonly infects via the oral or genital mucosa and replicates in the stratified squamous epithelium, followed by uptake into ramifying unmyelinated sensory nerve fibers within the stratified squamous epithelium. The virus is then transported to the cell body of the neuron in the dorsal root ganglion, where it persists in a latent cellular infection (Cunningham A L et al. *J Infect Dis*. (2006) 194 (Supplement 1): S11-S18).

The genome of Herpes Simplex Viruses (HSV-1 and HSV-2) contains about 85 open reading frames, such that HSV can generate at least 85 unique proteins. These genes encode 4 major classes of proteins: (1) those associated with the outermost external lipid bilayer of HSV (the envelope), (2) the internal protein coat (the capsid), (3) an intermediate complex connecting the envelope with the capsid coat (the tegument), and (4) proteins responsible for replication and infection.

Examples of envelope proteins include UL1 (gL), UL10 (gM), UL20, UL22, UL27 (gB), UL43, UL44 (gC), UL45, UL49A, UL53 (gK), US4 (gG), US5 (gJ), US6 (gD), US7 (gI), US8 (gE), and US10. Examples of capsid proteins include UL6, UL18, UL19, UL35, and UL38. Tegument proteins include UL11, UL13, UL21, UL36, UL37, UL41, UL45, UL46, UL47, UL48, UL49, US9, and US10. Other HSV proteins include UL2, UL3, UL4, UL5, UL7, UL8, UL9, UL12, UL14, UL15, UL16, UL17, UL23, UL24, UL25, UL26, UL26.5, UL28, UL29, UL30, UL31, UL32, UL33, UL34, UL39, UL40, UL42, UL50, UL51, UL52, UL54, UL55, UL56, US1, US2, US3, US81, US11, US12, ICP0, and ICP4.

Since the envelope (most external portion of an HSV particle) is the first to encounter target cells, the present disclosure encompasses antigenic polypeptides associated with the envelope as immunogenic agents. In brief, surface and membrane proteins—glycoprotein D (gD), glycoprotein B (gB), glycoprotein H (gH), glycoprotein L (gL)—as single antigens or in combination with or without adjuvants may be used as HSV vaccine antigens.

In some embodiments, HSV vaccines comprise RNA (e.g., mRNA) encoding HSV (HSV-1 or HSV-2) glycoprotein D.

In some embodiments, HSV vaccines comprise RNA (e.g., mRNA) encoding HSV (HSV-1 or HSV-2) glycoprotein B.

In some embodiments, HSV vaccines comprise RNA (e.g., mRNA) encoding HSV (HSV-1 or HSV-2) glycoprotein D and glycoprotein C.

In some embodiments, HSV vaccines comprise RNA (e.g., mRNA) encoding HSV (HSV-1 or HSV-2) glycoprotein D and glycoprotein E (or glycoprotein I).

In some embodiments, HSV vaccines comprise RNA (e.g., mRNA) encoding HSV (HSV-1 or HSV-2) glycoprotein B and glycoprotein C.

In some embodiments, HSV vaccines comprise RNA (e.g., mRNA) encoding HSV (HSV-1 or HSV-2) glycoprotein B and glycoprotein E (or glycoprotein I).

In some embodiments, HSV vaccines comprise RNA (e.g., mRNA) encoding a HSV (HSV-1 or HSV-2) antigenic polypeptide having at least 95%, at least 96%, at least 97%, at least 98% or at least 99% identity with HSV (HSV-1 or HSV-2) glycoprotein D and has HSV (HSV-1 or HSV-2) glycoprotein D activity.

In some embodiments, HSV vaccines comprise RNA (e.g., mRNA) encoding a HSV (HSV-1 or HSV-2) antigenic polypeptide having at least 95%, at least 96%, at least 97%, at least 98% or at least 99% identity with HSV (HSV-1 or HSV-2) glycoprotein C and has HSV (HSV-1 or HSV-2) glycoprotein C activity.

In some embodiments, HSV vaccines comprise RNA (e.g., mRNA) encoding a HSV (HSV-1 or HSV-2) antigenic polypeptide having at least 95%, at least 96%, at least 97%, at least 98% or at least 99% identity with HSV (HSV-1 or HSV-2) glycoprotein B and has HSV (HSV-1 or HSV-2) glycoprotein B activity.

In some embodiments, HSV vaccines comprise RNA (e.g., mRNA) encoding a HSV (HSV-1 or HSV-2) antigenic polypeptide having at least 95%, at least 96%, at least 97%, at least 98% or at least 99% identity with HSV (HSV-1 or HSV-2) glycoprotein E and has HSV (HSV-1 or HSV-2) glycoprotein E activity.

In some embodiments, HSV vaccines comprise RNA (e.g., mRNA) encoding a HSV (HSV-1 or HSV-2) antigenic polypeptide having at least 95%, at least 96%, at least 97%, at least 98%, or at least 99% identity with HSV (HSV-1 or HSV-2) glycoprotein I and has HSV (HSV-1 or HSV-2) glycoprotein I activity.

Glycoprotein "activity" of the present disclosure is described below.

Glycoprotein C (gC) is a glycoprotein involved in viral attachment to host cells; e.g., it acts as an attachment protein that mediates binding of the HSV-2 virus to host adhesion receptors, namely cell surface heparan sulfate and/or chondroitin sulfate. gC plays a role in host immune evasion (aka viral immunoevasion) by inhibiting the host complement cascade activation. In particular, gC binds to and/or interacts with host complement component C3b; this interaction then inhibits the host immune response by disregulating the complement cascade (e.g., binds host complement C3b to block neutralization of virus).

Glycoprotein D (gD) is an envelope glycoprotein that binds to cell surface receptors and/or is involved in cell attachment via poliovirus receptor-related protein and/or herpesvirus entry mediator, facilitating virus entry. gD binds to the potential host cell entry receptors (tumor necrosis factor receptor superfamily, member 14 (TNFRSF14)/herpesvirus entry mediator (HVEM), poliovirus receptor-related protein 1 (PVRL1) and or poliovirus receptor-related protein 2 (PVRL2), and is proposed to trigger fusion with host membrane by recruiting the fusion machinery composed of, for example, gB and gH/gL. gD interacts with host cell receptors TNFRSF14 and/or PVRL1 and/or PVRL2 and (1) interacts (via profusion domain) with gB; an interaction which can occur in the absence of related HSV glycoproteins, e.g., gH and/or gL; and (2) gD interacts (via profusion domain) with gH/gL heterodimer, an interaction which can occur in the absence of gB. As such, gD associates with the gB-gH/gL-gD complex. gD also interacts (via C-terminus) with UL11 tegument protein.

Glycoprotein B (gB) is a viral glycoprotein involved in the viral cell activity of herpes simplex virus (HSV) and is required for the fusion of the HSV's envelope with the cellular membrane. It is the most highly conserved of all surface glycoproteins and primarily acts as a fusion protein, constituting the core fusion machinery. gB, a class III membrane fusion glycoprotein, is a type-1 transmembrane protein trimer of five structural domains. Domain I includes two internal fusion loops and is thought to insert into the cellular membrane during virus-cell fusion. Domain II appears to interact with gH/gL during the fusion process, domain III contains an elongated alpha helix, and domain IV interacts with cellular receptors.

In epithelial cells, the heterodimer glycoprotein E/glycoproteinI (gE/gI) is required for the cell-to-cell spread of the virus, by sorting nascent virions to cell junctions. Once the virus reaches the cell junctions, virus particles can spread to adjacent cells extremely rapidly through interactions with cellular receptors that accumulate at these junctions. By similarity, it is implicated in basolateral spread in polarized cells. In neuronal cells, gE/gI is essential for the anterograde spread of the infection throughout the host nervous system. Together with US9, the heterodimer gE/gI is involved in the sorting and transport of viral structural components toward axon tips. The heterodimer gE/gI serves as a receptor for the Fc part of host IgG. Dissociation of gE/gI from IgG occurs at acidic pH, thus may be involved in anti-HSV antibodies bipolar bridging, followed by intracellular endocytosis and degradation, thereby interfering with host IgG-mediated immune responses. gE/gI interacts (via C-terminus) with VP22 tegument protein; this interaction is necessary for the recruitment of VP22 to the Golgi and its packaging into virions.

In any of the embodiments described herein, the RNA may have at least one modification, including at least one chemical modification.

HSV RNA (e.g., mRNA) vaccines, as provided herein may be used to induce a balanced immune response, comprising both cellular and humoral immunity, without many of the risks associated with DNA vaccination.

The entire contents of International Application No. PCT/US2015/002740 are incorporated herein by reference.

It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Nucleic Acids/Polynucleotides

HSV vaccines, as provided herein, comprise at least one (one or more) ribonucleic acid (RNA) polynucleotide having an open reading frame encoding at least one HSV antigenic polypeptide. The term "nucleic acid," in its broadest sense, includes any compound and/or substance that comprises a polymer of nucleotides. These polymers are referred to as polynucleotides.

In some embodiments, at least one RNA polynucleotide is encoded by at least one nucleic acid sequence selected from any of SEQ ID NO: 1-23, 54-64, or homologs having at least 80% identity with a nucleic acid sequence selected from any one of SEQ ID NO: 1-23 or 54-64. In some embodiments, at least one RNA polynucleotide is encoded by at least one nucleic acid sequence selected from any one of SEQ ID NO: 1-23, 54-64 or homologs having at least 90% (e.g. 90%, 91%, 92%, 93%, 94%, 95%, 96%, 97%, 98%, 99%, 99.8%, or 99.9%) identity with a nucleic acid sequence selected from any one of SEQ ID NO: 1-23 or 54-64. In some embodiments, at least one RNA polynucleotide is encoded by at least one fragment of a nucleic acid sequence selected from any one of SEQ ID NO: 1-23 or 54-64. In some embodiments, the at least one RNA polynucleotide has at least one chemical modification.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA), or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ, or ex vivo. The skilled artisan will appreciate that, except where otherwise noted, polynucleotide sequences set forth in the instant application will recite "T"s in a representative DNA sequence but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

It should be understood that the mRNA polynucleotides of the vaccines as provided herein are synthetic molecules, i.e., they are not naturally-occurring molecules. That is, the mRNA polynucleotides of the present disclosure are isolated mRNA polynucleotides. As is known in the art, "isolated polynucleotides" refer to polynucleotides that are substantially physically separated from other cellular material (e.g., separated from cells and/or systems that produce the polynucleotides) or from other material that hinders their use in the vaccines of the present disclosure. Isolated polynucleotides are substantially pure in that they have been substantially separated from the substances with which they may be associated in living or viral systems. Thus, mRNA polynucleotide vaccines are not associated with living or viral systems, such as cells or viruses. The mRNA polynucleotide vaccines do not include viral components (e.g., viral capsids, viral enzymes, or other viral proteins, for example, those needed for viral-based replication), and the mRNA polynucleotide vaccines are not packaged within, encapsulated within, linked to, or otherwise associated with a virus or viral particle. In some embodiments, the mRNA vaccines comprise a lipid nanoparticle that consists of, or consists essentially of, one or more mRNA polynucleotides (e.g., mRNA polynucleotides encoding one or more HSV antigen(s)). The basic components of an mRNA molecule typically include at least one coding region, a 5' untranslated region (UTR), a 3' UTR, a 5' cap, and a poly-A tail. Polynucleotides of the present disclosure may function as mRNA but can be distinguished from wild-type mRNA in their functional and/or structural design features which serve to overcome existing problems of effective polypeptide expression using nucleic-acid based therapeutics. In some embodiments, the RNA is a messenger RNA (mRNA) having an open reading frame encoding at least one HSV antigen. In some embodiments, the RNA (e.g., mRNA) further comprises a (at least one) 5' UTR, 3' UTR, a polyA tail and/or a 5' cap.

In some embodiments, a RNA polynucleotide of a HSV vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide of a HSV vaccine encodes at least 10, 20, 30, 40, 50, 60, 70, 80, 90 or 100 antigenic polypeptides. In some embodiments, a RNA polynucleotide of a HSV vaccine encodes at least 100 or at least 200 antigenic polypeptides. In some embodiments, a RNA polynucleotide of a HSV vaccine encodes 1-10, 5-15, 10-20, 15-25, 20-30, 25-35, 30-40, 35-45, 40-50, 1-50, 1-100, 2-50, or 2-100 antigenic polypeptides.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove, or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.), and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares between 65% and 75% or about 80% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, the HSV vaccine includes at least one RNA polynucleotide having an open reading frame encoding at least one HSV antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp (5') G [the ARCA cap]; G(5')ppp(5')A; G(5')ppp(5')G; m7G (5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G (5')ppp(5')G (New England BioLabs, Ipswich, Mass.). Cap 1 structure may be generated using both Vaccinia Virus Capping Enzyme and a 2'-O methyl-transferase to generate m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72, or greater than 72 hours.

In some embodiments, a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Antigens/Antigenic Polypeptides

In some embodiments, a HSV vaccine comprises at least one RNA (e.g., mRNA) polynucleotide having an open reading frame encoding HSV-2 glycoprotein B (e.g., SEQ ID NO: 1, 6, 12, 18, 66, or 71).

In some embodiments, a HSV vaccine comprises at least one RNA (e.g., mRNA) polynucleotide having an open reading frame encoding HSV-2 glycoprotein C (e.g., SEQ ID NO: 2, 7, 13, 19, 67, or 72).

In some embodiments, a HSV vaccine comprises at least one RNA (e.g., mRNA) polynucleotide having an open reading frame encoding HSV-2 glycoprotein D (e.g., SEQ ID NO: 3, 11, 14, 20, 68, or 75).

In some embodiments, a HSV vaccine comprises at least one RNA (e.g., mRNA) polynucleotide having an open reading frame encoding HSV-2 glycoprotein E (e.g., SEQ ID NO: 4, 8, 15, 21, 69, or 73).

In some embodiments, a HSV vaccine comprises at least one RNA (e.g., mRNA) polynucleotide having an open reading frame encoding HSV-2 glycoprotein I (e.g., SEQ ID NO: 5, 10, 13, 16, 22, 70, or 74).

In some embodiments, a HSV vaccine comprises at least one RNA (e.g., mRNA) polynucleotide having an open reading frame encoding HSV-2 ICP4 protein (e.g., SEQ ID NO: 9, 23, or 77).

In some embodiments, a HSV vaccine comprises at least one RNA (e.g., mRNA) polynucleotide having an open reading frame encoding HSV-2 ICP0 protein (e.g., SEQ ID NO: 17 or 76).

In some embodiments, a HSV vaccine comprises at least one RNA (e.g. mRNA) polynucleotide encoded by a nucleic acid selected from any one of SEQ ID NO: 1-23 or 54-64 (e.g., from Tables 1 or 3). In some embodiments, a HSV vaccine comprises at least one RNA (e.g. mRNA) polynucleotide that comprises a nucleic acid selected from any one of SEQ ID NO: 90-124 (e.g., from Tables 1 or 3).

In some embodiments, a HSV vaccine comprises at least one RNA (e.g., mRNA) having at least one modification, including at least one chemical modification.

In some embodiments, a HSV antigenic polypeptide is longer than 25 amino acids and shorter than 50 amino acids. The term "antigenic polypeptide" includes full length polypeptides/proteins as well as immunogenic fragments thereof (immunogenic fragments capable of inducing an immune response to HSV). Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer, or tetramer. Polypeptides may also comprise single chain or multichain polypeptides such as antibodies or insulin and may be associated or linked. Most commonly, disulfide linkages are found in multichain polypeptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, the term "variant mimic" is one which contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic, for example, phenylalanine may act as an inactivating substitution for tyrosine; or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants which differ by one or more amino acid alterations, for example, substitutions, additions or deletions of amino acid residues that still maintain one or more of the properties of the parent or starting polypeptide.

"Paralogs" are genes (or proteins) related by duplication within a genome. Orthologs retain the same function in the course of evolution, whereas paralogs evolve new functions, even if these are related to the original one.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In alternative embodiments, sequences for (or encoding) signal sequences, termination sequences, transmembrane domains, linkers, multimerization domains (such as, e.g., foldon regions) and the like may be substituted with alternative sequences which achieve the same or a similar function. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides, the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide, respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group ($NH_2$)) and a C-terminus (terminated by an amino acid with a free carboxyl group (COOH)). Proteins are, in some cases, made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al., (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication.

Multiprotein and Multicomponent Vaccines

The present disclosure encompasses HSV vaccines comprising multiple RNA (e.g., mRNA) polynucleotides, each encoding a single antigenic polypeptide, as well as HSV vaccines comprising a single RNA polynucleotide encoding more than one antigenic polypeptide (e.g., as a fusion polypeptide). Thus, it should be understood that a vaccine composition comprising a RNA polynucleotide having an open reading frame encoding a first HSV antigenic polypeptide and a RNA polynucleotide having an open reading frame encoding a second HSV antigenic polypeptide encompasses (a) vaccines that comprise a first RNA polynucleotide encoding a first HSV antigenic polypeptide and a second RNA polynucleotide encoding a second HSV antigenic polypeptide, and (b) vaccines that comprise a single RNA polynucleotide encoding a first and second HSV antigenic polypeptide (e.g., as a fusion polypeptide). HSV RNA (e.g., mRNA) vaccines of the present disclosure, in some embodiments, comprise 2-10 (e.g., 2, 3, 4, 5, 6, 7, 8, 9 or 10), or more RNA polynucleotides having an open reading frame, each of which encodes a different HSV antigenic polypeptide (or a single RNA polynucleotide encoding 2-10, or more, different HSV antigenic polypeptides).

In some embodiments, a RNA (e.g., mRNA) polynucleotide encodes a HSV antigenic polypeptide fused to a signal peptide (e.g., SEQ ID NO: 281 or SEQ ID NO: 282). Thus, HSV vaccines comprising at least one ribonucleic acid (RNA) polynucleotide having an open reading frame encoding a signal peptide linked to a HSV antigenic peptide are provided.

Further provided herein are HSV vaccines comprising any HSV antigenic polypeptides disclosed herein fused to signal peptides. The signal peptide may be fused to the N- or C-terminus of the HSV antigenic polypeptides.

Signal Peptides

In some embodiments, antigenic polypeptides encoded by HSV polynucleotides comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include of three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodominance of certain signal peptides are much more versatile than previously anticipated.

Signal peptides typically function to facilitate the targeting of newly synthesized protein to the endoplasmic reticulum (ER) for processing. ER processing produces a mature Envelope protein, wherein the signal peptide is cleaved, typically by a signal peptidase of the host cell. A signal peptide may also facilitate the targeting of the protein to the cell membrane. HSV vaccines of the present disclosure may comprise, for example, RNA polynucleotides encoding an artificial signal peptide, wherein the signal peptide coding sequence is operably linked to and is in frame with the coding sequence of the HSV antigenic polypeptide. Thus, HSV vaccines of the present disclosure, in some embodiments, produce an antigenic polypeptide comprising a HSV antigenic polypeptide fused to a signal peptide. In some embodiments, a signal peptide is fused to the N-terminus of the HSV antigenic polypeptide. In some embodiments, a signal peptide is fused to the C-terminus of the HSV antigenic polypeptide.

In some embodiments, the signal peptide fused to the HSV antigenic polypeptide is an artificial signal peptide. In some embodiments, an artificial signal peptide fused to the HSV antigenic polypeptide encoded by the HSV RNA (e.g., mRNA) vaccine is obtained from an immunoglobulin protein, e.g., an IgE signal peptide or an IgG signal peptide. In some embodiments, a signal peptide fused to the HSV antigenic polypeptide encoded by a HSV RNA (e.g., mRNA) vaccine is an Ig heavy chain epsilon-1 signal peptide (IgE HC SP) having the sequence of: MDWTWILFLVAAATRVHS (SEQ ID NO: 79). In some embodiments, a signal peptide fused to a HSV antigenic polypeptide encoded by the HSV RNA (e.g., mRNA) vaccine is an IgGk chain V-III region HAH signal peptide (IgGk SP) having the sequence of METPAQLLFLLLLWLPDTTG (SEQ ID NO: 78). In some embodiments, the HSV antigenic polypeptide encoded by a HSV RNA (e.g., mRNA) vaccine has an amino acid sequence set forth in one of SEQ ID NO: 24-53 or 66-77 fused to a signal peptide of SEQ ID NO: 78-82. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature HSV antigenic polypeptide produced by HSV RNA (e.g., mRNA) vaccine of the present disclosure typically does not comprise a signal peptide.

Chemical Modifications

RNA (e.g., mRNA) vaccines of the present disclosure comprise, in some embodiments, at least one ribonucleic acid (RNA) polynucleotide having an open reading frame encoding at least one herpes simplex virus (HSV) antigenic polypeptide, wherein said RNA comprises at least one chemical modification.

The terms "chemical modification" and "chemically modified" refer to modification with respect to adenosine (A), guanosine (G), uridine (U), thymidine (T), or cytidine (C) ribonucleosides or deoxyribnucleosides in at least one of their position, pattern, percent or population. Generally, these terms do not refer to the ribonucleotide modifications in naturally-occurring 5'-terminal mRNA cap moieties.

Modifications of polynucleotides include, without limitation, those described herein, and include, but are expressly not limited to, those modifications that comprise chemical modifications. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

With respect to a polypeptide, the term "modification" refers to a modification relative to the canonical set of 20 amino acids. Polypeptides, as provided herein, are also considered "modified" if they contain amino acid substitutions, insertions, or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two, or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those polynucleotides having at least one chemical modification. One example of such non-standard base pairing is the base pairing between the modified nucleotide inosine and adenine, cytosine, or uracil. Any combination of base/sugar or linker may be incorporated into polynucleotides of the present disclosure.

Modifications of polynucleotides (e.g., RNA polynucleotides, such as mRNA polynucleotides), including but not limited to chemical modification, that are useful in the compositions, vaccines, methods and synthetic processes of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo) adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl) adenine; 6 (methyl)adenine; 6-(alkyl)adenine; 6-(methyl) adenine; 7 (deaza)adenine; 8 (alkenyl)adenine; 8 (alkynyl) adenine; 8 (amino)adenine; 8 (thioalkyl)adenine; 8-(alkenyl) adenine; 8-(alkyl)adenine; 8-(alkynyl)adenine; 8-(amino) adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodo-adenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethyl cytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azido-cytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methyl aminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-

2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonyl ethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonyl ethylenyl)-4 (thio)pseudouracil; 1 (aminocarbonyl ethyl enyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 1-Ethyl-pseudo-UTP; 2 (thio) pseudouracil; 2' deoxy uridine; 2' fluorouridine; 2-(thio) uracil; 2,4-(dithio)pseudouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio)uracil; 5 (propynyl)uracil; 5 (trifluoromethyl)uracil; 5-(2-aminopropyl)uracil; 5-(alkyl)-2-(thio) pseudouracil; 5-(alkyl)-2,4 (dithio)pseudouracil; 5-(alkyl)-4 (thio)pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl) uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio) pseudouracil; 5-(methyl)pseudouracil; 5-(methylaminomethyl)-2 (thio)uracil; 5-(methylaminomethyl)-2,4(dithio) uracil; 5-(methylaminomethyl)-4-(thio)uracil; 5-(propynyl) uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; P seudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl)pseudouridine TP; (E)-5-(2-Bromo-vinyl)ara-uridine TP; (E)-5-(2-Bromo-vinyl)uridine TP; (Z)-5-(2-Bromo-vinyl)ara-uridine TP; (Z)-5-(2-Bromo-vinyl) uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl)pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6- tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenyl ethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl) isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanosine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nebularine; O6-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl) pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and combinations of two or more thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polyribonucleotide (e.g., RNA polyribonucleotide, such as mRNA polyribonucleotide) includes a combination of at least two (e.g., 2, 3, 4 or more) of the aforementioned modified nucleobases. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polyribonucleotide includes a combination of at least two (e.g., 2, 3, 4 or more) of the aforementioned modified nucleobases, including but not limited to chemical modifications.

In some embodiments, polynucleotides (e.g., RNA polynucleotides, such as mRNA polynucleotides) comprise pseudouridine (ψ) and 5-methyl-cytidine (m5C). In some embodiments, the polyribonucleotides (e.g., RNA, such as mRNA) comprise 1-methyl-pseudouridine (m1ψ). In some embodiments, the polyribonucleotides (e.g., RNA, such as mRNA) comprise 1-ethyl-pseudouridine (e1ψ). In some embodiments, the polyribonucleotides (e.g., RNA, such as mRNA) comprise 1-methyl-pseudouridine (m1ψ) and 5-methyl-cytidine (m5C). In some embodiments, the polyribonucleotides (e.g., RNA, such as mRNA) comprise 1-ethyl-pseudouridine (e1ψ) and 5-methyl-cytidine (m5C). In some embodiments, the polyribonucleotides (e.g., RNA, such as mRNA) comprise 2-thiouridine (s2U). In some embodiments, the polyribonucleotides (e.g., RNA, such as mRNA) comprise 2-thiouridine and 5-methyl-cytidine (m5C). In some embodiments, the polyribonucleotides (e.g., RNA, such as mRNA) comprise methoxy-uridine (mo5U). In some embodiments, the polyribonucleotides (e.g., RNA, such as mRNA) comprise 5-methoxy-uridine (mo5U) and 5-methyl-cytidine (m5C). In some embodiments, the polyribonucleotides (e.g., RNA, such as mRNA) comprise 2'-O-methyl uridine. In some embodiments, the polyribonucleotides (e.g., RNA, such as mRNA) comprise 2'-O-methyl uridine and 5-methyl-cytidine (m5C). In some embodiments, the polyribonucleotides (e.g., RNA, such as mRNA) comprise N6-methyl-adenosine (m6A). In some embodiments, the polyribonucleotides (e.g., RNA, such as mRNA) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) with a particular modification. For example, a polynucleotide can be uniformly modified with 1-methyl-pseudouridine, meaning that all uridine residues in the mRNA sequence are replaced with 1-methyl-pseudouridine. Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and nucleosides having a modified uridine include 1-methyl-pseudouridine (m1ψ), 1-ethyl-pseudouridine (e1ψ), 5-methoxy uridine, 2-thio uridine, 5-cyano uridine, 2'-O-methyl uridine, and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, and 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may be any one of nucleotides A, G, U, C, or any one of the combinations A+G, A+U, A+C, G+U, G+C, U+C, A+G+U, A+G+C, G+U+C, or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4, or more unique structures). In some embodiments, at least 5%, at least 10%, at least 25%, at least 50%, at least 80%, at least 90%, or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4, or more unique structures).

Thus, in some embodiments, the RNA vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxy-carbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine($\tau m^5s^2U$), 1-taurinomethyl-4-thio-pseudouridine, 5-methyl-uridine ($m^5U$, i.e., having the nucleobase deoxythymine), 1-methyl-pseudouridine ($m^1\psi$), 1-ethyl-pseudouridine (e1ψ), 5-methyl-2-thio-uridine (m5s$^2$U), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3$ ψ), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4{}_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl)

adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6{}_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6{}_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2{}_2G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2{}_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, 06-methyl-guanosine, 2'-F-ara-guanosine, and 2'-F-guanosine.

HSV Vaccines

In Vitro Transcription of RNA (e.g., mRNA)

HSV vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, the at least one RNA polynucleotide has at least one chemical modification. The at least one chemical modification may include, but is expressly not limited to, any modification described herein.

In vitro transcription of RNA is known in the art and is described in WO2014/152027, which is incorporated by reference herein in its entirety. For example, in some embodiments, the RNA transcript is generated using a non-amplified, linearized DNA template in an in vitro transcription reaction to generate the RNA transcript. In some embodiments, the RNA transcript is capped via enzymatic capping. In some embodiments, the RNA transcript is purified via chromatographic methods, e.g., use of an oligo dT substrate. Some embodiments exclude the use of DNase. In some embodiments, the RNA transcript is synthesized from a non-amplified, linear DNA template coding for the gene of interest via an enzymatic in vitro transcription reaction utilizing a T7 phage RNA polymerase and nucleotide triphosphates of the desired chemistry. Any number of RNA polymerases or variants may be used in the method of the present invention. The polymerase may be selected from, but is not limited to, a phage RNA polymerase, e.g., a T7 RNA polymerase, a T3 RNA polymerase, a SP6 RNa polymerase, and/or mutant polymerases such as, but not limited to, polymerases able to incorporate modified nucleic acids and/or modified nucleotides, including chemically modified nucleic acids and/or nucleotides.

In some embodiments, a non-amplified, linearized plasmid DNA is utilized as the template DNA for in vitro transcription. In some embodiments, the template DNA is isolated DNA. In some embodiments, the template DNA is cDNA. In some embodiments, the cDNA is formed by reverse transcription of a RNA polynucleotide, for example, but not limited to HSV RNA, e.g. HSV mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA or RNA beginning with a start codon (e.g., methionine (ATG or AUG)), and ending with a stop codon (e.g., TAA, TAG or TGA, or UAA, UAG or UGA) and typically encodes a polypeptide (e.g., protein). It will be understood that the sequences disclosed herein may further comprise additional elements, e.g., 5' and 3' UTRs, but that those elements, unlike the ORF, need not necessarily be present in a vaccine of the present disclosure. A "polyA tail" is a region of mRNA that is downstream, e.g., directly downstream (i.e., 3'), from the 3' UTR that contains multiple consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 adenosine monophosphates. In some embodiments, a polyA tail contains 50 to 250 adenosine monophosphates. In a relevant biological setting (e.g., in cells, in vivo), the poly(A) tail functions to protect mRNA from enzymatic degradation, e.g., in the cytoplasm, and aids in transcription termination, export of the mRNA from the nucleus, and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides.

Methods of Treatment

Provided herein are compositions (e.g., pharmaceutical compositions), methods, kits and reagents for prevention and/or treatment of HSV in humans and other mammals. HSV RNA (e.g. mRNA) vaccines can be used as therapeutic or prophylactic agents. They may be used in medicine to prevent and/or treat infectious disease. In exemplary aspects, the HSV RNA (e.g. mRNA) vaccines of the present disclosure are used to provide prophylactic protection from HSV. Prophylactic protection from HSV can be achieved following administration of a HSV RNA (e.g. mRNA) vaccine of the present disclosure. Vaccines can be administered once, twice, three times, four times or more, but it is likely sufficient to administer the vaccine once (optionally followed by a single booster). It is possible, although less desirable, to administer the vaccine to an infected individual to achieve a therapeutic response. Dosing may need to be adjusted accordingly.

In some embodiments, the HSV vaccines of the present disclosure can be used as a method of preventing a HSV infection in a subject, the method comprising administering to said subject at least one HSV vaccine of this invention. In other embodiments, the HSV vaccines of this invention can be used as a method of inhibiting a primary HSV infection in a subject, the method comprising administering to said subject at least one HSV vaccine of this invention. In other embodiments, the HSV vaccines of this invention can be used as a method of treating a HSV infection in a subject, the method comprising administering to said subject at least one HSV vaccine of this invention. In other embodiments, the HSV vaccines of this invention can be used as a method of reducing an incidence of HSV infection in a subject, the method comprising administering to said subject at least one HSV vaccine of this invention. In other embodiments, the HSV vaccines of this invention can be used as a method of inhibiting spread of HSV from a first subject infected with HSV to a second subject not infected with HSV, the method comprising administering to at least one of said first subject sand said second subject at least one HSV vaccine of this invention.

A method of eliciting an immune response in a subject against a HSV is provided in aspects of the present disclosure. The method involves administering to the subject a HSV RNA vaccine comprising at least one RNA (e.g. mRNA) polynucleotide having an open reading frame encoding at least one HSV antigenic polypeptide, thereby inducing in the subject an immune response specific to HSV antigenic polypeptide, wherein anti-antigenic polypeptide antibody titer in the subject is increased following vaccination relative to anti-antigenic polypeptide antibody titer in a subject vaccinated with a prophylactically effective dose of a traditional vaccine against the HSV. An “anti-antigenic polypeptide antibody” is a serum antibody the binds specifically to the antigenic polypeptide.

A prophylactically effective dose is a therapeutically effective dose that prevents infection with the virus at a clinically acceptable level. In some embodiments, the therapeutically effective dose is a dose listed in a package insert for the vaccine. A traditional vaccine, as used herein, refers to a vaccine other than the RNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the HSV.

In some embodiments, the anti-antigenic polypeptide antibody titer in the subject is increased 1 log following vaccination relative to anti-antigenic polypeptide antibody titer in a subject vaccinated with a prophylactically effective dose of a traditional vaccine against the HSV.

In some embodiments, the anti-antigenic polypeptide antibody titer in the subject is increased 2 log following vaccination relative to anti-antigenic polypeptide antibody titer in a subject vaccinated with a prophylactically effective dose of a traditional vaccine against the HSV.

In some embodiments, the anti-antigenic polypeptide antibody titer in the subject is increased 3 log following vaccination relative to anti-antigenic polypeptide antibody titer in a subject vaccinated with a prophylactically effective dose of a traditional vaccine against the HSV.

In some embodiments, the anti-antigenic polypeptide antibody titer in the subject is increased 5 log following vaccination relative to anti-antigenic polypeptide antibody titer in a subject vaccinated with a prophylactically effective dose of a traditional vaccine against the HSV.

In some embodiments, the anti-antigenic polypeptide antibody titer in the subject is increased 10 log following vaccination relative to anti-antigenic polypeptide antibody titer in a subject vaccinated with a prophylactically effective dose of a traditional vaccine against the HSV.

A method of eliciting an immune response in a subject against a HSV is provided in other aspects of the invention. The method involves administering to the subject a HSV RNA (e.g. mRNA) vaccine comprising at least one RNA polynucleotide having an open reading frame encoding at least one HSV antigenic polypeptide, thereby inducing in the subject an immune response specific to HSV antigenic polypeptide, wherein the immune response in the subject is equivalent to an immune response in a subject vaccinated with a traditional vaccine against the HSV at 2 times to 100 times the dosage level relative to the RNA vaccine.

In some embodiments, the immune response in the subject is equivalent to an immune response in a subject vaccinated with a traditional vaccine at twice the dosage level relative to the HSV RNA (e.g. mRNA) vaccine.

In some embodiments, the immune response in the subject is equivalent to an immune response in a subject vaccinated with a traditional vaccine at three times the dosage level relative to the HSV RNA (e.g. mRNA) vaccine.

In some embodiments, the immune response in the subject is equivalent to an immune response in a subject vaccinated with a traditional vaccine at 4 times the dosage level relative to the HSV RNA (e.g. mRNA) vaccine.

In some embodiments, the immune response in the subject is equivalent to an immune response in a subject vaccinated with a traditional vaccine at 5 times the dosage level relative to the HSV RNA (e.g. mRNA) vaccine.

In some embodiments, the immune response in the subject is equivalent to an immune response in a subject vaccinated with a traditional vaccine at 10 times the dosage level relative to the HSV RNA (e.g. mRNA) vaccine.

In some embodiments, the immune response in the subject is equivalent to an immune response in a subject vaccinated with a traditional vaccine at 50 times the dosage level relative to the HSV RNA (e.g. mRNA) vaccine.

In some embodiments, the immune response in the subject is equivalent to an immune response in a subject vaccinated with a traditional vaccine at 100 times the dosage level relative to the HSV RNA (e.g. mRNA) vaccine.

In some embodiments, the immune response in the subject is equivalent to an immune response in a subject vaccinated with a traditional vaccine at 10 times to 1000 times the dosage level relative to the HSV RNA (e.g. mRNA) vaccine.

In some embodiments, the immune response in the subject is equivalent to an immune response in a subject vaccinated with a traditional vaccine at 100 times to 1000 times the dosage level relative to the HSV RNA (e.g. mRNA) vaccine.

In other embodiments, the immune response is assessed by determining anti-antigenic polypeptide antibody titer in the subject.

In other aspects, the invention is a method of eliciting an immune response in a subject against a HSV by administering to the subject a HSV RNA (e.g. mRNA) vaccine comprising at least one RNA (e.g. mRNA) polynucleotide having an open reading frame encoding at least one HSV antigenic polypeptide, thereby inducing in the subject an immune response specific to HSV antigenic polypeptide, wherein the immune response in the subject is induced 2 days to 10 weeks earlier relative to an immune response induced in a subject vaccinated with a prophylactically effective dose of a traditional vaccine against the HSV. In some embodiments, the immune response in the subject is induced in a subject vaccinated with a prophylactically effective dose of a traditional vaccine at 2 times to 100 times the dosage level relative to the RNA (e.g. mRNA) vaccine.

In some embodiments, the immune response in the subject is induced 2 days earlier relative to an immune response induced in a subject vaccinated with a prophylactically effective dose of a traditional vaccine.

In some embodiments, the immune response in the subject is induced 3 days earlier relative to an immune response induced in a subject vaccinated a prophylactically effective dose of a traditional vaccine.

In some embodiments, the immune response in the subject is induced 1 week earlier relative to an immune response induced in a subject vaccinated with a prophylactically effective dose of a traditional vaccine.

In some embodiments, the immune response in the subject is induced 2 weeks earlier relative to an immune response induced in a subject vaccinated with a prophylactically effective dose of a traditional vaccine.

In some embodiments, the immune response in the subject is induced 3 weeks earlier relative to an immune response induced in a subject vaccinated with a prophylactically effective dose of a traditional vaccine.

In some embodiments, the immune response in the subject is induced 5 weeks earlier relative to an immune response induced in a subject vaccinated with a prophylactically effective dose of a traditional vaccine.

In some embodiments, the immune response in the subject is induced 10 weeks earlier relative to an immune response induced in a subject vaccinated with a prophylactically effective dose of a traditional vaccine.

Aspects of the present disclosure further include a method of eliciting an immune response in a subject against a HSV by administering to the subject a HSV RNA (e.g. mRNA) vaccine having an open reading frame encoding a first antigenic polypeptide, wherein the RNA polynucleotide does not include a stabilization element, and wherein an adjuvant is not coformulated or co-administered with the vaccine.

Broad Spectrum HSV Vaccines

It is envisioned that there may be situations where persons are at risk for infection with more than one strain of HSV. RNA (mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of HSV, a combination vaccine can be administered that includes RNA (e.g. mRNA) encoding at least one antigenic polypeptide protein (or antigenic portion thereof) of a first HSV and further includes RNA (e.g. mRNA) encoding at least one antigenic polypeptide protein (or antigenic portion thereof) of a second HSV. RNAs (mRNAs) can be coformulated, for example, in a single lipid nanoparticle (LNP) or can be formulated in separate LNPs destined for co-administration.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. typhimurium, H. pylori, V. cholera, S. marcesens, S. flexneri, T. pallidum, L. pneumophila, B. burgdorferei, C. difficile, R. meliloti, A. tumefaciens, R. lupini, B. clarridgeiae, P. mirabilis, B. subtilus, L. monocytogenes, P. aeruginosa*, and *E. coli*, among others are known.

A “flagellin polypeptide,” as used herein, refers to a full length flagellin protein, immunogenic fragments thereof, and peptides having at least 50% sequence identity to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8), and SEQ ID NO: 89, 125 or 126. In some embodiments, the flagellin polypeptide has at least 60%, 70%, 75%, 80%, 90%, 95%, 97%, 98%, or 99% sequence identity to a flagellin protein or immunogenic fragments thereof (e.g., SEQ ID NO: 89, 125 or 126).

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region," and "variable domain or region." "At least a portion of a hinge region," as used herein, refers to any part of the hinge region of the flagellin, or the entirety of the hinge region. In other embodiments, an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin-like sequences that activate TLR5 and contain a 13 amino acid motif that is 53% or more identical to the *Salmonella* sequence in 88-100 of FliC (LQRVRELAVQSAN; SEQ ID NO: 127).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue, and an arginine residue. In some embodiments, the linker is 1-30, 1-25, 1-25, 5-10, 5, 15, or 5-20 amino acids in length.

In other embodiments, the RNA (e.g., mRNA) vaccine includes at least two separate RNA polynucleotides, one encoding one or more antigenic polypeptides and the other encoding the flagellin polypeptide. The at least two RNA (e.g. mRNA) polynucleotides may be co-formulated in a carrier such as a lipid nanoparticle.

Therapeutic and Prophylactic Compositions

Provided herein are compositions (e.g., pharmaceutical compositions), methods, kits and reagents for prevention, treatment or diagnosis of HSV in humans and other mammals, for example. HSV RNA (e.g., mRNA) vaccines can be used as therapeutic or prophylactic agents. They may be used in medicine to prevent and/or treat infectious disease. In some embodiments, the HSV vaccines of the invention can be envisioned for use in the priming of immune effector cells, for example, to activate peripheral blood mononuclear cells (PBMCs) ex vivo, which are then infused (re-infused) into a subject.

In exemplary embodiments, a HSV vaccine containing RNA polynucleotides as described herein can be administered to a subject (e.g., a mammalian subject, such as a human subject), and the RNA polynucleotides are translated in vivo to produce an antigenic polypeptide.

The HSV RNA (e.g., mRNA) vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue, or organism is contacted with an effective amount of a composition containing a HSV RNA (e.g. mRNA) vaccine that contains a polynucleotide that has at least one a translatable region encoding an antigenic polypeptide.

An "effective amount" of the HSV RNA (e.g. mRNA) vaccine is provided based, at least in part, on the target tissue, target cell type, means of administration, physical characteristics of the polynucleotide (e.g., size, and extent of modified nucleosides), and other components of the HSV RNA (e.g. mRNA) vaccine, and other determinants. In general, an effective amount of the HSV RNA (e.g. mRNA) vaccine composition provides an induced or boosted immune response as a function of antigen production in the cell. In general, an effective amount of the HSV RNA (e.g. mRNA) vaccine containing RNA polynucleotides having at least one chemical modifications are preferably more efficient than a composition containing a corresponding unmodified RNA polynucleotides encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administration to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA (e.g., mRNA) vaccines (including polynucleotides their encoded polypeptides) in accordance with the present disclosure may be used for treatment of HSV.

HSV RNA (e.g., mRNA) vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

HSV RNA (e.g., mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months, or 1 year.

In some embodiments, HSV RNA (e.g., mRNA) vaccines may be administered intramuscularly or intradermally, similarly to the administration of inactivated vaccines known in the art.

The HSV RNA (e.g., mRNA) vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers and produce responses early than commercially available anti-virals.

Provided herein are pharmaceutical compositions including HSV RNA (e.g., mRNA) vaccines and RNA vaccine compositions and/or complexes optionally in combination with one or more pharmaceutically acceptable excipients.

HSV RNA (e.g., mRNA) vaccines may be formulated or administered alone or in conjunction with one or more other components. For instance, HSV RNA (e.g. mRNA) vaccines (vaccine compositions) may comprise other components including, but not limited to, adjuvants.

In some embodiments, RNA (e.g., mRNA) RNA vaccines do not include an adjuvant (they are adjuvant free).

HSV RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free, or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, HSV RNA (e.g., mRNA) vaccines are administered to humans, human patients, or subjects. For the purposes of the present disclosure, the phrase "active ingredient" generally refers to the RNA (e.g. mRNA) vaccines or the polynucleotides contained therein, for example, RNA polynucleotides (e.g., mRNA polynucleotides) encoding antigenic polypeptides.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

HSV RNA (e.g., mRNA) vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients, such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with HSV RNA (e.g. mRNA) vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail, are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments, the length of the 3'-poly(A) tail may be an essential element with respect to the stability of the individual mRNA.

In some embodiments, the RNA vaccine may include one or more stabilizing elements. Stabilizing elements may include, for instance, a histone stem-loop. A stem-loop binding protein (SLBP), a 32 kDa protein, has been identified. It is associated with the histone stem-loop at the 3'-end of the histone messages in both the nucleus and the cytoplasm. Its expression level is regulated by the cell cycle; it is peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA vaccine may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments, the RNA vaccine may have one or more AU-rich sequences removed. These sequences, sometimes referred to as AURES, are destabilizing sequences found in the 3'UTR. The AURES may be removed from the RNA vaccines. Alternatively, the AURES may remain in the RNA vaccine.

Nanoparticle Formulations

In some embodiments, HSV RNA (e.g., mRNA) vaccines are formulated in a nanoparticle. In some embodiments, HSV RNA (e.g. mRNA) vaccines are formulated in a lipid nanoparticle. In some embodiments, HSV RNA (e.g. mRNA) vaccines are formulated in a lipid-polycation complex, referred to as a cationic lipid nanoparticle. The formation of the lipid nanoparticle may be accomplished by methods known in the art and/or as described in U.S. Publication No. 2012/0178702, herein incorporated by reference in its entirety. As a non-limiting example, the polycation may include a cationic peptide or a polypeptide such as, but not limited to, polylysine, polyornithine and/or polyarginine and the cationic peptides described in International Publication No. WO2012/013326 or U.S. Publication No. US2013/0142818; each of which is herein incorporated by reference in its entirety. In some embodiments, HSV RNA (e.g. mRNA) vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components, and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid was shown to more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35% to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1, and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0%, and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC, and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200, and DLin-KC2-DMA.

In some embodiments, a HSV RNA (e.g., mRNA) vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, (12Z,15Z)—N,N-dimethyl-2-nonylhenicosa-12,15-dien-1-amine, N,N-dimethyl-1-[(1S,2R)-2-octylcyclopropyl]heptadecan-8-amine, PEGylated lipids, and amino alcohol lipids.

In some embodiments, the lipid is

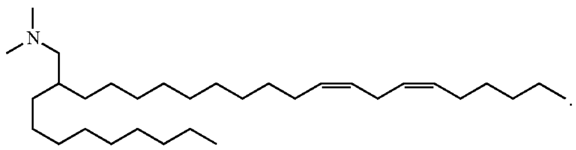 [SMILES: CCCCC/C=C\C/C=C\CCCCCCCCCC(CCCCCCCCC)CN(C)C]

In some embodiments, the lipid is

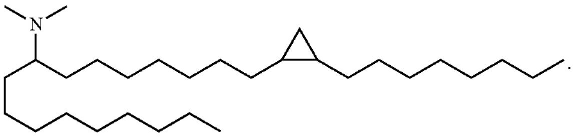 [SMILES: CCCCCCCCCC(CCCCCCCC1CC1CCCCCCCC)N(C)C]

In some embodiments, the lipid may be a cationic lipid such as, but not limited to, DLin-DMA, DLin-D-DMA, DLin-MC3-DMA, DLin-KC2-DMA, DODMA, and amino alcohol lipids. The amino alcohol cationic lipid may be the lipids described in and/or made by the methods described in U.S. Publication No. US2013/0150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US2013/0150625); 2-amino-3-[(9Z)-octadec-9-en-1-yloxy]-2-{[(9Z)-octadec-9-en-1-yloxy]methyl}propan-1-ol (Compound 2 in US2013/0150625); 2-amino-3-[(9Z,12Z)-octadeca-9,12-dien-1-yloxy]-2-[(octyloxy)methyl]propan-1-ol (Compound 3 in US2013/0150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US2013/0150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate, and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate; (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid: 5-25% neutral lipid (non-cationic lipid): 25-55% sterol: 0.5-15% PEG-lipid.

In some embodiments, a lipid nanoparticle formulation includes 25% to 75% on a molar basis of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, e.g., 35% to 65%, 45% to 65%, 60%, 57.5%, 50% or 40% on a molar basis.

In some embodiments, a lipid nanoparticle formulation includes 0.5% to 15% on a molar basis of the neutral lipid (non-cationic lipid), e.g., 3% to 12%, 5% to 10% or 15%, 10%, or 7.5% on a molar basis. Examples of neutral lipids include, without limitation, DSPC, POPC, DPPC, DOPE, and SM. In some embodiments, the formulation includes 5% to 50% on a molar basis of the sterol (e.g., 15% to 45%, 20% to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5% to 10%, 0.5% to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), and PEG-cDMA (further discussed in Reyes et al. *J. Controlled Release,* 107, 276-287 (2005) the content of which is herein incorporated by reference in its entirety).

In some embodiments, lipid nanoparticle formulations include 25-75% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 7.5% of the neutral lipid, 31% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1- yl) 9-((4-(dimethylamino)butanoyl)oxy)heptadecanedioate, 10% of the neutral lipid, 38.5% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 15% of the neutral lipid, 40% of the sterol, and 5% of the PEG or PEG-modified lipid on a molar basis.

In some embodiments, lipid nanoparticle formulations include 57.2% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (*J. Controlled Release,* 107, 276-287 (2005), the content of which is herein incorporated by reference in its entirety), 7.5% of the neutral lipid, 31.5% of the sterol, and 3.5% of the PEG or PEG-modified lipid on a molar basis.

In some embodiments, lipid nanoparticle formulations consist essentially of a lipid mixture in molar ratios of 20-70% cationic lipid: 5-45% neutral lipid (non-cationic lipid): 20-55% cholesterol: 0.5-15% PEG-modified lipid. In some embodiments, lipid nanoparticle formulations consist essentially of a lipid mixture in a molar ratio of 20-60% cationic lipid: 5-25% neutral lipid (non-cationic lipid): 25-55% cholesterol: 0.5-15% PEG-modified lipid.

In some embodiments, the molar lipid ratio is 50/10/38.5/1.5 (mol % cationic lipid/neutral lipid (non-cationic lipid), e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA), or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid, and a structural lipid, and optionally comprise a non-cationic lipid. As a non-limiting example, a lipid nanoparticle may comprise 40-60% of a cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of a cationic lipid, 5-15% of a non-cationic lipid, 1-2% of a PEG lipid, and 30-50% of a structural lipid. As another non-limiting example, the lipid nanoparticle may comprise 50% cationic lipid, 10% non-cationic lipid, 1.5% PEG lipid, and 38.5% structural lipid. As yet another non-limiting example, the lipid nanoparticle may comprise 55% cationic lipid, 10% non-cationic lipid, 2.5% PEG lipid, and 32.5% structural lipid. In some embodiments, the cationic lipid may be any cationic lipid described herein such as, but not limited to, 2,2-dilinoleyl-4-dimethylaminoethyl-[1,3]-dioxolane (DLin-KC2-DMA), dilinoleyl-methyl-4-dimethyl aminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the lipid nanoparticle formulations described herein may comprise a cationic lipid, a non-cationic lipid, a PEG lipid and a structural lipid. As a non-limiting example, the lipid nanoparticle may comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle may comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle may comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle may comprise 55% of the cationic lipid di((Z)-non-2-en-1-yl) 9-((4-(dimethylamino)butanoyl)oxy)heptadecanedioate, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding HSV), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, or 40-200 nm. In some embodiments, a nanoparticle (e.g., a lipid nanoparticle) has a mean diameter of 50-150 nm, 50-200 nm, 80-100 nm, or 80-200 nm.

Liposomes, Lipoplexes, and Lipid Nanoparticles

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. *Cancer Biology & Therapy* 2006 5(12)1708-1713); herein incorporated by reference in its entirety) and hyaluronan-coated liposomes (Quiet Therapeutics, Israel).

In some embodiments, the RNA vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. US2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water-soluble conjugate. The polymer conjugate may have a structure as described in U.S. Publication No. 2013/0059360, the content of which is herein incorporated by reference in its entirety. In some aspects, polymer conjugates with the polynucleotides of the present invention may be made using the methods and/or segmented polymeric reagents described in U.S. Publication No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al. (*Science* 2013, 339, 971-975), herein incorporated by reference in its entirety). As shown by Rodriguez et al., the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA (e.g. mRNA) vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In other embodiments, the nanoparticle may comprise PEG and a conjugate of CD47 or a derivative thereof. In yet other embodiments, the nanoparticle may comprise both the "self" peptide described above and the membrane protein CD47.

In some embodiments, a "self" peptide and/or CD47 protein may be conjugated to a virus-like particle or pseudovirion, as described herein for delivery of the RNA (e.g. mRNA) vaccines of the present invention.

In other embodiments, RNA (e.g. mRNA) vaccine pharmaceutical compositions comprise the polynucleotides of the present invention and a conjugate, which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA (e.g. mRNA) vaccine. As a non-limiting example, the carbohydrate carrier may include, but is not limited to, an anhydride-modified phytoglycogen or glycogen-type material, phtoglycogen octenyl succinate, phytoglycogen beta-dextrin, or anhydride-modified phytoglycogen beta-dextrin. (See e.g., International Publication No. WO2012/109121, the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA (e.g. mRNA) vaccines, within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbon.

In some embodiments, an immune response may be elicited by delivering a lipid nanoparticle which may include a nanospecies, a polymer and an immunogen. (U.S. Publication No. 2012/0189700 and International Publication No. WO2012/099805, each of which is herein incorporated by reference in its entirety).

The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), and genital (e.g., vaginal, cervical and urethral membranes). Nanoparticles larger than 10-200 nm, which are preferred for higher drug encapsulation efficiency and the ability to provide the sustained delivery of a wide array of drugs, have been thought to be too large to rapidly diffuse through mucosal barriers. Mucus is continuously secreted, shed, discarded or digested, and recycled so most of the trapped particles may be removed from the mucosal tissue within seconds or within a few hours. Large polymeric nanoparticles (200 nm to 500 nm in diameter) which have been coated densely with a low molecular weight polyethylene glycol (PEG) diffused through mucus only 4- to 6-fold lower than the same particles diffusing in water (Lai et al. *PNAS* 2007 104(5): 1482-487; Lai et al. *Adv Drug Deliv Rev.* 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (e.g., a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO2012/082165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG, trimethylene carbonate, and polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718, U.S. Publication 2010/0003337, and U.S. Pat. No. 8,263,665, each of which is herein incorporated by reference in its entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:2597-2600, the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

In some embodiments, the RNA (e.g., mRNA) vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. *Cancer Biology & Therapy* 2006 5(12)1708-1713, herein incorporated by reference in its entirety)), and hyaluronan-coated liposomes (Quiet Therapeutics, Israel).

In some embodiments, the RNA (e.g. mRNA) vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. 2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water-soluble conjugate. The polymer conjugate may have a structure as described in U.S. Application No. 2013/0059360, the content of which is herein incorporated by reference in its entirety. In some aspects, polymer conjugates with the polynucleotides of the present invention may be made using the methods and/or segmented polymeric reagents described in U.S. Patent Application No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the content of which is herein incorporated by reference in its entirety.

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle (see e.g., U.S. Publication 2010/0215580 and U.S. Publication 2008/0166414 and US2013/0164343 the content of each of which is herein incorporated by reference in its entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In other embodiments, the mucus penetrating lipid nanoparticles may be a hypotonic formulation comprising a mucosal penetration enhancing coating. The formulation may be hypotonice for the epithelium to which it is being delivered.

Non-limiting examples of hypotonic formulations may be found in International Publication No. WO2013/110028, the content of which is herein incorporated by reference in its entirety.

In some embodiments, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (see e.g., Ensign et al. *Biomaterials* 2013, 34(28):6922-9, the content of which is herein incorporated by reference in its entirety).

In some embodiments, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. *Cancer Res.* 2008 68:9788-9798; Strumberg et al. *Int J Clin Pharmacol Ther* 2012 50:76-78; Santel et al., *Gene Ther* 2006 13:1222-1234; Santel et al., *Gene Ther* 2006 13:1360-1370; Gutbier et al., *Pulm Pharmacol. Ther.* 2010 23:334-344; Kaufmann et al. *Microvasc Res* 2010 80:286-293; Weide et al. *J Immunother.* 2009 32:498-507; Weide et al. *J Immunother.* 2008 31:180-188; Pascolo, *Expert Opin. Biol. Ther.* 4:1285-1294; Fotin-Mleczek et al., 2011 *J Immunother.* 34:1-15; Song et al., *Nature Biotechnol.* 2005, 23:709-717; Peer et al., *Proc Natl Acad Sci USA.* 2007 6; 104:4095-4100; deFougerolles *Hum Gene Ther.* 2008 19:125-132; each of which is incorporated herein by reference in its entirety).

In some embodiments, such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. *Mol Ther.* 2010 18:1357-1364; Song et al., *Nat Biotechnol.* 2005 23:709-717; Judge et al., *J Clin Invest.* 2009 119:661-673; Kaufmann et al., *Microvasc Res* 2010 80:286-293; Santel et al., *Gene Ther* 2006 13:1222-1234; Santel et al., *Gene Ther* 2006 13:1360-1370; Gutbier et al., *Pulm Pharmacol. Ther.* 2010 23:334-344; Basha et al., *Mol. Ther.* 2011 19:2186-2200; Fenske and Cullis, *Expert Opin Drug Deliv.* 2008 5:25-44; Peer et al., *Science.* 2008 319:627-630; Peer and Lieberman, *Gene Ther.* 2011 18:1127-1133; each of which is incorporated herein by reference in its entirety). One example of passive targeting of formulations to liver cells includes the DLin-DMA, DLin-KC2-DMA, and DLin-MC3-DMA-based lipid nanoparticle formulations which have been shown to bind to apolipoprotein E and promote binding and uptake of these formulations into hepatocytes in vivo (Akinc et al. *Mol Ther.* 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., *Curr Drug Discov Technol.* 2011 8:197-206; Musacchio and Torchilin, *Front Biosci.* 2011 16:1388-1412; Yu et al., *Mol Membr Biol.* 2010 27:286-298; Patil et al., *Crit Rev Ther Drug Carrier Syst.* 2008 25:1-61; Benoit et al., *Biomacromolecules.* 2011 12:2708-2714; Zhao et al., *Expert Opin Drug Deliv.* 2008 5:309-319; Akinc et al., *Mol Ther.* 2010 18:1357-1364; Srinivasan et al., *Methods Mol Biol.* 2012 820:105-116; Ben-Arie et al., *Methods Mol Biol.* 2012 757:497-507; Peer 2010 *J Control Release.* 20:63-68; Peer et al., *Proc Natl Acad Sci USA.* 2007 104:4095-4100; Kim et al., *Methods Mol Biol.* 2011 721:339-353; Subramanya et al., *Mol Ther.* 2010 18:2028-2037; Song et al., *Nat Biotechnol.* 2005 23:709-717; Peer et al., *Science.* 2008 319:627-630; Peer and Lieberman, *Gene Ther.* 2011 18:1127-1133; each of which is incorporated herein by reference in its entirety).

In some embodiments, the RNA (e.g., mRNA) vaccine is formulated as a solid lipid nanoparticle. A solid lipid nanoparticle (SLN) may be spherical with an average diameter between 10 to 1000 nm. SLNs possess a solid lipid core matrix that can solubilize lipophilic molecules and may be stabilized with surfactants and/or emulsifiers. In other embodiments, the lipid nanoparticle may be a self-assembly lipid-polymer nanoparticle (see Zhang et al., *ACS Nano,* 2008, 2 (8), pp 1696-1702; the content of which is herein incorporated by reference in its entirety). As a non-limiting example, the SLN may be the SLN described in International Publication No. WO2013/105101, the content of which is herein incorporated by reference in its entirety. As another non-limiting example, the SLN may be made by the methods or processes described in International Publication No. WO2013/105101, the content of which is herein incorporated by reference in its entirety.

Liposomes, lipoplexes, or lipid nanoparticles may be used to improve the efficacy of polynucleotides directed protein production as these formulations may be able to increase cell transfection by the RNA (e.g. mRNA) vaccine; and/or increase the translation of encoded protein. One such example involves the use of lipid encapsulation to enable the effective systemic delivery of polyplex plasmid DNA (Heyes et al., *Mol Ther.* 2007 15:713-720; herein incorporated by reference in its entirety). The liposomes, lipoplexes, or lipid nanoparticles may also be used to increase the stability of the polynucleotide.

In some embodiments, the RNA (e.g., mRNA) vaccines of the present invention can be formulated for controlled release and/or targeted delivery. As used herein, "controlled release" refers to a pharmaceutical composition or compound release profile that conforms to a particular pattern of release to effect a therapeutic outcome. In some embodiments, the RNA vaccines may be encapsulated into a delivery agent described herein and/or known in the art for controlled release and/or targeted delivery. As used herein, the term "encapsulate" means to enclose, surround, or encase. As it relates to the formulation of the compounds of the invention, encapsulation may be substantial, complete, or partial. The term "substantially encapsulated" means that at least greater than 50, 60, 70, 80, 85, 90, 95, 96, 97, 98, 99, 99.9, 99.99 or greater than 99.999% of the pharmaceutical composition or compound of the invention may be enclosed, surrounded, or encased within the delivery agent. "Partially encapsulation" means that less than 10, 10, 20, 30, 40, 50% or less of the pharmaceutical composition or compound of the invention may be enclosed, surrounded, or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the present disclosure are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012/131104 and WO2012/131106; the contents of each of which is herein incorporated by reference in its entirety).

In other embodiments, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel, and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In other embodiments, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA (e.g. mRNA) vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA (e.g., mRNA) vaccine controlled release and/or targeted delivery formulation may comprise at least one degradable polyester which may contain polycationic side chains. Degradable polyesters include, but are not limited to, poly(serine ester), poly(L- lactide-co-L-lysine), poly(4-hydroxy-L-proline ester), and combinations thereof. In other embodiments, the degradable polyesters may include a PEG conjugation to form a PEGylated polymer.

In some embodiments, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In other embodiments, the RNA vaccine controlled release delivery formulation comprising at least one polynucleotide may be the controlled release polymer system described in U.S. Publication No. 2013/0130348, herein incorporated by reference in its entirety.

In some embodiments, the RNA (e.g., mRNA) vaccines of the present invention may be encapsulated in a therapeutic nanoparticle, referred to herein as "therapeutic nanoparticle RNA vaccines." Therapeutic nanoparticles may be formulated by methods described herein and known in the art such as, but not limited to, International Publication Nos. WO2010/005740, WO2010/030763, WO2010/005721, WO2010/005723, and WO2012/054923, U.S. Publication Nos. US2011/0262491, US2010/0104645, US2010/0087337, US2010/0068285, US2011/0274759, US2010/0068286, US2012/0288541, US2013/0123351 and US2013/0230567, and U.S. Pat. Nos. 8,206,747, 8,293,276, 8,318,208 and 8,318,211, the content of each of which is herein incorporated by reference in its entirety. In other embodiments, therapeutic polymer nanoparticles may be identified by the methods described in U.S. Publication No. US2012/0140790, the content of which is herein incorporated by reference in its entirety.

In some embodiments, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months, and years. As a non-limiting example, the sustained release nanoparticle may comprise a polymer and a therapeutic agent such as, but not limited to, the polynucleotides of the present invention (see International Publication No. 2010/075072 and U.S. Publication Nos. US2010/0216804, US2011/0217377 and US2012/0201859, each of which is herein incorporated by reference in its entirety). In another non-limiting example, the sustained release formulation may comprise agents which permit persistent bioavailability such as, but not limited to, crystals, macromolecular gels and/or particulate suspensions (see U.S. Publication No. US2013/0150295, the content of which is herein incorporated by reference in its entirety).

In some embodiments, the therapeutic nanoparticle RNA (e.g. mRNA) vaccines may be formulated to be target specific. As a non-limiting example, the therapeutic nanoparticles may include a corticosteroid (see International Publication No. WO2011/084518, herein incorporated by reference in its entirety). As a non-limiting example, the therapeutic nanoparticles may be formulated in nanoparticles described in International Publication Nos. WO2008/121949, WO2010/005726, WO2010/005725, WO2011/084521 and U.S. Publication Nos. US2010/0069426, US2012/0004293 and US2010/0104655, each of which is herein incorporated by reference in its entirety.

In some embodiments, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), or combinations thereof. In yet other embodiments, the diblock copolymer may be a high-X diblock copolymer such as those described in International Publication No. WO2013/120052, the content of which is herein incorporated by reference in its entirety.

As a non-limiting example, the therapeutic nanoparticle comprises a PLGA-PEG block copolymer (see U.S. Publication No. US2012/0004293 and U.S. Pat. No. 8,236,330, each of which is herein incorporated by reference in its entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012/166923, the content of each of which is herein incorporated by reference in its entirety). In yet another non-limiting example, the therapeutic nanoparticle is a stealth nanoparticle or a target-specific stealth nanoparticle as described in U.S. Publication No. 2013/0172406, the content of which is herein incorporated by reference in its entirety.

In some embodiments, the therapeutic nanoparticle may comprise a multiblock copolymer (see e.g., U.S. Pat. Nos. 8,263,665 and 8,287,910 and U.S. Publication No. 2013/0195987, the content of each of which is herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) used as a TGF-beta1 gene delivery vehicle in Lee et al. "Thermosensitive Hydrogel as a Tgf-β1 Gene Delivery Vehicle Enhances Diabetic Wound Healing." *Pharmaceutical Research,* 2003 20(12): 1995-2000; and used as a controlled gene delivery system in Li et al. "Controlled Gene Delivery System Based on Thermosensitive Biodegradable Hydrogel" *Pharmaceutical Research* 2003 20(6):884-888; and Chang et al., "Non-ionic amphiphilic biodegradable PEG-PLGA-PEG copolymer enhances gene delivery efficiency in rat skeletal muscle." *J Controlled Release.* 2007 118:245-253; each of which is herein incorporated by reference in its entirety). The RNA (e.g., mRNA) vaccines of the present disclosure may be formulated in lipid nanoparticles comprising the PEG-PLGA-PEG block copolymer.

In some embodiments, the therapeutic nanoparticle may comprise a multiblock copolymer (see e.g., U.S. Pat. Nos.

8,263,665 and 8,287,910 and U.S. Publication No. 2013/0195987, the content of each of which is herein incorporated by reference in its entirety).

In some embodiments, the block copolymers described herein may be included in a polyion complex comprising a non-polymeric micelle and the block copolymer. (see e.g., U.S. Publication No. 2012/0076836, herein incorporated by reference in its entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates, and combinations thereof.

In some embodiments, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Publication No. WO2013/032829 or U.S. Publication No. 2013/0121954, the content of which is herein incorporated by reference in its entirety. In some aspects, the poly(vinyl ester) polymers may be conjugated to the polynucleotides described herein.

In some embodiments, the therapeutic nanoparticle may comprise at least one diblock copolymer. The diblock copolymer may be, but it not limited to, a poly(lactic) acid-poly (ethylene)glycol copolymer (see e.g., International Publication No. WO2013/044219; herein incorporated by reference in its entirety). As a non-limiting example, the therapeutic nanoparticle may be used to treat cancer (see International Publication No. WO2013/044219, herein incorporated by reference in its entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethyleneimine, poly(amidoamine) dendrimers, poly(beta-amino esters) (see e.g., U.S. Pat. No. 8,287,849, herein incorporated by reference in its entirety), and combinations thereof. In other embodiments, the nanoparticles described herein may comprise an amine cationic lipid such as those described in International Publication No. WO2013/059496, the content of which is herein incorporated by reference in its entirety. In some aspects, the cationic lipids may have an amino-amine or an amino-amide moiety.

In some embodiments, the therapeutic nanoparticles may comprise at least one degradable polyester, which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGylated polymer.

In other embodiments, the therapeutic nanoparticle may include a conjugation of at least one targeting ligand. The targeting ligand may be any ligand known in the art such as, but not limited to, a monoclonal antibody (Kirpotin et al, *Cancer Res.* 2006 66:6732-6740, herein incorporated by reference in its entirety).

In some embodiments, the therapeutic nanoparticle may be formulated in an aqueous solution, which may be used to target cancer (see International Publication No. WO2011/084513 and U.S. Publication No. 2011/0294717, each of which is herein incorporated by reference in its entirety).

In some embodiments, the therapeutic nanoparticle RNA (e.g. mRNA) vaccines, e.g., therapeutic nanoparticles comprising at least one RNA vaccine may be formulated using the methods described by Podobinski et a in U.S. Pat. No. 8,404,799, the content of which is herein incorporated by reference in its entirety.

In some embodiments, the RNA (e.g., mRNA) vaccines may be encapsulated in, linked to and/or associated with synthetic nanocarriers. Synthetic nanocarriers include, but are not limited to, those described in International Publication Nos. WO2010/005740, WO2012/149454, and WO2013/019669, and U.S. Publication Nos. US2011/0262491, US2010/0104645, US2010/0087337, and US2012/0244222, each of which is herein incorporated by reference in its entirety. The synthetic nanocarriers may be formulated using methods known in the art and/or described herein. As a non-limiting example, the synthetic nanocarriers may be formulated by the methods described in International Publication Nos. WO2010/005740, WO2010/030763, and WO2012/013501, and U.S. Publication Nos. US2011/0262491, US2010/0104645, US2010/0087337, and US2012/024422, each of which is herein incorporated by reference in its entirety. In other embodiments, the synthetic nanocarrier formulations may be lyophilized by methods described in International Publication No. WO2011/072218 and U.S. Pat. No. 8,211,473, the content of each of which is herein incorporated by reference in its entirety. In yet other embodiments, formulations of the present invention, including, but not limited to, synthetic nanocarriers, may be lyophilized or reconstituted by the methods described in U.S. Publication No. 2013/0230568, the content of which is herein incorporated by reference in its entirety.

In some embodiments, the synthetic nanocarriers may contain reactive groups to release the polynucleotides described herein (see International Publication No. WO2012/092552 and U.S. Publication No. US2012/0171229, each of which is herein incorporated by reference in its entirety).

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Publication No. WO2010/123569 and U.S. Publication No. 2011/0223201, each of which is herein incorporated by reference in its entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA (e.g. mRNA) vaccines after 24 hours and/or at a pH of 4.5 (see International Publication Nos. WO2010/138193 and WO2010/138194 and U.S. Publication Nos. US2011/0020388 and US2011/0027217, each of which is herein incorporated by reference in its entirety).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Publication No.

WO2010/138192 and U.S. Publication No. 2010/0303850, each of which is herein incorporated by reference in its entirety.

In some embodiments, the RNA (e.g. mRNA) vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encodes at least one antigen. As a non-limiting example, the synthetic nanocarrier may include at least one antigen and an excipient for a vaccine dosage form (see International Publication No. WO2011/150264 and U.S. Publication No. 2011/0293723, each of which is herein incorporated by reference in its entirety). As another non-limiting example, a vaccine dosage form may include at least two synthetic nanocarriers with the same or different antigens and an excipient (see International Publication No. WO2011/150249 and U.S. Publication No. 2011/0293701, each of which is herein incorporated by reference in its entirety). The vaccine dosage form may be selected by methods described herein, known in the art, and/or described in International Publication No. WO2011/150258 and U.S. Publication No. US2012/0027806, each of which is herein incorporated by reference in its entirety.

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA), and an apolar fraction or part of said apolar fraction of a total lipid extract of a mycobacterium (see e.g., U.S. Pat. No. 8,241,610; herein incorporated by reference in its entirety). In other embodiments, the synthetic nanocarrier may comprise at least one polynucleotide and an adjuvant. As a non-limiting example, the synthetic nanocarrier comprising an adjuvant may be formulated by the methods described in International Publication No. WO2011/150240 and U.S. Publication No. US2011/0293700, each of which is herein incorporated by reference in its entirety.

In some embodiments, the synthetic nanocarrier may encapsulate at least one polynucleotide which encodes a peptide, fragment, or region from a virus. As a non-limiting example, the synthetic nanocarrier may include, but is not limited to, the nanocarriers described in International Publication Nos. WO2012/024621, WO2012/02629, and WO2012/024632 and U.S. Publication Nos. US2012/0064110, US2012/0058153, and US2012/0058154, each of which is herein incorporated by reference in its entirety.

In some embodiments, the synthetic nanocarrier may be coupled to a polynucleotide which may be able to trigger a humoral and/or cytotoxic T lymphocyte (CTL) response (see e.g., International Publication No. WO2013/019669, herein incorporated by reference in its entirety).

In some embodiments, the RNA (e.g. mRNA) vaccine may be encapsulated in, linked to and/or associated with zwitterionic lipids. Non-limiting examples of zwitterionic lipids and methods of using zwitterionic lipids are described in U.S. Publication No. 2013/0216607, the content of which is herein incorporated by reference in its entirety. In some aspects, the zwitterionic lipids may be used in the liposomes and lipid nanoparticles described herein.

In some embodiments, the RNA (e.g. mRNA) vaccine may be formulated in colloid nanocarriers as described in U.S. Publication No. 2013/0197100, the content of which is herein incorporated by reference in its entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Publication No. 2012/0282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA (e.g. mRNA) vaccines may be delivered using smaller LNPs. Such particles may comprise a diameter from below 0.1 μm up to 100 nm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, or less than 975 μm.

In other embodiments, RNA (e.g., mRNA) vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nm, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm, and/or from about 70 to about 90 nm.

In some embodiments, such LNPs are synthesized using methods comprising microfluidic mixers. Exemplary microfluidic mixers may include, but are not limited to a slit interdigitial micromixers including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing. Langmuir. 2012. 28:3633-40) have been published (Belliveau, N. M. et al., Microfluidic synthesis of highly potent limit-size lipid nanoparticles for in vivo delivery of siRNA. *Molecular Therapy-Nucleic Acids.* 2012. 1:e37; Chen, D. et al., Rapid discovery of potent siRNA-containing lipid nanoparticles enabled by controlled microfluidic formulation. *J Am Chem Soc.* 2012. 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams down flow through channels present in a herringbone pattern, causing rotational flow and folding the fluids around each other. This method may also comprise a surface for fluid mixing wherein the surface changes orientations during fluid cycling. Methods of generating LNPs using SHM include those disclosed in U.S. Publication Nos. 2004/0262223 and 2012/0276209, each of which is expressly incorporated herein by reference in its entirety.

In some embodiments, the RNA (e.g. mRNA) vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet ((IJMM) from the Institut für Mikrotechnik Mainz GmbH, Mainz Germany).

In some embodiments, the RNA (e.g., mRNA) vaccines of the present disclosure may be formulated in lipid nanoparticles created using microfluidic technology (see Whitesides, George M. The Origins and the Future of Microfluidics. *Nature,* 2006 442: 368-373; and Abraham et al. Chaotic Mixer for Microchannels. *Science,* 2002 295: 647-651; each of which is herein incorporated by reference in its entirety). As a non-limiting example, controlled microfluidic formulation includes a passive method for mixing streams of steady pressure-driven flows in micro channels at a low Reynolds number (see e.g., Abraham et al. Chaotic Mixer for Microchannels. *Science,* 2002 295: 647651; which is herein incorporated by reference in its entirety).

In some embodiments, the RNA (e.g., mRNA) vaccines of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the RNA (e.g., mRNA) vaccines of the invention may be formulated for delivery using the drug encapsulating microspheres described in International Publication No. WO2013/063468 or U.S. Pat. No. 8,440,614, each of which is herein incorporated by reference in its entirety. The microspheres may comprise a compound of the formula (I), (II), (III), (IV), (V) or (VI) as described in International Publication No. WO2013/063468, the content of which is herein incorporated by reference in its entirety.

In other aspects, the amino acid, peptide, polypeptide, lipids are useful in delivering the RNA (e.g. mRNA) vaccines of the invention to cells (see International Publication No. WO2013/063468, the contents of which is herein incorporated by reference in its entirety).

In some embodiments, the RNA (e.g., mRNA) vaccines of the present disclosure may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm, and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some aspects, the lipid nanoparticle may be a limit size lipid nanoparticle described in International Publication No. WO2013/059922, the content of which is herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and a 1-palmitoyl-2-oleoyl phosphatidylcholine (POPC). In other aspects, the limit size lipid nanoparticle may comprise a polyethylene glycol-lipid such as, but not limited to, DLPE-PEG, DMPE-PEG, DPPC-PEG, and DSPE-PEG.

In some embodiments, the RNA (e.g. mRNA) vaccines may be delivered, localized, and/or concentrated in a specific location using the delivery methods described in International Publication No. WO2013/063530, the content of which is herein incorporated by reference in its entirety. As a non-limiting example, a subject may be administered an empty polymeric particle prior to, simultaneously with or after delivering the RNA (e.g. mRNA) vaccines to the subject. The empty polymeric particle undergoes a change in volume once in contact with the subject and becomes lodged, embedded, immobilized or entrapped at a specific location in the subject.

In some embodiments, the RNA (e.g. mRNA) vaccines may be formulated in an active substance release system (see e.g., U.S. Publication No. US2013/0102545, the content of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA (e.g., mRNA) vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Publication No. WO2013/052167, herein incorporated by reference in its entirety. As another non-limiting example, the nanoparticle described in International Publication No. WO2013/052167, herein incorporated by reference in its entirety, may be used to deliver the RNA vaccines described herein.

In some embodiments, the RNA (e.g., mRNA) vaccines may be formulated in porous nanoparticle-supported lipid bilayers (protocells). Protocells are described in International Publication No. WO2013/056132, the content of which is herein incorporated by reference in its entirety.

In some embodiments, the RNA (e.g., mRNA) vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the content of which is herein incorporated by reference in its entirety. As another non-limiting example, the polymer nanoparticle for oral and parenteral formulations may be made by the methods described in European Patent No. EP2073848B1, the content of which is herein incorporated by reference in its entirety.

In other embodiments, the RNA (e.g., mRNA) vaccines described herein may be formulated in nanoparticles used in imaging. The nanoparticles may be liposome nanoparticles such as those described in U.S. Publication No. 20130129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., U.S. Publication No. US2013/0129636, the contents of which is herein incorporated by reference in its entirety).

In some embodiments, the nanoparticles which may be used in the present invention are formed by the methods described in U.S. Patent Application No. 2013/0130348, the content of which is herein incorporated by reference in its entirety.

The nanoparticles of the present invention may further include nutrients such as, but not limited to, those which deficiencies can lead to health hazards from anemia to neural tube defects (see e.g., the nanoparticles described in International Patent Publication No. WO2013/072929, the contents of which is herein incorporated by reference in its entirety). As a non-limiting example, the nutrient may be iron in the form of ferrous, ferric salts, or elemental iron, iodine, folic acid, vitamins or micronutrients.

In some embodiments, the RNA (e.g., mRNA) vaccines of the present invention may be formulated in a swellable nanoparticle. The swellable nanoparticle may be, but is not limited to, those described in U.S. Pat. No. 8,440,231, the content of which is herein incorporated by reference in its entirety. As a non-limiting embodiment, the swellable nanoparticle may be used for delivery of the RNA (e.g., mRNA) vaccines of the present invention to the pulmonary system (see e.g., U.S. Pat. No. 8,440,231, the content of which is herein incorporated by reference in its entirety).

The RNA (e.g., mRNA) vaccines of the present invention may be formulated in polyanhydride nanoparticles such as, but not limited to, those described in U.S. Pat. No. 8,449,916, the content of which is herein incorporated by reference in its entirety. The nanoparticles and microparticles of the present invention may be geometrically engineered to modulate macrophage and/or the immune response. In some aspects, the geometrically engineered particles may have varied shapes, sizes, and/or surface charges in order to incorporated the polynucleotides of the present invention for targeted delivery such as, but not limited to, pulmonary delivery (see e.g., International Publication No. WO2013/082111, the content of which is herein incorporated by reference in its entirety). Other physical features the geometrically engineering particles may have include, but are not limited to, fenestrations, angled arms, asymmetry, surface roughness, and charge, which can alter the interactions with cells and tissues. As a non-limiting example, nanoparticles of the present invention may be made by the methods described in International Publication No. WO2013/082111, the content of which is herein incorporated by reference in its entirety.

In some embodiments, the nanoparticles of the present invention may be water soluble nanoparticles such as, but not limited to, those described in International Publication No. WO2013/090601, the content of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments, the nanoparticles of the present invention may be developed by the methods described in U.S. Publication No. US2013/0172406, the content of which is herein incorporated by reference in its entirety.

In some embodiments, the nanoparticles of the present invention are stealth nanoparticles or target-specific stealth nanoparticles such as, but not limited to, those described in U.S. Publication No. 2013/0172406, the content of which is herein incorporated by reference in its entirety. The nanoparticles of the present invention may be made by the methods described in U.S. Publication No. 2013/0172406, the content of which is herein incorporated by reference in its entirety.

In other embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in U.S. Publication No. 2013/0171646, the content of which is herein incorporated by reference in its entirety. The nanoparticle may comprise a nucleic acid such as, but not limited to, polynucleotides described herein and/or known in the art.

At least one of the nanoparticles of the present invention may be embedded in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Publication No. WO2013/123523, the content of which is herein incorporated by reference in its entirety.

In some embodiments, a nanoparticle comprises compounds of Formula (I):

(I)

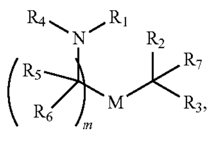

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ(R)$_2$, and unsubstituted $C_{1-6}$ alkyl, where Q is selected from a carbocycle, heterocycle, —OR, —O$(CH_2)_n$N(R)$_2$, —C(O)OR, —OC(O)R, —$CX_3$, —$CX_2$H, —$CXH_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)$R_8$, —O$(CH_2)_n$OR, —N(R)C(═$NR_9$)N(R)$_2$, —N(R)C(═$CHR_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═$NR_9$)N(R)$_2$, —N(OR)C(═$CHR_9$)N(R)$_2$, —C(═$NR_9$)N(R)$_2$, —C(═$NR_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N(R)$_2$, —C(O)OR, —OC(O)R, —$CX_3$, —$CX_2$H, —$CXH_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)$R_8$, —O$(CH_2)_n$OR, —N(R)C(═$NR_9$)N(R)$_2$, —N(R)C(═$CHR_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═$NR_9$)N(R)$_2$, —N(OR)C(═$CHR_9$)N(R)$_2$, —C(═$NR_9$)N(R)$_2$, —C(═$NR_9$)R, —C(O)N(R)OR, and a 5- to 14-membered heterocycloalkyl having one or more heteroatoms selected from N, O, and S which is substituted with one or more substituents selected from oxo (═O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is $—(CH_2)_nQ$ or $—(CH_2)_nCHQR$, where Q is $—N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

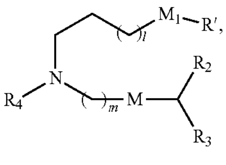

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

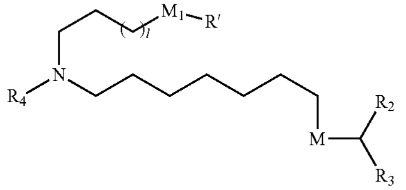

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

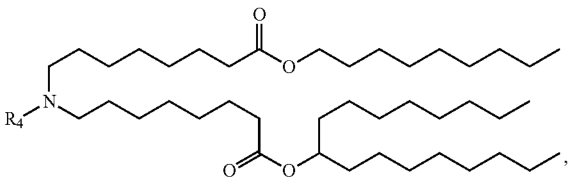

, (IIb)

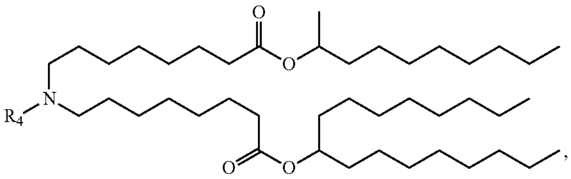

, (IIc)

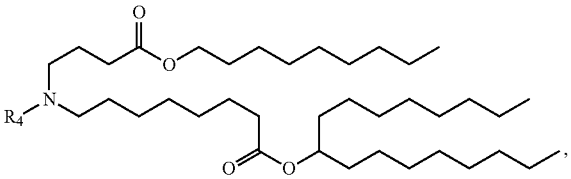

, or

-continued (IIe)

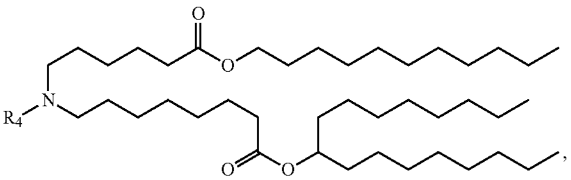

or a salt or isomer thereof, wherein $R_4$ is as described herein.

In some embodiments, a subset of compounds of Formula (I) includes those of Formula (IId):

(IId)

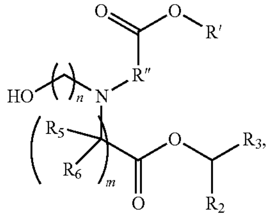

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)

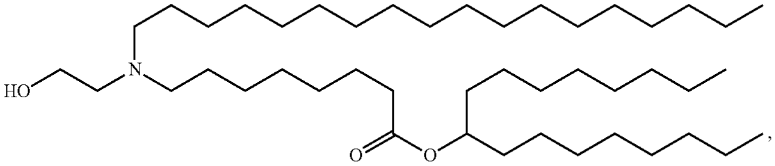

(Compound 2)

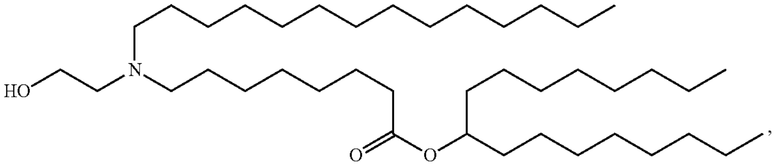

(Compound 3)

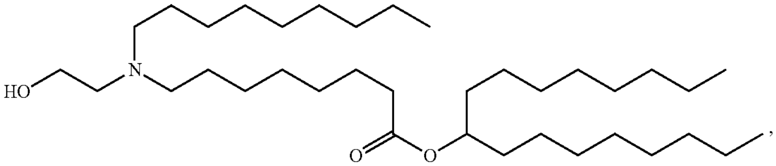

(Compound 4)

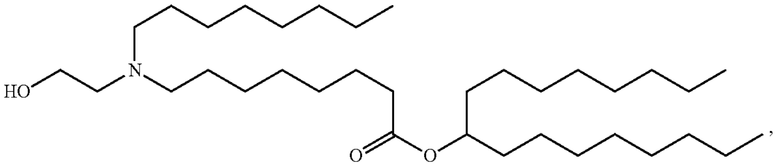

(Compound 5)

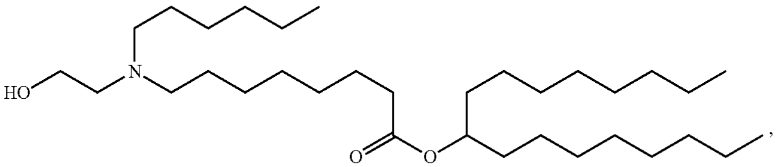

-continued
(Compound 6)
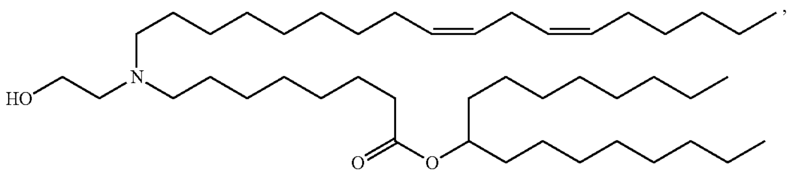
(Compound 7)
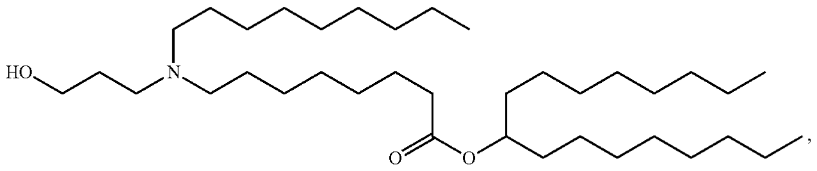
(Compound 8)
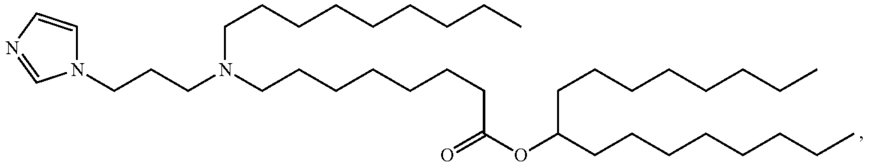
(Compound 9)
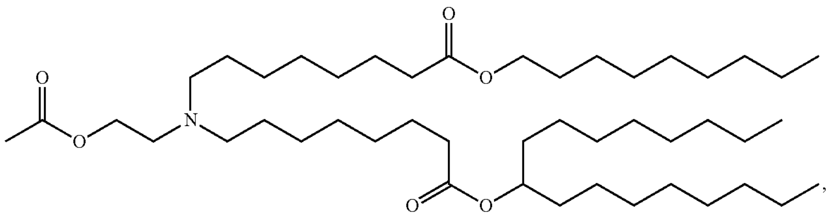
(Compound 10)
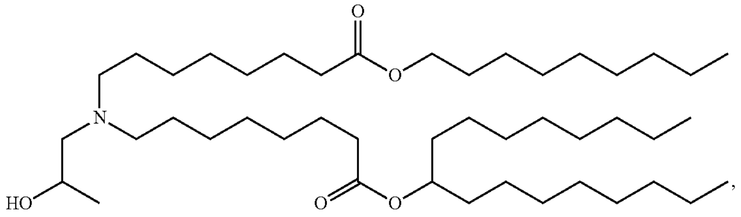
(Compound 11)
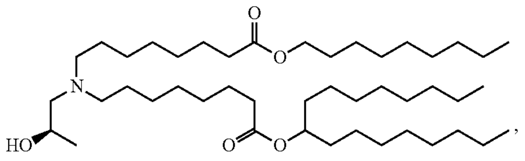
(Compound 12)
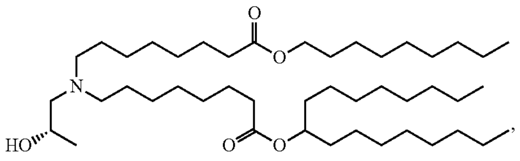
(Compound 13)
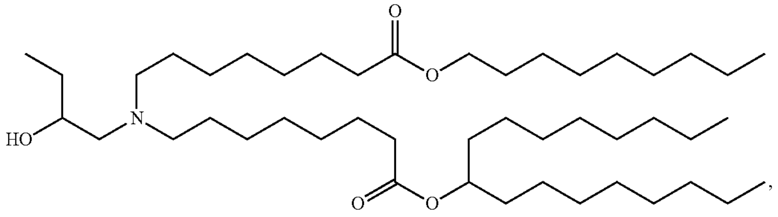
(Compound 14)
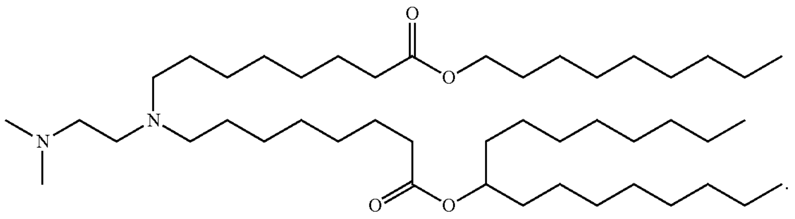

-continued
(Compound 15)
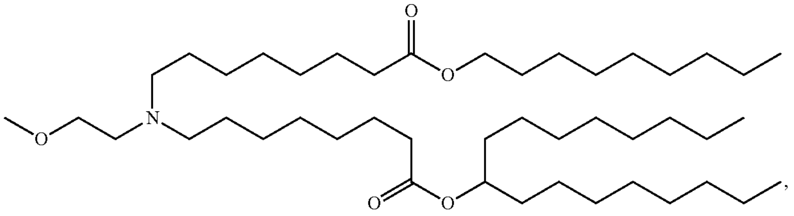
(Compound 16)
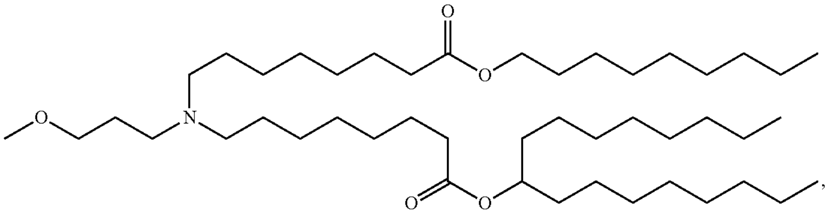
(Compound 17)
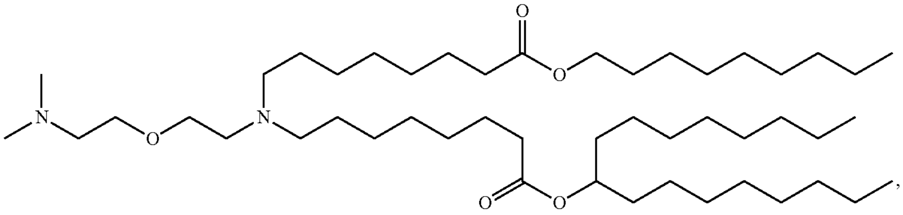
(Compound 18)
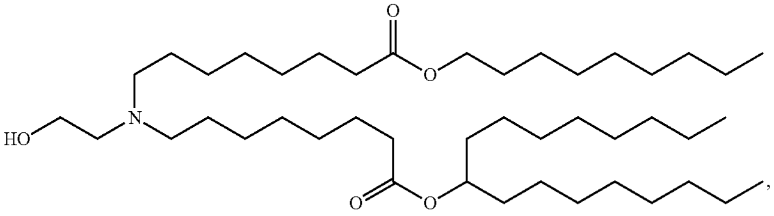
(Compound 19)
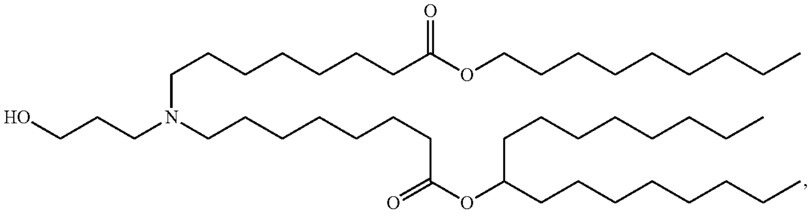
(Compound 20)
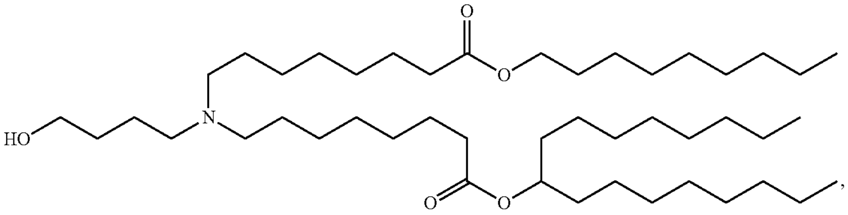
(Compound 21)
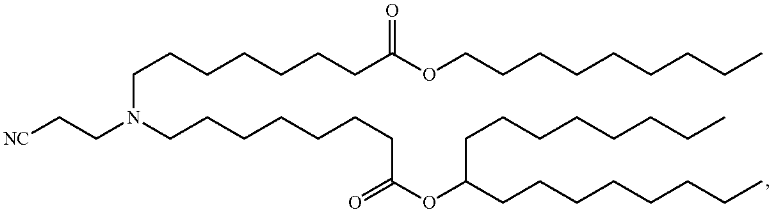

-continued
(Compound 22)
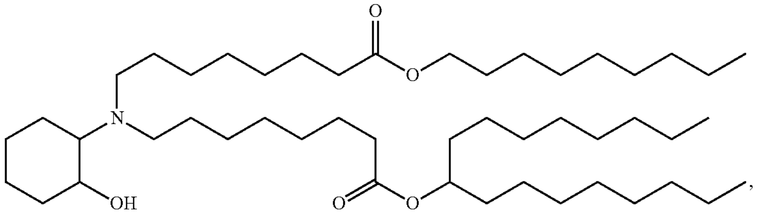
(Compound 23)
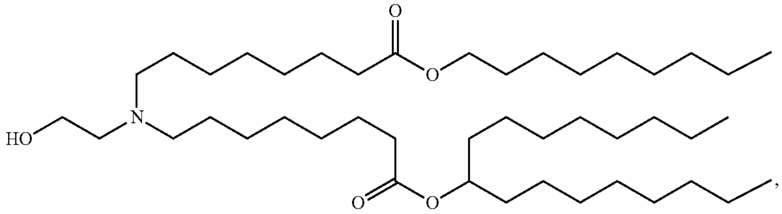
(Compound 24)
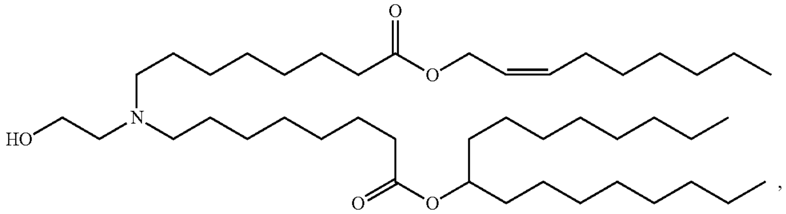
(Compound 25)
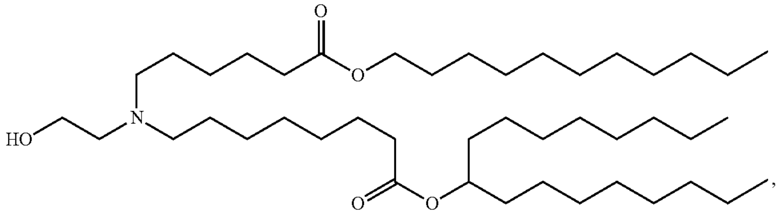
(Compound 26)
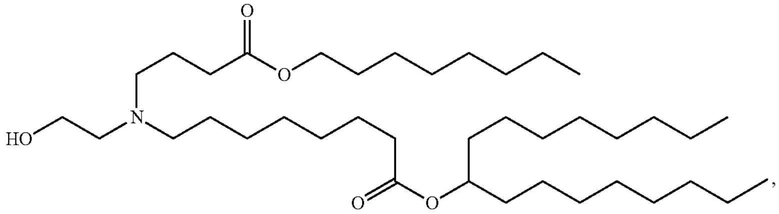
(Compound 27)
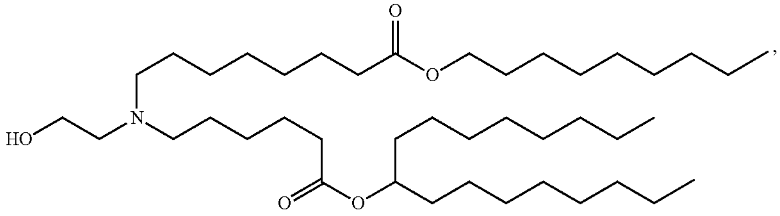
(Compound 28)
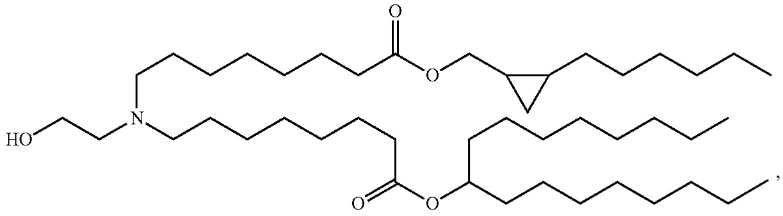

-continued
(Compound 29)
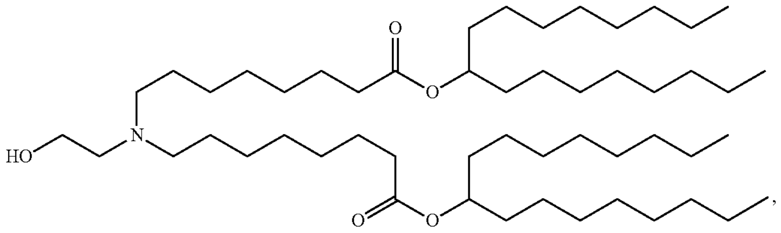
(Compound 30)
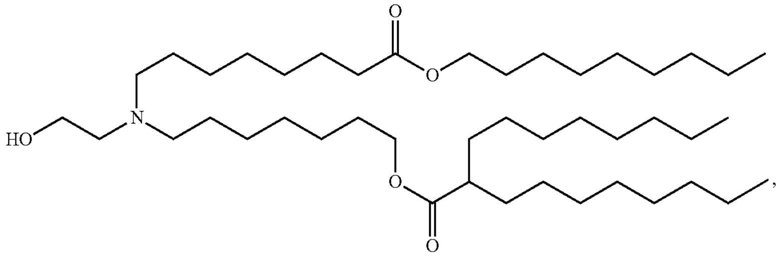
(Compound 31)
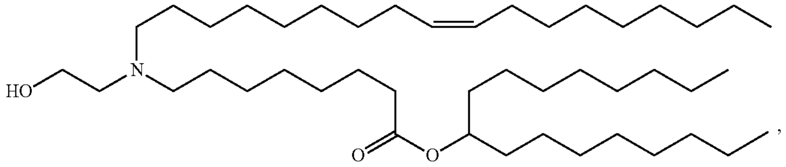
(Compound 32)
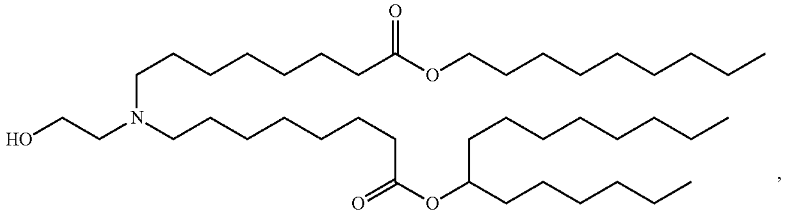
(Compound 33)
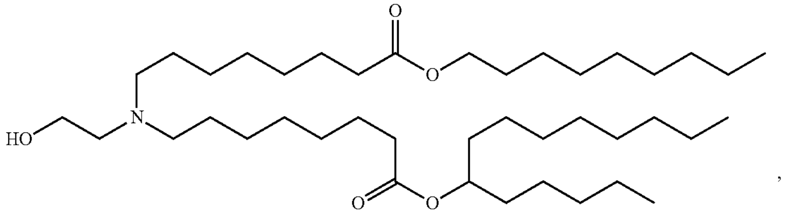
(Compound 34)
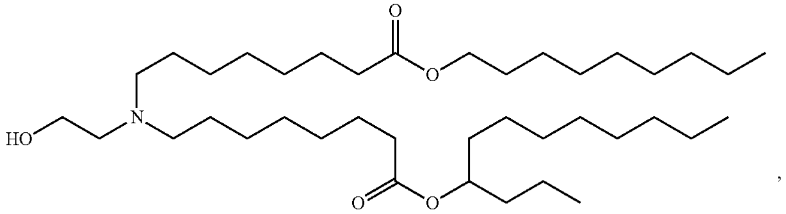
(Compound 35)
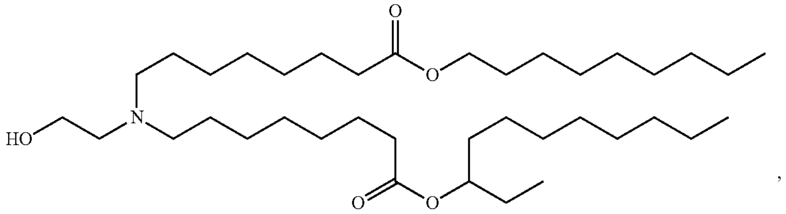

-continued
(Compound 36)
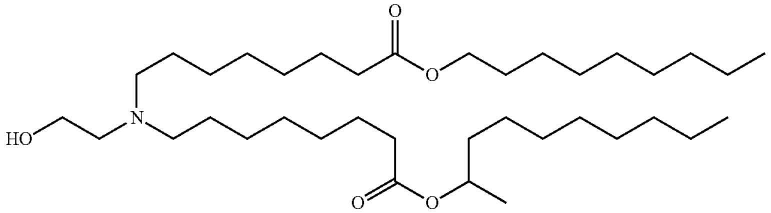
,
(Compound 37)
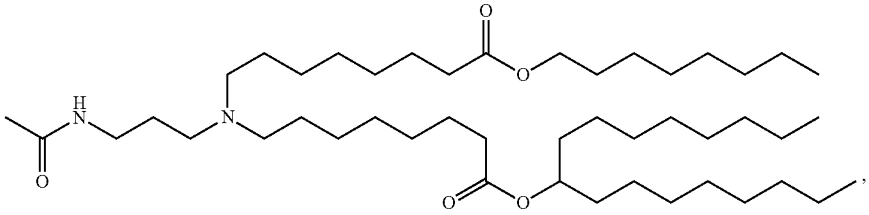
,
(Compound 38)
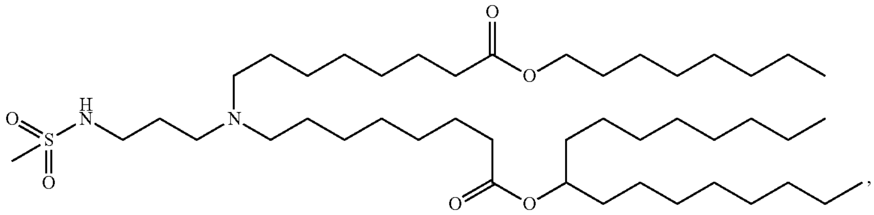
,
(Compound 39)
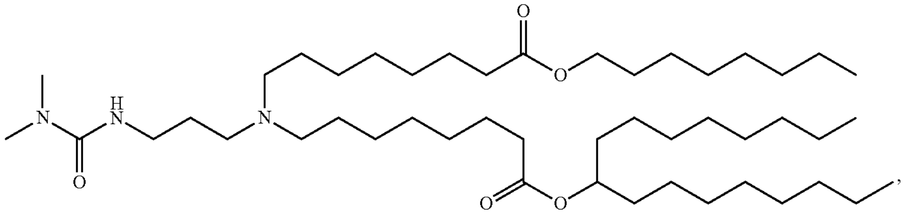
,
(Compound 40)
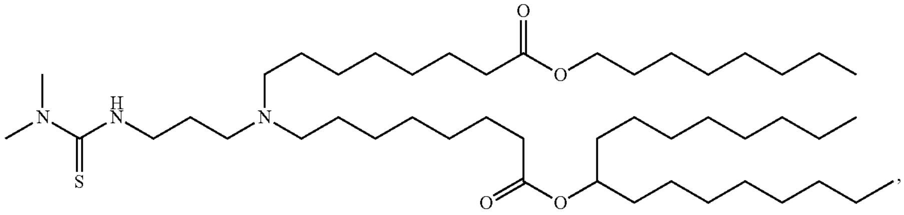
,
(Compound 41)
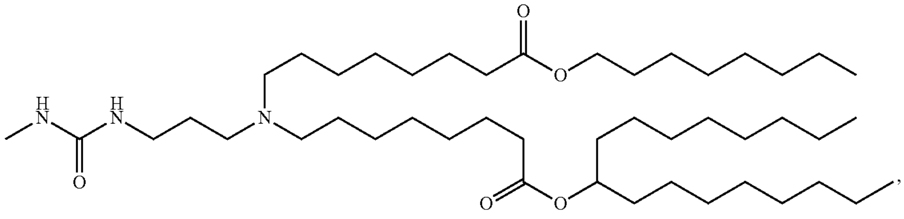
,
(Compound 42)
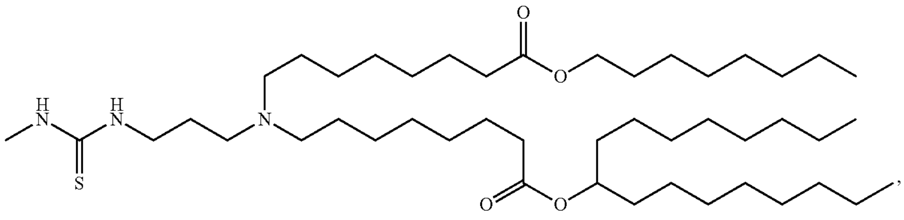
, -continued
(Compound 43)
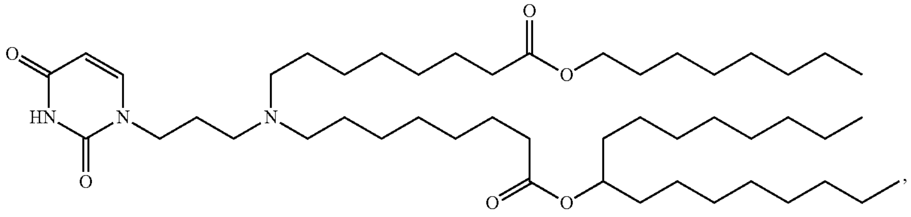
(Compound 44
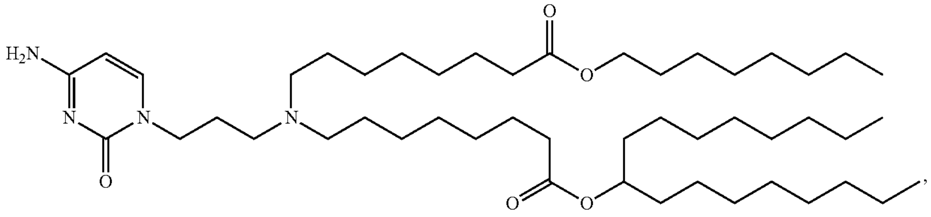
(Compound 45)
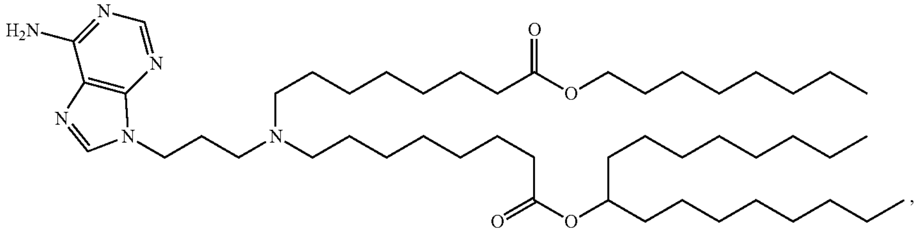
(Compound 46)
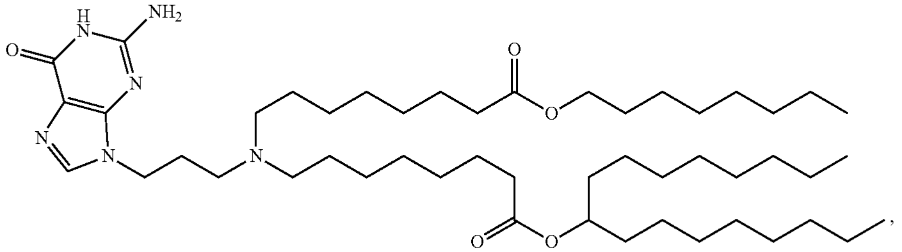
(Compound 47)
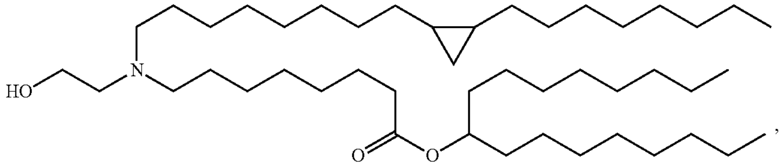
(Compound 48)
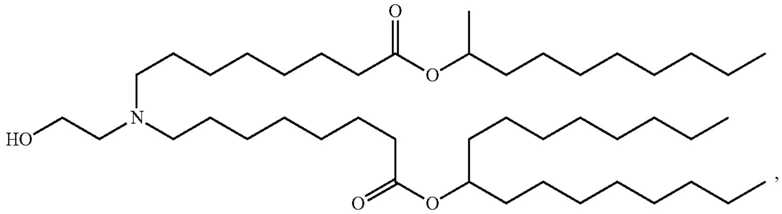
(Compound 49)
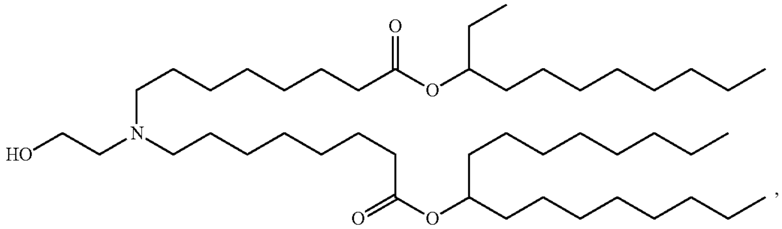

-continued
(Compound 50)
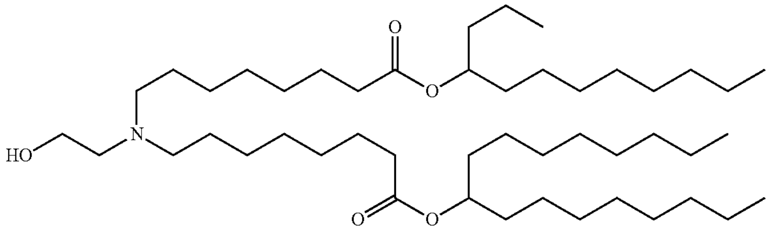
,
(Compound 51)
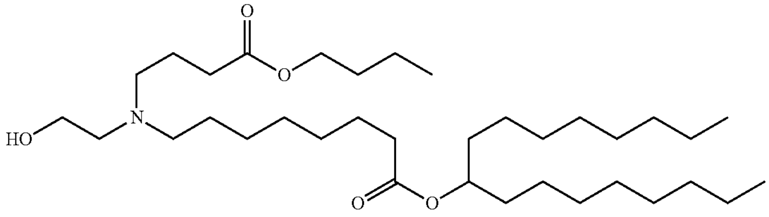
,
(Compound 52)
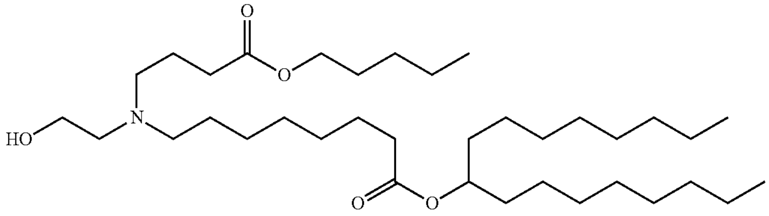
,
(Compound 53)
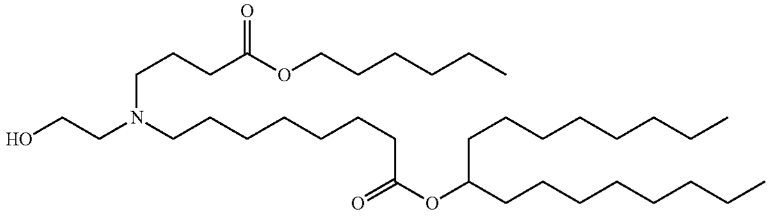
,
(Compound 54)
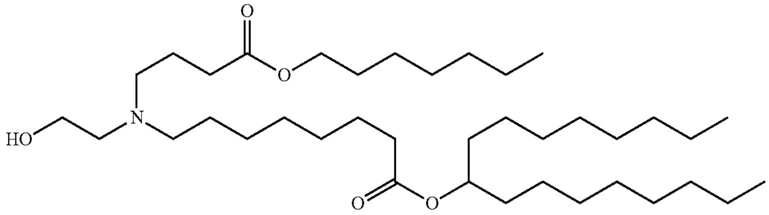
,
(Compound 55)
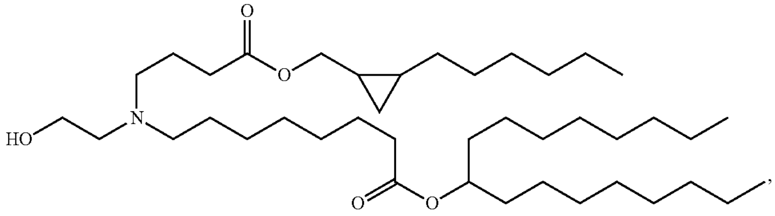
,
(Compound 56)
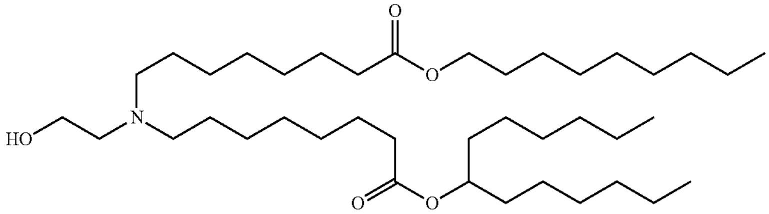
, -continued
(Compound 57)
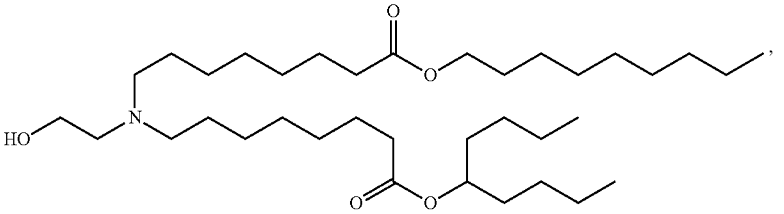
(Compound 58)
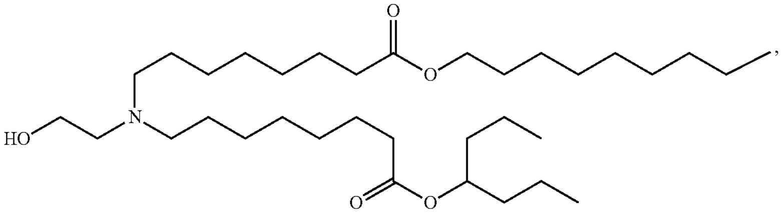
(Compound 59)
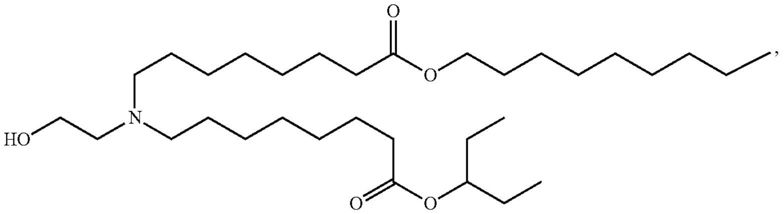
(Compound 60)
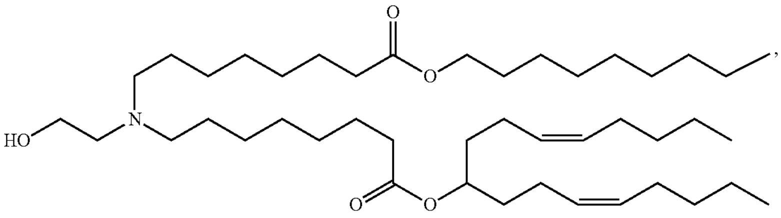
and
(Compound 61)
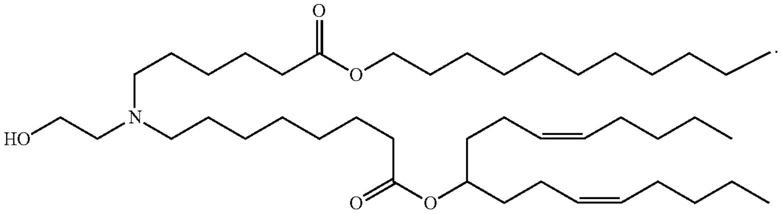
In further embodiments, the compound of Formula (I) is selected from the group consisting of:
(Compound 62)
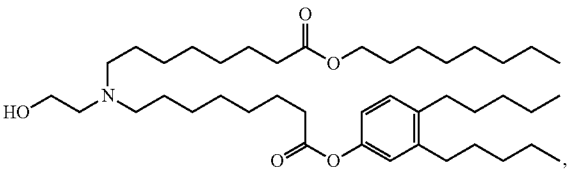
-continued
(Compound 63)
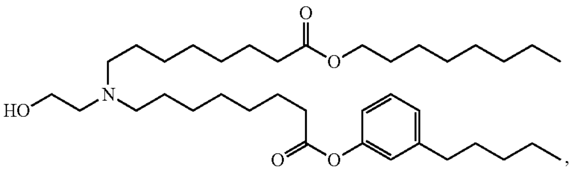
and -continued
(Compound 64)
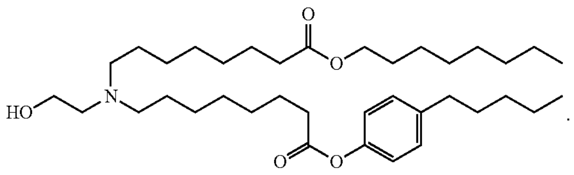
In further embodiments, the compound of Formula (I) is selected from the group consisting of:

(Compound 65)
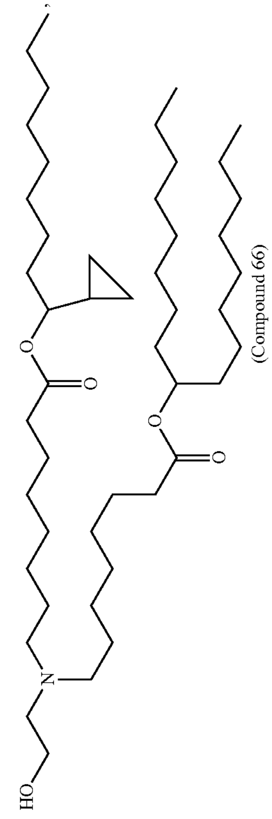
,
(Compound 66)
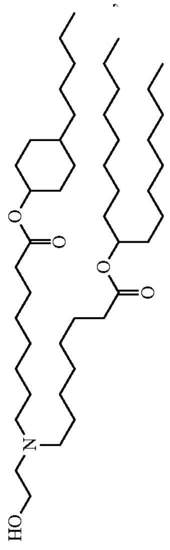
,
(Compound 67)
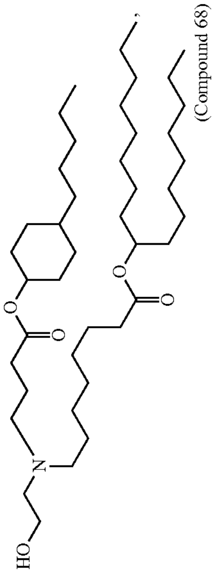
,
(Compound 68)
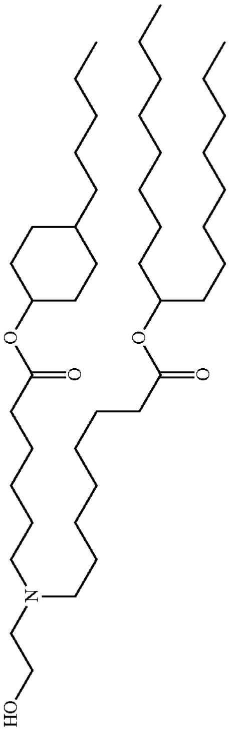
(Compound 69)
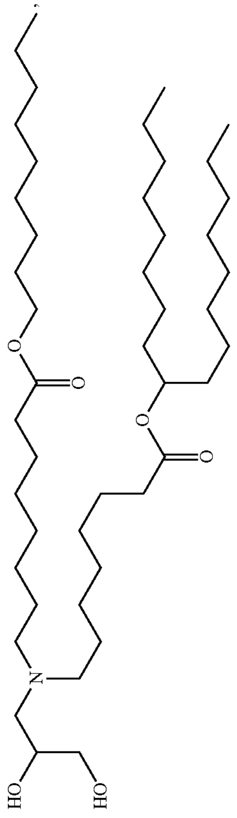
, -continued
(Compound 70)
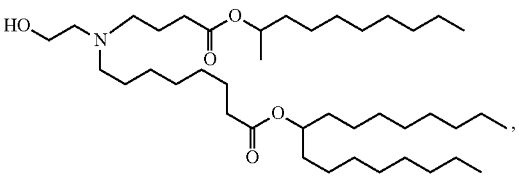
,
(Compound 71)
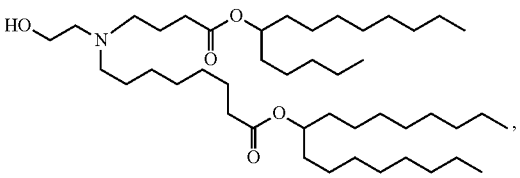
,
(Compound 72)
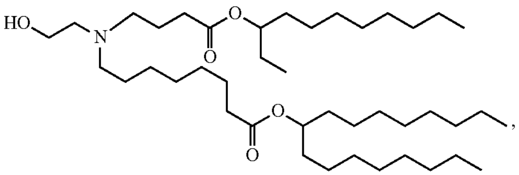
,
(Compound 73)
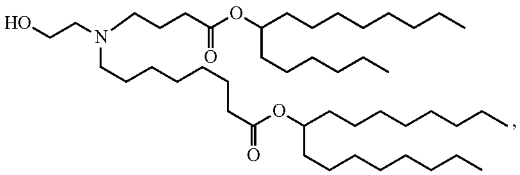
,
(Compound 74)
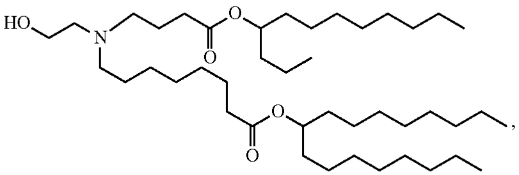
,
(Compound 75)
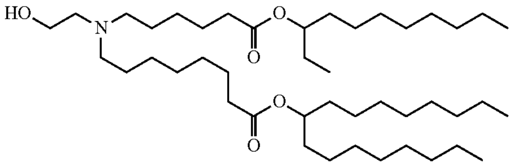
,
(Compound 76)
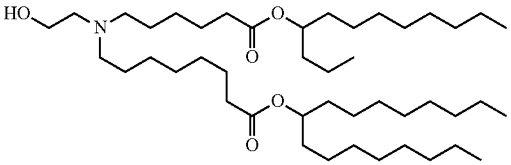
,
(Compound 77)
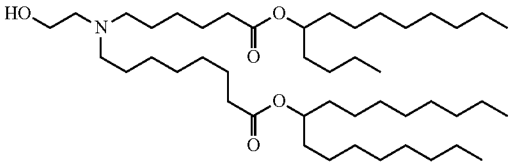
,
(Compound 78)
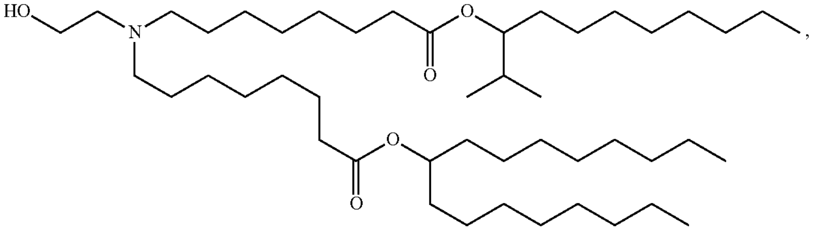
, -continued
(Compound 79)
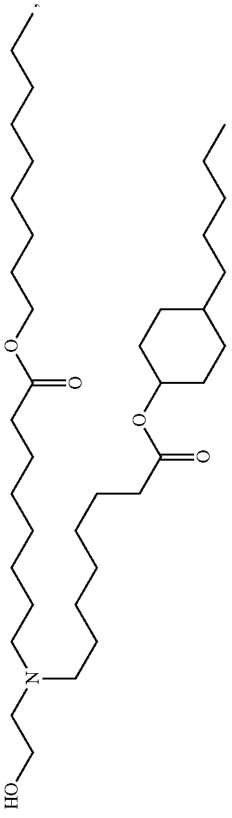
,
(Compound 80)
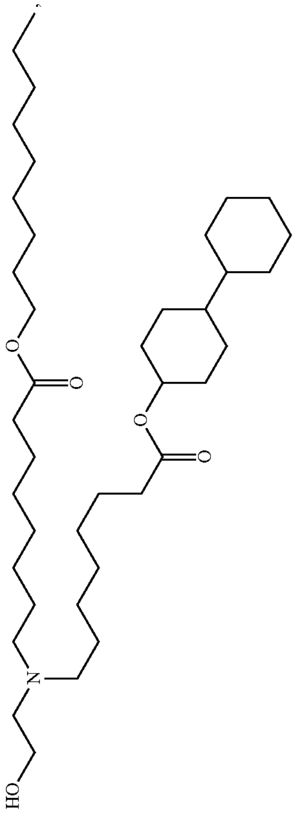
,
(Compound 81)
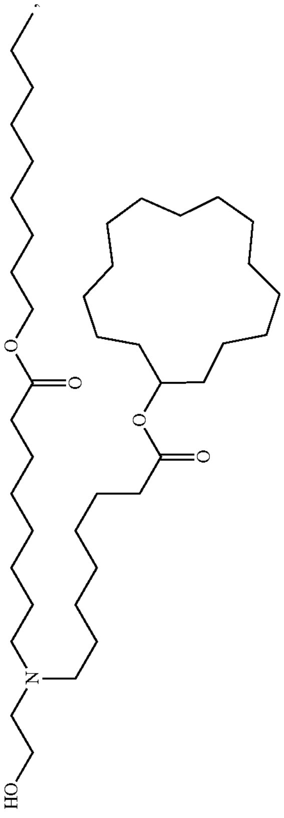
,
(Compound 82)
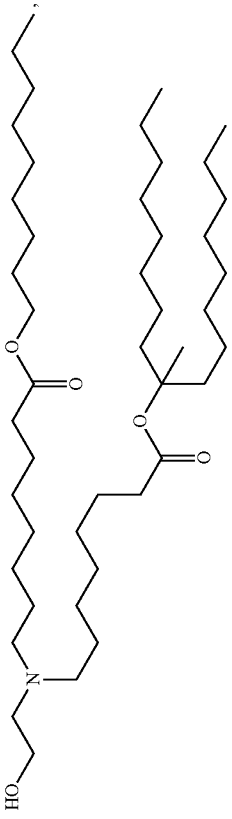
, -continued
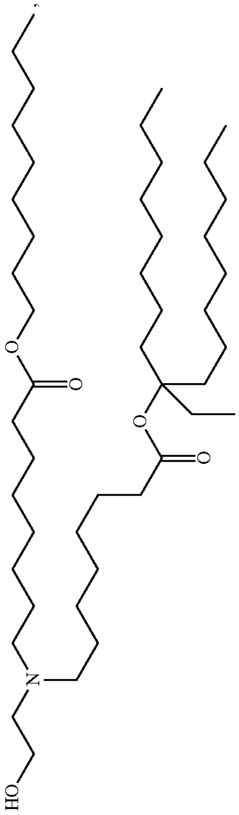,
(Compound 83)
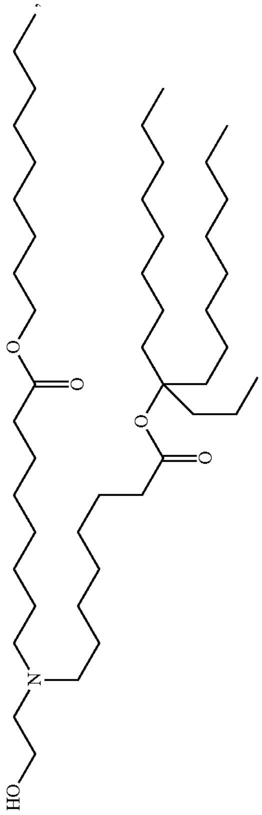,
(Compound 84)
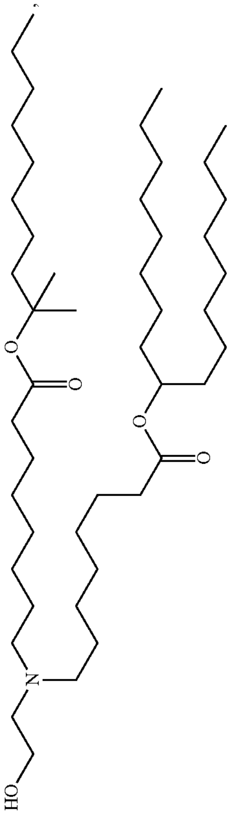,
(Compound 85)
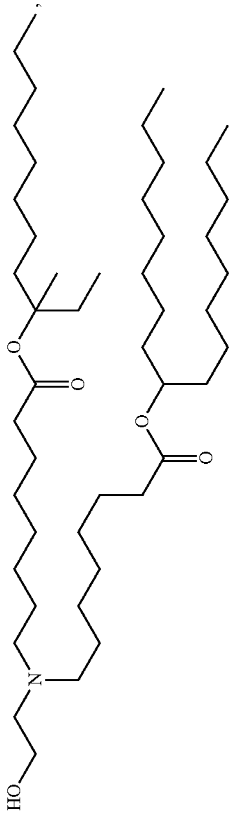,
(Compound 86)

-continued
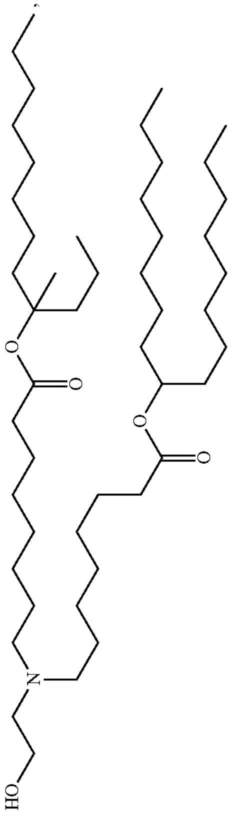
(Compound 87)
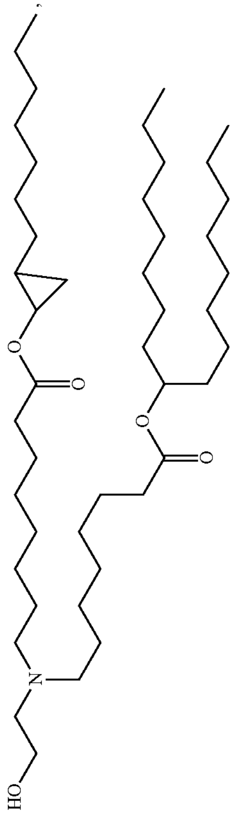
(Compound 88)
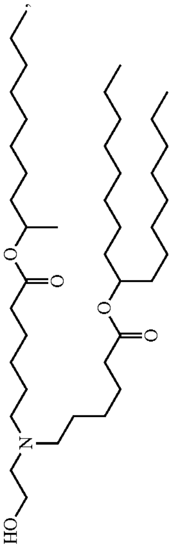
(Compound 89)
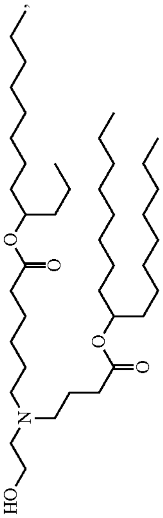
(Compound 90)
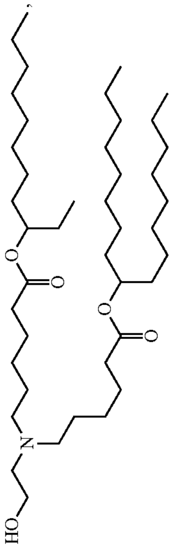
(Compound 91)
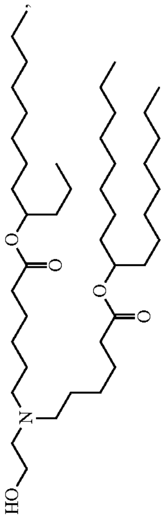
(Compound 92)

-continued
(Compound 93)
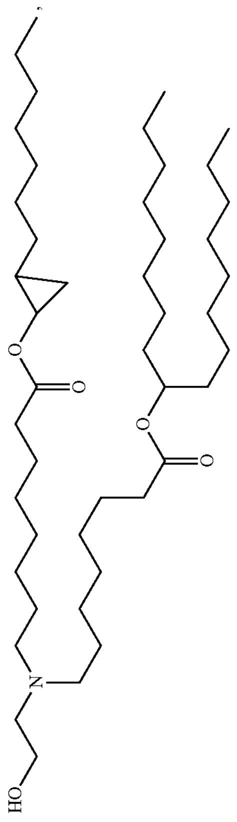
(Compound 94)
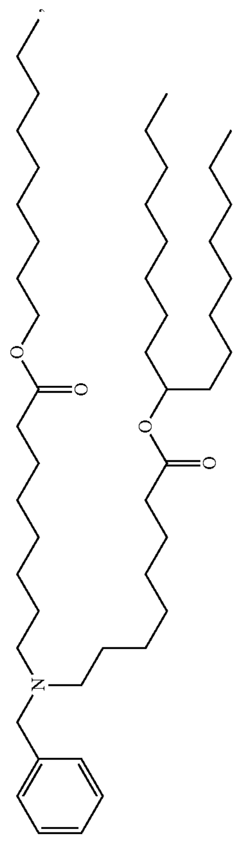
(Compound 95)
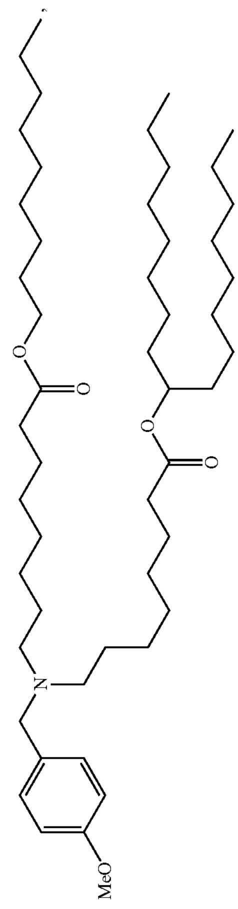
(Compound 96)
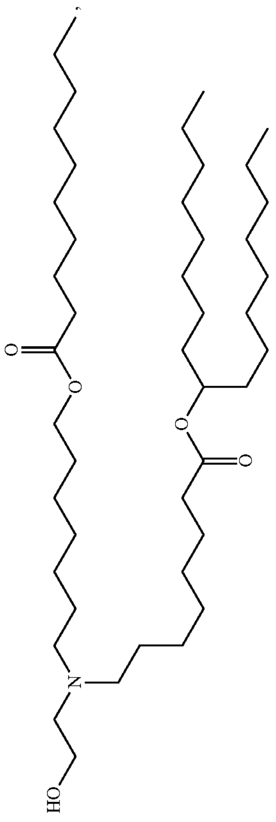

-continued
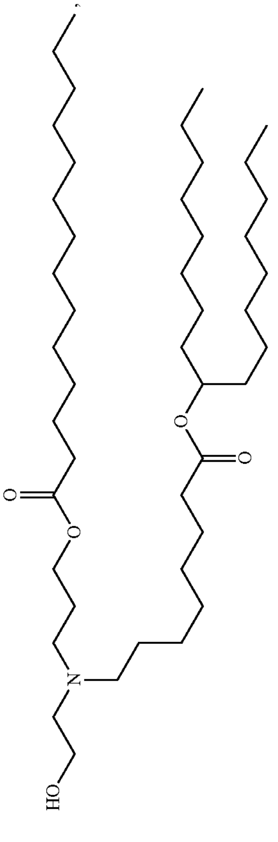
(Compound 97)
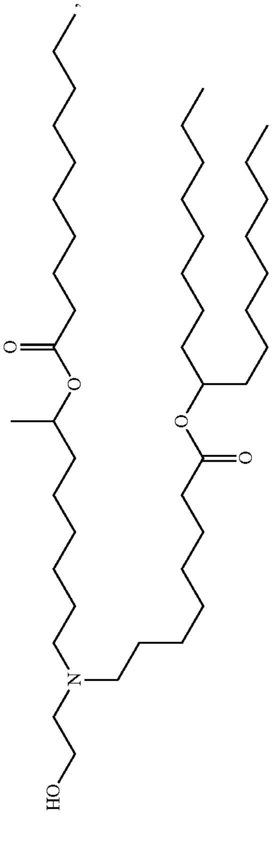
(Compound 98)
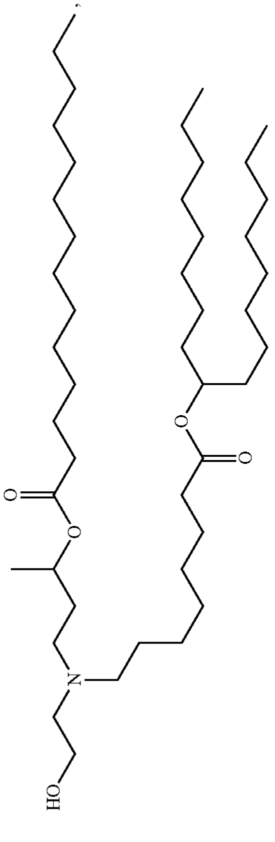
(Compound 99)

-continued
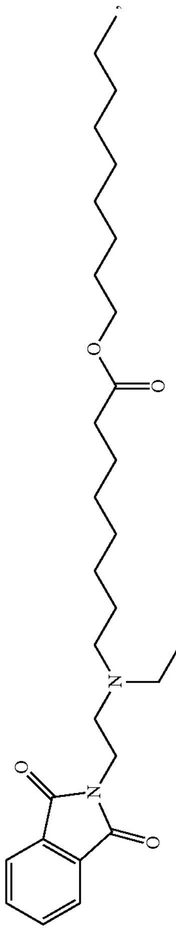
(Compound 100)
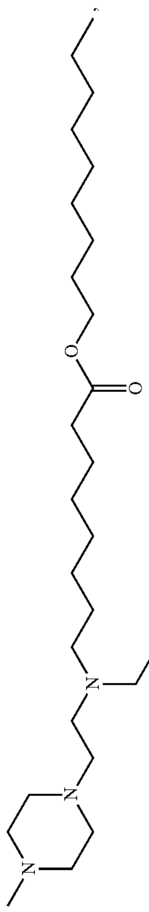
(Compound 101)
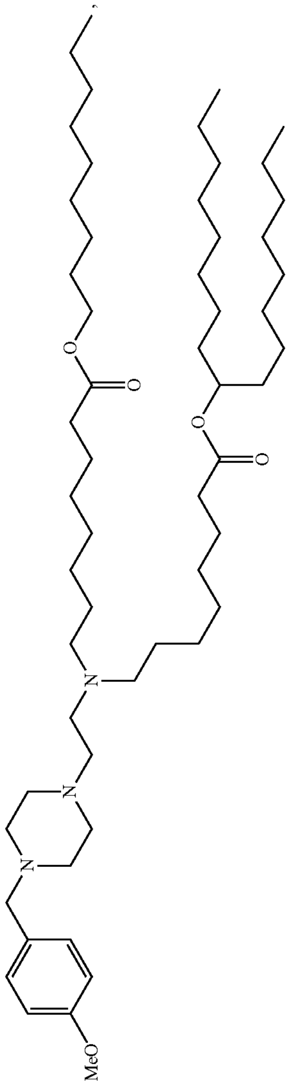
(Compound 102)

-continued
(Compound 103)
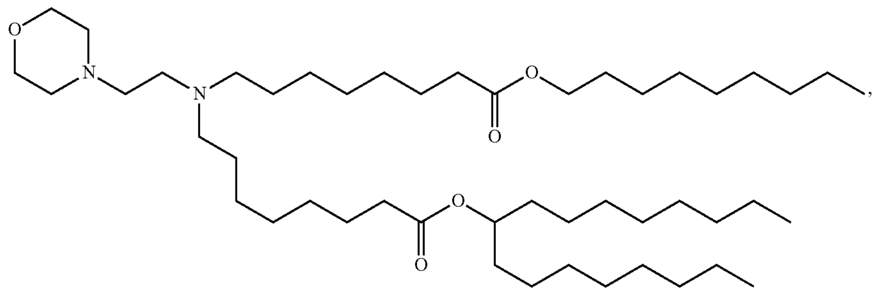
(Compound 104)
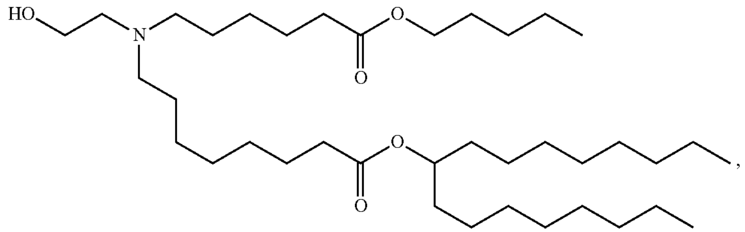
(Compound 105)
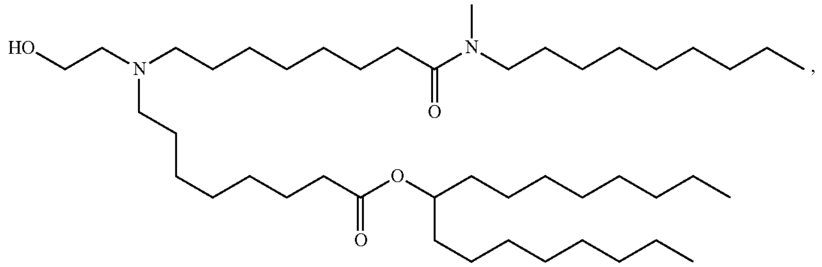
(Compound 106)
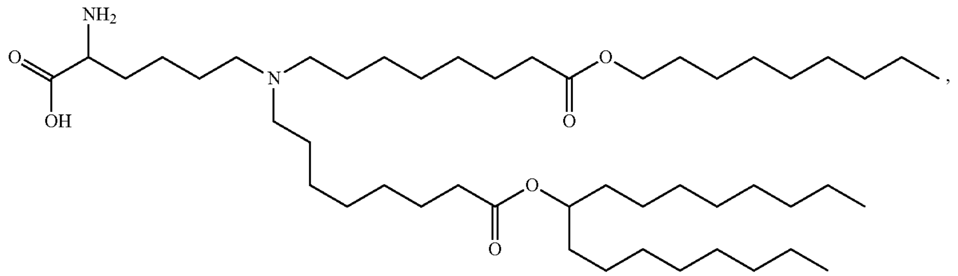

-continued
(Compound 107)
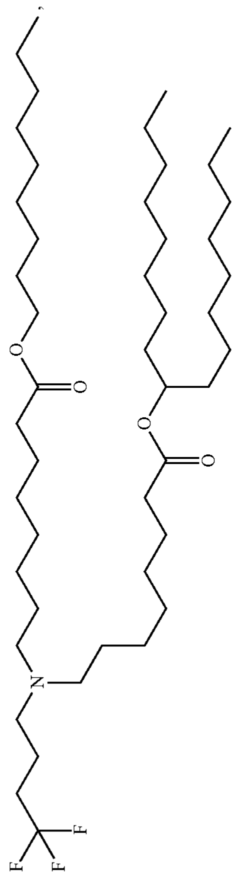
(Compound 108)
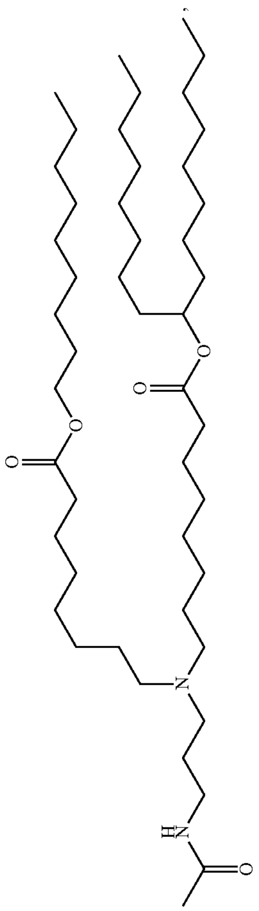
(Compound 109)
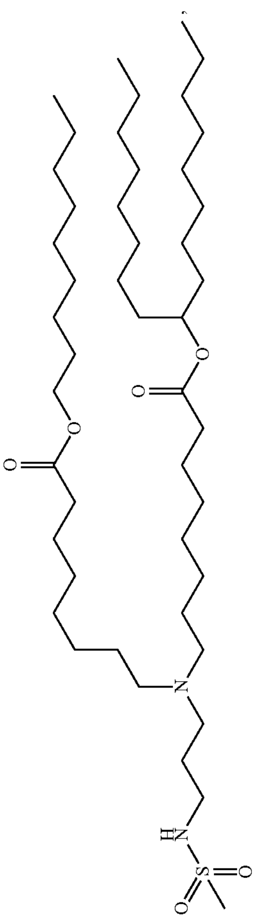
(Compound 110)
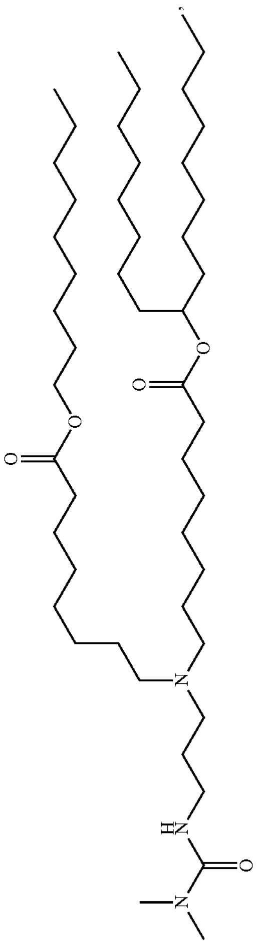

-continued
(Compound 111)
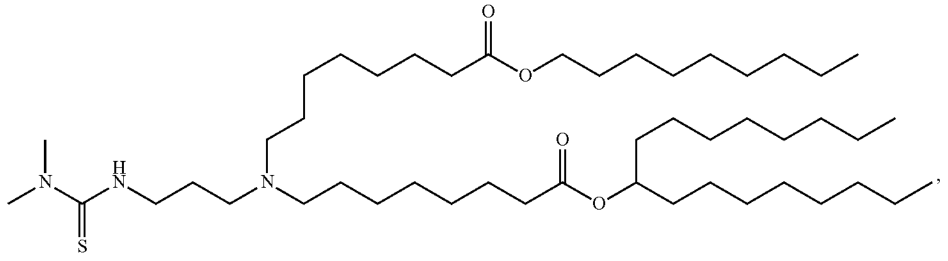
(Compound 112)
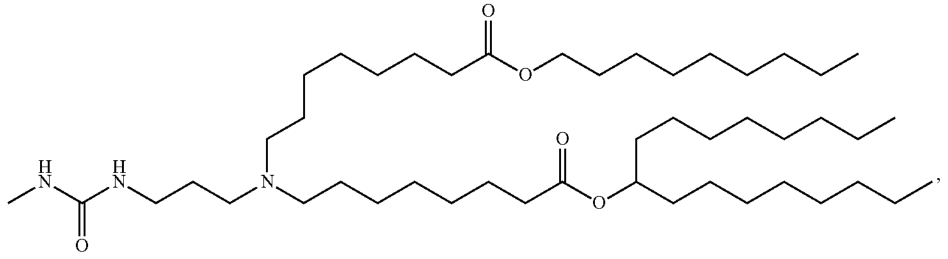
(Compound 113)
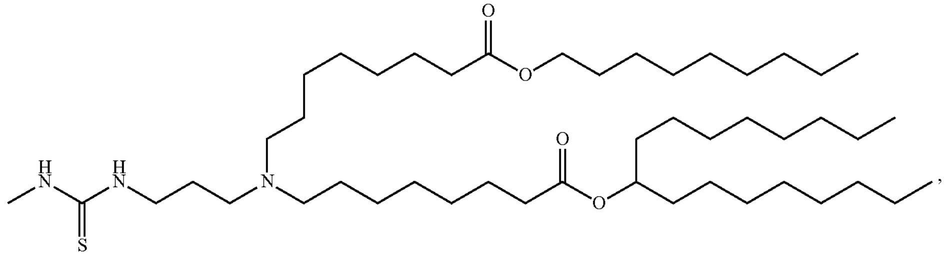
(Compound 114)
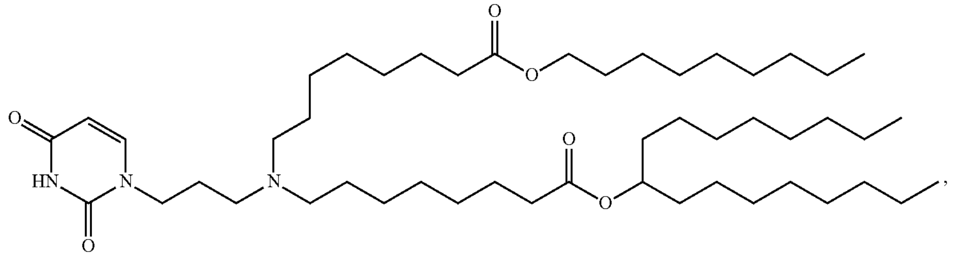

-continued
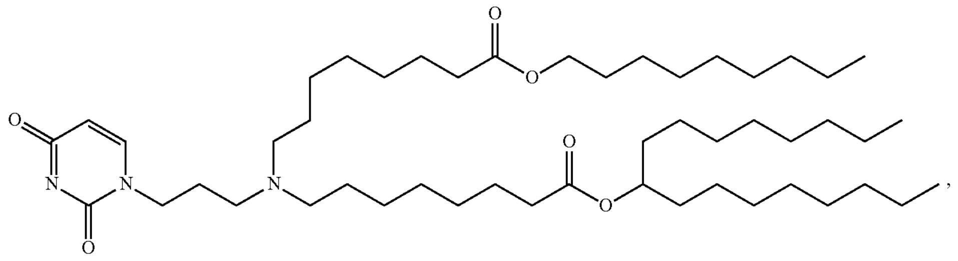
(Compound 115)
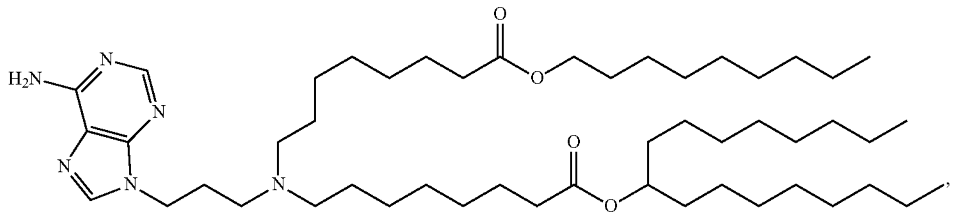
(Compound 116)
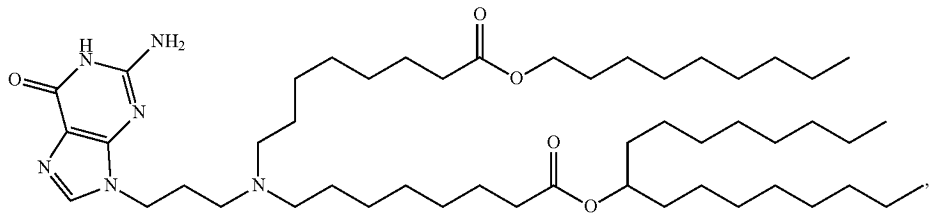
(Compound 117)
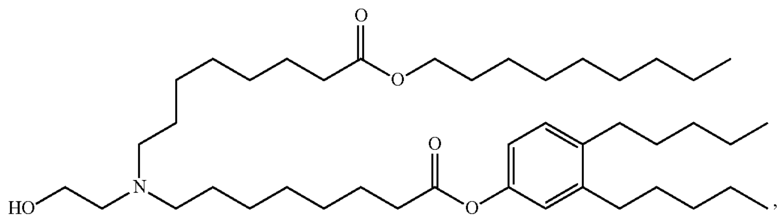
(Compound 118)

-continued
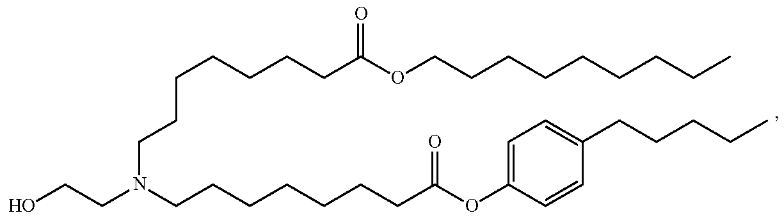
(Compound 119)
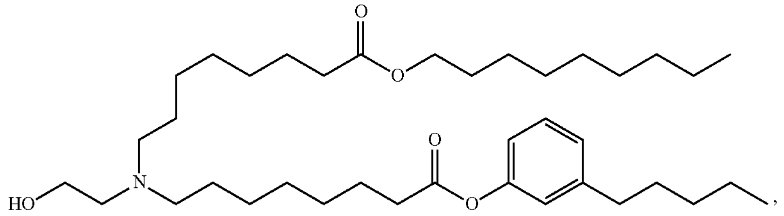
(Compound 120)
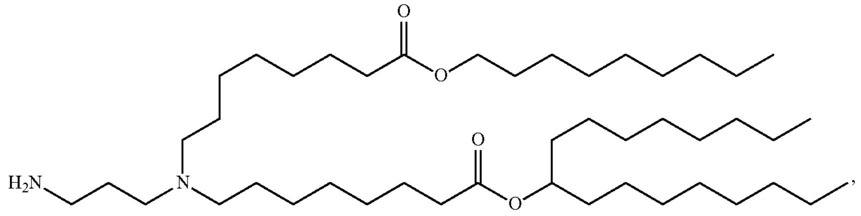
(Compound 121)
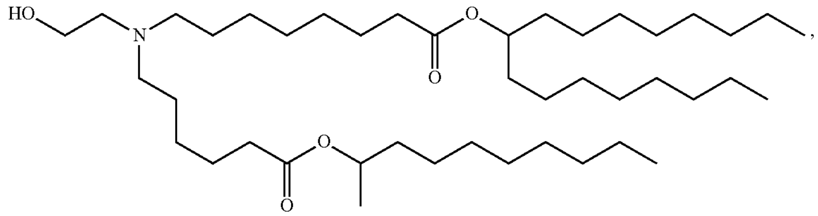
(Compound 122)

-continued
(Compound 123)
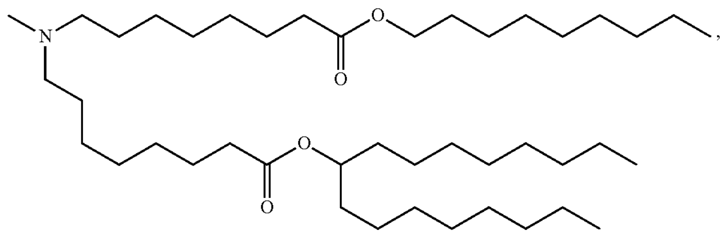
(Compound 124)
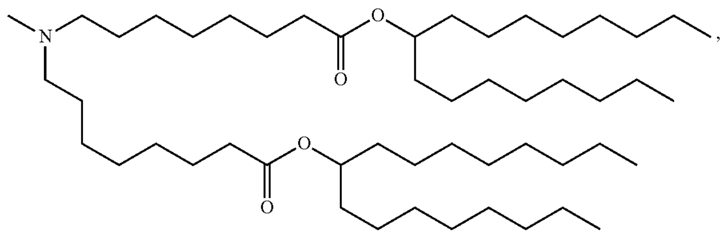
(Compound 125)
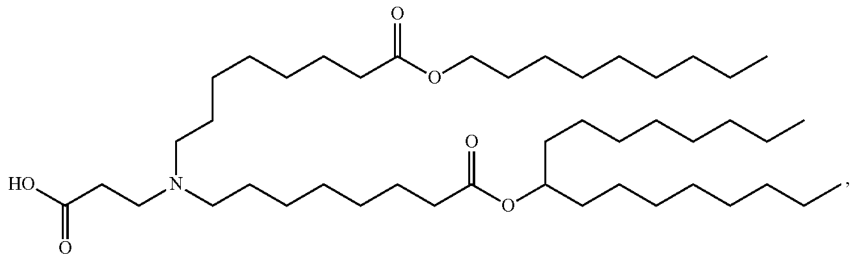
(Compound 126)
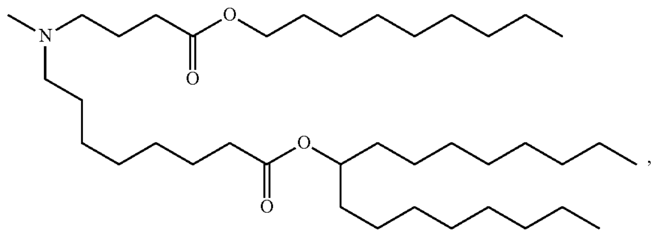

-continued
(Compound 127)
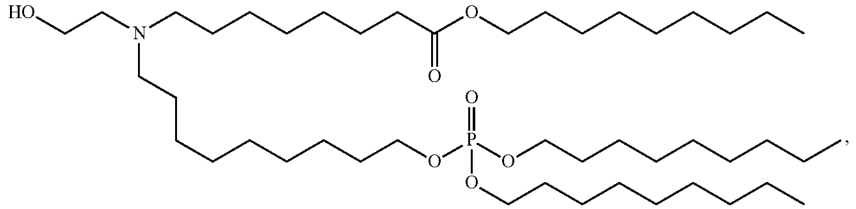
(Compound 128)
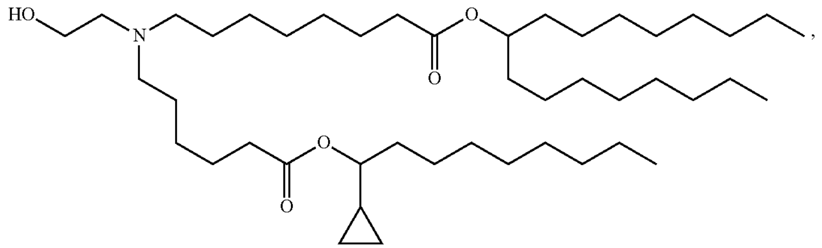
(Compound 129)
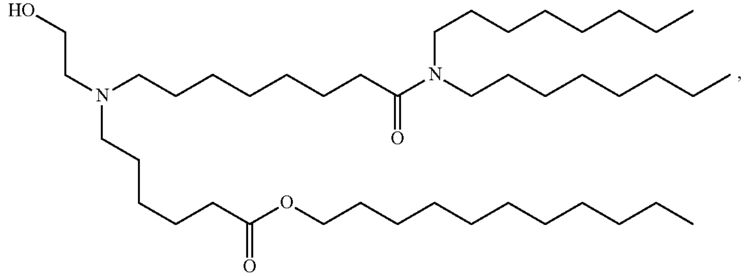
(Compound 130)
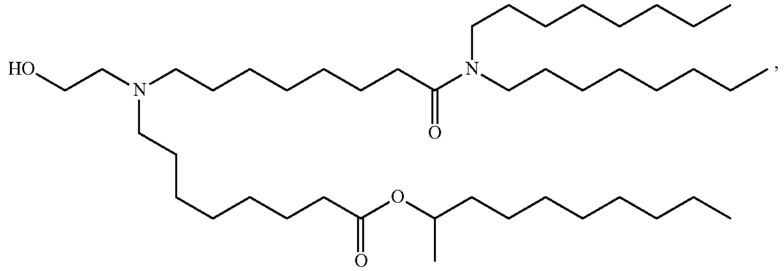
, -continued
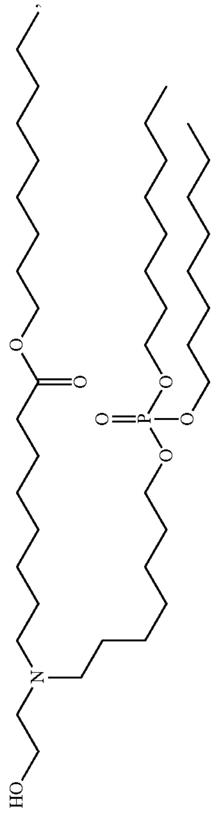
,
(Compound 131)
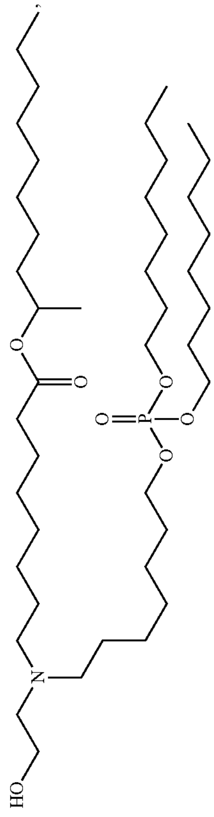
,
(Compound 132)
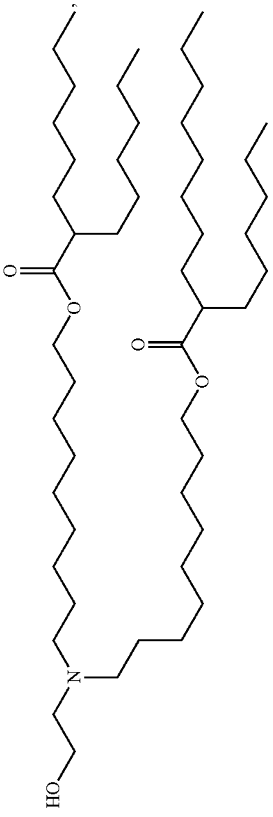
,
(Compound 133)
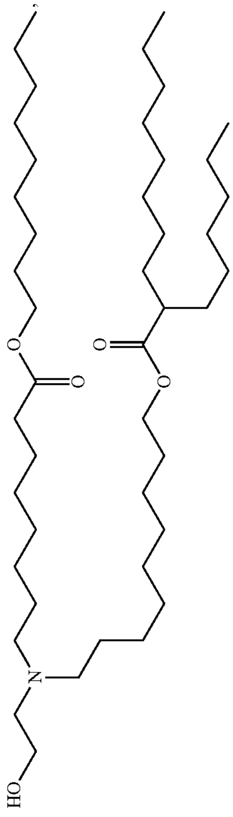
,
(Compound 134)

-continued
(Compound 135)
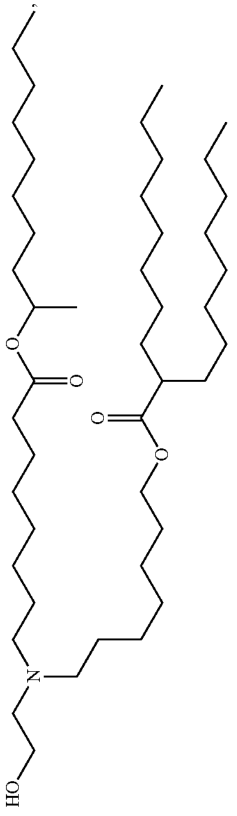
(Compound 136)
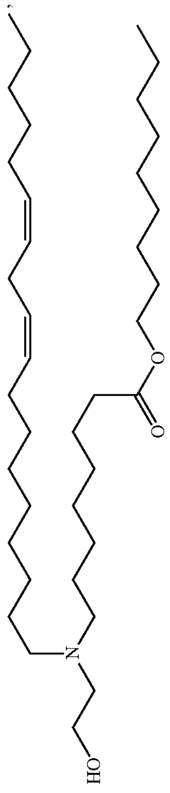
(Compound 137)
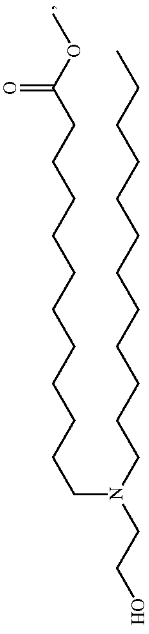
(Compound 138)
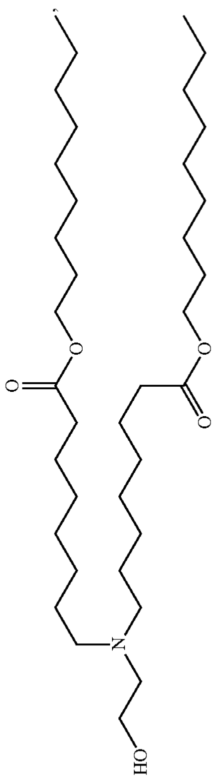
(Compound 139)
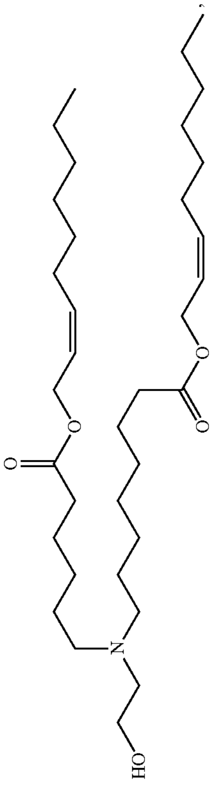

-continued
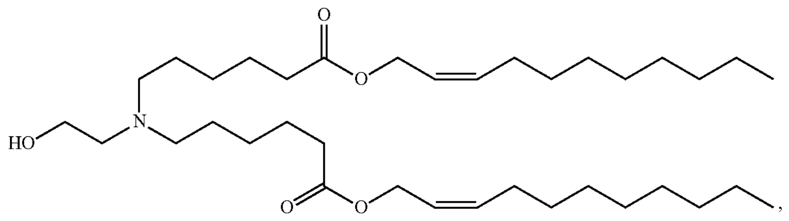
(Compound 140)
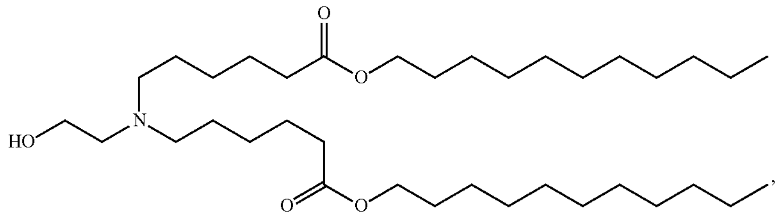
(Compound 141)
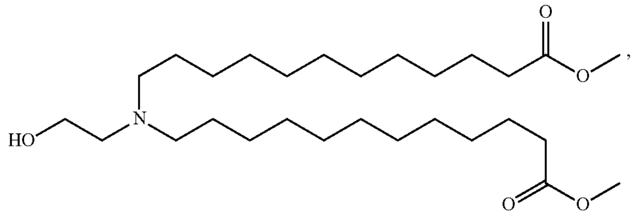
(Compound 142)
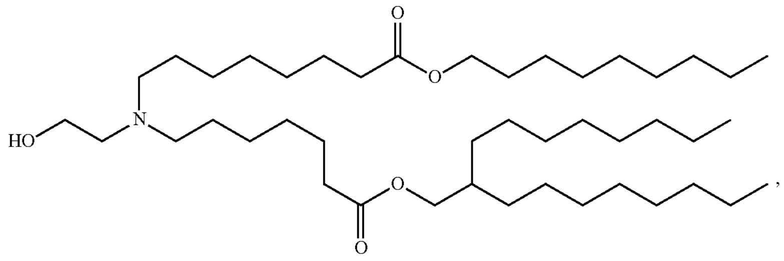
(Compound 143)

-continued
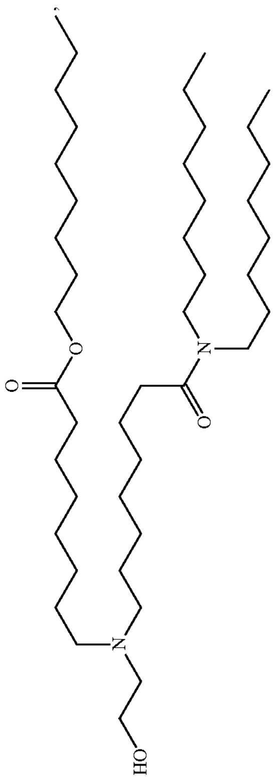
(Compound 144)
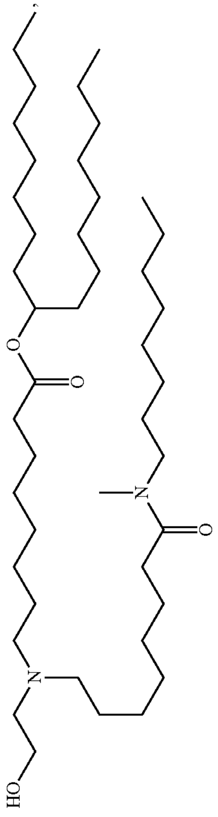
(Compound 145)
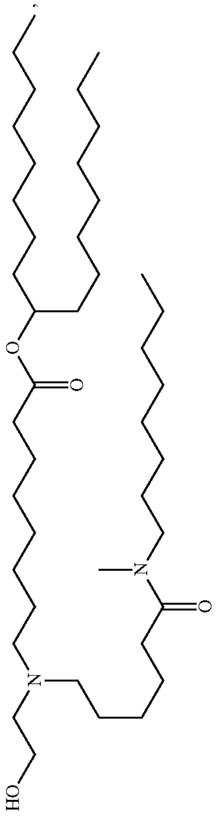
(Compound 146)
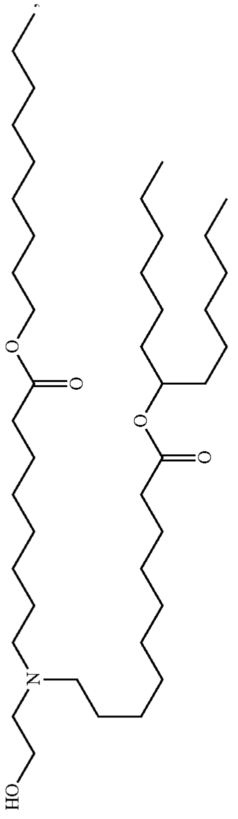
(Compound 147)

-continued
(Compound 148)
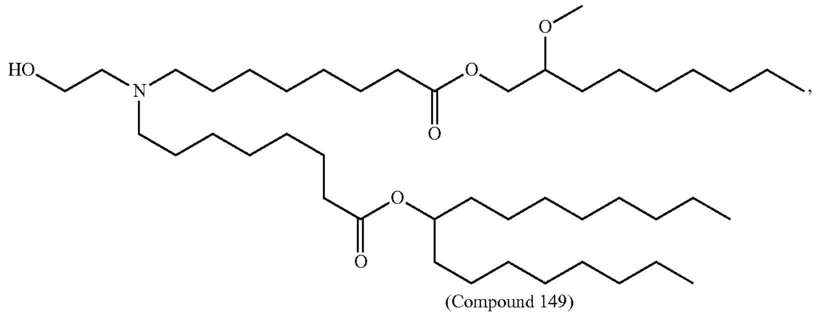
(Compound 149)
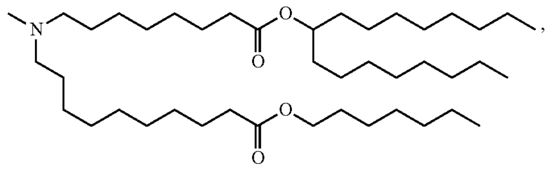
(Compound 150)
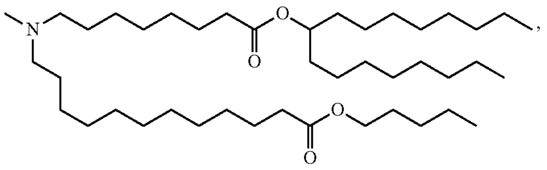
(Compound 151)
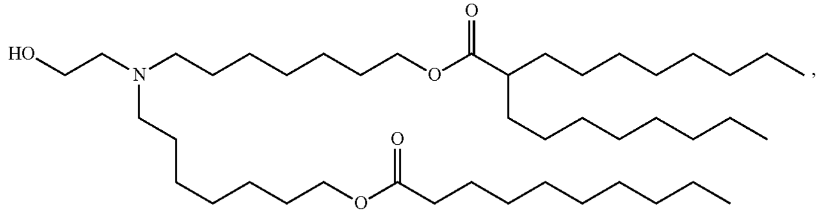
(Compound 152)
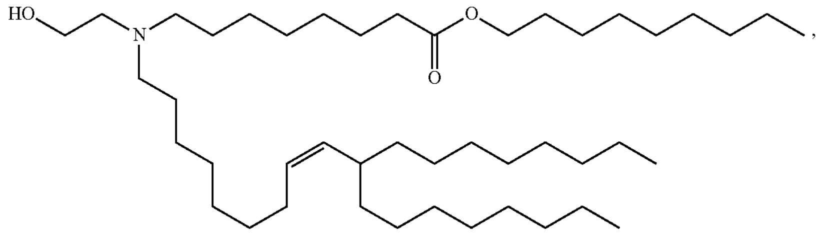

-continued
(Compound 153)
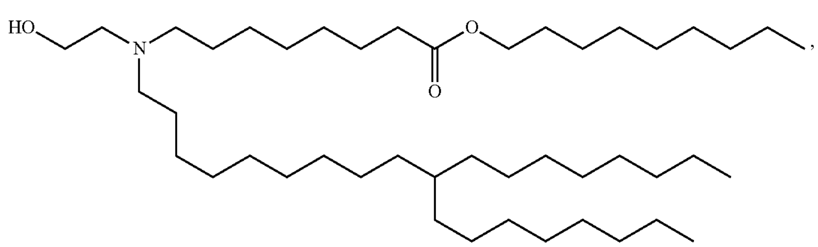,
(Compound 154)
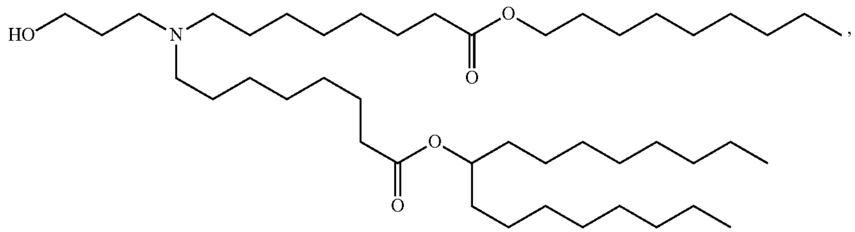,
(Compound 155)
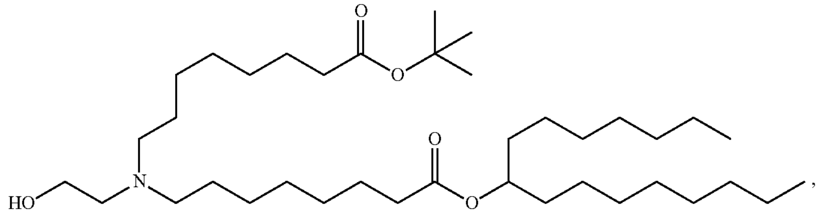,
(Compound 156)
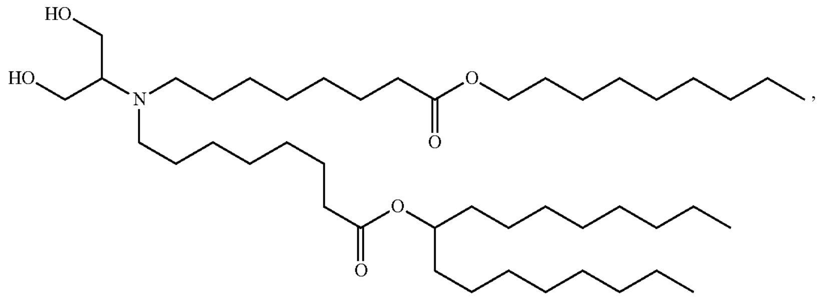, -continued
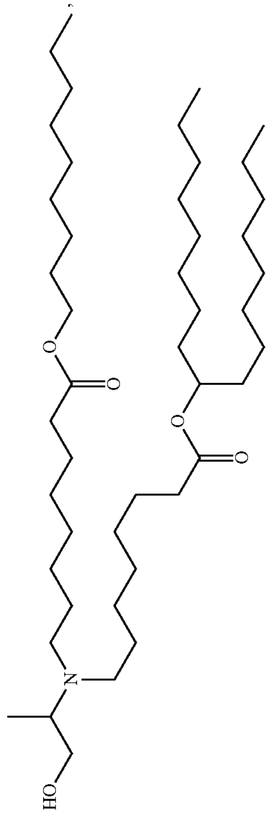
(Compound 157)
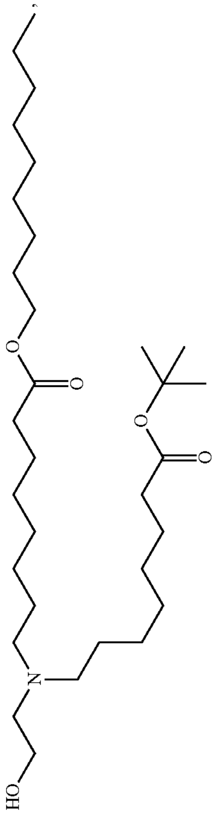
(Compound 158)
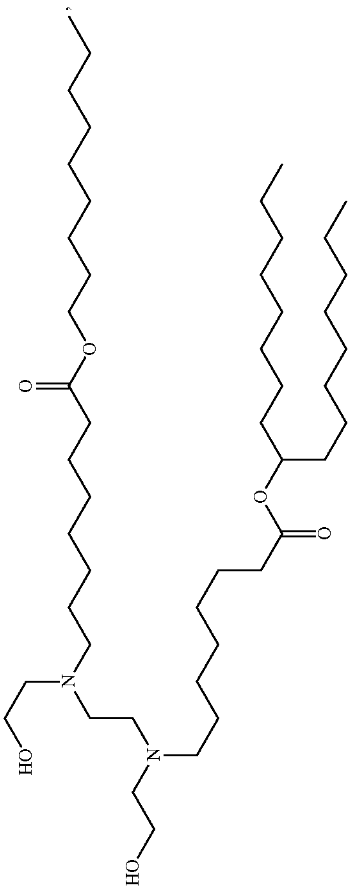
(Compound 159)

-continued
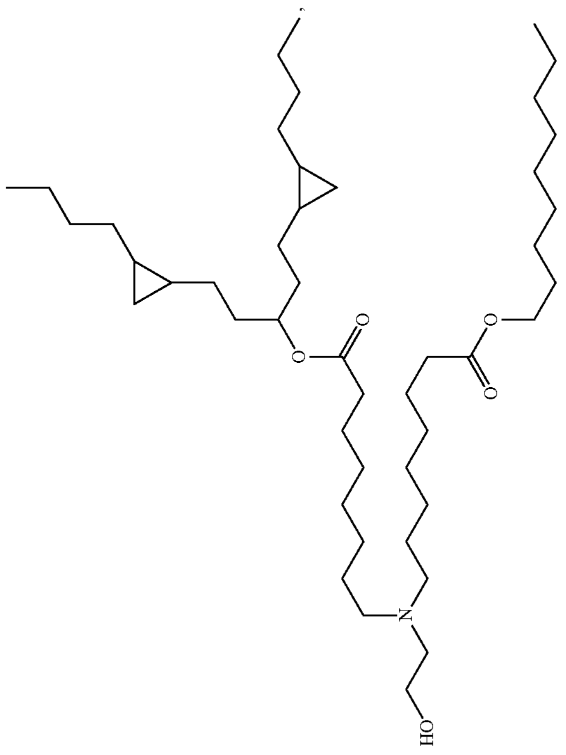
(Compound 160)
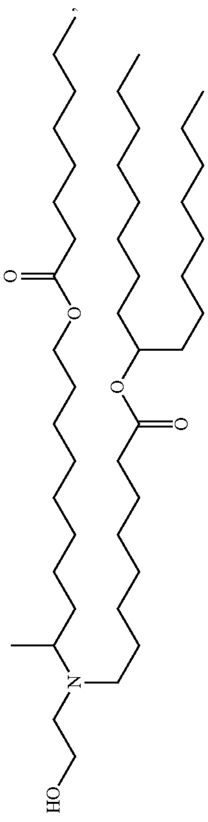
(Compound 161)
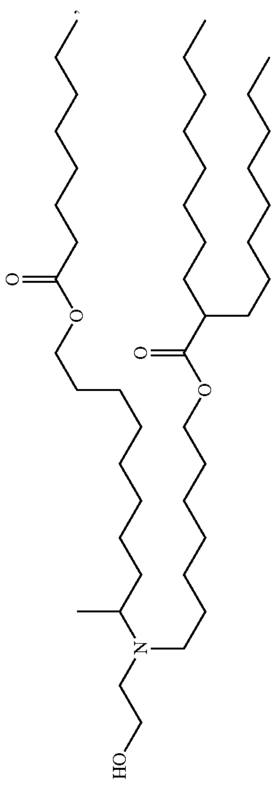
(Compound 162)

-continued
(Compound 163)
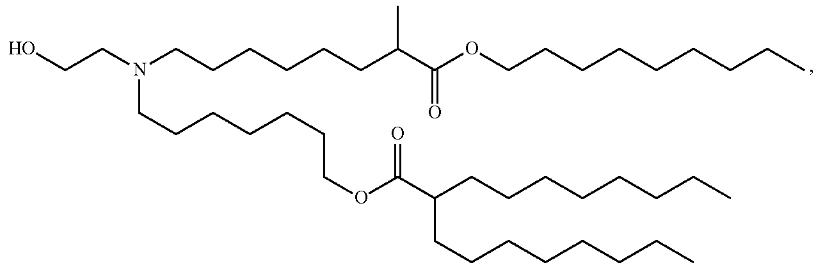
,
(Compound 164)
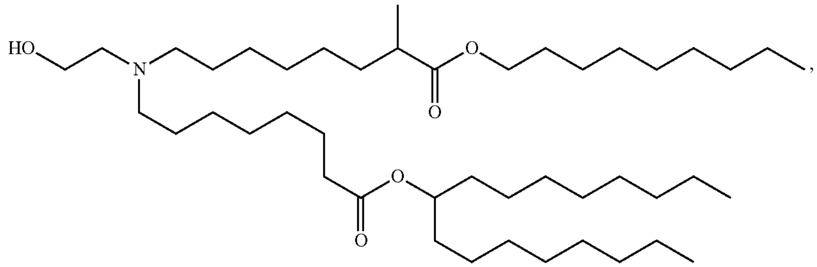
,
(Compound 165)
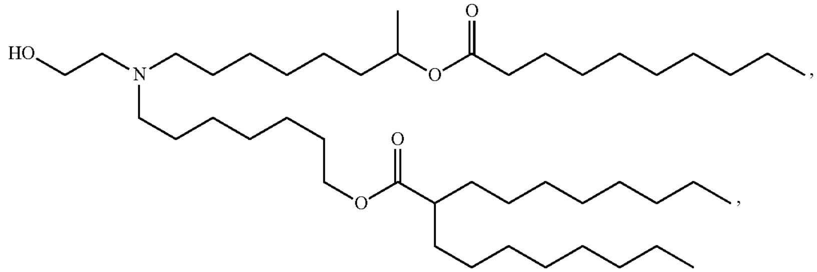
,
(Compound 166)
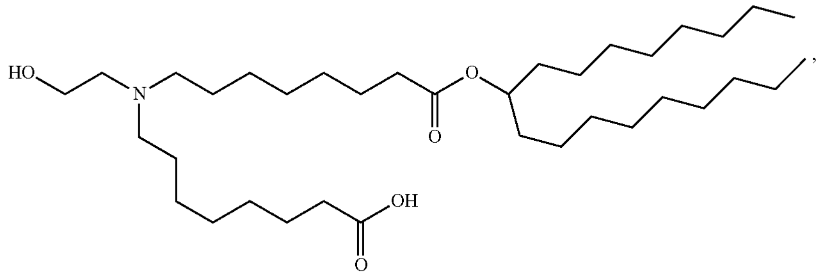
, -continued
(Compound 167)
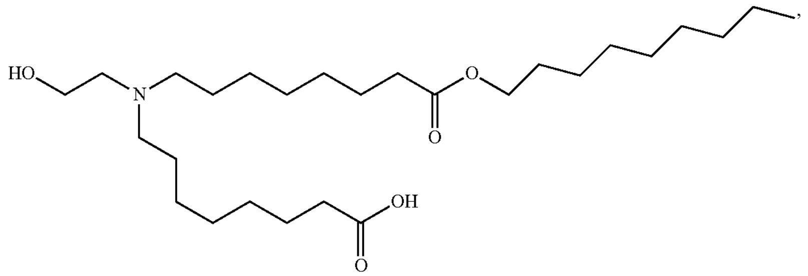
(Compound 168)
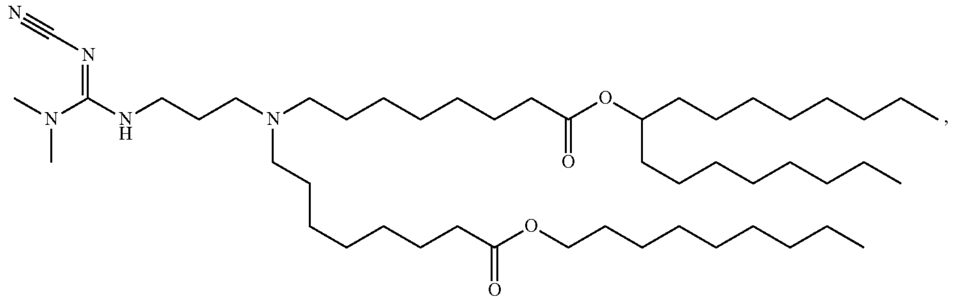
(Compound 169)
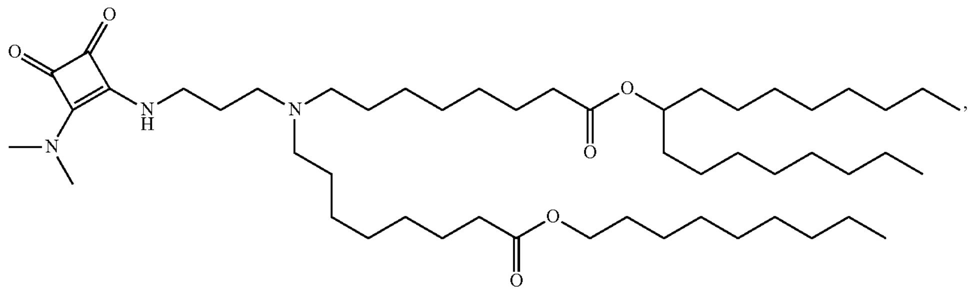

-continued
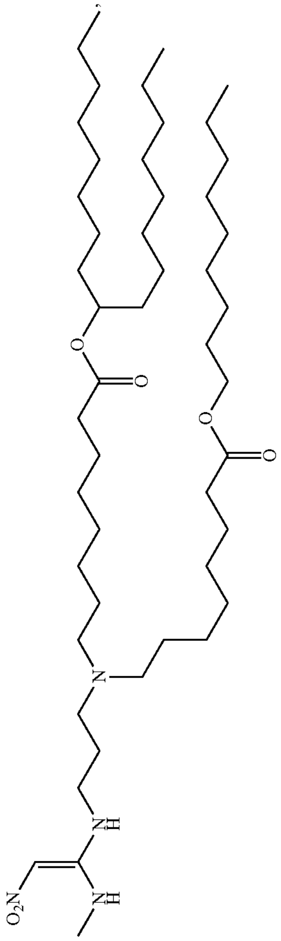
(Compound 170)
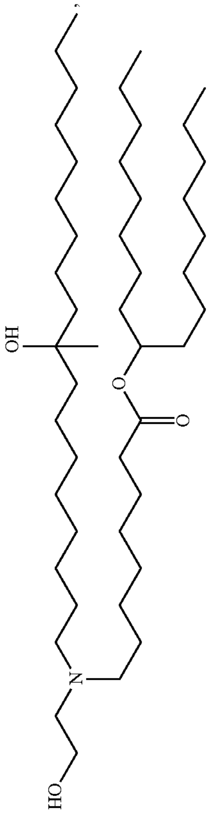
(Compound 171)
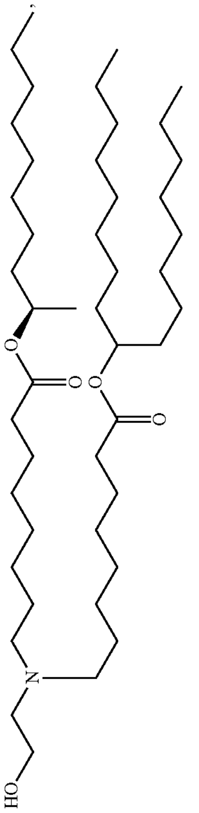
(Compound 172)
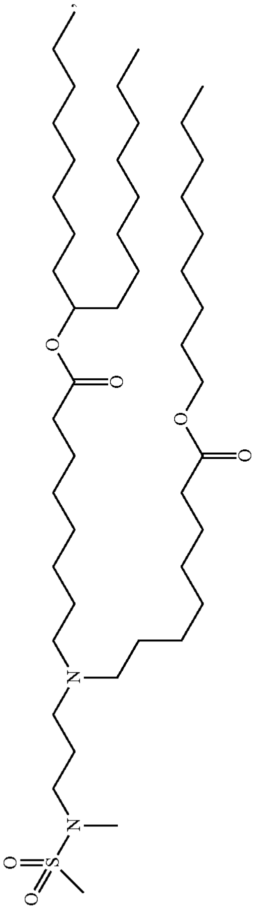
(Compound 173)

-continued
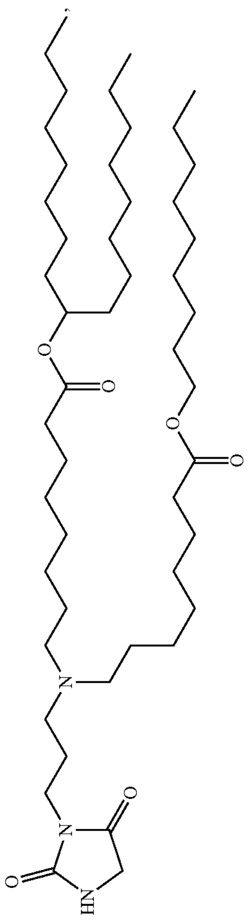
(Compound 174)
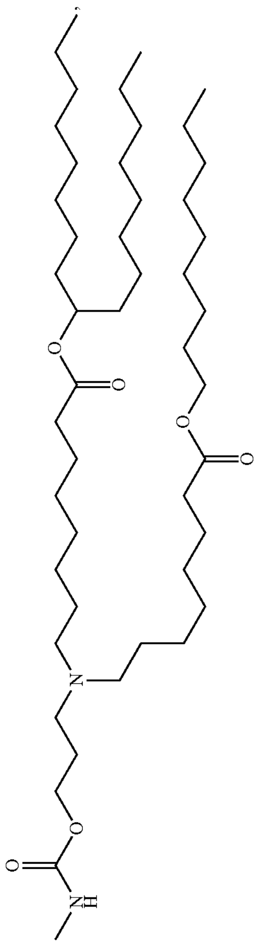
(Compound 175)
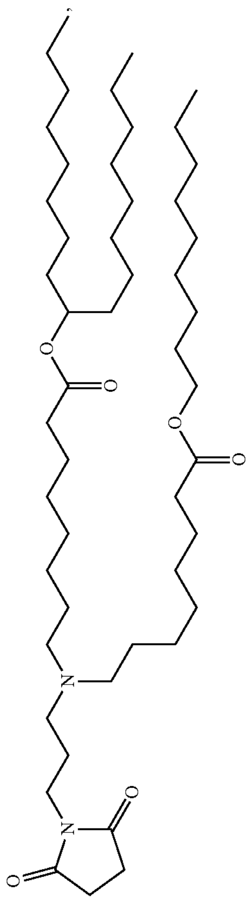
(Compound 176)
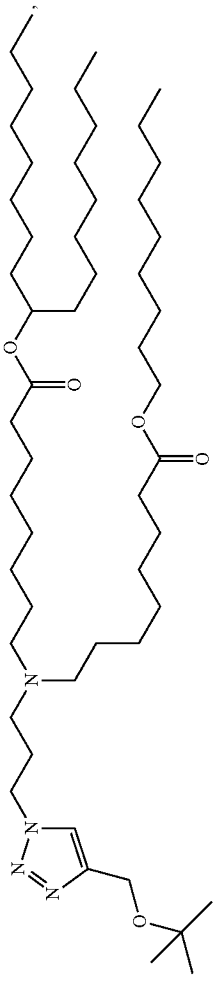
(Compound 177)

-continued
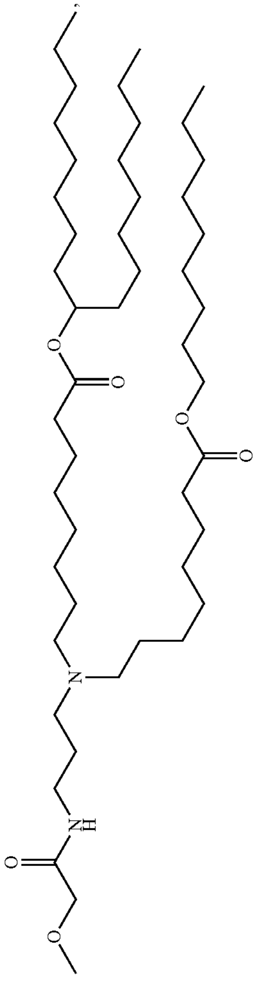
(Compound 178)
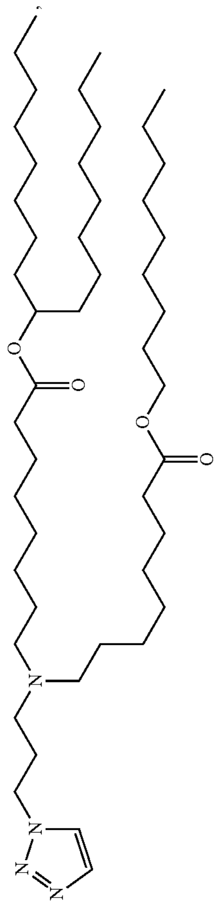
(Compound 179)
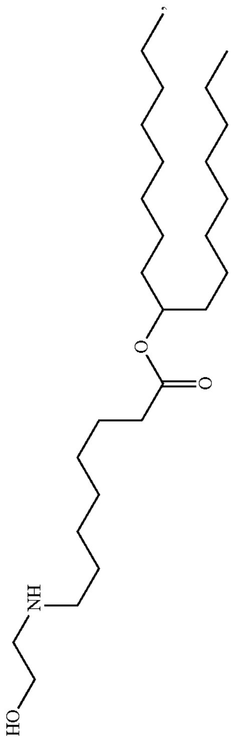
(Compound 180)
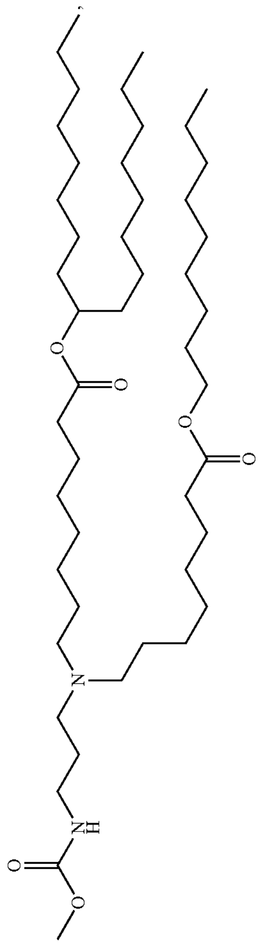
(Compound 181)

-continued
(Compound 182)
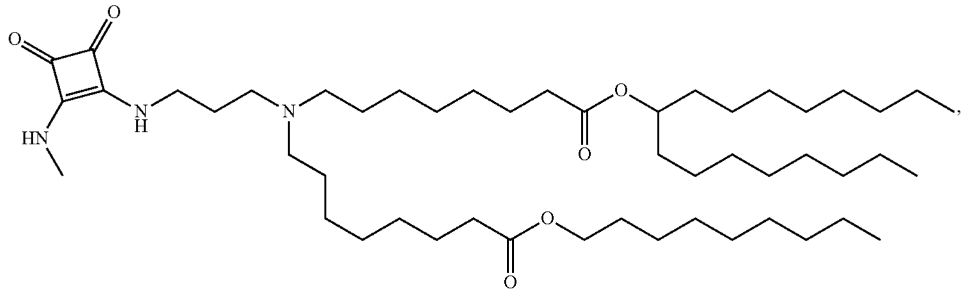
(Compound 183)
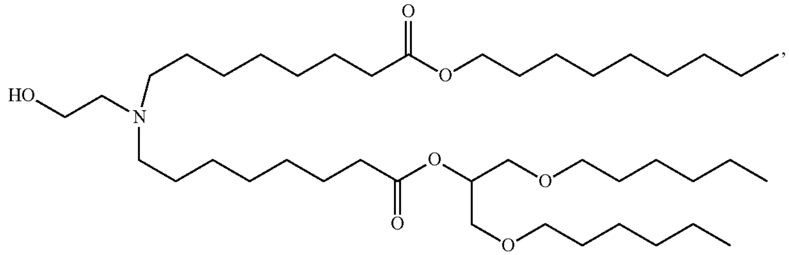
(Compound 184)
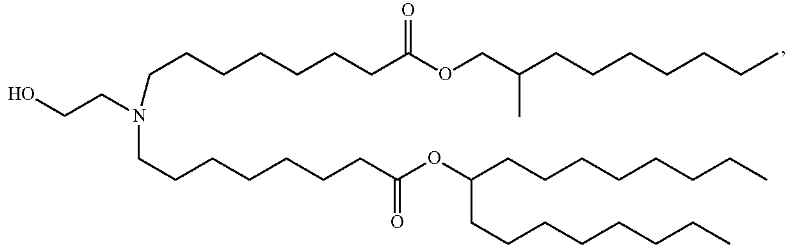
(Compound 185)
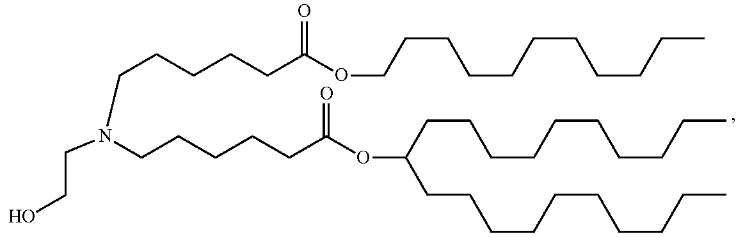

-continued
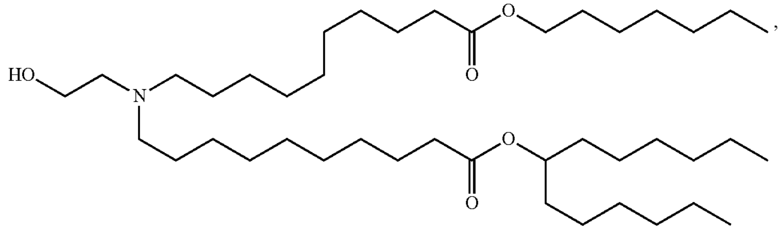
(Compound 186)
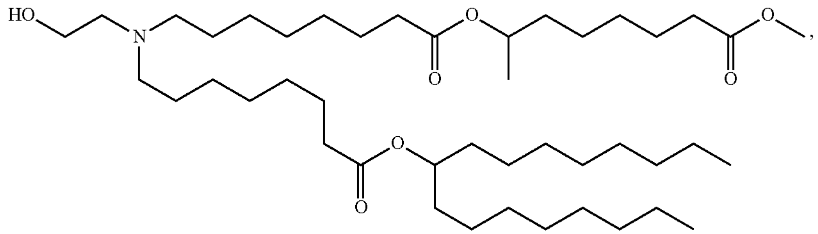
(Compound 187)
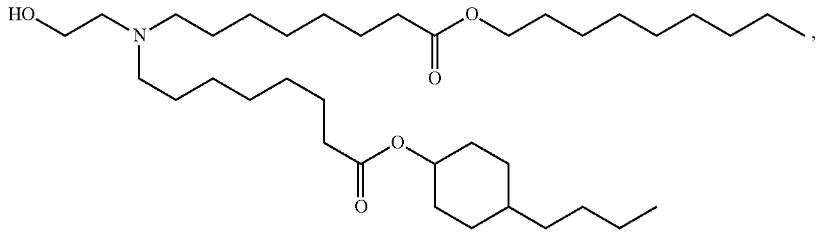
(Compound 188)
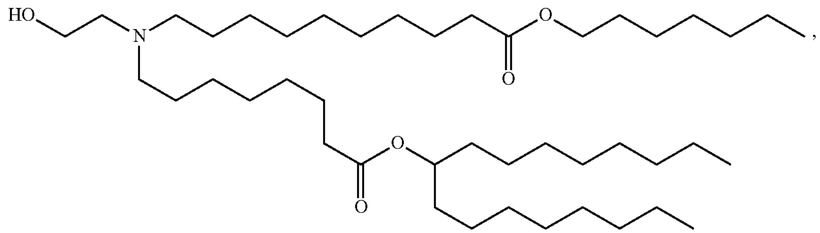
(Compound 189)

-continued
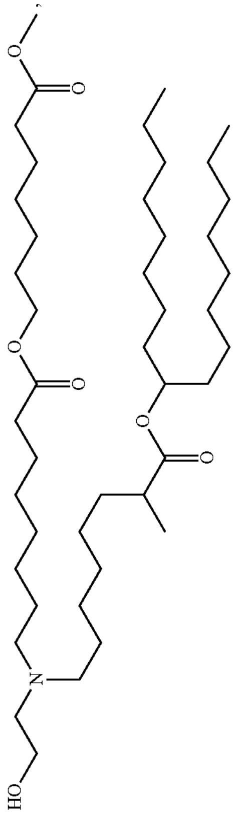
(Compound 190)
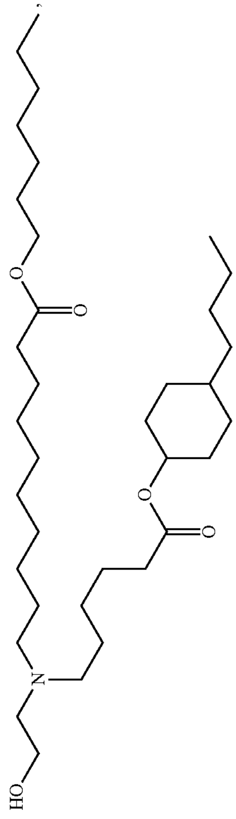
(Compound 191)
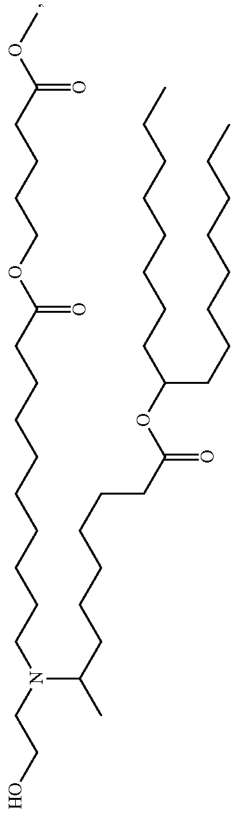
(Compound 192)
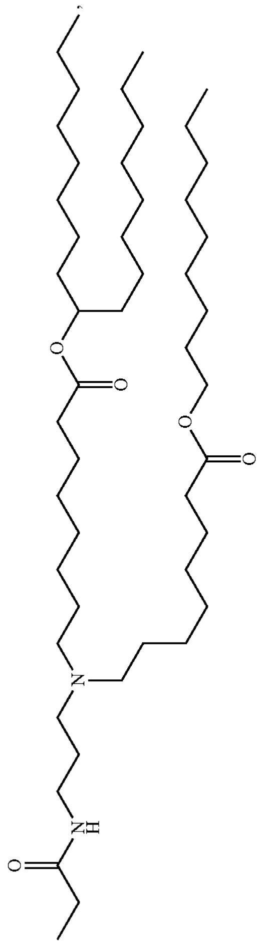
(Compound 193)

-continued
(Compound 194)
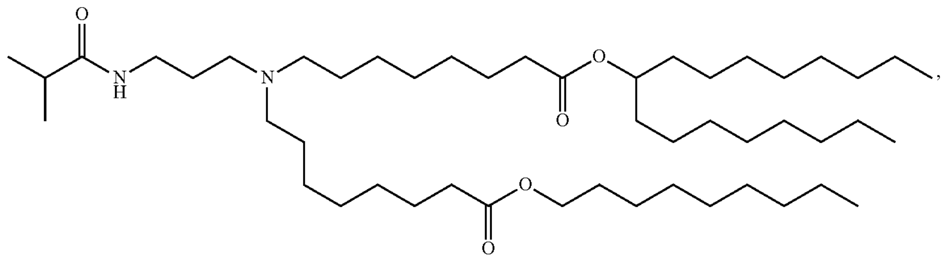
(Compound 195)
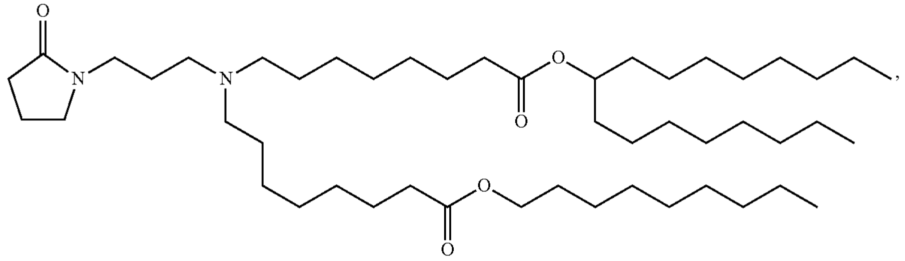
(Compound 196)
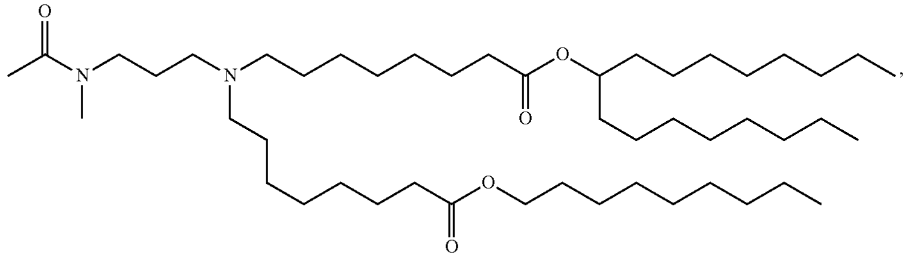
(Compound 197)
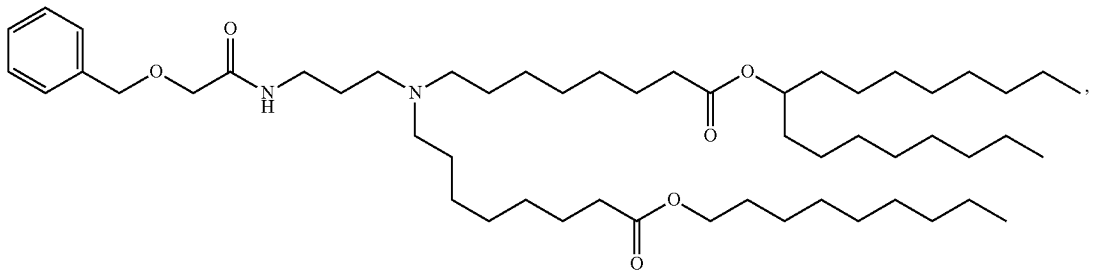

-continued
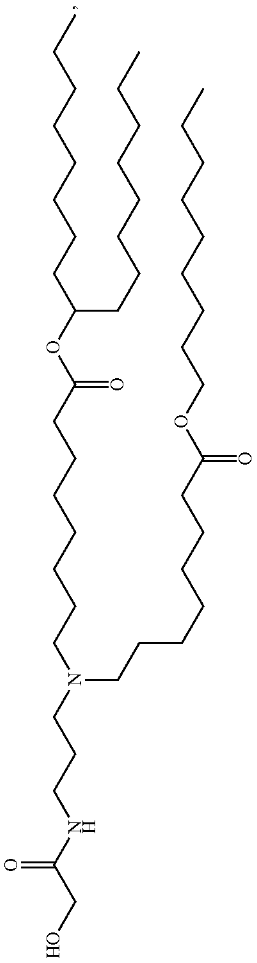
(Compound 198)
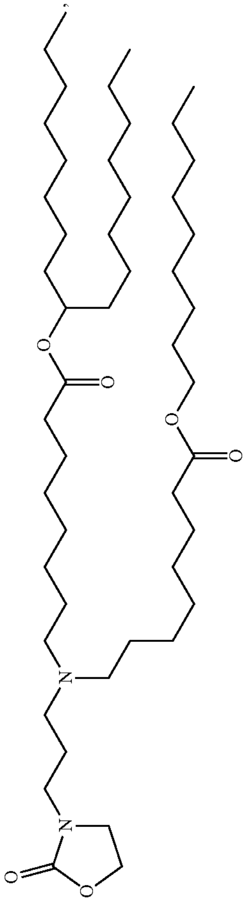
(Compound 199)
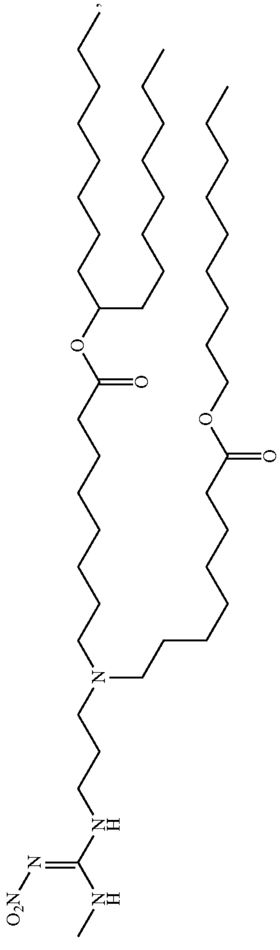
(Compound 200)
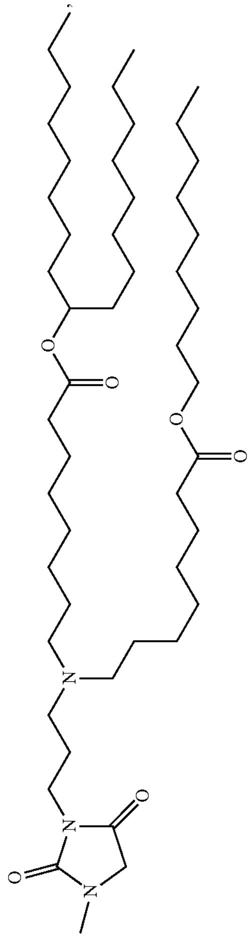
(Compound 201)

-continued
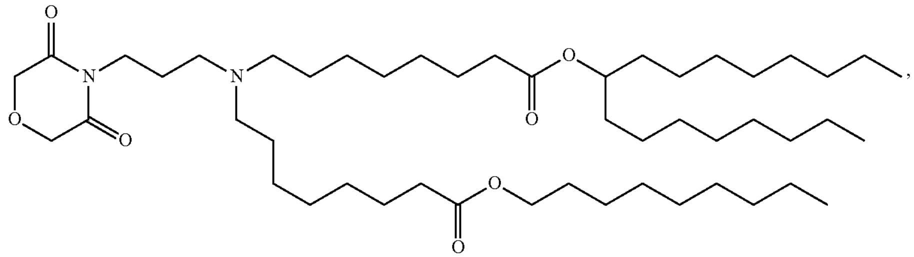,
(Compound 202)
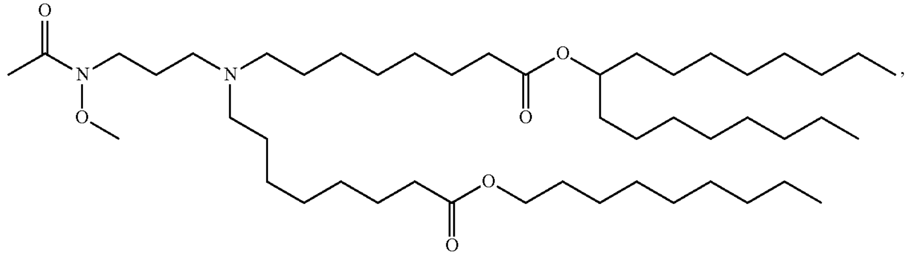,
(Compound 203)
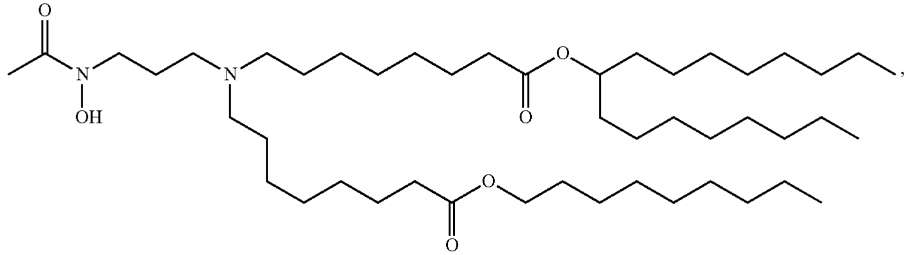,
(Compound 204)
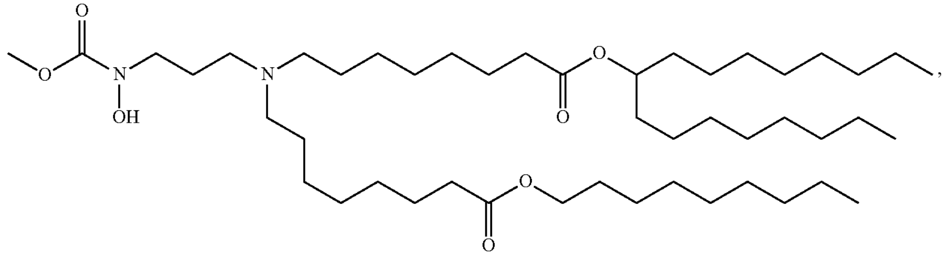,
(Compound 205)

-continued
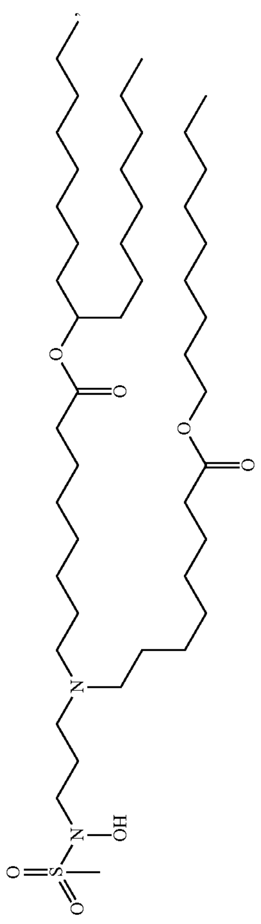
(Compound 206)
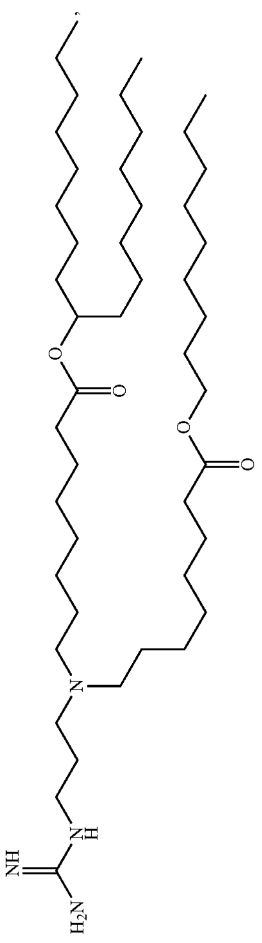
(Compound 207)
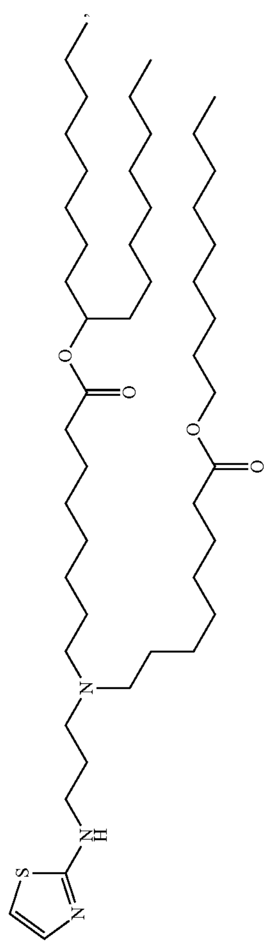
(Compound 208)
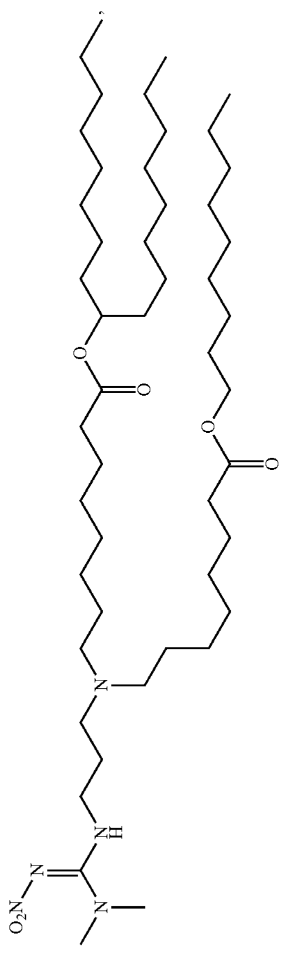
(Compound 209)

-continued
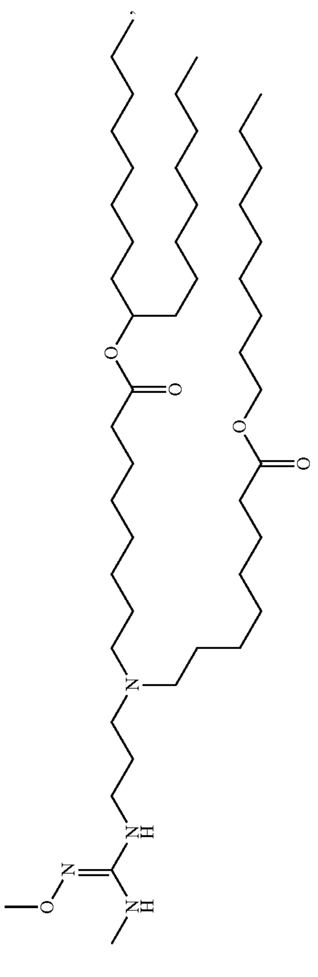
(Compound 210)
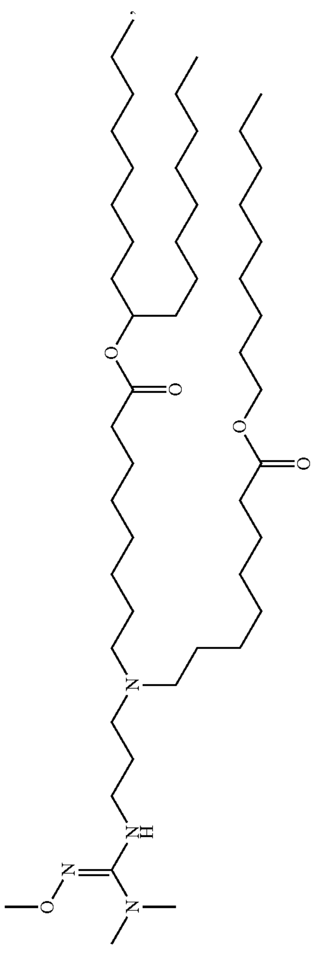
(Compound 211)
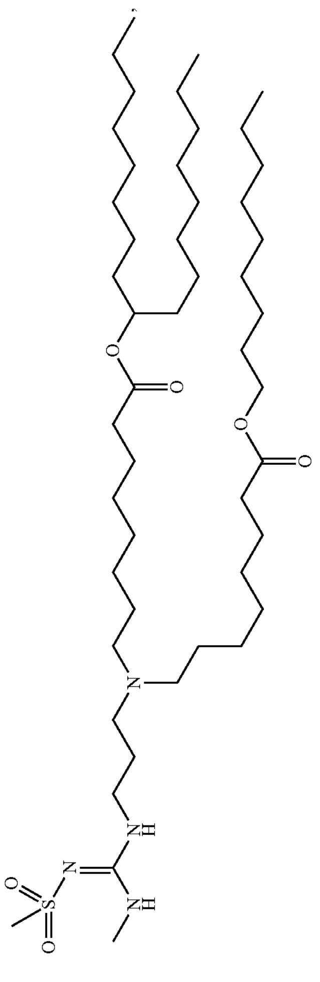
(Compound 212)

-continued
(Compound 213)
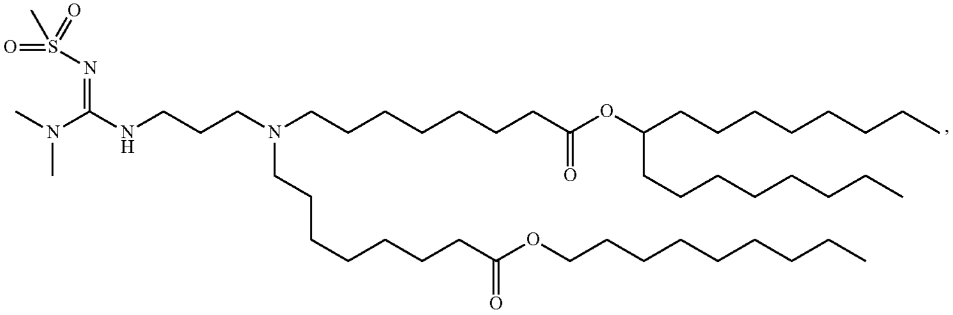
(Compound 214)
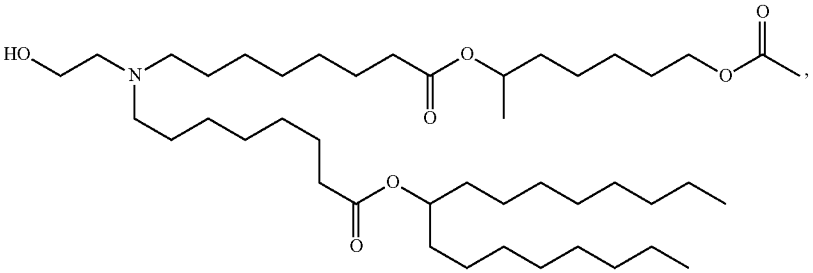
(Compound 215)
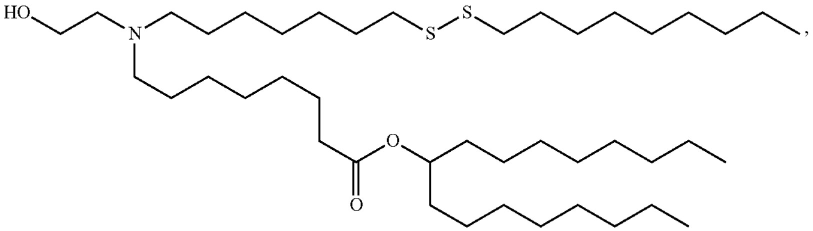
(Compound 216)
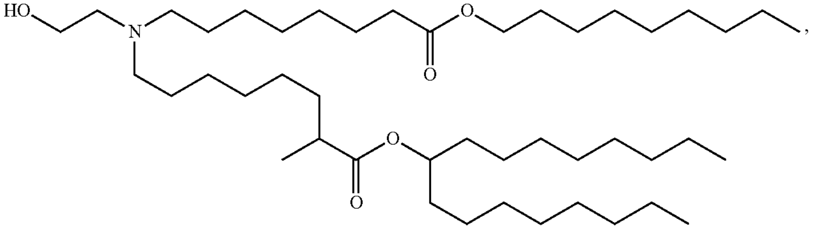

-continued
(Compound 217)
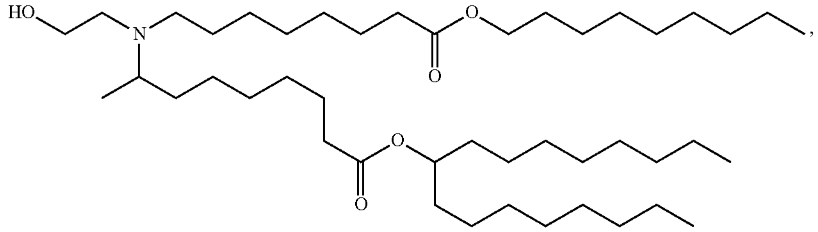
(Compound 218)
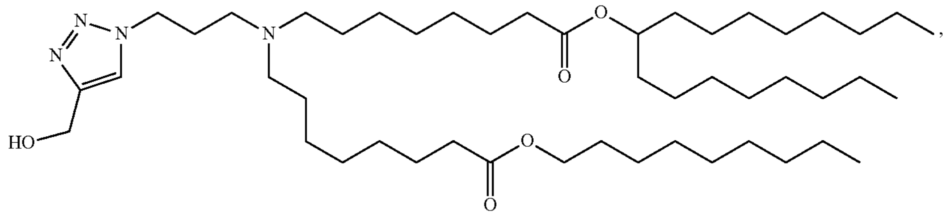
(Compound 219)
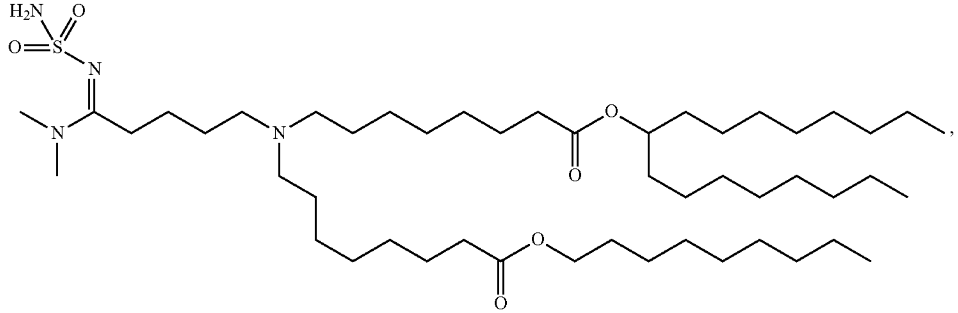
(Compound 220)
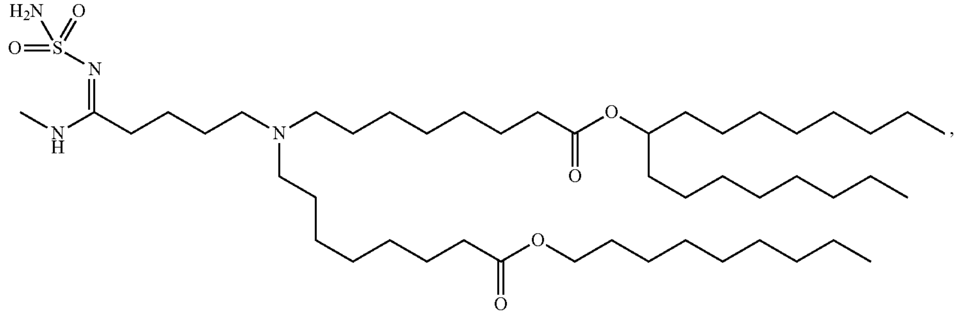

-continued
(Compound 221)
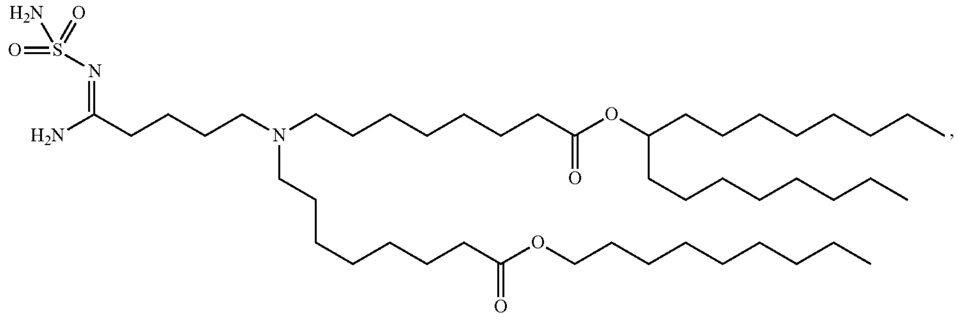
(Compound 222)
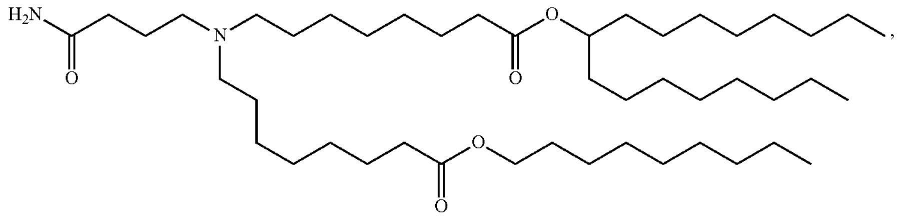
(Compound 223)
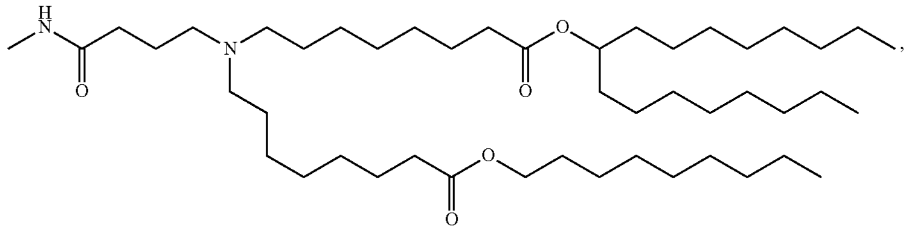
(Compound 224)
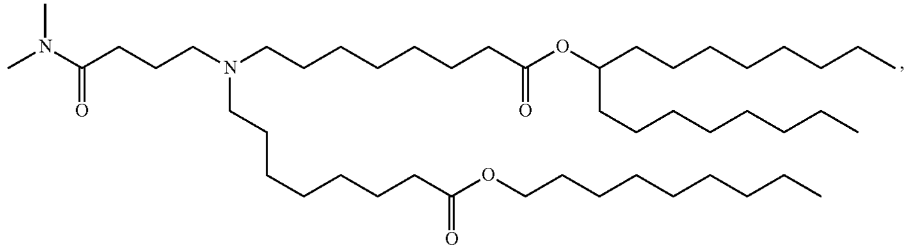

-continued
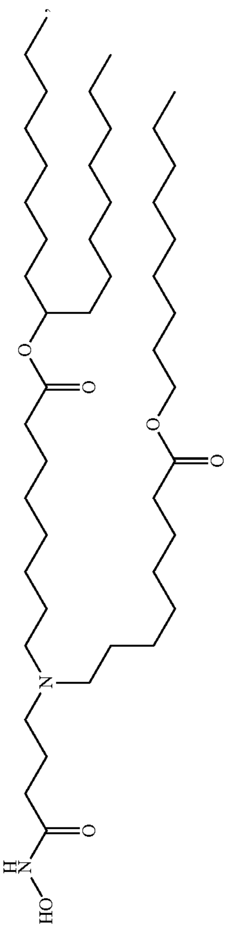
(Compound 225)
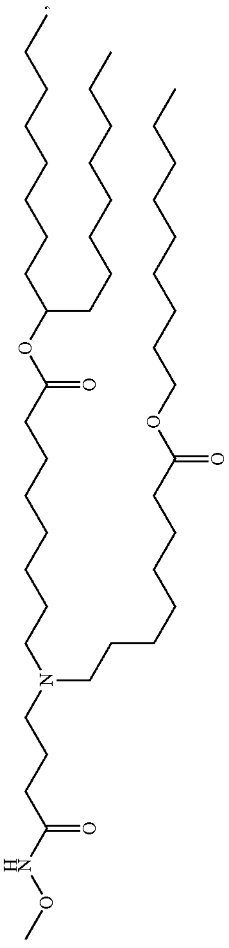
(Compound 226)
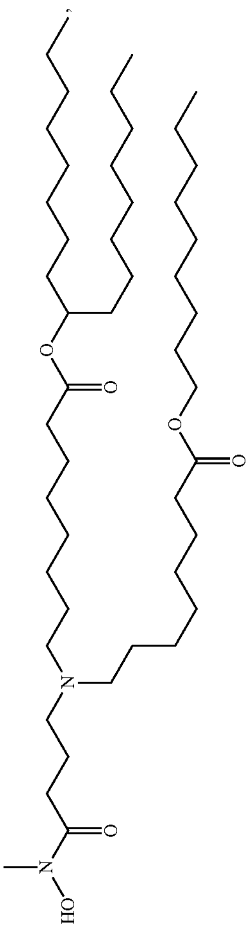
(Compound 227)
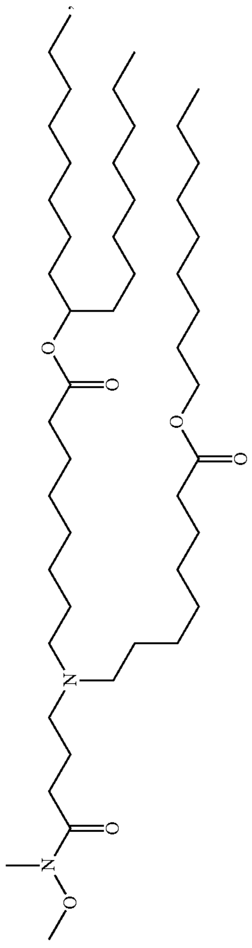
(Compound 228)

-continued
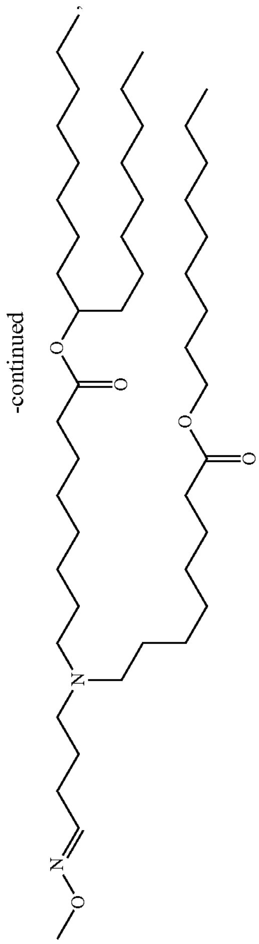
(Compound 229)
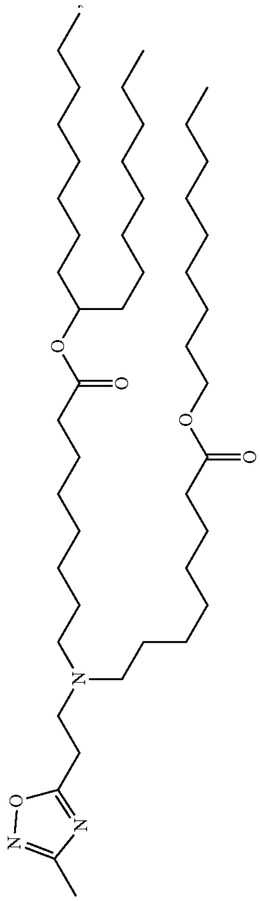
(Compound 230)
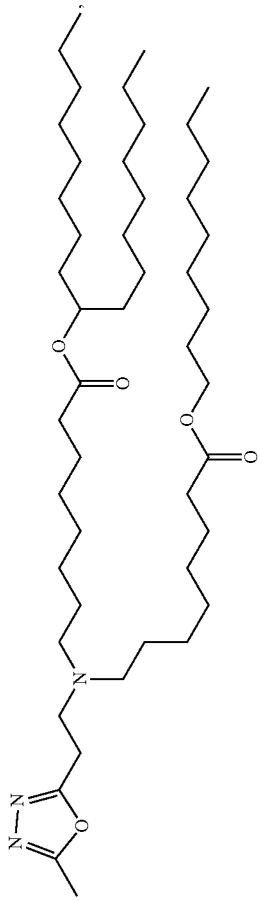
(Compound 231)
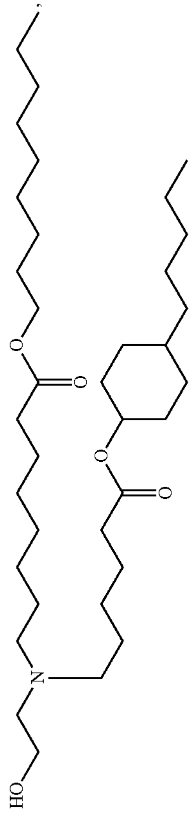
(Compound 232)

and salts and isomers thereof.

In some embodiments, a nanoparticle comprises the following compound:

(Compound 233)

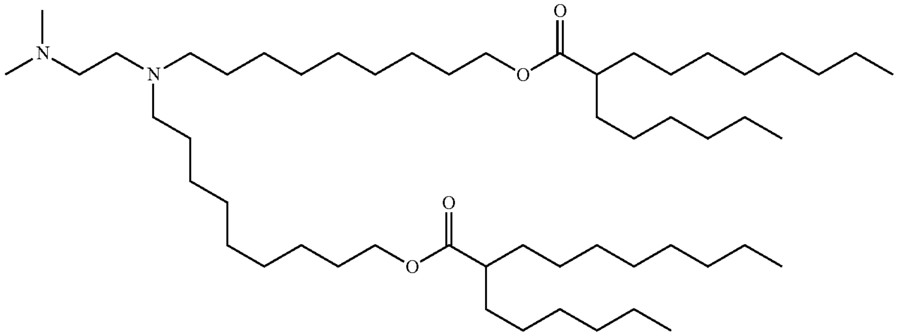

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, the disclosure features a pharmaceutical composition comprising a nanoparticle composition according to the preceding embodiments and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In some embodiments, the disclosure provides a method of delivering a therapeutic and/or prophylactic (e.g., RNA, such as mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In some embodiments, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In some embodiments, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In some embodiments, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In some embodiments, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId)

or (IIe) and methods of making a nanoparticle composition including a lipid component comprising the compound of Formula (I), (IA), (II), (IIa), (IIb), (IIc), (IId) or (IIe).

Modes of Vaccine Administration

HSV RNA (e.g., mRNA) vaccines may be administered by any route which results in a therapeutically effective outcome. These include, but are not limited, to intradermal, intramuscular, and/or subcutaneous administration. The present disclosure provides methods comprising administering RNA (e.g., mRNA) vaccines to a subject in need thereof. The exact amount required will vary from subject to subject, depending on the species, age, and general condition of the subject, the severity of the disease, the particular composition, its mode of administration, its mode of activity, and the like. HSV RNA (e.g., mRNA) vaccines compositions are typically formulated in dosage unit form for ease of administration and uniformity of dosage. It will be understood, however, that the total daily usage of HSV RNA (e.g., mRNA) vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, HSV RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013/078199, herein incorporated by reference in its entirety). The desired dosage may be delivered three times a day, two times a day, once a day, every other day, every third day, every week, every two weeks, every three weeks, every four weeks, every 2 months, every 3 months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, HSV RNA (e.g., mRNA) vaccine compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg, or about 0.005 mg/kg.

In some embodiments, HSV RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, HSV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a HSV RNA (e.g., mRNA) vaccine composition may be administered three or four times.

In some embodiments, HSV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg, or 0.400 mg.

In some embodiments, the RNA (e.g., mRNA) vaccine for use in a method of vaccinating a subject is administered the subject a single dosage of between 10 μg/kg and 400 μg/kg of the nucleic acid vaccine in an effective amount to vaccinate the subject. In some embodiments, the RNA (e.g., mRNA) vaccine for use in a method of vaccinating a subject is administered to the subject via a single dosage of between 10 μg and 400 μg of the nucleic acid vaccine in an effective amount to vaccinate the subject.

A RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

HSV RNA (e.g., mRNA) Vaccine Formulations and Methods of Use

Some aspects of the present disclosure provide formulations of the HSV RNA (e.g., mRNA) vaccine, wherein the HSV RNA vaccine is formulated in an effective amount to produce an antigen specific immune response in a subject (e.g., production of antibodies specific to an anti-HSV antigenic polypeptide). "An effective amount" is a dose of a HSV RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-HSV antigenic polypeptide antibody titer produced in a subject administered a HSV RNA (e.g., mRNA) vaccine as provided herein. An antibody titer is a measurement of the amount of antibodies within a subject, for example, antibodies that are specific to a particular antigen (e.g., an anti-HSV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the HSV RNA (e.g., mRNA) vaccine.

In some embodiments, an anti-HSV antigenic polypeptide antibody titer produced in a subject is increased by at least 1 log relative to a control. For example, anti-HSV antigenic polypeptide antibody titer produced in a subject may be increased by at least 1.5, at least 2, at least 2.5, or at least 3 log relative to a control. In some embodiments, the anti-HSV antigenic polypeptide antibody titer produced in the subject is increased by 1, 1.5, 2, 2.5 or 3 log relative to a control. In some embodiments, the anti-HSV antigenic polypeptide antibody titer produced in the subject is increased by 1-3 log relative to a control. For example, the anti-HSV antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-HSV antigenic polypeptide antibody titer produced in a subject is increased at least 2 times relative to a control. For example, the anti-HSV antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-HSV antigenic polypeptide antibody titer produced in the subject is increased 2, 3, 4, 5, 6, 7, 8, 9, or 10 times relative to a control. In some embodiments, the anti-HSV antigenic polypeptide antibody titer produced in a subject is increased 2-10 times relative to a control. For example, the anti-HSV antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-HSV antigenic polypeptide antibody titer produced in a subject who has not been administered a HSV RNA (e.g., mRNA) vaccine. In some embodiments, a control is an anti-HSV antigenic polypeptide antibody titer produced in a subject who has been administered a live attenuated HSV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-HSV antigenic polypeptide antibody titer produced in a subject administered inactivated HSV vaccine. In some embodiments, a control is an anti-HSV antigenic polypeptide antibody titer produced in a subject administered a recombinant or purified HSV protein vaccine. Recombinant protein vaccines typically include protein antigens that either have been produced in a heterologous expression system (e.g., bacteria or yeast) or purified from large amounts of the pathogenic organism. In some embodiments, a control is an anti-HSV antigenic polypeptide antibody titer produced in a subject who has been administered a HSV virus-like particle (VLP) vaccine (e.g., particles that contain viral capsid protein but lack a viral genome and, therefore, cannot replicate/produce progeny virus). In some embodiments, the control is a VLP HSV vaccine that comprises prefusion or postfusion F proteins, or that comprises a combination of the two.

In some embodiments, an effective amount of a HSV RNA (e.g., mRNA) vaccine is a dose that is reduced compared to the standard of care dose of a recombinant HSV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified HSV protein vaccine, or a live attenuated or inactivated HSV vaccine, or a HSV VLP vaccine, that a physician/clinician or other medical professional would administer to a subject to treat or prevent HSV, or a HSV-related condition, while following the standard of care guideline for treating or preventing HSV, or a HSV-related condition.

In some embodiments, the anti-HSV antigenic polypeptide antibody titer produced in a subject administered an effective amount of a HSV RNA (e.g., mRNA) vaccine is equivalent to an anti-HSV antigenic polypeptide antibody titer produced in a control subject administered a standard of care dose of a recombinant or purified HSV protein vaccine, or a live attenuated or inactivated HSV vaccine, or a HSV VLP vaccine.

In some embodiments, an effective amount of a HSV RNA (e.g., mRNA) vaccine is a dose equivalent to an at least 2-fold reduction in a standard of care dose of a recombinant or purified HSV protein vaccine. For example, an effective amount of a HSV RNA (e.g., mRNA) vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified HSV protein vaccine. In some embodiments, an effective amount of a HSV RNA vaccine is a dose equivalent to an at least at least 100-fold, at least 500-fold, or at least 1000-fold reduction in a standard of care dose of a recombinant or purified HSV protein vaccine. In some embodiments, an effective amount of a HSV RNA (e.g., mRNA) vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified HSV protein vaccine. In some embodiments, the anti-HSV antigenic polypeptide antibody titer produced in a subject administered an effective amount of a HSV RNA vaccine is equivalent to an anti-HSV antigenic polypeptide antibody titer produced in a control subject administered the standard of care dose of a recombinant or purified HSV protein vaccine, or a live attenuated or inactivated HSV vaccine, or a HSV VLP vaccine. In some embodiments, an effective amount of a HSV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified HSV protein vaccine, wherein the anti-HSV antigenic polypeptide antibody titer produced in the subject is equivalent to an anti-HSV antigenic polypeptide antibody titer produced in a control subject administered the standard of care dose of a recombinant or purified HSV protein vaccine, or a live attenuated or inactivated HSV vaccine, or a HSV VLP vaccine.

In some embodiments, the effective amount of a HSV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant HSV protein vaccine. In some embodiments, such as the foregoing, the anti-HSV antigenic polypeptide antibody titer produced in the subject is equivalent to an anti-HSV antigenic polypeptide antibody titer produced in a control subject administered the standard of care dose of a recombinant or purified HSV protein vaccine, or a live attenuated or inactivated HSV vaccine, or a HSV VLP vaccine. In some embodiments, the effective amount is a dose equivalent to (or equivalent to and at least) a 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant HSV protein vaccine. In some embodiments, such as the foregoing, an anti-HSV antigenic polypeptide antibody titer produced in the subject is equivalent to an anti-HSV antigenic polypeptide antibody titer produced in a control subject administered the standard of care dose of a recombinant or purified HSV protein vaccine, or a live attenuated or inactivated HSV vaccine, or a HSV VLP vaccine.

In some embodiments, the effective amount of a HSV RNA (e.g., mRNA) vaccine is a total dose of 50-1000 μg. In some embodiments, the effective amount of a HSV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a HSV RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 μg administered to the subject a total of two times. In some embodiments, the effective amount of a HSV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a HSV RNA (e.g., mRNA) vaccine is a total dose of 25, 50, 100, 150, 200, 250, 300, 350, 400, 450, or 500 μg administered to the subject a total of two times.

Additional Embodiments

1. A herpes simplex virus (HSV) vaccine, comprising: at least one messenger ribonucleic acid (mRNA) polynucleotide having a 5' terminal cap, an open reading frame encoding at least one HSV antigenic polypeptide, and a 3' polyA tail.
2. The vaccine of paragraph 1, wherein the at least one mRNA polynucleotide is encoded by a sequence identified by any one of SEQ ID NO: 1-23 or 54-64, or a fragment of a sequence identified by any one of SEQ ID NO: 1-23 or 54-64.
3. The vaccine of paragraph 1, wherein the at least one mRNA polynucleotide comprises a sequence identified by any one of SEQ ID NO: 90-124, or a fragment of a sequence identified by any one of SEQ ID NO: 90-124.
4. The vaccine of paragraph 1, wherein the at least one antigenic polypeptide comprises a sequence identified by any one of SEQ ID NO: 24-53 or 66-77, or a fragment of a sequence identified by any one of SEQ ID NO: 24-53 or 66-77.
5. The vaccine of any one of paragraphs 1-4, wherein the 5' terminal cap is or comprises 7mG(5')ppp(5')NlmpNp.
6. The vaccine of any one of paragraphs 1-5, wherein 100% of the uracil in the open reading frame is modified to include N1-methyl pseudouridine at the 5-position of the uracil.
7. The vaccine of any one of paragraphs 1-6, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG) 2000-DMG.
8. The vaccine of paragraph 7, wherein the lipid nanoparticle further comprises trisodium citrate buffer, sucrose and water.
9. A herpes simplex virus (HSV) vaccine, comprising: at least one messenger ribonucleic acid (mRNA) polynucleotide comprising a sequence identified by any one of SEQ ID NO: 90-124 or a fragment thereof, having a 5' terminal cap 7mG(5')ppp(5')NlmpNp and a 3' polyA tail, wherein the uracil nucleotides of the sequence identified by any one of SEQ ID NO: 90-124 are modified to include N1-methyl pseudouridine at the 5-position of the uracil nucleotide.
10. A herpes simplex virus (HSV) vaccine, comprising: at least one messenger ribonucleic acid (mRNA) polynucleotide comprising a sequence identified by any one of SEQ ID NO: 90, having a 5' terminal cap 7mG(5')ppp(5') NlmpNp and a 3' polyA tail, wherein the uracil nucleotides of the sequence identified by any one of SEQ ID NO: 90 are modified to include N1-methyl pseudouridine at the 5-position of the uracil nucleotide.
11. A HSV vaccine, comprising: at least one messenger ribonucleic acid (mRNA) polynucleotide comprising a sequence identified by any one of SEQ ID NO: 91, having a 5' terminal cap 7mG(5')ppp(5') NlmpNp and a 3' polyA tail, wherein the uracil nucleotides of the sequence identified by any one of SEQ ID NO: 91 are modified to include N1-methyl pseudouridine at the 5-position of the uracil nucleotide.
12. A HSV vaccine, comprising: at least one messenger ribonucleic acid (mRNA) polynucleotide comprising a sequence identified by any one of SEQ ID NO: 92, having a 5' terminal cap 7mG(5')ppp(5') NlmpNp and a 3' polyA tail, wherein the uracil nucleotides of the sequence identified by any one of SEQ ID NO: 92 are modified to include N1-methyl pseudouridine at the 5-position of the uracil nucleotide.
13. A HSV vaccine, comprising: at least one messenger ribonucleic acid (mRNA) polynucleotide comprising a sequence identified by any one of SEQ ID NO: 93, having a 5' terminal cap 7mG(5')ppp(5') NlmpNp and a 3' polyA tail, wherein the uracil nucleotides of the sequence identified by any one of SEQ ID NO: 93 are modified to include N1-methyl pseudouridine at the 5-position of the uracil nucleotide.
14. A HSV vaccine, comprising: at least one messenger ribonucleic acid (mRNA) polynucleotide comprising a sequence identified by any one of SEQ ID NO: 94, having a 5' terminal cap 7mG(5')ppp(5') NlmpNp and a 3' polyA tail, wherein the uracil nucleotides of the sequence identified by any one of SEQ ID NO: 94 are modified to include N1-methyl pseudouridine at the 5-position of the uracil nucleotide.
15. A HSV vaccine, comprising: at least one messenger ribonucleic acid (mRNA) polynucleotide comprising a sequence identified by any one of SEQ ID NO: 95, having a 5' terminal cap 7mG(5')ppp(5') NlmpNp and a 3' polyA tail, wherein the uracil nucleotides of the sequence identified by any one of SEQ ID NO: 95 are modified to include N1-methyl pseudouridine at the 5-position of the uracil nucleotide.
16. A HSV vaccine, comprising: at least one messenger ribonucleic acid (mRNA) polynucleotide comprising a sequence identified by any one of SEQ ID NO: 96, having a 5' terminal cap 7mG(5')ppp(5') NlmpNp and a 3' polyA tail, wherein the uracil nucleotides of the sequence identified by any one of SEQ ID NO: 96 are modified to include N1-methyl pseudouridine at the 5-position of the uracil nucleotide.
17. A HSV vaccine, comprising: at least one messenger ribonucleic acid (mRNA) polynucleotide comprising a sequence identified by any one of SEQ ID NO: 97, having a 5' terminal cap 7mG(5')ppp(5') NlmpNp and a 3' polyA tail, wherein the uracil nucleotides of the sequence identified by any one of SEQ ID NO: 97 are modified to include N1-methyl pseudouridine at the 5-position of the uracil nucleotide.
18. A HSV vaccine, comprising: at least one messenger ribonucleic acid (mRNA) polynucleotide comprising a sequence identified by any one of SEQ ID NO: 98, having a 5' terminal cap 7mG(5')ppp(5') NlmpNp and a 3' polyA tail, wherein the uracil nucleotides of the sequence identified by any one of SEQ ID NO: 98 are modified to include N1-methyl pseudouridine at the 5-position of the uracil nucleotide.
19. A HSV vaccine, comprising: at least one messenger ribonucleic acid (mRNA) polynucleotide comprising a sequence identified by any one of SEQ ID NO: 99, having a 5' terminal cap 7mG(5')ppp(5') NlmpNp and a 3' polyA tail, wherein the uracil nucleotides of the sequence identified by any one of SEQ ID NO: 99 are modified to include N1-methyl pseudouridine at the 5-position of the uracil nucleotide.
20. A HSV vaccine, comprising: at least one messenger ribonucleic acid (mRNA) polynucleotide comprising a sequence identified by any one of SEQ ID NO: 100, having a 5' terminal cap 7mG(5')ppp(5') NlmpNp and a 3' polyA tail, wherein the uracil nucleotides of the sequence identified by any one of SEQ ID NO: 100 are modified to include N1-methyl pseudouridine at the 5-position of the uracil nucleotide.
21. A HSV vaccine, comprising: at least one messenger ribonucleic acid (mRNA) polynucleotide comprising a sequence identified by any one of SEQ ID NO: 101, having a 5' terminal cap 7mG(5')ppp(5')

NlmpNp and a 3' polyA tail, wherein the uracil nucleotides of the sequence identified by any one of SEQ ID NO: 101 are modified to include N1-methyl pseudouridine at the 5-position of the uracil nucleotide.

22. A HSV vaccine, comprising:

at least one messenger ribonucleic acid (mRNA) polynucleotide comprising a sequence identified by any one of SEQ ID NO: 102, having a 5' terminal cap 7mG(5')ppp(5') NlmpNp and a 3' polyA tail, wherein the uracil nucleotides of the sequence identified by any one of SEQ ID NO: 102 are modified to include N1-methyl pseudouridine at the 5-position of the uracil nucleotide.

23. A HSV vaccine, comprising:

at least one messenger ribonucleic acid (mRNA) polynucleotide comprising a sequence identified by any one of SEQ ID NO: 103, having a 5' terminal cap 7mG(5')ppp(5') NlmpNp and a 3' polyA tail, wherein the uracil nucleotides of the sequence identified by any one of SEQ ID NO: 103 are modified to include N1-methyl pseudouridine at the 5-position of the uracil nucleotide.

24. A HSV vaccine, comprising:

at least one messenger ribonucleic acid (mRNA) polynucleotide comprising a sequence identified by any one of SEQ ID NO: 104, having a 5' terminal cap 7mG(5')ppp(5') NlmpNp and a 3' polyA tail, wherein the uracil nucleotides of the sequence identified by any one of SEQ ID NO: 104 are modified to include N1-methyl pseudouridine at the 5-position of the uracil nucleotide.

25. A HSV vaccine, comprising:

at least one messenger ribonucleic acid (mRNA) polynucleotide comprising a sequence identified by any one of SEQ ID NO: 105, having a 5' terminal cap 7mG(5')ppp(5') NlmpNp and a 3' polyA tail, wherein the uracil nucleotides of the sequence identified by any one of SEQ ID NO: 105 are modified to include N1-methyl pseudouridine at the 5-position of the uracil nucleotide.

26. A HSV vaccine, comprising:

at least one messenger ribonucleic acid (mRNA) polynucleotide comprising a sequence identified by any one of SEQ ID NO: 106, having a 5' terminal cap 7mG(5')ppp(5') NlmpNp and a 3' polyA tail, wherein the uracil nucleotides of the sequence identified by any one of SEQ ID NO: 106 are modified to include N1-methyl pseudouridine at the 5-position of the uracil nucleotide.

27. A HSV vaccine, comprising:

at least one messenger ribonucleic acid (mRNA) polynucleotide comprising a sequence identified by any one of SEQ ID NO: 107, having a 5' terminal cap 7mG(5')ppp(5') NlmpNp and a 3' polyA tail, wherein the uracil nucleotides of the sequence identified by any one of SEQ ID NO: 107 are modified to include N1-methyl pseudouridine at the 5-position of the uracil nucleotide.

28. A HSV vaccine, comprising:

at least one messenger ribonucleic acid (mRNA) polynucleotide comprising a sequence identified by any one of SEQ ID NO: 108, having a 5' terminal cap 7mG(5')ppp(5') NlmpNp and a 3' polyA tail, wherein the uracil nucleotides of the sequence identified by any one of SEQ ID NO: 108 are modified to include N1-methyl pseudouridine at the 5-position of the uracil nucleotide.

29. A HSV vaccine, comprising:

at least one messenger ribonucleic acid (mRNA) polynucleotide comprising a sequence identified by any one of SEQ ID NO: 109, having a 5' terminal cap 7mG(5')ppp(5') NlmpNp and a 3' polyA tail, wherein the uracil nucleotides of the sequence identified by any one of SEQ ID NO: 109 are modified to include N1-methyl pseudouridine at the 5-position of the uracil nucleotide.

30. A HSV vaccine, comprising:

at least one messenger ribonucleic acid (mRNA) polynucleotide comprising a sequence identified by any one of SEQ ID NO: 110, having a 5' terminal cap 7mG(5')ppp(5') NlmpNp and a 3' polyA tail, wherein the uracil nucleotides of the sequence identified by any one of SEQ ID NO: 110 are modified to include N1-methyl pseudouridine at the 5-position of the uracil nucleotide.

31. A HSV vaccine, comprising:

at least one messenger ribonucleic acid (mRNA) polynucleotide comprising a sequence identified by any one of SEQ ID NO: 111, having a 5' terminal cap 7mG(5')ppp(5') NlmpNp and a 3' polyA tail, wherein the uracil nucleotides of the sequence identified by any one of SEQ ID NO: 111 are modified to include N1-methyl pseudouridine at the 5-position of the uracil nucleotide.

32. A HSV vaccine, comprising:

at least one messenger ribonucleic acid (mRNA) polynucleotide comprising a sequence identified by any one of SEQ ID NO: 112, having a 5' terminal cap 7mG(5')ppp(5') NlmpNp and a 3' polyA tail, wherein the uracil nucleotides of the sequence identified by any one of SEQ ID NO: 112 are modified to include N1-methyl pseudouridine at the 5-position of the uracil nucleotide.

33. A HSV vaccine, comprising:

at least one messenger ribonucleic acid (mRNA) polynucleotide comprising a sequence identified by any one of SEQ ID NO: 113, having a 5' terminal cap 7mG(5')ppp(5') NlmpNp and a 3' polyA tail, wherein the uracil nucleotides of the sequence identified by any one of SEQ ID NO: 113 are modified to include N1-methyl pseudouridine at the 5-position of the uracil nucleotide.

34. A HSV vaccine, comprising:

at least one messenger ribonucleic acid (mRNA) polynucleotide comprising a sequence identified by any one of SEQ ID NO: 114, having a 5' terminal cap 7mG(5')ppp(5') NlmpNp and a 3' polyA tail, wherein the uracil nucleotides of the sequence identified by any one of SEQ ID NO: 114 are modified to include N1-methyl pseudouridine at the 5-position of the uracil nucleotide.

35. A HSV vaccine, comprising:

at least one messenger ribonucleic acid (mRNA) polynucleotide comprising a sequence identified by any one of SEQ ID NO: 115, having a 5' terminal cap 7mG(5')ppp(5') NlmpNp and a 3' polyA tail, wherein the uracil nucleotides of the sequence identified by any one of SEQ ID NO: 115 are modified to include N1-methyl pseudouridine at the 5-position of the uracil nucleotide.

36. A HSV vaccine, comprising:

at least one messenger ribonucleic acid (mRNA) polynucleotide comprising a sequence identified by any one of SEQ ID NO: 116, having a 5' terminal cap 7mG(5')ppp(5') NlmpNp and a 3' polyA tail, wherein the uracil nucleotides of the sequence identified by any one of SEQ ID NO: 116 are modified to include N1-methyl pseudouridine at the 5-position of the uracil nucleotide.

37. A HSV vaccine, comprising:

at least one messenger ribonucleic acid (mRNA) polynucleotide comprising a sequence identified by any one of SEQ ID NO: 117, having a 5' terminal cap 7mG(5')ppp(5') NlmpNp and a 3' polyA tail, wherein the uracil nucleotides of the sequence identified by any one of SEQ ID NO: 117 are modified to include N1-methyl pseudouridine at the 5-position of the uracil nucleotide.

38. A HSV vaccine, comprising:

at least one messenger ribonucleic acid (mRNA) polynucleotide comprising a sequence identified by any one of SEQ ID NO: 118, having a 5' terminal cap 7mG(5')ppp(5')NlmpNp and a 3' polyA tail, wherein the uracil nucleotides of the sequence identified by any one of SEQ ID NO: 118 are modified to include N1-methyl pseudouridine at the 5-position of the uracil nucleotide.

39. A HSV vaccine, comprising:

at least one messenger ribonucleic acid (mRNA) polynucleotide comprising a sequence identified by any one of SEQ ID NO: 119, having a 5' terminal cap 7mG(5')ppp(5')NlmpNp and a 3' polyA tail, wherein the uracil nucleotides of the sequence identified by any one of SEQ ID NO: 119 are modified to include N1-methyl pseudouridine at the 5-position of the uracil nucleotide.

40. A HSV vaccine, comprising:

at least one messenger ribonucleic acid (mRNA) polynucleotide comprising a sequence identified by any one of SEQ ID NO: 120, having a 5' terminal cap 7mG(5')ppp(5')NlmpNp and a 3' polyA tail, wherein the uracil nucleotides of the sequence identified by any one of SEQ ID NO: 120 are modified to include N1-methyl pseudouridine at the 5-position of the uracil nucleotide.

41. A HSV vaccine, comprising:

at least one messenger ribonucleic acid (mRNA) polynucleotide comprising a sequence identified by any one of SEQ ID NO: 121, having a 5' terminal cap 7mG(5')ppp(5')NlmpNp and a 3' polyA tail, wherein the uracil nucleotides of the sequence identified by any one of SEQ ID NO: 121 are modified to include N1-methyl pseudouridine at the 5-position of the uracil nucleotide.

42. A HSV vaccine, comprising:

at least one messenger ribonucleic acid (mRNA) polynucleotide comprising a sequence identified by any one of SEQ ID NO: 122, having a 5' terminal cap 7mG(5')ppp(5')NlmpNp and a 3' polyA tail, wherein the uracil nucleotides of the sequence identified by any one of SEQ ID NO: 122 are modified to include N1-methyl pseudouridine at the 5-position of the uracil nucleotide.

43. A HSV vaccine, comprising:

at least one messenger ribonucleic acid (mRNA) polynucleotide comprising a sequence identified by any one of SEQ ID NO: 123, having a 5' terminal cap 7mG(5')ppp(5')NlmpNp and a 3' polyA tail, wherein the uracil nucleotides of the sequence identified by any one of SEQ ID NO: 123 are modified to include N1-methyl pseudouridine at the 5-position of the uracil nucleotide.

44. A HSV vaccine, comprising:

at least one messenger ribonucleic acid (mRNA) polynucleotide comprising a sequence identified by any one of SEQ ID NO: 124, having a 5' terminal cap 7mG(5')ppp(5')NlmpNp and a 3' polyA tail, wherein the uracil nucleotides of the sequence identified by any one of SEQ ID NO: 124 are modified to include N1-methyl pseudouridine at the 5-position of the uracil nucleotide.

45. The vaccine of any one of paragraphs 9-44 formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

46. The vaccine of any one of paragraphs 1-45 formulated in a lipid nanoparticle comprising at least one cationic lipid selected from compounds of Formula (I):

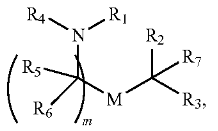

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ(R)$_2$, and unsubstituted $C_{1-6}$ alkyl, where Q is selected from a carbocycle, heterocycle, —OR, —O$(CH_2)_n$N(R)$_2$, —C(O)OR, —OC(O)R, —$CX_3$, —$CX_2$H, —$CXH_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)$R_8$, —O$(CH_2)_n$OR, —N(R)C(=N$R_9$)N(R)$_2$, —N(R)C(=CH$R_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=N$R_9$)N(R)$_2$, —N(OR)C(=CH$R_9$)N(R)$_2$, —C(=N$R_9$)N(R)$_2$, —C(=N$R_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

47. The vaccine of paragraph 46, wherein a subset of compounds of Formula (I) includes those in which when $R_4$ is —$(CH_2)_n$Q, —$(CH_2)_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

48. The vaccine of paragraph 46, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)N$(R)_2$, —C(=N$R_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

49. The vaccine of paragraph 46, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)R, —C(O)N(R)OR, and —C(=N$R_9$)N$(R)_2$, and each n is independently selected from 1, 2, 3, 4, and 5; and when Q is a 5- to 14-membered heterocycle and (i) $R_4$ is —$(CH_2)_n$Q in which n is 1 or 2, or (ii) $R_4$ is —$(CH_2)_n$CHQR in which n is 1, or (iii) $R_4$ is —CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

50. The vaccine of paragraph 46, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)

$N(R)_2$, —C(=$NR_9$)R, —C(O)N(R)OR, and —C(=$NR_9$)N$(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2$R, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

51. The vaccine of paragraph 46, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

52. The vaccine of paragraph 46, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

53. The vaccine of paragraph 46, wherein a subset of compounds of Formula (I) includes those of Formula (IA):

(IA)

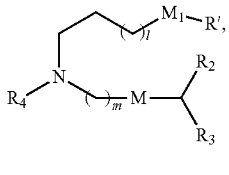

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of “including,” “comprising,” or “having,”

"containing," "involving," and variations thereof herein, is meant to encompass the items listed thereafter.

EXAMPLES

Example 1: Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the content of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2: Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3'desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1);

(b) a 5' triphosphate segment, which may include the coding region of a polypeptide and a normal 3'OH (SEG. 2); and (c) a 5' monophosphate segment for the 3' end of the chimeric polynucleotide (e.g., the tail) comprising cordycepin or no 3'OH (SEG. 3).

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG.2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA may be performed using 2×KAPA HIFI™ HotStart ReadyMix by Kapa Biosystems (Woburn, Mass.). This system includes 2× KAPA ReadyMix 12.5 μl; Forward Primer (10 μM) 0.75 μl; Reverse Primer (10 μM) 0.75 μl; Template cDNA 100 ng; and $dH_20$ diluted to 25.0 μl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, Calif.) per manufacturer's instructions (up to 5 μg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4: In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 μg |
| 2) | 10x transcription buffer (400 mM Tris-HCl pH 8.0, 190 mM $MgCl_2$, 50 mM DTT, 10 mM Spermidine) | 2.0 μl |

-continued

| | | |
|---|---|---|
| 3) | Custom NTPs (25 mM each) | 0.2 µl |
| 4) | RNase Inhibitor | 20 U |
| 5) | T7 RNA polymerase | 3000 U |
| 6) | $dH_20$ | up to 20.0 µl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, Tex.) following the manufacturer's instructions. This kit can purify up to 500 µg of RNA. Following the cleanup, the RNA polynucleotide may be quantified using the NanoDrop™ and analyzed by agarose gel electrophoresis to confirm the RNA polynucleotide is the proper size and that no degradation of the RNA has occurred.

Example 5: Enzymatic Capping

Capping of a RNA polynucleotide is performed as follows where the mixture includes: IVT RNA 60 µg-180 µg and $dH_20$ up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 µl); 20 mM GTP (5.0 µl); 20 mM S-Adenosyl Methionine (2.5 µl); RNase Inhibitor (100 U); 2'-O-Methyltransferase (400 U); Vaccinia capping enzyme (Guanylyl transferase) (40 U); $dH_20$ (Up to 28 µl); and incubation at 37° C. for 30 minutes for 60 µg RNA or up to 2 hours for 180 µg of RNA.

The RNA polynucleotide may then be purified using Ambion's MEGACLEAR™ Kit (Austin, Tex.) following the manufacturer's instructions. Following the cleanup, the RNA may be quantified using the NANODROP™ (ThermoFisher, Waltham, Mass.) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing capped IVT RNA (100 µl); RNase Inhibitor (20 U); 10× Tailing Buffer (0.5 M Tris-HCl (pH 8.0), 2.5 M NaCl, 100 mM $MgCl_2$)(12.0 µl); 20 mM ATP (6.0 µl); Poly-A Polymerase (20 U); $dH_20$ up to 123.5 µl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 µg). Poly-A Polymerase may be a recombinant enzyme expressed in yeast.

It should be understood that the processivity or integrity of the polyA tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7: Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24, and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 8: Agarose Gel Electrophoresis of Modified RNA or RTPCR Products

Individual RNA polynucleotides (200-400 ng in a 20 µl volume) or reverse transcribed PCR products (200-400 ng) may be loaded into a well on a non-denaturing 1.2% Agarose E-Gel (Invitrogen, Carlsbad, Calif.) and run for 12-15 minutes, according to the manufacturer protocol.

Example 9: Nanodrop Modified RNA Quantification and UV Spectral Data

Chemically modified RNA polynucleotides in TE buffer (1 µl) are used for NANODROP™ UV absorbance readings to quantitate the yield of each polynucleotide from an chemical synthesis or in vitro transcription reaction.

Example 10: Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 11: Immunogenicity Study

The instant study is designed to test the immunogenicity in mice of candidate HSV vaccines comprising a mRNA polynucleotide encoding one or a combination of HSV proteins.

Mice are immunized intravenously (IV), intramuscularly (IM), intranasally (IN), or intradermally (ID) with candidate HSV vaccines with and without adjuvant. A total of four immunizations are given at 3 week intervals (i.e., at weeks 0, 3, 6, and 9), and sera are collected after each immunization until weeks 33-51. Serum antibody titers against glycoprotein C or glycoprotein D are determined by ELISA. Sera collected from each mouse during weeks 10-16 are pooled, and total IgGs are purified by using ammonium sulfate (Sigma) precipitation followed by DEAE (Pierce) batch purification. Following dialysis against PBS, the purified antibodies are used for immunoelectron microscopy, antibody-affinity testing, and an in vitro protection assay.

Example 12: HSV Rodent Challenge

The instant study is designed to test the efficacy in cotton rats of candidate HSV vaccines against a lethal challenge using a HSV vaccine comprising a chemically modified or unmodified mRNA encoding one or a combination of HSV proteins. Cotton rats are challenged with a lethal dose of HSV.

Animals are immunized intravenously (IV), intramuscularly (IM), intranasally (IN), or intradermally (ID) at week 0 and week 3 with candidate HSV vaccines with and without adjuvant. The animals are then challenged with a lethal dose of HSV on week 7 via IV, IM or ID. Endpoint is day 13 post infection, death, or euthanasia. Animals displaying severe illness as determined by >30% weight loss, extreme lethargy, or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %), the non-cationic lipid is DSPC (10 mol %), the PEG lipid is PEG-DOMG (1.5 mol %) and the structural lipid is cholesterol (38.5 mol %), for example.

Example 13: HSV Non-Human Primate Challenge

The instant study is designed to test the efficacy in African Green Monkey of candidate HSV vaccines against a non-lethal challenge using a HSV vaccine comprising a chemically modified or unmodified mRNA encoding one or a combination of HSV proteins. Animals are challenged with an attenuated dose of HSV.

Animals are immunized intravenously (IV), intramuscularly (IM), or intradermally (ID) at week 0 and week 3 with candidate HSV vaccines with and without adjuvant. The animals are then challenged with an attenuated dose of HSV on week 7 via IV, IM or ID. Endpoint is day 13 post infection. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %), the non-cationic lipid is DSPC (10 mol %), the PEG lipid is PEG-DOMG (1.5 mol %) and the structural lipid is cholesterol (38.5 mol %), for example.

Example 14: Microneutralization Assay

Nine serial 2-fold dilutions (1:50-1:12,800) of simian or human serum are made in 50 μl virus growth medium (VGM) with trypsin in 96 well microtiter plates. Fifty microliters of HSV are added to the serum dilutions and allowed to incubate for 60 minutes at RT. Positive control wells of HSV without sera and negative control wells without HSV or sera are included in triplicate on each plate. While the serum-HSV mixtures incubate, a single cell suspension of cells are prepared by trypsinizing (Gibco 0.5% bovine pancrease trypsin in EDTA) a confluent monolayer and suspended cells are transferred to a 50 ml centrifuge tube, topped with sterile PBS and gently mixed. The cells are then pelleted at 200 g for 5 minutes, supernatant aspirated and cells resuspended in PBS. This procedure is repeated once and the cells are resuspended at a concentration of $3\times10^5$/ml in VGM with porcine trypsin. Then, 100 μl of cells are added to the serum-virus mixtures and the plates incubated at 35° C. in $CO_2$ for 5 days. The plates are fixed with 80% acetone in phosphate buffered saline (PBS) for 15 minutes at RT, air dried and then blocked for 30 minutes containing PBS with 0.5% gelatin and 2% FCS. An antibody to glycoprotein C or glycoprotein D is diluted in PBS with 0.5% gelatin/2% FCS/0.5% Tween 20 and incubated at RT for 2 hours. Wells are washed and horse radish peroxidase conjugated goat anti-mouse IgG added, followed by another 2 hour incubation. After washing, O-phenylenediamine dihydrochloride is added and the neutralization titer is defined as the titer of serum that reduced color development by 50% compared to the positive control wells.

One having ordinary skill in the art will recognize that the nucleotide sequences found in Table 1 below may be modified, for example but not limited to, for increased expression and RNA stability, and as such are covered by the present invention. Derivatives and variants thereof of the sequences found in Table 1 are considered covered by the present invention.

Each of the sequences described herein encompasses a chemically modified sequence or an unmodified sequence that includes no modified nucleotides.

TABLE 1

| HSV Nucleic Acid Sequences | |
|---|---|
| Strain | Nucleic Acid Sequence |
| HSV-2 gB_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGAGAGGTGGTGGCTTAGTT<br>TGCGCGCTGGTTGTCGGGGCGCTCGTAGCCGCCGTGGCGTCGGCCGCCCCTGCGGCT<br>CCTCGCGCTAGCGGAGGCGTAGCCGCAACAGTTGCGGCGAACGGGGGTCCAGCCTC<br>TCAGCCTCCTCCCGTCCCGAGCCCTGCGACCACCAAGGCTAGAAAGCGGAAGACCA<br>AGAAACCGCCCAAGCGCCCCGAGGCCACCCCGCCCCCCGATGCCAACGCGACTGTC<br>GCCGCTGGCCATGCGACGCTTCGCGCTCATCTGAGGGAGATCAAGGTTGAAAATGCT<br>GATGCCCAATTTTACGTGTGCCCGCCCCCGACGGGCGCCACGGTTGTGCAGTTTGAA<br>CAGCCGCGGCGCTGTCCGACGCGGCCAGAAGGCCAGAACTATACGGAGGGCATAGC<br>GGTGGTCTTTAAGGAAAACATCGCCCCGTACAAATTTAAGGCCACAATGTACTACAA<br>AGACGTGACAGTTTCGCAAGTGTGGTTTGGCCACAGATACTCGCAGTTTATGGGAAT<br>CTTCGAAGATAGAGCCCCTGTTCCCTTCGAGGAAGTCATCGACAAGATTAATGCCAA<br>AGGGGTATGCCGTTCCACGGCCAAATACGTGCGCAACAATATGGAGACCACCGCCT<br>TTCACCGGGATGATCACGAGACCGACATGGAGCTTAAGCCGGCGAAGGTCGCCACG<br>CGTACCTCCCGGGGTTGGCACACCACAGATCTTAAGTACAATCCCTCGCGAGTTGAA<br>GCATTCCATCGGTATGGAACTACCGTTAACTGCATCGTTGAGGAGGTGGATGCGCGG<br>TCGGTGTACCCTTACGATGAGTTTGTGTTAGCGACCGGCGATTTTGTGTACATGTCCC<br>CGTTTTACGGCTACCGGGAGGGGTCGCACACCGAACATACCTCGTACGCCGCTGACA<br>GGTTCAAGCAGGTCGATGGCTTTTACGCGCGCGATCTCACCACGAAGGCCCGGGCCA<br>CGTCACCGACGACCAGGAACTTGCTCACGACCCCCAAGTTCACCGTCGCTTGGGATT<br>GGGTCCCAAAGCGTCCGGCGGTCTGCACGATGACCAAATGGCAGGAGGTGGACGAA<br>ATGCTCCGCGCAGAATACGGCGGCTCCTTCCGCTTCTCGTCCGACGCCATCTCGACA<br>ACCTTCACCACCAATCTGACCCAGTACAGTCTGTCGCGCGTTGATTTAGGAGACTGC<br>ATTGGCCGGGATGCCCGGGAGGCCATCGACAGAATGTTTGCGCGTAAGTACAATGC<br>CACACATATTAAGGTGGGCCAGCCGCAATACTACCTTGCCACGGGCGGCTTTCTCAT<br>CGCGTACCAGCCCCTTCTCTCAAATACGCTCGCTGAACTGTACGTGCGGGAGTATAT<br>GAGGGAACAGGACCGCAAGCCCCGCAATGCCACGCCTGCGCCACTACGAGAGGCGC<br>CTTCAGCTAATGCGTCGGTGGAACGTATCAAGACCACCTCCTCAATAGAGTTCGCCC<br>GGCTGCAATTTACGTACAACCACATCCAGCGCCACGTGAACGACATGCTGGGCCGC<br>ATCGCTGTCGCCTGGTGCGAGCTGCAGAATCACGAGCTGACTCTTTGGAACGAGGCC<br>CGAAAACTCAACCCCAACGCGATCGCCTCCGCAACAGTCGGTAGACGGGTGAGCGC<br>TCGCATGCTAGGAGATGTCATGGCTGTGTCCACCTGCGTGCCCGTCGCTCCGGACAA<br>CGTGATTGTGCAGAATTCGATGCGGGTCTTGATAATAGGCTGGAGCCTCGGTGGCCA<br>TGCTTCTTGCCCCTTGGGCCTCCCCCCAGCCCCTCCTCCCCTTCCTGCACCCGTACCC<br>CCGTGGTCTTTGAATAAAGTCTGAGTGGGCGGC (SEQ ID NO: 1) |
| HSV-2 gC_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGGCCCTTGGACGGGTAGG<br>CCTAGCCGTGGGCCTGTGGGGCCTACTGTGGGTGGGTGTGGTCGTGGTGCTGGCCAA<br>TGCCTCCCCCGGACGCACGATAACGGTGGGCCCGCGAGGCAACGCGAGCAATGCTG<br>CCCCCTCCGCGTCCCCGCGGAACGCATCCGCCCCCCGAACCACACCCACGCCCCCAC<br>AACCCCGCAAAGCGACGAAATCCAAGGCCTCCACCGCCAAACCGGCTCCGCCCCCC<br>AAGACCGGACCCCCGAAGACATCCTCGGAGCCCGTGCGATGCAACCGCCACGACCC<br>GCTGGCCCGGTACGGCTCGCGGGTGCAAATCCGATGCCGGTTTCCCAACTCCACGAG<br>GACTGAGTCCCGTCTCCAGATCTGGCGTTATGCCACGGCGACGGACGCCGAAATCGG<br>AACAGCGCCTAGCTTAGAAGAGGTGATGGTGAACGTGTCGGCCCCGCCCGGGGGCC<br>AACTGGTGTATGACAGTGCCCCCAACCGAACGGACCCGCATGTAATCTGGGCGGAG<br>GGCGCCGGCCCGGGCGCCAGCCCGCGCCTGTACTCGGTTGTCGGCCCGCTGGGTCGG<br>CAGCGGCTCATCATCGAAGAGTTAACCCTGGAGACACAGGGCATGTACTATTGGGT<br>GTGGGGCCGGACGGACCGCCCGTCCGCCTACGGGACCTGGGTCCGCGTTCGAGTATT<br>TCGCCCTCCGTCGCTGACCATCCACCCCCACGCGGTGCTGGAGGGCCAGCCGTTTAA<br>GGCGACGTGCACGGCCGCAACCTACTACCCGGGCAACCGCGCGGAGTTCGTCTGGTT<br>TGAGGACGGTCGCCGCGTATTCGATCCGGCACAGATACACACGCAGACGCAGGAGA<br>ACCCCGACGGCTTTTCCACCGTCTCCACCGTGACCTCCGCGGCCGTCGGCGGGCAGG<br>GCCCCCCTCGCACCTTCACCTGCCAGCTGACGTGGCACCGCGACTCCGTGTCGTTCT<br>CTCGGCGCAACGCCAGCGGCACGGCCTCGGTTCTGCCGCGGCCGACCATTACCATGG<br>AGTTTACAGGCGACCATGCGGTCTGCACGGCCGGCTGTGTGCCCGAGGGGGTCACGT<br>TTGCTTGGTTCCTGGGGGATGACTCCTCGCCGGCGGAAAAGGTGGCCGTCGCGTCCC<br>AGACATCGTGCGGGCGCCCCGGCACCGCCACGATCCGCTCCACCCTGCCGGTCTCGT<br>ACGAGCAGACCGAGTACATCTGTAGACTGGCGGGATACCCGGACGGAATTCCGGTC<br>CTAGAGCACCACGGAAGCCACCAGCCCCCGCCGCGGGACCCAACCGAGCGGCAGGT<br>GATCCGGGCGGTGGAGGGGGCGGGGATCGGAGTGGCTGTCCTTGTCGCGGTGGTTC<br>TGGCCGGGACCGCGGTAGTGTACCTGACCCATGCCTCCTCGGTACGCTATCGTCGGC<br>TGCGGTAATGATAATAGGCTGGAGCCTCGGTGGCCATGCTTCTTGCCCCTTGGGCCT<br>CCCCCCAGCCCCTCCTCCCCTTCCTGCACCCGTACCCCCGTGGTCTTTGAATAAAGTC<br>TGAGTGGGCGGC (SEQ ID NO: 2) |
| HSV-2 gD_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGGGGCGTTTGACCTCCGGC<br>GTCGGGACGGCGGCCCTGCTAGTTGTCGCGGTGGGACTCCGCGTCGTCTGCGCCAAA<br>TACGCCTTAGCAGACCCCTCGCTTAAGATGGCCGATCCCAATCGATTTCGCGGGAAG<br>AACCTTCCGGTTTTGGACCAGCTGACCGACCCCCCGGGGTGAAGCGTGTTTACCAC<br>ATTCAGCCGAGCCTGGAGGACCCGTTCCAGCCCCCCAGCATCCCGATCACTGTGTAC<br>TACGCAGTGCTGGAACGTGCCTGCCGCAGCGTGCTCCTACATGCCCCATCGGAGGCC<br>CCCCAGATCGTGCGCGGGGCTTCGGACGAGGCCCGAAAGCACACGTACAACCTGAC<br>CATCGCCTGGTATCGCATGGGAGACAATTGCGCTATCCCCATCACGGTTATGGAATA |

TABLE 1-continued

| | |
|---|---|
| | CACCGAGTGCCCCTACAACAAGTCGTTGGGGGTCTGCCCCATCCGAACGCAGCCCCG<br>CTGGAGCTACTATGACAGCTTTAGCGCCGTCAGCGAGGATAACCTGGGATTCCTGAT<br>GCACGCCCCCGCCTTCGAGACCGCGGGTACGTACCTGCGGCTAGTGAAGATAAACG<br>ACTGGACGGAGATCACACAATTTATCCTGGAGCACCGGGCCCGCGCCTCCTGCAAGT<br>ACGCTCTCCCCCTGCGCATCCCCCCGGCAGCGTGCCTCACCTCGAAGGCCTACCAAC<br>AGGGCGTGACGGTCGACAGCATCGGGATGCTACCCCGCTTTATCCCCGAAAACCAG<br>CGCACCGTCGCCCTATACAGCTTAAAAATCGCCGGGTGGCACGGCCCCAAGCCCCC<br>GTACACCAGCACCCTGCTGCCGCCGGAGCTGTCCGACACCACCAACGCCACGCAAC<br>CCGAACTCGTTCCGGAAGACCCCGAGGACTCGGCCCTCTTAGAGGATCCCGCCGGG<br>ACGGTGTCTTCGCAGATCCCCCCAAACTGGCACATCCCGTCGATCCAGGACGTCGCA<br>CCGCACCACGCCCCCGCCGCCCCCAGCAACCCGGGCCTGATCATCGGCGCGCTGGCC<br>GGCAGTACCCTGGCGGTGCTGGTCATCGGCGGTATTGCGTTTTGGGTACGCCGCCGC<br>GCTCAGATGGCCCCCAAGCGCCTACGTCTCCCCCACATCCGGGATGACGACGCGCCC<br>CCCTCGCACCAGCCATTGTTTTACTAGTGATAATAGGCTGGAGCCTCGGTGGCCATG<br>CTTCTTGCCCCTTGGGCCTCCCCCCAGCCCCTCCTCCCCTTCCTGCACCCGTACCCCC<br>GTGGTCTTTGAATAAAGTCTGAGTGGGCGGC (SEQ ID NO: 3) |
| HSV-2 gE_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGGCTAGGGGGGCCGGGTT<br>GGTTTTTTTTGTTGGAGTTTGGGTCGTAAGCTGCCTCGCGGCAGCGCCCAGAACGTC<br>CTGGAAACGCGTAACCTCGGGCGAAGACGTGGTGTTACTCCCCGCGCCGGCGGGGC<br>CGGAAGAACGCACTCGGGCCCACAAACTACTGTGGGCAGCGGAACCGCTGGATGCC<br>TGCGGTCCCCTGAGGCCGTCATGGGTGGCACTGTGGCCCCCCCGACGAGTGCTTGAG<br>ACGGTTGTCGATGCGGCGTGCATGCGCGCCCCGGAACCGCTCGCTATCGCATACAGT<br>CCCCCGTTCCCTGCGGGCGACGAGGGACTTTATTCGGAGTTGGCGTGGCGCGATCGC<br>GTAGCCGTGGTCAACGAGAGTTTAGTTATCTACGGGGCCCTGGAGACGGACAGTGG<br>TCTGTACACCCTGTCAGTGGTGGGCCTATCCGACGAGGCCCGCCAAGTGGCGTCCGT<br>GGTTCTCGTCGTCGAGCCCGCCCCTGTGCCTACCCCGACCCCCGATGACTACGACGA<br>GGAGGATGACGCGGGCGTGAGCGAACGCACGCCCGTCAGCGTTCCCCCCCCAACAC<br>CCCCCCGACGTCCCCCCGTCGCCCCCCCGACGCACCCTCGTGTTATCCCTGAGGTGA<br>GCCACGTGCGGGGGGTGACGGTCCACATGGAAACCCCGGAGGCCATTCTGTTTGCG<br>CCAGGGGAGACGTTTGGGACGAACGTCTCCATCCACGCAATTGCCCACGACGACGG<br>TCCGTACGCCATGGACGTCGTCTGGATGCGATTTGATGTCCCGTCCTCGTGCGCCGA<br>GATGCGGATCTATGAAGCATGTCTGTATCACCCGCAGCTGCCTGAGTGTCTGTCTCC<br>GGCCGATGCGCCGTGCGCCGTAAGTTCGTGGGCGTACCGCCTGGCGGTCCGCAGCTA<br>CGCCGGCTGCTCCAGGACTACGCCCCCACCTCGATGTTTTGCTGAAGCTCGCATGGA<br>ACCGGTCCCCGGGTTGGCGTGGCTCGCATCAACTGTTAATCTGGAATTCCAGCATGC<br>CTCTCCCCAACACGCCGGCCTCTATCTGTGTGTGGTGTATGTGGACGACCATATCCAT<br>GCCTGGGGCCACATGACCATCTCCACAGCGGCCCAGTACCGGAATGCGGTGGTGGA<br>ACAGCATCTCCCCCAGCGCCAGCCCGAGCCCGTAGAACCCACCCGACCGCATGTGA<br>GAGCCCCCCCTCCCGCACCCTCCGCGAGAGGCCCGTTACGCTTAGGTGCGGTCCTGG<br>GGGCGGCCCTGTTGCTCGCGGCCCTCGGGCTATCCGCCTGGGCGTGCATGACCTGCT<br>GGCGCAGGCGCAGTTGGCGGGCGGTTAAAAGTCGGGCCTCGGCGACCGGCCCCACT<br>TACATTCGAGTAGCGGATAGCGAGCTGTACGCGGACTGGAGTTCGGACTCAGAGGG<br>CGAGCGCGACGGTTCCCTGTGGCAGGACCCTCCGGAGAGACCCGACTCACCGTCCA<br>CAAATGGATCCGGCTTTGAGATCTTATCCCCAACGGCGCCCTCTGTATACCCCCATA<br>GCGAAGGGCGTAAATCGCGCCGCCCGCTCACCACCTTTGGTTCAGGAAGCCCGGGA<br>CGTCGTCACTCCCAGGCGTCCTATTCTTCCGTCTTATGGTAATGATAATAGGCTGGAG<br>CCTCGGTGGCCATGCTTCTTGCCCCTTGGGCCTCCCCCCAGCCCCTCCTCCCCTTCCT<br>GCACCCGTACCCCCGTGGTCTTTGAATAAAGTCTGAGTGGGCGGC (SEQ ID NO: 4) |
| HSV-2 gI_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGCCCGGCCGCTCGCTGCAG<br>GGCCTGGCGATCCTGGGCCTGTGGGTCTGCGCCACCGGCCTGGTCGTCCGCGGCCCC<br>ACGGTCAGTCTGGTCTCAGACTCACTCGTGGATGCCGGGGCCGTGGGGCCCCAGGGC<br>TTCGTGGAAGAGGACCTGCGTGTTTTCGGGGAGCTTCATTTTGTGGGGGCCCAGGTC<br>CCCCACACAAACTACTACGACGGCATCATCGAGCTGTTTCACTACCCCCTGGGGAAC<br>CACTGCCCCCGCGTTGTACACGTGGTCACACTGACCGCATGCCCCCGCCGCCCCGCC<br>GTGGCGTTCACCTTGTGTCGCTCGACGCACCACGCCCACAGCCCCGCCTATCCGACC<br>CTGGAGCTGGGTCTGGCGCGGCAGCCGCTTCTGCGGGTTCGAACGGCAACGCGCGA<br>CTATGCCGGTCTGTATGTCCTGCGCGTATGGGTCGGCAGCGCGACGAACGCCAGCCT<br>GTTTGTTTTGGGGGTGGCGCTCTCTGCCAACGGGACGTTTGTGTATAACGGCTCGGA<br>CTACGGCTCCTGCGATCCGGCGCAGCTTCCCTTTTCGGCCCCGCGCCTGGGACCCTC<br>GAGCGTATACACCCCCGGAGCCTCCCGGCCCACCCCTCCACGGACAACGACATCAC<br>CGTCCTCCCCACGAGACCCGACCCCCGCCCCCGGGGACACAGGGACGCCTGCTCCC<br>GCGAGCGGCGAGAGAGCCCCGCCCAATTCCACGCGATCGGCCAGCGAATCGAGACA<br>CAGGCTAACCGTAGCCCAGGTAATCCAGATCGCCATACCGGCGTCCATCATCGCCTT<br>TGTGTTTCTGGGCAGCTGTATCTGCTTCATCCATAGATGCCAGCGCCGATACAGGCG<br>CCCCCGCGGCCAGATTTACAACCCCGGGGGCGTTTCCTGCGCGGTCAACGAGGCGGC<br>CATGGCCCGCCTCGGAGCCGAGCTGCGATCCCACCCAAACACCCCCCCCAAACCCC<br>GACGCCGTTCGTCGTCGTCCACGACCATGCCTTCCCTAACGTCGATAGCTGAGGAAT<br>CGGAGCCAGGTCCAGTCGTGCTGCTGTCCGTCAGTCCTCGGCCCCGCAGTGGCCCGA<br>CGGCCCCCCAAGAGGTCTAGTGATAATAGGCTGGAGCCTCGGTGGCCATGCTTCTTG<br>CCCCTTGGGCCTCCCCCCAGCCCCTCCTCCCCTTCCTGCACCCGTACCCCCGTGGTCT<br>TTGAATAAAGTCTGAGTGGGCGGC (SEQ ID NO: 5) |
| HSV-2<br>SgB_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGCGCGGGGGGGGCTTAGT<br>TTGCGCGCTGGTCGTGGGGGCGCTCGTAGCCGCGGTCGCGTCGGCGGCTCCGGCTGC<br>CCCACGCGCTTCAGGTGGTGTCGCTGCGACCGTTGCGGCGAATGGTGGTCCCGCCAG |

TABLE 1-continued

| | |
|---|---|
| | CCAACCGCCTCCCGTCCCGAGCCCCGCGACCACTAAGGCCCGGAAGCGGAAGACCA<br>AGAAGCCACCCAAGCGGCCCGAGGCGACTCCGCCCCCAGACGCCAACGCGACCGTC<br>GCCGCCGGCCACGCCACTCTGCGTGCGCACCTGCGGGAAATCAAGGTCGAGAACGC<br>GGACGCCCAGTTTTACGTGTGCCCGCCGCCGACTGGCGCCACGGTGGTGCAGTTTGA<br>GCAACCTAGGCGCTGCCCGACGCGACCAGAGGGGCAGAACTACACCGAGGGCATAG<br>CGGTGGTCTTTAAGGAAAACATCGCCCCGTACAAATTCAAGGCCACCATGTACTACA<br>AAGACGTGACCGTGTCGCAGGTGTGGTTCGGCCACCGCTACTCCCAGTTTATGGGGA<br>TATTCGAGGACCGCGCCCCCGTTCCCTTCGAAGAGGTGATTGACAAAATTAACGCCA<br>AGGGGGTCTGCCGCAGTACGGCGAAGTACGTCCGGAACAACATGGAGACCACTGCC<br>TTCCACCGGGACGACCACGAAACAGACATGGAGCTCAAACCGGCGAAAGTCGCCAC<br>GCGCACGAGCCGGGGGTGGCACACCACCGACCTCAAATACAATCCTTCGCGGGTGG<br>AAGCATTCCATCGGTATGGCACGACCGTCAACTGTATCGTAGAGGAGGTGGATGCG<br>CGGTCGGTGTACCCCTACGATGAGTTCGTGCTGGCAACGGGCGATTTTGTGTACATG<br>TCCCCTTTTTACGGCTACCGGGAAGGTAGTCACACCGAGCACACCAGTTACGCCGCC<br>GACCGCTTTAAGCAAGTGGACGGCTTCTACGCGCGCGACCTCACCACAAAGGCCCG<br>GGCCACGTCGCCGACGACCCGCAATTTGCTGACGACCCCCAAGTTTACCGTGGCCTG<br>GGACTGGGTGCCTAAGCGACCGGCGGTCTGTACCATGACAAAGTGGCAGGAGGTGG<br>ACGAAATGCTCCGCGCTGAATACGGTGGCTCTTTCCGCTTCTCTTCCGACGCCATCTC<br>CACCACGTTCACCACCAACCTGACCCAATACTCGCTCTCGAGAGTCGATCTGGGAGA<br>CTGCATTGGCCGGGATGCCCGCGAGGCAATTGACCGCATGTTCGCGCGCAAGTACA<br>ACGCTACGCACATAAAGGTTGGCCAACCCCAGTACTACCTAGCCACGGGGGGCTTCC<br>TCATCGCTTATCAACCCCTCCTCAGCAACACGCTCGCCGAGCTGTACGTGCGGGAAT<br>ATATGCGGGAACAGGACCGCAAACCCCGAAACGCCACGCCCGCGCCGCTGCGGGAA<br>GCACCGAGCGCCAACGCGTCCGTGGAGCGCATCAAGACGACATCCTCGATTGAGTTT<br>GCTCGTCTGCAGTTTACGTATAACCACATACAGCGCCATGTAAACGACATGCTCGGG<br>CGCATCGCCGTCGCGTGGTGCGAGCTCCAAAATCACGAGCTCACTCTGTGGAACGAG<br>GCACGCAAGCTCAATCCCAACGCCATCGCATCCGCCACCGTAGGCCGGCGGGTGAG<br>CGCTCGCATGCTCGGGGATGTCATGGCCGTCTCCACGTGCGTGCCCGTCGCCCCGGA<br>CAACGTGATCGTGCAAAATAGCATGCGCGTTTCTTCGCGGCCGGGGACGTGCTACAG<br>CCGCCCGCTGGTTAGCTTTCGGTACGAAGACCAAGGCCCGCTGATTGAGGGGCAGCT<br>GGGTGAGAACAACGAGCTGCGCCTCACCCGCGATGCGTTAGAGCCGTGTACCGTCG<br>GCCACCGGCGCTACTTCATCTTCGGAGGGGGATACGTATACTTCGAAGAATATGCGT<br>ACTCTCACCAATTGAGTCGCGCCGATGTCACCACTGTTAGCACCTTCATCGACCTGA<br>ACATCACCATGCTGGAGGACCACGAGTTCGTGCCCCTGGAGGTCTACACACGCCACG<br>AGATCAAGGATTCCGGCCTACTGGACTACACCGAAGTCCAGAGACGAAATCAGCTG<br>CACGATCTCCGCTTTGCTGACATCGATACTGTTATCCGCGCCGACGCCAACGCCGCC<br>ATGTTCGCAGGTCTGTGTGCGTTTTTCGAGGGTATGGGTGACTTAGGGCGCGCGGTG<br>GGCAAGGTCGTCATGGGGGTAGTCGGGGGCGTGGTGTCGGCCGTCTCGGGCGTCTCC<br>TCCTTTATGTCTAACCCCTGATAATAGGCTGGAGCCTCGGTGGCCATGCTTCTTGCCC<br>CTTGGGCCTCCCCCCAGCCCCTCCTCCCCTTCCTGCACCCGTACCCCCGTGGTCTTTG<br>AATAAAGTCTGAGTGGGCGGC (SEQ ID NO: 6) |
| HSV-2<br>SgC_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGGCCCTTGGACGGGTGGG<br>CCTAGCCGTGGGCCTGTGGGGCCTGCTGTGGGTGGGTGTTGTCGTGGTGCTGGCCAA<br>TGCCTCCCCTGGACGCACGATAACGGTGGGCCCGCGGGGGAACGCGAGCAATGCCG<br>CCCCATCCGCGTCCCCGCGGAACGCATCCGCCCCCCGAACCACACCCACTCCCCCCC<br>AACCCCGCAAAGCGACGAAAAGTAAGGCCTCCACCGCCAAACCGGCCCCGCCCCCC<br>AAGACCGGGCCCCCGAAGACATCTTCTGAGCCCGTGCGCTGCAACCGCCACGACCC<br>GCTGGCCCGGTACGGCTCGCGGGTGCAAATCCGATGTCGATTTCCCAACTCCACTCG<br>CACGGAATCCCGCCTCCAGATCTGGCGTTATGCCACGGCGACGGACGCCGAGATTG<br>GAACTGCGCCTAGCTTAGAGGAGGTGATGGTAAACGTGTCGGCCCCGCCCGGGGGC<br>CAACTGGTGTATGATAGCGCACCTAACCGAACGGACCCGCACGTGATTTGGGCGGA<br>GGGCGCCGGACCTGGCGCCTCACCGCGGCTGTACTCGGTCGTCGGGCCGCTGGGTCG<br>GCAGAGACTTATCATCGAAGAGCTGACCCTCGAGACACAGGGCATGTATTATTGGGT<br>GTGGGGCCGGACGGACCGCCCGTCCGCGTACGGGACCTGGGTGCGCGTTCGCGTGTT<br>CCGCCCTCCTTCGCTGACCATCCACCCCCACGCGGTGCTGGAGGGCCAGCCGTTTAA<br>AGCGACGTGCACCGCCGCCACCTACTACCCGGGCAACCGCGCGGAGTTCGTCTGGTT<br>CGAGGACGGTCGCCGGGTATTCGATCCGGCCCAGATACATACGCAGACGCAGGAAA<br>ACCCCGACGGCTTTTCCACCGTCTCCACCGTGACCTCCGCGGCCGTCGGCGGCCAGG<br>GCCCCCCGCGCACCTTCACCTGTCAGCTGACGTGGCACCGCGACTCCGTGTCGTTCT<br>CTCGGCGCAATGCCAGCGGCACGGCATCGGTGCTGCCACGGCCAACCATTACCATG<br>GAGTTTACGGGCGACCATGCGGTCTGCACGGCCGGCTGTGTGCCCGAGGGGGTGAC<br>GTTTGCCTGGTTCCTGGGGGACGACTCCTCGCCGGCCGAGAAGGTGGCCGTCGCGTC<br>CCAGACCTCGTGCGGTCGCCCCGGCACCGCCACGATCCGCTCCACACTGCCGGTCTC<br>GTACGAGCAGACCGAGTACATCTGCCGGCTGGCGGGATACCCGGACGGAATTCCGG<br>TCCTAGAGCACCATGGCAGCCACCAGCCCCCGCCGCGGGACCCCACCGAACGGCAG<br>GTGATTCGGGCAGTGGAAGGGTGATAATAGGCTGGAGCCTCGGTGGCCATGCTTCTT<br>GCCCCTTGGGCCTCCCCCCAGCCCCTCCTCCCCTTCCTGCACCCGTACCCCCGTGGTC<br>TTTGAATAAAGTCTGAGTGGGCGGC (SEQ ID NO: 7) |
| HSV-2<br>SgE_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGGCTCGCGGGGCCGGGTT<br>GGTGTTTTTTGTTGGAGTTTGGGTCGTATCGTGCCTGGCGGCAGCACCCAGAACGTC<br>CTGGAAACGGGTTACCTCGGGCGAGGACGTGGTGTTGCTTCCGGCGCCCGCGGGGC<br>CGGAGGAACGCACACGGGCCCACAAACTACTGTGGGCCGCGGAACCCCTGGATGCC<br>TGCGGTCCCCTGAGGCCGTCGTGGGTGGCGCTGTGGCCCCCGCGACGGGTGCTCGAA<br>ACGGTCGTGGATGCGGCGTGCATGCGCGCCCCGGAACCGCTCGCCATAGCATACAG<br>TCCCCCGTTCCCCGCGGGCGACGAGGGACTGTATTCGGAGTTGGCGTGGCGCGATCG<br>CGTAGCCGTGGTCAACGAGAGTCTGGTCATCTACGGGGCCCTGGAGACGGACAGCG |

TABLE 1-continued

| | |
|---|---|
| | GTCTGTACACCCTGTCCGTGGTCGGCCTAAGCGACGAGGCGCGCCAAGTGGCGTCGG<br>TGGTTCTGGTCGTGGAGCCCGCCCCTGTGCCGACCCCGACCCCGACGACTACGACG<br>AAGAAGACGACGCGGGCGTGAGCGAACGCACGCCGGTCAGCGTACCCCCCCCGACC<br>CCACCCCGTCGTCCCCCCGTCGCCCCCCCTACGCACCCTCGTGTTATCCCCGAGGTGT<br>CCCACGTGCGCGGGGTAACGGTCCATATGGAGACCCCGGAGGCCATTCTGTTTGCCC<br>CCGGAGAGACGTTTGGGACGAACGTCTCCATCCACGCCATTGCCCATGACGACGGTC<br>CGTACGCCATGGACGTCGTCTGGATGCGGTTTGACGTGCCGTCCTCGTGCGCCGAGA<br>TGCGGATCTACGAAGCTTGTCTGTATCACCCGCAGCTTCCAGAATGTCTATCTCCGG<br>CCGACGCGCCGTGCGCTGTAAGTTCCTGGGCGTACCGCCTGGCGGTCCGCAGCTACG<br>CCGGCTGTTCCAGGACTACGCCCCCGCCGCGATGTTTTGCCGAGGCTCGCATGGAAC<br>CGGTCCCGGGGTTGGCGTGGTTAGCCTCCACCGTCAACCTGGAATTCCAGCACGCCT<br>CCCCTCAGCACGCCGGCCTTTACCTGTGCGTGGTGTACGTGGACGATCATATCCACG<br>CCTGGGGCCACATGACCATCTCTACCGCGGCGCAGTACCGGAACGCGGTGGTGGAA<br>CAGCACTTGCCCCAGCGCCAGCCTGAACCCGTCGAGCCCACCCGCCCGCACGTAAG<br>AGCACCCCCTCCCGCGCCTTCCGCGCGCGGCCCGCTGCGCTGATAATAGGCTGGAGC<br>CTCGGTGGCCATGCTTCTTGCCCCTTGGGCCTCCCCCCAGCCCCTCCTCCCCTTCCTG<br>CACCCGTACCCCCGTGGTCTTTGAATAAAGTCTGAGTGGGCGGC (SEQ ID NO: 8) |
| HSV-2 ICP-4 | TCAAGCTTTTGGACCCTCGTACAGAAGCTAATACGACTCACTATAGGGAAATAAGAG<br>AGAAAAGAAGAGTAAGAAGAAATATAAGAGCCACCATGTCGGCGGAGCAGCGGAA<br>GAAGAAGAAGACGACGACGACGACGCAGGGCCGCGGGGCCGAGGTCGCGATGGCG<br>GACGAGGACGGGGGACGTCTCCGGGCCGCGGCGGAGACGACCGGCGGCCCCGGATC<br>TCCGGATCCAGCCGACGGACCGCCGCCCACCCCGAACCCGGACCGTCGCCCCGCCG<br>CGCGGCCCGGGTTCGGGTGGCACGGTGGGCCGGAGGAGAACGAAGACGAGGCCGA<br>CGACGCCGCCGCCGATGCCGATGCCGACGAGGCGGCCCCGGCGTCCGGGGAGGCCG<br>TCGACGAGCCTGCCGCGGACGGCGTCGTCTCGCCGCGGCAGCTGGCCCTGCTGGCCT<br>CGATGGTGGACGAGGCCGTTCGCACGATCCCGTCGCCCCCCCGGAGCGCGACGGC<br>GCGCAAGAAGAAGCGGCCCGCTCGCCTTCTCCGCCGCGGACCCCCTCCATGCGCGCC<br>GATTATGGCGAGGAGAACGACGACGACGACGACGACGACGATGACGACGACCGCG<br>ACGCGGGCCGCTGGGTCCGCGGACCGGAGACGACGTCCGCGGTCCGCGGGGCGTAC<br>CCGGACCCCATGGCCAGCCTGTCGCCGCGACCCCCGGCGCCCCGCCGACACCACCA<br>CCACCACCACCACCGCCGCCGGCGCGCCCCCCGCCGGCGCTCGGCCGCCTCTGACTC<br>ATCAAAATCCGGATCCTCGTCGTCGGCGTCCTCCGCCTCCTCCTCCGCCTCCTCCTCC<br>TCGTCTGCATCCGCCTCCTCGTCTGACGACGACGACGACGACGACGCCGCCCGCGCC<br>CCCGCCAGCGCCGCAGACCACGCCGCGGGCGGGACCCTCGGCGCGGACGACGAGGA<br>GGCGGGGGTGCCCGCGAGGGCCCCGGGGGCGGCGCCCCGGCCGAGCCCGCCCAGG<br>GCCGAGCCCGCCCCGGCCCGGACCCCCGCGGCGACCGCGGGCCGCCTGGAGCGCCG<br>CCGGGCCCGCGCGGCGGTGGCCGGCCGCGACGCCACGGGCCGCTTCACGGCCGGGC<br>GGCCCCGGCGGGTCGAGCTGGACGCCGACGCGGCCTCCGGCGCCTTCTACGCGCGC<br>TACCGCGACGGGTACGTCAGCGGGGAGCCGTGGCCCGGGGCCGGCCCCCCGCCCCC<br>GGGGCGCGTGCTGTACGGCGGGCTGGGCGACAGCCGCCCCGGCCTCTGGGGGGCGC<br>CCGAGGCGGAGGAGGCGCGGGCCCGGTTCGAGGCCTCGGGCGCCCCGGCGCCCGTG<br>TGGGCGCCCGAGCTGGGCGACGCGGCGCAGCAGTACGCCCTGATCACGCGGCTGCT<br>GTACACGCCGGACGCGGAGGCGATGGGGTGGCTCCAGAACCCGCGCGTGGCGCCCG<br>GGGACGTGGCGCTGGACCAGGCCTGCTTCCGGATCTCGGGCGCGGCGCGCAACAGC<br>AGCTCCTTCATCTCCGGCAGCGTGGCGCGGGCCGTGCCCCACCTGGGGTACGCCATG<br>GCGGCGGGCCGCTTCGGCTGGGGCCTGGCGCACGTGGCGGCCGCCGTGGCCATGAG<br>CCGCCGCTACGACCGCGCGCAGAAGGGCTTCCTGCTGACCAGCCTGCGCCGCGCCTA<br>CGCGCCCCTGCTGGCGCGCGAGAACGCGGCGCTGACCGGGGCGCGAACCCCCGACG<br>ACGGCGGCGACGCCAACCGCCACGACGGCGACGACGCCCGCGGGAAGCCCGCCGCC<br>GCCGCCGCCCCGTTGCCGTCGGCGGCGGCGTCGCCGGCCGACGAGCGCGCGGTGCC<br>CGCCGGCTACGGCGCCGCGGGGGTGCTCGCCGCCCTGGGGCGCCTGAGCGCCGCGC<br>CCGCCTCCGCGCCGGCCGGGGCCGACGACGACGACGACGACGGCGCCGGCGGT<br>GGTGGCGGCGGCCGGCGCGCGGAGGCGGGCCGCGTGGCCGTGGAGTGCCTGGCCGC<br>CTGCCGCGGGATCCTGGAGGCGCTGGCGGAGGGCTTCGACGGCGACCTGGCGGCCG<br>TGCCGGGGCTGGCCGGAGCCCGGCCCGCCGCGCCCCCGCGCCCGGGGCCCGCGGGC<br>GCGGCCGCCCCGCCGCACGCCGACGCGCCCCGCCTGCGCGCCTGGCTGCGCGAGCT<br>GCGGTTCGTGCGCGACGCGCTGGTGCTGATGCGCCTGCGCGGGGACCTGCGCGTGGC<br>CGGCGGCAGCGAGGCCGCCGTGGCCGCCGTGCGCGCCGTGAGCCTGGTCGCCGGGG<br>CCCTGGGCCCGGCGCTGCCGCGGAGCCCGCGCCTGCTGAGCTCCGCCGCCGCCGCCG<br>CCGCGGACCTGCTCTTCCAGAACCAGAGCCTGCGCCCCCTGCTGGCCGACACCGTCG<br>CCGCGGCCGACTCGCTCGCCGCGCCCGCCTCCGCGCCGCGGGAGGCCGCGGACGCC<br>CCCCGCCCCGCGGCCGCCCCTCCCGCGGGGGCCGCGCCCCCCGCCCCGCCGACGCCG<br>CCGCCGCGGCCGCCGCGCCCCGCGGCGCTGACCCGCCGGCCCGCCGAGGGCCCCGA<br>CCCGCAGGGCGGCTGGCGCCGCCAGCCGCCGGGGCCCAGCCACACGCCGGCGCCCT<br>CGGCCGCCGCCCTGGAGGCCTACTGCGCCCCGCGGGCCGTGGCCGAGCTCACGGAC<br>CACCCGCTCTTCCCCGCGCCGTGGCGCCCGGCCCTCATGTTCGACCCGCGCGCGCTG<br>GCCTCGCTGGCCGCGCGCTGCGCCGCCCCGCCCCCCGGCGGCGCGCCCGCCGCCTTC<br>GGCCCGCTGCGCGCCTCGGGCCCGCTGCGCCGCGCGGCGGCCTGGATGCGCCAGGT<br>GCCCGACCCGGAGGACGTGCGCGTGGTGATCCTCTACTCGCCGCTGCCGGGCGAGG<br>ACCTGGCCGCGGGCCGCGCCGGGGGCGGGCCCCCCCGGAGTGGTCCGCCGAGCGC<br>GGCGGGCTGTCCTGCCTGCTGGCGGCCCTGGGCAACCGGCTCTGCGGGCCCGCCACG<br>GCCGCCTGGGCGGGCAACTGGACCGGCGCCCCCGACGTCTCGGCGCTGGGCGCGCA<br>GGGCGTGCTGCTGCTGTCCACGCGGGACCTGGCCTTCGCCGGCGCCGTGGAGTTCCT<br>GGGGCTGCTGGCCGGCGCCTGCGACCGCCGCCTCATCGTCGTCAACGCCGTGCGCGC<br>CGCGGCCTGGCCCGCCGCTGCCCCCGTGGTCTCGCGGCAGCACGCCTACCTGGCCTG<br>CGAGGTGCTGCCCGCCGTGCAGTGCGCCGTGCGCTGGCCGGCGGCGCGGGACCTGC<br>GCCGCACCGTGCTGGCCTCCGGCCGCGTGTTCGGGCCGGGGGTCTTCGCGCGCGTGG<br>AGGCCGCGCACGCGCGCCTGTACCCCGACGCGCCGCCGCTGCGCCTCTGCCGCGGG<br>GCCAACGTGCGGTACCGCGTGCGCACGCGCTTCGGCCCCGACACGCTGGTGCCCATG |

TABLE 1-continued

| | |
|---|---|
| | TCCCCGCGCGAGTACCGCCGCGCCGTGCTCCCGGCGCTGGACGGCCGGGCCGCCGC<br>CTCGGGCGCGGGCGACGCCATGGCGCCCGGCGCGCCGGACTTCTGCGAGGACGAGG<br>CGCACTCGCACCGCGCCTGCGCGCGCTGGGGCCTGGGCGCGCCGCTGCGGCCCGTCT<br>ACGTGGCGCTGGGGCGCGACGCCGTGCGCGGCGGCCCGGCGGAGCTGCGCGGGCCG<br>CGGCGGGAGTTCTGCGCGCGGGCGCTGCTCGAGCCCGACGGCGACGCGCCCCCGCT<br>GGTGCTGCGCGACGACGCGGACGCGGGCCCGCCCCCGCAGATACGCTGGGCGTCGG<br>CCGCGGGCCGCGCGGGGACGGTGCTGGCCGCGGCGGGCGGCGGCGTGGAGGTGGTG<br>GGGACCGCCGCGGGGCTGGCCACGCCGCCGAGGCGCGAGCCCGTGGACATGGACGC<br>GGAGCTGGAGGACGACGACGACGGACTGTTTGGGGAGTGATGATAATAGGCTGGAG<br>CCTCGGTGGCCATGCTTCTTGCCCCTTGGGCCTCCCCCCAGCCCCTCCTCCCCTTCCT<br>GCACCCGTACCCCCGTGGTCTTTGAATAAAGTCTGAGTGGGCGGC (SEQ ID NO: 9) |
| HSV-2 SgI_DX | TCAAGCTTTTGGACCCTCGTACAGAAGCTAATACGACTCACTATAGGGAAATAAGAG<br>AGAAAAGAAGAGTAAGAAGAAATATAAGAGCCACCATGCCCGGCCGCTCGCTGCAG<br>GGCCTGGCGATCCTGGGCCTGTGGGTCTGCGCCACCGGCCTGGTCGTCCGCGGCCCC<br>ACGGTCAGTCTGGTCTCAGACTCACTCGTGGATGCCGGGGCCGTGGGGCCCCAGGGC<br>TTCGTGGAAGAGGACCTGCGTGTTTTCGGGGAGCTTCATTTTGTGGGGGCCCAGGTC<br>CCCCACACAAACTACTACGACGGCATCATCGAGCTGTTTCACTACCCCCTGGGGAAC<br>CACTGCCCCCGCGTTGTACACGTGGTCACACTGACCGCATGCCCCCGCCGCCCCGCC<br>GTGGCGTTCACCTTGTGTCGCTCGACGCACCACGCCCACAGCCCCGCCTATCCGACC<br>CTGGAGCTGGGTCTGGCGCGGCAGCCGCTTCTGCGGGTTCGAACGGCAACGCGCGA<br>CTATGCCGGTCTGTATGTCCTGCGCGTATGGGTCGGCAGCGCGACGAACGCCAGCCT<br>GTTTGTTTTGGGGGTGGCGCTCTCTGCCAACGGGACGTTTGTGTATAACGGCTCGGA<br>CTACGGCTCCTGCGATCCGGCGCAGCTTCCCTTTTCGGCCCCGCGCCTGGGACCCTC<br>GAGCGTATACACCCCCGGAGCCTCCCGGCCCACCCCTCCACGGACAACGACATCCCC<br>GTCCTCCCCTAGAGACCCGACCCCCGCCCCCGGGGACACAGGAACGCCTGCGCCCG<br>CGAGCGGCGAGAGAGCCCCGCCCAATTCCACGCGATCGGCCAGCGAATCGAGACAC<br>AGGCTAACCGTAGCCCAGGTAATCCAGTGATAATAGGCTGGAGCCTCGGTGGCCAT<br>GCTTCTTGCCCCTTGGGCCTCCCCCCAGCCCCTCCTCCCCTTCCTGCACCCGTACCCC<br>CGTGGTCTTTGAATAAAGTCTGAGTGGGCGGC (SEQ ID NO: 10) |
| HSV-2 SgD | TCAAGCTTTTGGACCCTCGTACAGAAGCTAATACGACTCACTATAGGGAAATAAGAG<br>AGAAAAGAAGAGTAAGAAGAAATATAAGAGCCACCATGGGGCGTTTGACCTCCGGC<br>GTCGGGACGGCGGCCCTGCTAGTTGTCGCGGTGGGACTCCGCGTCGTCTGCGCCAAA<br>TACGCCTTAGCAGACCCCTCGCTTAAGATGGCCGATCCCAATCGATTTCGCGGGAAG<br>AACCTTCCGGTTTTGGACCAGCTGACCGACCCCCCCGGGGTGAAGCGTGTTTACCAC<br>ATTCAGCCGAGCCTGGAGGACCCGTTCCAGCCCCCCAGCATCCCGATCACTGTGTAC<br>TACGCAGTGCTGGAACGTGCCTGCCGCAGCGTGCTCCTACATGCCCCATCGGAGGCC<br>CCCCAGATCGTGCGCGGGGCTTCGGACGAGGCCCGAAAGCACACGTACAACCTGAC<br>CATCGCCTGGTATCGCATGGGAGACAATTGCGCTATCCCCATCACGGTTATGGAATA<br>CACCGAGTGCCCCTACAACAAGTCGTTGGGGGTCTGCCCCATCCGAACGCAGCCCCG<br>CTGGAGCTACTATGACAGCTTTAGCGCCGTCAGCGAGGATAACCTGGGATTCCTGAT<br>GCACGCCCCCGCCTTCGAGACCGCGGGTACGTACCTGCGGCTAGTGAAGATAAACG<br>ACTGGACGGAGATCACACAATTTATCCTGGAGCACCGGGCCCGCGCCTCCTGCAAGT<br>ACGCTCTCCCCCTGCGCATCCCCCCGGCAGCGTGCCTCACCTCGAAGGCCTACCAAC<br>AGGGCGTGACGGTCGACAGCATCGGGATGCTACCCCGCTTTATCCCCGAAAACCAG<br>CGCACCGTCGCCCTATACAGCTTAAAAATCGCCGGGTGGCACGGCCCCAAGCCCCC<br>GTACACCAGCACCCTGCTGCCGCCGGAGCTGTCCGACACCACCAACGCCACGCAAC<br>CCGAACTCGTTCCGGAAGACCCCGAGGACTCGGCCCTCTTAGAGGATCCCGCCGGG<br>ACGGTGTCTTCGCAGATCCCCCCAAACTGGCACATCCCGTCGATCCAGGACGTCGCG<br>CCGCACCACGCCCCCGCCGCCCCCAGCAACCCGTGATAATAGGCTGGAGCCTCGGT<br>GGCCATGCTTCTTGCCCCTTGGGCCTCCCCCCAGCCCCTCCTCCCCTTCCTGCACCCG<br>TACCCCCGTGGTCTTTGAATAAAGTCTGAGTGGGCGGC (SEQ ID NO: 11) |
| HSV-2 gB | ATGCGCGGGGGGGGCTTGGTTTGCGCGCTGGTCGTGGGGGCGCTGGTGGCCGCGGT<br>GGCGTCGGCGGCCCCGGCGGCCCCCCGCGCCTCGGGCGGCGTGGCCGCGACCGTCG<br>CGGCGAACGGGGGTCCCGCCTCCCAGCCGCCCCCCGTCCCGAGCCCCGCGACCACC<br>AAGGCCCGGAAGCGGAAAACCAAAAAGCCGCCCAAGCGGCCCGAGGCGACCCCGC<br>CCCCCGACGCCAACGCGACCGTCGCCGCCGGCCACGCCACGCTGCGCGCGCACCTG<br>CGGGAAATCAAGGTCGAGAACGCCGATGCCCAGTTTTACGTGTGCCCGCCCCCGAC<br>GGGCGCCACGGTGGTGCAGTTTGAGCAGCCGCGCCGCTGCCCGACGCGCCCGGAGG<br>GGCAGAACTACACGGAGGGCATCGCGGTGGTCTTCAAGGAGAACATCGCCCCGTAC<br>AAATTCAAGGCCACCATGTACTACAAAGACGTGACCGTGTCGCAGGTGTGGTTCGGC<br>CACCGCTACTCCCAGTTTATGGGGATATTCGAGGACCGCGCCCCCGTTCCCTTCGAG<br>GAGGTGATCGACAAGATTAACGCCAAGGGGGTCTGCCGCTCCACGGCCAAGTACGT<br>GCGGAACAACATGGAGACCACCGCGTTTCACCGGGACGACCACGAGACCGACATGG<br>AGCTCAAGCCGGCGAAGGTCGCCACGCGCACGAGCCGGGGGTGGCACACCACCGAC<br>CTCAAGTACAACCCCTCGCGGGTGGAGGCGTTCCATCGGTACGGCACGACGGTCAA<br>CTGCATCGTCGAGGAGGTGGACGCGCGGTCGGTGTACCCGTACGATGAGTTTGTGCT<br>GGCGACGGGCGACTTTGTGTACATGTCCCCGTTTTACGGCTACCGGGAGGGGTCGCA<br>CACCGAGCACACCAGCTACGCCGCCGACCGCTTCAAGCAGGTCGACGGCTTCTACG<br>CGCGCGACCTCACCACGAAGGCCCGGGCCACGTCGCCGACGACCCGCAACTTGCTG<br>ACGACCCCCAAGTTTACCGTGGCCTGGGACTGGGTGCCGAAGCGACCGGCGGTCTG<br>CACCATGACCAAGTGGCAGGAGGTGGACGAGATGCTCCGCGCCGAGTACGGCGGCT<br>CCTTCCGCTTCTCCTCCGACGCCATCTCGACCACCTTCACCACCAACCTGACCCAGTA<br>CTCGCTCTCGCGCGTCGACCTGGGCGACTGCATCGGCCGGGATGCCCGCGAGGCCAT<br>CGACCGCATGTTTGCGCGCAAGTACAACGCCACGCACATCAAGGTGGGCCAGCCGC<br>AGTACTACCTGGCCACGGGGGGCTTCCTCATCGCGTACCAGCCCCTCCTCAGCAACA<br>CGCTCGCCGAGCTGTACGTGCGGGAGTACATGCGGGAGCAGGACCGCAAGCCCCGG<br>AATGCCACGCCCGCGCCACTGCGGGAGGCGCCCAGCGCCAACGCGTCCGTGGAGCG |

TABLE 1-continued

| | |
|---|---|
| | CATCAAGACCACCTCCTCGATCGAGTTCGCCCGGCTGCAGTTTACGTATAACCACAT<br>ACAGCGCCACGTGAACGACATGCTGGGGCGCATCGCCGTCGCGTGGTGCGAGCTGC<br>AGAACCACGAGCTGACTCTCTGGAACGAGGCCCGCAAGCTCAACCCCAACGCCATC<br>GCCTCCGCCACCGTCGGCCGGCGGGTGAGCGCGCGCATGCTCGGAGACGTCATGGC<br>CGTCTCCACGTGCGTGCCCGTCGCCCCGGACAACGTGATCGTGCAGAACTCGATGCG<br>CGTCAGCTCGCGGCCGGGGACGTGCTACAGCCGCCCCCTGGTCAGCTTTCGGTACGA<br>AGACCAGGGCCCGCTGATCGAGGGGCAGCTGGGCGAGAACAACGAGCTGCGCCTCA<br>CCCGCGACGCGCTCGAGCCGTGCACCGTGGGCCACCGGCGCTACTTCATCTTCGGCG<br>GGGGCTACGTGTACTTCGAGGAGTACGCGTACTCTCACCAGCTGAGTCGCGCCGACG<br>TCACCACCGTCAGCACCTTCATCGACCTGAACATCACCATGCTGGAGGACCACGAGT<br>TTGTGCCCCTGGAGGTCTACACGCGCCACGAGATCAAGGACAGCGGCCTGCTGGACT<br>ACACGGAGGTCCAGCGCCGCAACCAGCTGCACGACCTGCGCTTTGCCGACATCGAC<br>ACGGTCATCCGCGCCGACGCCAACGCCGCCATGTTCGCGGGGCTGTGCGCGTTCTTC<br>GAGGGGATGGGGGACTTGGGGCGCGCGGTCGGCAAGGTCGTCATGGGAGTAGTGGG<br>GGGCGTGGTGTCGGCCGTCTCGGGCGTGTCCTCCTTTATGTCCAACCCCTTCGGGGC<br>GCTTGCCGTGGGGCTGCTGGTCCTGGCCGGCCTGGTCGCGGCCTTCTTCGCCTTCCGC<br>TACGTCCTGCAACTGCAACGCAATCCCATGAAGGCCCTGTATCCGCTCACCACCAAG<br>GAACTCAAGACTTCCGACCCCGGGGGCGTGGGCGGGGAGGGGGAGGAAGGCGCGG<br>AGGGGGGCGGGTTTGACGAGGCCAAGTTGGCCGAGGCCCGAGAAATGATCCGATAT<br>ATGGCTTTGGTGTCGGCCATGGAGCGCACGGAACACAAGGCCAGAAAGAAGGGCAC<br>GAGCGCCCTGCTCAGCTCCAAGGTCACCAACATGGTTCTGCGCAAGCGCAACAAAG<br>CCAGGTACTCTCCGCTCCACAACGAGGACGAGGCCGGAGACGAAGACGAGCTCTAA<br>(SEQ ID NO: 12) |
| HSV-2 gC | ATGGCCCTTGGACGGGTGGGCCTAGCCGTGGGCCTGTGGGGCCTGCTGTGGGTGGGT<br>GTGGTCGTGGTGCTGGCCAATGCCTCCCCCGGACGCACGATAACGGTGGGCCCGCG<br>GGGGAACGCGAGCAATGCCGCCCCCTCCGCGTCCCCGCGGAACGCATCCGCCCCCC<br>GAACCACACCCACGCCCCCCCAACCCCGCAAGGCGACGAAAAGTAAGGCCTCCACC<br>GCCAAACCGGCCCCGCCCCCCAAGACCGGGCCCCCGAAGACATCCTCGGAGCCCGT<br>GCGATGCAACCGCCACGACCCGCTGGCCCGGTACGGCTCGCGGGTGCAAATCCGAT<br>GCCGGTTTCCCAACTCCACCCGCACGGAGTCCCGCCTCCAGATCTGGCGTTATGCCA<br>CGGCGACGGACGCCGAGATCGGAACGGCGCCTAGCTTAGAGGAGGTGATGGTAAAC<br>GTGTCGGCCCCGCCCGGGGGCCAACTGGTGTATGACAGCGCCCCCAACCGAACGGA<br>CCCGCACGTGATCTGGGCGGAGGGCGCCGGCCCGGGCGCCAGCCCGCGGCTGTACT<br>CGGTCGTCGGGCCGCTGGGTCGGCAGCGGCTCATCATCGAAGAGCTGACCCTGGAG<br>ACCCAGGGCATGTACTACTGGGTGTGGGGCCGGACGGACCGCCCGTCCGCGTACGG<br>GACCTGGGTGCGCGTTCGCGTGTTCCGCCCTCCGTCGCTGACCATCCACCCCCACGC<br>GGTGCTGGAGGGCCAGCCGTTTAAGGCGACGTGCACGGCCGCCACCTACTACCCGG<br>GCAACCGCGCGGAGTTCGTCTGGTTCGAGGACGGTCGCCGGGTATTCGATCCGGCCC<br>AGATACACACGCAGACGCAGGAGAACCCCGACGGCTTTTCCACCGTCTCCACCGTG<br>ACCTCCGCGGCCGTCGGCGGCCAGGGCCCCCCGCGCACCTTCACCTGCCAGCTGACG<br>TGGCACCGCGACTCCGTGTCGTTCTCTCGGCGCAACGCCAGCGGCACGGCATCGGTG<br>CTGCCGCGGCCAACCATTACCATGGAGTTTACGGGCGACCATGCGGTCTGCACGGCC<br>GGCTGTGTGCCCGAGGGGGTGACGTTTGCCTGGTTCCTGGGGGACGACTCCTCGCCG<br>GCGGAGAAGGTGGCCGTCGCGTCCCAGACATCGTGCGGGCGCCCCGGCACCGCCAC<br>GATCCGCTCCACCCTGCCGGTCTCGTACGAGCAGACCGAGTACATCTGCCGGCTGGC<br>GGGATACCCGGACGGAATTCCGGTCCTAGAGCACCACGGCAGCCACCAGCCCCCGC<br>CGCGGGACCCCACCGAGCGGCAGGTGATCCGGGCGGTGGAGGGGGCGGGGATCGG<br>AGTGGCTGTCCTTGTCGCGGTGGTTCTGGCCGGGACCGCGGTAGTGTACCTCACCCA<br>CGCCTCCTCGGTGCGCTATCGTCGGCTGCGGTAA (SEQ ID NO: 13) |
| HSV-2 gD | ATGGGGCGTTTGACCTCCGGCGTCGGGACGGCGGCCCTGCTAGTTGTCGCGGTGGGA<br>CTCCGCGTCGTCTGCGCCAAATACGCCTTAGCAGACCCCTCGCTTAAGATGGCCGAT<br>CCCAATCGATTTCGCGGGAAGAACCTTCCGGTTTTGGACCAGCTGACCGACCCCCCC<br>GGGGTGAAGCGTGTTTACCACATTCAGCCGAGCCTGGAGGACCCGTTCCAGCCCCCC<br>AGCATCCCGATCACTGTGTACTACGCAGTGCTGGAACGTGCCTGCCGCAGCGTGCTC<br>CTACATGCCCCATCGGAGGCCCCCCAGATCGTGCGCGGGGCTTCGGACGAGGCCCG<br>AAAGCACACGTACAACCTGACCATCGCCTGGTATCGCATGGGAGACAATTGCGCTAT<br>CCCCATCACGGTTATGGAATACACCGAGTGCCCCTACAACAAGTCGTTGGGGGTCTG<br>CCCCATCCGAACGCAGCCCCGCTGGAGCTACTATGACAGCTTTAGCGCCGTCAGCGA<br>GGATAACCTGGGATTCCTGATGCACGCCCCCGCCTTCGAGACCGCGGGTACGTACCT<br>GCGGCTAGTGAAGATAAACGACTGGACGGAGATCACACAATTTATCCTGGAGCACC<br>GGGCCCGCGCCTCCTGCAAGTACGCTCTCCCCCTGCGCATCCCCCCGGCAGCGTGCC<br>TCACCTCGAAGGCCTACCAACAGGGCGTGACGGTCGACAGCATCGGGATGCTACCC<br>CGCTTTATCCCCGAAAACCAGCGCACCGTCGCCCTATACAGCTTAAAAATCGCCGGG<br>TGGCACGGCCCCAAGCCCCCGTACACCAGCACCCTGCTGCCGCCGGAGCTGTCCGAC<br>ACCACCAACGCCACGCAACCCGAACTCGTTCCGGAAGACCCCGAGGACTCGGCCCT<br>CTTAGAGGATCCCGCCGGGACGGTGTCTTCGCAGATCCCCCCAAACTGGCACATCCC<br>GTCGATCCAGGACGTCGCGCCGCACCACGCCCCCGCCGCCCCCAGCAACCCGGGCC<br>TGATCATCGGCGCGCTGGCCGGCAGTACCCTGGCGGTGCTGGTCATCGGCGGTATTG<br>CGTTTTGGGTACGCCGCCGCGCTCAGATGGCCCCCAAGCGCCTACGTCTCCCCCACA<br>TCCGGGATGACGACGCGCCCCCCTCGCACCAGCCATTGTTTTACTAG (SEQ ID NO:<br>14) |
| HSV-2 gE | ATGGCTCGCGGGGCCGGGTTGGTGTTTTTTGTTGGAGTTTGGGTCGTATCGTGCCTGG<br>CGGCAGCACCCAGAACGTCCTGGAAACGGGTAACCTCGGGCGAGGACGTGGTGTTG<br>CTTCCGGCGCCCGCGGGGCCGGAGGAACGCACCCGGGCCCACAAACTACTGTGGGC<br>CGCGGAACCCCTGGATGCCTGCGGTCCCCTGCGCCCGTCGTGGGTGGCGCTGTGGCC<br>CCCCCGACGGGTGCTCGAGACGGTCGTGGATGCGGCGTGCATGCGCGCCCCGGAAC<br>CGCTCGCCATAGCATACAGTCCCCCGTTCCCCGCGGGCGACGAGGGACTGTATTCGG |

TABLE 1-continued

| | |
|---|---|
| | AGTTGGCGTGGCGCGATCGCGTAGCCGTGGTCAACGAGAGTCTGGTCATCTACGGG<br>GCCCTGGAGACGGACAGCGGTCTGTACACCCTGTCCGTGGTCGGCCTAAGCGACGA<br>GGCGCGCCAAGTGGCGTCGGTGGTTCTGGTCGTGGAGCCCGCCCCTGTGCCGACCCC<br>GACCCCCGACGACTACGACGAAGAAGACGACGCGGGCGTGAGCGAACGCACGCCG<br>GTCAGCGTTCCCCCCCCAACCCCCCCCCGTCGTCCCCCCGTCGCCCCCCCGACGCAC<br>CCTCGTGTTATCCCCGAGGTGTCCCACGTGCGCGGGGTAACGGTCCATATGGAGACC<br>CCGGAGGCCATTCTGTTTGCCCCCGGGGAGACGTTTGGGACGAACGTCTCCATCCAC<br>GCCATTGCCCACGACGACGGTCCGTACGCCATGGACGTCGTCTGGATGCGGTTTGAC<br>GTGCCGTCCTCGTGCGCCGAGATGCGGATCTACGAAGCTTGTCTGTATCACCCGCAG<br>CTTCCAGAGTGTCTATCTCCGGCCGACGCGCCGTGCGCCGTAAGTTCCTGGGCGTAC<br>CGCCTGGCGGTCCGCAGCTACGCCGGCTGTTCCAGGACTACGCCCCCGCCGCGATGT<br>TTTGCCGAGGCTCGCATGGAACCGGTCCCGGGGTTGGCGTGGCTGGCCTCCACCGTC<br>AATCTGGAATTCCAGCACGCCTCCCCCCAGCACGCCGGCCTCTACCTGTGCGTGGTG<br>TACGTGGACGATCATATCCACGCCTGGGGCCACATGACCATCAGCACCGCGGCGCA<br>GTACCGGAACGCGGTGGTGGAACAGCACCTCCCCCAGCGCCAGCCCGAGCCCGTCG<br>AGCCCACCCGCCCGCACGTGAGAGCCCCCCCTCCCGCGCCCTCCGCGCGCGGCCCGC<br>TGCGCCTCGGGGCGGTGCTGGGGGCGGCCCTGTTGCTGGCCGCCCTCGGGCTGTCCG<br>CGTGGGCGTGCATGACCTGCTGGCGCAGGCGCTCCTGGCGGGCGGTTAAAAGCCGG<br>GCCTCGGCGACGGGCCCCACTTACATTCGCGTGGCGGACAGCGAGCTGTACGCGGA<br>CTGGAGTTCGGACAGCGAGGGGGAGCGCGACGGGTCCCTGTGGCAGGACCCTCCGG<br>AGAGACCCGACTCTCCCTCCACAAATGGATCCGGCTTTGAGATCTTATCACCAACGG<br>CTCCGTCTGTATACCCCCATAGCGAGGGGCGTAAATCTCGCCGCCCGCTCACCACCT<br>TTGGTTCGGGAAGCCCGGCCGTCGTCACTCCCAGGCCTCCTATTCGTCCGTCCTCTG<br>GTAA (SEQ ID NO: 15) |
| HSV-2 gI | ATGCCCGGCCGCTCGCTGCAGGGCCTGGCGATCCTGGGCCTGTGGGTCTGCGCCACC<br>GGCCTGGTCGTCCGCGGCCCCACGGTCAGTCTGGTCTCAGACTCACTCGTGGATGCC<br>GGGGCCGTGGGGCCCCAGGGCTTCGTGGAAGAGGACCTGCGTGTTTTCGGGGAGCT<br>TCATTTTGTGGGGGCCCAGGTCCCCCACACAAACTACTACGACGGCATCATCGAGCT<br>GTTTCACTACCCCCTGGGGAACCACTGCCCCCGCGTTGTACACGTGGTCACACTGAC<br>CGCATGCCCCCGCCGCCCCGCCGTGGCGTTCACCTTGTGTCGCTCGACGCACCACGC<br>CCACAGCCCCGCCTATCCGACCCTGGAGCTGGGTCTGGCGCGGCAGCCGCTTCTGCG<br>GGTTCGAACGGCAACGCGCGACTATGCCGGTCTGTATGTCCTGCGCGTATGGGTCGG<br>CAGCGCGACGAACGCCAGCCTGTTTGTTTTGGGGGTGGCGCTCTCTGCCAACGGGAC<br>GTTTGTGTATAACGGCTCGGACTACGGCTCCTGCGATCCGGCGCAGCTTCCCTTTTCG<br>GCCCCGCGCCTGGGACCCTCGAGCGTATACACCCCCGGAGCCTCCCGGCCCACCCCT<br>CCACGGACAACGACATCCCCGTCCTCCCCCCGAGACCCGACCCCCGCCCCCGGGGA<br>CACAGGGACGCCCGCGCCCGCGAGCGGCGAGAGAGCCCCGCCCAATTCCACGCGAT<br>CGGCCAGCGAATCGAGACACAGGCTAACCGTAGCCCAGGTAATCCAGATCGCCATA<br>CCGGCGTCCATCATCGCCTTTGTGTTTCTGGGCAGCTGTATCTGCTTCATCCATAGAT<br>GCCAGCGCCGATACAGGCGCCCCCGCGGCCAGATTTACAACCCCGGGGGCGTTTCCT<br>GCGCGGTCAACGAGGCGGCCATGGCCCGCCTCGGAGCCGAGCTGCGATCCCACCCA<br>AACACCCCCCCCAAACCCCGACGCCGTTCGTCGTCGTCCACGACCATGCCTTCCCTA<br>ACGTCGATAGCTGAGGAATCGGAGCCAGGTCCAGTCGTGCTGCTGTCCGTCAGTCCT<br>CGGCCCCGCAGTGGCCCGACGGCCCCCAAGAGGTCTAG (SEQ ID NO: 16) |
| ICP0-2 \| BASED on strain HG52 (inactivated by deletion of the nuclear localization signal and zinc-binding ring finger) | ATGGAACCCCGGCCCGGCACGAGCTCCCGGGCGGACCCCGGCCCCGAGCGGCCGCC<br>GCGGCAGACCCCCGGCACGCAGCCCGCCGCCCCGCACGCCTGGGGGATGCTCAACG<br>ACATGCAGTGGCTCGCCAGCAGCGACTCGGAGGAGGAGACCGAGGTGGGAATCTCT<br>GACGACGACCTTCACCGCGACTCCACCTCCGAGGCGGGCAGCACGGACACGGAGAT<br>GTTCGAGGCGGGCCTGATGGACGCGGCCACGCCCCCGGCCCGGCCCCCGGCCGAGC<br>GCCAGGGCAGCCCCACGCCCGCCGACGCGCAGGGATCCTGTGGGGGTGGGCCCGTG<br>GGTGAGGAGGAAGCGGAAGCGGGAGGGGGGGGCGACGTGAACACCCCGGTGGCGT<br>ACCTGATAGTGGGCGTGACCGCCAGCGGGTCGTTCAGCACCATCCCGATAGTGAAC<br>GACCCCCGGACCCGCGTGGAGGCCGAGGCGGCCGTGCGGGCCGGCACGGCCGTGGA<br>CTTTATCTGGACGGGCAACCCGCGGACGGCCCCGCGCTCCCTGTCGCTGGGGGGACA<br>CACGGTCCGCGCCCTGTCGCCCACCCCCCCGTGGCCCGGCACGGACGACGAGGACG<br>ATGACCTGGCCGACGTGGACTACGTCCCGCCCGCCCCCCGAAGAGCGCCCCGGCGC<br>GGGGGCGGCGGTGCGGGGGCGACCCGCGGAACCTCCCAGCCCGCCGCGACCCGACC<br>GGCGCCCCCTGGCGCCCCGCGGAGCAGCAGCAGCGGCGGCGCCCCGTTGCGGGCGG<br>GGGTGGGATCTGGGTCTGGGGGCGGCCCTGCCGTCGCGGCCGTCGTGCCGAGAGTG<br>GCCTCTCTTCCCCCTGCGGCCGGCGGGGGGCGCGCGCAGGCGCGGCGGGTGGGCGA<br>AGACGCCGCGGCGGCGGAGGGCAGGACGCCCCCCGCGAGACAGCCCCGCGCGGCC<br>CAGGAGCCCCCCATAGTCATCAGCGACTCTCCCCCGCCGTCTCCGCGCCGCCCCGCG<br>GGCCCCGGGCCGCTCTCCTTTGTCTCCTCCTCCTCCGCACAGGTGTCCTCGGCCCCG<br>GGGGGGGAGGTCTGCCACAGTCGTCGGGGCGCGCCGCGCGCCCCCGCGCGGCCGTC<br>GCCCCGCGCGTCCGGAGTCCGCCCCGCGCCGCCGCCGCCCCCGTGGTGTCTGCGAGC<br>GCGGACGCGGCCGGGCCCGCGCCGCCCGCCGTGCCGGTGGACGCGCACCGCGCGCC<br>CCGGTCGCGCATGACCCAGGCTCAGACCGACACCCAAGCACAGAGTCTGGGCCGGG<br>CAGGCGCGACCGACGCGCGCGGGTCGGGAGGGCCGGGCGCGGAGGGAGGATCGGG<br>CCCCGCGGCCTCGTCCTCCGCCTCTTCCTCCGCCGCCCCGCGCTCGCCCCTCGCCCCC<br>CAGGGGGTGGGGGCCAAGAGGGCGGCGCCGCGCCGGGCCCCGGACTCGGACTCGG<br>GCGACCGCGGCCACGGGCCGCTCGCCCCGGCGTCCGCGGGCGCCGCGCCCCCGTCG<br>GCGTCTCCGTCGTCCCAGGCCGCGGTCGCCGCCGCCTCCTCCTCCTCCGCCTCCTCCT<br>CCTCCGCCTCCTCCTCCTCCGCCTCCTCCTCCTCCGCCTCCTCCTCCTCCGCCTCCTCC<br>TCCTCCGCCTCCTCCTCCTCCGCCTCTTCCTCTGCGGGCGGGGCTGGTGGGAGCGTCG<br>CGTCCGCGTCCGGCGCTGGGGAGAGACGAGAAACCTCCCTCGGCCCCCGCGCTGCT<br>GCGCCGCGGGGGCCGAGGAAGTGTGCCAGGAAGACGCGCCACGCGGAGGGCGGCC<br>CCGAGCCCGGGGCCCGCGACCCGGCGCCCGGCCTCACGCGCTACCTGCCCATCGCG<br>GGGGTCTCGAGCGTCGTGGCCCTGGCGCCTTACGTGAACAAGACGGTCACGGGGGA |

TABLE 1-continued

| | |
|---|---|
| | CTGCCTGCCCGTCCTGGACATGGAGACGGGCCACATAGGGGCCTACGTGGTCCTCGT<br>GGACCAGACGGGGAACGTGGCGGACCTGCTGCGGGCCGCGGCCCCCGCGTGGAGCC<br>GCCGCACCCTGCTCCCCGAGCACGCGCGCAACTGCGTGAGGCCCCCCGACTACCCG<br>ACGCCCCCCGCGTCGGAGTGGAACAGCCTCTGGATGACCCCGGTGGGCAACATGCT<br>CTTTGACCAGGGCACCCTGGTGGGCGCGCTGGACTTCCACGGCCTCCGGTCGCGCCA<br>CCCGTGGTCTCGGGAGCAGGGCGCGCCCGCGCCGGCCGGCGACGCCCCCGCGGGCC<br>ACGGGGAGTAG (SEQ ID NO: 17) |
| HSV-2 SgB | ATGCGCGGGGGGGGCTTGGTTTGCGCGCTGGTCGTGGGGGCGCTGGTGGCCGCGGT<br>GGCGTCGGCGGCCCCGGCGGCCCCCCGCGCCTCGGGCGGCGTGGCCGCGACCGTCG<br>CGGCGAACGGGGGTCCCGCCTCCCAGCCGCCCCCCGTCCCGAGCCCCGCGACCACC<br>AAGGCCCGGAAGCGGAAAACCAAAAAGCCGCCCAAGCGGCCCGAGGCGACCCCGC<br>CCCCCGACGCCAACGCGACCGTCGCCGCCGGCCACGCCACGCTGCGCGCGCACCTG<br>CGGGAAATCAAGGTCGAGAACGCCGATGCCCAGTTTTACGTGTGCCCGCCCCCGAC<br>GGGCGCCACGGTGGTGCAGTTTGAGCAGCCGCGCCGCTGCCCGACGCGCCCGGAGG<br>GGCAGAACTACACGGAGGGCATCGCGGTGGTCTTCAAGGAGAACATCGCCCCGTAC<br>AAATTCAAGGCCACCATGTACTACAAAGACGTGACCGTGTCGCAGGTGTGGTTCGGC<br>CACCGCTACTCCCAGTTTATGGGGATATTCGAGGACCGCGCCCCCGTTCCCTTCGAG<br>GAGGTGATCGACAAGATTAACGCCAAGGGGGTCTGCCGCTCCACGGCCAAGTACGT<br>GCGGAACAACATGGAGACCACCGCGTTTCACCGGGACGACCACGAGACCGACATGG<br>AGCTCAAGCCGGCGAAGGTCGCCACGCGCACGAGCCGGGGGTGGCACACCACCGAC<br>CTCAAGTACAACCCCTCGCGGGTGGAGGCGTTCCATCGGTACGGCACGACGGTCAA<br>CTGCATCGTCGAGGAGGTGGACGCGCGGTCGGTGTACCCGTACGATGAGTTTGTGCT<br>GGCGACGGGCGACTTTGTGTACATGTCCCCGTTTTACGGCTACCGGGAGGGGTCGCA<br>CACCGAGCACACCAGCTACGCCGCCGACCGCTTCAAGCAGGTCGACGGCTTCTACG<br>CGCGCGACCTCACCACGAAGGCCCGGGCCACGTCGCCGACGACCCGCAACTTGCTG<br>ACGACCCCCAAGTTTACCGTGGCCTGGGACTGGGTGCCGAAGCGACCGGCGGTCTG<br>CACCATGACCAAGTGGCAGGAGGTGGACGAGATGCTCCGCGCCGAGTACGGCGGCT<br>CCTTCCGCTTCTCCTCCGACGCCATCTCGACCACCTTCACCACCAACCTGACCCAGTA<br>CTCGCTCTCGCGCGTCGACCTGGGCGACTGCATCGGCCGGGATGCCCGCGAGGCCAT<br>CGACCGCATGTTTGCGCGCAAGTACAACGCCACGCACATCAAGGTGGGCCAGCCGC<br>AGTACTACCTGGCCACGGGGGGCTTCCTCATCGCGTACCAGCCCCTCCTCAGCAACA<br>CGCTCGCCGAGCTGTACGTGCGGGAGTACATGCGGGAGCAGGACCGCAAGCCCCGG<br>AATGCCACGCCCGCGCCACTGCGGGAGGCGCCCAGCGCCAACGCGTCCGTGGAGCG<br>CATCAAGACCACCTCCTCGATCGAGTTCGCCCGGCTGCAGTTTACGTATAACCACAT<br>ACAGCGCCACGTGAACGACATGCTGGGGCGCATCGCCGTCGCGTGGTGCGAGCTGC<br>AGAACCACGAGCTGACTCTCTGGAACGAGGCCCGCAAGCTCAACCCCAACGCCATC<br>GCCTCCGCCACCGTCGGCCGGCGGGTGAGCGCGCGCATGCTCGGAGACGTCATGGC<br>CGTCTCCACGTGCGTGCCCGTCGCCCCGGACAACGTGATCGTGCAGAACTCGATGCG<br>CGTCAGCTCGCGGCCGGGGACGTGCTACAGCCGCCCCCTGGTCAGCTTTCGGTACGA<br>AGACCAGGGCCCGCTGATCGAGGGGCAGCTGGGCGAGAACAACGAGCTGCGCCTCA<br>CCCGCGACGCGCTCGAGCCGTGCACCGTGGGCCACCGGCGCTACTTCATCTTCGGCG<br>GGGGCTACGTGTACTTCGAGGAGTACGCGTACTCTCACCAGCTGAGTCGCGCCGACG<br>TCACCACCGTCAGCACCTTCATCGACCTGAACATCACCATGCTGGAGGACCACGAGT<br>TTGTGCCCCTGGAGGTCTACACGCGCCACGAGATCAAGGACAGCGGCCTGCTGGACT<br>ACACGGAGGTCCAGCGCCGCAACCAGCTGCACGACCTGCGCTTTGCCGACATCGAC<br>ACGGTCATCCGCGCCGACGCCAACGCCGCCATGTTCGCGGGGCTGTGCGCGTTCTTC<br>GAGGGGATGGGGGACTTGGGGCGCGCGGTCGGCAAGGTCGTCATGGGAGTAGTGGG<br>GGGCGTGGTGTCGGCCGTCTCGGGCGTGTCCTCCTTTATGTCCAACCCC (SEQ ID NO:<br>18) |
| HSV-2 SgC | ATGGCCCTTGGACGGGTGGGCCTAGCCGTGGGCCTGTGGGGCCTGCTGTGGGTGGGT<br>GTGGTCGTGGTGCTGGCCAATGCCTCCCCGGACGCACGATAACGGTGGGCCCGCG<br>GGGGAACGCGAGCAATGCCGCCCCCTCCGCGTCCCCGCGGAACGCATCCGCCCCCC<br>GAACCACACCCACGCCCCCCCAACCCCGCAAGGCGACGAAAAGTAAGGCCTCCACC<br>GCCAAACCGGCCCCGCCCCCCAAGACCGGGCCCCCGAAGACATCCTCGGAGCCCGT<br>GCGATGCAACCGCCACGACCCGCTGGCCCGGTACGGCTCGCGGGTGCAAATCCGAT<br>GCCGGTTTCCCAACTCCACCCGCACGGAGTCCCGCCTCCAGATCTGGCGTTATGCCA<br>CGGCGACGGACGCCGAGATCGGAACGGCGCCTAGCTTAGAGGAGGTGATGGTAAAC<br>GTGTCGGCCCCGCCCGGGGGCCAACTGGTGTATGACAGCGCCCCCAACCGAACGGA<br>CCCGCACGTGATCTGGGCGGAGGGCGCCGGCCCGGGCGCCAGCCCGCGGCTGTACT<br>CGGTCGTCGGGCCGCTGGGTCGGCAGCGGCTCATCATCGAAGAGCTGACCCTGGAG<br>ACCCAGGGCATGTACTACTGGGTGTGGGGCCGGACGGACCGCCCGTCCGCGTACGG<br>GACCTGGGTGCGCGTTCGCGTGTTCCGCCCTCCGTCGCTGACCATCCACCCCCACGC<br>GGTGCTGGAGGGCCAGCCGTTTAAGGCGACGTGCACGGCCGCCACCTACTACCCGG<br>GCAACCGCGCGGAGTTCGTCTGGTTCGAGGACGGTCGCCGGGTATTCGATCCGGCCC<br>AGATACACACGCAGACGCAGGAGAACCCCGACGGCTTTTCCACCGTCTCCACCGTG<br>ACCTCCGCGGCCGTCGGCGGCCAGGGCCCCCCGCGCACCTTCACCTGCCAGCTGACG<br>TGGCACCGCGACTCCGTGTCGTTCTCTCGGCGCAACGCCAGCGGCACGGCATCGGTG<br>CTGCCGCGGCCAACCATTACCATGGAGTTTACGGGCGACCATGCGGTCTGCACGGCC<br>GGCTGTGTGCCCGAGGGGGTGACGTTTGCCTGGTTCCTGGGGGACGACTCCTCGCCG<br>GCGGAGAAGGTGGCCGTCGCGTCCCAGACATCGTGCGGGCGCCCCGGCACCGCCAC<br>GATCCGCTCCACCCTGCCGGTCTCGTACGAGCAGACCGAGTACATCTGCCGGCTGGC<br>GGGATACCCGGACGGAATTCCGGTCCTAGAGCACCACGGCAGCCACCAGCCCCCGC<br>CGCGGGACCCCACCGAGCGGCAGGTGATCCGGGCGGTGGAGGGG (SEQ ID NO: 19) |
| HSV-2 SgD | ATGGGGCGTTTGACCTCCGGCGTCGGGACGGCGGCCCTGCTAGTTGTCGCGGTGGGA<br>CTCCGCGTCGTCTGCGCCAAATACGCCTTAGCAGACCCCTCGCTTAAGATGGCCGAT<br>CCCAATCGATTTCGCGGGAAGAACCTTCCGGTTTTGGACCAGCTGACCGACCCCCCC<br>GGGGTGAAGCGTGTTTACCACATTCAGCCGAGCCTGGAGGACCCGTTCCAGCCCCCC |

TABLE 1-continued

| | |
|---|---|
| | AGCATCCCGATCACTGTGTACTACGCAGTGCTGGAACGTGCCTGCCGCAGCGTGCTC<br>CTACATGCCCCATCGGAGGCCCCCCAGATCGTGCGCGGGGCTTCGGACGAGGCCCG<br>AAAGCACACGTACAACCTGACCATCGCCTGGTATCGCATGGGAGACAATTGCGCTAT<br>CCCCATCACGGTTATGGAATACACCGAGTGCCCCTACAACAAGTCGTTGGGGGTCTG<br>CCCCATCCGAACGCAGCCCCGCTGGAGCTACTATGACAGCTTTAGCGCCGTCAGCGA<br>GGATAACCTGGGATTCCTGATGCACGCCCCCGCCTTCGAGACCGCGGGTACGTACCT<br>GCGGCTAGTGAAGATAAACGACTGGACGGAGATCACACAATTTATCCTGGAGCACC<br>GGGCCCGCGCCTCCTGCAAGTACGCTCTCCCCCTGCGCATCCCCCCGGCAGCGTGCC<br>TCACCTCGAAGGCCTACCAACAGGGCGTGACGGTCGACAGCATCGGGATGCTACCC<br>CGCTTTATCCCCGAAAACCAGCGCACCGTCGCCCTATACAGCTTAAAAATCGCCGGG<br>TGGCACGGCCCCAAGCCCCCGTACACCAGCACCCTGCTGCCGCCGGAGCTGTCCGAC<br>ACCACCAACGCCACGCAACCCGAACTCGTTCCGGAAGACCCCGAGGACTCGGCCCT<br>CTTAGAGGATCCCGCCGGGACGGTGTCTTCGCAGATCCCCCCAAACTGGCACATCCC<br>GTCGATCCAGGACGTCGCGCCGCACCACGCCCCCGCCGCCCCCAGCAACCCG (SEQ<br>ID NO: 20) |
| HSV-2 SgE | ATGGCTCGCGGGGCCGGGTTGGTGTTTTTTGTTGGAGTTTGGGTCGTATCGTGCCTGG<br>CGGCAGCACCCAGAACGTCCTGGAAACGGGTAACCTCGGGCGAGGACGTGGTGTTG<br>CTTCCGGCGCCCGCGGGGCCGGAGGAACGCACCCGGGCCCACAAACTACTGTGGGC<br>CGCGGAACCCCTGGATGCCTGCGGTCCCCTGCGCCCGTCGTGGGTGGCGCTGTGGCC<br>CCCCCGACGGGTGCTCGAGACGGTCGTGGATGCGGCGTGCATGCGCGCCCCGGAAC<br>CGCTCGCCATAGCATACAGTCCCCCGTTCCCCGCGGGCGACGAGGGACTGTATTCGG<br>AGTTGGCGTGGCGCGATCGCGTAGCCGTGGTCAACGAGAGTCTGGTCATCTACGGG<br>GCCCTGGAGACGGACAGCGGTCTGTACACCCTGTCCGTGGTCGGCCTAAGCGACGA<br>GGCGCGCCAAGTGGCGTCGGTGGTTCTGGTCGTGGAGCCCGCCCCTGTGCCGACCCC<br>GACCCCCGACGACTACGACGAAGAAGACGACGCGGGCGTGAGCGAACGCACGCCG<br>GTCAGCGTTCCCCCCCCAACCCCCCCCCGTCGTCCCCCCGTCGCCCCCCCGACGCAC<br>CCTCGTGTTATCCCCGAGGTGTCCCACGTGCGCGGGGTAACGGTCCATATGGAGACC<br>CCGGAGGCCATTCTGTTTGCCCCCGGGGAGACGTTTGGGACGAACGTCTCCATCCAC<br>GCCATTGCCCACGACGACGGTCCGTACGCCATGGACGTCGTCTGGATGCGGTTTGAC<br>GTGCCGTCCTCGTGCGCCGAGATGCGGATCTACGAAGCTTGTCTGTATCACCCGCAG<br>CTTCCAGAGTGTCTATCTCCGGCCGACGCGCCGTGCGCCGTAAGTTCCTGGGCGTAC<br>CGCCTGGCGGTCCGCAGCTACGCCGGCTGTTCCAGGACTACGCCCCCGCCGCGATGT<br>TTTGCCGAGGCTCGCATGGAACCGGTCCCGGGGTTGGCGTGGCTGGCCTCCACCGTC<br>AATCTGGAATTCCAGCACGCCTCCCCCCAGCACGCCGGCCTCTACCTGTGCGTGGTG<br>TACGTGGACGATCATATCCACGCCTGGGGCCACATGACCATCAGCACCGCGGCGCA<br>GTACCGGAACGCGGTGGTGGAACAGCACCTCCCCCAGCGCCAGCCCGAGCCCGTCG<br>AGCCCACCCGCCCGCACGTGAGAGCCCCCCCTCCCGCGCCCTCCGCGCGCGGCCCGC<br>TGCGC (SEQ ID NO: 21) |
| HSV-2 SgI | ATGCCCGGCCGCTCGCTGCAGGGCCTGGCGATCCTGGGCCTGTGGGTCTGCGCCACC<br>GGCCTGGTCGTCCGCGGCCCCACGGTCAGTCTGGTCTCAGACTCACTCGTGGATGCC<br>GGGGCCGTGGGGCCCCAGGGCTTCGTGGAAGAGGACCTGCGTGTTTTCGGGGAGCT<br>TCATTTTGTGGGGGCCCAGGTCCCCCACACAAACTACTACGACGGCATCATCGAGCT<br>GTTTCACTACCCCCTGGGGAACCACTGCCCCCGCGTTGTACACGTGGTCACACTGAC<br>CGCATGCCCCCGCCGCCCCGCCGTGGCGTTCACCTTGTGTCGCTCGACGCACCACGC<br>CCACAGCCCCGCCTATCCGACCCTGGAGCTGGGTCTGGCGCGGCAGCCGCTTCTGCG<br>GGTTCGAACGGCAACGCGCGACTATGCCGGTCTGTATGTCCTGCGCGTATGGGTCGG<br>CAGCGCGACGAACGCCAGCCTGTTTGTTTTGGGGGTGGCGCTCTCTGCCAACGGGAC<br>GTTTGTGTATAACGGCTCGGACTACGGCTCCTGCGATCCGGCGCAGCTTCCCTTTTCG<br>GCCCCGCGCCTGGGACCCTCGAGCGTATACACCCCCGGAGCCTCCCGGCCCACCCCT<br>CCACGGACAACGACATCCCCGTCCTCCCCCCGAGACCCGACCCCCGCCCCCGGGGA<br>CACAGGGACGCCCGCGCCCGCGAGCGGCGAGAGAGCCCCGCCCAATTCCACGCGAT<br>CGGCCAGCGAATCGAGACACAGGCTAACCGTAGCCCAGGTAATCCAG (SEQ ID NO:<br>22) |
| HSV-2 ICP-4; Based on strain HG52; (inactivated by deletion of nuclear localization signal and alanine substitution for key residues in the transactivation region) | ATGTCGGCGGAGCAGCGGAAGAAGAAGAAGACGACGACGACGACGCAGGGCCGCG<br>GGGCCGAGGTCGCGATGGCGGACGAGGACGGGGGACGTCTCCGGGCCGCGGCGGA<br>GACGACCGGCGGCCCCGGATCTCCGGATCCAGCCGACGGACCGCCGCCCACCCCGA<br>ACCCGGACCGTCGCCCCGCCGCGCGGCCCGGGTTCGGGTGGCACGGTGGGCCGGAG<br>GAGAACGAAGACGAGGCCGACGACGCCGCCGCCGATGCCGATGCCGACGAGGCGG<br>CCCCGGCGTCCGGGGAGGCCGTCGACGAGCCTGCCGCGGACGGCGTCGTCTCGCCG<br>CGGCAGCTGGCCCTGCTGGCCTCGATGGTGGACGAGGCCGTTCGCACGATCCCGTCG<br>CCCCCCCCGGAGCGCGACGGCGCGCAAGAAGAAGCGGCCCGCTCGCCTTCTCCGCC<br>GCGGACCCCCTCCATGCGCGCCGATTATGGCGAGGAGAACGACGACGACGACGACG<br>ACGACGATGACGACGACCGCGACGCGGGCCGCTGGGTCCGCGGACCGGAGACGACG<br>TCCGCGGTCCGCGGGGCGTACCCGGACCCCATGGCCAGCCTGTCGCCGCGACCCCCG<br>GCGCCCCGCCGACACCACCACCACCACCACCACCGCCGCCGGCGCGCCCCCCGCCG<br>GCGCTCGGCCGCCTCTGACTCATCAAAATCCGGATCCTCGTCGTCGGCGTCCTCCGC<br>CTCCTCCTCCGCCTCCTCCTCCTCGTCTGCATCCGCCTCCTCGTCTGACGACGACGAC<br>GACGACGACGCCGCCCGCGCCCCCGCCAGCGCCGCAGACCACGCCGCGGGCGGGAC<br>CCTCGGCGCGGACGACGAGGAGGCGGGGGTGCCCGCGAGGGCCCCGGGGGCGGCG<br>CCCCGGCCGAGCCCGCCCAGGGCCGAGCCCGCCCCGGCCCGGACCCCCGCGGCGAC<br>CGCGGGCCGCCTGGAGCGCCGCCGGGCCCGCGCGGCGGTGGCCGGCCGCGACGCCA<br>CGGGCCGCTTCACGGCCGGGCGGCCCCGGCGGGTCGAGCTGGACGCCGACGCGGCC<br>TCCGGCGCCTTCTACGCGCGCTACCGCGACGGGTACGTCAGCGGGGAGCCGTGGCCC<br>GGGGCCGGCCCCCCGCCCCCGGGGCGCGTGCTGTACGGCGGGCTGGGCGACAGCCG<br>CCCCGGCCTCTGGGGGGCGCCCGAGGCGGAGGAGGCGCGGGCCCGGTTCGAGGCCT<br>CGGGCGCCCCGGCGCCCGTGTGGGCGCCCGAGCTGGGCGACGCGGCGCAGCAGTAC<br>GCCCTGATCACGCGGCTGCTGTACACGCCGGACGCGGAGGCGATGGGGTGGCTCCA |

TABLE 1-continued

GAACCCGCGCGTGGCGCCCGGGGACGTGGCGCTGGACCAGGCCTGCTTCCGGATCT
CGGGCGCGGCGCGCAACAGCAGCTCCTTCATCTCCGGCAGCGTGGCGCGGGCCGTG
CCCCACCTGGGGTACGCCATGGCGGCGGGCCGCTTCGGCTGGGGCCTGGCGCACGT
GGCGGCCGCCGTGGCCATGAGCCGCCGCTACGACCGCGCGCAGAAGGGCTTCCTGC
TGACCAGCCTGCGCCGCGCCTACGCGCCCCTGCTGGCGCGCGAGAACGCGGCGCTG
ACCGGGGCGCGAACCCCCGACGACGGCGGCGACGCCAACCGCCACGACGGCGACG
ACGCCCGCGGGAAGCCCGCCGCCGCCGCCGCCCCGTTGCCGTCGGCGGCGGCGTCG
CCGGCCGACGAGCGCGCGGTGCCCGCCGGCTACGGCGCCGCGGGGGTGCTCGCCGC
CCTGGGGCGCCTGAGCGCCGCGCCCGCCTCCGCGCCGGCCGGGGCCGACGACGACG
ACGACGACGACGGCGCCGGCGGTGGTGGCGGCGGCCGGCGCGCGGAGGCGGGCCG
CGTGGCCGTGGAGTGCCTGGCCGCCTGCCGCGGGATCCTGGAGGCGCTGGCGGAGG
GCTTCGACGGCGACCTGGCGGCCGTGCCGGGGCTGGCCGGAGCCCGGCCCGCCGCG
CCCCCGCGCCCGGGCCCGCGGGCGCGGCCGCCCCGCCGCACGCCGACGCGCCCCG
CCTGCGCGCCTGGCTGCGCGAGCTGCGGTTCGTGCGCGACGCGCTGGTGCTGATGCG
CCTGCGCGGGGACCTGCGCGTGGCCGGCGGCAGCGAGGCCGCCGTGGCCGCCGTGC
GCGCCGTGAGCCTGGTCGCCGGGGCCCTGGGCCCGGCGCTGCCGCGGAGCCCGCGC
CTGCTGAGCTCCGCCGCCGCCGCCGCCGCGGACCTGCTCTTCCAGAACCAGAGCCTG
CGCCCCCTGCTGGCCGACACCGTCGCCGCGGCCGACTCGCTCGCCGCGCCCGCCTCC
GCGCCGCGGGAGGCCGCGGACGCCCCCGCCCCGCGGCCGCCCCTCCCGCGGGGGC
CGCGCCCCCCGCCCCGCCGACGCCGCCGCCGCGGCCGCCGCGCCCCGCGGCGCTGA
CCCGCCGGCCCGCCGAGGGCCCCGACCCGCAGGGCGGCTGGCGCCGCCAGCCGCCG
GGGCCCAGCCACACGCCGGCGCCCTCGGCCGCCGCCCTGGAGGCCTACTGCGCCCC
GCGGGCCGTGGCCGAGCTCACGGACCACCCGCTCTTCCCCGCGCCGTGGCGCCCGGC
CCTCATGTTCGACCCGCGCGCGCTGGCCTCGCTGGCCGCGCGCTGCGCCGCCCCGCC
CCCCGGCGGCGCGCCCGCCGCCTTCGGCCCGCTGCGCGCCTCGGGCCCGCTGCGCCG
CGCGGCGGCCTGGATGCGCCAGGTGCCCGACCCGGAGGACGTGCGCGTGGTGATCC
TCTACTCGCCGCTGCCGGGCGAGGACCTGGCCGCGGGCCGCGCCGGGGGCGGGCCC
CCCCCGGAGTGGTCCGCCGAGCGCGGCGGGCTGTCCTGCCTGCTGGCGGCCCTGGGC
AACCGGCTCTGCGGGCCCGCCACGGCCGCCTGGGCGGGCAACTGGACCGGCGCCCC
CGACGTCTCGGCGCTGGGCGCGCAGGGCGTGCTGCTGCTGTCCACGCGGGACCTGGC
CTTCGCCGGCGCCGTGGAGTTCCTGGGGCTGCTGGCCGGCGCCTGCGACCGCCGCCT
CATCGTCGTCAACGCCGTGCGCGCCGCGGCCTGGCCCGCCGCTGCCCCCGTGGTCTC
GCGGCAGCACGCCTACCTGGCCTGCGAGGTGCTGCCCGCCGTGCAGTGCGCCGTGCG
CTGGCCGGCGGCGCGGGACCTGCGCCGCACCGTGCTGGCCTCCGGCCGCGTGTTCGG
GCCGGGGGTCTTCGCGCGCGTGGAGGCCGCGCACGCGCGCCTGTACCCCGACGCGC
CGCCGCTGCGCCTCTGCCGCGGGGCCAACGTGCGGTACCGCGTGCGCACGCGCTTCG
GCCCCGACACGCTGGTGCCCATGTCCCCGCGCGAGTACCGCCGCGCCGTGCTCCCGG
CGCTGGACGGCCGGGCCGCCGCCTCGGGCGCGGGCGACGCCATGGCGCCCGGCGCG
CCGGACTTCTGCGAGGACGAGGCGCACTCGCACCGCGCCTGCGCGCGCTGGGGCCT
GGGCGCGCCGCTGCGGCCCGTCTACGTGGCGCTGGGGCGCGACGCCGTGCGCGGCG
GCCCGGCGGAGCTGCGCGGGCCGCGGCGGGAGTTCTGCGCGCGGGCGCTGCTCGAG
CCCGACGGCGACGCGCCCCCGCTGGTGCTGCGCGACGACGCGGACGCGGGCCCGCC
CCCGCAGATACGCTGGGCGTCGGCCGCGGGCCGCGCGGGGACGGTGCTGGCCGCGG
CGGGCGGCGGCGTGGAGGTGGTGGGGACCGCCGCGGGGCTGGCCACGCCGCCGAGG
CGCGAGCCCGTGGACATGGACGCGGAGCTGGAGGACGACGACGACGGACTGTTTGG
GGAGTGA (SEQ ID NO: 23)

MRK_HSV-2
gB, SQ-032178
CX-000747

TCAAGCTTTTGGACCCTCGTACAGAAGCTAATACGACTCACTATAGGGAAATAAGAG
AGAAAAGAAGAGTAAGAAGAAATATAAGAGCCACCATGAGAGGTGGTGGCTTAGTT
TGCGCGCTGGTTGTCGGGGCGCTCGTAGCCGCCGTGGCGTCGGCCGCCCCTGCGGCT
CCTCGCGCTAGCGGAGGCGTAGCCGCAACAGTTGCGGCGAACGGGGTCCAGCCTC
TCAGCCTCCTCCCGTCCCGAGCCCTGCGACCACCAAGGCTAGAAAGCGGAAGACCA
AGAAACCGCCCAAGCGCCCCGAGGCCACCCCGCCCCCCGATGCCAACGCGACTGTC
GCCGCTGGCCATGCGACGCTTCGCGCTCATCTGAGGGAGATCAAGGTTGAAAATGCT
GATGCCCAATTTTACGTGTGCCCGCCCCCGACGGGCGCCACGGTTGTGCAGTTTGAA
CAGCCGCGGCGCTGTCCGACGCGGCCAGAAGGCCAGAACTATACGGAGGGCATAGC
GGTGGTCTTTAAGGAAAACATCGCCCCGTACAAATTTAAGGCCACAATGTACTACAA
AGACGTGACAGTTTCGCAAGTGTGGTTTGGCCACAGATACTCGCAGTTTATGGGAAT
CTTCGAAGATAGAGCCCCTGTTCCCTTCGAGGAAGTCATCGACAAGATTAATGCCAA
AGGGGTATGCCGTTCCACGGCCAAATACGTGCGCAACAATATGGAGACCACCGCCT
TTCACCGGGATGATCACGAGACCGACATGGAGCTTAAGCCGGCGAAGGTCGCCACG
CGTACCTCCCGGGGTTGGCACACCACAGATCTTAAGTACAATCCCTCGCGAGTTGAA
GCATTCCATCGGTATGGAACTACCGTTAACTGCATCGTTGAGGAGGTGGATGCGCGG
TCGGTGTACCCTTACGATGAGTTTGTGTTAGCGACCGGCGATTTTGTGTACATGTCCC
CGTTTTACGGCTACCGGGAGGGGTCGCACACCGAACATACCTCGTACGCCGCTGACA
GGTTCAAGCAGGTCGATGGCTTTTACGCGCGCGATCTCACCACGAAGGCCCGGGCCA
CGTCACCGACGACCAGGAACTTGCTCACGACCCCCAAGTTCACCGTCGCTTGGGATT
GGGTCCCAAAGCGTCCGGCGGTCTGCACGATGACCAAATGGCAGGAGGTGGACGAA
ATGCTCCGCGCAGAATACGGCGGCTCCTTCCGCTTCTCGTCCGACGCCATCTCGACA
ACCTTCACCACCAATCTGACCCAGTACAGTCTGTCGCGCGTTGATTTAGGAGACTGC
ATTGGCCGGGATGCCCGGGAGGCCATCGACAGAATGTTTGCGCGTAAGTACAATGC
CACACATATTAAGGTGGGCCAGCCGCAATACTACCTTGCCACGGGCGGCTTTCTCAT
CGCGTACCAGCCCCTTCTCTCAAATACGCTCGCTGAACTGTACGTGCGGGAGTATAT
GAGGGAACAGGACCGCAAGCCCCGCAATGCCACGCCTGCGCCACTACGAGAGGCGC
CTTCAGCTAATGCGTCGGTGGAACGTATCAAGACCACCTCCTCAATAGAGTTCGCCC
GGCTGCAATTTACGTACAACCACATCCAGCGCCACGTGAACGACATGCTGGGCCGC
ATCGCTGTCGCCTGGTGCGAGCTGCAGAATCACGAGCTGACTCTTTGGAACGAGGCC
CGAAAACTCAACCCCAACGCGATCGCCTCCGCAACAGTCGGTAGACGGGTGAGCGC
TCGCATGCTAGGAGATGTCATGGCTGTGTCCACCTGCGTGCCCGTCGCTCCGGACAA
CGTGATTGTGCAGAATTCGATGCGGGTCTCATCGCGGCCGGGCACCTGCTACAGCAG

TABLE 1-continued

| | |
|---|---|
| | GCCCCTCGTCAGCTTCCGGTACGAAGACCAGGGCCCGCTGATTGAAGGGCAACTGG<br>GAGAGAACAATGAGCTGCGCCTCACCCGCGACGCGCTCGAACCCTGCACCGTCGGA<br>CATCGGAGATATTTCATCTTCGGAGGGGGCTACGTGTACTTCGAAGAGTATGCCTAC<br>TCTCACCAGCTGAGTAGAGCCGACGTCACTACCGTCAGCACCTTTATTGACCTGAAT<br>ATCACCATGCTGGAGGACCACGAGTTTGTGCCCCTGGAAGTTTACACTCGCCACGAA<br>ATCAAAGACTCCGGCCTGTTGGATTACACGGAGGTTCAGAGGCGGAACCAGCTGCA<br>TGACCTGCGCTTTGCCGACATCGACACCGTCATCCGCGCCGATGCCAACGCTGCCAT<br>GTTCGCGGGGCTGTGCGCGTTCTTCGAGGGGATGGGTGACTTGGGGCGCGCCGTCGG<br>CAAGGTCGTCATGGGAGTAGTGGGGGGCGTTGTGAGTGCCGTCAGCGGCGTGTCCTC<br>CTTCATGTCCAATCCATTCGGAGCGCTTGCTGTGGGGCTGCTGGTCCTGGCCGGGCT<br>GGTAGCCGCCTTCTTCGCCTTTCGATATGTTCTGCAACTGCAACGCAATCCCATGAA<br>AGCTCTATATCCGCTCACCACCAAGGAGCTAAAGACGTCAGATCCAGGAGGCGTGG<br>GCGGGGAAGGGGAAGAGGGCGCGGAGGGCGGAGGGTTTGACGAAGCCAAATTGGC<br>CGAGGCTCGTGAAATGATCCGATATATGGCACTAGTGTCGGCGATGGAAAGGACCG<br>AACATAAGGCCCGAAAGAAGGGCACGTCGGCGCTGCTCTCATCCAAGGTCACCAAC<br>ATGGTACTGCGCAAGCGCAACAAAGCCAGGTACTCTCCGCTCCATAACGAGGACGA<br>GGCGGGAGATGAGGATGAGCTCTAATGATAATAGGCTGGAGCCTCGGTGGCCATGC<br>TTCTTGCCCCTTGGGCCTCCCCCCAGCCCCTCCTCCCCTTCCTGCACCCGTACCCCCG<br>TGGTCTTTGAATAAAGTCTGAGTGGGCGGC (SEQ ID NO: 54) |
| MRK_HSV-2<br>gC, SQ-032179<br>CX-000670 | TCAAGCTTTTGGACCCTCGTACAGAAGCTAATACGACTCACTATAGGGAAATAAGAG<br>AGAAAAGAAGAGTAAGAAGAAATATAAGAGCCACCATGGCCCTTGGACGGGTAGG<br>CCTAGCCGTGGGCCTGTGGGGCCTACTGTGGGTGGGTGTGGTCGTGGTGCTGGCCAA<br>TGCCTCCCCCGGACGCACGATAACGGTGGGCCCGCGAGGCAACGCGAGCAATGCTG<br>CCCCCTCCGCGTCCCCGCGGAACGCATCCGCCCCCCGAACCACACCCACGCCCCCAC<br>AACCCCGCAAAGCGACGAAATCCAAGGCCTCCACCGCCAAACCGGCTCCGCCCCCC<br>AAGACCGGACCCCCGAAGACATCCTCGGAGCCCGTGCGATGCAACCGCCACGACCC<br>GCTGGCCCGGTACGGCTCGCGGGTGCAAATCCGATGCCGGTTTCCCAACTCCACGAG<br>GACTGAGTCCCGTCTCCAGATCTGGCGTTATGCCACGGCGACGGACGCCGAAATCGG<br>AACAGCGCCTAGCTTAGAAGAGGTGATGGTGAACGTGTCGGCCCCGCCCGGGGGCC<br>AACTGGTGTATGACAGTGCCCCCAACCGAACGGACCCGCATGTAATCTGGGCGGAG<br>GGCGCCGGCCCGGGCGCCAGCCCGCGCCTGTACTCGGTTGTCGGCCCGCTGGGTCGG<br>CAGCGGCTCATCATCGAAGAGTTAACCCTGGAGACACAGGGCATGTACTATTGGGT<br>GTGGGGCCGGACGGACCGCCCGTCCGCCTACGGGACCTGGGTCCGCGTTCGAGTATT<br>TCGCCCTCCGTCGCTGACCATCCACCCCCACGCGGTGCTGGAGGGCCAGCCGTTTAA<br>GGCGACGTGCACGGCCGCAACCTACTACCCGGGCAACCGCGCGGAGTTCGTCTGGTT<br>TGAGGACGGTCGCCGCGTATTCGATCCGGCACAGATACACACGCAGACGCAGGAGA<br>ACCCCGACGGCTTTTCCACCGTCTCCACCGTGACCTCCGCGGCCGTCGGCGGGCAGG<br>GCCCCCCTCGCACCTTCACCTGCCAGCTGACGTGGCACCGCGACTCCGTGTCGTTCT<br>CTCGGCGCAACGCCAGCGGCACGGCCTCGGTTCTGCCGCGGCCGACCATTACCATGG<br>AGTTTACAGGCGACCATGCGGTCTGCACGGCCGGCTGTGTGCCCGAGGGGGTCACGT<br>TTGCTTGGTTCCTGGGGGATGACTCCTCGCCGGCGGAAAAGGTGGCCGTCGCGTCCC<br>AGACATCGTGCGGGCGCCCCGGCACCGCCACGATCCGCTCCACCCTGCCGGTCTCGT<br>ACGAGCAGACCGAGTACATCTGTAGACTGGCGGGATACCCGGACGGAATTCCGGTC<br>CTAGAGCACCACGGAAGCCACCAGCCCCCGCCGCGGGACCCAACCGAGCGGCAGGT<br>GATCCGGGCGGTGGAGGGGGCGGGGATCGGAGTGGCTGTCCTTGTCGCGGTGGTTC<br>TGGCCGGGACCGCGGTAGTGTACCTGACCCATGCCTCCTCGGTACGCTATCGTCGGC<br>TGCGGTAATGATAATAGGCTGGAGCCTCGGTGGCCATGCTTCTTGCCCCTTGGGCCT<br>CCCCCCAGCCCCTCCTCCCCTTCCTGCACCCGTACCCCCGTGGTCTTTGAATAAAGTC<br>TGAGTGGGCGGC (SEQ ID NO: 55) |
| MRK_HSV-2<br>gD, SQ-032180,<br>CX-001301 | TCAAGCTTTTGGACCCTCGTACAGAAGCTAATACGACTCACTATAGGGAAATAAGAG<br>AGAAAAGAAGAGTAAGAAGAAATATAAGAGCCACCATGGGGCGTTTGACCTCCGGC<br>GTCGGGACGGCGGCCCTGCTAGTTGTCGCGGTGGGACTCCGCGTCGTCTGCGCCAAA<br>TACGCCTTAGCAGACCCCTCGCTTAAGATGGCCGATCCCAATCGATTTCGCGGGAAG<br>AACCTTCCGGTTTTGGACCAGCTGACCGACCCCCCGGGGTGAAGCGTGTTTACCAC<br>ATTCAGCCGAGCCTGGAGGACCCGTTCCAGCCCCCCAGCATCCCGATCACTGTGTAC<br>TACGCAGTGCTGGAACGTGCCTGCCGCAGCGTGCTCCTACATGCCCCATCGGAGGCC<br>CCCCAGATCGTGCGCGGGGCTTCGGACGAGGCCCGAAAGCACACGTACAACCTGAC<br>CATCGCCTGGTATCGCATGGGAGACAATTGCGCTATCCCCATCACGGTTATGGAATA<br>CACCGAGTGCCCCTACAACAAGTCGTTGGGGGTCTGCCCCATCCGAACGCAGCCCCG<br>CTGGAGCTACTATGACAGCTTTAGCGCCGTCAGCGAGGATAACCTGGGATTCCTGAT<br>GCACGCCCCCGCCTTCGAGACCGCGGGTACGTACCTGCGGCTAGTGAAGATAAACG<br>ACTGGACGGAGATCACACAATTTATCCTGGAGCACCGGGCCCGCGCCTCCTGCAAGT<br>ACGCTCTCCCCCTGCGCATCCCCCCGGCAGCGTGCCTCACCTCGAAGGCCTACCAAC<br>AGGGCGTGACGGTCGACAGCATCGGGATGCTACCCCGCTTTATCCCCGAAAACCAG<br>CGCACCGTCGCCCTATACAGCTTAAAAATCGCCGGGTGGCACGGCCCCAAGCCCCC<br>GTACACCAGCACCCTGCTGCCGCCGGAGCTGTCCGACACCACCAACGCCACGCAAC<br>CCGAACTCGTTCCGGAAGACCCCGAGGACTCGGCCCTCTTAGAGGATCCCGCCGGG<br>ACGGTGTCTTCGCAGATCCCCCCAAACTGGCACATCCCGTCGATCCAGGACGTCGCA<br>CCGCACCACGCCCCCGCCGCCCCCAGCAACCCGGGCCTGATCATCGGCGCGCTGGCC<br>GGCAGTACCCTGGCGGTGCTGGTCATCGGCGGTATTGCGTTTTGGGTACGCCGCCGC<br>GCTCAGATGGCCCCCAAGCGCCTACGTCTCCCCCACATCCGGGATGACGACGCGCCC<br>CCCTCGCACCAGCCATTGTTTTACTAGTGATAATAGGCTGGAGCCTCGGTGGCCATG<br>CTTCTTGCCCCTTGGGCCTCCCCCCAGCCCCTCCTCCCCTTCCTGCACCCGTACCCCC<br>GTGGTCTTTGAATAAAGTCTGAGTGGGCGGC (SEQ ID NO: 56) |

TABLE 1-continued

| | |
|---|---|
| MRK_HSV-2 gE, SQ-032181, CX-001391 | TCAAGCTTTTGGACCCTCGTACAGAAGCTAATACGACTCACTATAGGGAAATAAGAG<br>AGAAAAGAAGAGTAAGAAGAAATATAAGAGCCACCATGGCTAGGGGGGCCGGGTT<br>GGTTTTTTTTGTTGGAGTTTGGGTCGTAAGCTGCCTCGCGGCAGCGCCCAGAACGTC<br>CTGGAAACGCGTAACCTCGGGCGAAGACGTGGTGTTACTCCCCGCGCCGGCGGGGC<br>CGGAAGAACGCACTCGGGCCCACAAACTACTGTGGGCAGCGGAACCGCTGGATGCC<br>TGCGGTCCCCTGAGGCCGTCATGGGTGGCACTGTGGCCCCCCCGACGAGTGCTTGAG<br>ACGGTTGTCGATGCGGCGTGCATGCGCGCCCCGGAACCGCTCGCTATCGCATACAGT<br>CCCCCGTTCCCTGCGGGCGACGAGGGACTTTATTCGGAGTTGGCGTGGCGCGATCGC<br>GTAGCCGTGGTCAACGAGAGTTTAGTTATCTACGGGGCCCTGGAGACGGACAGTGG<br>TCTGTACACCCTGTCAGTGGTGGGCCTATCCGACGAGGCCCGCCAAGTGGCGTCCGT<br>GGTTCTCGTCGTCGAGCCCGCCCCTGTGCCTACCCCGACCCCCGATGACTACGACGA<br>GGAGGATGACGCGGGCGTGAGCGAACGCACGCCCGTCAGCGTTCCCCCCCCAACAC<br>CCCCCCGACGTCCCCCCGTCGCCCCCCCGACGCACCCTCGTGTTATCCCTGAGGTGA<br>GCCACGTGCGGGGGGTGACGGTCCACATGGAAACCCCGGAGGCCATTCTGTTTGCG<br>CCAGGGGAGACGTTTGGGACGAACGTCTCCATCCACGCAATTGCCCACGACGACGG<br>TCCGTACGCCATGGACGTCGTCTGGATGCGATTTGATGTCCCGTCCTCGTGCGCCGA<br>GATGCGGATCTATGAAGCATGTCTGTATCACCCGCAGCTGCCTGAGTGTCTGTCTCC<br>GGCCGATGCGCCGTGCGCCGTAAGTTCGTGGGCGTACCGCCTGGCGGTCCGCAGCTA<br>CGCCGGCTGCTCCAGGACTACGCCCCCACCTCGATGTTTTGCTGAAGCTCGCATGGA<br>ACCGGTCCCCGGGTTGGCGTGGCTCGCATCAACTGTTAATCTGGAATTCCAGCATGC<br>CTCTCCCCAACACGCCGGCCTCTATCTGTGTGTGGTGTATGTGGACGACCATATCCAT<br>GCCTGGGGCCACATGACCATCTCCACAGCGGCCCAGTACCGGAATGCGGTGGTGGA<br>ACAGCATCTCCCCCAGCGCCAGCCCGAGCCCGTAGAACCCACCCGACCGCATGTGA<br>GAGCCCCCCCTCCCGCACCCTCCGCGAGAGGCCCGTTACGCTTAGGTGCGGTCCTGG<br>GGGCGGCCCTGTTGCTCGCGGCCCTCGGGCTATCCGCCTGGGCGTGCATGACCTGCT<br>GGCGCAGGCGCAGTTGGCGGGCGGTTAAAAGTCGGGCCTCGGCGACCGGCCCCACT<br>TACATTCGAGTAGCGGATAGCGAGCTGTACGCGGACTGGAGTTCGGACTCAGAGGG<br>CGAGCGCGACGGTTCCCTGTGGCAGGACCCTCCGGAGAGACCCGACTCACCGTCCA<br>CAAATGGATCCGGCTTTGAGATCTTATCCCCAACGGCGCCCTCTGTATACCCCCATA<br>GCGAAGGGCGTAAATCGCGCCGCCCGCTCACCACCTTTGGTTCAGGAAGCCCGGGA<br>CGTCGTCACTCCCAGGCGTCCTATTCTTCCGTCTTATGGTAATGATAATAGGCTGGAG<br>CCTCGGTGGCCATGCTTCTTGCCCCTTGGGCCTCCCCCCAGCCCCTCCTCCCCTTCCT<br>GCACCCGTACCCCCGTGGTCTTTGAATAAAGTCTGAGTGGGCGGC (SEQ ID NO: 57) |
| MRK_HSV-2 gI SQ-032182 CX-000645 | TCAAGCTTTTGGACCCTCGTACAGAAGCTAATACGACTCACTATAGGGAAATAAGAG<br>AGAAAAGAAGAGTAAGAAGAAATATAAGAGCCACCATGCCCGGCCGCTCGCTGCAG<br>GGCCTGGCGATCCTGGGCCTGTGGGTCTGCGCCACCGGCCTGGTCGTCCGCGGCCCC<br>ACGGTCAGTCTGGTCTCAGACTCACTCGTGGATGCCGGGGCCGTGGGGCCCCAGGGC<br>TTCGTGGAAGAGGACCTGCGTGTTTTCGGGGAGCTTCATTTTGTGGGGGCCCAGGTC<br>CCCCACACAAACTACTACGACGGCATCATCGAGCTGTTTCACTACCCCCTGGGGAAC<br>CACTGCCCCCGCGTTGTACACGTGGTCACACTGACCGCATGCCCCCGCCGCCCCGCC<br>GTGGCGTTCACCTTGTGTCGCTCGACGCACCACGCCCACAGCCCCGCCTATCCGACC<br>CTGGAGCTGGGTCTGGCGCGGCAGCCGCTTCTGCGGGTTCGAACGGCAACGCGCGA<br>CTATGCCGGTCTGTATGTCCTGCGCGTATGGGTCGGCAGCGCGACGAACGCCAGCCT<br>GTTTGTTTTGGGGGTGGCGCTCTCTGCCAACGGGACGTTTGTGTATAACGGCTCGGA<br>CTACGGCTCCTGCGATCCGGCGCAGCTTCCCTTTTCGGCCCCGCGCCTGGGACCCTC<br>GAGCGTATACACCCCCGGAGCCTCCCGGCCCACCCCTCCACGGACAACGACATCAC<br>CGTCCTCCCCACGAGACCCGACCCCCGCCCCCGGGGACACAGGGACGCCTGCTCCC<br>GCGAGCGGCGAGAGAGCCCCGCCCAATTCCACGCGATCGGCCAGCGAATCGAGACA<br>CAGGCTAACCGTAGCCCAGGTAATCCAGATCGCCATACCGGCGTCCATCATCGCCTT<br>TGTGTTTCTGGGCAGCTGTATCTGCTTCATCCATAGATGCCAGCGCCGATACAGGCG<br>CCCCCGCGGCCAGATTTACAACCCCGGGGGCGTTTCCTGCGCGGTCAACGAGGCGGC<br>CATGGCCCGCCTCGGAGCCGAGCTGCGATCCCACCCAAACACCCCCCCCAAACCCC<br>GACGCCGTTCGTCGTCGTCCACGACCATGCCTTCCCTAACGTCGATAGCTGAGGAAT<br>CGGAGCCAGGTCCAGTCGTGCTGCTGTCCGTCAGTCCTCGGCCCCGCAGTGGCCCGA<br>CGGCCCCCCAAGAGGTCTAGTGATAATAGGCTGGAGCCTCGGTGGCCATGCTTCTTG<br>CCCCTTGGGCCTCCCCCCAGCCCCTCCTCCCCTTCCTGCACCCGTACCCCCGTGGTCT<br>TTGAATAAAGTCTGAGTGGGCGGC (SEQ ID NO: 58) |
| MRK_HSV-2 SgB, SQ-032210, CX-000655 | TCAAGCTTTTGGACCCTCGTACAGAAGCTAATACGACTCACTATAGGGAAATAAGAG<br>AGAAAAGAAGAGTAAGAAGAAATATAAGAGCCACCATGCGCGGGGGGGGCTTAGT<br>TTGCGCGCTGGTCGTGGGGGCGCTCGTAGCCGCGGTCGCGTCGGCGGCTCCGGCTGC<br>CCCACGCGCTTCAGGTGGTGTCGCTGCGACCGTTGCGGCGAATGGTGGTCCCGCCAG<br>CCAACCGCCTCCCGTCCCGAGCCCCGCGACCACTAAGGCCCGGAAGCGGAAGACCA<br>AGAAGCCACCCAAGCGGCCCGAGGCGACTCCGCCCCCAGACGCCAACGCGACCGTC<br>GCCGCCGGCCACGCCACTCTGCGTGCGCACCTGCGGGAAATCAAGGTCGAGAACGC<br>GGACGCCCAGTTTTACGTGTGCCCGCCGCCGACTGGCGCCACGGTGGTGCAGTTTGA<br>GCAACCTAGGCGCTGCCCGACGCGACCAGAGGGGCAGAACTACACCGAGGGCATAG<br>CGGTGGTCTTTAAGGAAAACATCGCCCCGTACAAATTCAAGGCCACCATGTACTACA<br>AAGACGTGACCGTGTCGCAGGTGTGGTTCGGCCACCGCTACTCCCAGTTTATGGGGA<br>TATTCGAGGACCGCGCCCCCGTTCCCTTCGAAGAGGTGATTGACAAAATTAACGCCA<br>AGGGGGTCTGCCGCAGTACGGCGAAGTACGTCCGGAACAACATGGAGACCACTGCC<br>TTCCACCGGGACGACCACGAAACAGACATGGAGCTCAAACCGGCGAAAGTCGCCAC<br>GCGCACGAGCCGGGGGTGGCACACCACCGACCTCAAATACAATCCTTCGCGGGTGG<br>AAGCATTCCATCGGTATGGCACGACCGTCAACTGTATCGTAGAGGAGGTGGATGCG<br>CGGTCGGTGTACCCCTACGATGAGTTCGTGCTGGCAACGGGCGATTTTGTGTACATG<br>TCCCCTTTTTACGGCTACCGGGAAGGTAGTCACACCGAGCACACCAGTTACGCCGCC<br>GACCGCTTTAAGCAAGTGGACGGCTTCTACGCGCGCGACCTCACCACAAAGGCCCG<br>GGCCACGTCGCCGACGACCCGCAATTTGCTGACGACCCCCAAGTTTACCGTGGCCTG |

TABLE 1-continued

| | |
|---|---|
| | GGACTGGGTGCCTAAGCGACCGGCGGTCTGTACCATGACAAAGTGGCAGGAGGTGG<br>ACGAAATGCTCCGCGCTGAATACGGTGGCTCTTTCCGCTTCTCTTCCGACGCCATCTC<br>CACCACGTTCACCACCAACCTGACCCAATACTCGCTCTCGAGAGTCGATCTGGGAGA<br>CTGCATTGGCCGGGATGCCCGCGAGGCAATTGACCGCATGTTCGCGCGCAAGTACA<br>ACGCTACGCACATAAAGGTTGGCCAACCCCAGTACTACCTAGCCACGGGGGGCTTCC<br>TCATCGCTTATCAACCCCTCCTCAGCAACACGCTCGCCGAGCTGTACGTGCGGGAAT<br>ATATGCGGGAACAGGACCGCAAACCCCGAAACGCCACGCCCGCGCCGCTGCGGGAA<br>GCACCGAGCGCCAACGCGTCCGTGGAGCGCATCAAGACGACATCCTCGATTGAGTTT<br>GCTCGTCTGCAGTTTACGTATAACCACATACAGCGCCATGTAAACGACATGCTCGGG<br>CGCATCGCCGTCGCGTGGTGCGAGCTCCAAAATCACGAGCTCACTCTGTGGAACGAG<br>GCACGCAAGCTCAATCCCAACGCCATCGCATCCGCCACCGTAGGCCGGCGGGTGAG<br>CGCTCGCATGCTCGGGGATGTCATGGCCGTCTCCACGTGCGTGCCCGTCGCCCCGGA<br>CAACGTGATCGTGCAAAATAGCATGCGCGTTTCTTCGCGGCCGGGGACGTGCTACAG<br>CCGCCCGCTGGTTAGCTTTCGGTACGAAGACCAAGGCCCGCTGATTGAGGGGCAGCT<br>GGGTGAGAACAACGAGCTGCGCCTCACCCGCGATGCGTTAGAGCCGTGTACCGTCG<br>GCCACCGGCGCTACTTCATCTTCGGAGGGGGATACGTATACTTCGAAGAATATGCGT<br>ACTCTCACCAATTGAGTCGCGCCGATGTCACCACTGTTAGCACCTTCATCGACCTGA<br>ACATCACCATGCTGGAGGACCACGAGTTCGTGCCCCTGGAGGTCTACACACGCCACG<br>AGATCAAGGATTCCGGCCTACTGGACTACACCGAAGTCCAGAGACGAAATCAGCTG<br>CACGATCTCCGCTTTGCTGACATCGATACTGTTATCCGCGCCGACGCCAACGCCGCC<br>ATGTTCGCAGGTCTGTGTGCGTTTTTCGAGGGTATGGGTGACTTAGGGCGCGCGGTG<br>GGCAAGGTCGTCATGGGGGTAGTCGGGGGCGTGGTGTCGGCCGTCTCGGGCGTCTCC<br>TCCTTTATGTCTAACCCCTGATAATAGGCTGGAGCCTCGGTGGCCATGCTTCTTGCCC<br>CTTGGGCCTCCCCCCAGCCCCTCCTCCCCTTCCTGCACCCGTACCCCCGTGGTCTTTG<br>AATAAAGTCTGAGTGGGCGGC (SEQ ID NO: 59) |
| MRK_HSV-2<br>SgC, SQ-<br>032835, CX-<br>000616 | TCAAGCTTTTGGACCCTCGTACAGAAGCTAATACGACTCACTATAGGGAAATAAGAG<br>AGAAAAGAAGAGTAAGAAGAAATATAAGAGCCACCATGGCACTGGGAAGAGTGGG<br>ATTGGCCGTCGGACTGTGGGGACTGCTGTGGGTGGGAGTCGTCGTCGTCCTGGCTAA<br>CGCCTCACCCGGTCGGACTATCACTGTGGGACCCAGGGGGAACGCCTCTAACGCCGC<br>GCCCTCAGCTAGCCCCAGGAATGCCAGCGCTCCCAGGACCACCCCGACTCCTCCGCA<br>ACCCCGCAAGGCGACCAAGTCCAAGGCGTCCACTGCCAAGCCAGCGCCTCCGCCTA<br>AGACTGGCCCCCCTAAGACCTCCAGCGAACCTGTGCGGTGCAACCGGCACGACCCT<br>CTGGCACGCTACGGATCGCGGGTCCAAATCCGGTGTCGGTTCCCGAACAGCACTCGG<br>ACCGAATCGCGGCTCCAGATTTGGAGATACGCAACTGCCACTGATGCCGAGATCGG<br>CACTGCCCCAAGCCTTGAGGAGGTCATGGTCAACGTGTCAGCTCCTCCTGGAGGCCA<br>GCTGGTGTACGACTCCGCTCCGAACCGAACCGACCCGCACGTCATCTGGGCCGAAG<br>GAGCCGGTCCTGGTGCATCGCCGAGGTTGTACTCGGTAGTGGGTCCCCTGGGGAGAC<br>AGCGGCTGATCATCGAAGAACTGACTCTGGAGACTCAGGGCATGTACTATTGGGTGT<br>GGGGCAGAACCGATAGACCATCCGCATACGGAACCTGGGTGCGCGTGAGAGTGTTC<br>AGACCCCCGTCCTTGACAATCCACCCGCATGCGGTGCTCGAAGGGCAGCCCTTCAAG<br>GCCACTTGCACTGCGGCCACTTACTACCCTGGAAACCGGGCCGAATTCGTGTGGTTC<br>GAGGATGGACGGAGGGTGTTCGACCCGGCGCAGATTCATACGCAGACTCAGGAAAA<br>CCCGGACGGCTTCTCCACCGTGTCCACTGTGACTTCGGCCGCTGTGGGAGGACAAGG<br>ACCGCCACGCACCTTCACCTGTCAGCTGACCTGGCACCGCGACAGCGTGTCCTTTAG<br>CCGGCGGAACGCATCAGGCACTGCCTCCGTGTTGCCTCGCCCAACCATTACCATGGA<br>GTTCACCGGAGATCACGCCGTGTGCACTGCTGGCTGCGTCCCCGAAGGCGTGACCTT<br>CGCCTGGTTTCTCGGGGACGACTCATCCCCGGCGGAAAAGGTGGCCGTGGCCTCTCA<br>GACCAGCTGCGGTAGACCGGGAACCGCCACCATCCGCTCCACTCTGCCGGTGTCGTA<br>CGAGCAGACCGAGTACATTTGTCGCCTGGCCGGATACCCGGACGGTATCCCAGTGCT<br>CGAACACCACGGCAGCCATCAGCCTCCGCCGAGAGATCCTACCGAGCGCCAGGTCA<br>TCCGGGCCGTGGAAGGATGATAATAGGCTGGAGCCTCGGTGGCCATGCTTCTTGCCC<br>CTTGGGCCTCCCCCCAGCCCCTCCTCCCCTTCCTGCACCCGTACCCCCGTGGTCTTTG<br>AATAAAGTCTGAGTGGGCGGC (SEQ ID NO: 60) |
| MRK_HSV-2<br>SgE, SQ-<br>032211, CX-<br>003794 | TCAAGCTTTTGGACCCTCGTACAGAAGCTAATACGACTCACTATAGGGAAATAAGAG<br>AGAAAAGAAGAGTAAGAAGAAATATAAGAGCCACCATGGCTCGCGGGGCCGGGTT<br>GGTGTTTTTTGTTGGAGTTTGGGTCGTATCGTGCCTGGCGGCAGCACCCAGAACGTC<br>CTGGAAACGGGTTACCTCGGGCGAGGACGTGGTGTTGCTTCCGGCGCCCGCGGGGC<br>CGGAGGAACGCACACGGGCCCACAAACTACTGTGGGCCGCGGAACCCCTGGATGCC<br>TGCGGTCCCCTGAGGCCGTCGTGGGTGGCGCTGTGGCCCCCGCGACGGGTGCTCGAA<br>ACGGTCGTGGATGCGGCGTGCATGCGCGCCCCGGAACCGCTCGCCATAGCATACAG<br>TCCCCCGTTCCCCGCGGGCGACGAGGGACTGTATTCGGAGTTGGCGTGGCGCGATCG<br>CGTAGCCGTGGTCAACGAGAGTCTGGTCATCTACGGGGCCCTGGAGACGGACAGCG<br>GTCTGTACACCCTGTCCGTGGTCGGCCTAAGCGACGAGGCGCGCCAAGTGGCGTCGG<br>TGGTTCTGGTCGTGGAGCCCGCCCCTGTGCCGACCCCGACCCCCGACGACTACGACG<br>AAGAAGACGACGCGGGCGTGAGCGAACGCACGCCGGTCAGCGTACCCCCCCCGACC<br>CCACCCCGTCGTCCCCCCGTCGCCCCCCCTACGCACCCTCGTGTTATCCCCGAGGTGT<br>CCCACGTGCGCGGGGTAACGGTCCATATGGAGACCCCGGAGGCCATTCTGTTTGCCC<br>CCGGAGAGACGTTTGGGACGAACGTCTCCATCCACGCCATTGCCCATGACGACGGTC<br>CGTACGCCATGGACGTCGTCTGGATGCGGTTTGACGTGCCGTCCTCGTGCGCCGAGA<br>TGCGGATCTACGAAGCTTGTCTGTATCACCCGCAGCTTCCAGAATGTCTATCTCCGG<br>CCGACGCGCCGTGCGCTGTAAGTTCCTGGGCGTACCGCCTGGCGGTCCGCAGCTACG<br>CCGGCTGTTCCAGGACTACGCCCCCGCCGCGATGTTTTGCCGAGGCTCGCATGGAAC<br>CGGTCCCGGGGTTGGCGTGGTTAGCCTCCACCGTCAACCTGGAATTCCAGCACGCCT<br>CCCCTCAGCACGCCGGCCTTTACCTGTGCGTGGTGTACGTGGACGATCATATCCACG<br>CCTGGGGCCACATGACCATCTCTACCGCGGCGCAGTACCGGAACGCGGTGGTGGAA |

TABLE 1-continued

| | |
|---|---|
| | CAGCACTTGCCCCAGCGCCAGCCTGAACCCGTCGAGCCCACCCGCCCGCACGTAAG<br>AGCACCCCCTCCCGCGCCTTCCGCGCGCGGCCCGCTGCGCTGATAATAGGCTGGAGC<br>CTCGGTGGCCATGCTTCTTGCCCCTTGGGCCTCCCCCCAGCCCCTCCTCCCCTTCCTG<br>CACCCGTACCCCCGTGGTCTTTGAATAAAGTCTGAGTGGGCGGC (SEQ ID NO: 61) |
| MRK_HSV-2<br>SgI, SQ-<br>032323, CX-<br>002683 | TCAAGCTTTTGGACCCTCGTACAGAAGCTAATACGACTCACTATAGGGAAATAAGAG<br>AGAAAAGAAGAGTAAGAAGAAATATAAGAGCCACCATGCCCGGCCGCTCGCTGCAG<br>GGCCTGGCGATCCTGGGCCTGTGGGTCTGCGCCACCGGCCTGGTCGTCCGCGGCCCC<br>ACGGTCAGTCTGGTCTCAGACTCACTCGTGGATGCCGGGGCCGTGGGGCCCCAGGGC<br>TTCGTGGAAGAGGACCTGCGTGTTTTCGGGGAGCTTCATTTTGTGGGGGCCCAGGTC<br>CCCCACACAAACTACTACGACGGCATCATCGAGCTGTTTCACTACCCCCTGGGGAAC<br>CACTGCCCCCGCGTTGTACACGTGGTCACACTGACCGCATGCCCCCGCCGCCCCGCC<br>GTGGCGTTCACCTTGTGTCGCTCGACGCACCACGCCCACAGCCCCGCCTATCCGACC<br>CTGGAGCTGGGTCTGGCGCGGCAGCCGCTTCTGCGGGTTCGAACGGCAACGCGCGA<br>CTATGCCGGTCTGTATGTCCTGCGCGTATGGGTCGGCAGCGCGACGAACGCCAGCCT<br>GTTTGTTTTGGGGGTGGCGCTCTCTGCCAACGGGACGTTTGTGTATAACGGCTCGGA<br>CTACGGCTCCTGCGATCCGGCGCAGCTTCCCTTTTCGGCCCCGCGCCTGGGACCCTC<br>GAGCGTATACACCCCCGGAGCCTCCCGGCCCACCCCTCCACGGACAACGACATCCCC<br>GTCCTCCCCTAGAGACCCGACCCCCGCCCCCGGGGACACAGGAACGCCTGCGCCCG<br>CGAGCGGCGAGAGAGCCCCGCCCAATTCCACGCGATCGGCCAGCGAATCGAGACAC<br>AGGCTAACCGTAGCCCAGGTAATCCAGTGATAATAGGCTGGAGCCTCGGTGGCCAT<br>GCTTCTTGCCCCTTGGGCCTCCCCCCAGCCCCTCCTCCCCTTCCTGCACCCGTACCCC<br>CGTGGTCTTTGAATAAAGTCTGAGTGGGCGGC (SEQ ID NO: 62) |
| MRK_HSV-2<br>SgD, SQ-<br>032172, CX-<br>004714 | TCAAGCTTTTGGACCCTCGTACAGAAGCTAATACGACTCACTATAGGGAAATAAGAG<br>AGAAAAGAAGAGTAAGAAGAAATATAAGAGCCACCATGGGGCGTTTGACCTCCGGC<br>GTCGGGACGGCGGCCCTGCTAGTTGTCGCGGTGGGACTCCGCGTCGTCTGCGCCAAA<br>TACGCCTTAGCAGACCCCTCGCTTAAGATGGCCGATCCCAATCGATTTCGCGGGAAG<br>AACCTTCCGGTTTTGGACCAGCTGACCGACCCCCCGGGGTGAAGCGTGTTTACCAC<br>ATTCAGCCGAGCCTGGAGGACCCGTTCCAGCCCCCCAGCATCCCGATCACTGTGTAC<br>TACGCAGTGCTGGAACGTGCCTGCCGCAGCGTGCTCCTACATGCCCCATCGGAGGCC<br>CCCCAGATCGTGCGCGGGGCTTCGGACGAGGCCCGAAAGCACACGTACAACCTGAC<br>CATCGCCTGGTATCGCATGGGAGACAATTGCGCTATCCCCATCACGGTTATGGAATA<br>CACCGAGTGCCCCTACAACAAGTCGTTGGGGGTCTGCCCCATCCGAACGCAGCCCCG<br>CTGGAGCTACTATGACAGCTTTAGCGCCGTCAGCGAGGATAACCTGGGATTCCT GAT<br>GCACGCCCCCGCCTTCGAGACCGCGGGTACGTACCTGCGGCTAGTGAAGATAAACG<br>ACTGGACGGAGATCACACAATTTATCCTGGAGCACCGGGCCCGCGCCTCCTGCAAGT<br>ACGCTCTCCCCCTGCGCATCCCCCCGGCAGCGTGCCTCACCTCGAAGGCCTACCAAC<br>AGGGCGTGACGGTCGACAGCATCGGGATGCTACCCCGCTTTATCCCCGAAAACCAG<br>CGCACCGTCGCCCTATACAGCTTAAAAATCGCCGGGTGGCACGGCCCCAAGCCCCC<br>GTACACCAGCACCCTGCTGCCGCCGGAGCTGTCCGACACCACCAACGCCACGCAAC<br>CCGAACTCGTTCCGGAAGACCCCGAGGACTCGGCCCTCTTAGAGGATCCCGCCGGG<br>ACGGTGTCTTCGCAGATCCCCCCAAACTGGCACATCCCGTCGATCCAGGACGTCGCG<br>CCGCACCACGCCCCCGCCGCCCCCAGCAACCCGTGATAATAGGCTGGAGCCTCGGT<br>GGCCATGCTTCTTGCCCCTTGGGCCTCCCCCCAGCCCCTCCTCCCCTTCCTGCACCCG<br>TACCCCCGTGGTCTTTGAATAAAGTCTGAGTGGGCGGC (SEQ ID NO: 63) |
| MRK_HSV-2<br>ICP-0, SQ-<br>032521, CX-<br>004422 | TCAAGCTTTTGGACCCTCGTACAGAAGCTAATACGACTCACTATAGGGAAATAAGAG<br>AGAAAAGAAGAGTAAGAAGAAATATAAGAGCCACCATGGAACCGCGGCCTGGTAC<br>TTCATCCCGCGCCGATCCTGGACCGGAACGGCCACCTCGCCAGACCCCTGGAACGCA<br>GCCTGCAGCCCCTCACGCCTGGGGGATGCTGAATGATATGCAGTGGCTGGCCTCAAG<br>CGACTCCGAGGAAGAGACAGAGGTCGGCATCTCCGACGATGATCTCCATCGGGATT<br>CTACTTCGGAAGCGGGCTCCACCGACACAGAGATGTTCGAGGCCGGCCTGATGGAT<br>GCTGCGACCCCTCCCGCAAGACCGCCTGCCGAACGCCAAGGCTCGCCGACCCCTGCT<br>GACGCCCAGGGTTCGTGCGGTGGAGGCCCTGTGGGGGAGGAGGAAGCTGAAGCCGG<br>AGGCGGTGGAGATGTCAACACCCCGGTGGCCTACCTGATCGTGGGCGTGACTGCCA<br>GCGGATCCTTCTCGACCATCCCCATTGTCAACGATCCCCGCACTCGGGTCGAAGCGG<br>AGGCCGCAGTGCGGGCTGGAACTGCCGTGGACTTCATTTGGACTGGCAATCCCAGG<br>ACCGCTCCCCGGTCACTGTCCCTGGGAGGACACACCGTCCGCGCCCTGTCACCAACT<br>CCCCCGTGGCCTGGAACCGATGACGAGGACGACGACCTGGCCGATGTGGACTACGT<br>GCCCCCTGCCCCAAGACGGGCTCCACGGAGAGGAGGCGGAGGCGCCGGTGCCACCA<br>GGGGCACCAGCCAACCCGCTGCCACCCGGCCTGCTCCTCCTGGGGCCCCGAGATCCT<br>CCTCATCCGGCGGGGCACCTCTGAGAGCAGGAGTGGGCTCAGGCTCCGGAGGAGGA<br>CCCGCCGTGGCAGCTGTGGTCCCGCGAGTGGCCTCCTTGCCTCCGGCCGCAGGAGGC<br>GGCCGGGCCCAGGCCAGAAGGGTGGGGGAGGACGCGGCAGCCGCCGAAGGGCGCA<br>CTCCTCCAGCGCGCCAACCAAGAGCAGCGCAAGAGCCTCCGATCGTGATCTCCGATA<br>GCCCCCCACCGTCACCTCGCAGACCAGCCGGACCCGGGCCTCTGTCGTTCGTGAGCT<br>CCAGCTCGGCCCAGGTGTCGAGCGGACCTGGCGGTGGTGGACTCCCTCAGAGCAGC<br>GGCAGAGCTGCCAGACCTCGCGCCGCCGTGGCCCCGAGGGTCAGGTCGCCGCCGAG<br>AGCAGCTGCCGCCCCAGTGGTGTCCGCCTCAGCCGACGCCGCCGGTCCCGCGCCTCC<br>TGCTGTGCCAGTGGACGCCCATAGAGCGCCGCGGAGCAGAATGACTCAGGCACAGA<br>CTGACACCCAGGCCCAGTCGCTCGGTAGGGCTGGAGCCACCGACGCCAGAGGATCG<br>GGCGGACCCGGAGCCGAAGGAGGGTCCGGTCCCGCCGCTTCCTCCTCCGCGTCCTCA<br>TCAGCCGCTCCGCGCTCACCGCTCGCACCCCAGGGTGTCGGAGCAAAGCGAGCAGC<br>TCCTCGCCGGGCCCCTGACTCCGACTCAGGAGATCGGGGCCACGGACCACTCGCGCC<br>TGCCAGCGCTGGAGCGGCTCCTCCATCGGCTTCCCCATCCTCGCAAGCAGCCGTGGC<br>CGCCGCATCCTCAAGCTCGGCGTCCTCTAGCTCAGCGAGCTCCTCCAGCGCCTCGTC<br>CTCGTCCGCCTCCAGCAGCTCAGCCTCCTCGTCCTCGGCCTCCTCATCGTCCGCCTCC<br>TCCTCCGCTGGAGGTGCCGGAGGATCGGTCGCATCCGCTTCCGGCGCAGGGGAGCG<br>CCGAGAAACGTCCCTGGGTCCGCGGGCAGCTGCTCCGAGGGGTCCTCGCAAGTGCG |

TABLE 1-continued

| | |
|---|---|
| | CGCGGAAAACTCGGCACGCGGAGGGAGGACCGGAACCTGGCGCGAGAGATCCTGC<br>GCCTGGACTGACCCGGTACCTCCCCATTGCCGGGGTGTCCAGCGTGGTGGCACTTGC<br>CCCGTACGTCAACAAGACCGTGACCGGGGACTGTCTCCCCGTGCTCGACATGGAGAC<br>TGGACACATTGGCGCGTATGTGGTCCTGGTGGATCAGACCGGTAATGTGGCCGACCT<br>TTTGAGAGCAGCGGCCCCAGCATGGTCCCGCAGAACCCTGCTGCCTGAGCACGCCA<br>GGAATTGCGTGCGGCCGCCGGACTACCCGACTCCGCCCGCCAGCGAATGGAACTCA<br>CTGTGGATGACTCCCGTGGGCAACATGCTGTTCGATCAGGGGACCCTGGTCGGAGCC<br>CTGGATTTTCACGGCCTGCGCTCCAGACATCCGTGGTCTAGGGAACAGGGTGCTCCT<br>GCTCCCGCGGGTGATGCCCCTGCTGGCCACGGCGAATAGTGATAATAGGCTGGAGC<br>CTCGGTGGCCATGCTTCTTGCCCCTTGGGCCTCCCCCCAGCCCCTCCTCCCCTTCCTG<br>CACCCGTACCCCCGTGGTCTTTGAATAAAGTCTGAGTGGGCGGC (SEQ ID NO: 64) |
| MRK_HSV-2<br>ICP-4, SQ-<br>032440, CX-<br>002146 | TCAAGCTTTTGGACCCTCGTACAGAAGCTAATACGACTCACTATAGGGAAATAAGAG<br>AGAAAAGAAGAGTAAGAAGAAATATAAGAGCCACCATGTCGGCCGAGCAGCGCAA<br>GAAGAAGAAAACGACCACCACTACCCAGGGCAGAGGAGCCGAAGTCGCCATGGCC<br>GATGAAGATGGCGGGAGGCTGCGGGCCGCCGCTGAAACCACCGGAGGACCGGGATC<br>CCCTGACCCTGCGGACGGCCCACCTCCCACACCGAACCCGGACAGACGGCCTGCTG<br>CAAGGCCCGGTTTCGGATGGCACGGGGGACCCGAAGAGAACGAGGACGAAGCCGA<br>TGACGCCGCGGCGGATGCAGACGCCGACGAGGCGGCTCCCGCTTCGGGAGAAGCGG<br>TGGACGAACCGGCCGCCGATGGAGTGGTCAGCCCCCGCCAGCTCGCGCTGCTCGCGT<br>CCATGGTGGATGAAGCCGTGAGAACTATCCCCTCACCTCCGCCGGAACGGGATGGA<br>GCTCAAGAGGAAGCCGCCAGAAGCCCGTCCCCTCCGAGAACTCCATCCATGCGGGC<br>CGACTACGGCGAAGAGAATGACGACGATGATGACGACGATGATGACGATGACCGCG<br>ATGCCGGACGGTGGGTCCGCGGACCTGAGACTACCTCCGCCGTGCGCGGAGCCTAC<br>CCTGATCCGATGGCCTCACTTAGCCCCCGGCCACCCGCCCCCCGCCGCCACCACCAC<br>CATCATCACCACCGCAGAAGAAGGGCTCCCAGGCGCAGATCAGCAGCTTCCGACAG<br>CTCGAAGTCCGGCTCCTCGTCCTCCGCCAGCAGCGCATCCTCGTCAGCGTCCTCATC<br>GTCCAGCGCCTCGGCGAGCTCCTCCGACGATGACGACGACGACGATGCCGCCAGAG<br>CTCCGGCATCAGCCGCGGACCATGCCGCCGGAGGAACCCTCGGTGCCGACGACGAG<br>GAGGCCGGCGTGCCTGCCCGCGCTCCGGGAGCTGCTCCTAGGCCTTCACCACCCCGG<br>GCGGAGCCAGCCCCTGCCAGAACGCCAGCAGCCACCGCTGGGCGATTGGAGAGGCG<br>GAGAGCCCGGGCCGCCGTGGCCGGTCGGGATGCCACCGGCCGCTTCACTGCCGGAC<br>GCCCTCGGCGCGTCGAACTGGACGCAGACGCCGCCTCGGGCGCGTTCTACGCCCGCT<br>ATCGGGACGGTTATGTGTCCGGCGAGCCTTGGCCTGGTGCCGGTCCTCCTCCGCCTG<br>GGAGAGTGCTCTACGGGGGTCTGGGTGATTCTCGGCCAGGGTTGTGGGGAGCCCCC<br>GAGGCGGAGGAAGCCAGAGCCCGCTTCGAAGCATCCGGAGCACCGGCCCCTGTGTG<br>GGCGCCGGAACTGGGCGACGCCGCCCAACAATACGCCCTGATCACACGCCTGCTCT<br>ACACTCCGGACGCCGAAGCCATGGGCTGGCTGCAGAACCCGAGAGTGGCCCCGGGT<br>GATGTGGCCCTGGACCAGGCATGCTTCAGGATTAGCGGAGCCGCGAGAAACTCGAG<br>CAGCTTTATCTCAGGATCTGTGGCCCGAGCCGTGCCGCACCTGGGCTACGCGATGGC<br>CGCCGGACGCTTCGGATGGGGGCTGGCCCATGTCGCTGCCGCGGTGGCGATGTCCCG<br>GCGGTACGACCGGGCTCAGAAGGGTTTCCTCCTCACCAGCCTCCGGAGGGCATACGC<br>CCCGTTGCTGGCTCGGGAGAACGCCGCTCTGACTGGCGCCCGCACTCCTGATGACGG<br>TGGCGACGCCAACCGCCACGACGGCGACGATGCACGGGGAAAGCCCGCGGCCGCCG<br>CCGCCCCCCTTCCTAGCGCAGCCGCTTCGCCTGCCGACGAACGGGCTGTCCCTGCCG<br>GATACGGAGCCGCCGGTGTGCTGGCGGCCCTTGGGAGACTGTCAGCCGCGCCTGCTT<br>CAGCGCCGGCCGGAGCCGACGATGACGACGACGACGATGGAGCCGGAGGAGGGGG<br>CGGCGGTCGGAGAGCAGAAGCCGGCAGGGTGGCAGTCGAATGCCTTGCTGCCTGTC<br>GCGGGATCCTCGAGGCGTTGGCCGAAGGCTTCGACGGCGACCTGGCGGCAGTGCCT<br>GGCCTGGCCGGCGCCCGCCCCGCTGCCCCTCCACGGCCCGGTCCGGCCGGGGCCGC<br>AGCCCCTCCGCATGCTGACGCGCCTCGCCTCAGAGCATGGCTGAGAGAATTGAGATT<br>TGTGCGGGATGCGCTGGTCCTTATGCGCCTGAGGGGGGATCTGAGGGTGGCCGGAG<br>GTTCCGAGGCGGCCGTGGCTGCTGTGCGGGCCGTGTCCCTGGTGGCCGGTGCGCTGG<br>GTCCCGCTCTGCCGCGGTCCCCTAGATTGCTTTCCTCAGCGGCCGCCGCCGCAGCCG<br>ATCTGCTCTTTCAGAACCAAAGCCTCAGGCCGCTGCTGGCCGACACTGTCGCCGCTG<br>CGGACTCCCTCGCTGCCCCAGCCTCGGCCCCAAGAGAGGCTGCCGATGCCCCTCGCC<br>CCGCCGCGGCCCCGCCTGCCGGAGCAGCGCCGCCTGCACCCCCTACTCCCCCCCCGC<br>GACCGCCACGCCCAGCCGCTCTTACCAGAAGGCCAGCTGAGGGTCCTGACCCGCAG<br>GGCGGCTGGCGCAGACAGCCCCCGGGACCTTCCCACACTCCCGCCCCATCTGCGGCT<br>GCCCTTGAAGCATACTGTGCCCCGAGAGCTGTGGCGGAGCTGACCGACCACCCTCTG<br>TTCCCTGCACCTTGGCGGCCTGCCCTGATGTTTGACCCGAGAGCGTTGGCCTCCCTGG<br>CGGCCAGATGTGCGGCCCCGCCTCCCGGAGGAGCCCCAGCTGCATTCGGACCTCTGC<br>GGGCATCCGGACCACTGCGGCGCGCTGCTGCATGGATGCGGCAAGTGCCGGACCCT<br>GAGGACGTTCGCGTGGTCATTCTTTACTCCCCCCTGCCGGGAGAAGATCTCGCCGCC<br>GGCCGCGCGGGAGGAGGCCCTCCACCCGAGTGGTCCGCTGAACGGGGAGGCCTGTC<br>CTGCCTGCTGGCTGCCCTGGGAAACCGCCTGTGCGGACCAGCTACTGCCGCCTGGGC<br>TGGAAACTGGACCGGCGCACCCGATGTGTCAGCCCTCGGAGCGCAGGGAGTGCTGC<br>TGCTGTCAACTCGCGACCTGGCATTCGCCGGAGCTGTGGAGTTCCTGGGTCTGCTTG<br>CCGGCGCGTGCGACCGGAGATTGATCGTCGTGAACGCTGTCAGAGCGGCCGCTTGG<br>CCTGCCGCTGCTCCGGTGGTCAGCCGGCAGCACGCATATCTGGCCTGCGAGGTGCTG<br>CCCGCCGTGCAGTGTGCCGTGCGGTGGCCAGCGGCCAGAGACTTGCGACGGACCGT<br>GCTGGCCTCCGGTAGGGTCTTTGGCCCCGGAGTGTTCGCCCGCGTGGAGGCCGCCCA<br>TGCCAGACTGTACCCCGACGCACCGCCCCTGAGACTGTGCCGGGGAGCCAACGTGC<br>GGTACAGAGTCCGCACCCGCTTCGGACCCGATACTCTGGTGCCAATGTCACCGCGGG<br>AATATAGGAGAGCCGTGCTCCCGGCACTGGACGGCAGAGCCGCCGCATCCGGTGCT<br>GGGGACGCGATGGCACCCGGAGCCCCCGACTTTTGCGAGGATGAAGCCCACAGCCA<br>TCGGGCCTGTGCCAGATGGGGCCTGGGTGCCCCTCTTCGCCCCGTGTACGTGGCCCT<br>GGGGAGAGATGCCGTCCGCGGTGGACCAGCCGAGCTGAGAGGCCCACGCCGGGAAT<br>TTTGCGCTCGGGCCCTGCTCGAGCCCGATGGAGATGCGCCTCCCCTTGTGCTGCGCG<br>ACGACGCTGACGCCGGCCCACCTCCGCAAATCCGGTGGGCCAGCGCCGCCGGTCGA |

TABLE 1-continued

| | |
|---|---|
| | GCAGGAACGGTGTTGGCAGCAGCCGGAGGAGGAGTCGAAGTGGTCGGAACCGCGG<br>CTGGACTGGCAACCCCGCCAAGGCGCGAACCTGTGGATATGGACGCCGAGCTGGAG<br>GATGACGACGATGGCCTTTTCGGCGAGTGATGATAATAGGCTGGAGCCTCGGTGGCC<br>ATGCTTCTTGCCCCTTGGGCCTCCCCCCAGCCCCTCCTCCCCTTCCTGCACCCGTACC<br>CCCGTGGTCTTTGAATAAAGTCTGAGTGGGCGGC (SEQ ID NO: 65) |

HSV mRNA Sequences

It should eb understood that the vaccines as provided herein may include a mRNA polynucleotide with or without a 5' UTR and/or 3' UTR. It should also be understood that any of the 5' UTR and/or 3' UTR sequences underlined below may be omitted, modified, or substituted with a different 5' UTR and/or 3 'UTR.

| Strain | Nucleic Acid Sequence |
|---|---|
| HSV-2 gB_DX | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGAGAGGUGGUGGCUU<br>AGUUUGCGCGCUGGUUGUCGGGGCGCUCGUAGCCGCCGUGGCGUCGGCCGCCCCU<br>GCGGCUCCUCGCGCUAGCGGAGGCGUAGCCGCAACAGUUGCGGCGAACGGGGGUC<br>CAGCCUCUCAGCCUCCUCCCGUCCCGAGCCCUGCGACCACCAAGGCUAGAAAGCG<br>GAAGACCAAGAAACCGCCCAAGCGCCCCGAGGCCACCCCGCCCCCCGAUGCCAACG<br>CGACUGUCGCCGCUGGCCAUGCGACGCUUCGCGCUCAUCUGAGGGAGAUCAAGGU<br>UGAAAAUGCUGAUGCCCAAUUUUACGUGUGCCCGCCCCCGACGGGCGCCACGGUU<br>GUGCAGUUUGAACAGCCGCGGCGCUGUCCGACGCGGCCAGAAGGCCAGAACUAUA<br>CGGAGGGCAUAGCGGUGGUCUUUAAGGAAAACAUCGCCCCGUACAAAUUUAAGGC<br>CACAAUGUACUACAAAGACGUGACAGUUUCGCAAGUGUGGUUUGGCCACAGAUAC<br>UCGCAGUUUAUGGGAAUCUUCGAAGAUAGAGCCCCUGUUCCCUUCGAGGAAGUCA<br>UCGACAAGAUUAAUGCCAAAGGGGUAUGCCGUUCCACGGCCAAAUACGUGCGCAA<br>CAAUAUGGAGACCACCGCCUUUCACCGGGAUGAUCACGAGACCGACAUGGAGCUU<br>AAGCCGGCGAAGGUCGCCACGCGUACCUCCCGGGGUUGGCACACCACAGAUCUUA<br>AGUACAAUCCCUCGCGAGUUGAAGCAUUCCAUCGGUAUGGAACUACCGUUAACUG<br>CAUCGUUGAGGAGGUGGAUGCGCGGUCGGUGUACCCUUACGAUGAGUUUGUGUU<br>AGCGACCGGCGAUUUUGUGUACAUGUCCCCGUUUUACGGCUACCGGGAGGGGUCG<br>CACACCGAACAUACCUCGUACGCCGCUGACAGGUUCAAGCAGGUCGAUGGCUUUU<br>ACGCGCGCGAUCUCACCACGAAGGCCCGGGCCACGUCACCGACGACCAGGAACUU<br>GCUCACGACCCCCAAGUUCACCGUCGCUUGGGAUUGGGUCCCAAAGCGUCCGGCG<br>GUCUGCACGAUGACCAAAUGGCAGGAGGUGGACGAAAUGCUCCGCGCAGAAUACG<br>GCGGCUCCUUCCGCUUCUCGUCCGACGCCAUCUCGACAACCUUCACCACCAAUCU<br>GACCCAGUACAGUCUGUCGCGCGUUGAUUUAGGAGACUGCAUUGGCCGGGAUGCC<br>CGGGAGGCCAUCGACAGAAUGUUUGCGCGUAAGUACAAUGCCACACAUAUUAAGG<br>UGGGCCAGCCGCAAUACUACCUUGCCACGGGCGGCUUUCUCAUCGCGUACCAGCC<br>CCUUCUCUCAAAUACGCUCGCUGAACUGUACGUGCGGGAGUAUAUGAGGGAACAG<br>GACCGCAAGCCCCGCAAUGCCACGCCUGCGCCACUACGAGAGGCGCCUUCAGCUA<br>AUGCGUCGGUGGAACGUAUCAAGACCACCUCCUCAAUAGAGUUCGCCCGGCUGCA<br>AUUUACGUACAACCACAUCCAGCGCCACGUGAACGACAUGCUGGGCCGCAUCGCU<br>GUCGCCUGGUGCGAGCUGCAGAAUCACGAGCUGACUCUUUGGAACGAGGCCCGAA<br>AACUCAACCCCAACGCGAUCGCCUCCGCAACAGUCGGUAGACGGGUGAGCGCUCG<br>CAUGCUAGGAGAUGUCAUGGCUGUGUCCACCUGCGUGCCCGUCGCUCCGGACAAC<br>GUGAUUGUGCAGAAUUCGAUGCGGGUCUUGAUAAUAGGCUGGAGCCUCGGUGGC<br>CAUGCUUCUUGCCCCUUGGGCCUCCCCCCAGCCCCUCCUCCCCUUCCUGCACCCGU<br>ACCCCCGUGGUCUUUGAAUAAAGUCUGAGUGGGCGGC (SEQ ID NO: 90) |
| HSV-2 gC_DX | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCCCUUGGACGGGU<br>AGGCCUAGCCGUGGGCCUGUGGGGCCUACUGUGGGUGGGUGUGGUCGUGGUGCU<br>GGCCAAUGCCUCCCCCGGACGCACGAUAACGGUGGGCCCGCGAGGCAACGCGAGC<br>AAUGCUGCCCCCUCCGCGUCCCCGCGGAACGCAUCCGCCCCCCGAACCACACCCAC<br>GCCCCCACAACCCCGCAAAGCGACGAAAUCCAAGGCCUCCACCGCCAAACCGGCUC<br>CGCCCCCCAAGACCGGACCCCCGAAGACAUCCUCGGAGCCCGUGCGAUGCAACCGC<br>CACGACCCGCUGGCCCGGUACGGCUCGCGGGUGCAAAUCCGAUGCCGGUUUCCCA<br>ACUCCACGAGGACUGAGUCCCGUCUCCAGAUCUGGCGUUAUGCCACGGCGACGGA<br>CGCCGAAAUCGGAACAGCGCCUAGCUUAGAAGAGGUGAUGGUGAACGUGUCGGCC<br>CCGCCCGGGGGCCAACUGGUGUAUGACAGUGCCCCCAACCGAACGGACCCGCAUG<br>UAAUCUGGGCGGAGGGCGCCGGCCCGGGCGCCAGCCCGCGCCUGUACUCGGUUGU<br>CGGCCCGCUGGGUCGGCAGCGGCUCAUCAUCGAAGAGUUAACCCUGGAGACACAG<br>GGCAUGUACUAUUGGGUGUGGGGCCGGACGGACCGCCCGUCCGCCUACGGGACCU<br>GGGUCCGCGUUCGAGUAUUUCGCCCUCCGUCGCUGACCAUCCACCCCCACGCGGU<br>GCUGGAGGGCCAGCCGUUUAAGGCGACGUGCACGGCCGCAACCUACUACCCGGGC<br>AACCGCGCGGAGUUCGUCUGGUUUGAGGACGGUCGCCGCGUAUUCGAUCCGGCAC<br>AGAUACACACGCAGACGCAGGAGAACCCCGACGGCUUUUCCACCGUCUCCACCGU<br>GACCUCCGCGGCCGUCGGCGGGCAGGGCCCCCCUCGCACCUUCACCUGCCAGCUGA<br>CGUGGCACCGCGACUCCGUGUCGUUCUCUCGGCGCAACGCCAGCGGCACGGCCUC<br>GGUUCUGCCGCGGCCGACCAUUACCAUGGAGUUUACAGGCGACCAUGCGGUCUGC<br>ACGGCCGGCUGUGUGCCCGAGGGGGUCACGUUUGCUUGGUUCCUGGGGGAUGACU<br>CCUCGCCGGCGGAAAAGGUGGCCGUCGCGUCCCAGACAUCGUGCGGGCGCCCCGG<br>CACCGCCACGAUCCGCUCCACCCUGCCGGUCUCGUACGAGCAGACCGAGUACAUC<br>UGUAGACUGGCGGGAUACCCGGACGGAAUUCCGGUCCUAGAGCACCACGGAAGCC<br>ACCAGCCCCCGCCGCGGGACCCAACCGAGCGGCAGGUGAUCCGGGCGGUGGAGGG<br>GGCGGGGAUCGGAGUGGCUGUCCUUGUCGCGGUGGUUCUGGCCGGGACCGCGGUA<br>GUGUACCUGACCCAUGCCUCCUCGGUACGCUAUCGUCGGCUGCGGUAAUGAUAAU |

TABLE 1-continued

| | |
|---|---|
| | AGGCUGGAGCCUCGGUGGCCAUGCUUCUUGCCCCUUGGGCCUCCCCCCAGCCCCU<br>CCUCCCCUUCCUGCACCCGUACCCCCGUGGUCUUUGAAUAAAGUCUGAGUGGGCG<br>GC (SEQ ID NO: 91) |
| HSV-2 gD_DX | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGGGCGUUUGACCUC<br>CGGCGUCGGGACGGCGGCCCUGCUAGUUGUCGCGGUGGGACUCCGCGUCGUCUGC<br>GCCAAAUACGCCUUAGCAGACCCCUCGCUUAAGAUGGCCGAUCCCAAUCGAUUUC<br>GCGGGAAGAACCUUCCGGUUUUGGACCAGCUGACCGACCCCCCGGGGUGAAGCG<br>UGUUUACCACAUUCAGCCGAGCCUGGAGGACCCGUUCCAGCCCCCCAGCAUCCCG<br>AUCACUGUGUACUACGCAGUGCUGGAACGUGCCUGCCGCAGCGUGCUCCUACAUG<br>CCCCAUCGGAGGCCCCCAGAUCGUGCGCGGGGCUUCGGACGAGGCCCGAAAGCA<br>CACGUACAACCUGACCAUCGCCUGGUAUCGCAUGGGAGACAAUUGCGCUAUCCCC<br>AUCACGGUUAUGGAAUACACCGAGUGCCCCUACAACAAGUCGUUGGGGGUCUGCC<br>CCAUCCGAACGCAGCCCCGCUGGAGCUACUAUGACAGCUUUAGCGCCGUCAGCGA<br>GGAUAACCUGGGAUUCCUGAUGCACGCCCCCGCCUUCGAGACCGCGGGUACGUAC<br>CUGCGGCUAGUGAAGAUAAACGACUGGACGGAGAUCACACAAUUUAUCCUGGAGC<br>ACCGGGCCCGCGCCUCCUGCAAGUACGCUCUCCCCCUGCGCAUCCCCCCGGCAGCG<br>UGCCUCACCUCGAAGGCCUACCAACAGGGCGUGACGGUCGACAGCAUCGGGAUGC<br>UACCCCGCUUUAUCCCCGAAAACCAGCGCACCGUCGCCCUAUACAGCUUAAAAAU<br>CGCCGGGUGGCACGGCCCCAAGCCCCCGUACACCAGCACCCUGCUGCCGCCGGAGC<br>UGUCCGACACCACCAACGCCACGCAACCCGAACUCGUUCCGGAAGACCCCGAGGA<br>CUCGGCCCUCUUAGAGGAUCCCGCCGGGACGGUGUCUUCGCAGAUCCCCCCAAAC<br>UGGCACAUCCCGUCGAUCCAGGACGUCGCACCGCACCACGCCCCCGCCGCCCCCAG<br>CAACCCGGGCCUGAUCAUCGGCGCGCUGGCCGGCAGUACCCUGGCGGUGCUGGUC<br>AUCGGCGGUAUUGCGUUUUGGGUACGCCGCCGCGCUCAGAUGGCCCCCAAGCGCC<br>UACGUCUCCCCCACAUCCGGGAUGACGACGCGCCCCCCUCGCACCAGCCAUUGUU<br>UUACUAGUGAUAAUAGGCUGGAGCCUCGGUGGCCAUGCUUCUUGCCCCUUGGGCC<br>UCCCCCCAGCCCCUCCUCCCCUUCCUGCACCCGUACCCCCGUGGUCUUUGAAUAAA<br>GUCUGAGUGGGCGGC (SEQ ID NO: 92) |
| HSV-2 gE_DX | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCUAGGGGGGCCGG<br>GUUGGUUUUUUUUGUUGGAGUUUGGGUCGUAAGCUGCCUCGCGGCAGCGCCCAG<br>AACGUCCUGGAAACGCGUAACCUCGGGCGAAGACGUGGUGUUACUCCCCGCGCCG<br>GCGGGGCCGGAAGAACGCACUCGGGCCCACAAACUACUGUGGGCAGCGGAACCGC<br>UGGAUGCCUGCGGUCCCCUGAGGCCGUCAUGGGUGGCACUGUGGCCCCCCCGACG<br>AGUGCUUGAGACGGUUGUCGAUGCGGCGUGCAUGCGCGCCCCGGAACCGCUCGCU<br>AUCGCAUACAGUCCCCCGUUCCCUGCGGGCGACGAGGGACUUUAUUCGGAGUUGG<br>CGUGGCGCGAUCGCGUAGCCGUGGUCAACGAGAGUUUAGUUAUCUACGGGGCCCU<br>GGAGACGGACAGUGGUCUGUACACCCUGUCAGUGGUGGGCCUAUCCGACGAGGCC<br>CGCCAAGUGGCGUCCGUGGUUCUCGUCGUCGAGCCCGCCCCUGUGCCUACCCCGA<br>CCCCCGAUGACUACGACGAGGAGGAUGACGCGGGCGUGAGCGAACGCACGCCCGU<br>CAGCGUUCCCCCCCCAACACCCCCCCGACGUCCCCCCGUCGCCCCCCGACGCACC<br>CUCGUGUUAUCCCUGAGGUGAGCCACGUGCGGGGGGUGACGGUCCACAUGGAAAC<br>CCCGGAGGCCAUUCUGUUUGCGCCAGGGGAGACGUUUGGGACGAACGUCUCCAUC<br>CACGCAAUUGCCCACGACGACGGUCCGUACGCCAUGGACGUCGUCUGGAUGCGAU<br>UUGAUGUCCCGUCCUCGUGCGCCGAGAUGCGGAUCUAUGAAGCAUGUCUGUAUCA<br>CCCGCAGCUGCCUGAGUGUCUGUCUCCGGCCGAUGCGCCGUGCGCCGUAAGUUCG<br>UGGGCGUACCGCCUGGCGGUCCGCAGCUACGCCGGCUGCUCCAGGACUACGCCCC<br>CACCUCGAUGUUUUGCUGAAGCUCGCAUGGAACCGGUCCCCGGGUUGGCGUGGCU<br>CGCAUCAACUGUUAAUCUGGAAUUCCAGCAUGCCUCUCCCCAACACGCCGGCCUC<br>UAUCUGUGUGUGGUGUAUGUGGACGACCAUAUCCAUGCCUGGGGCCACAUGACCA<br>UCUCCACAGCGGCCCAGUACCGGAAUGCGGUGGUGGAACAGCAUCUCCCCCAGCG<br>CCAGCCCGAGCCCGUAGAACCCACCCGACCGCAUGUGAGAGCCCCCCUCCCGCAC<br>CCUCCGCGAGAGGCCCGUUACGCUUAGGUGCGGUCCUGGGGGCGGCCCUGUUGCU<br>CGCGGCCCUCGGGCUAUCCGCCUGGGCGUGCAUGACCUGCUGGCGCAGGCGCAGU<br>UGGCGGGCGGUUAAAAGUCGGGCCUCGGCGACCGGCCCCACUUACAUUCGAGUAG<br>CGGAUAGCGAGCUGUACGCGGACUGGAGUUCGGACUCAGAGGGCGAGCGCGACGG<br>UUCCCUGUGGCAGGACCCUCCGGAGAGACCCGACUCACCGUCCACAAAUGGAUCC<br>GGCUUUGAGAUCUUAUCCCCAACGGCGCCCUCUGUAUACCCCCAUAGCGAAGGGC<br>GUAAAUCGCGCCGCCCGCUCACCACCUUUGGUUCAGGAAGCCCGGGACGUCGUCA<br>CUCCCAGGCGUCCUAUUCUUCCGUCUUAUGGUAAUGAUAAUAGGCUGGAGCCUCG<br>GUGGCCAUGCUUCUUGCCCCUUGGGCCUCCCCCCAGCCCCUCCUCCCCUUCCUGCA<br>CCCGUACCCCCGUGGUCUUUGAAUAAAGUCUGAGUGGGCGGC (SEQ ID NO: 93) |
| HSV-2 gI_DX | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGCCCGGCCGCUCGCUG<br>CAGGGCCUGGCGAUCCUGGGCCUGUGGGUCUGCGCCACCGGCCUGGUCGUCCGCG<br>GCCCCACGGUCAGUCUGGUCUCAGACUCACUCGUGGAUGCCGGGGCCGUGGGGCC<br>CCAGGGCUUCGUGGAAGAGGACCUGCGUGUUUUCGGGGAGCUUCAUUUUGUGGG<br>GGCCCAGGUCCCCCACACAAACUACUACGACGGCAUCAUCGAGCUGUUUCACUAC<br>CCCCUGGGGAACCACUGCCCCCGCGUUGUACACGUGGUCACACUGACCGCAUGCC<br>CCCGCCGCCCCGCCGUGGCGUUCACCUUGUGUCGCUCGACGCACCACGCCCACAGC<br>CCCGCCUAUCCGACCCUGGAGCUGGGUCUGGCGCGGCAGCCGCUUCUGCGGGUUC<br>GAACGGCAACGCGCGACUAUGCCGGUCUGUAUGUCCUGCGCGUAUGGGUCGGCAG<br>CGCGACGAACGCCAGCCUGUUUGUUUUGGGGGUGGCGCUCUCUGCCAACGGGACG<br>UUUGUGUAUAACGGCUCGGACUACGGCUCCUGCGAUCCGGCGCAGCUUCCCUUUU<br>CGGCCCCGCGCCUGGGACCCUCGAGCGUAUACACCCCCGGAGCCUCCCGGCCCACC<br>CCUCCACGGACAACGACAUCACCGUCCUCCCCACGAGACCCGACCCCCGCCCCCGG |

TABLE 1-continued

GGACACAGGGACGCCUGCUCCCGCGAGCGGCGAGAGAGCCCCGCCCAAUUCCACG
CGAUCGGCCAGCGAAUCGAGACACAGGCUAACCGUAGCCCAGGUAAUCCAGAUCG
CCAUACCGGCGUCCAUCAUCGCCUUUGUGUUUCUGGGCAGCUGUAUCUGCUUCAU
CCAUAGAUGCCAGCGCCGAUACAGGCGCCCCCGCGGCCAGAUUUACAACCCCGGG
GGCGUUUCCUGCGCGGUCAACGAGGCGGCCAUGGCCCGCCUCGGAGCCGAGCUGC
GAUCCCACCCAAACACCCCCCCCAAACCCCGACGCCGUUCGUCGUCGUCCACGACC
AUGCCUUCCCUAACGUCGAUAGCUGAGGAAUCGGAGCCAGGUCCAGUCGUGCUGC
UGUCCGUCAGUCCUCGGCCCCGCAGUGGCCCGACGGCCCCCCAAGAGGUCUAGUG
AUAAUAGGCUGGAGCCUCGGUGGCCAUGCUUCUUGCCCCUUGGGCCUCCCCCCAG
CCCCUCCUCCCCUUCCUGCACCCGUACCCCCGUGGUCUUUGAAUAAAGUCUGAGU
GGGCGGC (SEQ ID NO: 94)

HSV-2
SgB_DX

UCAAGCUUUUGGACCCUCGUACAGAAGCUAAUACGACUCACUAUAGGGAAAUAAG
AGAGAAAAGAAGAGUAAGAAGAAAUAUAAGAGCCACCAUGCGCGGGGGGGGCUU
AGUUUGCGCGCUGGUCGUGGGGGCGCUCGUAGCCGCGGUCGCGUCGGCGGCUCCG
GCUGCCCCACGCGCUUCAGGUGGUGUCGCUGCGACCGUUGCGGCGAAUGGUGGUC
CCGCCAGCCAACCGCCUCCCGUCCCGAGCCCCGCGACCACUAAGGCCCGGAAGCGG
AAGACCAAGAAGCCACCCAAGCGGCCCGAGGCGACUCCGCCCCCAGACGCCAACG
CGACCGUCGCCGCCGGCCACGCCACUCUGCGUGCGCACCUGCGGGAAAUCAAGGU
CGAGAACGCGGACGCCCAGUUUUACGUGUGCCCGCCGCCGACUGGCGCCACGGUG
GUGCAGUUUGAGCAACCUAGGCGCUGCCCGACGCGACCAGAGGGGCAGAACUACA
CCGAGGGCAUAGCGGUGGUCUUUAAGGAAAACAUCGCCCCGUACAAAUUCAAGGC
CACCAUGUACUACAAAGACGUGACCGUGUCGCAGGUGUGGUUCGGCCACCGCUAC
UCCCAGUUUAUGGGGAUAUUCGAGGACCGCGCCCCCGUUCCCUUCGAAGAGGUGA
UUGACAAAAUUAACGCCAAGGGGGUCUGCCGCAGUACGGCGAAGUACGUCCGGAA
CAACAUGGAGACCACUGCCUUCCACCGGGACGACCACGAAACAGACAUGGAGCUC
AAACCGGCGAAAGUCGCCACGCGCACGAGCCGGGGGUGGCACACCACCGACCUCA
AAUACAAUCCUUCGCGGGUGGAAGCAUUCCAUCGGUAUGGCACGACCGUCAACUG
UAUCGUAGAGGAGGUGGAUGCGCGGUCGGUGUACCCCUACGAUGAGUUCGUGCU
GGCAACGGGCGAUUUUGUGUACAUGUCCCCUUUUUACGGCUACCGGGAAGGUAGU
CACACCGAGCACACCAGUUACGCCGCCGACCGCUUUAAGCAAGUGGACGGCUUCU
ACGCGCGCGACCUCACCACAAAGGCCCGGGCCACGUCGCCGACGACCCGCAAUUU
GCUGACGACCCCCAAGUUUACCGUGGCCUGGGACUGGGUGCCUAAGCGACCGGCG
GUCUGUACCAUGACAAAGUGGCAGGAGGUGGACGAAAUGCUCCGCGCUGAAUACG
GUGGCUCUUUCCGCUUCUCUUCCGACGCCAUCUCCACCACGUUCACCACCAACCU
GACCCAAUACUCGCUCUCGAGAGUCGAUCUGGGAGACUGCAUUGGCCGGGAUGCC
CGCGAGGCAAUUGACCGCAUGUUCGCGCGCAAGUACAACGCUACGCACAUAAAGG
UUGGCCAACCCCAGUACUACCUAGCCACGGGGGGCUUCCUCAUCGCUUAUCAACC
CCUCCUCAGCAACACGCUCGCCGAGCUGUACGUGCGGGAAUAUAUGCGGGAACAG
GACCGCAAACCCCGAAACGCCACGCCCGCGCCGCUGCGGGAAGCACCGAGCGCCA
ACGCGUCCGUGGAGCGCAUCAAGACGACAUCCUCGAUUGAGUUUGCUCGUCUGCA
GUUUACGUAUAACCACAUACAGCGCCAUGUAAACGACAUGCUCGGGCGCAUCGCC
GUCGCGUGGUGCGAGCUCCAAAAUCACGAGCUCACUCUGUGGAACGAGGCACGCA
AGCUCAAUCCCAACGCCAUCGCAUCCGCCACCGUAGGCCGGCGGGUGAGCGCUCG
CAUGCUCGGGGAUGUCAUGGCCGUCUCCACGUGCGUGCCCGUCGCCCCGGACAAC
GUGAUCGUGCAAAAUAGCAUGCGCGUUUCUUCGCGGCCGGGGACGUGCUACAGCC
GCCCGCUGGUUAGCUUUCGGUACGAAGACCAAGGCCCGCUGAUUGAGGGGCAGCU
GGGUGAGAACAACGAGCUGCGCCUCACCCGCGAUGCGUUAGAGCCGUGUACCGUC
GGCCACCGGCGCUACUUCAUCUUCGGAGGGGGAUACGUAUACUUCGAAGAAUAUG
CGUACUCUCACCAAUUGAGUCGCGCCGAUGUCACCACUGUUAGCACCUUCAUCGA
CCUGAACAUCACCAUGCUGGAGGACCACGAGUUCGUGCCCCUGGAGGUCUACACA
CGCCACGAGAUCAAGGAUUCCGGCCUACUGGACUACACCGAAGUCCAGAGACGAA
AUCAGCUGCACGAUCUCCGCUUUGCUGACAUCGAUACUGUUAUCCGCGCCGACGC
CAACGCCGCCAUGUUCGCAGGUCUGUGUGCGUUUUUCGAGGGUAUGGGUGACUUA
GGGCGCGCGGUGGGCAAGGUCGUCAUGGGGGUAGUCGGGGGCGUGGUGUCGGCC
GUCUCGGGCGUCUCCUCCUUUAUGUCUAACCCCUGAUAAUAGGCUGGAGCCUCGG
UGGCCAUGCUUCUUGCCCCUUGGGCCUCCCCCCAGCCCCUCCUCCCCUUCCUGCAC
CCGUACCCCCGUGGUCUUUGAAUAAAGUCUGAGUGGGCGGC (SEQ ID NO: 95)

HSV-2
SgC_DX

UCAAGCUUUUGGACCCUCGUACAGAAGCUAAUACGACUCACUAUAGGGAAAUAAG
AGAGAAAAGAAGAGUAAGAAGAAAUAUAAGAGCCACCAUGGCCCUUGGACGGGU
GGGCCUAGCCGUGGGCCUGUGGGGCCUGCUGUGGGUGGGUGUUGUCGUGGUGCU
GGCCAAUGCCUCCCCUGGACGCACGAUAACGGUGGGCCCGCGGGGGAACGCGAGC
AAUGCCGCCCCAUCCGCGUCCCCGCGGAACGCAUCCGCCCCCCGAACCACACCCAC
UCCCCCCCAACCCCGCAAAGCGACGAAAAGUAAGGCCUCCACCGCCAAACCGGCCC
CGCCCCCCAAGACCGGGCCCCCGAAGACAUCUUCUGAGCCCGUGCGCUGCAACCGC
CACGACCCGCUGGCCCGGUACGGCUCGCGGGUGCAAAUCCGAUGUCGAUUUCCCA
ACUCCACUCGCACGGAAUCCCGCCUCCAGAUCUGGCGUUAUGCCACGGCGACGGA
CGCCGAGAUUGGAACUGCGCCUAGCUUAGAGGAGGUGAUGGUAAACGUGUCGGCC
CCGCCCGGGGGCCAACUGGUGUAUGAUAGCGCACCUAACCGAACGGACCCGCACG
UGAUUUGGGCGGAGGGCGCCGGACCUGGCGCCUCACCGCGGCUGUACUCGGUCGU
CGGGCCGCUGGGUCGGCAGAGACUUAUCAUCGAAGAGCUGACCCUCGAGACACAG
GGCAUGUAUUAUUGGGUGUGGGGCCGGACGGACCGCCCGUCCGCGUACGGGACCU
GGGUGCGCGUUCGCGUGUUCCGCCCUCCUUCGCUGACCAUCCACCCCCACGCGGU
GCUGGAGGGCCAGCCGUUUAAAGCGACGUGCACCGCCGCCACCUACUACCCGGGC
AACCGCGCGGAGUUCGUCUGGUUCGAGGACGGUCGCCGGGUAUUCGAUCCGGCCC
AGAUACAUACGCAGACGCAGGAAAACCCCGACGGCUUUUCCACCGUCUCCACCGU
GACCUCCGCGGCCGUCGGCGGCCAGGGCCCCCCGCGCACCUUCACCUGUCAGCUGA
CGUGGCACCGCGACUCCGUGUCGUUCUCUCGGCGCAAUGCCAGCGGCACGGCAUC
GGUGCUGCCACGGCCAACCAUUACCAUGGAGUUUACGGGCGACCAUGCGGUCUGC

TABLE 1-continued

| | |
|---|---|
| | ACGGCCGGCUGUGUGCCCGAGGGGGUGACGUUUGCCUGGUUCCUGGGGGACGACU<br>CCUCGCCGGCCGAGAAGGUGGCCGUCGCGUCCCAGACCUCGUGCGGUCGCCCCGG<br>CACCGCCACGAUCCGCUCCACACUGCCGGUCUCGUACGAGCAGACCGAGUACAUC<br>UGCCGGCUGGCGGGAUACCCGGACGGAAUUCCGGUCCUAGAGCACCAUGGCAGCC<br>ACCAGCCCCCGCCGCGGGACCCCACCGAACGGCAGGUGAUUCGGGCAGUGGAAGG<br>GUGAUAAUAGGCUGGAGCCUCGGUGGCCAUGCUUCUUGCCCCUUGGGCCUCCCCC<br>CAGCCCCUCCUCCCCUUCCUGCACCCGUACCCCCGUGGUCUUUGAAUAAAGUCUG<br>AGUGGGCGGC (SEQ ID NO: 96) |
| HSV-2<br>SgE_DX | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCUCGCGGGGCCGG<br>GUUGGUGUUUUUUGUUGGAGUUUGGGUCGUAUCGUGCCUGGCGGCAGCACCCAG<br>AACGUCCUGGAAACGGGUUACCUCGGGCGAGGACGUGGUGUUGCUUCCGGCGCCC<br>GCGGGGCCGGAGGAACGCACACGGGCCCACAAACUACUGUGGGCCGCGGAACCCC<br>UGGAUGCCUGCGGUCCCCUGAGGCCGUCGUGGGUGGCGCUGUGGCCCCCGCGACG<br>GGUGCUCGAAACGGUCGUGGAUGCGGCGUGCAUGCGCGCCCCGGAACCGCUCGCC<br>AUAGCAUACAGUCCCCCGUUCCCCGCGGGCGACGAGGGACUGUAUUCGGAGUUGG<br>CGUGGCGCGAUCGCGUAGCCGUGGUCAACGAGAGUCUGGUCAUCUACGGGGCCCU<br>GGAGACGGACAGCGGUCUGUACACCCUGUCCGUGGUCGGCCUAAGCGACGAGGCG<br>CGCCAAGUGGCGUCGGUGGUUCUGGUCGUGGAGCCCGCCCCUGUGCCGACCCCGA<br>CCCCCGACGACUACGACGAAGAAGACGACGCGGGCGUGAGCGAACGCACGCCGGU<br>CAGCGUACCCCCCCCGACCCCACCCCGUCGUCCCCCCGUCGCCCCCCCUACGCACC<br>CUCGUGUUAUCCCCGAGGUGUCCCACGUGCGCGGGGUAACGGUCCAUAUGGAGAC<br>CCCGGAGGCCAUUCUGUUUGCCCCCGGAGAGACGUUUGGGACGAACGUCUCCAUC<br>CACGCCAUUGCCCAUGACGACGGUCCGUACGCCAUGGACGUCGUCUGGAUGCGGU<br>UUGACGUGCCGUCCUCGUGCGCCGAGAUGCGGAUCUACGAAGCUUGUCUGUAUCA<br>CCCGCAGCUUCCAGAAUGUCUAUCUCCGGCCGACGCGCCGUGCGCUGUAAGUUCC<br>UGGGCGUACCGCCUGGCGGUCCGCAGCUACGCCGGCUGUUCCAGGACUACGCCCC<br>CGCCGCGAUGUUUUGCCGAGGCUCGCAUGGAACCGGUCCCGGGGUUGGCGUGGUU<br>AGCCUCCACCGUCAACCUGGAAUUCCAGCACGCCUCCCCUCAGCACGCCGGCCUUU<br>ACCUGUGCGUGGUGUACGUGGACGAUCAUAUCCACGCCUGGGGCCACAUGACCAU<br>CUCUACCGCGGCGCAGUACCGGAACGCGGUGGUGGAACAGCACUUGCCCCAGCGC<br>CAGCCUGAACCCGUCGAGCCCACCCGCCCGCACGUAAGAGCACCCCCUCCCGCGCC<br>UUCCGCGCGCGGCCCGCUGCGCUGAUAAUAGGCUGGAGCCUCGGUGGCCAUGCUU<br>CUUGCCCCUUGGGCCUCCCCCCAGCCCCUCCUCCCCUUCCUGCACCCGUACCCCCG<br>UGGUCUUUGAAUAAAGUCUGAGUGGGCGGC (SEQ ID NO: 97) |
| HSV-2 ICP-4 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGUCGGCGGAGCAGCG<br>GAAGAAGAAGAAGACGACGACGACGACGCAGGGCCGCGGGGCCGAGGUCGCGAUG<br>GCGGACGAGGACGGGGGACGUCUCCGGGCCGCGGCGGAGACGACCGGCGGCCCCG<br>GAUCUCCGGAUCCAGCCGACGGACCGCCGCCCACCCCGAACCCGGACCGUCGCCCC<br>GCCGCGCGGCCCGGGUUCGGGUGGCACGGUGGGCCGGAGGAGAACGAAGACGAGG<br>CCGACGACGCCGCCGCCGAUGCCGAUGCCGACGAGGCGGCCCCGGCGUCCGGGGA<br>GGCCGUCGACGAGCCUGCCGCGGACGGCGUCGUCUCGCCGCGGCAGCUGGCCCUG<br>CUGGCCUCGAUGGUGGACGAGGCCGUUCGCACGAUCCCGUCGCCCCCCCCGGAGC<br>GCGACGGCGCGCAAGAAGAAGCGGCCCGCUCGCCUUCUCCGCCGCGGACCCCCUCC<br>AUGCGCGCCGAUUAUGGCGAGGAGAACGACGACGACGACGACGACGACGAUGACG<br>ACGACCGCGACGCGGGCCGCUGGGUCCGCGGACCGGAGACGACGUCCGCGGUCCG<br>CGGGGCGUACCCGGACCCCAUGGCCAGCCUGUCGCCGCGACCCCCGGCGCCCCGCC<br>GACACCACCACCACCACCACCACCGCCGCCGGCGCGCCCCCCGCCGGCGCUCGGCC<br>GCCUCUGACUCAUCAAAAUCCGGAUCCUCGUCGUCGGCGUCCUCCGCCUCCUCCU<br>CCGCCUCCUCCUCCUCGUCUGCAUCCGCCUCCUCGUCUGACGACGACGACGACGAC<br>GACGCCGCCCGCGCCCCCGCCAGCGCCGCAGACCACGCCGCGGGCGGGACCCUCGG<br>CGCGGACGACGAGGAGGCGGGGGUGCCCGCGAGGGCCCCGGGGGCGGCGCCCCGG<br>CCGAGCCCGCCCAGGGCCGAGCCCGCCCCGGCCCGGACCCCCGCGGCGACCGCGGG<br>CCGCCUGGAGCGCCGCCGGGCCCGCGCGGCGGUGGCCGGCCGCGACGCCACGGGCC<br>GCUUCACGGCCGGGCGGCCCCGGCGGGUCGAGCUGGACGCCGACGCGGCCUCCGG<br>CGCCUUCUACGCGCGCUACCGCGACGGGUACGUCAGCGGGGAGCCGUGGCCCGGG<br>GCCGGCCCCCGCCCCCGGGGCGCGUGCUGUACGGCGGGCUGGGCGACAGCCGCCC<br>CGGCCUCUGGGGGGCGCCCGAGGCGGAGGAGGCGCGGGCCCGGUUCGAGGCCUCG<br>GGCGCCCCGGCGCCCGUGUGGGCGCCCGAGCUGGGCGACGCGGCGCAGCAGUACG<br>CCCUGAUCACGCGGCUGCUGUACACGCCGGACGCGGAGGCGAUGGGGUGGCUCCA<br>GAACCCGCGCGUGGCGCCCGGGGACGUGGCGCUGGACCAGGCCUGCUUCCGGAUC<br>UCGGGCGCGGCGCGCAACAGCAGCUCCUUCAUCUCCGGCAGCGUGGCGCGGGCCG<br>UGCCCCACCUGGGGUACGCCAUGGCGGCGGGCCGCUUCGGCUGGGGCCUGGCGCA<br>CGUGGCGGCCGCCGUGGCCAUGAGCCGCCGCUACGACCGCGCGCAGAAGGGCUUC<br>CUGCUGACCAGCCUGCGCCGCGCCUACGCGCCCCUGCUGGCGCGCGAGAACGCGG<br>CGCUGACCGGGGCGCGAACCCCCGACGACGGCGGCGACGCCAACCGCCACGACGG<br>CGACGACGCCCGCGGGAAGCCCGCCGCCGCCGCCGCCCCGUUGCCGUCGGCGGCGG<br>CGUCGCCGGCCGACGAGCGCGCGGUGCCCGCCGGCUACGGCGCCGCGGGGGUGCU<br>CGCCGCCCUGGGGCGCCUGAGCGCCGCGCCCGCCUCCGCGCCGGCCGGGGCCGACG<br>ACGACGACGACGACGACGGCGCCGGCGGUGGUGGCGGCGGCCGGCGCGCGGAGGC<br>GGGCCGCGUGGCCGUGGAGUGCCUGGCCGCCUGCCGCGGGAUCCUGGAGGCGCUG<br>GCGGAGGGCUUCGACGGCGACCUGGCGGCCGUGCCGGGGCUGGCCGGAGCCCGGC<br>CCGCCGCGCCCCCGCGCCCGGGGCCCGCGGGCGCGGCCGCCCCGCCGCACGCCGAC<br>GCGCCCCGCCUGCGCGCCUGGCUGCGCGAGCUGCGGUUCGUGCGCGACGCGCUGG<br>UGCUGAUGCGCCUGCGCGGGGACCUGCGCGUGGCCGGCGGCAGCGAGGCCGCCGU<br>GGCCGCCGUGCGCGCCGUGAGCCUGGUCGCCGGGGCCCUGGGCCCGGCGCUGCCG<br>CGGAGCCCGCGCCUGCUGAGCUCCGCCGCCGCCGCCGCCGCGGACCUGCUCUUCCA |

TABLE 1-continued

GAACCAGAGCCUGCGCCCCCUGCUGGCCGACACCGUCGCCGCGGCCGACUCGCUCG
CCGCGCCCGCCUCCGCGCCGCGGGAGGCCGCGGACGCCCCCGCCCCGCGGCCGCC
CCUCCCGCGGGGGCCGCGCCCCCGCCCCGCCGACGCCGCCGCCGCGGCCGCCGCG
CCCCGCGGCGCUGACCCGCCGGCCCGCCGAGGGCCCCGACCCGCAGGGCGGCUGGC
GCCGCCAGCCGCCGGGGCCCAGCCACACGCCGGCGCCCUCGGCCGCCGCCCUGGAG
GCCUACUGCGCCCCGCGGGCCGUGGCCGAGCUCACGGACCACCCGCUCUUCCCCGC
GCCGUGGCGCCCGGCCCUCAUGUUCGACCCGCGCGCGCUGGCCUCGCUGGCCGCGC
GCUGCGCCGCCCCGCCCCCGGCGGCGCGCCCGCCGCCUUCGGCCCGCUGCGCGCC
UCGGGCCCGCUGCGCCGCGCGGCGGCCUGGAUGCGCCAGGUGCCCGACCCGGAGG
ACGUGCGCGUGGUGAUCCUCUACUCGCCGCUGCCGGGCGAGGACCUGGCCGCGGG
CCGCGCCGGGGGCGGGCCCCCCCGGAGUGGUCCGCCGAGCGCGGCGGGCUGUCC
UGCCUGCUGGCGGCCCUGGGCAACCGGCUCUGCGGGCCCGCCACGGCCGCCUGGG
CGGGCAACUGGACCGGCGCCCCCGACGUCUCGGCGCUGGGCGCGCAGGGCGUGCU
GCUGCUGUCCACGCGGGACCUGGCCUUCGCCGGCGCCGUGGAGUUCCUGGGGCUG
CUGGCCGGCGCCUGCGACCGCCGCCUCAUCGUCGUCAACGCCGUGCGCGCCGCGGC
CUGGCCCGCCGCUGCCCCCGUGGUCUCGCGGCAGCACGCCUACCUGGCCUGCGAG
GUGCUGCCCGCCGUGCAGUGCGCCGUGCGCUGGCCGGCGGCGCGGGACCUGCGCC
GCACCGUGCUGGCCUCCGGCCGCGUGUUCGGGCCGGGGGUCUUCGCGCGCGUGGA
GGCCGCGCACGCGCGCCUGUACCCCGACGCGCCGCCGCUGCGCCUCUGCCGCGGGG
CCAACGUGCGGUACCGCGUGCGCACGCGCUUCGGCCCCGACACGCUGGUGCCCAU
GUCCCCGCGCGAGUACCGCCGCGCCGUGCUCCCGGCGCUGGACGGCCGGGCCGCCG
CCUCGGGCGCGGGCGACGCCAUGGCGCCCGGCGCGCCGGACUUCUGCGAGGACGA
GGCGCACUCGCACCGCGCCUGCGCGCGCUGGGGCCUGGGCGCGCCGCUGCGGCCC
GUCUACGUGGCGCUGGGGCGCGACGCCGUGCGCGGCGGCCCGGCGGAGCUGCGCG
GGCCGCGGCGGGAGUUCUGCGCGCGGGCGCUGCUCGAGCCCGACGGCGACGCGCC
CCCGCUGGUGCUGCGCGACGACGCGGACGCGGGCCCGCCCCCGCAGAUACGCUGG
GCGUCGGCCGCGGGCCGCGCGGGGACGGUGCUGGCCGCGGCGGGCGGCGGCGUGG
AGGUGGUGGGGACCGCCGCGGGGCUGGCCACGCCGCCGAGGCGCGAGCCCGUGGA
CAUGGACGCGGAGCUGGAGGACGACGACGACGGACUGUUUGGGGAGUGAUGAUA
AUAGGCUGGAGCCUCGGUGGCCAUGCUUCUUGCCCCUUGGGCCUCCCCCCAGCCC
CUCCUCCCCUUCCUGCACCCGUACCCCCGUGGUCUUUGAAUAAAGUCUGAGUGGG
CGGC (SEQ ID NO: 98)

HSV-2 SgI_DX

UCAAGCUUUUGGACCCUCGUACAGAAGCUAAUACGACUCACUAUAGGGAAAUAAG
AGAGAAAAGAAGAGUAAGAAGAAAUAUAAGAGCCACCAUGCCCGGCCGCUCGCUG
CAGGGCCUGGCGAUCCUGGGCCUGUGGGUCUGCGCCACCGGCCUGGUCGUCCGCG
GCCCCACGGUCAGUCUGGUCUCAGACUCACUCGUGGAUGCCGGGGCCGUGGGGCC
CCAGGGCUUCGUGGAAGAGGACCUGCGUGUUUUCGGGGAGCUUCAUUUUGUGGG
GGCCCAGGUCCCCCACACAAACUACUACGACGGCAUCAUCGAGCUGUUUCACUAC
CCCCUGGGGAACCACUGCCCCCGCGUUGUACACGUGGUCACACUGACCGCAUGCC
CCCGCCGCCCCGCCGUGGCGUUCACCUUGUGUCGCUCGACGCACCACGCCCACAGC
CCCGCCUAUCCGACCCUGGAGCUGGGUCUGGCGCGGCAGCCGCUUCUGCGGGUUC
GAACGGCAACGCGCGACUAUGCCGGUCUGUAUGUCCUGCGCGUAUGGGUCGGCAG
CGCGACGAACGCCAGCCUGUUUGUUUUGGGGGUGGCGCUCUCUGCCAACGGGACG
UUUGUGUAUAACGGCUCGGACUACGGCUCCUGCGAUCCGGCGCAGCUUCCCUUUU
CGGCCCCGCGCCUGGGACCCUCGAGCGUAUACACCCCCGGAGCCUCCCGGCCCACC
CCUCCACGGACAACGACAUCCCCGUCCUCCCCUAGAGACCCGACCCCCGCCCCCGG
GGACACAGGAACGCCUGCGCCCGCGAGCGGCGAGAGAGCCCCGCCCAAUUCCACG
CGAUCGGCCAGCGAAUCGAGACACAGGCUAACCGUAGCCCAGGUAAUCCAGUGAU
AAUAGGCUGGAGCCUCGGUGGCCAUGCUUCUUGCCCCUUGGGCCUCCCCCCAGCC
CCUCCUCCCCUUCCUGCACCCGUACCCCCGUGGUCUUUGAAUAAAGUCUGAGUGG
GCGGC (SEQ ID NO: 99)

HSV-2 SgD

UCAAGCUUUUGGACCCUCGUACAGAAGCUAAUACGACUCACUAUAGGGAAAUAAG
AGAGAAAAGAAGAGUAAGAAGAAAUAUAAGAGCCACCAUGGGGCGUUUGACCUC
CGGCGUCGGGACGGCGGCCCUGCUAGUUGUCGCGGUGGGACUCCGCGUCGUCUGC
GCCAAAUACGCCUUAGCAGACCCCUCGCUUAAGAUGGCCGAUCCCAAUCGAUUUC
GCGGGAAGAACCUUCCGGUUUUGGACCAGCUGACCGACCCCCCGGGGUGAAGCG
UGUUUACCACAUUCAGCCGAGCCUGGAGGACCCGUUCCAGCCCCCCAGCAUCCCG
AUCACUGUGUACUACGCAGUGCUGGAACGUGCCUGCCGCAGCGUGCUCCUACAUG
CCCCAUCGGAGGCCCCCCAGAUCGUGCGCGGGGCUUCGGACGAGGCCCGAAAGCA
CACGUACAACCUGACCAUCGCCUGGUAUCGCAUGGGAGACAAUUGCGCUAUCCCC
AUCACGGUUAUGGAAUACACCGAGUGCCCCUACAACAAGUCGUUGGGGGUCUGCC
CCAUCCGAACGCAGCCCCGCUGGAGCUACUAUGACAGCUUUAGCGCCGUCAGCGA
GGAUAACCUGGGAUUCCUGAUGCACGCCCCCGCCUUCGAGACCGCGGGUACGUAC
CUGCGGCUAGUGAAGAUAAACGACUGGACGGAGAUCACACAAUUUAUCCUGGAGC
ACCGGGCCCGCGCCUCCUGCAAGUACGCUCUCCCCCUGCGCAUCCCCCCGGCAGCG
UGCCUCACCUCGAAGGCCUACCAACAGGGCGUGACGGUCGACAGCAUCGGGAUGC
UACCCCGCUUUAUCCCCGAAAACCAGCGCACCGUCGCCCUAUACAGCUUAAAAAU
CGCCGGGUGGCACGGCCCCAAGCCCCCGUACACCAGCACCCUGCUGCCGCCGGAGC
UGUCCGACACCACCAACGCCACGCAACCCGAACUCGUUCCGGAAGACCCCGAGGA
CUCGGCCCUCUUAGAGGAUCCCGCCGGGACGGUGUCUUCGCAGAUCCCCCCAAAC
UGGCACAUCCCGUCGAUCCAGGACGUCGCGCCGCACCACGCCCCCGCCGCCCCCAG
CAACCCGUGAUAAUAGGCUGGAGCCUCGGUGGCCAUGCUUCUUGCCCCUUGGGCC
UCCCCCCAGCCCCUCCUCCCCUUCCUGCACCCGUACCCCCGUGGUCUUUGAAUAAA
GUCUGAGUGGGCGGC (SEQ ID NO: 100)

HSV-2 gB

AUGCGCGGGGGGGGCUUGGUUUGCGCGCUGGUCGUGGGGGCGCUGGUGGCCGCGG
UGGCGUCGGCGGCCCCGGCGGCCCCCCGCGCCUCGGGCGGCGUGGCCGCGACCGUC
GCGGCGAACGGGGGUCCCGCCUCCCAGCCGCCCCCCGUCCCGAGCCCCGCGACCAC

TABLE 1-continued

| | |
|---|---|
| | CAAGGCCCGGAAGCGGAAAACCAAAAAGCCGCCCAAGCGGCCCGAGGCGACCCCG<br>CCCCCCGACGCCAACGCGACCGUCGCCGCCGGCCACGCCACGCUGCGCGCGCACCU<br>GCGGGAAAUCAAGGUCGAGAACGCCGAUGCCCAGUUUUACGUGUGCCCGCCCCCG<br>ACGGGCGCCACGGUGGUGCAGUUUGAGCAGCCGCGCCGCUGCCCGACGCGCCCGG<br>AGGGGCAGAACUACACGGAGGGCAUCGCGGUGGUCUUCAAGGAGAACAUCGCCCC<br>GUACAAAUUCAAGGCCACCAUGUACUACAAAGACGUGACCGUGUCGCAGGUGUGG<br>UUCGGCCACCGCUACUCCCAGUUUAUGGGGAUAUUCGAGGACCGCGCCCCCGUUC<br>CCUUCGAGGAGGUGAUCGACAAGAUUAACGCCAAGGGGGUCUGCCGCUCCACGGC<br>CAAGUACGUGCGGAACAACAUGGAGACCACCGCGUUUCACCGGGACGACCACGAG<br>ACCGACAUGGAGCUCAAGCCGGCGAAGGUCGCCACGCGCACGAGCCGGGGGUGGC<br>ACACCACCGACCUCAAGUACAACCCCUCGCGGGUGGAGGCGUUCCAUCGGUACGG<br>CACGACGGUCAACUGCAUCGUCGAGGAGGUGGACGCGCGGUCGGUGUACCCGUAC<br>GAUGAGUUUGUGCUGGCGACGGGCGACUUUGUGUACAUGUCCCCGUUUUACGGCU<br>ACCGGGAGGGGUCGCACACCGAGCACACCAGCUACGCCGCCGACCGCUUCAAGCA<br>GGUCGACGGCUUCUACGCGCGCGACCUCACCACGAAGGCCCGGGCCACGUCGCCG<br>ACGACCCGCAACUUGCUGACGACCCCCAAGUUUACCGUGGCCUGGGACUGGGUGC<br>CGAAGCGACCGGCGGUCUGCACCAUGACCAAGUGGCAGGAGGUGGACGAGAUGCU<br>CCGCGCCGAGUACGGCGGCUCCUUCCGCUUCUCCUCCGACGCCAUCUCGACCACCU<br>UCACCACCAACCUGACCCAGUACUCGCUCUCGCGCGUCGACCUGGGCGACUGCAU<br>CGGCCGGGAUGCCCGCGAGGCCAUCGACCGCAUGUUUGCGCGCAAGUACAACGCC<br>ACGCACAUCAAGGUGGGCCAGCCGCAGUACUACCUGGCCACGGGGGGCUUCCUCA<br>UCGCGUACCAGCCCCUCCUCAGCAACACGCUCGCCGAGCUGUACGUGCGGGAGUA<br>CAUGCGGGAGCAGGACCGCAAGCCCCGGAAUGCCACGCCCGCGCCACUGCGGGAG<br>GCGCCCAGCGCCAACGCGUCCGUGGAGCGCAUCAAGACCACCUCCUCGAUCGAGU<br>UCGCCCGGCUGCAGUUUACGUAUAACCACAUACAGCGCCACGUGAACGACAUGCU<br>GGGGCGCAUCGCCGUCGCGUGGUGCGAGCUGCAGAACCACGAGCUGACUCUCUGG<br>AACGAGGCCCGCAAGCUCAACCCCAACGCCAUCGCCUCCGCCACCGUCGGCCGGCG<br>GGUGAGCGCGCGCAUGCUCGGAGACGUCAUGGCCGUCUCCACGUGCGUGCCCGUC<br>GCCCCGGACAACGUGAUCGUGCAGAACUCGAUGCGCGUCAGCUCGCGGCCGGGGA<br>CGUGCUACAGCCGCCCCCUGGUCAGCUUUCGGUACGAAGACCAGGGCCCGCUGAU<br>CGAGGGGCAGCUGGGCGAGAACAACGAGCUGCGCCUCACCCGCGACGCGCUCGAG<br>CCGUGCACCGUGGGCCACCGGCGCUACUUCAUCUUCGGCGGGGGCUACGUGUACU<br>UCGAGGAGUACGCGUACUCUCACCAGCUGAGUCGCGCCGACGUCACCACCGUCAG<br>CACCUUCAUCGACCUGAACAUCACCAUGCUGGAGGACCACGAGUUUGUGCCCCUG<br>GAGGUCUACACGCGCCACGAGAUCAAGGACAGCGGCCUGCUGGACUACACGGAGG<br>UCCAGCGCCGCAACCAGCUGCACGACCUGCGCUUUGCCGACAUCGACACGGUCAU<br>CCGCGCCGACGCCAACGCCGCCAUGUUCGCGGGGCUGUGCGCGUUCUUCGAGGGG<br>AUGGGGGACUUGGGGCGCGCGGUCGGCAAGGUCGUCAUGGGAGUAGUGGGGGC<br>GUGGUGUCGGCCGUCUCGGGCGUGUCCUCCUUUAUGUCCAACCCCUUCGGGGCGC<br>UUGCCGUGGGGCUGCUGGUCCUGGCCGGCCUGGUCGCGGCCUUCUUCGCCUUCCG<br>CUACGUCCUGCAACUGCAACGCAAUCCCAUGAAGGCCCUGUAUCCGCUCACCACC<br>AAGGAACUCAAGACUUCCGACCCCGGGGGCGUGGGCGGGGAGGGGGAGGAAGGCG<br>CGGAGGGGGGCGGGUUUGACGAGGCCAAGUUGGCCGAGGCCCGAGAAAUGAUCCG<br>AUAUAUGGCUUUGGUGUCGGCCAUGGAGCGCACGGAACACAAGGCCAGAAAGAA<br>GGGCACGAGCGCCCUGCUCAGCUCCAAGGUCACCAACAUGGUUCUGCGCAAGCGC<br>AACAAAGCCAGGUACUCUCCGCUCCACAACGAGGACGAGGCCGGAGACGAAGACG<br>AGCUCUAA (SEQ ID NO: 101) |
| HSV-2 gC | AUGGCCCUUGGACGGGUGGGCCUAGCCGUGGGCCUGUGGGGCCUGCUGUGGGUGG<br>GUGUGGUCGUGGUGCUGGCCAAUGCCUCCCCCGGACGCACGAUAACGGUGGGCCC<br>GCGGGGGAACGCGAGCAAUGCCGCCCCCUCCGCGUCCCCGCGGAACGCAUCCGCCC<br>CCCGAACCACACCCACGCCCCCCAACCCCGCAAGGCGACGAAAAGUAAGGCCUCC<br>ACCGCCAAACCGGCCCCGCCCCCCAAGACCGGGCCCCCGAAGACAUCCUCGGAGCC<br>CGUGCGAUGCAACCGCCACGACCCGCUGGCCCGGUACGGCUCGCGGGUGCAAAUC<br>CGAUGCCGGUUUCCCAACUCCACCCGCACGGAGUCCCGCCUCCAGAUCUGGCGUU<br>AUGCCACGGCGACGGACGCCGAGAUCGGAACGGCGCCUAGCUUAGAGGAGGUGAU<br>GGUAAACGUGUCGGCCCCGCCCGGGGGCCAACUGGUGUAUGACAGCGCCCCCAAC<br>CGAACGGACCCGCACGUGAUCUGGGCGGAGGGCGCCGGCCCGGGCGCCAGCCCGC<br>GGCUGUACUCGGUCGUCGGGCCGCUGGGUCGGCAGCGGCUCAUCAUCGAAGAGCU<br>GACCCUGGAGACCCAGGGCAUGUACUACUGGGUGUGGGGCCGGACGGACCGCCCG<br>UCCGCGUACGGGACCUGGGUGCGCGUUCGCGUGUUCCGCCCUCCGUCGCUGACCA<br>UCCACCCCCACGCGGUGCUGGAGGGCCAGCCGUUUAAGGCGACGUGCACGGCCGC<br>CACCUACUACCCGGGCAACCGCGCGGAGUUCGUCUGGUUCGAGGACGGUCGCCGG<br>GUAUUCGAUCCGGCCCAGAUACACACGCAGACGCAGGAGAACCCCGACGGCUUUU<br>CCACCGUCUCCACCGUGACCUCCGCGGCCGUCGGCGGCCAGGGCCCCCCGCGCACC<br>UUCACCUGCCAGCUGACGUGGCACCGCGACUCCGUGUCGUUCUCUCGGCGCAACG<br>CCAGCGGCACGGCAUCGGUGCUGCCGCGGCCAACCAUUACCAUGGAGUUUACGGG<br>CGACCAUGCGGUCUGCACGGCCGGCUGUGUGCCCGAGGGGGUGACGUUUGCCUGG<br>UUCCUGGGGGACGACUCCUCGCCGGCGGAGAAGGUGGCCGUCGCGUCCCAGACAU<br>CGUGCGGGCGCCCCGGCACCGCCACGAUCCGCUCCACCCUGCCGGUCUCGUACGAG<br>CAGACCGAGUACAUCUGCCGGCUGGCGGGAUACCCGGACGGAAUUCCGGUCCUAG<br>AGCACCACGGCAGCCACCAGCCCCCGCCGCGGGACCCCACCGAGCGGCAGGUGAUC<br>CGGGCGGUGGAGGGGGCGGGGAUCGGAGUGGCUGUCCUUGUCGCGGUGGUUCUG<br>GCCGGGACCGCGGUAGUGUACCUCACCCACGCCUCCUCGGUGCGCUAUCGUCGGC<br>UGCGGUAA (SEQ ID NO: 102) |
| HSV-2 gD | AUGGGGCGUUUGACCUCCGGCGUCGGGACGGCGGCCCUGCUAGUUGUCGCGGUGG<br>GACUCCGCGUCGUCUGCGCCAAAUACGCCUUAGCAGACCCCUCGCUUAAGAUGGC<br>CGAUCCCAAUCGAUUUCGCGGGAAGAACCUUCCGGUUUUGGACCAGCUGACCGAC<br>CCCCCCGGGGUGAAGCGUGUUUACCACAUUCAGCCGAGCCUGGAGGACCCGUUCC |

TABLE 1-continued

| | |
|---|---|
| | AGCCCCCCAGCAUCCCGAUCACUGUGUACUACGCAGUGCUGGAACGUGCCUGCCG<br>CAGCGUGCUCCUACAUGCCCCAUCGGAGGCCCCCCAGAUCGUGCGCGGGGCUUCG<br>GACGAGGCCCGAAAGCACACGUACAACCUGACCAUCGCCUGGUAUCGCAUGGGAG<br>ACAAUUGCGCUAUCCCCAUCACGGUUAUGGAAUACACCGAGUGCCCCUACAACAA<br>GUCGUUGGGGGUCUGCCCCAUCCGAACGCAGCCCCGCUGGAGCUACUAUGACAGC<br>UUUAGCGCCGUCAGCGAGGAUAACCUGGGAUUCCUGAUGCACGCCCCCGCCUUCG<br>AGACCGCGGGUACGUACCUGCGGCUAGUGAAGAUAAACGACUGGACGGAGAUCAC<br>ACAAUUUAUCCUGGAGCACCGGGCCCGCGCCUCCUGCAAGUACGCUCUCCCCCUG<br>CGCAUCCCCCCGGCAGCGUGCCUCACCUCGAAGGCCUACCAACAGGGCGUGACGG<br>UCGACAGCAUCGGGAUGCUACCCCGCUUUAUCCCCGAAAACCAGCGCACCGUCGC<br>CCUAUACAGCUUAAAAAUCGCCGGGUGGCACGGCCCCAAGCCCCCGUACACCAGC<br>ACCCUGCUGCCGCCGGAGCUGUCCGACACCACCAACGCCACGCAACCCGAACUCGU<br>UCCGGAAGACCCCGAGGACUCGGCCCUCUUAGAGGAUCCCGCCGGGACGGUGUCU<br>UCGCAGAUCCCCCCAAACUGGCACAUCCCGUCGAUCCAGGACGUCGCGCCGCACC<br>ACGCCCCCGCCGCCCCCAGCAACCCGGGCCUGAUCAUCGGCGCGCUGGCCGGCAGU<br>ACCCUGGCGGUGCUGGUCAUCGGCGGUAUUGCGUUUUGGGUACGCCGCCGCGCUC<br>AGAUGGCCCCCAAGCGCCUACGUCUCCCCCACAUCCGGGAUGACGACGCGCCCCCC<br>UCGCACCAGCCAUUGUUUUACUAG (SEQ ID NO: 103) |
| HSV-2 gE | AUGGCUCGCGGGGCCGGGUUGGUGUUUUUUGUUGGAGUUUGGGUCGUAUCGUGC<br>CUGGCGGCAGCACCCAGAACGUCCUGGAAACGGGUAACCUCGGGCGAGGACGUGG<br>UGUUGCUUCCGGCGCCCGCGGGGCCGGAGGAACGCACCCGGGCCCACAAACUACU<br>GUGGGCCGCGGAACCCCUGGAUGCCUGCGGUCCCCUGCGCCCGUCGUGGGUGGCG<br>CUGUGGCCCCCCCGACGGGUGCUCGAGACGGUCGUGGAUGCGGCGUGCAUGCGCG<br>CCCCGGAACCGCUCGCCAUAGCAUACAGUCCCCCGUUCCCCGCGGGCGACGAGGG<br>ACUGUAUUCGGAGUUGGCGUGGCGCGAUCGCGUAGCCGUGGUCAACGAGAGUCUG<br>GUCAUCUACGGGGCCCUGGAGACGGACAGCGGUCUGUACACCCUGUCCGUGGUCG<br>GCCUAAGCGACGAGGCGCGCCAAGUGGCGUCGGUGGUUCUGGUCGUGGAGCCCGC<br>CCCUGUGCCGACCCCGACCCCCGACGACUACGACGAAGAAGACGACGCGGGCGUG<br>AGCGAACGCACGCCGGUCAGCGUUCCCCCCCAACCCCCCCCGUCGUCCCCCCGU<br>CGCCCCCCCGACGCACCCUCGUGUUAUCCCCGAGGUGUCCCACGUGCGCGGGGUA<br>ACGGUCCAUAUGGAGACCCCGGAGGCCAUUCUGUUUGCCCCCGGGGAGACGUUUG<br>GGACGAACGUCUCCAUCCACGCCAUUGCCCACGACGACGGUCCGUACGCCAUGGA<br>CGUCGUCUGGAUGCGGUUUGACGUGCCGUCCUCGUGCGCCGAGAUGCGGAUCUAC<br>GAAGCUUGUCUGUAUCACCCGCAGCUUCCAGAGUGUCUAUCUCCGGCCGACGCGC<br>CGUGCGCCGUAAGUUCCUGGGCGUACCGCCUGGCGGUCCGCAGCUACGCCGGCUG<br>UUCCAGGACUACGCCCCCGCCGCGAUGUUUUGCCGAGGCUCGCAUGGAACCGGUC<br>CCGGGGUUGGCGUGGCUGGCCUCCACCGUCAAUCUGGAAUUCCAGCACGCCUCCC<br>CCCAGCACGCCGGCCUCUACCUGUGCGUGGUGUACGUGGACGAUCAUAUCCACGC<br>CUGGGGCCACAUGACCAUCAGCACCGCGGCGCAGUACCGGAACGCGGUGGUGGAA<br>CAGCACCUCCCCCAGCGCCAGCCCGAGCCCGUCGAGCCCACCCGCCCGCACGUGAG<br>AGCCCCCCCUCCCGCGCCCUCCGCGCGCGGCCCGCUGCGCCUCGGGGCGGUGCUGG<br>GGGCGGCCCUGUUGCUGGCCGCCCUCGGGCUGUCCGCGUGGGCGUGCAUGACCUG<br>CUGGCGCAGGCGCUCCUGGCGGGCGGUUAAAAGCCGGGCCUCGGCGACGGGCCCC<br>ACUUACAUUCGCGUGGCGGACAGCGAGCUGUACGCGGACUGGAGUUCGGACAGCG<br>AGGGGGAGCGCGACGGGUCCCUGUGGCAGGACCCUCCGGAGAGACCCGACUCUCC<br>CUCCACAAAUGGAUCCGGCUUUGAGAUCUUAUCACCAACGGCUCCGUCUGUAUAC<br>CCCCAUAGCGAGGGGCGUAAAUCUCGCCGCCCGCUCACCACCUUUGGUUCGGGAA<br>GCCCGGGCCGUCGUCACUCCCAGGCCUCCUAUUCGUCCGUCCUCUGGUAA (SEQ ID<br>NO: 104) |
| HSV-2 gI | AUGCCCGGCCGCUCGCUGCAGGGCCUGGCGAUCCUGGGCCUGUGGGUCUGCGCCA<br>CCGGCCUGGUCGUCCGCGGCCCCACGGUCAGUCUGGUCUCAGACUCACUCGUGGA<br>UGCCGGGGCCGUGGGGCCCCAGGGCUUCGUGGAAGAGGACCUGCGUGUUUUCGGG<br>GAGCUUCAUUUUGUGGGGGCCCAGGUCCCCCACACAAACUACUACGACGGCAUCA<br>UCGAGCUGUUUCACUACCCCCUGGGGAACCACUGCCCCCGCGUUGUACACGUGGU<br>CACACUGACCGCAUGCCCCCGCCGCCCCGCCGUGGCGUUCACCUUGUGUCGCUCGA<br>CGCACCACGCCCACAGCCCCGCCUAUCCGACCCUGGAGCUGGGUCUGGCGCGGCA<br>GCCGCUUCUGCGGGUUCGAACGGCAACGCGCGACUAUGCCGGUCUGUAUGUCCUG<br>CGCGUAUGGGUCGGCAGCGCGACGAACGCCAGCCUGUUUGUUUUGGGGGUGGCGC<br>UCUCUGCCAACGGGACGUUUGUGUAUAACGGCUCGGACUACGGCUCCUGCGAUCC<br>GGCGCAGCUUCCCUUUUCGGCCCCGCGCCUGGGACCCUCGAGCGUAUACACCCCC<br>GGAGCCUCCCGGCCCACCCCUCCACGGACAACGACAUCCCCGUCCUCCCCCCGAGA<br>CCCGACCCCCGCCCCCGGGGACACAGGGACGCCCGCGCCCGCGAGCGGCGAGAGAG<br>CCCCGCCCAAUUCCACGCGAUCGGCCAGCGAAUCGAGACACAGGCUAACCGUAGC<br>CCAGGUAAUCCAGAUCGCCAUACCGGCGUCCAUCAUCGCCUUUGUGUUUCUGGGC<br>AGCUGUAUCUGCUUCAUCCAUAGAUGCCAGCGCCGAUACAGGCGCCCCCGCGGCC<br>AGAUUUACAACCCCGGGGGCGUUUCCUGCGCGGUCAACGAGGCGGCCAUGGCCCG<br>CCUCGGAGCCGAGCUGCGAUCCCACCCAAACACCCCCCCCAAACCCCGACGCCGUU<br>CGUCGUCGUCCACGACCAUGCCUUCCCUAACGUCGAUAGCUGAGGAAUCGGAGCC<br>AGGUCCAGUCGUGCUGCUGUCCGUCAGUCCUCGGCCCCGCAGUGGCCCGACGGCC<br>CCCCAAGAGGUCUAG (SEQ ID NO: 105) |

TABLE 1-continued

| | |
|---|---|
| ICP0-2 \| Based on strain HG52 (inactivated by deletion of the nuclear localization signal and zinc-binding ring finger) | AUGGAACCCCGGCCCGGCACGAGCUCCCGGGCGGACCCCGGCCCCGAGCGGCCGCC<br>GCGGCAGACCCCCGGCACGCAGCCCGCCGCCCCGCACGCCUGGGGGAUGCUCAACG<br>ACAUGCAGUGGCUCGCCAGCAGCGACUCGGAGGAGGAGACCGAGGUGGGAAUCUC<br>UGACGACGACCUUCACCGCGACUCCACCUCCGAGGCGGGCAGCACGGACACGGAG<br>AUGUUCGAGGCGGGCCUGAUGGACGCGGCCACGCCCCCGGCCCGGCCCCCGGCCG<br>AGCGCCAGGGCAGCCCCACGCCCGCCGACGCGCAGGGAUCCUGUGGGGGUGGGCC<br>CGUGGGUGAGGAGGAAGCGGAAGCGGGAGGGGGGGGCGACGUGAACACCCCGGU<br>GGCGUACCUGAUAGUGGGCGUGACCGCCAGCGGGUCGUUCAGCACCAUCCCGAUA<br>GUGAACGACCCCCGGACCCGCGUGGAGGCCGAGGCGGCCGUGCGGGCCGGCACGG<br>CCGUGGACUUUAUCUGGACGGGCAACCCGCGGACGGCCCCGCGCUCCCUGUCGCU<br>GGGGGGACACACGGUCCGCGCCCUGUCGCCCACCCCCCCGUGGCCCGGCACGGACG<br>ACGAGGACGAUGACCUGGCCGACGUGGACUACGUCCCGCCCGCCCCCGAAGAGC<br>GCCCCGGCGCGGGGGCGGCGGUGCGGGGCGACCCGCGGAACCUCCCAGCCCGCC<br>GCGACCCGACCGGCGCCCCCUGGCGCCCCGCGGAGCAGCAGCAGCGGCGGCGCCCC<br>GUUGCGGGCGGGGGUGGGAUCUGGGUCUGGGGGCGGCCCUGCCGUCGCGGCCGUC<br>GUGCCGAGAGUGGCCUCUCUUCCCCCUGCGGCCGGCGGGGGGCGCGCGCAGGCGC<br>GGCGGGUGGGCGAAGACGCCGCGGCGGCGGAGGGCAGGACGCCCCCCGCGAGACA<br>GCCCCGCGCGGCCCAGGAGCCCCCCAUAGUCAUCAGCGACUCUCCCCCGCCGUCUC<br>CGCGCCGCCCCGCGGGCCCCGGGCCGCUCUCCUUUGUCUCCUCCUCCUCCGCACAG<br>GUGUCCUCGGGCCCCGGGGGGGGAGGUCUGCCACAGUCGUCGGGGCGCGCCGCGC<br>GCCCCCGCGCGGCCGUCGCCCCGCGCGUCCGGAGUCCGCCCCGCGCCGCCGCCGCC<br>CCCGUGGUGUCUGCGAGCGCGGACGCGGCCGGGCCCGCGCCGCCCGCCGUGCCGG<br>UGGACGCGCACCGCGCGCCCCGGUCGCGCAUGACCCAGGCUCAGACCGACACCCA<br>AGCACAGAGUCUGGGCCGGGCAGGCGCGACCGACGCGCGCGGGUCGGGAGGGCCG<br>GGCGCGGAGGGAGGAUCGGGCCCCGCGGCCUCGUCCUCCGCCUCUUCCUCCGCCG<br>CCCCGCGCUCGCCCCUCGCCCCCCAGGGGGUGGGGGCCAAGAGGGCGGCGCCGCGC<br>CGGGCCCCGGACUCGGACUCGGGCGACCGCGGCCACGGGCCGCUCGCCCCGGCGUC<br>CGCGGGCGCCGCGCCCCCGUCGGCGUCUCCGUCGUCCCAGGCCGCGGUCGCCGCCG<br>CCUCCUCCUCCUCCGCCUCCUCCUCCUCCGCCUCCUCCUCCUCCGCCUCCUCCUCC<br>UCCGCCUCCUCCUCCUCCGCCUCCUCCUCCUCCGCCUCCUCCUCCUCCGCCUCUUC<br>CUCUGCGGGCGGGGCUGGUGGGAGCGUCGCGUCCGCGUCCGGCGCUGGGGAGAGA<br>CGAGAAACCUCCCUCGGCCCCCGCGCUGCUGCGCCGCGGGGCCGAGGAAGUGUG<br>CCAGGAAGACGCGCCACGCGGAGGGCGGCCCCGAGCCCGGGGCCCGCGACCCGGC<br>GCCCGGCCUCACGCGCUACCUGCCCAUCGCGGGGGUCUCGAGCGUCGUGGCCCUG<br>GCGCCUUACGUGAACAAGACGGUCACGGGGGACUGCCUGCCCGUCCUGGACAUGG<br>AGACGGGCCACAUAGGGGCCUACGUGGUCCUCGUGGACCAGACGGGGAACGUGGC<br>GGACCUGCUGCGGGCCGCGGCCCCCGCGUGGAGCCGCCGCACCCUGCUCCCCGAGC<br>ACGCGCGCAACUGCGUGAGGCCCCCCGACUACCCGACGCCCCCCGCGUCGGAGUG<br>GAACAGCCUCUGGAUGACCCCGGUGGGCAACAUGCUCUUUGACCAGGGCACCCUG<br>GUGGGCGCGCUGGACUUCCACGGCCUCCGGUCGCGCCACCCGUGGUCUCGGGAGC<br>AGGGCGCGCCCGCGCCGGCCGGCGACGCCCCCGCGGGCCACGGGGAGUAG (SEQ ID NO: 106) |
| HSV-2 SgB | AUGCGCGGGGGGGGCUUGGUUUGCGCGCUGGUCGUGGGGGCGCUGGUGGCCGCGG<br>UGGCGUCGGCGGCCCCGGCGGCCCCCCGCGCCUCGGGCGGCGUGGCCGCGACCGUC<br>GCGGCGAACGGGGGUCCCGCCUCCCAGCCGCCCCCCGUCCCGAGCCCCGCGACCAC<br>CAAGGCCCGGAAGCGGAAAACCAAAAAGCCGCCCAAGCGGCCCGAGGCGACCCCG<br>CCCCCCGACGCCAACGCGACCGUCGCCGCCGGCCACGCCACGCUGCGCGCGCACCU<br>GCGGGAAAUCAAGGUCGAGAACGCCGAUGCCCAGUUUUACGUGUGCCCGCCCCCG<br>ACGGGCGCCACGGUGGUGCAGUUUGAGCAGCCGCGCCGCUGCCCGACGCGCCCGG<br>AGGGGCAGAACUACACGGAGGGCAUCGCGGUGGUCUUCAAGGAGAACAUCGCCCC<br>GUACAAAUUCAAGGCCACCAUGUACUACAAAGACGUGACCGUGUCGCAGGUGUGG<br>UUCGGCCACCGCUACUCCCAGUUUAUGGGGAUAUUCGAGGACCGCGCCCCCGUUC<br>CCUUCGAGGAGGUGAUCGACAAGAUUAACGCCAAGGGGGUCUGCCGCUCCACGGC<br>CAAGUACGUGCGGAACAACAUGGAGACCACCGCGUUUCACCGGGACGACCACGAG<br>ACCGACAUGGAGCUCAAGCCGGCGAAGGUCGCCACGCGCACGAGCCGGGGGUGGC<br>ACACCACCGACCUCAAGUACAACCCCUCGCGGGUGGAGGCGUUCCAUCGGUACGG<br>CACGACGGUCAACUGCAUCGUCGAGGAGGUGGACGCGCGGUCGGUGUACCCGUAC<br>GAUGAGUUUGUGCUGGCGACGGGCGACUUUGUGUACAUGUCCCCGUUUUACGGCU<br>ACCGGGAGGGGUCGCACACCGAGCACACCAGCUACGCCGCCGACCGCUUCAAGCA<br>GGUCGACGGCUUCUACGCGCGCGACCUCACCACGAAGGCCCGGGCCACGUCGCCG<br>ACGACCCGCAACUUGCUGACGACCCCCAAGUUUACCGUGGCCUGGGACUGGGUGC<br>CGAAGCGACCGGCGGUCUGCACCAUGACCAAGUGGCAGGAGGUGGACGAGAUGCU<br>CCGCGCCGAGUACGGCGGCUCCUUCCGCUUCUCCUCCGACGCCAUCUCGACCACCU<br>UCACCACCAACCUGACCCAGUACUCGCUCUCGCGCGUCGACCUGGGCGACUGCAU<br>CGGCCGGGAUGCCCGCGAGGCCAUCGACCGCAUGUUUGCGCGCAAGUACAACGCC<br>ACGCACAUCAAGGUGGGCCAGCCGCAGUACUACCUGGCCACGGGGGGCUUCCUCA<br>UCGCGUACCAGCCCCUCCUCAGCAACACGCUCGCCGAGCUGUACGUGCGGGAGUA<br>CAUGCGGGAGCAGGACCGCAAGCCCCGGAAUGCCACGCCCGCGCCACUGCGGGAG<br>GCGCCCAGCGCCAACGCGUCCGUGGAGCGCAUCAAGACCACCUCCUCGAUCGAGU<br>UCGCCCGGCUGCAGUUUACGUAUAACCACAUACAGCGCCACGUGAACGACAUGCU<br>GGGGCGCAUCGCCGUCGCGUGGUGCGAGCUGCAGAACCACGAGCUGACUCUCUGG<br>AACGAGGCCCGCAAGCUCAACCCCAACGCCAUCGCCUCCGCCACCGUCGGCCGGCG<br>GGUGAGCGCGCGCAUGCUCGGAGACGUCAUGGCCGUCUCCACGUGCGUGCCCGUC<br>GCCCCGGACAACGUGAUCGUGCAGAACUCGAUGCGCGUCAGCUCGCGGCCGGGGA<br>CGUGCUACAGCCGCCCCCUGGUCAGCUUUCGGUACGAAGACCAGGGCCCGCUGAU<br>CGAGGGGCAGCUGGGCGAGAACAACGAGCUGCGCCUCACCCGCGACGCGCUCGAG<br>CCGUGCACCGUGGGCCACCGGCGCUACUUCAUCUUCGGCGGGGGCUACGUGUACU<br>UCGAGGAGUACGCGUACUCUCACCAGCUGAGUCGCGCCGACGUCACCACCGUCAG |

TABLE 1-continued

| | |
|---|---|
| | CACCUUCAUCGACCUGAACAUCACCAUGCUGGAGGACCACGAGUUUGUGCCCCUG GAGGUCUACACGCGCCACGAGAUCAAGGACAGCGGCCUGCUGGACUACACGGAGG UCCAGCGCCGCAACCAGCUGCACGACCUGCGCUUUGCCGACAUCGACACGGUCAU CCGCGCCGACGCCAACGCCGCCAUGUUCGCGGGGCUGUGCGCGUUCUUCGAGGGG AUGGGGGACUUGGGGCGCGCGGUCGGCAAGGUCGUCAUGGGAGUAGUGGGGGC GUGGUGUCGGCCGUCUCGGGCGUGUCCUCCUUUAUGUCCAACCCC (SEQ ID NO: 107) |
| HSV-2 SgC | AUGGCCCUUGGACGGGUGGGCCUAGCCGUGGGCCUGUGGGGCCUGCUGUGGGUGG GUGUGGUCGUGGUGCUGGCCAAUGCCUCCCCCGGACGCACGAUAACGGUGGGCCC GCGGGGGAACGCGAGCAAUGCCGCCCCCUCCGCGUCCCCGCGGAACGCAUCCGCCC CCCGAACCACACCCACGCCCCCCAACCCCGCAAGGCGACGAAAAGUAAGGCCUCC ACCGCCAAACCGGCCCCGCCCCCCAAGACCGGGCCCCCGAAGACAUCCUCGGAGCC CGUGCGAUGCAACCGCCACGACCCGCUGGCCCGGUACGGCUCGCGGGUGCAAAUC CGAUGCCGGUUUCCCAACUCCACCCGCACGGAGUCCCGCCUCCAGAUCUGGCGUU AUGCCACGGCGACGGACGCCGAGAUCGGAACGGCGCCUAGCUUAGAGGAGGUGAU GGUAAACGUGUCGGCCCCGCCCGGGGGCCAACUGGUGUAUGACAGCGCCCCCAAC CGAACGGACCCGCACGUGAUCUGGGCGGAGGGCGCCGGCCCGGGCGCCAGCCCGC GGCUGUACUCGGUCGUCGGGCCGCUGGGUCGGCAGCGGCUCAUCAUCGAAGAGCU GACCCUGGAGACCCAGGGCAUGUACUACUGGGUGUGGGGCCGGACGGACCGCCCG UCCGCGUACGGGACCUGGGUGCGCGUUCGCGUGUUCCGCCCUCCGUCGCUGACCA UCCACCCCCACGCGGUGCUGGAGGGCCAGCCGUUUAAGGCGACGUGCACGGCCGC CACCUACUACCCGGGCAACCGCGCGGAGUUCGUCUGGUUCGAGGACGGUCGCCGG GUAUUCGAUCCGGCCCAGAUACACACGCAGACGCAGGAGAACCCCGACGGCUUUU CCACCGUCUCCACCGUGACCUCCGCGGCCGUCGGCGGCCAGGGCCCCCCGCGCACC UUCACCUGCCAGCUGACGUGGCACCGCGACUCCGUGUCGUUCUCUCGGCGCAACG CCAGCGGCACGGCAUCGGUGCUGCCGCGGCCAACCAUUACCAUGGAGUUUACGGG CGACCAUGCGGUCUGCACGGCCGGCUGUGUGCCCGAGGGGGUGACGUUUGCCUGG UUCCUGGGGGACGACUCCUCGCCGGCGGAGAAGGUGGCCGUCGCGUCCCAGACAU CGUGCGGGCGCCCCGGCACCGCCACGAUCCGCUCCACCCUGCCGGUCUCGUACGAG CAGACCGAGUACAUCUGCCGGCUGGCGGGAUACCCGGACGGAAUUCCGGUCCUAG AGCACCACGGCAGCCACCAGCCCCCGCCGCGGGACCCCACCGAGCGGCAGGUGAUC CGGGCGGUGGAGGGG (SEQ ID NO: 108) |
| HSV-2 SgD | AUGGGGCGUUUGACCUCCGGCGUCGGGACGGCGGCCCUGCUAGUUGUCGCGGUGG GACUCCGCGUCGUCUGCGCCAAAUACGCCUUAGCAGACCCCUCGCUUAAGAUGGC CGAUCCCAAUCGAUUUCGCGGAAGAACCUUCCGGUUUUGGACCAGCUGACCGAC CCCCCCGGGGUGAAGCGUGUUUACCACAUUCAGCCGAGCCUGGAGGACCCGUUCC AGCCCCCCAGCAUCCCGAUCACUGUGUACUACGCAGUGCUGGAACGUGCCUGCCG CAGCGUGCUCCUACAUGCCCCAUCGGAGGCCCCCCAGAUCGUGCGCGGGGCUUCG GACGAGGCCCGAAAGCACACGUACAACCUGACCAUCGCCUGGUAUCGCAUGGGAG ACAAUUGCGCUAUCCCCAUCACGGUUAUGGAAUACACCGAGUGCCCCUACAACAA GUCGUUGGGGGUCUGCCCCAUCCGAACGCAGCCCCGCUGGAGCUACUAUGACAGC UUUAGCGCCGUCAGCGAGGAUAACCUGGGAUUCCUGAUGCACGCCCCCGCCUUCG AGACCGCGGGUACGUACCUGCGGCUAGUGAAGAUAAACGACUGGACGGAGAUCAC ACAAUUUAUCCUGGAGCACCGGGCCCGCGCCUCCUGCAAGUACGCUCUCCCCCUG CGCAUCCCCCCGGCAGCGUGCCUCACCUCGAAGGCCUACCAACAGGGCGUGACGG UCGACAGCAUCGGGAUGCUACCCCGCUUUAUCCCCGAAAACCAGCGCACCGUCGC CCUAUACAGCUUAAAAAUCGCCGGGUGGCACGGCCCCAAGCCCCCGUACACCAGC ACCCUGCUGCCGCCGGAGCUGUCCGACACCACCAACGCCACGCAACCCGAACUCGU UCCGGAAGACCCCGAGGACUCGGCCCUCUUAGAGGAUCCCGCCGGGACGGUGUCU UCGCAGAUCCCCCCAAACUGGCACAUCCCGUCGAUCCAGGACGUCGCGCCGCACC ACGCCCCCGCCGCCCCCAGCAACCCG (SEQ ID NO: 109) |
| HSV-2 SgE | AUGGCUCGCGGGGCCGGGUUGGUGUUUUUUGUUGGAGUUUGGGUCGUAUCGUGC CUGGCGGCAGCACCCAGAACGUCCUGGAAACGGGUAACCUCGGGCGAGGACGUGG UGUUGCUUCCGGCGCCCGCGGGGCCGGAGGAACGCACCCGGGCCCACAAACUACU GUGGGCCGCGGAACCCCUGGAUGCCUGCGGUCCCCUGCGCCCGUCGUGGGUGGCG CUGUGGCCCCCCCGACGGGUGCUCGAGACGGUCGUGGAUGCGGCGUGCAUGCGCG CCCCGGAACCGCUCGCCAUAGCAUACAGUCCCCCGUUCCCCGCGGGCGACGAGGG ACUGUAUUCGGAGUUGGCGUGGCGCGAUCGCGUAGCCGUGGUCAACGAGAGUCUG GUCAUCUACGGGGCCCUGGAGACGGACAGCGGUCUGUACACCCUGUCCGUGGUCG GCCUAAGCGACGAGGCGCGCCAAGUGGCGUCGGUGGUUCUGGUCGUGGAGCCCGC CCCUGUGCCGACCCCGACCCCCGACGACUACGACGAAGAAGACGACGCGGGCGUG AGCGAACGCACGCCGGUCAGCGUUCCCCCCCCAACCCCCCCCCGUCGUCCCCCCGU CGCCCCCCCGACGCACCCUCGUGUUAUCCCCGAGGUGUCCCACGUGCGCGGGGUA ACGGUCCAUAUGGAGACCCCGGAGGCCAUUCUGUUUGCCCCCGGGGAGACGUUUG GGACGAACGUCUCCAUCCACGCCAUUGCCCACGACGACGGUCCGUACGCCAUGGA CGUCGUCUGGAUGCGGUUUGACGUGCCGUCCUCGUGCGCCGAGAUGCGGAUCUAC GAAGCUUGUCUGUAUCACCCGCAGCUUCCAGAGUGUCUAUCUCCGGCCGACGCGC CGUGCGCCGUAAGUUCCUGGGCGUACCGCCUGGCGGUCCGCAGCUACGCCGGCUG UUCCAGGACUACGCCCCCGCCGCGAUGUUUUGCCGAGGCUCGCAUGGAACCGGUC CCGGGGUUGGCGUGGCUGGCCUCCACCGUCAAUCUGGAAUUCCAGCACGCCUCCC CCCAGCACGCCGGCCUCUACCUGUGCGUGGUGUACGUGGACGAUCAUAUCCACGC CUGGGGCCACAUGACCAUCAGCACCGCGGCGCAGUACCGGAACGCGGUGGUGGAA CAGCACCUCCCCCAGCGCCAGCCCGAGCCCGUCGAGCCCACCCGCCCGCACGUGAG AGCCCCCCCUCCCGCGCCCUCCGCGCGCGGCCCGCUGCGC (SEQ ID NO: 110) |

TABLE 1-continued

| | |
|---|---|
| HSV-2 SgI | AUGCCCGGCCGCUCGCUGCAGGGCCUGGCGAUCCUGGGCCUGUGGGUCUGCGCCA<br>CCGGCCUGGUCGUCCGCGGCCCCACGGUCAGUCUGGUCUCAGACUCACUCGUGGA<br>UGCCGGGGCCGUGGGGCCCCAGGGCUUCGUGGAAGAGGACCUGCGUGUUUUCGGG<br>GAGCUUCAUUUUGUGGGGGCCCAGGUCCCCCACACAAACUACUACGACGGCAUCA<br>UCGAGCUGUUUCACUACCCCCUGGGGAACCACUGCCCCCGCGUUGUACACGUGGU<br>CACACUGACCGCAUGCCCCCGCCGCCCCGCCGUGGCGUUCACCUUGUGUCGCUCGA<br>CGCACCACGCCCACAGCCCCGCCUAUCCGACCCUGGAGCUGGGUCUGGCGCGGCA<br>GCCGCUUCUGCGGGUUCGAACGGCAACGCGCGACUAUGCCGGUCUGUAUGUCCUG<br>CGCGUAUGGGUCGGCAGCGCGACGAACGCCAGCCUGUUUGUUUUGGGGGUGGCGC<br>UCUCUGCCAACGGGACGUUUGUGUAUAACGGCUCGGACUACGGCUCCUGCGAUCC<br>GGCGCAGCUUCCCUUUUCGGCCCCGCGCCUGGGACCCUCGAGCGUAUACACCCCC<br>GGAGCCUCCCGGCCCACCCCUCCACGGACAACGACAUCCCCGUCCUCCCCCCGAGA<br>CCCGACCCCCGCCCCCGGGGACACAGGGACGCCCGCGCCCGCGAGCGGCGAGAGAG<br>CCCCGCCCAAUUCCACGCGAUCGGCCAGCGAAUCGAGACACAGGCUAACCGUAGC<br>CCAGGUAAUCCAG (SEQ ID NO: 111) |
| HSV-2 ICP-4; Based on strain HG52; (inactivated by deletion of nuclear localization signal and alanine substitution for key residues in the transactivation region) | AUGUCGGCGGAGCAGCGGAAGAAGAAGAAGACGACGACGACGACGCAGGGCCGCG<br>GGGCCGAGGUCGCGAUGGCGGACGAGGACGGGGGACGUCUCCGGGCCGCGGCGGA<br>GACGACCGGCGGCCCCGGAUCUCCGGAUCCAGCCGACGGACCGCCGCCCACCCCGA<br>ACCCGGACCGUCGCCCCGCCGCGCGGCCCGGGUUCGGGUGGCACGGUGGGCCGGA<br>GGAGAACGAAGACGAGGCCGACGACGCCGCCGCCGAUGCCGAUGCCGACGAGGCG<br>GCCCCGGCGUCCGGGGAGGCCGUCGACGAGCCUGCCGCGGACGGCGUCGUCUCGC<br>CGCGGCAGCUGGCCCUGCUGGCCUCGAUGGUGGACGAGGCCGUUCGCACGAUCCC<br>GUCGCCCCCCCGGAGCGCGACGGCGCGCAAGAAGAAGCGGCCCGCUCGCCUUCU<br>CCGCCGCGGACCCCCUCCAUGCGCGCCGAUUAUGGCGAGGAGAACGACGACGACG<br>ACGACGACGACGAUGACGACGACCGCGACGCGGGCCGCUGGGUCCGCGGACCGGA<br>GACGACGUCCGCGGUCCGCGGGGCGUACCCGGACCCCAUGGCCAGCCUGUCGCCG<br>CGACCCCCGGCGCCCCGCCGACACCACCACCACCACCACCACCGCCGCCGGCGCGC<br>CCCCCGCCGGCGCUCGGCCGCCUCUGACUCAUCAAAAUCCGGAUCCUCGUCGUCG<br>GCGUCCUCCGCCUCCUCCUCCGCCUCCUCCUCCUCGUCUGCAUCCGCCUCCUCGUC<br>UGACGACGACGACGACGACGACGCCGCCCGCGCCCCCGCCAGCGCCGCAGACCACG<br>CCGCGGGCGGGACCCUCGGCGCGGACGACGAGGAGGCGGGGGUGCCCGCGAGGGC<br>CCCGGGGGCGGCGCCCCGGCCGAGCCCGCCCAGGGCCGAGCCCGCCCCGGCCCGGA<br>CCCCCGCGGCGACCGCGGGCCGCCUGGAGCGCCGCCGGGCCCGCGCGGCGGUGGCC<br>GGCCGCGACGCCACGGGCCGCUUCACGGCCGGGCGGCCCCGGCGGGUCGAGCUGG<br>ACGCCGACGCGGCCUCCGGCGCCUUCUACGCGCGCUACCGCGACGGGUACGUCAG<br>CGGGGAGCCGUGGCCCGGGGCCGGCCCCCCGCCCCCGGGGCGCGUGCUGUACGGC<br>GGGCUGGGCGACAGCCGCCCCGGCCUCUGGGGGGCGCCCGAGGCGGAGGAGGCGC<br>GGGCCCGGUUCGAGGCCUCGGGCGCCCCGGCGCCCGUGUGGGCGCCCGAGCUGGG<br>CGACGCGGCGCAGCAGUACGCCCUGAUCACGCGGCUGCUGUACACGCCGGACGCG<br>GAGGCGAUGGGGUGGCUCCAGAACCCGCGCGUGGCGCCCGGGGACGUGGCGCUGG<br>ACCAGGCCUGCUUCCGGAUCUCGGGCGCGGCGCGCAACAGCAGCUCCUUCAUCUC<br>CGGCAGCGUGGCGCGGGCCGUGCCCCACCUGGGGUACGCCAUGGCGGCGGGCCGC<br>UUCGGCUGGGGCCUGGCGCACGUGGCGGCCGCCGUGGCCAUGAGCCGCCGCUACG<br>ACCGCGCGCAGAAGGGCUUCCUGCUGACCAGCCUGCGCCGCGCCUACGCGCCCCU<br>GCUGGCGCGCGAGAACGCGGCGCUGACCGGGGCGCGAACCCCCGACGACGGCGGC<br>GACGCCAACCGCCACGACGGCGACGACGCCCGCGGGAAGCCCGCCGCCGCCGCCGC<br>CCCGUUGCCGUCGGCGGCGGCGUCGCCGGCCGACGAGCGCGCGGUGCCCGCCGGC<br>UACGGCGCCGCGGGGGUGCUCGCCGCCCUGGGGCGCCUGAGCGCCGCGCCCGCCU<br>CCGCGCCGGCCGGGGCCGACGACGACGACGACGACGGCGCCGGCGGUGGUGG<br>CGGCGGCCGGCGCGCGGAGGCGGGCCGCGUGGCCGUGGAGUGCCUGGCCGCCUGC<br>CGCGGGAUCCUGGAGGCGCUGGCGGAGGGCUUCGACGGCGACCUGGCGGCCGUGC<br>CGGGGCUGGCCGGAGCCCGGCCCGCCGCGCCCCCGCGCCCGGGGCCCGCGGGCGCG<br>GCCGCCCCGCCGCACGCCGACGCGCCCCGCCUGCGCGCCUGGCUGCGCGAGCUGCG<br>GUUCGUGCGCGACGCGCUGGUGCUGAUGCGCCUGCGCGGGGACCUGCGCGUGGCC<br>GGCGGCAGCGAGGCCGCCGUGGCCGCCGUGCGCGCCGUGAGCCUGGUCGCCGGGG<br>CCCUGGGCCCGGCGCUGCCGCGGAGCCCGCGCCUGCUGAGCUCCGCCGCCGCCGCC<br>GCCGCGGACCUGCUCUUCCAGAACCAGAGCCUGCGCCCCCUGCUGGCCGACACCG<br>UCGCCGCGGCCGACUCGCUCGCCGCGCCCGCCUCCGCGCCGCGGGAGGCCGCGGAC<br>GCCCCCCGCCCCGCGGCCGCCCCUCCCGCGGGGGCCGCGCCCCCCGCCCCGCCGAC<br>GCCGCCGCCGCGGCCGCCGCGCCCCGCGGCGCUGACCCGCCGGCCCGCCGAGGGCC<br>CCGACCCGCAGGGCGGCUGGCGCCGCCAGCCGCCGGGGCCCAGCCACACGCCGGCG<br>CCCUCGGCCGCCGCCCUGGAGGCCUACUGCGCCCCGCGGGCCGUGGCCGAGCUCAC<br>GGACCACCCGCUCUUCCCCGCGCCGUGGCGCCCGGCCCUCAUGUUCGACCCGCGCG<br>CGCUGGCCUCGCUGGCCGCGCGCUGCGCCGCCCCGCCCCCGGCGGCGCGCCCGCC<br>GCCUUCGGCCCGCUGCGCGCCUCGGGCCCGCUGCGCCGCGCGGCGGCCUGGAUGC<br>GCCAGGUGCCCGACCCGGAGGACGUGCGCGUGGUGAUCCUCUACUCGCCGCUGCC<br>GGGCGAGGACCUGGCCGCGGGCCGCGCCGGGGGCGGGCCCCCCCCGGAGUGGUCC<br>GCCGAGCGCGGCGGGCUGUCCUGCCUGCUGGCGGCCCUGGGCAACCGGCUCUGCG<br>GGCCCGCCACGGCCGCCUGGGCGGGCAACUGGACCGGCGCCCCCGACGUCUCGGC<br>GCUGGGCGCGCAGGGCGUGCUGCUGCUGUCCACGCGGGACCUGGCCUUCGCCGGC<br>GCCGUGGAGUUCCUGGGGCUGCUGGCCGGCGCCUGCGACCGCCGCCUCAUCGUCG<br>UCAACGCCGUGCGCGCCGCGGCCUGGCCCGCCGCUGCCCCCGUGGUCUCGCGGCAG<br>CACGCCUACCUGGCCUGCGAGGUGCUGCCCGCCGUGCAGUGCGCCGUGCGCUGGC<br>CGGCGGCGCGGGACCUGCGCCGCACCGUGCUGGCCUCCGGCCGCGUGUUCGGGCC<br>GGGGGUCUUCGCGCGCGUGGAGGCCGCGCACGCGCGCCUGUACCCCGACGCGCCG<br>CCGCUGCGCCUCUGCCGCGGGGCCAACGUGCGGUACCGCGUGCGCACGCGCUUCG<br>GCCCCGACACGCUGGUGCCCAUGUCCCCGCGCGAGUACCGCCGCGCCGUGCUCCCG<br>GCGCUGGACGGCCGGGCCGCCGCCUCGGGCGCGGGCGACGCCAUGGCGCCCGGCG |

TABLE 1-continued

| | |
|---|---|
| | CGCCGGACUUCUGCGAGGACGAGGCGCACUCGCACCGCGCCUGCGCGCGCUGGGG<br>CCUGGGCGCGCCGCUGCGGCCCGUCUACGUGGCGCUGGGGCGCGACGCCGUGCGC<br>GGCGGCCCGGCGGAGCUGCGCGGGCCGCGGCGGGAGUUCUGCGCGCGGGCGCUGC<br>UCGAGCCCGACGGCGACGCGCCCCCGCUGGUGCUGCGCGACGACGCGGACGCGGG<br>CCCGCCCCCGCAGAUACGCUGGGCGUCGGCCGCGGGCCGCGCGGGGACGGUGCUG<br>GCCGCGGCGGGCGGCGGCGUGGAGGUGGUGGGGACCGCCGCGGGGCUGGCCACGC<br>CGCCGAGGCGCGAGCCCGUGGACAUGGACGCGGAGCUGGAGGACGACGACGACGG<br>ACUGUUUGGGGAGUGA (SEQ ID NO: 112) |
| MRK_HSV-2<br>gB, SQ-032178,<br>CX-000747 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGAGAGGUGGUGGCUU<br>AGUUUGCGCGCUGGUUGUCGGGGCGCUCGUAGCCGCCGUGGCGUCGGCCGCCCCU<br>GCGGCUCCUCGCGCUAGCGGAGGCGUAGCCGCAACAGUUGCGGCGAACGGGGGUC<br>CAGCCUCUCAGCCUCCUCCCGUCCCGAGCCCUGCGACCACCAAGGCUAGAAAGCG<br>GAAGACCAAGAAACCGCCCAAGCGCCCCGAGGCCACCCCGCCCCCCGAUGCCAACG<br>CGACUGUCGCCGCUGGCCAUGCGACGCUUCGCGCUCAUCUGAGGGAGAUCAAGGU<br>UGAAAAUGCUGAUGCCCAAUUUUACGUGUGCCCGCCCCCGACGGGCGCCACGGUU<br>GUGCAGUUUGAACAGCCGCGGCGCUGUCCGACGCGGCCAGAAGGCCAGAACUAUA<br>CGGAGGGCAUAGCGGUGGUCUUUAAGGAAAACAUCGCCCCGUACAAAUUUAAGGC<br>CACAAUGUACUACAAAGACGUGACAGUUUCGCAAGUGUGGUUUGGCCACAGAUAC<br>UCGCAGUUUAUGGGAAUCUUCGAAGAUAGAGCCCCUGUUCCCUUCGAGGAAGUCA<br>UCGACAAGAUUAAUGCCAAAGGGGUAUGCCGUUCCACGGCCAAAUACGUGCGCAA<br>CAAUAUGGAGACCACCGCCUUUCACCGGGAUGAUCACGAGACCGACAUGGAGCUU<br>AAGCCGGCGAAGGUCGCCACGCGUACCUCCCGGGGUUGGCACACCACAGAUCUUA<br>AGUACAAUCCCUCGCGAGUUGAAGCAUUCCAUCGGUAUGGAACUACCGUUAACUG<br>CAUCGUUGAGGAGGUGGAUGCGCGGUCGGUGUACCCUUACGAUGAGUUUGUGUU<br>AGCGACCGGCGAUUUUGUGUACAUGUCCCCGUUUUACGGCUACCGGGAGGGGUCG<br>CACACCGAACAUACCUCGUACGCCGCUGACAGGUUCAAGCAGGUCGAUGGCUUUU<br>ACGCGCGCGAUCUCACCACGAAGGCCCGGGCCACGUCACCGACGACCAGGAACUU<br>GCUCACGACCCCCAAGUUCACCGUCGCUUGGGAUUGGGUCCCAAAGCGUCCGGCG<br>GUCUGCACGAUGACCAAAUGGCAGGAGGUGGACGAAAUGCUCCGCGCAGAAUACG<br>GCGGCUCCUUCCGCUUCUCGUCCGACGCCAUCUCGACAACCUUCACCACCAAUCU<br>GACCCAGUACAGUCUGUCGCGCGUUGAUUUAGGAGACUGCAUUGGCCGGGAUGCC<br>CGGGAGGCCAUCGACAGAAUGUUUGCGCGUAAGUACAAUGCCACACAUAUUAAGG<br>UGGGCCAGCCGCAAUACUACCUUGCCACGGGCGGCUUUCUCAUCGCGUACCAGCC<br>CCUUCUCUCAAAUACGCUCGCUGAACUGUACGUGCGGGAGUAUAUGAGGGAACAG<br>GACCGCAAGCCCCGCAAUGCCACGCCUGCGCCACUACGAGAGGCGCCUUCAGCUA<br>AUGCGUCGGUGGAACGUAUCAAGACCACCUCCUCAAUAGAGUUCGCCCGGCUGCA<br>AUUUACGUACAACCACAUCCAGCGCCACGUGAACGACAUGCUGGGCCGCAUCGCU<br>GUCGCCUGGUGCGAGCUGCAGAAUCACGAGCUGACUCUUUGGAACGAGGCCCGAA<br>AACUCAACCCCAACGCGAUCGCCUCCGCAACAGUCGGUAGACGGGUGAGCGCUCG<br>CAUGCUAGGAGAUGUCAUGGCUGUGUCCACCUGCGUGCCCGUCGCUCCGGACAAC<br>GUGAUUGUGCAGAAUUCGAUGCGGGUCUCAUCGCGGCCGGGCACCUGCUACAGCA<br>GGCCCCUCGUCAGCUUCCGGUACGAAGACCAGGGCCCGCUGAUUGAAGGGCAACU<br>GGGAGAGAACAAUGAGCUGCGCCUCACCCGCGACGCGCUCGAACCCUGCACCGUC<br>GGACAUCGGAGAUAUUUCAUCUUCGGAGGGGGCUACGUGUACUUCGAAGAGUAU<br>GCCUACUCUCACCAGCUGAGUAGAGCCGACGUCACUACCGUCAGCACCUUUAUUG<br>ACCUGAAUAUCACCAUGCUGGAGGACCACGAGUUUGUGCCCCUGGAAGUUUACAC<br>UCGCCACGAAAUCAAAGACUCCGGCCUGUUGGAUUACACGGAGGUUCAGAGGCGG<br>AACCAGCUGCAUGACCUGCGCUUUGCCGACAUCGACACCGUCAUCCGCGCCGAUG<br>CCAACGCUGCCAUGUUCGCGGGGCUGUGCGCGUUCUUCGAGGGGAUGGGUGACUU<br>GGGGCGCGCCGUCGGCAAGGUCGUCAUGGGAGUAGUGGGGGGCGUUGUGAGUGC<br>CGUCAGCGGCGUGUCCUCCUUCAUGUCCAAUCCAUUCGGAGCGCUUGCUGUGGGG<br>CUGCUGGUCCUGGCCGGGCUGGUAGCCGCCUUCUUCGCCUUUCGAUAUGUUCUGC<br>AACUGCAACGCAAUCCCAUGAAAGCUCUAUAUCCGCUCACCACCAAGGAGCUAAA<br>GACGUCAGAUCCAGGAGGCGUGGGCGGGGAAGGGGAAGAGGGCGCGGAGGGCGG<br>AGGGUUUGACGAAGCCAAAUUGGCCGAGGCUCGUGAAAUGAUCCGAUAUAUGGC<br>ACUAGUGUCGGCGAUGGAAAGGACCGAACAUAAGGCCCGAAAGAAGGGCACGUCG<br>GCGCUGCUCUCAUCCAAGGUCACCAACAUGGUACUGCGCAAGCGCAACAAAGCCA<br>GGUACUCUCCGCUCCAUAACGAGGACGAGGCGGGAGAUGAGGAUGAGCUCUAAUG<br>AUAAUAGGCUGGAGCCUCGGUGGCCAUGCUUCUUGCCCCUUGGGCCUCCCCCCAG<br>CCCCUCCUCCCCUUCCUGCACCCGUACCCCCGUGGUCUUUGAAUAAAGUCUGAGU<br>GGGCGGC (SEQ ID NO: 113) |
| MRK_HSV-2<br>gC, SQ-032179,<br>CX-000670 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCCCUUGGACGGGU<br>AGGCCUAGCCGUGGGCCUGUGGGGCCUACUGUGGGUGGGUGUGGUCGUGGUGCU<br>GGCCAAUGCCUCCCCCGGACGCACGAUAACGGUGGGCCCGCGAGGCAACGCGAGC<br>AAUGCUGCCCCCUCCGCGUCCCCGCGGAACGCAUCCGCCCCCCGAACCACACCCAC<br>GCCCCCACAACCCCGCAAAGCGACGAAAUCCAAGGCCUCCACCGCCAAACCGGCUC<br>CGCCCCCCAAGACCGGACCCCCGAAGACAUCCUCGGAGCCCGUGCGAUGCAACCGC<br>CACGACCCGCUGGCCCGGUACGGCUCGCGGGUGCAAAUCCGAUGCCGGUUUCCCA<br>ACUCCACGAGGACUGAGUCCCGUCUCCAGAUCUGGCGUUAUGCCACGGCGACGGA<br>CGCCGAAAUCGGAACAGCGCCUAGCUUAGAAGAGGUGAUGGUGAACGUGUCGGCC<br>CCGCCCGGGGGCCAACUGGUGUAUGACAGUGCCCCCAACCGAACGGACCCGCAUG<br>UAAUCUGGGCGGAGGGCGCCGGCCCGGGCGCCAGCCCGCGCCUGUACUCGGUUGU<br>CGGCCCGCUGGGUCGGCAGCGGCUCAUCAUCGAAGAGUUAACCCUGGAGACACAG<br>GGCAUGUACUAUUGGGUGUGGGGCCGGACGGACCGCCCGUCCGCCUACGGGACCU<br>GGGUCCGCGUUCGAGUAUUUCGCCCUCCGUCGCUGACCAUCCACCCCCACGCGGU<br>GCUGGAGGGCCAGCCGUUUAAGGCGACGUGCACGGCCGCAACCUACUACCCGGGC |

TABLE 1-continued

| | |
|---|---|
| | AACCGCGCGGAGUUCGUCUGGUUUGAGGACGGUCGCCGCGUAUUCGAUCCGGCAC<br>AGAUACACACGCAGACGCAGGAGAACCCCGACGGCUUUUCCACCGUCUCCACCGU<br>GACCUCCGCGGCCGUCGGCGGGCAGGGCCCCCCUCGCACCUUCACCUGCCAGCUGA<br>CGUGGCACCGCGACUCCGUGUCGUUCUCUCGGCGCAACGCCAGCGGCACGGCCUC<br>GGUUCUGCCGCGGCCGACCAUUACCAUGGAGUUUACAGGCGACCAUGCGGUCUGC<br>ACGGCCGGCUGUGUGCCCGAGGGGGUCACGUUUGCUUGGUUCCUGGGGGAUGACU<br>CCUCGCCGGCGGAAAAGGUGGCCGUCGCGUCCCAGACAUCGUGCGGGCGCCCCGG<br>CACCGCCACGAUCCGCUCCACCCUGCCGGUCUCGUACGAGCAGACCGAGUACAUC<br>UGUAGACUGGCGGGAUACCCGGACGGAAUUCCGGUCCUAGAGCACCACGGAAGCC<br>ACCAGCCCCCGCCGCGGGACCCAACCGAGCGGCAGGUGAUCCGGGCGGUGGAGGG<br>GGCGGGGAUCGGAGUGGCUGUCCUUGUCGCGGUGGUUCUGGCCGGGACCGCGGUA<br>GUGUACCUGACCCAUGCCUCCUCGGUACGCUAUCGUCGGCUGCGGUAAUGAUAAU<br>AGGCUGGAGCCUCGGUGGCCAUGCUUCUUGCCCCUUGGGCCUCCCCCCAGCCCCU<br>CCUCCCCUUCCUGCACCCGUACCCCCGUGGUCUUUGAAUAAAGUCUGAGUGGGCG<br>GC (SEQ ID NO: 114) |
| MRK_HSV-2<br>gD, SQ-032180,<br>CX-001301 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGGGCGUUUGACCUC<br>CGGCGUCGGGACGGCGGCCCUGCUAGUUGUCGCGGUGGGACUCCGCGUCGUCUGC<br>GCCAAAUACGCCUUAGCAGACCCCUCGCUUAAGAUGGCCGAUCCCAAUCGAUUUC<br>GCGGGAAGAACCUUCCGGUUUUGGACCAGCUGACCGACCCCCCGGGGUGAAGCG<br>UGUUUACCACAUUCAGCCGAGCCUGGAGGACCCGUUCCAGCCCCCCAGCAUCCCG<br>AUCACUGUGUACUACGCAGUGCUGGAACGUGCCUGCCGCAGCGUGCUCCUACAUG<br>CCCCAUCGGAGGCCCCCCAGAUCGUGCGCGGGGCUUCGGACGAGGCCCGAAAGCA<br>CACGUACAACCUGACCAUCGCCUGGUAUCGCAUGGGAGACAAUUGCGCUAUCCCC<br>AUCACGGUUAUGGAAUACACCGAGUGCCCCUACAACAAGUCGUUGGGGGUCUGCC<br>CCAUCCGAACGCAGCCCCGCUGGAGCUACUAUGACAGCUUUAGCGCCGUCAGCGA<br>GGAUAACCUGGGAUUCCUGAUGCACGCCCCCGCCUUCGAGACCGCGGGUACGUAC<br>CUGCGGCUAGUGAAGAUAAACGACUGGACGGAGAUCACACAAUUUAUCCUGGAGC<br>ACCGGGCCCGCGCCUCCUGCAAGUACGCUCUCCCCCUGCGCAUCCCCCCGGCAGCG<br>UGCCUCACCUCGAAGGCCUACCAACAGGGCGUGACGGUCGACAGCAUCGGGAUGC<br>UACCCCGCUUUAUCCCCGAAAACCAGCGCACCGUCGCCCUAUACAGCUUAAAAAU<br>CGCCGGGUGGCACGGCCCCAAGCCCCCGUACACCAGCACCCUGCUGCCGCCGGAGC<br>UGUCCGACACCACCAACGCCACGCAACCCGAACUCGUUCCGGAAGACCCCGAGGA<br>CUCGGCCCUCUUAGAGGAUCCCGCCGGGACGGUGUCUUCGCAGAUCCCCCCAAAC<br>UGGCACAUCCCGUCGAUCCAGGACGUCGCACCGCACCACGCCCCCGCCGCCCCCAG<br>CAACCCGGGCCUGAUCAUCGGCGCGCUGGCCGGCAGUACCCUGGCGGUGCUGGUC<br>AUCGGCGGUAUUGCGUUUUGGGUACGCCGCCGCGCUCAGAUGGCCCCCAAGCGCC<br>UACGUCUCCCCCACAUCCGGGAUGACGACGCGCCCCCCUCGCACCAGCCAUUGUU<br>UUACUAGUGAUAAUAGGCUGGAGCCUCGGUGGCCAUGCUUCUUGCCCCUUGGGCC<br>UCCCCCCAGCCCCUCCUCCCCUUCCUGCACCCGUACCCCCGUGGUCUUUGAAUAAA<br>GUCUGAGUGGGCGGC (SEQ ID NO: 115) |
| MRK_HSV-2<br>gE, SQ-032181,<br>CX-001391 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCUAGGGGGGCCGG<br>GUUGGUUUUUUUUGUUGGAGUUUGGGUCGUAAGCUGCCUCGCGGCAGCGCCCAG<br>AACGUCCUGGAAACGCGUAACCUCGGGCGAAGACGUGGUGUUACUCCCCGCGCCG<br>GCGGGGCCGGAAGAACGCACUCGGGCCCACAAACUACUGUGGGCAGCGGAACCGC<br>UGGAUGCCUGCGGUCCCCUGAGGCCGUCAUGGGUGGCACUGUGGCCCCCCCGACG<br>AGUGCUUGAGACGGUUGUCGAUGCGGCGUGCAUGCGCGCCCCGGAACCGCUCGCU<br>AUCGCAUACAGUCCCCCGUUCCCUGCGGGCGACGAGGGACUUUAUUCGGAGUUGG<br>CGUGGCGCGAUCGCGUAGCCGUGGUCAACGAGAGUUUAGUUAUCUACGGGGCCCU<br>GGAGACGGACAGUGGUCUGUACACCCUGUCAGUGGUGGGCCUAUCCGACGAGGCC<br>CGCCAAGUGGCGUCCGUGGUUCUCGUCGUCGAGCCCGCCCCUGUGCCUACCCCGA<br>CCCCCGAUGACUACGACGAGGAGGAUGACGCGGGCGUGAGCGAACGCACGCCCGU<br>CAGCGUUCCCCCCCAACACCCCCCCGACGUCCCCCCGUCGCCCCCCCGACGCACC<br>CUCGUGUUAUCCCUGAGGUGAGCCACGUGCGGGGGGUGACGGUCCACAUGGAAAC<br>CCCGGAGGCCAUUCUGUUUGCGCCAGGGGAGACGUUUGGGACGAACGUCUCCAUC<br>CACGCAAUUGCCCACGACGACGGUCCGUACGCCAUGGACGUCGUCUGGAUGCGAU<br>UUGAUGUCCCGUCCUCGUGCGCCGAGAUGCGGAUCUAUGAAGCAUGUCUGUAUCA<br>CCCGCAGCUGCCUGAGUGUCUGUCUCCGGCCGAUGCGCCGUGCGCCGUAAGUUCG<br>UGGGCGUACCGCCUGGCGGUCCGCAGCUACGCCGGCUGCUCCAGGACUACGCCCC<br>CACCUCGAUGUUUUGCUGAAGCUCGCAUGGAACCGGUCCCCGGGUUGGCGUGGCU<br>CGCAUCAACUGUUAAUCUGGAAUUCCAGCAUGCCUCUCCCCAACACGCCGGCCUC<br>UAUCUGUGUGUGGUGUAUGUGGACGACCAUAUCCAUGCCUGGGGCCACAUGACCA<br>UCUCCACAGCGGCCCAGUACCGGAAUGCGGUGGUGGAACAGCAUCUCCCCCAGCG<br>CCAGCCCGAGCCCGUAGAACCCACCCGACCGCAUGUGAGAGCCCCCCUCCCGCAC<br>CCUCCGCGAGAGGCCCGUUACGCUUAGGUGCGGUCCUGGGGGCGGCCCUGUUGCU<br>CGCGGCCCUCGGGCUAUCCGCCUGGGCGUGCAUGACCUGCUGGCGCAGGCGCAGU<br>UGGCGGGCGGUUAAAAGUCGGGCCUCGGCGACCGGCCCCACUUACAUUCGAGUAG<br>CGGAUAGCGAGCUGUACGCGGACUGGAGUUCGGACUCAGAGGGCGAGCGCGACGG<br>UUCCCUGUGGCAGGACCCUCCGGAGAGACCCGACUCACCGUCCACAAAUGGAUCC<br>GGCUUUGAGAUCUUAUCCCCAACGGCGCCCUCUGUAUACCCCCAUAGCGAAGGGC<br>GUAAAUCGCGCCGCCCGCUCACCACCUUUGGUUCAGGAAGCCCGGGACGUCGUCA<br>CUCCCAGGCGUCCUAUUCUUCCGUCUUAUGGUAAUGAUAAUAGGCUGGAGCCUCG<br>GUGGCCAUGCUUCUUGCCCCUUGGGCCUCCCCCCAGCCCCUCCUCCCCUUCCUGCA<br>CCCGUACCCCCGUGGUCUUUGAAUAAAGUCUGAGUGGGCGGC (SEQ ID NO: 116) |

TABLE 1-continued

| | |
|---|---|
| MRK_HSV-2<br>gI, SQ-032182,<br>CX-000645 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGCCCGGCCGCUCGCUG<br>CAGGGCCUGGCGAUCCUGGGCCUGUGGGUCUGCGCCACCGGCCUGGUCGUCCGCG<br>GCCCCACGGUCAGUCUGGUCUCAGACUCACUCGUGGAUGCCGGGGCCGUGGGGCC<br>CCAGGGCUUCGUGGAAGAGGACCUGCGUGUUUUCGGGGAGCUUCAUUUUGUGGG<br>GGCCCAGGUCCCCCACACAAACUACUACGACGGCAUCAUCGAGCUGUUUCACUAC<br>CCCCUGGGGAACCACUGCCCCCGCGUUGUACACGUGGUCACACUGACCGCAUGCC<br>CCCGCCGCCCCGCCGUGGCGUUCACCUUGUGUCGCUCGACGCACCACGCCCACAGC<br>CCCGCCUAUCCGACCCUGGAGCUGGGUCUGGCGCGGCAGCCGCUUCUGCGGGUUC<br>GAACGGCAACGCGCGACUAUGCCGGUCUGUAUGUCCUGCGCGUAUGGGUCGGCAG<br>CGCGACGAACGCCAGCCUGUUUGUUUUGGGGGUGGCGCUCUCUGCCAACGGGACG<br>UUUGUGUAUAACGGCUCGGACUACGGCUCCUGCGAUCCGGCGCAGCUUCCCUUUU<br>CGGCCCCGCGCCUGGGACCCUCGAGCGUAUACACCCCCGGAGCCUCCCGGCCCACC<br>CCUCCACGGACAACGACAUCACCGUCCUCCCCACGAGACCCGACCCCCGCCCCCGG<br>GGACACAGGGACGCCUGCUCCCGCGAGCGGCGAGAGAGCCCCGCCCAAUUCCACG<br>CGAUCGGCCAGCGAAUCGAGACACAGGCUAACCGUAGCCCAGGUAAUCCAGAUCG<br>CCAUACCGGCGUCCAUCAUCGCCUUUGUGUUUCUGGGCAGCUGUAUCUGCUUCAU<br>CCAUAGAUGCCAGCGCCGAUACAGGCGCCCCCGCGGCCAGAUUUACAACCCCGGG<br>GGCGUUUCCUGCGCGGUCAACGAGGCGGCCAUGGCCCGCCUCGGAGCCGAGCUGC<br>GAUCCCACCCAAACACCCCCCCCAAACCCCGACGCCGUUCGUCGUCGUCCACGACC<br>AUGCCUUCCCUAACGUCGAUAGCUGAGGAAUCGGAGCCAGGUCCAGUCGUGCUGC<br>UGUCCGUCAGUCCUCGGCCCCGCAGUGGCCCGACGGCCCCCCAAGAGGUCUAGUG<br>AUAAUAGGCUGGAGCCUCGGUGGCCAUGCUUCUUGCCCCUUGGGCCUCCCCCCAG<br>CCCCUCCUCCCCUUCCUGCACCCGUACCCCCGUGGUCUUUGAAUAAAGUCUGAGU<br>GGGCGGC (SEQ ID NO: 117) |
| MRK_HSV-2<br>SgB, SQ-<br>032210, CX-<br>000655 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGCGCGGGGGGGGCUU<br>AGUUUGCGCGCUGGUCGUGGGGGCGCUCGUAGCCGCGGUCGCGUCGGCGGCUCCG<br>GCUGCCCCACGCGCUUCAGGUGGUGUCGCUGCGACCGUUGCGGCGAAUGGUGGUC<br>CCGCCAGCCAACCGCCUCCCGUCCCGAGCCCCGCGACCACUAAGGCCCGGAAGCGG<br>AAGACCAAGAAGCCACCCAAGCGGCCCGAGGCGACUCCGCCCCCAGACGCCAACG<br>CGACCGUCGCCGCCGGCCACGCCACUCUGCGUGCGCACCUGCGGGAAAUCAAGGU<br>CGAGAACGCGGACGCCCAGUUUUACGUGUGCCCGCCGCCGACUGGCGCCACGGUG<br>GUGCAGUUUGAGCAACCUAGGCGCUGCCCGACGCGACCAGAGGGGCAGAACUACA<br>CCGAGGGCAUAGCGGUGGUCUUUAAGGAAAACAUCGCCCCGUACAAAUUCAAGGC<br>CACCAUGUACUACAAAGACGUGACCGUGUCGCAGGUGUGGUUCGGCCACCGCUAC<br>UCCCAGUUUAUGGGGAUAUUCGAGGACCGCGCCCCCGUUCCCUUCGAAGAGGUGA<br>UUGACAAAAUUAACGCCAAGGGGGUCUGCCGCAGUACGGCGAAGUACGUCCGGAA<br>CAACAUGGAGACCACUGCCUUCCACCGGGACGACCACGAAACAGACAUGGAGCUC<br>AAACCGGCGAAAGUCGCCACGCGCACGAGCCGGGGGUGGCACACCACCGACCUCA<br>AAUACAAUCCUUCGCGGGUGGAAGCAUUCCAUCGGUAUGGCACGACCGUCAACUG<br>UAUCGUAGAGGAGGUGGAUGCGCGGUCGGUGUACCCCUACGAUGAGUUCGUGCU<br>GGCAACGGGCGAUUUUGUGUACAUGUCCCCUUUUUACGGCUACCGGGAAGGUAGU<br>CACACCGAGCACACCAGUUACGCCGCCGACCGCUUUAAGCAAGUGGACGGCUUCU<br>ACGCGCGCGACCUCACCACAAAGGCCCGGGCCACGUCGCCGACGACCCGCAAUUU<br>GCUGACGACCCCCAAGUUUACCGUGGCCUGGGACUGGGUGCCUAAGCGACCGGCG<br>GUCUGUACCAUGACAAAGUGGCAGGAGGUGGACGAAAUGCUCCGCGCUGAAUACG<br>GUGGCUCUUUCCGCUUCUCUUCCGACGCCAUCUCCACCACGUUCACCACCAACCU<br>GACCCAAUACUCGCUCUCGAGAGUCGAUCUGGGAGACUGCAUUGGCCGGGAUGCC<br>CGCGAGGCAAUUGACCGCAUGUUCGCGCGCAAGUACAACGCUACGCACAUAAAGG<br>UUGGCCAACCCCAGUACUACCUAGCCACGGGGGGCUUCCUCAUCGCUUAUCAACC<br>CCUCCUCAGCAACACGCUCGCCGAGCUGUACGUGCGGGAAUAUAUGCGGGAACAG<br>GACCGCAAACCCCGAAACGCCACGCCCGCGCCGCUGCGGGAAGCACCGAGCGCCA<br>ACGCGUCCGUGGAGCGCAUCAAGACGACAUCCUCGAUUGAGUUUGCUCGUCUGCA<br>GUUUACGUAUAACCACAUACAGCGCCAUGUAAACGACAUGCUCGGGCGCAUCGCC<br>GUCGCGUGGUGCGAGCUCCAAAAUCACGAGCUCACUCUGUGGAACGAGGCACGCA<br>AGCUCAAUCCCAACGCCAUCGCAUCCGCCACCGUAGGCCGGCGGGUGAGCGCUCG<br>CAUGCUCGGGGAUGUCAUGGCCGUCUCCACGUGCGUGCCCGUCGCCCCGGACAAC<br>GUGAUCGUGCAAAAUAGCAUGCGCGUUUCUUCGCGGCCGGGGACGUGCUACAGCC<br>GCCCGCUGGUUAGCUUUCGGUACGAAGACCAAGGCCCGCUGAUUGAGGGGCAGCU<br>GGGUGAGAACAACGAGCUGCGCCUCACCCGCGAUGCGUUAGAGCCGUGUACCGUC<br>GGCCACCGGCGCUACUUCAUCUUCGGAGGGGGAUACGUAUACUUCGAAGAAUAUG<br>CGUACUCUCACCAAUUGAGUCGCGCCGAUGUCACCACUGUUAGCACCUUCAUCGA<br>CCUGAACAUCACCAUGCUGGAGGACCACGAGUUCGUGCCCCUGGAGGUCUACACA<br>CGCCACGAGAUCAAGGAUUCCGGCCUACUGGACUACACCGAAGUCCAGAGACGAA<br>AUCAGCUGCACGAUCUCCGCUUUGCUGACAUCGAUACUGUUAUCCGCGCCGACGC<br>CAACGCCGCCAUGUUCGCAGGUCUGUGUGCGUUUUUCGAGGGUAUGGGUGACUUA<br>GGGCGCGCGGUGGGCAAGGUCGUCAUGGGGGUAGUCGGGGGCGUGGUGUCGGCC<br>GUCUCGGGCGUCUCCUCCUUUAUGUCUAACCCCUGAUAAUAGGCUGGAGCCUCGG<br>UGGCCAUGCUUCUUGCCCCUUGGGCCUCCCCCCAGCCCCUCCUCCCCUUCCUGCAC<br>CCGUACCCCCGUGGUCUUUGAAUAAAGUCUGAGUGGGCGGC (SEQ ID NO: 118) |
| MRK_HSV-2<br>SgC, SQ-<br>032835, CX-<br>000616 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCACUGGGAAGAGU<br>GGGAUUGGCCGUCGGACUGUGGGGACUGCUGUGGGUGGGAGUCGUCGUCGUCCU<br>GGCUAACGCCUCACCCGGUCGGACUAUCACUGUGGGACCCAGGGGGAACGCCUCU<br>AACGCCGCGCCCUCAGCUAGCCCCAGGAAUGCCAGCGCUCCCAGGACCACCCCGAC<br>UCCUCCGCAACCCCGCAAGGCGACCAAGUCCAAGGCGUCCACUGCCAAGCCAGCG |

TABLE 1-continued

| | |
|---|---|
| | CCUCCGCCUAAGACUGGCCCCCCUAAGACCUCCAGCGAACCUGUGCGGUGCAACC<br>GGCACGACCCUCUGGCACGCUACGGAUCGCGGGUCCAAAUCCGGUGUCGGUUCCC<br>GAACAGCACUCGGACCGAAUCGCGGCUCCAGAUUUGGAGAUACGCAACUGCCACU<br>GAUGCCGAGAUCGGCACUGCCCAAGCCUUGAGGAGGUCAUGGUCAACGUGUCAG<br>CUCCUCCUGGAGGCCAGCUGGUGUACGACUCCGCUCCGAACCGAACCGACCCGCA<br>CGUCAUCUGGGCCGAAGGAGCCGGUCCUGGUGCAUCGCCGAGGUUGUACUCGGUA<br>GUGGGUCCCCUGGGGAGACAGCGGCUGAUCAUCGAAGAACUGACUCUGGAGACUC<br>AGGGCAUGUACUAUUGGGUGUGGGGCAGAACCGAUAGACCAUCCGCAUACGGAAC<br>CUGGGUGCGCGUGAGAGUGUUCAGACCCCCGUCCUUGACAAUCCACCCGCAUGCG<br>GUGCUCGAAGGGCAGCCCUUCAAGGCCACUUGCACUGCGGCCACUUACUACCCUG<br>GAAACCGGGCCGAAUUCGUGUGGUUCGAGGAUGGACGGAGGGUGUUCGACCCGGC<br>GCAGAUUCAUACGCAGACUCAGGAAAACCCGGACGGCUUCUCCACCGUGUCCACU<br>GUGACUUCGGCCGCUGUGGGAGGACAAGGACCGCCACGCACCUUCACCUGUCAGC<br>UGACCUGGCACCGCGACAGCGUGUCCUUUAGCCGGCGGAACGCAUCAGGCACUGC<br>CUCCGUGUUGCCUCGCCCAACCAUUACCAUGGAGUUCACCGGAGAUCACGCCGUG<br>UGCACUGCUGGCUGCGUCCCCGAAGGCGUGACCUUCGCCUGGUUUCUCGGGGACG<br>ACUCAUCCCCGGCGGAAAAGGUGGCCGUGGCCUCUCAGACCAGCUGCGGUAGACC<br>GGGAACCGCCACCAUCCGCUCCACUCUGCCGGUGUCGUACGAGCAGACCGAGUAC<br>AUUUGUCGCCUGGCCGGAUACCCGGACGGUAUCCCAGUGCUCGAACACCACGGCA<br>GCCAUCAGCCUCCGCCGAGAGAUCCUACCGAGCGCCAGGUCAUCCGGGCCGUGGA<br>AGGAUGAUAAUAGGCUGGAGCCUCGGUGGCCAUGCUUCUUGCCCCUUGGGCCUCC<br>CCCCAGCCCCUCCUCCCCUUCCUGCACCCGUACCCCCGUGGUCUUUGAAUAAAGUC<br>UGAGUGGGCGGC (SEQ ID NO: 119) |
| MRK_HSV-2<br>SgE, SQ-<br>032211, CX-<br>003794 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGCUCGCGGGGCCGG<br>GUUGGUGUUUUUUGUUGGAGUUUGGGUCGUAUCGUGCCUGGCGGCAGCACCCAG<br>AACGUCCUGGAAACGGGUUACCUCGGGCGAGGACGUGGUGUUGCUUCCGGCGCCC<br>GCGGGGCCGGAGGAACGCACACGGGCCCACAAACUACUGUGGGCCGCGGAACCCC<br>UGGAUGCCUGCGGUCCCCUGAGGCCGUCGUGGGUGGCGCUGUGGCCCCCGCGACG<br>GGUGCUCGAAACGGUCGUGGAUGCGGCGUGCAUGCGCGCCCCGGAACCGCUCGCC<br>AUAGCAUACAGUCCCCCGUUCCCCGCGGGCGACGAGGGACUGUAUUCGGAGUUGG<br>CGUGGCGCGAUCGCGUAGCCGUGGUCAACGAGAGUCUGGUCAUCUACGGGGCCCU<br>GGAGACGGACAGCGGUCUGUACACCCUGUCCGUGGUCGGCCUAAGCGACGAGGCG<br>CGCCAAGUGGCGUCGGUGGUUCUGGUCGUGGAGCCCGCCCCUGUGCCGACCCCGA<br>CCCCCGACGACUACGACGAAGAAGACGACGCGGGCGUGAGCGAACGCACGCCGGU<br>CAGCGUACCCCCCCCGACCCCACCCCGUCGUCCCCCGUCGCCCCCCCUACGCACC<br>CUCGUGUUAUCCCCGAGGUGUCCCACGUGCGCGGGGUAACGGUCCAUAUGGAGAC<br>CCCGGAGGCCAUUCUGUUUGCCCCCGGAGAGACGUUUGGGACGAACGUCUCCAUC<br>CACGCCAUUGCCCAUGACGACGGUCCGUACGCCAUGGACGUCGUCUGGAUGCGGU<br>UUGACGUGCCGUCCUCGUGCGCCGAGAUGCGGAUCUACGAAGCUUGUCUGUAUCA<br>CCCGCAGCUUCCAGAAUGUCUAUCUCCGGCCGACGCGCCGUGCGCUGUAAGUUCC<br>UGGGCGUACCGCCUGGCGGUCCGCAGCUACGCCGGCUGUUCCAGGACUACGCCCC<br>CGCCGCGAUGUUUUGCCGAGGCUCGCAUGGAACCGGUCCCGGGGUUGGCGUGGUU<br>AGCCUCCACCGUCAACCUGGAAUUCCAGCACGCCUCCCCUCAGCACGCCGGCCUUU<br>ACCUGUGCGUGGUGUACGUGGACGAUCAUAUCCACGCCUGGGGCCACAUGACCAU<br>CUCUACCGCGGCGCAGUACCGGAACGCGGUGGUGGAACAGCACUUGCCCCAGCGC<br>CAGCCUGAACCCGUCGAGCCCACCCGCCCGCACGUAAGAGCACCCCCUCCCGCGCC<br>UUCCGCGCGCGGCCCGCUGCGCUGAUAAUAGGCUGGAGCCUCGGUGGCCAUGCUU<br>CUUGCCCCUUGGGCCUCCCCCCAGCCCCUCCUCCCCUUCCUGCACCCGUACCCCCG<br>UGGUCUUUGAAUAAAGUCUGAGUGGGCGGC (SEQ ID NO: 120) |
| MRK_HSV-2<br>SgI, SQ-<br>032323, CX-<br>002683 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGCCCGGCCGCUCGCUG<br>CAGGGCCUGGCGAUCCUGGGCCUGUGGGUCUGCGCCACCGGCCUGGUCGUCCGCG<br>GCCCCACGGUCAGUCUGGUCUCAGACUCACUCGUGGAUGCCGGGGCCGUGGGGCC<br>CCAGGGCUUCGUGGAAGAGGACCUGCGUGUUUUCGGGGAGCUUCAUUUUGUGGG<br>GGCCCAGGUCCCCCACACAAACUACUACGACGGCAUCAUCGAGCUGUUUCACUAC<br>CCCCUGGGGAACCACUGCCCCCGCGUUGUACACGUGGUCACACUGACCGCAUGCC<br>CCCGCCGCCCCGCCGUGGCGUUCACCUUGUGUCGCUCGACGCACCACGCCCACAGC<br>CCCGCCUAUCCGACCCUGGAGCUGGGUCUGGCGCGGCAGCCGCUUCUGCGGGUUC<br>GAACGGCAACGCGCGACUAUGCCGGUCUGUAUGUCCUGCGCGUAUGGGUCGGCAG<br>CGCGACGAACGCCAGCCUGUUUGUUUUGGGGGUGGCGCUCUCUGCCAACGGGACG<br>UUUGUGUAUAACGGCUCGGACUACGGCUCCUGCGAUCCGGCGCAGCUUCCCUUUU<br>CGGCCCCGCGCCUGGGACCCUCGAGCGUAUACACCCCCGGAGCCUCCCGGCCCACC<br>CCUCCACGGACAACGACAUCCCCGUCCUCCCCUAGAGACCCGACCCCCGCCCCCGG<br>GGACACAGGAACGCCUGCGCCCGCGAGCGGCGAGAGAGCCCCGCCCAAUUCCACG<br>CGAUCGGCCAGCGAAUCGAGACACAGGCUAACCGUAGCCCAGGUAAUCCAGUGAU<br>AAUAGGCUGGAGCCUCGGUGGCCAUGCUUCUUGCCCCUUGGGCCUCCCCCCAGCC<br>CCUCCUCCCCUUCCUGCACCCGUACCCCCGUGGUCUUUGAAUAAAGUCUGAGUGG<br>GCGGC (SEQ ID NO: 121) |
| MRK_HSV-2<br>SgD, SQ-<br>032172, CX-<br>004714 | UCAAGCUUUUGGACCCUCGUACAGAAGCUAAUACGACUCACUAUAGGGAAAUAAG<br>AGAGAAAAGAAGAGUAAGAAGAAAUAUAAGAGCCACCAUGGGGCGUUUGACCUC<br>CGGCGUCGGGACGGCGGCCCUGCUAGUUGUCGCGGUGGGACUCCGCGUCGUCUGC<br>GCCAAAUACGCCUUAGCAGACCCCUCGCUUAAGAUGGCCGAUCCCAAUCGAUUUC<br>GCGGGAAGAACCUUCCGGUUUUGGACCAGCUGACCGACCCCCCGGGGUGAAGCG<br>UGUUUACCACAUUCAGCCGAGCCUGGAGGACCCGUUCCAGCCCCCCAGCAUCCCG<br>AUCACUGUGUACUACGCAGUGCUGGAACGUGCCUGCCGCAGCGUGCUCCUACAUG<br>CCCCAUCGGAGGCCCCCCAGAUCGUGCGCGGGGCUUCGGACGAGGCCCGAAAGCA |

TABLE 1-continued

| | |
|---|---|
| | CACGUACAACCUGACCAUCGCCUGGUAUCGCAUGGGAGACAAUUGCGCUAUCCCCAUCACGGUUAUGGAAUACACCGAGUGCCCCUACAACAAGUCGUUGGGGGUCUGCCCCAUCCGAACGCAGCCCCGCUGGAGCUACUAUGACAGCUUUAGCGCCGUCAGCGAGGAUAACCUGGGAUUCCUGAUGCACGCCCCCGCCUUCGAGACCGCGGGUACGUACCUGCGGCUAGUGAAGAUAAACGACUGGACGGAGAUCACACAAUUUAUCCUGGAGCACCGGGCCCGCGCCUCCUGCAAGUACGCUCUCCCCCUGCGCAUCCCCCCGGCAGCGUGCCUCACCUCGAAGGCCUACCAACAGGGCGUGACGGUCGACAGCAUCGGGAUGCUACCCCGCUUUAUCCCCGAAAACCAGCGCACCGUCGCCCUAUACAGCUUAAAAAUCGCCGGGUGGCACGGCCCCAAGCCCCCGUACACCAGCACCCUGCUGCCGCCGGAGCUGUCCGACACCACCAACGCCACGCAACCCGAACUCGUUCCGGAAGACCCCGAGGACUCGGCCCUCUUAGAGGAUCCCGCCGGGACGGUGUCUUCGCAGAUCCCCCCAAACUGGCACAUCCCGUCGAUCCAGGACGUCGCGCCGCACCACGCCCCCGCCGCCCCCAGCAACCCGUGAUAAUAGGCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC (SEQ ID NO: 122) |
| MRK_HSV-2 ICP-0, SQ-032521, CX-004422 | UCAAGCUUUUGGACCCUCGUACAGAAGCUAAUACGACUCACUAUAGGGAAAUAAGAGAGAAAAGAAGAGUAAGAAGAAAUAUAAGAGCCACCAUGGAACCGCGGCCUGGUACUUCAUCCCGCGCCGAUCCUGGACCGGAACGGCCACCUCGCCAGACCCCUGGAACGCAGCCUGCAGCCCCUCACGCCUGGGGGAUGCUGAAUGAUAUGCAGUGGCUGGCCUCAAGCGACUCCGAGGAAGAGACAGAGGUCGGCAUCUCCGACGAUGAUCUCCAUCGGGAUUCUACUUCGGAAGCGGGCUCCACCGACACAGAGAUGUUCGAGGCCGGCCUGAUGGAUGCUGCGACCCCUCCCGCAAGACCGCCUGCCGAACGCCAAGGCUCGCCGACCCCUGCUGACGCCCAGGGUUCGUGCGGUGGAGGCCCUGUGGGGGAGGAGGAAGCUGAAGCCGGAGGCGGUGGAGAUGUCAACACCCCGGUGGCCUACCUGAUCGUGGGCGUGACUGCCAGCGGAUCCUUCUCGACCAUCCCCAUUGUCAACGAUCCCCGCACUCGGGUCGAAGCGGAGGCCGCAGUGCGGGCUGGAACUGCCGUGGACUUCAUUUGGACUGGCAAUCCCAGGACCGCUCCCCGGUCACUGUCCCUGGGAGGACACACCGUCCGCGCCCUGUCACCAACUCCCCCGUGGCCUGGAACCGAUGACGAGGACGACGACCUGGCCGAUGUGGACUACGUGCCCCCUGCCCCAAGACGGGCUCCACGGAGAGGAGGCGGAGGCGCCGGUGCCACCAGGGGCACCAGCCAACCCGCUGCCACCCGGCCUGCUCCUCCUGGGGCCCCGAGAUCCUCCUCAUCCGGCGGGGCACCUCUGAGAGCAGGAGUGGGCUCAGGCUCCGGAGGAGGACCCGCCGUGGCAGCUGUGGUCCCGCGAGUGGCCUCCUUGCCUCCGGCCGCAGGAGGCGGCCGGGCCCAGGCCAGAAGGGUGGGGGAGGACGCGGCAGCCGCCGAAGGGCGCACUCCUCCAGCGCGCCAACCAAGAGCAGCGCAAGAGCCUCCGAUCGUGAUCUCCGAUAGCCCCCCACCGUCACCUCGCAGACCAGCCGGACCCGGGCCUCUGUCGUUCGUGAGCUCCAGCUCGGCCCAGGUGUCGAGCGGACCUGGCGGUGGUGGACUCCCUCAGAGCAGCGGCAGAGCUGCCAGACCUCGCGCCGCCGUGGCCCCGAGGGUCAGGUCGCCGCCGAGAGCAGCUGCCGCCCCAGUGGUGUCCGCCUCAGCCGACGCCGCCGGUCCCGCGCCUCCUGCUGUGCCAGUGGACGCCCAUAGAGCGCCGCGGAGCAGAAUGACUCAGGCACAGACUGACACCCAGGCCCAGUCGCUCGGUAGGGCUGGAGCCACCGACGCCAGAGGAUCGGGCGGACCCGGAGCCGAAGGAGGGUCCGGUCCCGCCGCUUCCUCCUCCGCGUCCUCAUCAGCCGCUCCGCGCUCACCGCUCGCACCCCAGGGUGUCGGAGCAAAGCGAGCAGCUCCUCGCCGGGCCCCUGACUCCGACUCAGGAGAUCGGGGCCACGGACCACUCGCGCCUGCCAGCGCUGGAGCGGCUCCUCCAUCGGCUUCCCCAUCCUCGCAAGCAGCCGUGGCCGCCGCAUCCUCAAGCUCGGCGUCCUCUAGCUCAGCGAGCUCCUCCAGCGCCUCGUCCUCGUCCGCCUCCAGCAGCUCAGCCUCCUCGUCCUCGGCCUCCUCAUCGUCCGCCUCCUCCUCCGCUGGAGGUGCCGGAGGAUCGGUCGCAUCCGCUUCCGGCGCAGGGGAGCGCCGAGAAACGUCCCUGGGUCCGCGGGCAGCUGCUCCGAGGGGUCCUCGCAAGUGCGCGCGGAAAACUCGGCACGCGGAGGGAGGACCGGAACCUGGCGCGAGAGAUCCUGCGCCUGGACUGACCCGGUACCUCCCCAUUGCCGGGGUGUCCAGCGUGGUGGCACUUGCCCCGUACGUCAACAAGACCGUGACCGGGGACUGUCUCCCCGUGCUCGACAUGGAGACUGGACACAUUGGCGCGUAUGUGGUCCUGGUGGAUCAGACCGGUAAUGUGGCCGACCUUUUGAGAGCAGCGGCCCCAGCAUGGUCCCGCAGAACCCUGCUGCCUGAGCACGCCAGGAAUUGCGUGCGGCCGCCGGACUACCCGACUCCGCCCGCCAGCGAAUGGAACUCACUGUGGAUGACUCCCGUGGGCAACAUGCUGUUCGAUCAGGGGACCCUGGUCGGAGCCCUGGAUUUUCACGGCCUGCGCUCCAGACAUCCGUGGUCUAGGGAACAGGGUGCUCCUGCUCCCGCGGGUGAUGCCCCUGCUGGCCACGGCGAAUAGUGAUAAUAGGCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC (SEQ ID NO: 123) |
| MRK_HSV-2 ICP-4, SQ-032440, CX-002146 | UCAAGCUUUUGGACCCUCGUACAGAAGCUAAUACGACUCACUAUAGGGAAAUAAGAGAGAAAAGAAGAGUAAGAAGAAAUAUAAGAGCCACCAUGUCGGCCGAGCAGCGCAAGAAGAAGAAAACGACCACCACUACCCAGGGCAGAGGAGCCGAAGUCGCCAUGGCCGAUGAAGAUGGCGGGAGGCUGCGGGCCGCCGCUGAAACCACCGGAGGACCGGGAUCCCCUGACCCUGCGGACGGCCCACCUCCCACACCGAACCCGGACAGACGGCCUGCUGCAAGGCCCGGUUUCGGAUGGCACGGGGGACCCGAAGAGAACGAGGACGAAGCCGAUGACGCCGCGGCGGAUGCAGACGCCGACGAGGCGGCUCCCGCUUCGGGAGAAGCGGUGGACGAACCGGCCGCCGAUGGAGUGGUCAGCCCCCGCCAGCUCGCGCUGCUCGCGUCCAUGGUGGAUGAAGCCGUGAGAACUAUCCCCUCACCUCCGCCGGAACGGGAUGGAGCUCAAGAGGAAGCCGCCAGAAGCCCGUCCCCUCCGAGAACUCCAUCCAUGCGGGCCGACUACGGCGAAGAGAAUGACGACGAUGAUGACGACGAUGAUGACGAUGACCGCGAUGCCGGACGGUGGGUCCGCGGACCUGAGACUACCUCCGCCGUGCGCGGAGCCUACCCUGAUCCGAUGGCCUCACUUAGCCCCCGGCCACCCGCCCCCCGCCGCCACCACCACCAUCAUCACCACCGCAGAAGAAGGGCUCCCAGGCGCAGAUCAGCAGCUUCCGACAGCUCGAAGUCCGGCUCCUCGUCCUCCGCCAGCAGCGCAUCCUCGUCAGCGUCCUCAUCGUCCAGCGCCUCGGCGAGCUCCUCCGACGAUGACGACGACGACGAUGCCGCCAGAGCUCCGGCAUCAGCCGCGGACCAUGCCGCCGGAGGAACCC |

TABLE 1-continued

| |
|---|
| UCGGUGCCGACGACGAGGAGGCCGGCGUGCCUGCCCGCGCUCCGGGAGCUGCUCC<br>UAGGCCUUCACCACCCCGGGCGGAGCCAGCCCCUGCCAGAACGCCAGCAGCCACCG<br>CUGGGCGAUUGGAGAGGCGGAGAGCCCGGGCCGCCGUGGCCGGUCGGGAUGCCAC<br>CGGCCGCUUCACUGCCGGACGCCCUCGGCGCGUCGAACUGGACGCAGACGCCGCC<br>UCGGGCGCGUUCUACGCCCGCUAUCGGGACGGUUAUGUGUCCGGCGAGCCUUGGC<br>CUGGUGCCGGUCCUCCUCCGCCUGGGAGAGUGCUCUACGGGGGUCUGGGUGAUUC<br>UCGGCCAGGGUUGUGGGGAGCCCCCGAGGCGGAGGAAGCCAGAGCCCGCUUCGAA<br>GCAUCCGGAGCACCGGCCCCUGUGUGGGCGCCGGAACUGGGCGACGCCGCCCAAC<br>AAUACGCCCUGAUCACACGCCUGCUCUACACUCCGGACGCCGAAGCCAUGGGCUG<br>GCUGCAGAACCCGAGAGUGGCCCCGGGUGAUGUGGCCCUGGACCAGGCAUGCUUC<br>AGGAUUAGCGGAGCCGCGAGAAACUCGAGCAGCUUUAUCUCAGGAUCUGUGGCCC<br>GAGCCGUGCCGCACCUGGGCUACGCGAUGGCCGCCGGACGCUUCGGAUGGGGGCU<br>GGCCCAUGUCGCUGCCGCGGUGGCGAUGUCCCGGCGGUACGACCGGGCUCAGAAG<br>GGUUUCCUCCUCACCAGCCUCCGGAGGGCAUACGCCCCGUUGCUGGCUCGGGAGA<br>ACGCCGCUCUGACUGGCGCCCGCACUCCUGAUGACGGUGGCGACGCCAACCGCCA<br>CGACGGCGACGAUGCACGGGGAAAGCCCGCGGCCGCCGCCGCCCCCCUUCCUAGC<br>GCAGCCGCUUCGCCUGCCGACGAACGGGCUGUCCCUGCCGGAUACGGAGCCGCCG<br>GUGUGCUGGCGGCCCUUGGGAGACUGUCAGCCGCGCCUGCUUCAGCGCCGGCCGG<br>AGCCGACGAUGACGACGACGACGAUGGAGCCGGAGGAGGGGGCGGCGGUCGGAGA<br>GCAGAAGCCGGCAGGGUGGCAGUCGAAUGCCUUGCUGCCUGUCGCGGGAUCCUCG<br>AGGCGUUGGCCGAAGGCUUCGACGGCGACCUGGCGGCAGUGCCUGGCCUGGCCGG<br>CGCCCGCCCCGCUGCCCCUCCACGGCCCGGUCCGGCCGGGGCCGCAGCCCCUCCGC<br>AUGCUGACGCGCCUCGCCUCAGAGCAUGGCUGAGAGAAUUGAGAUUUGUGCGGGA<br>UGCGCUGGUCCUUAUGCGCCUGAGGGGGGAUCUGAGGGUGGCCGGAGGUUCCGAG<br>GCGGCCGUGGCUGCUGUGCGGGCCGUGUCCCUGGUGGCCGGUGCGCUGGGUCCCG<br>CUCUGCCGCGGUCCCCUAGAUUGCUUUCCUCAGCGGCCGCCGCCGCAGCCGAUCU<br>GCUCUUUCAGAACCAAAGCCUCAGGCCGCUGCUGGCCGACACUGUCGCCGCUGCG<br>GACUCCCUCGCUGCCCCAGCCUCGGCCCCAAGAGAGGCUGCCGAUGCCCCUCGCCC<br>CGCCGCGGCCCCGCCUGCCGGAGCAGCGCCGCCUGCACCCCCUACUCCCCCCCCGC<br>GACCGCCACGCCCAGCCGCUCUUACCAGAAGGCCAGCUGAGGGUCCUGACCCGCA<br>GGGCGGCUGGCGCAGACAGCCCCCGGGACCUUCCCACACUCCCGCCCCAUCUGCGG<br>CUGCCCUUGAAGCAUACUGUGCCCCGAGAGCUGUGGCGGAGCUGACCGACCACCC<br>UCUGUUCCCUGCACCUUGGCGGCCUGCCCUGAUGUUUGACCCGAGAGCGUUGGCC<br>UCCCUGGCGGCCAGAUGUGCGGCCCCGCCUCCCGGAGGAGCCCCAGCUGCAUUCG<br>GACCUCUGCGGGCAUCCGGACCACUGCGGCGCGCUGCUGCAUGGAUGCGGCAAGU<br>GCCGGACCCUGAGGACGUUCGCGUGGUCAUUCUUUACUCCCCCCUGCCGGGAGAA<br>GAUCUCGCCGCCGGCCGCGCGGGAGGAGGCCCUCCACCCGAGUGGUCCGCUGAAC<br>GGGGAGGCCUGUCCUGCCUGCUGGCUGCCCUGGGAAACCGCCUGUGCGGACCAGC<br>UACUGCCGCCUGGGCUGGAAACUGGACCGGCGCACCCGAUGUGUCAGCCCUCGGA<br>GCGCAGGGAGUGCUGCUGCUGUCAACUCGCGACCUGGCAUUCGCCGGAGCUGUGG<br>AGUUCCUGGGUCUGCUUGCCGGCGCGUGCGACCGGAGAUUGAUCGUCGUGAACGC<br>UGUCAGAGCGGCCGCUUGGCCUGCCGCUGCUCCGGUGGUCAGCCGGCAGCACGCA<br>UAUCUGGCCUGCGAGGUGCUGCCCGCCGUGCAGUGUGCCGUGCGGUGGCCAGCGG<br>CCAGAGACUUGCGACGGACCGUGCUGGCCUCCGGUAGGGUCUUUGGCCCCGGAGU<br>GUUCGCCCGCGUGGAGGCCGCCCAUGCCAGACUGUACCCCGACGCACCGCCCCUG<br>AGACUGUGCCGGGGAGCCAACGUGCGGUACAGAGUCCGCACCCGCUUCGGACCCG<br>AUACUCUGGUGCCAAUGUCACCGCGGGAAUAUAGGAGAGCCGUGCUCCCGGCACU<br>GGACGGCAGAGCCGCCGCAUCCGGUGCUGGGGACGCGAUGGCACCCGGAGCCCCC<br>GACUUUUGCGAGGAUGAAGCCCACAGCCAUCGGGCCUGUGCCAGAUGGGGCCUGG<br>GUGCCCCUCUUCGCCCCGUGUACGUGGCCCUGGGGAGAGAUGCCGUCCGCGGUGG<br>ACCAGCCGAGCUGAGAGGCCCACGCCGGGAAUUUUGCGCUCGGGCCCUGCUCGAG<br>CCCGAUGGAGAUGCGCCUCCCCUUGUGCUGCGCGACGACGCUGACGCCGGCCCAC<br>CUCCGCAAAUCCGGUGGGCCAGCGCCGCCGGUCGAGCAGGAACGGUGUUGGCAGC<br>AGCCGGAGGAGGAGUCGAAGUGGUCGGAACCGCGGCUGGACUGGCAACCCCGCCA<br>AGGCGCGAACCUGUGGAUAUGGACGCCGAGCUGGAGGAUGACGACGAUGGCCUUU<br>UCGGCGAGUGAUGAUAAUAGGCUGGAGCCUCGGUGGCCAUGCUUCUUGCCCCUUG<br>GGCCUCCCCCCAGCCCCUCCUCCCCUUCCUGCACCCGUACCCCCGUGGUCUUUGAA<br>UAAAGUCUGAGUGGGCGGC (SEQ ID NO: 124) |

The first underlined sequence is representative of the 5' UTR, which may be included in or omitted from any of the constructs listed in Table 1, or it may be modified or substituted with another 5' UTR comprising a different sequence.

The second underlined sequence is representative of the 3' UTR, which may be included in or omitted from any of the constructs listed in Table 1, or it may be modified or substituted with another 3' UTR comprising a different sequence.

TABLE 2

HSV Amino Acid Sequences

| Strain | Amino Acid Sequence |
|---|---|
| gi\|138220\|sp\|1306475.1\|GC_<br>HHV23 RecName:<br>Full = Envelope<br>glycoprotein C; Flags:<br>Precursor | MALGRVGLAVGLWGLLWVGVVVVLANASPGRTITVGPRGNASNAAPSASP<br>RNASAPRTTPTPPQPRKATKSKASTAKPAPPPKTGPPKTSSEPVRCNRHDPLA<br>RYGSRVQIRCRFPNSTRTESRLQIWRYATATDAEIGTAPSLEEVMVNVSAPPG<br>GQLVYDSAPNRTDPHVIWAEGAGPGASPRLYSVVGPLGRQRLIIEELTLETQG<br>MYYWVWGRTDRPSAYGTWVRVRVFRPPSLTIHPHAVLEGQPFKATCTAATY<br>YPGNRAEFVWFEDGRRVFDPAQIHTQTQENPDGFSTVSTVTSAAVGGQGPPR |

TABLE 2-continued

| HSV Amino Acid Sequences | |
|---|---|
| Strain | Amino Acid Sequence |
| | TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEGAGIGVAVLVAVVLAGTAVVYLT HASSVRYRRLR (SEQ ID NO: 24) |
| gi\|2842677\|sp\|Q89730.1\|GC_ HHV2H RecName: Full = Envelope glycoprotein C; Flags: Precursor | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTEFRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEGAGIGVAVLVAVVLAGTAVVYLT HASSVRYRRLR (SEQ ID NO: 25) |
| gi\|138219\|sp\|1303173.1\|GC_ HHV2G RecName: Full = Envelope glycoprotein C; AltName: Full = Glycoprotein F; Flags: Precursor | MALGRVGLTVGLWGLLWVGVVVVLANASPGRTITVGPRGNASNAAPSVPR NRSAPRTTPTPPQPRKATKSKASTAKPAPPPKTGPPKTSSEPVRCNRHDPLAR YGSRVQIRCRFPNSTRTESRLQIWRYATATDAEIGTAPSLEEVMVNVSAPPGG QLVYDSAPNRTDPHVIWAEGAGPGASPRLYSVVGPLGRQRLIIEELTLETQGM YYWVWGRTDRPSAYGTWVRVRVFRPPSLTIHPHAVLEGQPFKATCTAATYY PGNRAEFVWFEDGRRVFDPAQIHTQTQENPDGFSTVSTVTSAAVGGQGPPRT FTCQLTWHRDSVSFSRRNASGTASVLPRPTITMEFTGDHAVCTAGCVPEGVT FAWFLGDDSSPAEKVAVASQTSCGRPGTATIRSTLPVSYEQTEYICRLAGYPD GIPVLEHHGSHQPPPRDPTERQVIRAVEGAGIGVAVLVAVVLAGTAVVYLTH ASSVRYRRLR (SEQ ID NO: 26) |
| gi\|156072158\|gb\|ABU45430.1\| glycoprotein C [Human herpesvirus 2] | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTESRLQIWRYATATDAEIGTAPSLEEVMVNVSAPPG GQLVYDSPPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEGAGIGVAVLVAVVLAGTAVVYLT HASSVRYRRLR (SEQ ID NO: 27) |
| gi\|156072221\|gb\|ABU45459.1\| glycoprotein C [Human herpesvirus 2] | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTESRLQIWRYATATDAEIGTAPSLEEVMVNVSAPPG GQLVYDSAPNRTDPHVIWAEGAGPGASPRLYSVVGPLGRQRPIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEGAGIGVAVLVAVVLAGTAVVYLT HASSVRYRRLR (SEQ ID NO: 28) |
| gi\|807203116\|gb\|AKC59499.1\| envelope glycoprotein C [Human herpesvirus 2] | MALGRVGLAVGLWGLLWVGVVVVLANASPGRTITVGPRGNASNAAPSASP RNASAPRTTPTPPQPRKATKSKASPAKPAPPPKTGPPKTSSEPVRCNRHDPLA RYGSRVQIRCRFPNSTRTEFRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEGAGIGVAVLVAVVLAGTAVVYLT HASSVRYRRLR (SEQ ID NO: 29) |
| gi\|522172\|gb\|AAB60549.1\| glycoprotein C [Human herpesvirus 2] | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTEFRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP HGIPVLEHHGSHQPPPRDPTERQVIRAVEGAGIGVAVLVAVVLAGTAVVYLT HASSVRYRRLR (SEQ ID NO: 30) |
| gi\|392937653\|gb\|AFM93864.1\| virion glycoprotein C [Human herpesvirus 2 strain 186] | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTEFRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY |

TABLE 2-continued

HSV Amino Acid Sequences

| Strain | Amino Acid Sequence |
|---|---|
| | YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTKRQVIRAVEGAGIGVAVLVAVVLAGTAVVYLT HASSVRYRRLR (SEQ ID NO: 31) |
| gi\|330271\|gb\|AAA45842.1\| glycoprotein-D [Human herpesvirus 2] | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFTPENQRTVALYSLKI AGWHGPKPPYTSTLLPPELSDTTNATQPELVPEDPEDSALLEDPAGTVSSQIPP NWHIPSIQDVAPHHAPAAPANPGLIIGALAGSTLAALVIGGIAFWVRRRRSVA PKRLRLPHIRDDDAPPSHQPLFY (SEQ ID NO: 32) |
| gi\|56698864\|gb\|AAW23130.1\| glycoprotein-D [Human herpesvirus 2] | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNPGLIIGALAGSTLAALVIGGIAFWVRRRAQMAP KRPRLPHIRDDDAPPSHQPLFY (SEQ ID NO: 33) |
| gi\|405168231\|gb\|AFS18221.1\| virion glycoprotein D [Human herpesvirus 2] | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDTLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNPGLIIGALAGSTLAVLVIGGIAFWVRRRAQMAP KRLRLPHIRDDDAPPSHQPLFY (SEQ ID NO: 34) |
| gi\|674748224\|gb\|AIL27730.1\| glycoprotein D [Human herpesvirus 2] | MGRLTSGVGTAALLVVAVGLRVVYAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYMRLVKINDWTEITQFILEHR ARASCKYALPLRIPPAACLTSKAYQQGVTVDSIGMLPRFIPENQRTVALYSLKI AGWHGPKPPYTSTLLPPELSDTTNATQPELVPEDPEDSALLEDPAGTVSSQIPP NWHIPSIQDVAPHHAPAAPSNPGLIIGALAGSTLAALVIGGIAFWVRRRAQMA PKRLRLPHIRDDDAPPSHQPLFY (SEQ ID NO: 35) |
| gi\|674748211\|gb\|AIL27728.1\| glycoprotein D [Human herpesvirus 2] | MGRLTSGVGTAALLVVAVGLRVVYAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNPGLIIGALAGSTLAALVIGGIAFWVRRRAQMAP KRLRLPHIRDDDAPPSHQPLFY (SEQ ID NO: 36) |
| gi\|154744645\|gb\|ABS84899.1\| glycoprotein D [Human herpesvirus 2] | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAASEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNPGLIIGALAGSTLAVLVIGGIAFWVRRRAQMAP KRLRLPHIRDDDAPPSHQPLFY (SEQ ID NO: 37) |
| gi\|156072225\|gb\|ABU45461.1\| glycoprotein D [Human herpesvirus 2] | MGRLTSGVGTAALLVVAVGLRVVCAKYALADPSLKMADPNRFRGKNLPVL DRLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNPGLIIGALAGSTLAVLVIGGIAFWVRRRAQMAP KRLRLPHIRDDDAPPSHQPLFY (SEQ ID NO: 38) |
| gi\|82013827\|sp\|Q69467.1\| GD_HHV2H\| glycoprotein D | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA |

TABLE 2-continued

HSV Amino Acid Sequences

| Strain | Amino Acid Sequence |
|---|---|
| | GWHGPKPPYTSTLLPPELSDTTNATQPELVPEDPEDSALLEDPAGTVSSQIPPN<br>WHIPSIQDVAPHHAPAAPSNPGLIIGALAGSTLAVLVIGGIAFWVRRRAQMAP<br>KRLRLPHIRDDDAPPSHQPLFY (SEQ ID NO: 39) |
| gi\|522178\|gb\|AAB60554.1<br>glycoprotein D [Human<br>herpesvirus 2]\| | MGRLTSGVGTAALLVVAVGLRVVCAKYALADPSLKMADPNRFRGKNLPVL<br>DQLTDPPGVKRVYHIQPSLEDPFQPPSIPITVYYAVLERACRSVLLHAPSEAPQI<br>VRGASDEARKHTYNLTIAWYRMGDNCAIPITVMEYTECPYNKSLGVCPIRTQ<br>PRWSYYDSFSAVSEDNLGFLMHAPAFETAGTYLRLVKINDWTEITQFILEHRA<br>RASCKYALPLRIPPAACLTSKAYQQGVTVDSIGMLPRFIPENQRTVALYSLKIA<br>GWHGPKPPYTSTLLPPELSDTTNATQPELVPEDPEDSALLEDPAGTVSSQIPPN<br>WHIPSIQDVAPHHAPAAPSNPGLIIGALAGSTLAALVIGGIAFWVRRRAQMAP<br>KRLRLPHIRDDDAPPSHQPLFY (SEQ ID NO: 40) |
| gi\|674748163\|gb\|AIL27723.1\|<br>glycoprotein D [Human<br>herpesvirus 2] | MGRLTSGVGTAALLVVAVGLRVVCAKYALADPSLKMADPNRFRGKNLPVL<br>DQLTDPPGVKRVYHIQPSLEDPFQPPSIPITVYYAVLERACRSVLLHAPSEAPQI<br>VRGASDEARKHTYNLTIAWYRMGDNCAIPITVMEYTECPYNKSLGVCPIRTQ<br>PRWSYYDSFSAVSEDNLGFLMHAPAFETAGTYLRLVKINDWTEITQFILEHRA<br>RASCKYALPLRIPPAACLTSKAYQQGVTVDSIGMLPRFIPENQRTVALYSLKIA<br>GWHGPKPPYTSTLLPPELSDTTNATQPELVPEDPEDSALLEDPAGTVSSQIPPN<br>WHIPSIQDVAPHHAPAAPSNPGLIIGALAGSTLAALVIGGIAFWVRRRAQMAP<br>KRLRLPHIRDDDAPPSHQPLFY (SEQ ID NO: 41) |
| HSV-2 gB; accession<br>number HM011304 (isolate<br>00-10045) | MRGGGLVCALVVGALVAAVASAAPAAPRASGGVAATVAANGGPASQPPPV<br>PSPATTKARKRKTKKPPKRPEATPPPDANATVAAGHATLRAHLREIKVENAD<br>AQFYVCPPPTGATVVQFEQPRRCPTRPEGQNYTEGIAVVFKENIAPYKFKATM<br>YYKDVTVSQVWFGHRYSQFMGIFEDRAPVPFEEVIDKINAKGVCRSTAKYVR<br>NNMETTAFHRDDHETDMELKPAKVATRTSRGWHTTDLKYNPSRVEAFHRY<br>GTTVNCIVEEVDARSVYPYDEFVLATGDFVYMSPFYGYREGSHTEHTSYAAD<br>RFKQVDGFYARDLTTKARATSPTTRNLLTTPKFTVAWDWVPKRPAVCTMTK<br>WQEVDEMLRAEYGGSFRFSSDAISTTFTTNLTQYSLSRVDLGDCIGRDAREAI<br>DRMFARKYNATHIKVGQPQYYLATGGFLIAYQPLLSNTLAELYVREYMREQ<br>DRKPRNATPAPLREAPSANASVERIKTTSSIEFARLQFTYNHIQRHVNDMLGRI<br>AVAWCELQNHELTLWNEARKLNPNAIASATVGRRVSARMLGDVMAVSTCV<br>PVAPDNVIVQNSMRVSSRPGTCYSRPLVSFRYEDQGPLIEGQLGENNELRLTR<br>DALEPCTVGHRRYFIFGGGYVYFEEYAYSHQLSRADVTTVSTFIDLNITMLED<br>HEFVPLEVYTRHEIKDSGLLDYTEVQRRNQLHDLRFADIDTVIRADANAAMF<br>AGLCAFFEGMGDLGRAVGKVVMGVVGGVVSAVSGVSSFMSNPFGALAVGL<br>LVLAGLVAAFFAFRYVLQLQRNPMKALYPLTTKELKTSDPGGVGGEGEEGA<br>EGGGFDEAKLAEAREMIRYMALVSAMERTEHKARKKGTSALLSSKVTNMVL<br>RKRNKARYSPLHNEDEAGDEDEL (SEQ ID NO: 42) |
| HSV-2 gC; accession<br>number KP192856 (strain<br>333) | MALGRVGLAVGLWGLLWVGVVVVLANASPGRTITVGPRGNASNAAPSASP<br>RNASAPRTTPTPPQPRKATKSKASTAKPAPPPKTGPPKTSSEPVRCNRHDPLA<br>RYGSRVQIRCRFPNSTRTESRLQIWRYATATDAEIGTAPSLEEVMVNVSAPPG<br>GQLVYDSAPNRTDPHVIWAEGAGPGASPRLYSVVGPLGRQRLIIEELTLETQG<br>MYYWVWGRTDRPSAYGTWVRVRVFRPPSLTIHPHAVLEGQPFKATCTAATY<br>YPGNRAEFVWFEDGRRVFDPAQIHTQTQENPDGFSTVSTVTSAAVGGQGPPR<br>TFTCQLTWHRDSVSFSRRNASGTASVLPRPTITMEFTGDHAVCTAGCVPEGV<br>TFAWFLGDDSSPAEKVAVASQTSCGRPGTATIRSTLPVSYEQTEYICRLAGYP<br>DGIPVLEHHGSHQPPPRDPTERQVIRAVEGAGIGVAVLVAVVLAGTAVVYLT<br>HASSVRYRRLR (SEQ ID NO: 43) |
| HSV-2 gD; accession<br>number JN561323 (strain<br>HG52) | MGRLTSGVGTAALLVVAVGLRVVCAKYALADPSLKMADPNRFRGKNLPVL<br>DQLTDPPGVKRVYHIQPSLEDPFQPPSIPITVYYAVLERACRSVLLHAPSEAPQI<br>VRGASDEARKHTYNLTIAWYRMGDNCAIPITVMEYTECPYNKSLGVCPIRTQ<br>PRWSYYDSFSAVSEDNLGFLMHAPAFETAGTYLRLVKINDWTEITQFILEHRA<br>RASCKYALPLRIPPAACLTSKAYQQGVTVDSIGMLPRFIPENQRTVALYSLKIA<br>GWHGPKPPYTSTLLPPELSDTTNATQPELVPEDPEDSALLEDPAGTVSSQIPPN<br>WHIPSIQDVAPHHAPAAPSNPGLIIGALAGSTLAVLVIGGIAFWVRRRAQMAP<br>KRLRLPHIRDDDAPPSHQPLFY<br>(SEQ ID NO: 44) |
| HSV-2 gE; accession<br>number EU018094 (strain<br>333) | MARGAGLVFFVGVWVVSCLAAAPRTSWKRVTSGEDVVLLPAPAGPEERTRA<br>HKLLWAAEPLDACGPLRPSWVALWPPRRVLETVVDAACMRAPEPLAIAYSP<br>PFPAGDEGLYSELAWRDRVAVVNESLVIYGALETDSGLYTLSVVGLSDEARQ<br>VASVVLVVEPAPVPTPTPDDYDEEDDAGVSERTPVSVPPPTPPRRPPVAPPTH<br>PRVIPEVSHVRGVTVHMETPEAILFAPGETFGTNVSIHAIAHDDGPYAMDVV<br>WMRFDVPSSCAEMRIYEACLYHPQLPECLSPADAPCAVSSWAYRLAVRSYA<br>GCSRTTPPPRCFAEARMEPVPGLAWLASTVNLEFQHASPQHAGLYLCVVYVD<br>DHIHAWGHMTISTAAQYRNAVVEQHLPQRQPEPVEPTRPHVRAPPPAPSARG<br>PLRLGAVLGAALLLAALGLSAWACMTCWRRRSWRAVKSRASATGPTYIRVA<br>DSELYADWSSDSEGERDGSLWQDPPERPDSPSTNGSGFEILSPTAPSVYPHSE<br>GRKSRRPLTTFGSGSPGRRHSQASYSSVLW* (SEQ ID NO: 45) |

TABLE 2-continued

| HSV Amino Acid Sequences | |
|---|---|
| Strain | Amino Acid Sequence |
| HSV-2 gI; accession number KP192856 (strain 333) | MPGRSLQGLAILGLWVCATGLVVRGPTVSLVSDSLVDAGAVGPQGFVEEDL RVFGELHFVGAQVPHTNYYDGIIELFHYPLGNHCPRVVHVVTLTACPRRPAV AFTLCRSTHHAHSPAYPTLELGLARQPLLRVRTATRDYAGLYVLRVWVGSAT NASLFVLGVALSANGTFVYNGSDYGSCDPAQLPFSAPRLGPSSVYTPGASRPT PPRTTTSPSSPRDPTPAPGDTGTPAPASGERAPPNSTRSASESRHRLTVAQVIQI AIPASIIAFVFLGSCICFIHRCQRRYRRPRGQIYNPGGVSCAVNEAAMARLGAE LRSHPNTPPKPRRRSSSSTTMPSLTSIAEESEPGPVVLLSVSPRPRSGPTAPQEV (SEQ ID NO: 46) |
| HSV-2 ICP-0; Based on strain HG52(inactivated by deletion of the nuclear localization signal and zinc-binding ring finger) | MEPRPGTSSRADPGPERPPRQTPGTQPAAPHAWGMLNDMQWLASSDSEEET EVGISDDDLHRDSTSEAGSTDTEMFEAGLMDAATPPARPPAERQGSPTPADA QGSCGGGPVGEEEAEAGGGGDVNTPVAYLIVGVTASGSFSTIPIVNDPRTRVE AEAAVRAGTAVDFIWTGNPRTAPRSLSLGGHTVRALSPTPPWPGTDDEDDDL ADVDYVPPAPRRAPRRGGGAGATRGTSQPAATRPAPPGAPRSSSSGGAPLR AGVGSGSGGGPAVAAVVPRVASLPPAAGGGRAQARRVGEDAAAAEGRTPP ARQPRAAQEPPIVISDSPPPSPRRPAGPGPLSFVSSSSAQVSSGPGGGGLPQSSG RAARPRAAVAPRVRSPPRAAAAPVVSASADAAGPAPPAVPVDAHRAPRSRM TQAQTDTQAQSLGRAGATDARGSGGPGAEGGSGPAASSSASSSAAPRSPLAP QGVGAKRAAPRRAPDSDSGDRGHGPLAPASAGAAPPSASPSSQAAVAAASSS SASSSSASSSSASSSSASSSSASSSSASSSSASSSAGGAGGSVASASGAGERRET SLGPRAAAPRGPRKCARKTRHAEGGPEPGARDPAPGLTRYLPIAGVSSVVAL APYVNKTVTGDCLPVLDMETGHIGAYVVLVDQTGNVADLLRAAAPAWSRR TLLPEHARNCVRPPDYPTPPASEWNSLWMTPVGNMLFDQGTLVGALDFHGL RSRHPWSREQGAPAPAGDAPAGHGE (SEQ ID NO: 47) |
| HSV-2 SgB; (based on accession number HM011304; isolate 00-10045; truncated to remove transmembrane region) | MRGGGLVCALVVGALVAAVASAAPAAPRASGGVAATVAANGGPASQPPPV PSPATTKARKRKTKKPPKRPEATPPPDANATVAAGHATLRAHLREIKVENAD AQFYVCPPPTGATVVQFEQPRRCPTRPEGQNYTEGIAVVFKENIAPYKFKATM YYKDVTVSQVWFGHRYSQFMGIFEDRAPVPFEEVIDKINAKGVCRSTAKYVR NNMETTAFHRDDHETDMELKPAKVATRTSRGWHTTDLKYNPSRVEAFHRY GTTVNCIVEEVDARSVYPYDEFVLATGDFVYMSPFYGYREGSHTEHTSYAAD RFKQVDGFYARDLTTKARATSPTTRNLLTTPKFTVAWDWVPKRPAVCTMTK WQEVDEMLRAEYGGSFRFSSDAISTTFTTNLTQYSLSRVDLGDCIGRDAREAI DRMFARKYNATHIKVGQPQYYLATGGFLIAYQPLLSNTLAELYVREYMREQ DRKPRNATPAPLREAPSANASVERIKTTSSIEFARLQFTYNHIQRHVNDMLGRI AVAWCELQNHELTLWNEARKLNPNAIASATVGRRVSARMLGDVMAVSTCV PVAPDNVIVQNSMRVSSRPGTCYSRPLVSFRYEDQGPLIEGQLGENNELRLTR DALEPCTVGHRRYFIFGGGYVYFEEYAYSHQLSRADVTTVSTFIDLNITMLED HEFVPLEVYTRHEIKDSGLLDYTEVQRRNQLHDLRFADIDTVIRADANAAMF AGLCAFFEGMGDLGRAVGKVVMGVVGGVVSAVSGVSSFMSNP (SEQ ID NO: 48) |
| HSV-2 SgC; (based on accession number KP192856; strain 333; truncated to remove transmembrane region | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTESRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEG (SEQ ID NO: 49) |
| HSV-2 SgD (based on accession number JN561323; strain HG52; truncated to remove transmembrane region) | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNP (SEQ ID NO: 50) |
| HSV-2 SgE; (based on accession number EU018094; strain 333; truncated to remove transmembrane region) | MARGAGLVFFVGVWVVSCLAAAPRTSWKRVTSGEDVVLLPAPAGPEERTRA HKLLWAAEPLDACGPLRPSWVALWPPRRVLETVVDAACMRAPEPLAIAYSP PFPAGDEGLYSELAWRDRVAVVNESLVIYGALETDSGLYTLSVVGLSDEARQ VASVVLVVEPAPVPTPTPDDYDEEDDAGVSERTPVSVPPPTPPRRPPVAPPTH PRVIPEVSHVRGVTVHMETPEAILFAPGETFGTNVSIHAIAHDDGPYAMDVV WMRFDVPSSCAEMRIYEACLYHPQLPECLSPADAPCAVSSWAYRLAVRSYA GCSRTTPPPRCFAEARMEPVPGLAWLASTVNLEFQHASPQHAGLYLCVVYVD DHIHAWGHMTISTAAQYRNAVVEQHLPQRQPEPVEPTRPHVRAPPPAPSARG PLR (SEQ ID NO: 51) |

TABLE 2-continued

HSV Amino Acid Sequences

| Strain | Amino Acid Sequence |
|---|---|
| HSV-2 SgI; based on accession number KP192856; strain 333; truncated to remove transmembrane region) | MPGRSLQGLAILGLWVCATGLVVRGPTVSLVSDSLVDAGAVGPQGFVEEDL RVFGELHFVGAQVPHTNYYDGIIELFHYPLGNHCPRVVHVVTLTACPRRPAV AFTLCRSTHHAHSPAYPTLELGLARQPLLRVRTATRDYAGLYVLRVWVGSAT NASLFVLGVALSANGTFVYNGSDYGSCDPAQLPFSAPRLGPSSVYTPGASRPT PPRTTTSPSSPRDPTPAPGDTGTPAPASGERAPPNSTRSASESRHRLTVAQVIQ (SEQ ID NO: 52) |
| HSV-2 ICP-4; Based on strain HG52; (inactivated by deletion of nuclear localization signal and alanine substitution for key residues in the transactivation region) | MSAEQRKKKKTTTTTQGRGAEVAMADEDGGRLRAAAETTGGPGSPDPADG PPPTPNPDRRPAARPGFGWHGGPEENEDEADDAAADADADEAAPASGEAVD EPAADGVVSPRQLALLASMVDEAVRTIPSPPPERDGAQEEAARSPSPPRTPSM RADYGEENDDDDDDDDDDDRDAGRWVRGPETTSAVRGAYPDPMASLSPRP PAPRRHHHHHHRRRRAPRRRSAASDSSKSGSSSSASSASSSASSSSSASASSS DDDDDDDAARAPASAADHAAGGTLGADDEEAGVPARAPGAAPRPSPPRAEP APARTPAATAGRLERRRARAAVAGRDATGRFTAGRPRRVELDADAASGAFY ARYRDGYVSGEPWPGAGPPPPGRVLYGGLGDSRPGLWGAPEAEEARARFEA SGAPAPVWAPELGDAAQQYALITRLLYTPDAEAMGWLQNPRVAPGDVALD QACFRISGAARNSSSFISGSVARAVPHLGYAMAAGRFGWGLAHVAAAVAMS RRYDRAQKGFLLTSLRRAYAPLLARENAALTGARTPDDGGDANRHDGDDAR GKPAAAAAPLPSAAASPADERAVPAGYGAAGVLAALGRLSAAPASAPAGAD DDDDDDGAGGGGGGRRAEAGRVAVECLAACRGILEALAEGFDGDLAAVPG LAGARPAAPPRPGPAGAAAPPHADAPRLRAWLRELRFVRDALVLMRLRGDL RVAGGSEAAVAAVRAVSLVAGALGPALPRSPRLLSSAAAAAADLLFQNQSL RPLLADTVAAADSLAAPASAPREAADAPRPAAAPPAGAAPPAPPTPPPRPPRP AALTRRPAEGPDPQGGWRRQPPGPSHTPAPSAAALEAYCAPRAVAELTDHPL FPAPWRPALMFDPRALASLAARCAAPPPGGAPAAFGPLRASGPLRRAAAWM RQVPDPEDVRVVILYSPLPGEDLAAGRAGGGPPPEWSAERGGLSCLLAALGN RLCGPATAAWAGNWTGAPDVSALGAQGVLLLSTRDLAFAGAVEFLGLLAG ACDRRLIVVNAVRAAAWPAAAPVVSRQHAYLACEVLPAVQCAVRWPAARD LRRTVLASGRVFGPGVFARVEAAHARLYPDAPPLRLCRGANVRYRVRTRFGP DTLVPMSPREYRRAVLPALDGRAAASGAGDAMAPGAPDFCEDEAHSHRACA RWGLGAPLRPVYVALGRDAVRGGPAELRGPRREFCARALLEPDGDAPPLVL RDDADAGPPPQIRWASAAGRAGTVLAAAGGGVEVVGTAAGLATPPRREPVD MDAELEDDDDGLFGE* (SEQ ID NO: 53) |
| MRK_HSV-2 gB, SQ-032178 | MRGGGLVCALVVGALVAAVASAAPAAPRASGGVAATVAANGGPASQPPPV PSPATTKARKRKTKKPPKRPEATPPPDANATVAAGHATLRAHLREIKVENAD AQFYVCPPPTGATVVQFEQPRRCPTRPEGQNYTEGIAVVFKENIAPYKFKATM YYKDVTVSQVWFGHRYSQFMGIFEDRAPVPFEEVIDKINAKGVCRSTAKYVR NNMETTAFHRDDHETDMELKPAKVATRTSRGWHTTDLKYNPSRVEAFHRY GTTVNCIVEEVDARSVYPYDEFVLATGDFVYMSPFYGYREGSHTEHTSYAAD RFKQVDGFYARDLTTKARATSPTTRNLLTTPKFTVAWDWVPKRPAVCTMTK WQEVDEMLRAEYGGSFRFSSDAISTTFTTNLTQYSLSRVDLGDCIGRDAREAI DRMFARKYNATHIKVGQPQYYLATGGFLIAYQPLLSNTLAELYVREYMREQ DRKPRNATPAPLREAPSANASVERIKTTSSIEFARLQFTYNHIQRHVNDMLGRI AVAWCELQNHELTLWNEARKLNPNAIASATVGRRVSARMLGDVMAVSTCV PVAPDNVIVQNSMRVSSRPGTCYSRPLVSFRYEDQGPLIEGQLGENNELRLTR DALEPCTVGHRRYFIFGGGYVYFEEYAYSHQLSRADVTTVSTFIDLNITMLED HEFVPLEVYTRHEIKDSGLLDYTEVQRRNQLHDLRFADIDTVIRADANAAMF AGLCAFFEGMGDLGRAVGKVVMGVVGGVVSAVSGVSSFMSNPFGALAVGL LVLAGLVAAFFAFRYVLQLQRNPMKALYPLTTKELKTSDPGGVGGEGEEGA EGGGFDEAKLAEAREMIRYMALVSAMERTEHKARKKGTSALLSSKVTNMVL RKRNKARYSPLHNEDEAGDEDEL (SEQ ID NO: 66) |
| MRK_HSV-2 gC, SQ-032179 | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTESRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEGAGIGVAVLVAVVLAGTAVVYLT HASSVRYRRLR (SEQ ID NO: 67) |
| MRK_HSV-2 gD, SQ-032180 | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNPGLIIGALAGSTLAVLVIGGIAFWVRRRAQMAP KRLRLPHIRDDDAPPSHQPLFY (SEQ ID NO: 68) |

TABLE 2-continued

| HSV Amino Acid Sequences | |
|---|---|
| Strain | Amino Acid Sequence |
| MRK_HSV-2 gE, SQ-032181 | MARGAGLVFFVGVWVVSCLAAAPRTSWKRVTSGEDVVLLPAPAGPEERTRA HKLLWAAEPLDACGPLRPSWVALWPPRRVLETVVDAACMRAPEPLAIAYSP PFPAGDEGLYSELAWRDRVAVVNESLVIYGALETDSGLYTLSVVGLSDEARQ VASVVLVVEPAPVPTPTPDDYDEEDDAGVSERTPVSVPPPTPPRRPPVAPPTH PRVIPEVSHVRGVTVHMETPEAILFAPGETFGTNVSIHAIAHDDGPYAMDVV WMRFDVPSSCAEMRIYEACLYHPQLPECLSPADAPCAVSSWAYRLAVRSYA GCSRTTPPPRCFAEARMEPVPGLAWLASTVNLEFQHASPQHAGLYLCVVYVD DHIHAWGHMTISTAAQYRNAVVEQHLPQRQPEPVEPTRPHVRAPPPAPSARG PLRLGAVLGAALLLAALGLSAWACMTCWRRRSWRAVKSRASATGPTYIRVA DSELYADWSSDSEGERDGSLWQDPPERPDSPSTNGSGFEILSPTAPSVYPHSE GRKSRRPLTTFGSGSPGRRHSQASYSSVLW (SEQ ID NO: 69) |
| MRK_HSV-2 gI, SQ-032182 | MPGRSLQGLAILGLWVCATGLVVRGPTVSLVSDSLVDAGAVGPQGFVEEDL RVFGELHFVGAQVPHTNYYDGIIELFHYPLGNHCPRVVHVVTLTACPRRPAV AFTLCRSTHHAHSPAYPTLELGLARQPLLRVRTATRDYAGLYVLRVWVGSAT NASLFVLGVALSANGTFVYNGSDYGSCDPAQLPFSAPRLGPSSVYTPGASRPT PPRTTTSPSSPRDPTPAPGDTGTPAPASGERAPPNSTRSASESRHRLTVAQVIQI AIPASIIAFVFLGSCICFIHRCQRRYRRPRGQIYNPGGVSCAVNEAAMARLGAE LRSHPNTPPKPRRRSSSSTTMPSLTSIAEESEPGPVVLLSVSPRPRSGPTAPQEV (SEQ ID NO: 70) |
| MRK_HSV-2 SgB, SQ-032210 | MRGGGLVCALVVGALVAAVASAAPAAPRASGGVAATVAANGGPASQPPPV PSPATTKARKRKTKKPPKRPEATPPPDANATVAAGHATLRAHLREIKVENAD AQFYVCPPPTGATVVQFEQPRRCPTRPEGQNYTEGIAVVFKENIAPYKFKATM YYKDVTVSQVWFGHRYSQFMGIFEDRAPVPFEEVIDKINAKGVCRSTAKYVR NNMETTAFHRDDHETDMELKPAKVATRTSRGWHTTDLKYNPSRVEAFHRY GTTVNCIVEEVDARSVYPYDEFVLATGDFVYMSPFYGYREGSHTEHTSYAAD RFKQVDGFYARDLTTKARATSPTTRNLLTTPKFTVAWDWVPKRPAVCTMTK WQEVDEMLRAEYGGSFRFSSDAISTTFTTNLTQYSLSRVDLGDCIGRDAREAI DRMFARKYNATHIKVGQPQYYLATGGFLIAYQPLLSNTLAELYVREYMREQ DRKPRNATPAPLREAPSANASVERIKTTSSIEFARLQFTYNHIQRHVNDMLGRI AVAWCELQNHELTLWNEARKLNPNAIASATVGRRVSARMLGDVMAVSTCV PVAPDNVIVQNSMRVSSRPGTCYSRPLVSFRYEDQGPLIEGQLGENNELRLTR DALEPCTVGHRRYFIFGGGYVYFEEYAYSHQLSRADVTTVSTFIDLNITMLED HEFVPLEVYTRHEIKDSGLLDYTEVQRRNQLHDLRFADIDTVIRADANAAMF AGLCAFFEGMGDLGRAVGKVVMGVVGGVVSAVSGVSSFMSNP (SEQ ID NO: 71) |
| MRK_HSV-2 SgC, SQ-032835 | MALGRVGLAVGLWGLLWVGVVVVLANASPGRTITVGPRGNASNAAPSASP RNASAPRTTPTPPQPRKATKSKASTAKPAPPPKTGPPKTSSEPVRCNRHDPLA RYGSRVQIRCRFPNSTRTESRLQIWRYATATDAEIGTAPSLEEVMVNVSAPPG GQLVYDSAPNRTDPHVIWAEGAGPGASPRLYSVVGPLGRQRLIIEELTLETQG MYYWVWGRTDRPSAYGTWVRVRVFRPPSLTIHPHAVLEGQPFKATCTAATY YPGNRAEFVWFEDGRRVFDPAQIHTQTQENPDGFSTVSTVTSAAVGGQGPPR TFTCQLTWHRDSVSFSRRNASGTASVLPRPTITMEFTGDHAVCTAGCVPEGV TFAWFLGDDSSPAEKVAVASQTSCGRPGTATIRSTLPVSYEQTEYICRLAGYP DGIPVLEHHGSHQPPPRDPTERQVIRAVEG (SEQ ID NO: 72) |
| MRK_HSV-2 SgE, SQ-032211 | MARGAGLVFFVGVWVVSCLAAAPRTSWKRVTSGEDVVLLPAPAGPEERTRA HKLLWAAEPLDACGPLRPSWVALWPPRRVLETVVDAACMRAPEPLAIAYSP PFPAGDEGLYSELAWRDRVAVVNESLVIYGALETDSGLYTLSVVGLSDEARQ VASVVLVVEPAPVPTPTPDDYDEEDDAGVSERTPVSVPPPTPPRRPPVAPPTH PRVIPEVSHVRGVTVHMETPEAILFAPGETFGTNVSIHAIAHDDGPYAMDVV WMRFDVPSSCAEMRIYEACLYHPQLPECLSPADAPCAVSSWAYRLAVRSYA GCSRTTPPPRCFAEARMEPVPGLAWLASTVNLEFQHASPQHAGLYLCVVYVD DHIHAWGHMTISTAAQYRNAVVEQHLPQRQPEPVEPTRPHVRAPPPAPSARG PLR (SEQ ID NO: 73) |
| MRK_HSV-2 SgI, SQ-032323 | MPGRSLQGLAILGLWVCATGLVVRGPTVSLVSDSLVDAGAVGPQGFVEEDL RVFGELHFVGAQVPHTNYYDGIIELFHYPLGNHCPRVVHVVTLTACPRRPAV AFTLCRSTHHAHSPAYPTLELGLARQPLLRVRTATRDYAGLYVLRVWVGSAT NASLFVLGVALSANGTFVYNGSDYGSCDPAQLPFSAPRLGPSSVYTPGASRPT PPRTTTSPSSPRDPTPAPGDTGTPAPASGERAPPNSTRSASESRHRLTVAQVIQ (SEQ ID NO: 74) |
| MRK_HSV-2 SgD, SQ-032172 | MGRLTSGVGTAALLVVAVGLRVVCAKYALADPSLKMADPNRFRGKNLPVL DQLTDPPGVKRVYHIQPSLEDPFQPPSIPITVYYAVLERACRSVLLHAPSEAPQI VRGASDEARKHTYNLTIAWYRMGDNCAIPITVMEYTECPYNKSLGVCPIRTQ PRWSYYDSFSAVSEDNLGFLMHAPAFETAGTYLRLVKINDWTEITQFILEHRA RASCKYALPLRIPPAACLTSKAYQQGVTVDSIGMLPRFIPENQRTVALYSLKIA GWHGPKPPYTSTLLPPELSDTTNATQPELVPEDPEDSALLEDPAGTVSSQIPPN WHIPSIQDVAPHHAPAAPSNP (SEQ ID NO: 75) |

TABLE 2-continued

| HSV Amino Acid Sequences | |
|---|---|
| Strain | Amino Acid Sequence |
| MRK_HSV-2 ICP-0, SQ-032521 | MEPRPGTSSRADPGPERPPRQTPGTQPAAPHAWGMLNDMQWLASSDSEEET EVGISDDDLHRDSTSEAGSTDTEMFEAGLMDAATPPARPPAERQGSPTPADA QGSCGGGPVGEEEAEAGGGGDVNTPVAYLIVGVTASGSFSTIPIVNDPRTRVE AEAAVRAGTAVDFIWTGNPRTAPRSLSLGGHTVRALSPTPPWPGTDDEDDDL ADVDYVPPAPRRAPRRGGGGAGATRGTSQPAATRPAPPGAPRSSSSGGAPLR AGVGSGSGGGPAVAAVVPRVASLPPAAGGGRAQARRVGEDAAAAEGRTPP ARQPRAAQEPPIVISDSPPPSPRRPAGPGPLSFVSSSSAQVSSGPGGGGLPQSSG RAARPRAAVAPRVRSPPRAAAAPVVSASADAAGPAPPAVPVDAHRAPRSRM TQAQTDTQAQSLGRAGATDARGSGGPGAEGGSGPAASSSASSSAAPRSPLAP QGVGAKRAAPRRAPDSDSGDRGHGPLAPASAGAAPPSASPSSQAAVAAASSS SASSSSASSSSASSSSASSSSASSSSASSSSASSSSAGGAGGSVASASGAGERRET SLGPRAAAPRGPRKCARKTRHAEGGPEPGARDPAPGLTRYLPIAGVSSVVAL APYVNKTVTGDCLPVLDMETGHIGAYVVLVDQTGNVADLLRAAAPAWSRR TLLPEHARNCVRPPDYPTPPASEWNSLWMTPVGNMLFDQGTLVGALDFHGL RSRHPWSREQGAPAPAGDAPAGHGE (SEQ ID NO: 76) |
| MRK_HSV-2 ICP-4, SQ-032440 | MSAEQRKKKKTTTTTQGRGAEVAMADEDGGRLRAAAETTGGPGSPDPADG PPPTPNPDRRPAARPGFGWHGGPEENEDEADDAAADADADEAAPASGEAVD EPAADGVVSPRQLALLASMVDEAVRTIPSPPPERDGAQEEAARSPSPPRTPSM RADYGEENDDDDDDDDDDDRDAGRWVRGPETTSAVRGAYPDPMASLSPRP PAPRRHHHHHHRRRRAPRRRSAASDSSKSGSSSSASSASSSASSSSSASASSS DDDDDDDAARAPASAADHAAGGTLGADDEEAGVPARAPGAAPRPSPPRAEP APARTPAATAGRLERRRARAAVAGRDATGRFTAGRPRRVELDADAASGAFY ARYRDGYVSGEPWPGAGPPPPGRVLYGGLGDSRPGLWGAPEAEEARARFEA SGAPAPVWAPELGDAAQQYALITRLLYTPDAEAMGWLQNPRVAPGDVALD QACFRISGAARNSSSFISGSVARAVPHLGYAMAAGRFGWGLAHVAAAVAMS RRYDRAQKGFLLTSLRRAYAPLLARENAALTGARTPDDGGDANRHDGDDAR GKPAAAAAPLPSAAASPADERAVPAGYGAAGVLAALGRLSAAPASAPAGAD DDDDDDGAGGGGGGRRAEAGRVAVECLAACRGILEALAEGFDGDLAAVPG LAGARPAAPPRPGPAGAAAPPHADAPRLRAWLRELRFVRDALVLMRLRGDL RVAGGSEAAVAAVRAVSLVAGALGPALPRSPRLLSSAAAAAADLLFQNQSL RPLLADTVAAADSLAAPASAPREAADAPRPAAAPPAGAAPPAPPTPPPRPPRP AALTRRPAEGPDPQGGWRRQPPGPSHTPAPSAAALEAYCAPRAVAELTDHPL FPAPWRPALMFDPRALASLAARCAAPPPGGAPAAFGPLRASGPLRRAAAWM RQVPDPEDVRVVILYSPLPGEDLAAGRAGGGPPPEWSAERGGLSCLLAALGN RLCGPATAAWAGNWTGAPDVSALGAQGVLLLSTRDLAFAGAVEFLGLLAG ACDRRLIVVNAVRAAAWPAAAPVVSRQHAYLACEVLPAVQCAVRWPAARD LRRTVLASGRVFGPGVFARVEAAHARLYPDAPPLRLCRGANVRYRVRTRFGP DTLVPMSPREYRRAVLPALDGRAAASGAGDAMAPGAPDFCEDEAHSHRACA RWGLGAPLRPVYVALGRDAVRGGPAELRGPRREFCARALLEPDGDAPPLVL RDDADAGPPPQIRWASAAGRAGTVLAAAGGGVEVVGTAAGLATPPRREPVD MDAELEDDDDGLFGE (SEQ ID NO: 77) |

TABLE 3

| HSV strains/isolates, Envelope proteins/variants - *Homo sapiens* | | | |
|---|---|---|---|
| Strain | | NCBI Accession No. | Protein Accession No. |
| Human herpesvirus 2 strain CtSF | partial genome | KP334097.1 | P06475.1 (SwissProt/EMBL) |
| Human herpesvirus 2 strain GSC-56 | partial genome | KP334094.1 | |
| Human herpesvirus 2 strain 333 | partial genome | KP192856.1 | |
| Herpes simplex virus type 2 glycoprotein C and 18K protein genes | complete cds | M10053.1 | |
| Herpes simplex virus type 2 (strain 333) gene for glycoprotein C (gC-2) and 18K protein | | X01996.1 | |
| Human herpesvirus 2 MMA glycoprotein C (UL44) gene | complete cds | U12178.1 | |
| Human herpesvirus 2 strain 333 glycoprotein C (UL44) gene | complete cds | EU018087.1 | |
| Human herpesvirus 2 strain 1192 | partial genome | KP334095.1 | |

TABLE 3-continued

| HSV strains/isolates, Envelope proteins/variants - *Homo sapiens* | | | |
|---|---|---|---|
| Strain | | NCBI Accession No. | Protein Accession No. |
| Human herpesvirus 2 strain SD90e | complete genome | KF781518.1 | |
| Human herpesvirus 2 strain 333 (variant A4) glycoprotein C (UL44) gene | complete cds | EU018090.1 | |
| Human herpesvirus 2 strain 333 (variant ACS) glycoprotein C (UL44) gene | complete cds | EU018089.1 | |
| Human herpesvirus 2 glycoprotein C precursor (UL44) gene | complete cds | AF021341.1 | Q89730.1 (SwissProt/EMBL) YP_009137196.1 (GenBank) |
| Human herpesvirus 2 WTW1A glycoprotein C (UL44) gene | complete cds | U12179.1 | |
| Herpes simplex virus type 2 ul44 gene for glycoprotein C | isolate B4327UR | AJ297389.1 | |
| Human herpesvirus 2 strain HG52 | complete genome | JN561323.2 | |
| Herpes simplex virus type 2 (strain HG52) | complete genome | Z86099.2 | |
| Human herpesvirus 2 JDZ3 glycoprotein C (UL44) gene | complete cds | U12177.1 | |
| Herpes simplex virus type 2 glycoprotein F gene | | X01456.1 | P03173.1 (SwissProt/EMBL) |
| Human herpesvirus 2 strain 333 (variant AC1) glycoprotein C (UL44) gene | complete cds | EU018088.1 | ABU45430.1 GI:156072158 |
| Human herpesvirus 2 strain 333 (variant A2) glycoprotein C (UL44) gene | complete cds | EU018122.1 | ABU45459.1 GI:156072221 |
| Human herpesvirus 2 strain COH 3818 | partial genome | KP334096.1 | AKC59499.1 GI:807203116 |
| Human herpesvirus 2 strain CtSF-R | partial genome | KP334093.1 | |
| Human herpesvirus 2 CAM4B glycoprotein C (UL44) gene | complete cds | U12176.1 | AAB60549.1 GI:522172 |
| Human herpesvirus 2 Strain 186 (Broad Institute) | partial genome | JX112656.1 | AFM93864.1 GI:392937653 |
| Human herpesvirus 2 isolate 10045 from USA glycoprotein C (UL44) gene | partial cds | AY827344.1 | |
| Human herpesvirus 2 9788_00_802swab_1486 gC gene | partial cds | DQ236133.1 | |
| Human herpesvirus 2 isolate 8484 from USA glycoprotein C (UL44) gene | partial cds | AY827357.1 | |
| Human herpesvirus 2 isolate 8028 from USA glycoprotein C (UL44) gene | partial cds | AY827351.1 | |
| Human herpesvirus 2 isolate 8456 from USA glycoprotein C (UL44) gene | partial cds | | |
| Human herpesvirus 2 strain 16293 glycoprotein D (US6) gene | complete cds | AY779754.1 | Q69467.1 GI:82013827 (SwissProt/EMBL) YP_009137218.1 (BenBank) |
| Human herpesvirus 2 strain HG52 | complete genome | JN561323.2 | |
| Herpes simplex virus type 2 (strain HG52) | complete genome | Z86099.2 | |

TABLE 3-continued

HSV strains/isolates, Envelope proteins/variants - *Homo sapiens*

| Strain | | NCBI Accession No. | Protein Accession No. |
|---|---|---|---|
| Human herpesvirus 2 JDZ3 glycoprotein D (US6) gene | complete cds | U12181.1 | |
| HSV-2 genomic HindIII 1 region of short unique component U(s) with genes US2 to US8 | | X04798.1 | |
| Human herpesvirus 2 isolate pat5 glycoprotein D (US6) gene | complete cds | KF588422.1 | |
| Human herpesvirus 2 isolate pat14 glycoprotein D (US6) gene | complete cds | KM068891.1 | |
| Human herpesvirus 2 isolate pat13 glycoprotein D (US6) gene | complete cds | KM068890.1 | |
| Human herpesvirus 2 strain 2899 glycoprotein D (US6) gene | complete cds | AY779751.1 | |
| Human herpesvirus 2 strain CtSF | partial genome | KP334097.1 | |
| Human herpesvirus 2 strain COH 3818 | partial genome | KP334096.1 | |
| Human herpesvirus 2 strain GSC-56 | partial genome | KP334094.1 | |
| Human herpesvirus 2 strain CtSF-R | partial genome | KP334093.1 | |
| Human herpesvirus 2 strain 333 | partial genome | KP192856.1 | |
| Human herpesvirus 2 strain SD90e | complete genome | KF781518.1 | |
| Human herpesvirus 2 isolate Pt13 virion glycoprotein D (US6) gene | complete cds | JQ956362.1 | |
| Human herpesvirus 2 strain MS glycoprotein D gene | complete cds | EU445527.1 | |
| Human herpesvirus 2 strain 333 glycoprotein D (US6) gene | complete cds | EU018091.1 | |
| Human herpesvirus 2 isolate Pt21 virion glycoprotein D (US6) gene | complete cds | JQ956369.1 | |
| Human herpesvirus 2 isolate Pt05 virion glycoprotein D (US6) gene | complete cds | JQ956354.1 | |
| Human herpesvirus 2 isolate Pt01 virion glycoprotein D (US6) gene | complete cds | JQ956351.1 | |
| Human herpesvirus 2 strain 333 (variant AC2) glycoprotein D (US6) gene | complete cds | EU018092.1 | |
| Human herpesvirus 2 isolate Iranian glycoprotein D (us6) gene | complete cds | AY517492.1 | |
| Human herpesvirus 2 MMA glycoprotein D (US6) gene | complete cds | U12182.1 | AAB60554.1 GI:522178 |
| Human herpesvirus 2 glycoprotein D precursor (US6) gene | complete cds | AF021342.1 | |
| Human herpesvirus 2 CAM4B glycoprotein D (US6) gene | complete cds | U12180.1 | |
| Herpes simplex virus type 2 (HSV-2) glycoprotein D (gD-2) gene and flanks | K01408.1 | | |
| Human herpesvirus 2 isolate Pt11 virion glycoprotein D (US6) gene | complete cds | JQ956360.1 | |
| Human herpesvirus 2 strain 1192 | partial genome | KP334095.1 | |
| Human herpesvirus 2 isolate path glycoprotein D (US6) gene | complete cds | KF588423.1 | |

TABLE 3-continued

HSV strains/isolates, Envelope proteins/variants - *Homo sapiens*

| Strain | | NCBI Accession No. | Protein Accession No. |
|---|---|---|---|
| Human herpesvirus 2 isolate Pt25 virion glycoprotein D (US6) gene | complete cds | JQ956373.1 | |
| Human herpesvirus 2 strain 333 (variant AC1) glycoprotein D (US6) gene | complete cds | EU018124.1 | ABU45461.1 GI:156072225 |
| Human herpesvirus 2 isolate subject ID VRC11098 specimen 2002_346 glycoprotein D (US6) gene | complete cds | EU029158.1 | ABS84899.1 GI:154744645 |
| Human herpesvirus 2 isolate pat4 glycoprotein D (US6) gene | complete cds | KF588421.1 GI:674748162 | AIL27723.1 GI:674748163 |
| Human herpesvirus 2 isolate pat10 glycoprotein D (US6) gene | complete cds | KF588427.1 | |
| Human herpesvirus 2 isolate pat9 glycoprotein D (US6) gene | complete cds | KF588426.1 | AIL27728.1 GI:674748211 |
| Human herpesvirus 2 isolate pat8 glycoprotein D (US6) gene | complete cds | KF588425.1 | |
| Human herpesvirus 2 isolate pat7 glycoprotein D (US6) gene | complete cds | KF588424.1 | |
| Human herpesvirus 2 isolate pat3 glycoprotein D (US6) gene | complete cds | KF588420.1 | |
| Human herpesvirus 2 isolate pat2 glycoprotein D (US6) gene | complete cds | KF588419.1 | |
| Human herpesvirus 2 isolate pat1 glycoprotein D (US6) gene | complete cds | KF588418.1 | |
| Human herpesvirus 2 isolate pat11 glycoprotein D (US6) gene | complete cds | KF588428.1 | AIL27730.1 GI:674748224 |
| Human herpesvirus 2 isolate pat12 glycoprotein D (US6) gene | complete cds | KF588429.1 | |
| Human herpesvirus 2 strain 333 (variant A6) glycoprotein D (US6) gene | complete cds | EU018093.1 | ABU45435.1 GI:156072168 |
| Human herpesvirus 2 isolate Pt26 virion glycoprotein D (US6) gene | complete cds | JQ956374.1 | AFS18221.1 GI:405168231 |
| Human herpesvirus 2 strain 2589 glycoprotein D (US6) gene | complete cds | AY779750.1 | AAW23130.1 GI:56698864 |
| Herpes simplex virus type 2 glycoprotein-D gene | complete cds | K02373.1 | AAA45842.1 GI:330271 |
| HSV-1 | | | |
| Human herpesvirus 1 strain TFT401 | partial genome | JN420337.1 | |
| Human herpesvirus 1 strain 81L partial genome | KR052508.1 | | |
| Human herpesvirus 1 strain 5-4-2 | partial genome | KR011311.1 | |
| Human herpesvirus 1 strain 10-11-3 | partial genome | KR011309.1 | |
| Human herpesvirus 1 strain 10-6-2 | partial genome | KR011306.1 | |
| Human herpesvirus 1 strain 47M | partial genome | KR011305.1 | |
| Human herpesvirus 1 strain 31XL | partial genome | KR011304.1 | |
| Human herpesvirus 1 strain 10-1-2 | partial genome | KR011302.1 | |
| Human herpesvirus 1 strain 10-5-1 | partial genome | KR011301.1 | |
| Human herpesvirus 1 strain 76M | partial genome | KR011300.1 | |
| Human herpesvirus 1 strain 5-1-1 | partial genome | KR011299.1 | |

TABLE 3-continued

| HSV strains/isolates, Envelope proteins/variants - *Homo sapiens* | | | |
|---|---|---|---|
| Strain | | NCBI Accession No. | Protein Accession No. |
| Human herpesvirus 1 strain 10-6-1 | partial genome | KR011296.1 | |
| Human herpesvirus 1 strain 5-5-2 | partial genome | KR011295.1 | |
| Human herpesvirus 1 strain 11M | partial genome | KR011294.1 | |
| Human herpesvirus 1 strain 2-5-3 | partial genome | KR011292.1 | |
| Human herpesvirus 1 strain 10-14-1 | partial genome | KR011291.1 | |
| Human herpesvirus 1 strain 10-7-1 | partial genome | KR011290.1 | |
| Human herpesvirus 1 strain 2-4-2 | partial genome | KR011288.1 | |
| Human herpesvirus 1 strain 12-12-67 | partial genome | KR011286.1 | |
| Human herpesvirus 1 strain 5-2-1 | partial genome | KR011285.1 | |
| Human herpesvirus 1 strain 10-6-3 | partial genome | KR011284.1 | |
| Human herpesvirus 1 strain 3M | partial genome | KR011282.1 | |
| Human herpesvirus 1 strain 66S | partial genome | KR011281.1 | |
| Human herpesvirus 1 strain 36L | partial genome | KR011279.1 | |
| Human herpesvirus 1 strain 10-2-2 | partial genome | KR011277.1 | |
| Human herpesvirus 1 strain 57M | partial genome | KR011276.1 | |
| Human herpesvirus 1 strain 10-2-3 | partial genome | KR011274.1 | |
| Human herpesvirus 1 isolate RE | complete genome | KF498959.1 | |
| Human herpesvirus 1 strain E19 | partial genome | HM585511.2 | |
| Human herpesvirus 1 strain CR38 | partial genome | HM585508.2 | |
| Human herpesvirus 1 strain E13 | partial genome | HM585502.2 | |
| Human herpesvirus 1 strain E08 | partial genome | HM585498.2 | |
| Human herpesvirus 1 strain KOS | complete genome | JQ780693.1 | |
| Human herpesvirus 1 strain KOS | complete genome | JQ673480.1 | |
| Human herpesvirus 1 strain OD4 | partial genome | JN420342.1 | |
| Human herpesvirus 1 strain KOSc glycoprotein D (US6) gene | complete cds | EF157319.1 | |
| HSV1 glycoprotein D gene | J02217.1 | | |
| Herpes simplex virus type 1 glycoprotein D gene | complete cds | L09243.1 | |
| Human herpesvirus 1 strain 12-12-2 | partial genome | KR011298.1 | |
| Human herpesvirus 1 isolate HSV-1/0116209/India/2011 | complete genome | KJ847330.1 | |
| Human herpesvirus 1 strain R62 | partial genome | HM585515.2 | |
| Human herpesvirus 1 strain S25 | partial genome | HM585513.2 | |
| Human herpesvirus 1 strain KOSc(C2) glycoprotein D (US6) gene | complete cds | EF157322.1 | |
| Human herpesvirus 1 strain KOSc(AC4) glycoprotein D (US6) gene | complete cds | EF157321.1 | |
| Human herpesvirus 1 strain KOSc(AC3 | AC6) glycoprotein D (US6) gene | complete cds | |
| EF157320.1 | | | |

TABLE 3-continued

HSV strains/isolates, Envelope proteins/variants - *Homo sapiens*

| Strain | | NCBI Accession No. | Protein Accession No. |
|---|---|---|---|
| Herpes simplex virus type 1 glycoprotein D gene | complete cds | L09244.1 | |
| Herpes simplex virus type 1 glycoprotein D gene | complete cds | L09245.1 | |

TABLE 4

Signal Peptides

| Description | Sequence | SEQ ID NO: |
|---|---|---|
| HuIgGk signal peptide | METPAQLLFLLLLWLPDTTG | 78 |
| IgE heavy chain epsilon -1 signal peptide | MDWTWILFLVAAATRVHS | 79 |
| Japanese encephalitis PRM signal sequence | MLGSNSGQRVVFTILLLLVAPAYS | 80 |
| VSVg protein signal sequence | MKCLLYLAFLFIGVNCA | 81 |
| Japanese encephalitis JEV signal sequence | MWLVSLAIVTACAGA | 82 |

TABLE 5

| Name | Sequence | SEQ ID NO: |
|---|---|---|
| Flagellin Nucleic Acid Sequences | | |
| NT (5' UTR, ORF, 3' UTR) | TCAAGCTTTTGGACCCTCGTACAGAAGCTAATACGACTCACTATAGGGAA ATAAGAGAGAAAAGAAGAGTAAGAAGAAATATAAGAGCCACCATGGCA CAAGTCATTAATACAAACAGCCTGTCGCTGTTGACCCAGAATAACCTGAA CAAATCCCAGTCCGCACTGGGCACTGCTATCGAGCGTTTGTCTTCCGGTCT GCGTATCAACAGCGCGAAAGACGATGCGGCAGGACAGGCGATTGCTAAC CGTTTTACCGCGAACATCAAAGGTCTGACTCAGGCTTCCCGTAACGCTAA CGACGGTATCTCCATTGCGCAGACCACTGAAGGCGCGCTGAACGAAATC AACAACAACCTGCAGCGTGTGCGTGAACTGGCGGTTCAGTCTGCGAATGG TACTAACTCCCAGTCTGACCTCGACTCCATCCAGGCTGAAATCACCCAGC GCCTGAACGAAATCGACCGTGTATCCGGCCAGACTCAGTTCAACGGCGTG AAAGTCCTGGCGCAGGACAACACCCTGACCATCCAGGTTGGTGCCAACG ACGGTGAAACTATCGATATTGATTTAAAAGAAATCAGCTCTAAAACACTG GGACTTGATAAGCTTAATGTCCAAGATGCCTACACCCCGAAAGAAACTGC TGTAACCGTTGATAAAACTACCTATAAAAATGGTACAGATCCTATTACAG CCCAGAGCAATACTGATATCCAAACTGCAATTGGCGGTGGTGCAACGGG GGTTACTGGGGCTGATATCAAATTTAAAGATGGTCAATACTATTTAGATG TTAAAGGCGGTGCTTCTGCTGGTGTTTATAAAGCCACTTATGATGAAACT ACAAAGAAAGTTAATATTGATACGACTGATAAAACTCCGTTGGCAACTGC GGAAGCTACAGCTATTCGGGGAACGGCCACTATAACCCACAACCAAATT GCTGAAGTAACAAAAGAGGGTGTTGATACGACCACAGTTGCGGCTCAAC TTGCTGCAGCAGGGGTTACTGGCGCCGATAAGGACAATACTAGCCTTGTA AAACTATCGTTTGAGGATAAAAACGGTAAGGTTATTGATGGTGGCTATGC AGTGAAAATGGGCGACGATTTCTATGCCGCTACATATGATGAGAAAACA GGTGCAATTACTGCTAAAACCACTACTTATACAGATGGTACTGGCGTTGC TCAAACTGGAGCTGTGAAATTTGGTGGCGCAAATGGTAAATCTGAAGTTG TTACTGCTACCGATGGTAAGACTTACTTAGCAAGCGACCTTGACAAACAT AACTTCAGAACAGGCGGTGAGCTTAAAGAGGTTAATACAGATAAGACTG AAAACCCACTGCAGAAAATTGATGCTGCCTTGGCACAGGTTGATACACTT CGTTCTGACCTGGGTGCGGTTCAGAACCGTTTCAACTCCGCTATCACCAA CCTGGGCAATACCGTAAATAACCTGTCTTCTGCCCGTAGCCGTATCGAAG ATTCCGACTACGCAACCGAAGTCTCCAACATGTCTCGCGCGCAGATTCTG CAGCAGGCCGGTACCTCCGTTCTGGCGCAGGCGAACCAGGTTCCGCAAA ACGTCCTCTCTTTACTGCGTTGATAATAGGCTGGAGCCTCGGTGGCCATG CTTCTTGCCCCTTGGGCCTCCCCCCAGCCCCTCCTCCCCTTCCTGCACCCG TACCCCCGTGGTCTTTGAATAAAGTCTGAGTGGGCGGC | 83 |
| ORF Sequence, NT | ATGGCACAAGTCATTAATACAAACAGCCTGTCGCTGTTGACCCAGAATAA CCTGAACAAATCCCAGTCCGCACTGGGCACTGCTATCGAGCGTTTGTCTT CCGGTCTGCGTATCAACAGCGCGAAAGACGATGCGGCAGGACAGGCGAT TGCTAACCGTTTTACCGCGAACATCAAAGGTCTGACTCAGGCTTCCCGTA ACGCTAACGACGGTATCTCCATTGCGCAGACCACTGAAGGCGCGCTGAAC GAAATCAACAACAACCTGCAGCGTGTGCGTGAACTGGCGGTTCAGTCTGC GAATGGTACTAACTCCCAGTCTGACCTCGACTCCATCCAGGCTGAAATCA | 84 |

TABLE 5 -continued

| Name | Sequence | SEQ ID NO: |
|---|---|---|
| | CCCAGCGCCTGAACGAAATCGACCGTGTATCCGGCCAGACTCAGTTCAAC<br>GGCGTGAAAGTCCTGGCGCAGGACAACACCCTGACCATCCAGGTTGGTG<br>CCAACGACGGTGAAACTATCGATATTGATTTAAAAGAAATCAGCTCTAAA<br>ACACTGGGACTTGATAAGCTTAATGTCCAAGATGCCTACACCCCGAAAGA<br>AACTGCTGTAACCGTTGATAAAACTACCTATAAAAATGGTACAGATCCTA<br>TTACAGCCCAGAGCAATACTGATATCCAAACTGCAATTGGCGGTGGTGCA<br>ACGGGGGTTACTGGGGCTGATATCAAATTTAAAGATGGTCAATACTATTT<br>AGATGTTAAAGGCGGTGCTTCTGCTGGTGTTTATAAAGCCACTTATGATG<br>AAACTACAAAGAAAGTTAATATTGATACGACTGATAAAACTCCGTTGGCA<br>ACTGCGGAAGCTACAGCTATTCGGGGAACGGCCACTATAACCCACAACC<br>AAATTGCTGAAGTAACAAAAGAGGGTGTTGATACGACCACAGTTGCGGC<br>TCAACTTGCTGCAGCAGGGGTTACTGGCGCCGATAAGGACAATACTAGCC<br>TTGTAAAACTATCGTTTGAGGATAAAAACGGTAAGGTTATTGATGGTGGC<br>TATGCAGTGAAAATGGGCGACGATTTCTATGCCGCTACATATGATGAGAA<br>AACAGGTGCAATTACTGCTAAAACCACTACTTATACAGATGGTACTGGCG<br>TTGCTCAAACTGGAGCTGTGAAATTTGGTGGCGCAAATGGTAAATCTGAA<br>GTTGTTACTGCTACCGATGGTAAGACTTACTTAGCAAGCGACCTTGACAA<br>ACATAACTTCAGAACAGGCGGTGAGCTTAAAGAGGTTAATACAGATAAG<br>ACTGAAAACCCACTGCAGAAAATTGATGCTGCCTTGGCACAGGTTGATAC<br>ACTTCGTTCTGACCTGGGTGCGGTTCAGAACCGTTTCAACTCCGCTATCAC<br>CAACCTGGGCAATACCGTAAATAACCTGTCTTCTGCCCGTAGCCGTATCG<br>AAGATTCCGACTACGCAACCGAAGTCTCCAACATGTCTCGCGCGCAGATT<br>CTGCAGCAGGCCGGTACCTCCGTTCTGGCGCAGGCGAACCAGGTTCCGCA<br>AAACGTCCTCTCTTTACTGCGT | |
| mRNA Sequence (assumes T100 tail) | G*GGGAAAUAAGAGAGAAAAGAAGAGUAAGAAGAAAUAUAAGAGCCAC<br>CAUGGCACAAGUCAUUAAUACAAACAGCCUGUCGCUGUUGACCCAGAA<br>UAACCUGAACAAAUCCCAGUCCGCACUGGGCACUGCUAUCGAGCGUUU<br>GUCUUCCGGUCUGCGUAUCAACAGCGCGAAAGACGAUGCGGCAGGACA<br>GGCGAUUGCUAACCGUUUUACCGCGAACAUCAAAGGUCUGACUCAGGC<br>UUCCCGUAACGCUAACGACGGUAUCUCCAUUGCGCAGACCACUGAAGG<br>CGCGCUGAACGAAAUCAACAACAACCUGCAGCGUGUGCGUGAACUGGC<br>GGUUCAGUCUGCGAAUGGUACUAACUCCCAGUCUGACCUCGACUCCAU<br>CCAGGCUGAAAUCACCCAGCGCCUGAACGAAAUCGACCGUGUAUCCGG<br>CCAGACUCAGUUCAACGGCGUGAAAGUCCUGGCGCAGGACAACACCCU<br>GACCAUCCAGGUUGGUGCCAACGACGGUGAAACUAUCGAUAUUGAUUU<br>AAAAGAAAUCAGCUCUAAAACACUGGGACUUGAUAAGCUUAAUGUCCA<br>AGAUGCCUACACCCCGAAAGAAACUGCUGUAACCGUUGAUAAAACUAC<br>CUAUAAAAAUGGUACAGAUCCUAUUACAGCCCAGAGCAAUACUGAUAU<br>CCAAACUGCAAUUGGCGGUGGUGCAACGGGGGUUACUGGGGCUGAUAU<br>CAAAUUUAAAGAUGGUCAAUACUAUUUAGAUGUUAAAGGCGGUGCUUC<br>UGCUGGUGUUUAUAAAGCCACUUAUGAUGAAACUACAAAGAAAGUUAA<br>UAUUGAUACGACUGAUAAAACUCCGUUGGCAACUGCGGAAGCUACAGC<br>UAUUCGGGGAACGGCCACUAUAACCCACAACCAAAUUGCUGAAGUAAC<br>AAAAGAGGGUGUUGAUACGACCACAGUUGCGGCUCAACUUGCUGCAGC<br>AGGGGUUACUGGCGCCGAUAAGGACAAUACUAGCCUUGUAAAACUAUC<br>GUUUGAGGAUAAAAACGGUAAGGUUAUUGAUGGUGGCUAUGCAGUGA<br>AAAUGGGCGACGAUUUCUAUGCCGCUACAUAUGAUGAGAAAACAGGUG<br>CAAUUACUGCUAAAACCACUACUUAUACAGAUGGUACUGGCGUUGCUC<br>AAACUGGAGCUGUGAAAUUUGGUGGCGCAAAUGGUAAAUCUGAAGUU<br>GUUACUGCUACCGAUGGUAAGACUUACUUAGCAAGCGACCUUGACAAA<br>CAUAACUUCAGAACAGGCGGUGAGCUUAAAGAGGUUAAUACAGAUAAG<br>ACUGAAAACCCACUGCAGAAAAUUGAUGCUGCCUUGGCACAGGUUGAU<br>ACACUUCGUUCUGACCUGGGUGCGGUUCAGAACCGUUUCAACUCCGCU<br>AUCACCAACCUGGGCAAUACCGUAAAUAACCUGUCUUCUGCCCGUAGC<br>CGUAUCGAAGAUUCCGACUACGCAACCGAAGUCUCCAACAUGUCUCGC<br>GCGCAGAUUCUGCAGCAGGCCGGUACCUCCGUUCUGGCGCAGGCGAAC<br>CAGGUUCCGCAAAACGUCCUCUCUUUACUGCGUUGAUAAUAGGCUGGA<br>GCCUCGGUGGCCAUGCUUCUUGCCCCUUGGGCCUCCCCCCAGCCCCUCC<br>UCCCCUUCCUGCACCCGUACCCCCGUGGUCUUUGAAUAAAGUCUGAGU<br>GGGCGGCAAAAAAAAAAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAUCUAG | 85 |
| **Flagellin mRNA Sequences** | | |
| NT (5' UTR, ORF, 3' UTR) | UCAAGCUUUUGGACCCUCGUACAGAAGCUAAUACGACUCACUAUAGGG<br>AAAUAAGAGAGAAAAGAAGAGUAAGAAGAAAUAUAAGAGCCACCAUG<br>GCACAAGUCAUUAAUACAAACAGCCUGUCGCUGUUGACCCAGAAUAAC<br>CUGAACAAAUCCCAGUCCGCACUGGGCACUGCUAUCGAGCGUUUGUCU<br>UCCGGUCUGCGUAUCAACAGCGCGAAAGACGAUGCGGCAGGACAGGCG<br>AUUGCUAACCGUUUUACCGCGAACAUCAAAGGUCUGACUCAGGCUUCC<br>CGUAACGCUAACGACGGUAUCUCCAUUGCGCAGACCACUGAAGGCGCG<br>CUGAACGAAAUCAACAACAACCUGCAGCGUGUGCGUGAACUGGCGGUU<br>CAGUCUGCGAAUGGUACUAACUCCCAGUCUGACCUCGACUCCAUCCAG<br>GCUGAAAUCACCCAGCGCCUGAACGAAAUCGACCGUGUAUCCGGCCAG<br>ACUCAGUUCAACGGCGUGAAAGUCCUGGCGCAGGACAACACCCUGACC<br>AUCCAGGUUGGUGCCAACGACGGUGAAACUAUCGAUAUUGAUUUAAAA | 86 |

TABLE 5 -continued

| Name | Sequence | SEQ ID NO: |
|---|---|---|
| | GAAAUCAGCUCUAAAACACUGGGACUUGAUAAGCUUAAUGUCCAAGAU GCCUACACCCCGAAAGAAACUGCUGUAACCGUUGAUAAAACUACCUAU AAAAAUGGUACAGAUCCUAUUACAGCCCAGAGCAAUACUGAUAUCCAA ACUGCAAUUGGCGGUGGUGCAACGGGGGUUACUGGGGCUGAUAUCAAA UUUAAAGAUGGUCAAUACUAUUUAGAUGUUAAAGGCGGUGCUUCUGCU GGUGUUUAUAAAGCCACUUAUGAUGAAACUACAAAGAAAGUUAAUAU UGAUACGACUGAUAAAACUCCGUUGGCAACUGCGGAAGCUACAGCUAU UCGGGGAACGGCCACUAUAACCCACAACCAAAUUGCUGAAGUAACAAA AGAGGGUGUUGAUACGACCACAGUUGCGGCUCAACUUGCUGCAGCAGG GGUUACUGGCGCCGAUAAGGACAAUACUAGCCUUGUAAAACUAUCGUU UGAGGAUAAAAACGGUAAGGUUAUUGAUGGUGGCUAUGCAGUGAAAA UGGGCGACGAUUUCUAUGCCGCUACAUAUGAUGAGAAAACAGGUGCAA UUACUGCUAAAACCACUACUUAUACAGAUGGUACUGGCGUUGCUCAAA CUGGAGCUGUGAAAUUUGGUGGCGCAAAUGGUAAAUCUGAAGUUGUU ACUGCUACCGAUGGUAAGACUUACUUAGCAAGCGACCUUGACAAACAU AACUUCAGAACAGGCGGUGAGCUUAAAGAGGUUAAUACAGAUAAGACU GAAAACCCACUGCAGAAAAUUGAUGCUGCCUUGGCACAGGUUGAUACA CUUCGUUCUGACCUGGGUGCGGUUCAGAACCGUUUCAACUCCGCUAUC ACCAACCUGGGCAAUACCGUAAAUAACCUGUCUUCUGCCCGUAGCCGU AUCGAAGAUUCCGACUACGCAACCGAAGUCUCCAACAUGUCUCGCGCG CAGAUUCUGCAGCAGGCCGGUACCUCCGUUCUGGCGCAGGCGAACCAG GUUCCGCAAAACGUCCUCUCUUUACUGCGUUGAUAAUAGGCUGGAGCC UCGGUGGCCAUGCUUCUUGCCCCUUGGGCCUCCCCCCAGCCCCUCCUCC CCUUCCUGCACCCGUACCCCCGUGGUCUUUGAAUAAAGUCUGAGUGGG CGGC | |
| ORF Sequence, NT | AUGGCACAAGUCAUUAAUACAAACAGCCUGUCGCUGUUGACCCAGAAU AACCUGAACAAAUCCCAGUCCGCACUGGGCACUGCUAUCGAGCGUUUG UCUUCCGGUCUGCGUAUCAACAGCGCGAAAGACGAUGCGGCAGGACAG GCGAUUGCUAACCGUUUUACCGCGAACAUCAAAGGUCUGACUCAGGCU UCCCGUAACGCUAACGACGGUAUCUCCAUUGCGCAGACCACUGAAGGC GCGCUGAACGAAAUCAACAACAACCUGCAGCGUGUGCGUGAACUGGCG GUUCAGUCUGCGAAUGGUACUAACUCCCAGUCUGACCUCGACUCCAUC CAGGCUGAAAUCACCCAGCGCCUGAACGAAAUCGACCGUGUAUCCGGC CAGACUCAGUUCAACGGCGUGAAAGUCCUGGCGCAGGACAACACCCUG ACCAUCCAGGUUGGUGCCAACGACGGUGAAACUAUCGAUAUUGAUUUA AAAGAAAUCAGCUCUAAAACACUGGGACUUGAUAAGCUUAAUGUCCAA GAUGCCUACACCCCGAAAGAAACUGCUGUAACCGUUGAUAAAACUACC UAUAAAAAUGGUACAGAUCCUAUUACAGCCCAGAGCAAUACUGAUAUC CAAACUGCAAUUGGCGGUGGUGCAACGGGGGUUACUGGGGCUGAUAUC AAAUUUAAAGAUGGUCAAUACUAUUUAGAUGUUAAAGGCGGUGCUUC UGCUGGUGUUUAUAAAGCCACUUAUGAUGAAACUACAAAGAAAGUUAA UAUUGAUACGACUGAUAAAACUCCGUUGGCAACUGCGGAAGCUACAGC UAUUCGGGGAACGGCCACUAUAACCCACAACCAAAUUGCUGAAGUAAC AAAAGAGGGUGUUGAUACGACCACAGUUGCGGCUCAACUUGCUGCAGC AGGGGUUACUGGCGCCGAUAAGGACAAUACUAGCCUUGUAAAACUAUC GUUUGAGGAUAAAAACGGUAAGGUUAUUGAUGGUGGCUAUGCAGUGA AAAUGGGCGACGAUUUCUAUGCCGCUACAUAUGAUGAGAAAACAGGUG CAAUUACUGCUAAAACCACUACUUAUACAGAUGGUACUGGCGUUGCUC AAACUGGAGCUGUGAAAUUUGGUGGCGCAAAUGGUAAAUCUGAAGUU GUUACUGCUACCGAUGGUAAGACUUACUUAGCAAGCGACCUUGACAAA CAUAACUUCAGAACAGGCGGUGAGCUUAAAGAGGUUAAUACAGAUAAG ACUGAAAACCCACUGCAGAAAAUUGAUGCUGCCUUGGCACAGGUUGAU ACACUUCGUUCUGACCUGGGUGCGGUUCAGAACCGUUUCAACUCCGCU AUCACCAACCUGGGCAAUACCGUAAAUAACCUGUCUUCUGCCCGUAGC CGUAUCGAAGAUUCCGACUACGCAACCGAAGUCUCCAACAUGUCUCGC GCGCAGAUUCUGCAGCAGGCCGGUACCUCCGUUCUGGCGCAGGCGAAC CAGGUUCCGCAAAACGUCCUCUCUUUACUGCGU | 87 |
| mRNA Sequence (assumes T100 tail) | G*GGGAAAUAAGAGAGAAAAGAAGAGUAAGAAGAAAUAUAAGAGCCAC CAUGGCACAAGUCAUUAAUACAAACAGCCUGUCGCUGUUGACCCAGAA UAACCUGAACAAAUCCCAGUCCGCACUGGGCACUGCUAUCGAGCGUUU GUCUUCCGGUCUGCGUAUCAACAGCGCGAAAGACGAUGCGGCAGGACA GGCGAUUGCUAACCGUUUUACCGCGAACAUCAAAGGUCUGACUCAGGC UUCCCGUAACGCUAACGACGGUAUCUCCAUUGCGCAGACCACUGAAGG CGCGCUGAACGAAAUCAACAACAACCUGCAGCGUGUGCGUGAACUGGC GGUUCAGUCUGCGAAUGGUACUAACUCCCAGUCUGACCUCGACUCCAU CCAGGCUGAAAUCACCCAGCGCCUGAACGAAAUCGACCGUGUAUCCGG CCAGACUCAGUUCAACGGCGUGAAAGUCCUGGCGCAGGACAACACCCU GACCAUCCAGGUUGGUGCCAACGACGGUGAAACUAUCGAUAUUGAUUU AAAAGAAAUCAGCUCUAAAACACUGGGACUUGAUAAGCUUAAUGUCCA AGAUGCCUACACCCCGAAAGAAACUGCUGUAACCGUUGAUAAAACUAC CUAUAAAAAUGGUACAGAUCCUAUUACAGCCCAGAGCAAUACUGAUAU CCAAACUGCAAUUGGCGGUGGUGCAACGGGGGUUACUGGGGCUGAUAU CAAAUUUAAAGAUGGUCAAUACUAUUUAGAUGUUAAAGGCGGUGCUUC UGCUGGUGUUUAUAAAGCCACUUAUGAUGAAACUACAAAGAAAGUUAA UAUUGAUACGACUGAUAAAACUCCGUUGGCAACUGCGGAAGCUACAGC UAUUCGGGGAACGGCCACUAUAACCCACAACCAAAUUGCUGAAGUAAC | 88 |

TABLE 5 -continued

| Name | Sequence | SEQ ID NO: |
|---|---|---|
| | AAAAGAGGGUGUUGAUACGACCACAGUUGCGGCUCAACUUGCUGCAGC<br>AGGGGUUACUGGCGCCGAUAAGGACAAUACUAGCCUUGUAAAACUAUC<br>GUUUGAGGAUAAAAACGGUAAGGUUAUUGAUGGUGGCUAUGCAGUGA<br>AAAUGGGCGACGAUUUCUAUGCCGCUACAUAUGAUGAGAAAACAGGUG<br>CAAUUACUGCUAAAACCACUACUUAUACAGAUGGUACUGGCGUUGCUC<br>AAACUGGAGCUGUGAAAUUUGGUGGCGCAAAUGGUAAAUCUGAAGUU<br>GUUACUGCUACCGAUGGUAAGACUUACUUAGCAAGCGACCUUGACAAA<br>CAUAACUUCAGAACAGGCGGUGAGCUUAAAGAGGUUAAUACAGAUAAG<br>ACUGAAAACCCACUGCAGAAAAUUGAUGCUGCCUUGGCACAGGUUGAU<br>ACACUUCGUUCUGACCUGGGUGCGGUUCAGAACCGUUUCAACUCCGCU<br>AUCACCAACCUGGGCAAUACCGUAAAUAACCUGUCUUCUGCCCGUAGC<br>CGUAUCGAAGAUUCCGACUACGCAACCGAAGUCUCCAACAUGUCUCGC<br>GCGCAGAUUCUGCAGCAGGCCGGUACCUCCGUUCUGGCGCAGGCGAAC<br>CAGGUUCCGCAAAACGUCCUCUCUUUACUGCGU<u>UGAUAAUAGGCUGGA<br>GCCUCGGUGGCCAUGCUUCUUGCCCCUUGGGCCUCCCCCCAGCCCCUCC<br>UCCCCUUCCUGCACCCGUACCCCCGUGGUCUUUGAAUAAAGUCUGAGU<br>GGGCGG</u>CAAAAAAAAAAAAAAAAAAAAAAAAAAAAAAAAAAAAAAAA<br>AAAAAAAAAAAAAAAAAAAAAAAAAAAAAAAAAAAAAAAAAAAAAAA<br>AAAAAAAAAAAAAUCUAG | |

TABLE 6

Flagellin Amino Acid Sequences

| Name | Sequence | SEQ ID NO: |
|---|---|---|
| ORF Sequence, AA | MAQVINTNSLSLLTQNNLNKSQSALGTAIERLSSGLRINSAKDDAAGQAIANR<br>FTANIKGLTQASRNANDGISIAQTTEGALNEINNNLQRVRELAVQSANGTNS<br>QSDLDSIQAEITQRLNEIDRVSGQTQFNGVKVLAQDNTLTIQVGANDGETIDI<br>DLKEISSKTLGLDKLNVQDAYTPKETAVTVDKTTYKNGTDPITAQSNTDIQT<br>AIGGGATGVTGADIKFKDGQYYLDVKGGASAGVYKATYDETTKKVNIDTTD<br>KTPLATAEATAIRGTATITHNQIAEVTKEGVDTTTVAAQLAAAGVTGADKD<br>NTSLVKLSFEDKNGKVIDGGYAVKMGDDFYAATYDEKTGAITAKTTTYTDG<br>TGVAQTGAVKFGGANGKSEVVTATDGKTYLASDLDKHNFRTGGELKEVNT<br>DKTENPLQKIDAALAQVDTLRSDLGAVQNRFNSAITNLGNTVNNLSSARSRI<br>EDSDYATEVSNMSRAQILQQAGTSVLAQANQVPQNVLSLLR | 89 |
| Flagellin-GS linker-circumsporo-zoite protein | MAQVINTNSLSLLTQNNLNKSQSALGTAIERLSSGLRINSAKDDAAGQAIANR<br>FTANIKGLTQASRNANDGISIAQTTEGALNEINNNLQRVRELAVQSANSTNSQ<br>SDLDSIQAEITQRLNEIDRVSGQTQFNGVKVLAQDNTLTIQVGANDGETIDID<br>LKQINSQTLGLDTLNVQQKYKVSDTAATVTGYADTTIALDNSTFKASATGLG<br>GTDQKIDGDLKFDDTTGKYYAKVTVTGGTGKDGYYEVSVDKTNGEVTLAG<br>GATSPLTGGLPATATEDVKNVQVANADLTEAKAALTAAGVTGTASVVKMS<br>YTDNNGKTIDGGLAVKVGDDYYSATQNKDGSISINTTKYTADDGTSKTALN<br>KLGGADGKTEVVSIGGKTYAASKAEGHNFKAQPDLAEAAATTTENPLQKID<br>AALAQVDTLRSDLGAVQNRFNSAITNLGNTVNNLTSARSRIEDSDYATEVSN<br>MSRAQILQQAGTSVLAQANQVPQNVLSLLR<u>GGGGSGGGGSMMAPDPNANP<br>NANPNANPNANPNANPNANPNANPNANPNANPNANPNANPNANPNANPNA<br>NPNANPNANPNANPNANPNANPNKNNQGNGQGHNMPNDPNRNVDENANA<br>NNAVKNNNNEEPSDKHIEQYLKKIKNSISTEWSPCSVTCGNGIQVRIKPGSAN<br>KPKDELDYENDIEKKICKMEKCSSVFNVVNS</u> | 125 |
| Flagellin-RPVT linker-circumsporo-ozoite protein | MMAPDPNANPNANPNANPNANPNANPNANPNANPNANPNANPNANPNANP<br>NANPNANPNANPNANPNANPNANPNANPNANPNKNNQGNGQGHNMPNDP<br>NRNVDENANANNAVKNNNNEEPSDKHIEQYLKKIKNSISTEWSPCSVTCGN<br>GIQVRIKPGSANKPKDELDYENDIEKKICKMEKCSSVFNVVNS<u>RPVTMAQVI<br>NTNSLSLLTQNNLNKSQSALGTAIERLSSGLRINSAKDDAAGQAIANRFTANI<br>KGLTQASRNANDGISIAQTTEGALNEINNNLQRVRELAVQSANSTNSQSDLD<br>SIQAEITQRLNEIDRVSGQTQFNGVKVLAQDNTLTIQVGANDGETIDIDLKQIN<br>SQTLGLDTLNVQQKYKVSDTAATVTGYADTTIALDNSTFKASATGLGGTDQ<br>KIDGDLKFDDTTGKYYAKVTVTGGTGKDGYYEVSVDKTNGEVTLAGGATS<br>PLTGGLPATATEDVKNVQVANADLTEAKAALTAAGVTGTASVVKMSYTDN<br>NGKTIDGGLAVKVGDDYYSATQNKDGSISINTTKYTADDGTSKTALNKLGG<br>ADGKTEVVSIGGKTYAASKAEGHNFKAQPDLAEAAATTTENPLQKIDAALA<br>QVDTLRSDLGAVQNRFNSAITNLGNTVNNLTSARSRIEDSDYATEVSNMSRA<br>QILQQAGTSVLAQANQVPQNVLSLLR</u> | 126 |

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A messenger ribonucleic acid (mRNA) vaccine composition comprising:

(a) an mRNA polynucleotide having an open reading frame (ORF) encoding an HSV-2 glycoprotein B variant that comprises a transmembrane domain and is truncated at its C terminus, relative to a wild-type HSV-2 glycoprotein B;

(b) an mRNA polynucleotide having an ORF encoding an HSV-2 glycoprotein C variant that comprises a transmembrane domain and is truncated at its C terminus, relative to a wild-type HSV-2 glycoprotein C;

(c) an mRNA polynucleotide having an ORF encoding an HSV-2 glycoprotein D; and (d) a lipid nanoparticle comprising 20-60% ionizable cationic lipid, 0.5-15% polyethylene glycol (PEG)-modified lipid, 25-55% cholesterol, and 5-25% neutral lipid, wherein the ionizable lipid comprises a compound of Formula (I):

(I)

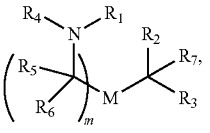

or a salt or isomer thereof, wherein:

$R_1$ is R"M'R' or $C_{5-20}$ alkenyl;

$R_2$ and $R_3$ are each independently selected from $C_{1-14}$ alkyl and $C_{2-14}$ alkenyl;

$R_4$ is $-(CH_2)_nQ$, wherein Q is OH and n is selected from 3, 4, and 5;

M and M' are each independently —OC(O)— or —C(O)O—;

$R_5$, $R_6$, and $R_7$ are each H;

R' is a linear $C_{1-12}$ alkyl, or $C_{1-12}$ alkyl substituted with $C_{6-9}$ alkyl;

R" is $C_{3-14}$ alkyl;

m is selected from 5, 6, 7, 8, 9, 10, 11, 12, and 13.

2. The mRNA vaccine composition of claim 1, wherein the mRNA vaccine composition further comprises an mRNA comprising an ORF encoding an HSV-2 ICP0, and an mRNA comprising an ORF encoding an HSV-2 ICP4.

3. The mRNA vaccine composition of claim 1, wherein the ionizable cationic lipid comprises Compound 25:

(Compound 25)

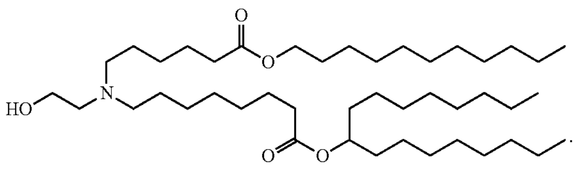

4. The mRNA vaccine composition of claim 1, wherein:

$R_1$ is R"M'R';

$R_2$ and $R_3$ are each independently $C_{1-14}$ alkyl;

$R_4$ is $-(CH_2)_nQ$, wherein Q is OH and n is 4;

M and M' are each independently —OC(O)—;

$R_5$, $R_6$, and $R_7$ are each H;

R' is $C_{1-12}$ alkyl substituted with $C_{6-9}$ alkyl;

R" is $C_{3-14}$ alkyl; and m is 6.

5. The mRNA vaccine composition of claim 1, wherein:

$R_1$ is $C_{5-20}$ alkenyl;

$R_2$ and $R_3$ are each independently $C_{1-14}$ alkyl;

$R_4$ is $-(CH_2)_nQ$, wherein Q is OH and n is 3;

M is —C(O)O—;

$R_5$, $R_6$, and $R_7$ are each H; and m is 6.

6. The mRNA vaccine composition of claim 1, wherein 100% of uracil nucleotides in the ORFs comprise 1-methylpseudouridine.

7. The mRNA vaccine composition of claim 6, wherein the ionizable cationic lipid comprises Compound 25:

(Compound 25)

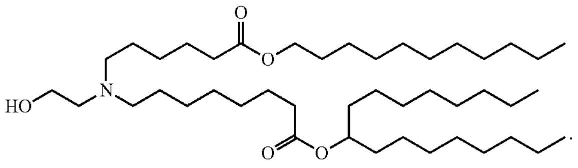

8. The mRNA vaccine composition of claim 6, wherein:

$R_1$ is R"M'R';

$R_2$ and $R_3$ are each independently $C_{1-14}$ alkyl;

$R_4$ is $-(CH_2)_nQ$, wherein Q is OH and n is 4;

M and M' are each independently —OC(O)—;

$R_5$, $R_6$, and $R_7$ are each H;

R' is $C_{1-12}$ alkyl substituted with $C_{6-9}$ alkyl;

R" is $C_{3-14}$ alkyl; and m is 6.

9. The mRNA vaccine composition of claim 6, wherein:

$R_1$ is $C_{5-20}$ alkenyl;

$R_2$ and $R_3$ are each independently $C_{1-14}$ alkyl;

$R_4$ is $-(CH_2)_nQ$, wherein Q is OH and n is 3;

M is —C(O)O—;

$R_5$, $R_6$, and $R_7$ are each H; and m is 6.

* * * * *

SEQUENCE LISTING

<160> NUMBER OF SEQ ID NOS: 127

<210> SEQ ID NO 1
<211> LENGTH: 1961
<212> TYPE: DNA
<213> ORGANISM: Human herpesvirus 2

<400> SEQUENCE: 1

```
tcaagctttt ggaccctcgt acagaagcta atacgactca ctatagggaa ataagagaga     60
aaagaagagt aagaagaaat ataagagcca ccatgagagg tggtggctta gtttgcgcgc    120
tggttgtcgg ggcgctcgta gccgccgtgg cgtcggccgc ccctgcggct cctcgcgcta    180
gcggaggcgt agccgcaaca gttgcggcga acgggggtcc agcctctcag cctcctcccg    240
tcccgagccc tgcgaccacc aaggctagaa agcggaagac caagaaaccg cccaagcgcc    300
ccgaggccac cccgcccccc gatgccaacg cgactgtcgc cgctggccat gcgacgcttc    360
gcgctcatct gagggagatc aaggttgaaa atgctgatgc ccaattttac gtgtgcccgc    420
ccccgacggg cgccacggtt gtgcagtttg aacagccgcg gcgctgtccg acgcggccag    480
aaggccagaa ctatacggag ggcatagcgg tggtctttaa ggaaaacatc gccccgtaca    540
aatttaaggc cacaatgtac tacaaagacg tgacagtttc gcaagtgtgg tttggccaca    600
gatactcgca gtttatggga atcttcgaag atagagcccc tgttcccttc gaggaagtca    660
tcgacaagat taatgccaaa ggggtatgcc gttccacggc caaatacgtg cgcaacaata    720
tggagaccac cgcctttcac cgggatgatc acgagaccga catggagctt aagccggcga    780
aggtcgccac gcgtacctcc cggggttggc acaccacaga tcttaagtac aatccctcgc    840
gagttgaagc attccatcgg tatggaacta ccgttaactg catcgttgag gaggtggatg    900
cgcggtcggt gtacccttac gatgagtttg tgttagcgac cggcgatttt gtgtacatgt    960
ccccgtttta cggctaccgg gaggggtcgc acaccgaaca tacctcgtac gccgctgaca   1020
ggttcaagca ggtcgatggc ttttacgcgc gcgatctcac cacgaaggcc cgggccacgt   1080
caccgacgac caggaacttg ctcacgaccc ccaagttcac cgtcgcttgg gattgggtcc   1140
caaagcgtcc ggcggtctgc acgatgacca aatggcagga ggtggacgaa atgctccgcg   1200
cagaatacgg cggctccttc cgcttctcgt ccgacgccat ctcgacaacc ttcaccacca   1260
atctgaccca gtacagtctg tcgcgcgttg atttaggaga ctgcattggc cgggatgccc   1320
gggaggccat cgacagaatg tttgcgcgta agtacaatgc cacacatatt aaggtgggcc   1380
agccgcaata ctaccttgcc acgggcggct ttctcatcgc gtaccagccc cttctctcaa   1440
atacgctcgc tgaactgtac gtgcgggagt atatgaggga acaggaccgc aagccccgca   1500
atgccacgcc tgcgccacta cgagaggcgc cttcagctaa tgcgtcggtg gaacgtatca   1560
agaccacctc ctcaatagag ttcgcccggc tgcaatttac gtacaaccac atccagcgcc   1620
acgtgaacga catgctgggc cgcatcgctg tcgcctggtg cgagctgcag aatcacgagc   1680
tgactctttg gaacgaggcc cgaaaactca accccaacgc gatcgcctcc gcaacagtcg   1740
gtagacgggt gagcgctcgc atgctaggag atgtcatggc tgtgtccacc tgcgtgcccg   1800
tcgctccgga caacgtgatt gtgcagaatt cgatgcgggt cttgataata ggctggagcc   1860
tcggtggcca tgcttcttgc cccttgggcc tccccccagc ccctcctccc cttcctgcac   1920
ccgtaccccc gtggtctttg aataaagtct gagtgggcgg c                       1961
```

<210> SEQ ID NO 2
<211> LENGTH: 1654

<212> TYPE: DNA
<213> ORGANISM: Human herpesvirus 2

<400> SEQUENCE: 2

```
tcaagctttt ggaccctcgt acagaagcta atacgactca ctatagggaa ataagagaga     60

aaagaagagt aagaagaaat ataagagcca ccatggccct tggacgggta ggcctagccg    120

tgggcctgtg gggcctactg tgggtgggtg tggtcgtggt gctggccaat gcctccccccg    180

gacgcacgat aacggtgggc ccgcgaggca acgcgagcaa tgctgccccc tccgcgtccc    240

cgcggaacgc atccgccccc cgaaccacac ccacgccccc acaaccccgc aaagcgacga    300

aatccaaggc ctccaccgcc aaaccggctc cgccccccaa gaccggaccc ccgaagacat    360

cctcggagcc cgtgcgatgc aaccgccacg acccgctggc ccggtacggc tcgcgggtgc    420

aaatccgatg ccggtttccc aactccacga ggactgagtc ccgtctccag atctggcgtt    480

atgccacggc gacggacgcc gaaatcggaa cagcgcctag cttagaagag gtgatggtga    540

acgtgtcggc cccgcccggg ggccaactgg tgtatgacag tgcccccaac cgaacggacc    600

cgcatgtaat ctgggcggag ggcgccggcc cgggcgccag cccgcgcctg tactcggttg    660

tcggcccgct gggtcggcag cggctcatca tcgaagagtt aaccctggag acacagggca    720

tgtactattg ggtgtggggc cggacggacc gcccgtccgc ctacgggacc tgggtccgcg    780

ttcgagtatt tcgccctccg tcgctgacca tccacccccca cgcggtgctg gagggccagc    840

cgtttaaggc gacgtgcacg gccgcaacct actacccggg caaccgcgcg gagttcgtct    900

ggtttgagga cggtcgccgc gtattcgatc cggcacagat acacacgcag acgcaggaga    960

accccgacgg cttttccacc gtctccaccg tgacctccgc ggccgtcggc gggcagggcc   1020

cccctcgcac cttcacctgc cagctgacgt ggcaccgcga ctccgtgtcg ttctctcggc   1080

gcaacgccag cggcacggcc tcggttctgc cgcggccgac cattaccatg gagtttacag   1140

gcgaccatgc ggtctgcacg gccggctgtg tgcccgaggg ggtcacgttt gcttggttcc   1200

tgggggatga ctcctcgccg gcggaaaagg tggccgtcgc gtcccagaca tcgtgcgggc   1260

gccccggcac cgccacgatc cgctccaccc tgccggtctc gtacgagcag accgagtaca   1320

tctgtagact ggcgggatac ccggacggaa ttccggtcct agagcaccac ggaagccacc   1380

agcccccgcc gcgggaccca accgagcggc aggtgatccg ggcggtggag ggggcgggga   1440

tcggagtggc tgtccttgtc gcggtggttc tggccgggac cgcggtagtg tacctgaccc   1500

atgcctcctc ggtacgctat cgtcggctgc ggtaatgata ataggctgga gcctcggtgg   1560

ccatgcttct tgccccttgg gcctcccccc agcccctcct ccccttcctg cacccgtacc   1620

cccgtggtct ttgaataaag tctgagtggg cggc                               1654
```

<210> SEQ ID NO 3
<211> LENGTH: 1393
<212> TYPE: DNA
<213> ORGANISM: Human herpesvirus 2

<400> SEQUENCE: 3

```
tcaagctttt ggaccctcgt acagaagcta atacgactca ctatagggaa ataagagaga     60

aaagaagagt aagaagaaat ataagagcca ccatggggcg tttgacctcc ggcgtcggga    120

cggcggccct gctagttgtc gcggtgggac tccgcgtcgt ctgcgccaaa tacgccttag    180

cagacccctc gcttaagatg gccgatccca atcgatttcg cgggaagaac cttccggttt    240

tggaccagct gaccgacccc cccggggtga agcgtgttta ccacattcag ccgagcctgg    300
```

-continued

```
aggacccgtt ccagcccccc agcatcccga tcactgtgta ctacgcagtg ctggaacgtg    360
cctgccgcag cgtgctccta catgccccat cggaggcccc ccagatcgtg cgcggggctt    420
cggacgaggc ccgaaagcac acgtacaacc tgaccatcgc ctggtatcgc atgggagaca    480
attgcgctat ccccatcacg gttatggaat acaccgagtg cccctacaac aagtcgttgg    540
gggtctgccc catccgaacg cagccccgct ggagctacta tgacagcttt agcgccgtca    600
gcgaggataa cctgggattc ctgatgcacg cccccgcctt cgagaccgcg ggtacgtacc    660
tgcggctagt gaagataaac gactggacgg agatcacaca atttatcctg gagcaccggg    720
cccgcgcctc ctgcaagtac gctctccccc tgcgcatccc cccggcagcg tgcctcacct    780
cgaaggccta ccaacagggc gtgacggtcg acagcatcgg gatgctaccc cgctttatcc    840
ccgaaaacca gcgcaccgtc gccctataca gcttaaaaat cgccgggtgg cacggcccca    900
agcccccgta caccagcacc ctgctgccgc cggagctgtc cgacaccacc aacgccacgc    960
aacccgaact cgttccggaa gaccccgagg actcggccct cttagaggat cccgccggga   1020
cggtgtcttc gcagatcccc ccaaactggc acatcccgtc gatccaggac gtcgcaccgc   1080
accacgcccc cgccgccccc agcaacccgg gcctgatcat cggcgcgctg gccggcagta   1140
ccctggcggt gctggtcatc ggcggtattg cgttttgggt acgccgccgc gctcagatgg   1200
cccccaagcg cctacgtctc ccccacatcc gggatgacga cgcgcccccc tcgcaccagc   1260
cattgtttta ctagtgataa taggctggag cctcggtggc catgcttctt gccccttggg   1320
cctcccccca gcccctcctc cccttcctgc acccgtaccc ccgtggtctt tgaataaagt   1380
ctgagtgggc ggc                                                      1393
```

<210> SEQ ID NO 4
<211> LENGTH: 1858
<212> TYPE: DNA
<213> ORGANISM: Human herpesvirus 2

<400> SEQUENCE: 4

```
tcaagctttt ggaccctcgt acagaagcta atacgactca ctatagggaa ataagagaga     60
aaagaagagt aagaagaaat ataagagcca ccatggctag gggggccggg ttggtttttt    120
ttgttggagt ttgggtcgta agctgcctcg cggcagcgcc cagaacgtcc tggaaacgcg    180
taacctcggg cgaagacgtg gtgttactcc ccgcgccggc ggggccggaa gaacgcactc    240
gggcccacaa actactgtgg gcagcggaac cgctggatgc ctgcggtccc ctgaggccgt    300
catgggtggc actgtggccc ccccgacgag tgcttgagac ggttgtcgat gcggcgtgca    360
tgcgcgcccc ggaaccgctc gctatcgcat acagtccccc gttccctgcg ggcgacgagg    420
gactttattc ggagttggcg tggcgcgatc gcgtagccgt ggtcaacgag agtttagtta    480
tctacggggc cctggagacg gacagtggtc tgtacaccct gtcagtggtg ggcctatccg    540
acgaggcccg ccaagtggcg tccgtggttc tcgtcgtcga gcccgcccct gtgcctaccc    600
cgacccccga tgactacgac gaggaggatg acgcgggcgt gagcgaacgc acgcccgtca    660
gcgttccccc cccaacaccc ccccgacgtc cccccgtcgc ccccccgacg caccctcgtg    720
ttatccctga ggtgagccac gtgcgggggg tgacggtcca catggaaacc ccggaggcca    780
ttctgtttgc gccaggggag acgtttggga cgaacgtctc catccacgca attgcccacg    840
acgacggtcc gtacgccatg gacgtcgtct ggatgcgatt tgatgtcccg tcctcgtgcg    900
ccgagatgcg gatctatgaa gcatgtctgt atcacccgca gctgcctgag tgtctgtctc    960
cggccgatgc gccgtgcgcc gtaagttcgt gggcgtaccg cctggcggtc cgcagctacg   1020
```

ccggctgctc caggactacg cccccacctc gatgttttgc tgaagctcgc atggaaccgg 1080
tccccgggtt ggcgtggctc gcatcaactg ttaatctgga attccagcat gcctctcccc 1140
aacacgccgg cctctatctg tgtgtggtgt atgtggacga ccatatccat gcctggggcc 1200
acatgaccat ctccacagcg gcccagtacc ggaatgcggt ggtggaacag catctccccc 1260
agcgccagcc cgagcccgta gaacccaccc gaccgcatgt gagagccccc cctcccgcac 1320
cctccgcgag aggcccgtta cgcttaggtg cggtcctggg ggcggccctg ttgctcgcgg 1380
ccctcgggct atccgcctgg gcgtgcatga cctgctggcg caggcgcagt tggcgggcgg 1440
ttaaaagtcg ggcctcggcg accggcccca cttacattcg agtagcggat agcgagctgt 1500
acgcggactg gagttcggac tcagagggcg agcgcgacgg ttccctgtgg caggaccctc 1560
cggagagacc cgactcaccg tccacaaatg gatccggctt tgagatctta tccccaacgg 1620
cgccctctgt ataccccccat agcgaagggc gtaaatcgcg ccgcccgctc accacctttg 1680
gttcaggaag cccgggacgt cgtcactccc aggcgtccta ttcttccgtc ttatggtaat 1740
gataataggc tggagcctcg gtggccatgc ttcttgcccc ttgggcctcc ccccagcccc 1800
tcctcccctt cctgcacccg tacccccgtg gtctttgaat aaagtctgag tgggcggc 1858

<210> SEQ ID NO 5
<211> LENGTH: 1330
<212> TYPE: DNA
<213> ORGANISM: Human herpesvirus 2

<400> SEQUENCE: 5
tcaagctttt ggaccctcgt acagaagcta atacgactca ctatagggaa ataagagaga 60
aaagaagagt aagaagaaat ataagagcca ccatgcccgg ccgctcgctg cagggcctgg 120
cgatcctggg cctgtgggtc tgcgccaccg gcctggtcgt ccgcggcccc acggtcagtc 180
tggtctcaga ctcactcgtg gatgccgggg ccgtggggcc ccagggcttc gtggaagagg 240
acctgcgtgt tttcggggag cttcattttg tgggggccca ggtcccccac acaaactact 300
acgacggcat catcgagctg tttcactacc ccctggggaa ccactgcccc cgcgttgtac 360
acgtggtcac actgaccgca tgcccccgcc gccccgccgt ggcgttcacc ttgtgtcgct 420
cgacgcacca cgcccacagc cccgcctatc cgaccctgga gctgggtctg gcgcggcagc 480
cgcttctgcg ggttcgaacg gcaacgcgcg actatgccgg tctgtatgtc ctgcgcgtat 540
gggtcggcag cgcgacgaac gccagcctgt ttgttttggg ggtggcgctc tctgccaacg 600
ggacgtttgt gtataacggc tcggactacg gctcctgcga tccggcgcag cttccctttt 660
cggccccgcg cctgggaccc tcgagcgtat acaccccccgg agcctcccgg cccacccctc 720
cacggacaac gacatcaccg tcctccccac gagacccgac ccccgccccc ggggacacag 780
ggacgcctgc tcccgcgagc ggcgagagag ccccgcccaa ttccacgcga tcggccagcg 840
aatcgagaca caggctaacc gtagcccagg taatccagat cgccataccg gcgtccatca 900
tcgcctttgt gtttctgggc agctgtatct gcttcatcca tagatgccag cgccgataca 960
ggcgcccccg cggccagatt tacaaccccg ggggcgtttc ctgcgcggtc aacgaggcgg 1020
ccatggcccg cctcggagcc gagctgcgat cccacccaaa cacccccccc aaaccccgac 1080
gccgttcgtc gtcgtccacg accatgcctt ccctaacgtc gatagctgag gaatcggagc 1140
caggtccagt cgtgctgctg tccgtcagtc ctcggccccg cagtggcccg acggcccccc 1200
aagaggtcta gtgataatag gctggagcct cggtggccat gcttcttgcc ccttgggcct 1260 cccccagcc cctcctcccc ttcctgcacc cgtacccccg tggtctttga ataaagtctg 1320
agtgggcggc 1330

<210> SEQ ID NO 6
<211> LENGTH: 2515
<212> TYPE: DNA
<213> ORGANISM: Human herpesvirus 2

<400> SEQUENCE: 6
tcaagctttt ggaccctcgt acagaagcta atacgactca ctatagggaa ataagagaga 60
aaagaagagt aagaagaaat ataagagcca ccatgcgcgg ggggggctta gtttgcgcgc 120
tggtcgtggg ggcgctcgta gccgcggtcg cgtcggcggc tccggctgcc ccacgcgctt 180
caggtggtgt cgctgcgacc gttgcggcga atggtggtcc cgccagccaa ccgcctcccg 240
tcccgagccc cgcgaccact aaggcccgga agcggaagac caagaagcca cccaagcggc 300
ccgaggcgac tccgccccca gacgccaacg cgaccgtcgc cgccggccac gccactctgc 360
gtgcgcacct gcgggaaatc aaggtcgaga acgcggacgc ccagttttac gtgtgcccgc 420
cgccgactgg cgccacggtg gtgcagtttg agcaacctag gcgctgcccg acgcgaccag 480
aggggcagaa ctacaccgag ggcatagcgg tggtctttaa ggaaaacatc gccccgtaca 540
aattcaaggc caccatgtac tacaaagacg tgaccgtgtc gcaggtgtgg ttcggccacc 600
gctactccca gtttatgggg atattcgagg accgcgcccc cgttcccttc gaagaggtga 660
ttgacaaaat taacgccaag ggggtctgcc gcagtacggc gaagtacgtc cggaacaaca 720
tggagaccac tgccttccac cgggacgacc acgaaacaga catggagctc aaaccggcga 780
aagtcgccac gcgcacgagc cgggggtggc acaccaccga cctcaaatac aatccttcgc 840
gggtggaagc attccatcgg tatggcacga ccgtcaactg tatcgtagag gaggtggatg 900
cgcggtcggt gtacccctac gatgagttcg tgctggcaac gggcgatttt gtgtacatgt 960
ccccttttta cggctaccgg gaaggtagtc acaccgagca caccagttac gccgccgacc 1020
gctttaagca agtggacggc ttctacgcgc gcgacctcac cacaaaggcc cgggccacgt 1080
cgccgacgac ccgcaatttg ctgacgaccc ccaagtttac cgtggcctgg gactgggtgc 1140
ctaagcgacc ggcggtctgt accatgacaa agtggcagga ggtggacgaa atgctccgcg 1200
ctgaatacgg tggctctttc cgcttctctt ccgacgccat ctccaccacg ttcaccacca 1260
acctgaccca atactcgctc tcgagagtcg atctgggaga ctgcattggc cgggatgccc 1320
gcgaggcaat tgaccgcatg ttcgcgcgca agtacaacgc tacgcacata aaggttggcc 1380
aaccccagta ctacctagcc acgggggggct tcctcatcgc ttatcaaccc ctcctcagca 1440
acacgctcgc cgagctgtac gtgcgggaat atatgcggga acaggaccgc aaaccccgaa 1500
acgccacgcc cgcgccgctg cgggaagcac cgagcgccaa cgcgtccgtg gagcgcatca 1560
agacgacatc ctcgattgag tttgctcgtc tgcagtttac gtataaccac atacagcgcc 1620
atgtaaacga catgctcggg cgcatcgccg tcgcgtggtg cgagctccaa aatcacgagc 1680
tcactctgtg gaacgaggca cgcaagctca atcccaacgc catcgcatcc gccaccgtag 1740
gccggcgggt gagcgctcgc atgctcgggg atgtcatggc cgtctccacg tgcgtgcccg 1800
tcgccccgga caacgtgatc gtgcaaaata gcatgcgcgt ttcttcgcgg ccggggacgt 1860
gctacagccg cccgctggtt agctttcggt acgaagacca aggcccgctg attgaggggc 1920
agctgggtga gaacaacgag ctgcgcctca cccgcgatgc gttagagccg tgtaccgtcg 1980
gccaccggcg ctacttcatc ttcggagggg gatacgtata cttcgaagaa tatgcgtact 2040

```
ctcaccaatt gagtcgcgcc gatgtcacca ctgttagcac cttcatcgac ctgaacatca   2100

ccatgctgga ggaccacgag ttcgtgcccc tggaggtcta cacacgccac gagatcaagg   2160

attccggcct actggactac accgaagtcc agagacgaaa tcagctgcac gatctccgct   2220

ttgctgacat cgatactgtt atccgcgccg acgccaacgc cgccatgttc gcaggtctgt   2280

gtgcgttttt cgagggtatg ggtgacttag ggcgcgcggt gggcaaggtc gtcatggggg   2340

tagtcggggg cgtggtgtcg gccgtctcgg gcgtctcctc ctttatgtct aacccctgat   2400

aataggctgg agcctcggtg gccatgcttc ttgccccttg ggcctccccc cagcccctcc   2460

tccccttcct gcacccgtac cccgtggtc tttgaataaa gtctgagtgg gcggc        2515
```

<210> SEQ ID NO 7
<211> LENGTH: 1552
<212> TYPE: DNA
<213> ORGANISM: Human herpesvirus 2

<400> SEQUENCE: 7

```
tcaagctttt ggaccctcgt acagaagcta atacgactca ctatagggaa ataagagaga     60

aaagaagagt aagaagaaat ataagagcca ccatggccct tggacgggtg ggcctagccg    120

tgggcctgtg gggcctgctg tgggtgggtg ttgtcgtggt gctggccaat gcctcccctg    180

gacgcacgat aacggtgggc ccgcggggga acgcgagcaa tgccgcccca tccgcgtccc    240

cgcggaacgc atccgccccc cgaaccacac ccactccccc ccaaccccgc aaagcgacga    300

aaagtaaggc ctccaccgcc aaaccggccc cgccccccaa gaccgggccc ccgaagacat    360

cttctgagcc cgtgcgctgc aaccgccacg acccgctggc ccggtacggc tcgcgggtgc    420

aaatccgatg tcgatttccc aactccactc gcacggaatc ccgcctccag atctggcgtt    480

atgccacggc gacggacgcc gagattggaa ctgcgcctag cttagaggag gtgatggtaa    540

acgtgtcggc cccgcccggg ggccaactgg tgtatgatag cgcacctaac cgaacggacc    600

cgcacgtgat ttgggcggag ggcgccggac ctggcgcctc accgcggctg tactcggtcg    660

tcgggccgct gggtcggcag agacttatca tcgaagagct gaccctcgag acacagggca    720

tgtattattg ggtgtggggc cggacggacc gcccgtccgc gtacgggacc tgggtgcgcg    780

ttcgcgtgtt ccgccctcct tcgctgacca tccaccccca cgcggtgctg gagggccagc    840

cgtttaaagc gacgtgcacc gccgccacct actacccggg caaccgcgcg gagttcgtct    900

ggttcgagga cggtcgccgg gtattcgatc cggcccagat acatacgcag acgcaggaaa    960

accccgacgg cttttccacc gtctccaccg tgacctccgc ggccgtcggc ggccagggcc   1020

ccccgcgcac cttcacctgt cagctgacgt ggcaccgcga ctccgtgtcg ttctctcggc   1080

gcaatgccag cggcacggca tcggtgctgc cacggccaac cattaccatg gagtttacgg   1140

gcgaccatgc ggtctgcacg gccggctgtg tgcccgaggg ggtgacgttt gcctggttcc   1200

tgggggacga ctcctcgccg gccgagaagg tggccgtcgc gtcccagacc tcgtgcggtc   1260

gccccggcac cgccacgatc cgctccacac tgccggtctc gtacgagcag accgagtaca   1320

tctgccggct ggcgggatac ccggacggaa ttccggtcct agagcaccat ggcagccacc   1380

agcccccgcc gcgggacccc accgaacggc aggtgattcg ggcagtggaa gggtgataat   1440

aggctggagc ctcggtggcc atgcttcttg ccccttgggc ctccccccag cccctcctcc   1500

ccttcctgca cccgtacccc cgtggtcttt gaataaagtc tgagtgggcg gc           1552
```

<210> SEQ ID NO 8

<211> LENGTH: 1462
<212> TYPE: DNA
<213> ORGANISM: Human herpesvirus 2

<400> SEQUENCE: 8
tcaagctttt ggaccctcgt acagaagcta atacgactca ctatagggaa ataagagaga 60
aaagaagagt aagaagaaat ataagagcca ccatggctcg cggggccggg ttggtgtttt 120
ttgttggagt ttgggtcgta tcgtgcctgg cggcagcacc cagaacgtcc tggaaacggg 180
ttacctcggg cgaggacgtg gtgttgcttc cggcgcccgc ggggccggag gaacgcacac 240
gggcccacaa actactgtgg gccgcggaac ccctggatgc ctgcggtccc ctgaggccgt 300
cgtgggtggc gctgtggccc ccgcgacggg tgctcgaaac ggtcgtggat gcggcgtgca 360
tgcgcgcccc ggaaccgctc gccatagcat acagtccccc gttccccgcg ggcgacgagg 420
gactgtattc ggagttggcg tggcgcgatc gcgtagccgt ggtcaacgag agtctggtca 480
tctacggggc cctggagacg gacagcggtc tgtacaccct gtccgtggtc ggcctaagcg 540
acgaggcgcg ccaagtggcg tcggtggttc tggtcgtgga gcccgcccct gtgccgaccc 600
cgacccccga cgactacgac gaagaagacg acgcgggcgt gagcgaacgc acgccggtca 660
gcgtaccccc cccgacccca ccccgtcgtc cccccgtcgc ccccccctacg caccctcgtg 720 ttatccccga ggtgtcccac gtgcgcgggg taacggtcca tatggagacc ccggaggcca 780
ttctgtttgc ccccggagag acgtttggga cgaacgtctc catccacgcc attgcccatg 840
acgacggtcc gtacgccatg gacgtcgtct ggatgcggtt tgacgtgccg tcctcgtgcg 900
ccgagatgcg gatctacgaa gcttgtctgt atcacccgca gcttccagaa tgtctatctc 960
cggccgacgc gccgtgcgct gtaagttcct gggcgtaccg cctggcggtc cgcagctacg 1020
ccggctgttc caggactacg cccccgccgc gatgttttgc cgaggctcgc atggaaccgg 1080
tcccggggtt ggcgtggtta gcctccaccg tcaacctgga attccagcac gcctcccctc 1140
agcacgccgg cctttacctg tgcgtggtgt acgtggacga tcatatccac gcctggggcc 1200
acatgaccat ctctaccgcg gcgcagtacc ggaacgcggt ggtggaacag cacttgcccc 1260
agcgccagcc tgaacccgtc gagcccaccc gcccgcacgt aagagcaccc cctcccgcgc 1320
cttccgcgcg cggcccgctg cgctgataat aggctggagc ctcggtggcc atgcttcttg 1380
ccccttgggc ctccccccag cccctcctcc ccttcctgca cccgtacccc cgtggtcttt 1440
gaataaagtc tgagtgggcg gc 1462

<210> SEQ ID NO 9
<211> LENGTH: 4096
<212> TYPE: DNA
<213> ORGANISM: Human herpesvirus 2

<400> SEQUENCE: 9
tcaagctttt ggaccctcgt acagaagcta atacgactca ctatagggaa ataagagaga 60
aaagaagagt aagaagaaat ataagagcca ccatgtcggc ggagcagcgg aagaagaaga 120
agacgacgac gacgacgcag ggccgcgggg ccgaggtcgc gatggcggac gaggacgggg 180
gacgtctccg ggccgcggcg gagacgaccg gcggccccgg atctccggat ccagccgacg 240
gaccgccgcc cacccccgaac ccggaccgtc gccccgccgc gcggcccggg ttcgggtggc 300
acggtgggcc ggaggagaac gaagacgagg ccgacgacgc cgccgccgat gccgatgccg 360
acgaggcggc cccggcgtcc ggggaggccg tcgacgagcc tgccgcggac ggcgtcgtct 420
cgccgcggca gctggccctg ctggcctcga tggtggacga ggccgttcgc acgatcccgt 480

-continued

```
cgccccccc ggagcgcgac ggcgcgcaag aagaagcggc ccgctcgcct tctccgccgc    540
ggaccccctc catgcgcgcc gattatggcg aggagaacga cgacgacgac gacgacgacg    600
atgacgacga ccgcgacgcg ggccgctggg tccgcggacc ggagacgacg tccgcggtcc    660
gcggggcgta cccggacccc atggccagcc tgtcgccgcg acccccggcg ccccgccgac    720
accaccacca ccaccaccac cgccgccggc gcgccccccg ccggcgctcg gccgcctctg    780
actcatcaaa atccggatcc tcgtcgtcgg cgtcctccgc ctcctcctcc gcctcctcct    840
cctcgtctgc atccgcctcc tcgtctgacg acgacgacga cgacgacgcc gcccgcgccc    900
ccgccagcgc cgcagaccac gccgcgggcg ggaccctcgg cgcggacgac gaggaggcgg    960
gggtgcccgc gagggccccg ggggcggcgc cccggccgag cccgcccagg gccgagcccg   1020
ccccggcccg gacccccgcg gcgaccgcgg gccgcctgga gcgccgccgg gcccgcgcgg   1080
cggtggccgg ccgcgacgcc acgggccgct tcacggccgg gcggccccgg cgggtcgagc   1140
tggacgccga cgcggcctcc ggcgccttct acgcgcgcta ccgcgacggg tacgtcagcg   1200
gggagccgtg gcccggggcc ggcccccgc ccccggggcg cgtgctgtac ggcgggctgg   1260
gcgacagccg ccccggcctc tggggggcgc ccgaggcgga ggaggcgcgg gcccggttcg   1320
aggcctcggg cgccccggcg cccgtgtggg cgcccgagct gggcgacgcg gcgcagcagt   1380
acgccctgat cacgcggctg ctgtacacgc cggacgcgga ggcgatgggg tggctccaga   1440
acccgcgcgt ggcgcccggg gacgtggcgc tggaccaggc ctgcttccgg atctcgggcg   1500
cggcgcgcaa cagcagctcc ttcatctccg gcagcgtggc gcgggccgtg ccccacctgg   1560
ggtacgccat ggcggcgggc cgcttcggct ggggcctggc gcacgtggcg gccgccgtgg   1620
ccatgagccg ccgctacgac cgcgcgcaga agggcttcct gctgaccagc ctgcgccgcg   1680
cctacgcgcc cctgctggcg cgcgagaacg cggcgctgac cggggcgcga acccccgacg   1740
acggcggcga cgccaaccgc cacgacggcg acgacgcccg cgggaagccc gccgccgccg   1800
ccgccccgtt gccgtcggcg gcggcgtcgc cggccgacga gcgcgcggtg cccgccggct   1860
acggcgccgc gggggtgctc gccgccctgg ggcgcctgag cgccgcgccc gcctccgcgc   1920
cggccggggc cgacgacgac gacgacgacg acggcgccgg cggtggtggc ggcggccggc   1980
gcgcggaggc gggccgcgtg gccgtggagt gcctggccgc ctgccgcggg atcctggagg   2040
cgctggcgga gggcttcgac ggcgacctgg cggccgtgcc ggggctggcc ggagcccggc   2100
ccgccgcgcc cccgcgcccg gggcccgcgg gcgcggccgc cccgccgcac gccgacgcgc   2160
cccgcctgcg cgcctggctg cgcgagctgc ggttcgtgcg cgacgcgctg gtgctgatgc   2220
gcctgcgcgg ggacctgcgc gtggccggcg gcagcgaggc cgccgtggcc gccgtgcgcg   2280
ccgtgagcct ggtcgccggg gccctgggcc cggcgctgcc gcggagcccg cgcctgctga   2340
gctccgccgc cgccgccgcc gcggacctgc tcttccagaa ccagagcctg cgccccctgc   2400
tggccgacac cgtcgccgcg gccgactcgc tcgccgcgcc cgcctccgcg ccgcgggagg   2460
ccgcggacgc cccccgcccc gcggccgccc ctcccgcggg ggccgcgccc cccgccccgc   2520
cgacgccgcc gccgcggccg ccgcgccccg cggcgctgac ccgccggccc gccgagggcc   2580
ccgacccgca gggcggctgg cgccgccagc cgccggggcc cagccacacg ccggcgccct   2640
cggccgccgc cctggaggcc tactgcgccc cgcgggccgt ggccgagctc acggaccacc   2700
cgctcttccc cgcgccgtgg cgcccggccc tcatgttcga cccgcgcgcg ctggcctcgc   2760
tggccgcgcg ctgcgccgcc ccgccccccg gcggcgcgcc cgccgccttc ggcccgctgc   2820
```

-continued gcgcctcggg cccgctgcgc cgcgcggcgg cctggatgcg ccaggtgccc gacccggagg 2880
acgtgcgcgt ggtgatcctc tactcgccgc tgccgggcga ggacctggcc gcgggccgcg 2940
ccgggggcgg gcccccccg gagtggtccg ccgagcgcgg cgggctgtcc tgcctgctgg 3000
cggccctggg caaccggctc tgcgggcccg ccacggccgc ctgggcgggc aactggaccg 3060
gcgcccccga cgtctcggcg ctgggcgcgc agggcgtgct gctgctgtcc acgcgggacc 3120
tggccttcgc cggcgccgtg gagttcctgg ggctgctggc cggcgcctgc gaccgccgcc 3180
tcatcgtcgt caacgccgtg cgcgccgcgg cctggcccgc cgctgccccc gtggtctcgc 3240
ggcagcacgc ctacctggcc tgcgaggtgc tgcccgccgt gcagtgcgcc gtgcgctggc 3300
cggcggcgcg ggacctgcgc cgcaccgtgc tggcctccgg ccgcgtgttc gggccggggg 3360
tcttcgcgcg cgtggaggcc gcgcacgcgc gcctgtaccc cgacgcgccg ccgctgcgcc 3420
tctgccgcgg ggccaacgtg cggtaccgcg tgcgcacgcg cttcggcccc gacacgctgg 3480
tgcccatgtc cccgcgcgag taccgccgcg ccgtgctccc ggcgctggac ggccgggccg 3540
ccgcctcggg cgcgggcgac gccatggcgc ccggcgcgcc ggacttctgc gaggacgagg 3600
cgcactcgca ccgcgcctgc gcgcgctggg gcctgggcgc gccgctgcgg cccgtctacg 3660
tggcgctggg gcgcgacgcc gtgcgcggcg gcccggcgga gctgcgcggg ccgcggcggg 3720
agttctgcgc gcgggcgctg ctcgagcccg acggcgacgc gcccccgctg gtgctgcgcg 3780
acgacgcgga cgcgggcccg cccccgcaga tacgctgggc gtcggccgcg ggccgcgcgg 3840
ggacggtgct ggccgcggcg ggcggcggcg tggaggtggt ggggaccgcc gcggggctgg 3900
ccacgccgcc gaggcgcgag cccgtggaca tggacgcgga gctggaggac gacgacgacg 3960
gactgtttgg ggagtgatga taataggctg gagcctcggt ggccatgctt cttgcccctt 4020
gggcctcccc ccagcccctc ctccccttcc tgcacccgta cccccgtggt ctttgaataa 4080
agtctgagtg ggcggc 4096

<210> SEQ ID NO 10
<211> LENGTH: 997
<212> TYPE: DNA
<213> ORGANISM: Human herpesvirus 2

<400> SEQUENCE: 10
tcaagctttt ggaccctcgt acagaagcta atacgactca ctatagggaa ataagagaga 60
aaagaagagt aagaagaaat ataagagcca ccatgcccgg ccgctcgctg cagggcctgg 120
cgatcctggg cctgtgggtc tgcgccaccg gcctggtcgt ccgcggcccc acggtcagtc 180
tggtctcaga ctcactcgtg gatgccgggg ccgtggggcc ccagggcttc gtggaagagg 240
acctgcgtgt tttcggggag cttcattttg tgggggccca ggtcccccac acaaactact 300
acgacggcat catcgagctg tttcactacc ccctggggaa ccactgcccc cgcgttgtac 360
acgtggtcac actgaccgca tgcccccgcc gccccgccgt ggcgttcacc ttgtgtcgct 420
cgacgcacca cgcccacagc cccgcctatc cgaccctgga gctgggtctg gcgcggcagc 480
cgcttctgcg ggttcgaacg gcaacgcgcg actatgccgg tctgtatgtc ctgcgcgtat 540
gggtcggcag cgcgacgaac gccagcctgt ttgttttggg ggtggcgctc tctgccaacg 600
ggacgtttgt gtataacggc tcggactacg gctcctgcga tccggcgcag cttccctttt 660
cggccccgcg cctgggaccc tcgagcgtat acacccccgg agcctcccgg cccaccccctc 720 cacggacaac gacatccccg tcctccccta gagacccgac cccgccccc ggggacacag 780 gaacgcctgc gcccgcgagc ggcgagagag ccccgcccaa ttccacgcga tcggccagcg 840

```
aatcgagaca caggctaacc gtagcccagg taatccagtg ataataggct ggagcctcgg    900

tggccatgct tcttgcccct tgggcctccc cccagcccct cctccccttc ctgcacccgt    960

acccccgtgg tctttgaata aagtctgagt gggcggc                             997


<210> SEQ ID NO 11
<211> LENGTH: 1228
<212> TYPE: DNA
<213> ORGANISM: Human herpesvirus 2

<400> SEQUENCE: 11

tcaagctttt ggaccctcgt acagaagcta atacgactca ctatagggaa ataagagaga     60

aaagaagagt aagaagaaat ataagagcca ccatggggcg tttgacctcc ggcgtcggga    120

cggcggccct gctagttgtc gcggtgggac tccgcgtcgt ctgcgccaaa tacgccttag    180

cagacccctc gcttaagatg gccgatccca atcgatttcg cgggaagaac cttccggttt    240

tggaccagct gaccgacccc cccggggtga agcgtgttta ccacattcag ccgagcctgg    300

aggacccgtt ccagcccccc agcatcccga tcactgtgta ctacgcagtg ctggaacgtg    360

cctgccgcag cgtgctccta catgccccat cggaggcccc ccagatcgtg cgcggggctt    420

cggacgaggc ccgaaagcac acgtacaacc tgaccatcgc ctggtatcgc atgggagaca    480

attgcgctat ccccatcacg gttatggaat acaccgagtg cccctacaac aagtcgttgg    540

gggtctgccc catccgaacg cagccccgct ggagctacta tgacagcttt agcgccgtca    600

gcgaggataa cctgggattc ctgatgcacg cccccgcctt cgagaccgcg ggtacgtacc    660

tgcggctagt gaagataaac gactggacgg agatcacaca atttatcctg gagcaccggg    720

cccgcgcctc ctgcaagtac gctctccccc tgcgcatccc cccggcagcg tgcctcacct    780

cgaaggccta ccaacagggc gtgacggtcg acagcatcgg gatgctaccc cgctttatcc    840

ccgaaaacca gcgcaccgtc gccctataca gcttaaaaat cgccgggtgg cacggcccca    900

agcccccgta caccagcacc ctgctgccgc cggagctgtc cgacaccacc aacgccacgc    960

aacccgaact cgttccggaa gaccccgagg actcggccct cttagaggat cccgccggga   1020

cggtgtcttc gcagatcccc ccaaactggc acatcccgtc gatccaggac gtcgcgccgc   1080

accacgcccc cgccgccccc agcaacccgt gataataggc tggagcctcg gtggccatgc   1140

ttcttgcccc ttgggcctcc ccccagcccc tcctcccctt cctgcacccg tacccccgtg   1200

gtctttgaat aaagtctgag tgggcggc                                      1228


<210> SEQ ID NO 12
<211> LENGTH: 2706
<212> TYPE: DNA
<213> ORGANISM: Human herpesvirus 2

<400> SEQUENCE: 12

atgcgcgggg ggggcttggt ttgcgcgctg gtcgtggggg cgctggtggc cgcggtggcg     60

tcggcggccc cggcggcccc ccgcgcctcg ggcggcgtgg ccgcgaccgt cgcggcgaac    120

gggggtcccg cctcccagcc gcccccgtc ccgagccccg cgaccaccaa ggcccggaag    180

cggaaaacca aaaagccgcc caagcggccc gaggcgaccc cgccccccga cgccaacgcg    240

accgtcgccg ccggccacgc cacgctgcgc gcgcacctgc gggaaatcaa ggtcgagaac    300

gccgatgccc agttttacgt gtgcccgccc ccgacgggcg ccacggtggt gcagtttgag    360

cagccgcgcc gctgcccgac gcgcccggag gggcagaact acacggaggg catcgcggtg    420
```

-continued

```
gtcttcaagg agaacatcgc cccgtacaaa ttcaaggcca ccatgtacta caaagacgtg    480
accgtgtcgc aggtgtggtt cggccaccgc tactcccagt ttatggggat attcgaggac    540
cgcgccccccg ttcccttcga ggaggtgatc gacaagatta acgccaaggg ggtctgccgc    600
tccacggcca agtacgtgcg gaacaacatg gagaccaccg cgtttcaccg ggacgaccac    660
gagaccgaca tggagctcaa gccggcgaag gtcgccacgc gcacgagccg ggggtggcac    720
accaccgacc tcaagtacaa cccctcgcgg gtggaggcgt tccatcggta cggcacgacg    780
gtcaactgca tcgtcgagga ggtggacgcg cggtcggtgt acccgtacga tgagtttgtg    840
ctggcgacgg gcgactttgt gtacatgtcc ccgttttacg gctaccggga ggggtcgcac    900
accgagcaca ccagctacgc cgccgaccgc ttcaagcagg tcgacggctt ctacgcgcgc    960
gacctcacca cgaaggcccg ggccacgtcg ccgacgaccc gcaacttgct gacgaccccc   1020
aagtttaccg tggcctggga ctgggtgccg aagcgaccgg cggtctgcac catgaccaag   1080
tggcaggagg tggacgagat gctccgcgcc gagtacggcg gctccttccg cttctcctcc   1140
gacgccatct cgaccacctt caccaccaac ctgacccagt actcgctctc gcgcgtcgac   1200
ctgggcgact gcatcggccg ggatgcccgc gaggccatcg accgcatgtt tgcgcgcaag   1260
tacaacgcca cgcacatcaa ggtgggccag ccgcagtact acctggccac gggggggcttc   1320
ctcatcgcgt accagcccct cctcagcaac acgctcgccg agctgtacgt gcgggagtac   1380
atgcgggagc aggaccgcaa gccccggaat gccacgcccg cgccactgcg ggaggcgccc   1440
agcgccaacg cgtccgtgga gcgcatcaag accacctcct cgatcgagtt cgcccggctg   1500
cagtttacgt ataaccacat acagcgccac gtgaacgaca tgctggggcg catcgccgtc   1560
gcgtggtgcg agctgcagaa ccacgagctg actctctgga acgaggcccg caagctcaac   1620
cccaacgcca tcgcctccgc caccgtcggc cggcgggtga gcgcgcgcat gctcggagac   1680
gtcatggccg tctccacgtg cgtgcccgtc gccccggaca acgtgatcgt gcagaactcg   1740
atgcgcgtca gctcgcggcc ggggacgtgc tacagccgcc ccctggtcag ctttcggtac   1800
gaagaccagg gcccgctgat cgaggggcag ctgggcgaga acaacgagct gcgcctcacc   1860
cgcgacgcgc tcgagccgtg caccgtgggc caccggcgct acttcatctt cggcgggggc   1920
tacgtgtact tcgaggagta cgcgtactct caccagctga gtcgcgccga cgtcaccacc   1980
gtcagcacct tcatcgacct gaacatcacc atgctggagg accacgagtt tgtgcccctg   2040
gaggtctaca cgcgccacga gatcaaggac agcggcctgc tggactacac ggaggtccag   2100
cgccgcaacc agctgcacga cctgcgcttt gccgacatcg acacggtcat ccgcgccgac   2160
gccaacgccg ccatgttcgc ggggctgtgc gcgttcttcg aggggatggg ggacttgggg   2220
cgcgcggtcg gcaaggtcgt catgggagta gtgggggggcg tggtgtcggc cgtctcgggc   2280
gtgtcctcct ttatgtccaa cccccttcggg gcgcttgccg tggggctgct ggtcctggcc   2340
ggcctggtcg cggccttctt cgccttccgc tacgtcctgc aactgcaacg caatcccatg   2400
aaggccctgt atccgctcac caccaaggaa ctcaagactt ccgaccccgg gggcgtgggc   2460
ggggaggggg aggaaggcgc ggagggggggc gggtttgacg aggccaagtt ggccgaggcc   2520
cgagaaatga tccgatatat ggctttggtg tcggccatgg agcgcacgga acacaaggcc   2580
agaaagaagg gcacgagcgc cctgctcagc tccaaggtca ccaacatggt tctgcgcaag   2640
cgcaacaaag ccaggtactc tccgctccac aacgaggacg aggccggaga cgaagacgag   2700
ctctaa                                                               2706
```

<210> SEQ ID NO 13
<211> LENGTH: 1443
<212> TYPE: DNA
<213> ORGANISM: Human herpesvirus 2

<400> SEQUENCE: 13
atggcccttg gacgggtggg cctagccgtg ggcctgtggg gcctgctgtg ggtgggtgtg 60
gtcgtggtgc tggccaatgc ctcccccgga cgcacgataa cggtgggccc gcgggggaac 120
gcgagcaatg ccgccccctc cgcgtccccg cggaacgcat ccgccccccg aaccacaccc 180
acgccccccc aaccccgcaa ggcgacgaaa agtaaggcct ccaccgccaa accggccccg 240
ccccccaaga ccgggccccc gaagacatcc tcggagcccg tgcgatgcaa ccgccacgac 300
ccgctggccc ggtacggctc gcgggtgcaa atccgatgcc ggtttcccaa ctccacccgc 360
acggagtccc gcctccagat ctggcgttat gccacggcga cggacgccga gatcggaacg 420
gcgcctagct tagaggaggt gatggtaaac gtgtcggccc cgcccggggg ccaactggtg 480
tatgacagcg cccccaaccg aacggacccg cacgtgatct gggcggaggg cgccggcccg 540
ggcgccagcc cgcggctgta ctcggtcgtc gggccgctgg gtcggcagcg gctcatcatc 600
gaagagctga ccctggagac ccagggcatg tactactggg tgtggggccg gacggaccgc 660
ccgtccgcgt acgggacctg ggtgcgcgtt cgcgtgttcc gccctccgtc gctgaccatc 720
cacccccacg cggtgctgga gggccagccg tttaaggcga cgtgcacggc cgccacctac 780
tacccgggca accgcgcgga gttcgtctgg ttcgaggacg gtcgccgggt attcgatccg 840
gcccagatac acacgcagac gcaggagaac cccgacggct tttccaccgt ctccaccgtg 900
acctccgcgg ccgtcggcgg ccagggcccc ccgcgcacct tcacctgcca gctgacgtgg 960
caccgcgact ccgtgtcgtt ctctcggcgc aacgccagcg gcacggcatc ggtgctgccg 1020
cggccaacca ttaccatgga gtttacgggc gaccatgcgg tctgcacggc cggctgtgtg 1080
cccgaggggg tgacgtttgc ctggttcctg ggggacgact cctcgccggc ggagaaggtg 1140
gccgtcgcgt cccagacatc gtgcgggcgc cccggcaccg ccacgatccg ctccaccctg 1200
ccggtctcgt acgagcagac cgagtacatc tgccggctgg cgggataccc ggacggaatt 1260
ccggtcctag agcaccacgg cagccaccag cccccgccgc gggaccccac cgagcggcag 1320
gtgatccggg cggtggaggg ggcggggatc ggagtggctg tccttgtcgc ggtggttctg 1380
gccgggaccg cggtagtgta cctcacccac gcctcctcgg tgcgctatcg tcggctgcgg 1440
taa 1443

<210> SEQ ID NO 14
<211> LENGTH: 1182
<212> TYPE: DNA
<213> ORGANISM: Human herpesvirus 2

<400> SEQUENCE: 14
atggggcgtt tgacctccgg cgtcgggacg gcggccctgc tagttgtcgc ggtgggactc 60
cgcgtcgtct gcgccaaata cgccttagca gacccctcgc ttaagatggc cgatcccaat 120
cgatttcgcg ggaagaacct tccggttttg gaccagctga ccgacccccc cggggtgaag 180
cgtgtttacc acattcagcc gagcctggag gacccgttcc agccccccag catcccgatc 240
actgtgtact acgcagtgct ggaacgtgcc tgccgcagcg tgctcctaca tgccccatcg 300
gaggcccccc agatcgtgcg cggggcttcg gacgaggccc gaaagcacac gtacaacctg 360
accatcgcct ggtatcgcat gggagacaat tgcgctatcc ccatcacggt tatggaatac 420

```
accgagtgcc cctacaacaa gtcgttgggg gtctgcccca tccgaacgca gccccgctgg    480

agctactatg acagctttag cgccgtcagc gaggataacc tgggattcct gatgcacgcc    540

cccgccttcg agaccgcggg tacgtacctg cggctagtga agataaacga ctggacggag    600

atcacacaat ttatcctgga gcaccgggcc cgcgcctcct gcaagtacgc tctcccctg    660

cgcatccccc cggcagcgtg cctcacctcg aaggcctacc aacagggcgt gacggtcgac    720

agcatcggga tgctaccccg ctttatcccc gaaaaccagc gcaccgtcgc cctatacagc    780

ttaaaaatcg ccgggtggca cggccccaag cccccgtaca ccagcaccct gctgccgccg    840

gagctgtccg acaccaccaa cgccacgcaa cccgaactcg ttccggaaga ccccgaggac    900

tcggccctct tagaggatcc cgccgggacg gtgtcttcgc agatcccccc aaactggcac    960

atcccgtcga tccaggacgt cgcgccgcac cacgcccccg ccgcccccag caacccgggc   1020

ctgatcatcg gcgcgctggc cggcagtacc ctggcggtgc tggtcatcgg cggtattgcg   1080

ttttgggtac gccgccgcgc tcagatggcc cccaagcgcc tacgtctccc ccacatccgg   1140

gatgacgacg cgccccctc gcaccagcca ttgttttact ag                       1182
```

<210> SEQ ID NO 15
<211> LENGTH: 1647
<212> TYPE: DNA
<213> ORGANISM: Human herpesvirus 2

<400> SEQUENCE: 15

```
atggctcgcg gggccgggtt ggtgtttttt gttggagttt gggtcgtatc gtgcctggcg     60

gcagcaccca gaacgtcctg gaaacgggta acctcgggcg aggacgtggt gttgcttccg    120

gcgcccgcgg ggccggagga acgcacccgg gcccacaaac tactgtgggc cgcggaaccc    180

ctggatgcct gcggtcccct gcgcccgtcg tgggtggcgc tgtggccccc ccgacgggtg    240

ctcgagacgg tcgtggatgc ggcgtgcatg cgcgccccgg aaccgctcgc catagcatac    300

agtcccccgt tccccgcggg cgacgaggga ctgtattcgg agttggcgtg gcgcgatcgc    360

gtagccgtgg tcaacgagag tctggtcatc tacggggccc tggagacgga cagcggtctg    420

tacaccctgt ccgtggtcgg cctaagcgac gaggcgcgcc aagtggcgtc ggtggttctg    480

gtcgtggagc ccgcccctgt gccgaccccg acccccgacg actacgacga agaagacgac    540

gcgggcgtga gcgaacgcac gccggtcagc gttcccccc caacccccc ccgtcgtccc    600

cccgtcgccc ccccgacgca ccctcgtgtt atccccgagg tgtcccacgt gcgcggggta    660

acggtccata tggagacccc ggaggccatt ctgtttgccc ccggggagac gtttgggacg    720

aacgtctcca tccacgccat tgcccacgac gacggtccgt acgccatgga cgtcgtctgg    780

atgcggtttg acgtgccgtc ctcgtgcgcc gagatgcgga tctacgaagc ttgtctgtat    840

cacccgcagc ttccagagtg tctatctccg gccgacgcgc cgtgcgccgt aagttcctgg    900

gcgtaccgcc tggcggtccg cagctacgcc ggctgttcca ggactacgcc cccgccgcga    960

tgttttgccg aggctcgcat ggaaccggtc ccggggttgg cgtggctggc ctccaccgtc   1020

aatctggaat tccagcacgc ctccccccag cacgccggcc tctacctgtg cgtggtgtac   1080

gtggacgatc atatccacgc ctggggccac atgaccatca gcaccgcggc gcagtaccgg   1140

aacgcggtgg tggaacagca cctcccccag cgccagcccg agcccgtcga gcccacccgc   1200

ccgcacgtga gagccccccc tcccgcgccc tccgcgcgcg gcccgctgcg cctcggggcg   1260

gtgctggggg cggccctgtt gctggccgcc ctcgggctgt ccgcgtgggc gtgcatgacc   1320

tgctggcgca ggcgctcctg gcgggcggtt aaaagccggg cctcggcgac gggccccact   1380
```

tacattcgcg tggcggacag cgagctgtac gcggactgga gttcggacag cgagggggag 1440
cgcgacgggt ccctgtggca ggaccctccg gagagacccg actctccctc cacaaatgga 1500
tccggctttg agatcttatc accaacggct ccgtctgtat acccccatag cgaggggcgt 1560
aaatctcgcc gcccgctcac cacctttggt tcgggaagcc cgggccgtcg tcactcccag 1620
gcctcctatt cgtccgtcct ctggtaa 1647

<210> SEQ ID NO 16
<211> LENGTH: 1119
<212> TYPE: DNA
<213> ORGANISM: Human herpesvirus 2

<400> SEQUENCE: 16
atgcccggcc gctcgctgca gggcctggcg atcctgggcc tgtgggtctg cgccaccggc 60
ctggtcgtcc gcggccccac ggtcagtctg gtctcagact cactcgtgga tgccggggcc 120
gtggggcccc agggcttcgt ggaagaggac ctgcgtgttt tcggggagct tcattttgtg 180
ggggcccagg tcccccacac aaactactac gacggcatca tcgagctgtt tcactacccc 240
ctggggaacc actgcccccg cgttgtacac gtggtcacac tgaccgcatg cccccgccgc 300
cccgccgtgg cgttcacctt gtgtcgctcg acgcaccacg cccacagccc cgcctatccg 360
accctggagc tgggtctggc gcggcagccg cttctgcggg ttcgaacggc aacgcgcgac 420
tatgccggtc tgtatgtcct gcgcgtatgg gtcggcagcg cgacgaacgc cagcctgttt 480
gttttggggg tggcgctctc tgccaacggg acgtttgtgt ataacggctc ggactacggc 540
tcctgcgatc cggcgcagct tcccttttcg gccccgcgcc tgggaccctc gagcgtatac 600
acccccggag cctcccggcc cacccctcca cggacaacga catccccgtc ctcccccga 660 gacccgaccc ccgcccccgg ggacacaggg acgcccgcgc ccgcgagcgg cgagagagcc 720
ccgcccaatt ccacgcgatc ggccagcgaa tcgagacaca ggctaaccgt agcccaggta 780
atccagatcg ccataccggc gtccatcatc gcctttgtgt ttctgggcag ctgtatctgc 840
ttcatccata gatgccagcg ccgatacagg cgcccccgcg gccagattta caaccccggg 900
ggcgtttcct gcgcggtcaa cgaggcggcc atggcccgcc tcggagccga gctgcgatcc 960
cacccaaaca cccccccaa accccgacgc cgttcgtcgt cgtccacgac catgccttcc 1020
ctaacgtcga tagctgagga atcggagcca ggtccagtcg tgctgctgtc cgtcagtcct 1080
cggccccgca gtggcccgac ggccccccaa gaggtctag 1119

<210> SEQ ID NO 17
<211> LENGTH: 2262
<212> TYPE: DNA
<213> ORGANISM: Artificial Sequence
<220> FEATURE:
<223> OTHER INFORMATION: Synthetic Polynucleotide

<400> SEQUENCE: 17
atggaacccc ggcccggcac gagctcccgg gcggaccccg gccccgagcg gccgccgcgg 60
cagacccccg gcacgcagcc cgccgccccg cacgcctggg ggatgctcaa cgacatgcag 120
tggctcgcca gcagcgactc ggaggaggag accgaggtgg gaatctctga cgacgacctt 180
caccgcgact ccacctccga ggcgggcagc acggacacgg agatgttcga ggcgggcctg 240
atggacgcgg ccacgccccc ggcccggccc ccggccgagc gccagggcag ccccacgccc 300
gccgacgcgc agggatcctg tgggggtggg cccgtgggtg aggaggaagc ggaagcggga 360

-continued

```
gggggggggcg acgtgaacac cccggtggcg tacctgatag tgggcgtgac cgccagcggg    420

tcgttcagca ccatcccgat agtgaacgac ccccggaccc gcgtggaggc cgaggcggcc    480

gtgcgggccg gcacggccgt ggactttatc tggacgggca acccgcggac ggccccgcgc    540

tccctgtcgc tgggggggaca cacggtccgc gccctgtcgc ccaccccccc gtggcccggc    600

acggacgacg aggacgatga cctggccgac gtggactacg tcccgcccgc cccccgaaga    660

gcgccccggc gcgggggcgg cggtgcgggg gcgacccgcg gaacctccca gcccgccgcg    720

acccgaccgg cgccccctgg cgccccgcgg agcagcagca gcggcggcgc cccgttgcgg    780

gcgggggtgg gatctgggtc tgggggcggc cctgccgtcg cggccgtcgt gccgagagtg    840

gcctctcttc cccctgcggc cggcgggggg cgcgcgcagg cgcggcgggt gggcgaagac    900

gccgcggcgg cggagggcag gacgcccccc gcgagacagc cccgcgcggc ccaggagccc    960

cccatagtca tcagcgactc tcccccgccg tctccgcgcc gccccgcggg ccccgggccg   1020

ctctcctttg tctcctcctc ctccgcacag gtgtcctcgg gccccggggg gggaggtctg   1080

ccacagtcgt cggggcgcgc cgcgcgcccc cgcgcggccg tcgccccgcg cgtccggagt   1140

ccgccccgcg ccgccgccgc ccccgtggtg tctgcgagcg cggacgcggc cgggcccgcg   1200

ccgcccgccg tgccggtgga cgcgcaccgc gcgccccggt cgcgcatgac ccaggctcag   1260

accgacaccc aagcacagag tctgggccgg gcaggcgcga ccgacgcgcg cgggtcggga   1320

gggccgggcg cggagggagg atcgggcccc gcggcctcgt cctccgcctc ttcctccgcc   1380

gccccgcgct cgcccctcgc cccccagggg gtgggggcca agagggcggc gccgcgccgg   1440

gccccggact cggactcggg cgaccgcggc cacgggccgc tcgccccggc gtccgcgggc   1500

gccgcgcccc cgtcggcgtc tccgtcgtcc caggccgcgg tcgccgccgc ctcctcctcc   1560

tccgcctcct cctcctccgc ctcctcctcc tccgcctcct cctcctccgc ctcctcctcc   1620

tccgcctcct cctcctccgc ctcctcctcc tccgcctctt cctctgcggg cggggctggt   1680

gggagcgtcg cgtccgcgtc cggcgctggg gagagacgag aaacctccct cggcccccgc   1740

gctgctgcgc cgcgggggcc gaggaagtgt gccaggaaga cgcgccacgc ggagggcggc   1800

cccgagcccg gggcccgcga cccggcgccc ggcctcacgc gctacctgcc catcgcgggg   1860

gtctcgagcg tcgtggccct ggcgccttac gtgaacaaga cggtcacggg ggactgcctg   1920

cccgtcctgg acatggagac gggccacata ggggcctacg tggtcctcgt ggaccagacg   1980

gggaacgtgg cggacctgct gcgggccgcg gcccccgcgt ggagccgccg caccctgctc   2040

cccgagcacg cgcgcaactg cgtgaggccc cccgactacc cgacgccccc cgcgtcggag   2100

tggaacagcc tctggatgac cccggtgggc aacatgctct ttgaccaggg caccctggtg   2160

ggcgcgctgg acttccacgg cctccggtcg cgccacccgt ggtctcggga gcagggcgcg   2220

cccgcgccgg ccggcgacgc ccccgcgggc cacggggagt ag                       2262
```

<210> SEQ ID NO 18
<211> LENGTH: 2304
<212> TYPE: DNA
<213> ORGANISM: Human herpesvirus 2

<400> SEQUENCE: 18

```
atgcgcgggg ggggcttggt ttgcgcgctg gtcgtggggg cgctggtggc cgcggtggcg     60

tcggcggccc cggcggcccc ccgcgcctcg ggcggcgtgg ccgcgaccgt cgcggcgaac    120

gggggtcccg cctcccagcc gcccccgtc ccgagccccg cgaccaccaa ggcccggaag    180

cggaaaacca aaaagccgcc caagcggccc gaggcgaccc cgccccccga cgccaacgcg    240
```

-continued

```
accgtcgccg ccggccacgc cacgctgcgc gcgcacctgc gggaaatcaa ggtcgagaac    300

gccgatgccc agttttacgt gtgcccgccc ccgacgggcg ccacggtggt gcagtttgag    360

cagccgcgcc gctgcccgac gcgcccggag gggcagaact acacggaggg catcgcggtg    420

gtcttcaagg agaacatcgc cccgtacaaa ttcaaggcca ccatgtacta caaagacgtg    480

accgtgtcgc aggtgtggtt cggccaccgc tactcccagt ttatggggat attcgaggac    540

cgcgcccccg ttcccttcga ggaggtgatc gacaagatta acgccaaggg ggtctgccgc    600

tccacggcca agtacgtgcg gaacaacatg gagaccaccg cgtttcaccg ggacgaccac    660

gagaccgaca tggagctcaa gccggcgaag gtcgccacgc gcacgagccg gggggtggcac   720

accaccgacc tcaagtacaa cccctcgcgg gtggaggcgt tccatcggta cggcacgacg    780

gtcaactgca tcgtcgagga ggtggacgcg cggtcggtgt acccgtacga tgagtttgtg    840

ctggcgacgg gcgactttgt gtacatgtcc ccgttttacg gctaccggga ggggtcgcac    900

accgagcaca ccagctacgc cgccgaccgc ttcaagcagg tcgacggctt ctacgcgcgc    960

gacctcacca cgaaggcccg ggccacgtcg ccgacgaccc gcaacttgct gacgaccccc   1020

aagtttaccg tggcctggga ctgggtgccg aagcgaccgg cggtctgcac catgaccaag   1080

tggcaggagg tggacgagat gctccgcgcc gagtacggcg gctccttccg cttctcctcc   1140

gacgccatct cgaccacctt caccaccaac ctgacccagt actcgctctc gcgcgtcgac   1200

ctgggcgact gcatcggccg ggatgcccgc gaggccatcg accgcatgtt tgcgcgcaag   1260

tacaacgcca cgcacatcaa ggtgggccag ccgcagtact acctggccac gggggggcttc  1320

ctcatcgcgt accagcccct cctcagcaac acgctcgccg agctgtacgt gcgggagtac   1380

atgcgggagc aggaccgcaa gccccggaat gccacgcccg cgccactgcg ggaggcgccc   1440

agcgccaacg cgtccgtgga gcgcatcaag accacctcct cgatcgagtt cgcccggctg   1500

cagtttacgt ataaccacat acagcgccac gtgaacgaca tgctggggcg catcgccgtc   1560

gcgtggtgcg agctgcagaa ccacgagctg actctctgga acgaggcccg caagctcaac   1620

cccaacgcca tcgcctccgc caccgtcggc cggcgggtga gcgcgcgcat gctcggagac   1680

gtcatggccg tctccacgtg cgtgcccgtc gccccggaca acgtgatcgt gcagaactcg   1740

atgcgcgtca gctcgcggcc ggggacgtgc tacagccgcc ccctggtcag ctttcggtac   1800

gaagaccagg gcccgctgat cgaggggcag ctgggcgaga acaacgagct gcgcctcacc   1860

cgcgacgcgc tcgagccgtg caccgtgggc caccggcgct acttcatctt cggcgggggc   1920

tacgtgtact tcgaggagta cgcgtactct caccagctga gtcgcgccga cgtcaccacc   1980

gtcagcacct tcatcgacct gaacatcacc atgctggagg accacgagtt tgtgcccctg   2040

gaggtctaca cgcgccacga gatcaaggac agcggcctgc tggactacac ggaggtccag   2100

cgccgcaacc agctgcacga cctgcgcttt gccgacatcg acacggtcat ccgcgccgac   2160

gccaacgccg ccatgttcgc ggggctgtgc gcgttcttcg aggggatggg ggacttgggg   2220

cgcgcggtcg gcaaggtcgt catgggagta gtgggggggcg tggtgtcggc cgtctcgggc  2280

gtgtcctcct ttatgtccaa cccc                                          2304
```

<210> SEQ ID NO 19
<211> LENGTH: 1341
<212> TYPE: DNA
<213> ORGANISM: Human herpesvirus 2

<400> SEQUENCE: 19

-continued

```
atggcccttg gacgggtggg cctagccgtg ggcctgtggg gcctgctgtg ggtgggtgtg      60

gtcgtggtgc tggccaatgc ctcccccgga cgcacgataa cggtgggccc gcgggggaac     120

gcgagcaatg ccgccccctc cgcgtccccg cggaacgcat ccgccccccg aaccacaccc     180

acgccccccc aaccccgcaa ggcgacgaaa agtaaggcct ccaccgccaa accggccccg     240

ccccccaaga ccgggccccc gaagacatcc tcggagcccg tgcgatgcaa ccgccacgac     300

ccgctggccc ggtacggctc gcgggtgcaa atccgatgcc ggtttcccaa ctccacccgc     360

acggagtccc gcctccagat ctggcgttat gccacggcga cggacgccga gatcggaacg     420

gcgcctagct tagaggaggt gatggtaaac gtgtcggccc cgcccggggg ccaactggtg     480

tatgacagcg cccccaaccg aacggacccg cacgtgatct gggcggaggg cgccggcccg     540

ggcgccagcc cgcggctgta ctcggtcgtc gggccgctgg gtcggcagcg gctcatcatc     600

gaagagctga ccctggagac ccagggcatg tactactggg tgtggggccg gacggaccgc     660

ccgtccgcgt acgggacctg ggtgcgcgtt cgcgtgttcc gccctccgtc gctgaccatc     720

cacccccacg cggtgctgga gggccagccg tttaaggcga cgtgcacggc cgccacctac     780

tacccgggca accgcgcgga gttcgtctgg ttcgaggacg gtcgccgggt attcgatccg     840

gcccagatac acacgcagac gcaggagaac cccgacggct tttccaccgt ctccaccgtg     900

acctccgcgg ccgtcggcgg ccagggcccc ccgcgcacct tcacctgcca gctgacgtgg     960

caccgcgact ccgtgtcgtt ctctcggcgc aacgccagcg gcacggcatc ggtgctgccg    1020

cggccaacca ttaccatgga gtttacgggc gaccatgcgg tctgcacggc cggctgtgtg    1080

cccgaggggg tgacgtttgc ctggttcctg ggggacgact cctcgccggc ggagaaggtg    1140

gccgtcgcgt cccagacatc gtgcgggcgc cccggcaccg ccacgatccg ctccaccctg    1200

ccggtctcgt acgagcagac cgagtacatc tgccggctgg cgggataccc ggacggaatt    1260

ccggtcctag agcaccacgg cagccaccag cccccgccgc gggaccccac cgagcggcag    1320

gtgatccggg cggtggaggg g                                              1341
```

<210> SEQ ID NO 20
<211> LENGTH: 1017
<212> TYPE: DNA
<213> ORGANISM: Human herpesvirus 2

<400> SEQUENCE: 20

```
atggggcgtt tgacctccgg cgtcgggacg gcggccctgc tagttgtcgc ggtgggactc      60

cgcgtcgtct gcgccaaata cgccttagca gacccctcgc ttaagatggc cgatcccaat     120

cgatttcgcg ggaagaacct tccggttttg gaccagctga ccgacccccc cggggtgaag     180

cgtgtttacc acattcagcc gagcctggag gacccgttcc agccccccag catcccgatc     240

actgtgtact acgcagtgct ggaacgtgcc tgccgcagcg tgctcctaca tgccccatcg     300

gaggcccccc agatcgtgcg cggggcttcg gacgaggccc gaaagcacac gtacaacctg     360

accatcgcct ggtatcgcat gggagacaat tgcgctatcc ccatcacggt tatggaatac     420

accgagtgcc cctacaacaa gtcgttgggg gtctgcccca tccgaacgca gccccgctgg     480

agctactatg acagctttag cgccgtcagc gaggataacc tgggattcct gatgcacgcc     540

cccgccttcg agaccgcggg tacgtacctg cggctagtga agataaacga ctggacggag     600

atcacacaat ttatcctgga gcaccgggcc cgcgcctcct gcaagtacgc tctccccctg     660

cgcatccccc cggcagcgtg cctcacctcg aaggcctacc aacagggcgt gacggtcgac     720

agcatcggga tgctaccccg ctttatcccc gaaaaccagc gcaccgtcgc cctatacagc     780
```

```
ttaaaaatcg ccgggtggca cggccccaag cccccgtaca ccagcaccct gctgccgccg    840

gagctgtccg acaccaccaa cgccacgcaa cccgaactcg ttccggaaga ccccgaggac    900

tcggccctct tagaggatcc cgccgggacg gtgtcttcgc agatcccccc aaactggcac    960

atcccgtcga tccaggacgt cgcgccgcac cacgcccccg ccgcccccag caacccg      1017
```

<210> SEQ ID NO 21
<211> LENGTH: 1251
<212> TYPE: DNA
<213> ORGANISM: Human herpesvirus 2

<400> SEQUENCE: 21

```
atggctcgcg gggccgggtt ggtgtttttt gttggagttt gggtcgtatc gtgcctggcg     60

gcagcaccca gaacgtcctg gaaacgggta acctcgggcg aggacgtggt gttgcttccg    120

gcgcccgcgg ggccggagga acgcacccgg gcccacaaac tactgtgggc cgcggaaccc    180

ctggatgcct gcggtcccct gcgcccgtcg tgggtggcgc tgtggccccc ccgacgggtg    240

ctcgagacgg tcgtggatgc ggcgtgcatg cgcgccccgg aaccgctcgc catagcatac    300

agtcccccgt tccccgcggg cgacgaggga ctgtattcgg agttggcgtg gcgcgatcgc    360

gtagccgtgg tcaacgagag tctggtcatc tacggggccc tggagacgga cagcggtctg    420

tacaccctgt ccgtggtcgg cctaagcgac gaggcgcgcc aagtggcgtc ggtggttctg    480

gtcgtggagc ccgcccctgt gccgacccccg accccccgacg actacgacga agaagacgac    540

gcgggcgtga gcgaacgcac gccggtcagc gttccccccc caaccccccc ccgtcgtccc    600

cccgtcgccc ccccgacgca ccctcgtgtt atccccgagg tgtcccacgt gcgcggggta    660

acggtccata tggagacccc ggaggccatt ctgtttgccc ccggggagac gtttgggacg    720

aacgtctcca tccacgccat tgcccacgac gacggtccgt acgccatgga cgtcgtctgg    780

atgcggtttg acgtgccgtc ctcgtgcgcc gagatgcgga tctacgaagc ttgtctgtat    840

cacccgcagc ttccagagtg tctatctccg gccgacgcgc cgtgcgccgt aagttcctgg    900

gcgtaccgcc tggcggtccg cagctacgcc ggctgttcca ggactacgcc cccgccgcga    960

tgttttgccg aggctcgcat ggaaccggtc ccggggttgg cgtggctggc ctccaccgtc   1020

aatctggaat tccagcacgc ctccccccag cacgccggcc tctacctgtg cgtggtgtac   1080

gtggacgatc atatccacgc ctggggccac atgaccatca gcaccgcggc gcagtaccgg   1140

aacgcggtgg tggaacagca cctcccccag cgccagcccg agcccgtcga gcccacccgc   1200

ccgcacgtga gagccccccc tcccgcgccc tccgcgcgcg gcccgctgcg c            1251
```

<210> SEQ ID NO 22
<211> LENGTH: 786
<212> TYPE: DNA
<213> ORGANISM: Human herpesvirus 2

<400> SEQUENCE: 22

```
atgcccggcc gctcgctgca gggcctggcg atcctgggcc tgtgggtctg cgccaccggc     60

ctggtcgtcc gcggccccac ggtcagtctg gtctcagact cactcgtgga tgccggggcc    120

gtggggcccc agggcttcgt ggaagaggac ctgcgtgttt tcggggagct tcattttgtg    180

ggggcccagg tcccccacac aaactactac gacggcatca tcgagctgtt tcactacccc    240

ctggggaacc actgcccccg cgttgtacac gtggtcacac tgaccgcatg cccccgccgc    300

cccgccgtgg cgttcacctt gtgtcgctcg acgcaccacg cccacagccc cgcctatccg    360
```

-continued accctggagc tgggtctggc gcggcagccg cttctgcggg ttcgaacggc aacgcgcgac 420
tatgccggtc tgtatgtcct gcgcgtatgg gtcggcagcg cgacgaacgc cagcctgttt 480
gttttggggg tggcgctctc tgccaacggg acgtttgtgt ataacggctc ggactacggc 540
tcctgcgatc cggcgcagct tcccttttcg gccccgcgcc tggaccctc gagcgtatac 600 acccccggag cctcccggcc cacccctcca cggacaacga catccccgtc ctccccccga 660
gacccgaccc ccgcccccgg ggacacaggg acgcccgcgc ccgcgagcgg cgagagagcc 720
ccgcccaatt ccacgcgatc ggccagcgaa tcgagacaca ggctaaccgt agcccaggta 780
atccag 786

<210> SEQ ID NO 23
<211> LENGTH: 3885
<212> TYPE: DNA
<213> ORGANISM: Artificial Sequence
<220> FEATURE:
<223> OTHER INFORMATION: Synthetic Polynucleotide

<400> SEQUENCE: 23
atgtcggcgg agcagcggaa gaagaagaag acgacgacga cgacgcaggg ccgcggggcc 60
gaggtcgcga tggcggacga ggacggggga cgtctccggg ccgcggcgga gacgaccggc 120
ggccccggat ctccggatcc agccgacgga ccgccgccca ccccgaaccc ggaccgtcgc 180
cccgccgcgc ggcccgggtt cgggtggcac ggtgggccgg aggagaacga agacgaggcc 240
gacgacgccg ccgccgatgc cgatgccgac gaggcggccc cggcgtccgg ggaggccgtc 300
gacgagcctg ccgcggacgg cgtcgtctcg ccgcggcagc tggccctgct ggcctcgatg 360
gtggacgagg ccgttcgcac gatcccgtcg cccccccggg agcgcgacgg cgcgcaagaa 420
gaagcggccc gctcgccttc tccgccgcgg accccctcca tgcgcgccga ttatggcgag 480
gagaacgacg acgacgacga cgacgacgat gacgacgacc gcgacgcggg ccgctgggtc 540
cgcggaccgg agacgacgtc cgcggtccgc ggggcgtacc cggaccccat ggccagcctg 600
tcgccgcgac ccccggcgcc ccgccgacac caccaccacc accaccaccg ccgccggcgc 660
gccccccgcc ggcgctcggc cgcctctgac tcatcaaaat ccggatcctc gtcgtcggcg 720
tcctccgcct cctcctccgc ctcctcctcc tcgtctgcat ccgcctcctc gtctgacgac 780
gacgacgacg acgacgccgc ccgcgccccc gccagcgccg cagaccacgc cgcgggcggg 840
accctcggcg cggacgacga ggaggcgggg gtgcccgcga gggccccggg ggcggcgccc 900
cggccgagcc cgcccagggc cgagcccgcc ccggcccgga cccccgcggc gaccgcgggc 960
cgcctggagc gccgccgggc ccgcgcggcg gtggccggcc gcgacgccac gggccgcttc 1020
acggccgggc ggccccggcg ggtcgagctg gacgccgacg cggcctccgg cgccttctac 1080
gcgcgctacc gcgacgggta cgtcagcggg gagccgtggc ccggggccgg ccccccgccc 1140
ccggggcgcg tgctgtacgg cgggctgggc gacagccgcc ccggcctctg gggggcgccc 1200
gaggcggagg aggcgcgggc ccggttcgag gcctcgggcg ccccggcgcc cgtgtgggcg 1260
cccgagctgg gcgacgcggc gcagcagtac gccctgatca cgcggctgct gtacacgccg 1320
gacgcggagg cgatggggtg gctccagaac ccgcgcgtgg cgcccgggga cgtggcgctg 1380
gaccaggcct gcttccggat ctcgggcgcg gcgcgcaaca gcagctcctt catctccggc 1440
agcgtggcgc gggccgtgcc ccacctgggg tacgccatgg cggcgggccg cttcggctgg 1500
ggcctggcgc acgtggcggc cgccgtggcc atgagccgcc gctacgaccg cgcgcagaag 1560
ggcttcctgc tgaccagcct gcgccgcgcc tacgcgcccc tgctggcgcg cgagaacgcg 1620
gcgctgaccg gggcgcgaac ccccgacgac ggcggcgacg ccaaccgcca cgacggcgac 1680
gacgcccgcg ggaagcccgc cgccgccgcc gccccgttgc cgtcggcggc ggcgtcgccg 1740
gccgacgagc gcgcggtgcc cgccggctac ggcgccgcgg gggtgctcgc cgccctgggg 1800
cgcctgagcg ccgcgcccgc ctccgcgccg gccggggccg acgacgacga cgacgacgac 1860
ggcgccggcg gtggtggcgg cggccggcgc gcggaggcgg gccgcgtggc cgtggagtgc 1920
ctggccgcct gccgcgggat cctggaggcg ctggcggagg gcttcgacgg cgacctggcg 1980
gccgtgccgg ggctggccgg agcccggccc gccgcgcccc cgcgcccggg gcccgcgggc 2040
gcggccgccc cgccgcacgc cgacgcgccc cgcctgcgcg cctggctgcg cgagctgcgg 2100
ttcgtgcgcg acgcgctggt gctgatgcgc ctgcgcgggg acctgcgcgt ggccggcggc 2160
agcgaggccg ccgtggccgc cgtgcgcgcc gtgagcctgg tcgccggggc cctgggcccg 2220
gcgctgccgc ggagcccgcg cctgctgagc tccgccgccg ccgccgccgc ggacctgctc 2280
ttccagaacc agagcctgcg cccccctgctg gccgacaccg tcgccgcggc cgactcgctc 2340
gccgcgcccg cctccgcgcc gcgggaggcc gcggacgccc cccgccccgc ggccgcccct 2400
cccgcggggg ccgcgccccc cgccccgccg acgccgccgc cgcggccgcc gcgccccgcg 2460
gcgctgaccc gccggcccgc cgagggcccc gacccgcagg gcggctggcg ccgccagccg 2520
ccggggccca gccacacgcc ggcgccctcg gccgccgccc tggaggccta ctgcgccccg 2580
cgggccgtgg ccgagctcac ggaccacccg ctcttccccg cgccgtggcg cccggccctc 2640
atgttcgacc cgcgcgcgct ggcctcgctg gccgcgcgct gcgccgcccc gccccccggc 2700
ggcgcgcccg ccgccttcgg cccgctgcgc gcctcgggcc cgctgcgccg cgcggcggcc 2760
tggatgcgcc aggtgcccga cccggaggac gtgcgcgtgg tgatcctcta ctcgccgctg 2820
ccgggcgagg acctggccgc gggccgcgcc gggggcgggc ccccccccgga gtggtccgcc 2880 gagcgcggcg ggctgtcctg cctgctggcg gccctgggca accggctctg cgggcccgcc 2940
acggccgcct gggcgggcaa ctggaccggc gcccccgacg tctcggcgct gggcgcgcag 3000
ggcgtgctgc tgctgtccac gcgggacctg gccttcgccg gcgccgtgga gttcctgggg 3060
ctgctggccg gcgcctgcga ccgccgcctc atcgtcgtca acgccgtgcg cgccgcggcc 3120
tggcccgccg ctgcccccgt ggtctcgcgg cagcacgcct acctggcctg cgaggtgctg 3180
cccgccgtgc agtgcgccgt gcgctggccg gcggcgcggg acctgcgccg caccgtgctg 3240
gcctccggcc gcgtgttcgg gccgggggtc ttcgcgcgcg tggaggccgc gcacgcgcgc 3300
ctgtaccccg acgcgccgcc gctgcgcctc tgccgcgggg ccaacgtgcg gtaccgcgtg 3360
cgcacgcgct tcggccccga cacgctggtg cccatgtccc cgcgcgagta ccgccgcgcc 3420
gtgctcccgg cgctggacgg ccgggccgcc gcctcgggcg cgggcgacgc catggcgccc 3480
ggcgcgccgg acttctgcga ggacgaggcg cactcgcacc gcgcctgcgc gcgctggggc 3540
ctgggcgcgc cgctgcggcc cgtctacgtg gcgctggggc gcgacgccgt gcgcggcggc 3600
ccggcggagc tgcgcgggcc gcggcgggag ttctgcgcgc gggcgctgct cgagcccgac 3660
ggcgacgcgc ccccgctggt gctgcgcgac gacgcggacg cgggcccgcc cccgcagata 3720
cgctgggcgt cggccgcggg ccgcgcgggg acggtgctgg ccgcggcggg cggcggcgtg 3780
gaggtggtgg ggaccgccgc ggggctggcc acgccgccga ggcgcgagcc cgtggacatg 3840
gacgcggagc tggaggacga cgacgacgga ctgtttgggg agtga 3885

<210> SEQ ID NO 24

<211> LENGTH: 480
<212> TYPE: PRT
<213> ORGANISM: Human herpesvirus 2

<400> SEQUENCE: 24

Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Ser Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu

-continued

```
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480


<210> SEQ ID NO 25
<211> LENGTH: 480
<212> TYPE: PRT
<213> ORGANISM: Human herpesvirus 2

<400> SEQUENCE: 25

Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Phe Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285
```

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480

<210> SEQ ID NO 26
<211> LENGTH: 479
<212> TYPE: PRT
<213> ORGANISM: Human herpesvirus 2

<400> SEQUENCE: 26

Met Ala Leu Gly Arg Val Gly Leu Thr Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Val
        35                  40                  45

Pro Arg Asn Arg Ser Ala Pro Arg Thr Thr Pro Thr Pro Pro Gln Pro
    50                  55                  60

Arg Lys Ala Thr Lys Ser Lys Ala Ser Thr Ala Lys Pro Ala Pro Pro
65                  70                  75                  80

Pro Lys Thr Gly Pro Pro Lys Thr Ser Ser Glu Pro Val Arg Cys Asn
                85                  90                  95

Arg His Asp Pro Leu Ala Arg Tyr Gly Ser Arg Val Gln Ile Arg Cys
            100                 105                 110

Arg Phe Pro Asn Ser Thr Arg Thr Glu Ser Arg Leu Gln Ile Trp Arg
        115                 120                 125

Tyr Ala Thr Ala Thr Asp Ala Glu Ile Gly Thr Ala Pro Ser Leu Glu
    130                 135                 140

Glu Val Met Val Asn Val Ser Ala Pro Pro Gly Gly Gln Leu Val Tyr
145                 150                 155                 160

Asp Ser Ala Pro Asn Arg Thr Asp Pro His Val Ile Trp Ala Glu Gly
                165                 170                 175

Ala Gly Pro Gly Ala Ser Pro Arg Leu Tyr Ser Val Val Gly Pro Leu
            180                 185                 190

Gly Arg Gln Arg Leu Ile Ile Glu Glu Leu Thr Leu Glu Thr Gln Gly
195 200 205

Met Tyr Tyr Trp Val Trp Gly Arg Thr Asp Arg Pro Ser Ala Tyr Gly
210 215 220

Thr Trp Val Arg Val Arg Val Phe Arg Pro Pro Ser Leu Thr Ile His
225 230 235 240

Pro His Ala Val Leu Glu Gly Gln Pro Phe Lys Ala Thr Cys Thr Ala
245 250 255

Ala Thr Tyr Tyr Pro Gly Asn Arg Ala Glu Phe Val Trp Phe Glu Asp
260 265 270

Gly Arg Arg Val Phe Asp Pro Ala Gln Ile His Thr Gln Thr Gln Glu
275 280 285

Asn Pro Asp Gly Phe Ser Thr Val Ser Thr Val Thr Ser Ala Ala Val
290 295 300

Gly Gly Gln Gly Pro Pro Arg Thr Phe Thr Cys Gln Leu Thr Trp His
305 310 315 320

Arg Asp Ser Val Ser Phe Ser Arg Arg Asn Ala Ser Gly Thr Ala Ser
325 330 335

Val Leu Pro Arg Pro Thr Ile Thr Met Glu Phe Thr Gly Asp His Ala
340 345 350

Val Cys Thr Ala Gly Cys Val Pro Glu Gly Val Thr Phe Ala Trp Phe
355 360 365

Leu Gly Asp Asp Ser Ser Pro Ala Glu Lys Val Ala Val Ala Ser Gln
370 375 380

Thr Ser Cys Gly Arg Pro Gly Thr Ala Thr Ile Arg Ser Thr Leu Pro
385 390 395 400

Val Ser Tyr Glu Gln Thr Glu Tyr Ile Cys Arg Leu Ala Gly Tyr Pro
405 410 415

Asp Gly Ile Pro Val Leu Glu His His Gly Ser His Gln Pro Pro Pro
420 425 430

Arg Asp Pro Thr Glu Arg Gln Val Ile Arg Ala Val Glu Gly Ala Gly
435 440 445

Ile Gly Val Ala Val Leu Val Ala Val Val Leu Ala Gly Thr Ala Val
450 455 460

Val Tyr Leu Thr His Ala Ser Ser Val Arg Tyr Arg Arg Leu Arg
465 470 475

<210> SEQ ID NO 27
<211> LENGTH: 480
<212> TYPE: PRT
<213> ORGANISM: Human herpesvirus 2

<400> SEQUENCE: 27

Met Ala Leu Gly Arg Val Gly Leu Ala Val Gly Leu Trp Gly Leu Leu
1 5 10 15

Trp Val Gly Val Val Val Val Leu Ala Asn Ala Ser Pro Gly Arg Thr
20 25 30

Ile Thr Val Gly Pro Arg Gly Asn Ala Ser Asn Ala Ala Pro Ser Ala
35 40 45

Ser Pro Arg Asn Ala Ser Ala Pro Arg Thr Thr Pro Thr Pro Pro Gln
50 55 60

Pro Arg Lys Ala Thr Lys Ser Lys Ala Ser Thr Ala Lys Pro Ala Pro
65 70 75 80

Pro Pro Lys Thr Gly Pro Pro Lys Thr Ser Ser Glu Pro Val Arg Cys

-continued

```
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Ser Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Pro Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480
```

<210> SEQ ID NO 28
<211> LENGTH: 480
<212> TYPE: PRT
<213> ORGANISM: Human herpesvirus 2

<400> SEQUENCE: 28

```
Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Ser Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Pro Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
```

```
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480


<210> SEQ ID NO 29
<211> LENGTH: 480
<212> TYPE: PRT
<213> ORGANISM: Human herpesvirus 2

<400> SEQUENCE: 29

Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Pro Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Phe Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300
```

```
Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480


<210> SEQ ID NO 30
<211> LENGTH: 480
<212> TYPE: PRT
<213> ORGANISM: Human herpesvirus 2

<400> SEQUENCE: 30

Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Phe Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205
```

Gly Met Tyr Tyr Trp Val Trp Gly Arg Thr Asp Arg Pro Ser Ala Tyr
210 215 220

Gly Thr Trp Val Arg Val Arg Val Phe Arg Pro Pro Ser Leu Thr Ile
225 230 235 240

His Pro His Ala Val Leu Glu Gly Gln Pro Phe Lys Ala Thr Cys Thr
245 250 255

Ala Ala Thr Tyr Tyr Pro Gly Asn Arg Ala Glu Phe Val Trp Phe Glu
260 265 270

Asp Gly Arg Arg Val Phe Asp Pro Ala Gln Ile His Thr Gln Thr Gln
275 280 285

Glu Asn Pro Asp Gly Phe Ser Thr Val Ser Thr Val Thr Ser Ala Ala
290 295 300

Val Gly Gly Gln Gly Pro Pro Arg Thr Phe Thr Cys Gln Leu Thr Trp
305 310 315 320

His Arg Asp Ser Val Ser Phe Ser Arg Arg Asn Ala Ser Gly Thr Ala
325 330 335

Ser Val Leu Pro Arg Pro Thr Ile Thr Met Glu Phe Thr Gly Asp His
340 345 350

Ala Val Cys Thr Ala Gly Cys Val Pro Glu Gly Val Thr Phe Ala Trp
355 360 365

Phe Leu Gly Asp Asp Ser Ser Pro Ala Glu Lys Val Ala Val Ala Ser
370 375 380

Gln Thr Ser Cys Gly Arg Pro Gly Thr Ala Thr Ile Arg Ser Thr Leu
385 390 395 400

Pro Val Ser Tyr Glu Gln Thr Glu Tyr Ile Cys Arg Leu Ala Gly Tyr
405 410 415

Pro His Gly Ile Pro Val Leu Glu His His Gly Ser His Gln Pro Pro
420 425 430

Pro Arg Asp Pro Thr Glu Arg Gln Val Ile Arg Ala Val Glu Gly Ala
435 440 445

Gly Ile Gly Val Ala Val Leu Val Ala Val Val Leu Ala Gly Thr Ala
450 455 460

Val Val Tyr Leu Thr His Ala Ser Ser Val Arg Tyr Arg Arg Leu Arg
465 470 475 480

<210> SEQ ID NO 31
<211> LENGTH: 480
<212> TYPE: PRT
<213> ORGANISM: Human herpesvirus 2

<400> SEQUENCE: 31

Met Ala Leu Gly Arg Val Gly Leu Ala Val Gly Leu Trp Gly Leu Leu
1 5 10 15

Trp Val Gly Val Val Val Val Leu Ala Asn Ala Ser Pro Gly Arg Thr
20 25 30

Ile Thr Val Gly Pro Arg Gly Asn Ala Ser Asn Ala Ala Pro Ser Ala
35 40 45

Ser Pro Arg Asn Ala Ser Ala Pro Arg Thr Thr Pro Thr Pro Pro Gln
50 55 60

Pro Arg Lys Ala Thr Lys Ser Lys Ala Ser Thr Ala Lys Pro Ala Pro
65 70 75 80

Pro Pro Lys Thr Gly Pro Pro Lys Thr Ser Ser Glu Pro Val Arg Cys
85 90 95

Asn Arg His Asp Pro Leu Ala Arg Tyr Gly Ser Arg Val Gln Ile Arg

```
            100                 105                 110

Cys Arg Phe Pro Asn Ser Thr Arg Thr Glu Phe Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Lys Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480
```

<210> SEQ ID NO 32
<211> LENGTH: 393
<212> TYPE: PRT
<213> ORGANISM: Human herpesvirus 2

<400> SEQUENCE: 32

-continued

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Thr Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ala Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Arg Ser
        355                 360                 365

Val Ala Pro Lys Arg Leu Arg Leu Pro His Ile Arg Asp Asp Asp Ala
    370                 375                 380

Pro Pro Ser His Gln Pro Leu Phe Tyr
385                 390
```

<210> SEQ ID NO 33
<211> LENGTH: 393
<212> TYPE: PRT

<213> ORGANISM: Human herpesvirus 2

<400> SEQUENCE: 33

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Ala Gln
        355                 360                 365

Met Ala Pro Lys Arg Pro Arg Leu Pro His Ile Arg Asp Asp Asp Ala
    370                 375                 380

Pro Pro Ser His Gln Pro Leu Phe Tyr
385                 390
```

<210> SEQ ID NO 34
<211> LENGTH: 393
<212> TYPE: PRT
<213> ORGANISM: Human herpesvirus 2

<400> SEQUENCE: 34

Met Gly Arg Leu Thr Ser Gly Val Gly Thr Ala Ala Leu Leu Val Val
1 5 10 15

Ala Val Gly Leu Arg Val Val Cys Ala Lys Tyr Ala Leu Ala Asp Pro
20 25 30

Ser Leu Lys Met Ala Asp Pro Asn Arg Phe Arg Gly Lys Asn Leu Pro
35 40 45

Val Leu Asp Gln Leu Thr Asp Pro Pro Gly Val Lys Arg Val Tyr His
50 55 60

Ile Gln Pro Ser Leu Glu Asp Pro Phe Gln Pro Pro Ser Ile Pro Ile
65 70 75 80

Thr Val Tyr Tyr Ala Val Leu Glu Arg Ala Cys Arg Ser Val Leu Leu
85 90 95

His Ala Pro Ser Glu Ala Pro Gln Ile Val Arg Gly Ala Ser Asp Glu
100 105 110

Ala Arg Lys His Thr Tyr Asn Leu Thr Ile Ala Trp Tyr Arg Met Gly
115 120 125

Asp Asn Cys Ala Ile Pro Ile Thr Val Met Glu Tyr Thr Glu Cys Pro
130 135 140

Tyr Asn Lys Ser Leu Gly Val Cys Pro Ile Arg Thr Gln Pro Arg Trp
145 150 155 160

Ser Tyr Tyr Asp Ser Phe Ser Ala Val Ser Glu Asp Thr Leu Gly Phe
165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro Gly Leu Ile Ile Gly Ala Leu Ala Gly Ser Thr Leu Ala
340 345 350

Val Leu Val Ile Gly Gly Ile Ala Phe Trp Val Arg Arg Arg Ala Gln
355 360 365

Met Ala Pro Lys Arg Leu Arg Leu Pro His Ile Arg Asp Asp Asp Ala
370 375 380

Pro Pro Ser His Gln Pro Leu Phe Tyr
385 390

<210> SEQ ID NO 35
<211> LENGTH: 393
<212> TYPE: PRT
<213> ORGANISM: Human herpesvirus 2

<400> SEQUENCE: 35

Met Gly Arg Leu Thr Ser Gly Val Gly Thr Ala Ala Leu Leu Val Val
1 5 10 15

Ala Val Gly Leu Arg Val Val Tyr Ala Lys Tyr Ala Leu Ala Asp Pro
20 25 30

Ser Leu Lys Met Ala Asp Pro Asn Arg Phe Arg Gly Lys Asn Leu Pro
35 40 45

Val Leu Asp Gln Leu Thr Asp Pro Pro Gly Val Lys Arg Val Tyr His
50 55 60

Ile Gln Pro Ser Leu Glu Asp Pro Phe Gln Pro Pro Ser Ile Pro Ile
65 70 75 80

Thr Val Tyr Tyr Ala Val Leu Glu Arg Ala Cys Arg Ser Val Leu Leu
85 90 95

His Ala Pro Ser Glu Ala Pro Gln Ile Val Arg Gly Ala Ser Asp Glu
100 105 110

Ala Arg Lys His Thr Tyr Asn Leu Thr Ile Ala Trp Tyr Arg Met Gly
115 120 125

Asp Asn Cys Ala Ile Pro Ile Thr Val Met Glu Tyr Thr Glu Cys Pro
130 135 140

Tyr Asn Lys Ser Leu Gly Val Cys Pro Ile Arg Thr Gln Pro Arg Trp
145 150 155 160

Ser Tyr Tyr Asp Ser Phe Ser Ala Val Ser Glu Asp Asn Leu Gly Phe
165 170 175

Leu Met His Ala Pro Ala Phe Glu Thr Ala Gly Thr Tyr Met Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro Gly Leu Ile Ile Gly Ala Leu Ala Gly Ser Thr Leu Ala
340 345 350

Ala Leu Val Ile Gly Gly Ile Ala Phe Trp Val Arg Arg Arg Ala Gln

```
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 36
<211> LENGTH: 393
<212> TYPE: PRT
<213> ORGANISM: Human herpesvirus 2

<400> SEQUENCE: 36

Met Gly Arg Leu Thr Ser Gly Val Gly Thr Ala Ala Leu Leu Val Val
1               5                   10                  15

Ala Val Gly Leu Arg Val Val Tyr Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335
```

```
Ser Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 37
<211> LENGTH: 393
<212> TYPE: PRT
<213> ORGANISM: Human herpesvirus 2

<400> SEQUENCE: 37

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Ala Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320
```

```
Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 38
<211> LENGTH: 393
<212> TYPE: PRT
<213> ORGANISM: Human herpesvirus 2

<400> SEQUENCE: 38

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Arg Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
```

290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro Gly Leu Ile Ile Gly Ala Leu Ala Gly Ser Thr Leu Ala
340 345 350

Val Leu Val Ile Gly Gly Ile Ala Phe Trp Val Arg Arg Arg Ala Gln
355 360 365

Met Ala Pro Lys Arg Leu Arg Leu Pro His Ile Arg Asp Asp Asp Ala
370 375 380

Pro Pro Ser His Gln Pro Leu Phe Tyr
385 390

<210> SEQ ID NO 39
<211> LENGTH: 393
<212> TYPE: PRT
<213> ORGANISM: Human herpesvirus 2

<400> SEQUENCE: 39

Met Gly Arg Leu Thr Ser Gly Val Gly Thr Ala Ala Leu Leu Val Val
1 5 10 15

Ala Val Gly Leu Arg Val Val Cys Ala Lys Tyr Ala Leu Ala Asp Pro
20 25 30

Ser Leu Lys Met Ala Asp Pro Asn Arg Phe Arg Gly Lys Asn Leu Pro
35 40 45

Val Leu Asp Gln Leu Thr Asp Pro Pro Gly Val Lys Arg Val Tyr His
50 55 60

Ile Gln Pro Ser Leu Glu Asp Pro Phe Gln Pro Pro Ser Ile Pro Ile
65 70 75 80

Thr Val Tyr Tyr Ala Val Leu Glu Arg Ala Cys Arg Ser Val Leu Leu
85 90 95

His Ala Pro Ser Glu Ala Pro Gln Ile Val Arg Gly Ala Ser Asp Glu
100 105 110

Ala Arg Lys His Thr Tyr Asn Leu Thr Ile Ala Trp Tyr Arg Met Gly
115 120 125

Asp Asn Cys Ala Ile Pro Ile Thr Val Met Glu Tyr Thr Glu Cys Pro
130 135 140

Tyr Asn Lys Ser Leu Gly Val Cys Pro Ile Arg Thr Gln Pro Arg Trp
145 150 155 160

Ser Tyr Tyr Asp Ser Phe Ser Ala Val Ser Glu Asp Asn Leu Gly Phe
165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

```
Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 40
<211> LENGTH: 393
<212> TYPE: PRT
<213> ORGANISM: Human herpesvirus 2

<400> SEQUENCE: 40

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255
```

```
Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 41
<211> LENGTH: 393
<212> TYPE: PRT
<213> ORGANISM: Human herpesvirus 2

<400> SEQUENCE: 41

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
```

```
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 42
<211> LENGTH: 901
<212> TYPE: PRT
<213> ORGANISM: Human herpesvirus 2

<400> SEQUENCE: 42

Met Arg Gly Gly Gly Leu Val Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Gln Pro Pro
        35                  40                  45

Pro Val Pro Ser Pro Ala Thr Thr Lys Ala Arg Lys Arg Lys Thr Lys
    50                  55                  60

Lys Pro Pro Lys Arg Pro Glu Ala Thr Pro Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205
```

```
Asn Met Glu Thr Thr Ala Phe His Arg Asp Asp His Glu Thr Asp Met
    210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
    290                 295                 300

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
                325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

Arg Ala Glu Tyr Gly Gly Ser Phe Arg Phe Ser Ser Asp Ala Ile Ser
    370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
        435                 440                 445

Ser Asn Thr Leu Ala Glu Leu Tyr Val Arg Glu Tyr Met Arg Glu Gln
    450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
        515                 520                 525

Glu Leu Thr Leu Trp Asn Glu Ala Arg Lys Leu Asn Pro Asn Ala Ile
    530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
        595                 600                 605

Gly Gln Leu Gly Glu Asn Asn Glu Leu Arg Leu Thr Arg Asp Ala Leu
    610                 615                 620

Glu Pro Cys Thr Val Gly His Arg Arg Tyr Phe Ile Phe Gly Gly Gly
```

625 630 635 640

Tyr Val Tyr Phe Glu Glu Tyr Ala Tyr Ser His Gln Leu Ser Arg Ala
645 650 655

Asp Val Thr Thr Val Ser Thr Phe Ile Asp Leu Asn Ile Thr Met Leu
660 665 670

Glu Asp His Glu Phe Val Pro Leu Glu Val Tyr Thr Arg His Glu Ile
675 680 685

Lys Asp Ser Gly Leu Leu Asp Tyr Thr Glu Val Gln Arg Arg Asn Gln
690 695 700

Leu His Asp Leu Arg Phe Ala Asp Ile Asp Thr Val Ile Arg Ala Asp
705 710 715 720

Ala Asn Ala Ala Met Phe Ala Gly Leu Cys Ala Phe Phe Glu Gly Met
725 730 735

Gly Asp Leu Gly Arg Ala Val Gly Lys Val Val Met Gly Val Val Gly
740 745 750

Gly Val Val Ser Ala Val Ser Gly Val Ser Ser Phe Met Ser Asn Pro
755 760 765

Phe Gly Ala Leu Ala Val Gly Leu Leu Val Leu Ala Gly Leu Val Ala
770 775 780

Ala Phe Phe Ala Phe Arg Tyr Val Leu Gln Leu Gln Arg Asn Pro Met
785 790 795 800

Lys Ala Leu Tyr Pro Leu Thr Thr Lys Glu Leu Lys Thr Ser Asp Pro
805 810 815

Gly Gly Val Gly Gly Glu Gly Glu Glu Gly Ala Glu Gly Gly Gly Phe
820 825 830

Asp Glu Ala Lys Leu Ala Glu Ala Arg Glu Met Ile Arg Tyr Met Ala
835 840 845

Leu Val Ser Ala Met Glu Arg Thr Glu His Lys Ala Arg Lys Lys Gly
850 855 860

Thr Ser Ala Leu Leu Ser Ser Lys Val Thr Asn Met Val Leu Arg Lys
865 870 875 880

Arg Asn Lys Ala Arg Tyr Ser Pro Leu His Asn Glu Asp Glu Ala Gly
885 890 895

Asp Glu Asp Glu Leu
900

<210> SEQ ID NO 43
<211> LENGTH: 480
<212> TYPE: PRT
<213> ORGANISM: Human herpesvirus 2

<400> SEQUENCE: 43

Met Ala Leu Gly Arg Val Gly Leu Ala Val Gly Leu Trp Gly Leu Leu
1 5 10 15

Trp Val Gly Val Val Val Val Leu Ala Asn Ala Ser Pro Gly Arg Thr
20 25 30

Ile Thr Val Gly Pro Arg Gly Asn Ala Ser Asn Ala Ala Pro Ser Ala
35 40 45

Ser Pro Arg Asn Ala Ser Ala Pro Arg Thr Thr Pro Thr Pro Pro Gln
50 55 60

Pro Arg Lys Ala Thr Lys Ser Lys Ala Ser Thr Ala Lys Pro Ala Pro
65 70 75 80

Pro Pro Lys Thr Gly Pro Pro Lys Thr Ser Ser Glu Pro Val Arg Cys
85 90 95

Asn Arg His Asp Pro Leu Ala Arg Tyr Gly Ser Arg Val Gln Ile Arg
100 105 110

Cys Arg Phe Pro Asn Ser Thr Arg Thr Glu Ser Arg Leu Gln Ile Trp
115 120 125

Arg Tyr Ala Thr Ala Thr Asp Ala Glu Ile Gly Thr Ala Pro Ser Leu
130 135 140

Glu Glu Val Met Val Asn Val Ser Ala Pro Pro Gly Gly Gln Leu Val
145 150 155 160

Tyr Asp Ser Ala Pro Asn Arg Thr Asp Pro His Val Ile Trp Ala Glu
165 170 175

Gly Ala Gly Pro Gly Ala Ser Pro Arg Leu Tyr Ser Val Val Gly Pro
180 185 190

Leu Gly Arg Gln Arg Leu Ile Ile Glu Glu Leu Thr Leu Glu Thr Gln
195 200 205

Gly Met Tyr Tyr Trp Val Trp Gly Arg Thr Asp Arg Pro Ser Ala Tyr
210 215 220

Gly Thr Trp Val Arg Val Arg Val Phe Arg Pro Pro Ser Leu Thr Ile
225 230 235 240

His Pro His Ala Val Leu Glu Gly Gln Pro Phe Lys Ala Thr Cys Thr
245 250 255

Ala Ala Thr Tyr Tyr Pro Gly Asn Arg Ala Glu Phe Val Trp Phe Glu
260 265 270

Asp Gly Arg Arg Val Phe Asp Pro Ala Gln Ile His Thr Gln Thr Gln
275 280 285

Glu Asn Pro Asp Gly Phe Ser Thr Val Ser Thr Val Thr Ser Ala Ala
290 295 300

Val Gly Gly Gln Gly Pro Pro Arg Thr Phe Thr Cys Gln Leu Thr Trp
305 310 315 320

His Arg Asp Ser Val Ser Phe Ser Arg Arg Asn Ala Ser Gly Thr Ala
325 330 335

Ser Val Leu Pro Arg Pro Thr Ile Thr Met Glu Phe Thr Gly Asp His
340 345 350

Ala Val Cys Thr Ala Gly Cys Val Pro Glu Gly Val Thr Phe Ala Trp
355 360 365

Phe Leu Gly Asp Asp Ser Ser Pro Ala Glu Lys Val Ala Val Ala Ser
370 375 380

Gln Thr Ser Cys Gly Arg Pro Gly Thr Ala Thr Ile Arg Ser Thr Leu
385 390 395 400

Pro Val Ser Tyr Glu Gln Thr Glu Tyr Ile Cys Arg Leu Ala Gly Tyr
405 410 415

Pro Asp Gly Ile Pro Val Leu Glu His His Gly Ser His Gln Pro Pro
420 425 430

Pro Arg Asp Pro Thr Glu Arg Gln Val Ile Arg Ala Val Glu Gly Ala
435 440 445

Gly Ile Gly Val Ala Val Leu Val Ala Val Val Leu Ala Gly Thr Ala
450 455 460

Val Val Tyr Leu Thr His Ala Ser Ser Val Arg Tyr Arg Arg Leu Arg
465 470 475 480

<210> SEQ ID NO 44
<211> LENGTH: 393
<212> TYPE: PRT
<213> ORGANISM: Human herpesvirus 2

<400> SEQUENCE: 44

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390
```

<210> SEQ ID NO 45
<211> LENGTH: 548

<212> TYPE: PRT
<213> ORGANISM: Human herpesvirus 2

<400> SEQUENCE: 45

Met Ala Arg Gly Ala Gly Leu Val Phe Phe Val Gly Val Trp Val Val
1 5 10 15

Ser Cys Leu Ala Ala Ala Pro Arg Thr Ser Trp Lys Arg Val Thr Ser
20 25 30

Gly Glu Asp Val Val Leu Leu Pro Ala Pro Ala Gly Pro Glu Glu Arg
35 40 45

Thr Arg Ala His Lys Leu Leu Trp Ala Ala Glu Pro Leu Asp Ala Cys
50 55 60

Gly Pro Leu Arg Pro Ser Trp Val Ala Leu Trp Pro Pro Arg Arg Val
65 70 75 80

Leu Glu Thr Val Val Asp Ala Ala Cys Met Arg Ala Pro Glu Pro Leu
85 90 95

Ala Ile Ala Tyr Ser Pro Pro Phe Pro Ala Gly Asp Glu Gly Leu Tyr
100 105 110

Ser Glu Leu Ala Trp Arg Asp Arg Val Ala Val Val Asn Glu Ser Leu
115 120 125

Val Ile Tyr Gly Ala Leu Glu Thr Asp Ser Gly Leu Tyr Thr Leu Ser
130 135 140

Val Val Gly Leu Ser Asp Glu Ala Arg Gln Val Ala Ser Val Val Leu
145 150 155 160

Val Val Glu Pro Ala Pro Val Pro Thr Pro Thr Pro Asp Asp Tyr Asp
165 170 175

Glu Glu Asp Asp Ala Gly Val Ser Glu Arg Thr Pro Val Ser Val Pro
180 185 190

Pro Pro Thr Pro Pro Arg Arg Pro Pro Val Ala Pro Pro Thr His Pro
195 200 205

Arg Val Ile Pro Glu Val Ser His Val Arg Gly Val Thr Val His Met
210 215 220

Glu Thr Pro Glu Ala Ile Leu Phe Ala Pro Gly Glu Thr Phe Gly Thr
225 230 235 240

Asn Val Ser Ile His Ala Ile Ala His Asp Asp Gly Pro Tyr Ala Met
245 250 255

Asp Val Val Trp Met Arg Phe Asp Val Pro Ser Ser Cys Ala Glu Met
260 265 270

Arg Ile Tyr Glu Ala Cys Leu Tyr His Pro Gln Leu Pro Glu Cys Leu
275 280 285

Ser Pro Ala Asp Ala Pro Cys Ala Val Ser Ser Trp Ala Tyr Arg Leu
290 295 300

Ala Val Arg Ser Tyr Ala Gly Cys Ser Arg Thr Thr Pro Pro Pro Arg
305 310 315 320

Cys Phe Ala Glu Ala Arg Met Glu Pro Val Pro Gly Leu Ala Trp Leu
325 330 335

Ala Ser Thr Val Asn Leu Glu Phe Gln His Ala Ser Pro Gln His Ala
340 345 350

Gly Leu Tyr Leu Cys Val Val Tyr Val Asp Asp His Ile His Ala Trp
355 360 365

Gly His Met Thr Ile Ser Thr Ala Ala Gln Tyr Arg Asn Ala Val Val
370 375 380

Glu Gln His Leu Pro Gln Arg Gln Pro Glu Pro Val Glu Pro Thr Arg
385 390 395 400

```
Pro His Val Arg Ala Pro Pro Pro Ala Pro Ser Ala Arg Gly Pro Leu
                405                 410                 415

Arg Leu Gly Ala Val Leu Gly Ala Ala Leu Leu Leu Ala Ala Leu Gly
            420                 425                 430

Leu Ser Ala Trp Ala Cys Met Thr Cys Trp Arg Arg Arg Ser Trp Arg
        435                 440                 445

Ala Val Lys Ser Arg Ala Ser Ala Thr Gly Pro Thr Tyr Ile Arg Val
    450                 455                 460

Ala Asp Ser Glu Leu Tyr Ala Asp Trp Ser Ser Asp Ser Glu Gly Glu
465                 470                 475                 480

Arg Asp Gly Ser Leu Trp Gln Asp Pro Pro Glu Arg Pro Asp Ser Pro
                485                 490                 495

Ser Thr Asn Gly Ser Gly Phe Glu Ile Leu Ser Pro Thr Ala Pro Ser
            500                 505                 510

Val Tyr Pro His Ser Glu Gly Arg Lys Ser Arg Arg Pro Leu Thr Thr
        515                 520                 525

Phe Gly Ser Gly Ser Pro Gly Arg Arg His Ser Gln Ala Ser Tyr Ser
    530                 535                 540

Ser Val Leu Trp
545


<210> SEQ ID NO 46
<211> LENGTH: 372
<212> TYPE: PRT
<213> ORGANISM: Human herpesvirus 2

<400> SEQUENCE: 46

Met Pro Gly Arg Ser Leu Gln Gly Leu Ala Ile Leu Gly Leu Trp Val
1               5                   10                  15

Cys Ala Thr Gly Leu Val Val Arg Gly Pro Thr Val Ser Leu Val Ser
            20                  25                  30

Asp Ser Leu Val Asp Ala Gly Ala Val Gly Pro Gln Gly Phe Val Glu
        35                  40                  45

Glu Asp Leu Arg Val Phe Gly Glu Leu His Phe Val Gly Ala Gln Val
    50                  55                  60

Pro His Thr Asn Tyr Tyr Asp Gly Ile Ile Glu Leu Phe His Tyr Pro
65                  70                  75                  80

Leu Gly Asn His Cys Pro Arg Val Val His Val Val Thr Leu Thr Ala
                85                  90                  95

Cys Pro Arg Arg Pro Ala Val Ala Phe Thr Leu Cys Arg Ser Thr His
            100                 105                 110

His Ala His Ser Pro Ala Tyr Pro Thr Leu Glu Leu Gly Leu Ala Arg
        115                 120                 125

Gln Pro Leu Leu Arg Val Arg Thr Ala Thr Arg Asp Tyr Ala Gly Leu
    130                 135                 140

Tyr Val Leu Arg Val Trp Val Gly Ser Ala Thr Asn Ala Ser Leu Phe
145                 150                 155                 160

Val Leu Gly Val Ala Leu Ser Ala Asn Gly Thr Phe Val Tyr Asn Gly
                165                 170                 175

Ser Asp Tyr Gly Ser Cys Asp Pro Ala Gln Leu Pro Phe Ser Ala Pro
            180                 185                 190

Arg Leu Gly Pro Ser Ser Val Tyr Thr Pro Gly Ala Ser Arg Pro Thr
        195                 200                 205

Pro Pro Arg Thr Thr Thr Ser Pro Ser Ser Pro Arg Asp Pro Thr Pro
```

```
    210                 215                 220

Ala Pro Gly Asp Thr Gly Thr Pro Ala Pro Ala Ser Gly Glu Arg Ala
225                 230                 235                 240

Pro Pro Asn Ser Thr Arg Ser Ala Ser Glu Ser Arg His Arg Leu Thr
                245                 250                 255

Val Ala Gln Val Ile Gln Ile Ala Ile Pro Ala Ser Ile Ile Ala Phe
            260                 265                 270

Val Phe Leu Gly Ser Cys Ile Cys Phe Ile His Arg Cys Gln Arg Arg
        275                 280                 285

Tyr Arg Arg Pro Arg Gly Gln Ile Tyr Asn Pro Gly Gly Val Ser Cys
    290                 295                 300

Ala Val Asn Glu Ala Ala Met Ala Arg Leu Gly Ala Glu Leu Arg Ser
305                 310                 315                 320

His Pro Asn Thr Pro Pro Lys Pro Arg Arg Arg Ser Ser Ser Ser Thr
                325                 330                 335

Thr Met Pro Ser Leu Thr Ser Ile Ala Glu Glu Ser Glu Pro Gly Pro
            340                 345                 350

Val Val Leu Leu Ser Val Ser Pro Arg Pro Arg Ser Gly Pro Thr Ala
        355                 360                 365

Pro Gln Glu Val
    370


<210> SEQ ID NO 47
<211> LENGTH: 753
<212> TYPE: PRT
<213> ORGANISM: Artificial Sequence
<220> FEATURE:
<223> OTHER INFORMATION: Synthetic Polypeptide

<400> SEQUENCE: 47

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95

Ser Pro Thr Pro Ala Asp Ala Gln Gly Ser Cys Gly Gly Gly Pro Val
            100                 105                 110

Gly Glu Glu Glu Ala Glu Ala Gly Gly Gly Gly Asp Val Asn Thr Pro
        115                 120                 125

Val Ala Tyr Leu Ile Val Gly Val Thr Ala Ser Gly Ser Phe Ser Thr
    130                 135                 140

Ile Pro Ile Val Asn Asp Pro Arg Thr Arg Val Glu Ala Glu Ala Ala
145                 150                 155                 160

Val Arg Ala Gly Thr Ala Val Asp Phe Ile Trp Thr Gly Asn Pro Arg
                165                 170                 175

Thr Ala Pro Arg Ser Leu Ser Leu Gly Gly His Thr Val Arg Ala Leu
            180                 185                 190

Ser Pro Thr Pro Pro Trp Pro Gly Thr Asp Asp Glu Asp Asp Asp Leu
```

```
        195                 200                 205

Ala Asp Val Asp Tyr Val Pro Pro Ala Pro Arg Arg Ala Pro Arg Arg
    210                 215                 220

Gly Gly Gly Gly Ala Gly Ala Thr Arg Gly Thr Ser Gln Pro Ala Ala
225                 230                 235                 240

Thr Arg Pro Ala Pro Pro Gly Ala Pro Arg Ser Ser Ser Ser Gly Gly
                245                 250                 255

Ala Pro Leu Arg Ala Gly Val Gly Ser Gly Ser Gly Gly Gly Pro Ala
            260                 265                 270

Val Ala Ala Val Val Pro Arg Val Ala Ser Leu Pro Pro Ala Ala Gly
        275                 280                 285

Gly Gly Arg Ala Gln Ala Arg Arg Val Gly Glu Asp Ala Ala Ala Ala
    290                 295                 300

Glu Gly Arg Thr Pro Pro Ala Arg Gln Pro Arg Ala Ala Gln Glu Pro
305                 310                 315                 320

Pro Ile Val Ile Ser Asp Ser Pro Pro Pro Ser Pro Arg Arg Pro Ala
                325                 330                 335

Gly Pro Gly Pro Leu Ser Phe Val Ser Ser Ser Ser Ala Gln Val Ser
            340                 345                 350

Ser Gly Pro Gly Gly Gly Gly Leu Pro Gln Ser Ser Gly Arg Ala Ala
        355                 360                 365

Arg Pro Arg Ala Ala Val Ala Pro Arg Val Arg Ser Pro Pro Arg Ala
    370                 375                 380

Ala Ala Ala Pro Val Val Ser Ala Ser Ala Asp Ala Ala Gly Pro Ala
385                 390                 395                 400

Pro Pro Ala Val Pro Val Asp Ala His Arg Ala Pro Arg Ser Arg Met
                405                 410                 415

Thr Gln Ala Gln Thr Asp Thr Gln Ala Gln Ser Leu Gly Arg Ala Gly
            420                 425                 430

Ala Thr Asp Ala Arg Gly Ser Gly Gly Pro Gly Ala Glu Gly Gly Ser
        435                 440                 445

Gly Pro Ala Ala Ser Ser Ser Ala Ser Ser Ser Ala Ala Pro Arg Ser
    450                 455                 460

Pro Leu Ala Pro Gln Gly Val Gly Ala Lys Arg Ala Ala Pro Arg Arg
465                 470                 475                 480

Ala Pro Asp Ser Asp Ser Gly Asp Arg Gly His Gly Pro Leu Ala Pro
                485                 490                 495

Ala Ser Ala Gly Ala Ala Pro Pro Ser Ala Ser Pro Ser Ser Gln Ala
            500                 505                 510

Ala Val Ala Ala Ala Ser Ser Ser Ser Ala Ser Ser Ser Ser Ala Ser
        515                 520                 525

Ser Ser Ser Ala Ser Ser Ser Ser Ala Ser Ser Ser Ser Ala Ser Ser
    530                 535                 540

Ser Ser Ala Ser Ser Ser Ser Ala Ser Ser Ser Ala Gly Gly Ala Gly
545                 550                 555                 560

Gly Ser Val Ala Ser Ala Ser Gly Ala Gly Glu Arg Arg Glu Thr Ser
                565                 570                 575

Leu Gly Pro Arg Ala Ala Ala Pro Arg Gly Pro Arg Lys Cys Ala Arg
            580                 585                 590

Lys Thr Arg His Ala Glu Gly Gly Pro Glu Pro Gly Ala Arg Asp Pro
        595                 600                 605

Ala Pro Gly Leu Thr Arg Tyr Leu Pro Ile Ala Gly Val Ser Ser Val
    610                 615                 620
```

Val Ala Leu Ala Pro Tyr Val Asn Lys Thr Val Thr Gly Asp Cys Leu
625 630 635 640

Pro Val Leu Asp Met Glu Thr Gly His Ile Gly Ala Tyr Val Val Leu
645 650 655

Val Asp Gln Thr Gly Asn Val Ala Asp Leu Leu Arg Ala Ala Ala Pro
660 665 670

Ala Trp Ser Arg Arg Thr Leu Leu Pro Glu His Ala Arg Asn Cys Val
675 680 685

Arg Pro Pro Asp Tyr Pro Thr Pro Pro Ala Ser Glu Trp Asn Ser Leu
690 695 700

Trp Met Thr Pro Val Gly Asn Met Leu Phe Asp Gln Gly Thr Leu Val
705 710 715 720

Gly Ala Leu Asp Phe His Gly Leu Arg Ser Arg His Pro Trp Ser Arg
725 730 735

Glu Gln Gly Ala Pro Ala Pro Ala Gly Asp Ala Pro Ala Gly His Gly
740 745 750

Glu

<210> SEQ ID NO 48
<211> LENGTH: 768
<212> TYPE: PRT
<213> ORGANISM: Artificial Sequence
<220> FEATURE:
<223> OTHER INFORMATION: Synthetic Polypeptide

<400> SEQUENCE: 48

Met Arg Gly Gly Gly Leu Val Cys Ala Leu Val Val Gly Ala Leu Val
1 5 10 15

Ala Ala Val Ala Ser Ala Ala Pro Ala Ala Pro Arg Ala Ser Gly Gly
20 25 30

Val Ala Ala Thr Val Ala Ala Asn Gly Gly Pro Ala Ser Gln Pro Pro
35 40 45

Pro Val Pro Ser Pro Ala Thr Thr Lys Ala Arg Lys Arg Lys Thr Lys
50 55 60

Lys Pro Pro Lys Arg Pro Glu Ala Thr Pro Pro Pro Asp Ala Asn Ala
65 70 75 80

Thr Val Ala Ala Gly His Ala Thr Leu Arg Ala His Leu Arg Glu Ile
85 90 95

Lys Val Glu Asn Ala Asp Ala Gln Phe Tyr Val Cys Pro Pro Pro Thr
100 105 110

Gly Ala Thr Val Val Gln Phe Glu Gln Pro Arg Arg Cys Pro Thr Arg
115 120 125

Pro Glu Gly Gln Asn Tyr Thr Glu Gly Ile Ala Val Val Phe Lys Glu
130 135 140

Asn Ile Ala Pro Tyr Lys Phe Lys Ala Thr Met Tyr Tyr Lys Asp Val
145 150 155 160

Thr Val Ser Gln Val Trp Phe Gly His Arg Tyr Ser Gln Phe Met Gly
165 170 175

Ile Phe Glu Asp Arg Ala Pro Val Pro Phe Glu Glu Val Ile Asp Lys
180 185 190

Ile Asn Ala Lys Gly Val Cys Arg Ser Thr Ala Lys Tyr Val Arg Asn
195 200 205

Asn Met Glu Thr Thr Ala Phe His Arg Asp Asp His Glu Thr Asp Met
210 215 220

-continued

```
Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
    290                 295                 300

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
                325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

Arg Ala Glu Tyr Gly Gly Ser Phe Arg Phe Ser Ser Asp Ala Ile Ser
    370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
        435                 440                 445

Ser Asn Thr Leu Ala Glu Leu Tyr Val Arg Glu Tyr Met Arg Glu Gln
    450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
        515                 520                 525

Glu Leu Thr Leu Trp Asn Glu Ala Arg Lys Leu Asn Pro Asn Ala Ile
    530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
        595                 600                 605

Gly Gln Leu Gly Glu Asn Asn Glu Leu Arg Leu Thr Arg Asp Ala Leu
    610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
```

645 650 655

Asp Val Thr Thr Val Ser Thr Phe Ile Asp Leu Asn Ile Thr Met Leu
660 665 670

Glu Asp His Glu Phe Val Pro Leu Glu Val Tyr Thr Arg His Glu Ile
675 680 685

Lys Asp Ser Gly Leu Leu Asp Tyr Thr Glu Val Gln Arg Arg Asn Gln
690 695 700

Leu His Asp Leu Arg Phe Ala Asp Ile Asp Thr Val Ile Arg Ala Asp
705 710 715 720

Ala Asn Ala Ala Met Phe Ala Gly Leu Cys Ala Phe Phe Glu Gly Met
725 730 735

Gly Asp Leu Gly Arg Ala Val Gly Lys Val Val Met Gly Val Val Gly
740 745 750

Gly Val Val Ser Ala Val Ser Gly Val Ser Ser Phe Met Ser Asn Pro
755 760 765

<210> SEQ ID NO 49
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 49

Met Ala Leu Gly Arg Val Gly Leu Ala Val Gly Leu Trp Gly Leu Leu
1 5 10 15

Trp Val Gly Val Val Val Val Leu Ala Asn Ala Ser Pro Gly Arg Thr
20 25 30

Ile Thr Val Gly Pro Arg Gly Asn Ala Ser Asn Ala Ala Pro Ser Ala
35 40 45

Ser Pro Arg Asn Ala Ser Ala Pro Arg Thr Thr Pro Thr Pro Pro Gln
50 55 60

Pro Arg Lys Ala Thr Lys Ser Lys Ala Ser Thr Ala Lys Pro Ala Pro
65 70 75 80

Pro Pro Lys Thr Gly Pro Pro Lys Thr Ser Ser Glu Pro Val Arg Cys
85 90 95

Asn Arg His Asp Pro Leu Ala Arg Tyr Gly Ser Arg Val Gln Ile Arg
100 105 110

Cys Arg Phe Pro Asn Ser Thr Arg Thr Glu Ser Arg Leu Gln Ile Trp
115 120 125

Arg Tyr Ala Thr Ala Thr Asp Ala Glu Ile Gly Thr Ala Pro Ser Leu
130 135 140

Glu Glu Val Met Val Asn Val Ser Ala Pro Pro Gly Gly Gln Leu Val
145 150 155 160

Tyr Asp Ser Ala Pro Asn Arg Thr Asp Pro His Val Ile Trp Ala Glu
165 170 175

Gly Ala Gly Pro Gly Ala Ser Pro Arg Leu Tyr Ser Val Val Gly Pro
180 185 190

Leu Gly Arg Gln Arg Leu Ile Ile Glu Glu Leu Thr Leu Glu Thr Gln
195 200 205

Gly Met Tyr Tyr Trp Val Trp Gly Arg Thr Asp Arg Pro Ser Ala Tyr
210 215 220

Gly Thr Trp Val Arg Val Arg Val Phe Arg Pro Pro Ser Leu Thr Ile
225 230 235 240

His Pro His Ala Val Leu Glu Gly Gln Pro Phe Lys Ala Thr Cys Thr

```
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly
        435                 440                 445


<210> SEQ ID NO 50
<211> LENGTH: 339
<212> TYPE: PRT
<213> ORGANISM: Artificial Sequence
<220> FEATURE:
<223> OTHER INFORMATION: Synthetic Polypeptide

<400> SEQUENCE: 50

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
```

165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro

<210> SEQ ID NO 51
<211> LENGTH: 417
<212> TYPE: PRT
<213> ORGANISM: Artificial Sequence
<220> FEATURE:
<223> OTHER INFORMATION: Synthetic Polypeptide

<400> SEQUENCE: 51

Met Ala Arg Gly Ala Gly Leu Val Phe Phe Val Gly Val Trp Val Val
1 5 10 15

Ser Cys Leu Ala Ala Ala Pro Arg Thr Ser Trp Lys Arg Val Thr Ser
20 25 30

Gly Glu Asp Val Val Leu Leu Pro Ala Pro Ala Gly Pro Glu Glu Arg
35 40 45

Thr Arg Ala His Lys Leu Leu Trp Ala Ala Glu Pro Leu Asp Ala Cys
50 55 60

Gly Pro Leu Arg Pro Ser Trp Val Ala Leu Trp Pro Pro Arg Arg Val
65 70 75 80

Leu Glu Thr Val Val Asp Ala Ala Cys Met Arg Ala Pro Glu Pro Leu
85 90 95

Ala Ile Ala Tyr Ser Pro Pro Phe Pro Ala Gly Asp Glu Gly Leu Tyr
100 105 110

Ser Glu Leu Ala Trp Arg Asp Arg Val Ala Val Val Asn Glu Ser Leu
115 120 125

Val Ile Tyr Gly Ala Leu Glu Thr Asp Ser Gly Leu Tyr Thr Leu Ser
130 135 140

Val Val Gly Leu Ser Asp Glu Ala Arg Gln Val Ala Ser Val Val Leu
145 150 155 160

Val Val Glu Pro Ala Pro Val Pro Thr Pro Thr Pro Asp Asp Tyr Asp
165 170 175

Glu Glu Asp Asp Ala Gly Val Ser Glu Arg Thr Pro Val Ser Val Pro
180 185 190

```
Pro Pro Thr Pro Pro Arg Arg Pro Pro Val Ala Pro Pro Thr His Pro
        195                 200                 205

Arg Val Ile Pro Glu Val Ser His Val Arg Gly Val Thr Val His Met
    210                 215                 220

Glu Thr Pro Glu Ala Ile Leu Phe Ala Pro Gly Glu Thr Phe Gly Thr
225                 230                 235                 240

Asn Val Ser Ile His Ala Ile Ala His Asp Asp Gly Pro Tyr Ala Met
                245                 250                 255

Asp Val Val Trp Met Arg Phe Asp Val Pro Ser Ser Cys Ala Glu Met
            260                 265                 270

Arg Ile Tyr Glu Ala Cys Leu Tyr His Pro Gln Leu Pro Glu Cys Leu
        275                 280                 285

Ser Pro Ala Asp Ala Pro Cys Ala Val Ser Ser Trp Ala Tyr Arg Leu
    290                 295                 300

Ala Val Arg Ser Tyr Ala Gly Cys Ser Arg Thr Thr Pro Pro Pro Arg
305                 310                 315                 320

Cys Phe Ala Glu Ala Arg Met Glu Pro Val Pro Gly Leu Ala Trp Leu
                325                 330                 335

Ala Ser Thr Val Asn Leu Glu Phe Gln His Ala Ser Pro Gln His Ala
            340                 345                 350

Gly Leu Tyr Leu Cys Val Val Tyr Val Asp Asp His Ile His Ala Trp
        355                 360                 365

Gly His Met Thr Ile Ser Thr Ala Ala Gln Tyr Arg Asn Ala Val Val
    370                 375                 380

Glu Gln His Leu Pro Gln Arg Gln Pro Glu Pro Val Glu Pro Thr Arg
385                 390                 395                 400

Pro His Val Arg Ala Pro Pro Pro Ala Pro Ser Ala Arg Gly Pro Leu
                405                 410                 415

Arg


<210> SEQ ID NO 52
<211> LENGTH: 262
<212> TYPE: PRT
<213> ORGANISM: Artificial Sequence
<220> FEATURE:
<223> OTHER INFORMATION: Synthetic Polypeptide

<400> SEQUENCE: 52

Met Pro Gly Arg Ser Leu Gln Gly Leu Ala Ile Leu Gly Leu Trp Val
1               5                   10                  15

Cys Ala Thr Gly Leu Val Val Arg Gly Pro Thr Val Ser Leu Val Ser
            20                  25                  30

Asp Ser Leu Val Asp Ala Gly Ala Val Gly Pro Gln Gly Phe Val Glu
        35                  40                  45

Glu Asp Leu Arg Val Phe Gly Glu Leu His Phe Val Gly Ala Gln Val
    50                  55                  60

Pro His Thr Asn Tyr Tyr Asp Gly Ile Ile Glu Leu Phe His Tyr Pro
65                  70                  75                  80

Leu Gly Asn His Cys Pro Arg Val Val His Val Val Thr Leu Thr Ala
                85                  90                  95

Cys Pro Arg Arg Pro Ala Val Ala Phe Thr Leu Cys Arg Ser Thr His
            100                 105                 110

His Ala His Ser Pro Ala Tyr Pro Thr Leu Glu Leu Gly Leu Ala Arg
        115                 120                 125
```

```
Gln Pro Leu Leu Arg Val Arg Thr Ala Thr Arg Asp Tyr Ala Gly Leu
    130                 135                 140

Tyr Val Leu Arg Val Trp Val Gly Ser Ala Thr Asn Ala Ser Leu Phe
145                 150                 155                 160

Val Leu Gly Val Ala Leu Ser Ala Asn Gly Thr Phe Val Tyr Asn Gly
                165                 170                 175

Ser Asp Tyr Gly Ser Cys Asp Pro Ala Gln Leu Pro Phe Ser Ala Pro
            180                 185                 190

Arg Leu Gly Pro Ser Ser Val Tyr Thr Pro Gly Ala Ser Arg Pro Thr
        195                 200                 205

Pro Pro Arg Thr Thr Thr Ser Pro Ser Ser Pro Arg Asp Pro Thr Pro
    210                 215                 220

Ala Pro Gly Asp Thr Gly Thr Pro Ala Pro Ala Ser Gly Glu Arg Ala
225                 230                 235                 240

Pro Pro Asn Ser Thr Arg Ser Ala Ser Glu Ser Arg His Arg Leu Thr
                245                 250                 255

Val Ala Gln Val Ile Gln
            260


<210> SEQ ID NO 53
<211> LENGTH: 1294
<212> TYPE: PRT
<213> ORGANISM: Artificial Sequence
<220> FEATURE:
<223> OTHER INFORMATION: Synthetic Polypeptide

<400> SEQUENCE: 53

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His His Arg Arg Arg Arg Ala Pro Arg Arg
    210                 215                 220
```

```
Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255

Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
                405                 410                 415

Pro Val Trp Ala Pro Glu Leu Gly Asp Ala Ala Gln Gln Tyr Ala Leu
            420                 425                 430

Ile Thr Arg Leu Leu Tyr Thr Pro Asp Ala Glu Ala Met Gly Trp Leu
        435                 440                 445

Gln Asn Pro Arg Val Ala Pro Gly Asp Val Ala Leu Asp Gln Ala Cys
    450                 455                 460

Phe Arg Ile Ser Gly Ala Ala Arg Asn Ser Ser Ser Phe Ile Ser Gly
465                 470                 475                 480

Ser Val Ala Arg Ala Val Pro His Leu Gly Tyr Ala Met Ala Ala Gly
                485                 490                 495

Arg Phe Gly Trp Gly Leu Ala His Val Ala Ala Ala Val Ala Met Ser
            500                 505                 510

Arg Arg Tyr Asp Arg Ala Gln Lys Gly Phe Leu Leu Thr Ser Leu Arg
        515                 520                 525

Arg Ala Tyr Ala Pro Leu Leu Ala Arg Glu Asn Ala Ala Leu Thr Gly
    530                 535                 540

Ala Arg Thr Pro Asp Asp Gly Gly Asp Ala Asn Arg His Asp Gly Asp
545                 550                 555                 560

Asp Ala Arg Gly Lys Pro Ala Ala Ala Ala Ala Pro Leu Pro Ser Ala
                565                 570                 575

Ala Ala Ser Pro Ala Asp Glu Arg Ala Val Pro Ala Gly Tyr Gly Ala
            580                 585                 590

Ala Gly Val Leu Ala Ala Leu Gly Arg Leu Ser Ala Ala Pro Ala Ser
        595                 600                 605

Ala Pro Ala Gly Ala Asp Asp Asp Asp Asp Asp Asp Gly Ala Gly Gly
    610                 615                 620

Gly Gly Gly Gly Arg Arg Ala Glu Ala Gly Arg Val Ala Val Glu Cys
625                 630                 635                 640

Leu Ala Ala Cys Arg Gly Ile Leu Glu Ala Leu Ala Glu Gly Phe Asp
```

-continued

```
                645                 650                 655

Gly Asp Leu Ala Ala Val Pro Gly Leu Ala Gly Ala Arg Pro Ala Ala
            660                 665                 670

Pro Pro Arg Pro Gly Pro Ala Gly Ala Ala Ala Pro Pro His Ala Asp
        675                 680                 685

Ala Pro Arg Leu Arg Ala Trp Leu Arg Glu Leu Arg Phe Val Arg Asp
    690                 695                 700

Ala Leu Val Leu Met Arg Leu Arg Gly Asp Leu Arg Val Ala Gly Gly
705                 710                 715                 720

Ser Glu Ala Ala Val Ala Ala Val Arg Ala Val Ser Leu Val Ala Gly
                725                 730                 735

Ala Leu Gly Pro Ala Leu Pro Arg Ser Pro Arg Leu Leu Ser Ser Ala
            740                 745                 750

Ala Ala Ala Ala Ala Asp Leu Leu Phe Gln Asn Gln Ser Leu Arg Pro
        755                 760                 765

Leu Leu Ala Asp Thr Val Ala Ala Ala Asp Ser Leu Ala Ala Pro Ala
    770                 775                 780

Ser Ala Pro Arg Glu Ala Ala Asp Ala Pro Arg Pro Ala Ala Ala Pro
785                 790                 795                 800

Pro Ala Gly Ala Ala Pro Pro Ala Pro Pro Thr Pro Pro Pro Arg Pro
                805                 810                 815

Pro Arg Pro Ala Ala Leu Thr Arg Arg Pro Ala Glu Gly Pro Asp Pro
            820                 825                 830

Gln Gly Gly Trp Arg Arg Gln Pro Pro Gly Pro Ser His Thr Pro Ala
        835                 840                 845

Pro Ser Ala Ala Ala Leu Glu Ala Tyr Cys Ala Pro Arg Ala Val Ala
    850                 855                 860

Glu Leu Thr Asp His Pro Leu Phe Pro Ala Pro Trp Arg Pro Ala Leu
865                 870                 875                 880

Met Phe Asp Pro Arg Ala Leu Ala Ser Leu Ala Ala Arg Cys Ala Ala
                885                 890                 895

Pro Pro Pro Gly Gly Ala Pro Ala Ala Phe Gly Pro Leu Arg Ala Ser
            900                 905                 910

Gly Pro Leu Arg Arg Ala Ala Ala Trp Met Arg Gln Val Pro Asp Pro
        915                 920                 925

Glu Asp Val Arg Val Val Ile Leu Tyr Ser Pro Leu Pro Gly Glu Asp
    930                 935                 940

Leu Ala Ala Gly Arg Ala Gly Gly Gly Pro Pro Pro Glu Trp Ser Ala
945                 950                 955                 960

Glu Arg Gly Gly Leu Ser Cys Leu Leu Ala Ala Leu Gly Asn Arg Leu
                965                 970                 975

Cys Gly Pro Ala Thr Ala Ala Trp Ala Gly Asn Trp Thr Gly Ala Pro
            980                 985                 990

Asp Val Ser Ala Leu Gly Ala Gln  Gly Val Leu Leu Leu  Ser Thr Arg
        995                 1000                1005

Asp Leu  Ala Phe Ala Gly Ala  Val Glu Phe Leu Gly  Leu Leu Ala
    1010                1015                1020

Gly Ala  Cys Asp Arg Arg Leu  Ile Val Val Asn Ala  Val Arg Ala
    1025                1030                1035

Ala Ala  Trp Pro Ala Ala Ala  Pro Val Val Ser Arg  Gln His Ala
    1040                1045                1050

Tyr Leu  Ala Cys Glu Val Leu  Pro Ala Val Gln Cys  Ala Val Arg
    1055                1060                1065
```

Trp Pro Ala Ala Arg Asp Leu Arg Arg Thr Val Leu Ala Ser Gly
1070 1075 1080

Arg Val Phe Gly Pro Gly Val Phe Ala Arg Val Glu Ala Ala His
1085 1090 1095

Ala Arg Leu Tyr Pro Asp Ala Pro Pro Leu Arg Leu Cys Arg Gly
1100 1105 1110

Ala Asn Val Arg Tyr Arg Val Arg Thr Arg Phe Gly Pro Asp Thr
1115 1120 1125

Leu Val Pro Met Ser Pro Arg Glu Tyr Arg Arg Ala Val Leu Pro
1130 1135 1140

Ala Leu Asp Gly Arg Ala Ala Ala Ser Gly Ala Gly Asp Ala Met
1145 1150 1155

Ala Pro Gly Ala Pro Asp Phe Cys Glu Asp Glu Ala His Ser His
1160 1165 1170

Arg Ala Cys Ala Arg Trp Gly Leu Gly Ala Pro Leu Arg Pro Val
1175 1180 1185

Tyr Val Ala Leu Gly Arg Asp Ala Val Arg Gly Gly Pro Ala Glu
1190 1195 1200

Leu Arg Gly Pro Arg Arg Glu Phe Cys Ala Arg Ala Leu Leu Glu
1205 1210 1215

Pro Asp Gly Asp Ala Pro Pro Leu Val Leu Arg Asp Asp Ala Asp
1220 1225 1230

Ala Gly Pro Pro Pro Gln Ile Arg Trp Ala Ser Ala Ala Gly Arg
1235 1240 1245

Ala Gly Thr Val Leu Ala Ala Ala Gly Gly Gly Val Glu Val Val
1250 1255 1260

Gly Thr Ala Ala Gly Leu Ala Thr Pro Pro Arg Arg Glu Pro Val
1265 1270 1275

Asp Met Asp Ala Glu Leu Glu Asp Asp Asp Asp Gly Leu Phe Gly
1280 1285 1290

Glu

<210> SEQ ID NO 54
<211> LENGTH: 2917
<212> TYPE: DNA
<213> ORGANISM: Artificial Sequence
<220> FEATURE:
<223> OTHER INFORMATION: Synthetic Polynucleotide

<400> SEQUENCE: 54
tcaagctttt ggaccctcgt acagaagcta atacgactca ctatagggaa ataagagaga 60
aaagaagagt aagaagaaat ataagagcca ccatgagagg tggtggctta gtttgcgcgc 120
tggttgtcgg ggcgctcgta gccgccgtgg cgtcggccgc ccctgcggct cctcgcgcta 180
gcggaggcgt agccgcaaca gttgcggcga acgggggtcc agcctctcag cctcctcccg 240
tcccgagccc tgcgaccacc aaggctagaa agcggaagac caagaaaccg cccaagcgcc 300
ccgaggccac cccgcccccc gatgccaacg cgactgtcgc cgctggccat gcgacgcttc 360
gcgctcatct gagggagatc aaggttgaaa atgctgatgc ccaattttac gtgtgcccgc 420
ccccgacggg cgccacggtt gtgcagtttg aacagccgcg gcgctgtccg acgcggccag 480
aaggccagaa ctatacggag ggcatagcgg tggtctttaa ggaaaacatc gccccgtaca 540
aatttaaggc cacaatgtac tacaaagacg tgacagtttc gcaagtgtgg tttggccaca 600
gatactcgca gtttatggga atcttcgaag atagagcccc tgttcccttc gaggaagtca 660

-continued

```
tcgacaagat taatgccaaa ggggtatgcc gttccacggc caaatacgtg cgcaacaata    720
tggagaccac cgcctttcac cgggatgatc acgagaccga catggagctt aagccggcga    780
aggtcgccac gcgtacctcc cggggttggc acaccacaga tcttaagtac aatccctcgc    840
gagttgaagc attccatcgg tatggaacta ccgttaactg catcgttgag gaggtggatg    900
cgcggtcggt gtacccttac gatgagtttg tgttagcgac cggcgatttt gtgtacatgt    960
ccccgtttta cggctaccgg gaggggtcgc acaccgaaca tacctcgtac gccgctgaca   1020
ggttcaagca ggtcgatggc ttttacgcgc gcgatctcac cacgaaggcc cgggccacgt   1080
caccgacgac caggaacttg ctcacgaccc ccaagttcac cgtcgcttgg gattgggtcc   1140
caaagcgtcc ggcggtctgc acgatgacca aatggcagga ggtggacgaa atgctccgcg   1200
cagaatacgg cggctccttc cgcttctcgt ccgacgccat ctcgacaacc ttcaccacca   1260
atctgaccca gtacagtctg tcgcgcgttg atttaggaga ctgcattggc cgggatgccc   1320
gggaggccat cgacagaatg tttgcgcgta agtacaatgc cacacatatt aaggtgggcc   1380
agccgcaata ctaccttgcc acgggcggct ttctcatcgc gtaccagccc cttctctcaa   1440
atacgctcgc tgaactgtac gtgcgggagt atatgaggga acaggaccgc aagccccgca   1500
atgccacgcc tgcgccacta cgagaggcgc cttcagctaa tgcgtcggtg gaacgtatca   1560
agaccacctc ctcaatagag ttcgcccggc tgcaatttac gtacaaccac atccagcgcc   1620
acgtgaacga catgctgggc cgcatcgctg tcgcctggtg cgagctgcag aatcacgagc   1680
tgactctttg gaacgaggcc cgaaaactca accccaacgc gatcgcctcc gcaacagtcg   1740
gtagacgggt gagcgctcgc atgctaggag atgtcatggc tgtgtccacc tgcgtgcccg   1800
tcgctccgga caacgtgatt gtgcagaatt cgatgcgggt ctcatcgcgg ccgggcacct   1860
gctacagcag gcccctcgtc agcttccggt acgaagacca gggcccgctg attgaagggc   1920
aactgggaga gaacaatgag ctgcgcctca cccgcgacgc gctcgaaccc tgcaccgtcg   1980
gacatcggag atatttcatc ttcggagggg gctacgtgta cttcgaagag tatgcctact   2040
ctcaccagct gagtagagcc gacgtcacta ccgtcagcac ctttattgac ctgaatatca   2100
ccatgctgga ggaccacgag tttgtgcccc tggaagttta cactcgccac gaaatcaaag   2160
actccggcct gttggattac acggaggttc agaggcggaa ccagctgcat gacctgcgct   2220
ttgccgacat cgacaccgtc atccgcgccg atgccaacgc tgccatgttc gcggggctgt   2280
gcgcgttctt cgaggggatg ggtgacttgg ggcgcgccgt cggcaaggtc gtcatgggag   2340
tagtgggggg cgttgtgagt gccgtcagcg gcgtgtcctc cttcatgtcc aatccattcg   2400
gagcgcttgc tgtggggctg ctggtcctgg ccgggctggt agccgccttc ttcgcctttc   2460
gatatgttct gcaactgcaa cgcaatccca tgaaagctct atatccgctc accaccaagg   2520
agctaaagac gtcagatcca ggaggcgtgg gcggggaagg ggaagagggc gcggagggcg   2580
gagggtttga cgaagccaaa ttggccgagg ctcgtgaaat gatccgatat atggcactag   2640
tgtcggcgat ggaaaggacc gaacataagg cccgaaagaa gggcacgtcg gcgctgctct   2700
catccaaggt caccaacatg gtactgcgca agcgcaacaa agccaggtac tctccgctcc   2760
ataacgagga cgaggcggga gatgaggatg agctctaatg ataataggct ggagcctcgg   2820
tggccatgct tcttgcccct tgggcctccc cccagcccct cctccccttc ctgcacccgt   2880
acccccgtgg tctttgaata aagtctgagt gggcggc                            2917
```

<210> SEQ ID NO 55

<211> LENGTH: 1654
<212> TYPE: DNA
<213> ORGANISM: Artificial Sequence
<220> FEATURE:
<223> OTHER INFORMATION: Synthetic Polynucleotide

<400> SEQUENCE: 55
tcaagctttt ggaccctcgt acagaagcta atacgactca ctatagggaa ataagagaga 60
aaagaagagt aagaagaaat ataagagcca ccatggccct tggacgggta ggcctagccg 120
tgggcctgtg gggcctactg tgggtgggtg tggtcgtggt gctggccaat gcctcccccg 180
gacgcacgat aacggtgggc ccgcgaggca acgcgagcaa tgctgccccc tccgcgtccc 240
cgcggaacgc atccgccccc cgaaccacac ccacgccccc acaaccccgc aaagcgacga 300
aatccaaggc ctccaccgcc aaaccggctc cgccccccaa gaccggaccc ccgaagacat 360
cctcggagcc cgtgcgatgc aaccgccacg acccgctggc ccggtacggc tcgcgggtgc 420
aaatccgatg ccggtttccc aactccacga ggactgagtc ccgtctccag atctggcgtt 480
atgccacggc gacggacgcc gaaatcggaa cagcgcctag cttagaagag gtgatggtga 540
acgtgtcggc cccgcccggg ggccaactgg tgtatgacag tgcccccaac cgaacggacc 600
cgcatgtaat ctgggcggag ggcgccggcc cgggcgccag cccgcgcctg tactcggttg 660
tcggcccgct gggtcggcag cggctcatca tcgaagagtt aaccctggag acacagggca 720
tgtactattg ggtgtggggc cggacggacc gcccgtccgc ctacgggacc tgggtccgcg 780
ttcgagtatt tcgccctccg tcgctgacca tccaccccca cgcggtgctg gagggccagc 840
cgtttaaggc gacgtgcacg gccgcaacct actacccggg caaccgcgcg gagttcgtct 900
ggtttgagga cggtcgccgc gtattcgatc cggcacagat acacacgcag acgcaggaga 960
accccgacgg cttttccacc gtctccaccg tgacctccgc ggccgtcggc gggcagggcc 1020
cccctcgcac cttcacctgc cagctgacgt ggcaccgcga ctccgtgtcg ttctctcggc 1080
gcaacgccag cggcacggcc tcggttctgc cgcggccgac cattaccatg gagtttacag 1140
gcgaccatgc ggtctgcacg gccggctgtg tgcccgaggg ggtcacgttt gcttggttcc 1200
tgggggatga ctcctcgccg gcggaaaagg tggccgtcgc gtcccagaca tcgtgcgggc 1260
gccccggcac cgccacgatc cgctccaccc tgccggtctc gtacgagcag accgagtaca 1320
tctgtagact ggcgggatac ccggacggaa ttccggtcct agagcaccac ggaagccacc 1380
agcccccgcc gcgggaccca accgagcggc aggtgatccg ggcggtggag ggggcgggga 1440
tcggagtggc tgtccttgtc gcggtggttc tggccgggac cgcggtagtg tacctgaccc 1500
atgcctcctc ggtacgctat cgtcggctgc ggtaatgata ataggctgga gcctcggtgg 1560
ccatgcttct tgccccttgg gcctcccccc agcccctcct ccccttcctg cacccgtacc 1620
cccgtggtct ttgaataaag tctgagtggg cggc 1654

<210> SEQ ID NO 56
<211> LENGTH: 1393
<212> TYPE: DNA
<213> ORGANISM: Artificial Sequence
<220> FEATURE:
<223> OTHER INFORMATION: Synthetic Polynucleotide

<400> SEQUENCE: 56
tcaagctttt ggaccctcgt acagaagcta atacgactca ctatagggaa ataagagaga 60
aaagaagagt aagaagaaat ataagagcca ccatggggcg tttgacctcc ggcgtcggga 120
cggcggccct gctagttgtc gcggtgggac tccgcgtcgt ctgcgccaaa tacgccttag 180

```
cagacccctc gcttaagatg gccgatccca atcgatttcg cgggaagaac cttccggttt    240

tggaccagct gaccgacccc cccggggtga agcgtgttta ccacattcag ccgagcctgg    300

aggacccgtt ccagcccccc agcatcccga tcactgtgta ctacgcagtg ctggaacgtg    360

cctgccgcag cgtgctccta catgccccat cggaggcccc ccagatcgtg cgcggggctt    420

cggacgaggc ccgaaagcac acgtacaacc tgaccatcgc ctggtatcgc atgggagaca    480

attgcgctat ccccatcacg gttatggaat acaccgagtg cccctacaac aagtcgttgg    540

gggtctgccc catccgaacg cagccccgct ggagctacta tgacagcttt agcgccgtca    600

gcgaggataa cctgggattc ctgatgcacg cccccgcctt cgagaccgcg ggtacgtacc    660

tgcggctagt gaagataaac gactggacgg agatcacaca atttatcctg gagcaccggg    720

cccgcgcctc ctgcaagtac gctctccccc tgcgcatccc cccggcagcg tgcctcacct    780

cgaaggccta ccaacagggc gtgacggtcg acagcatcgg gatgctaccc cgctttatcc    840

ccgaaaacca gcgcaccgtc gccctataca gcttaaaaat cgccgggtgg cacggcccca    900

agcccccgta caccagcacc ctgctgccgc cggagctgtc cgacaccacc aacgccacgc    960

aacccgaact cgttccggaa gaccccgagg actcggccct cttagaggat cccgccggga   1020

cggtgtcttc gcagatcccc ccaaactggc acatcccgtc gatccaggac gtcgcaccgc   1080

accacgcccc cgccgccccc agcaacccgg gcctgatcat cggcgcgctg gccggcagta   1140

ccctggcggt gctggtcatc ggcggtattg cgttttgggt acgccgccgc gctcagatgg   1200

cccccaagcg cctacgtctc ccccacatcc gggatgacga cgcgcccccc tcgcaccagc   1260

cattgtttta ctagtgataa taggctggag cctcggtggc catgcttctt gccccttggg   1320

cctcccccca gcccctcctc cccttcctgc acccgtaccc ccgtggtctt tgaataaagt   1380

ctgagtgggc ggc                                                      1393
```

<210> SEQ ID NO 57
<211> LENGTH: 1858
<212> TYPE: DNA
<213> ORGANISM: Artificial Sequence
<220> FEATURE:
<223> OTHER INFORMATION: Synthetic Polynucleotide

<400> SEQUENCE: 57

```
tcaagctttt ggaccctcgt acagaagcta atacgactca ctatagggaa ataagagaga     60

aaagaagagt aagaagaaat ataagagcca ccatggctag gggggccggg ttggtttttt    120

ttgttggagt ttgggtcgta agctgcctcg cggcagcgcc cagaacgtcc tggaaacgcg    180

taacctcggg cgaagacgtg gtgttactcc ccgcgccggc ggggccggaa gaacgcactc    240

gggcccacaa actactgtgg gcagcggaac cgctggatgc ctgcggtccc ctgaggccgt    300

catgggtggc actgtggccc ccccgacgag tgcttgagac ggttgtcgat gcggcgtgca    360

tgcgcgcccc ggaaccgctc gctatcgcat acagtccccc gttccctgcg ggcgacgagg    420

gactttattc ggagttggcg tggcgcgatc gcgtagccgt ggtcaacgag agtttagtta    480

tctacggggc cctggagacg gacagtggtc tgtacaccct gtcagtggtg ggcctatccg    540

acgaggcccg ccaagtggcg tccgtggttc tcgtcgtcga gcccgcccct gtgcctaccc    600

cgacccccga tgactacgac gaggaggatg acgcgggcgt gagcgaacgc acgcccgtca    660

gcgttccccc cccaacaccc ccccgacgtc cccccgtcgc ccccccgacg caccctcgtg    720

ttatccctga ggtgagccac gtgcgggggg tgacggtcca catggaaacc ccggaggcca    780
```

ttctgtttgc gccaggggag acgtttggga cgaacgtctc catccacgca attgcccacg 840
acgacggtcc gtacgccatg gacgtcgtct ggatgcgatt tgatgtcccg tcctcgtgcg 900
ccgagatgcg gatctatgaa gcatgtctgt atcacccgca gctgcctgag tgtctgtctc 960
cggccgatgc gccgtgcgcc gtaagttcgt gggcgtaccg cctggcggtc cgcagctacg 1020
ccggctgctc caggactacg cccccacctc gatgttttgc tgaagctcgc atggaaccgg 1080
tccccgggtt ggcgtggctc gcatcaactg ttaatctgga attccagcat gcctctcccc 1140
aacacgccgg cctctatctg tgtgtggtgt atgtggacga ccatatccat gcctggggcc 1200
acatgaccat ctccacagcg gcccagtacc ggaatgcggt ggtggaacag catctccccc 1260
agcgccagcc cgagcccgta gaacccaccc gaccgcatgt gagagccccc cctcccgcac 1320
cctccgcgag aggcccgtta cgcttaggtg cggtcctggg ggcggccctg ttgctcgcgg 1380
ccctcgggct atccgcctgg gcgtgcatga cctgctggcg caggcgcagt tggcgggcgg 1440
ttaaaagtcg ggcctcggcg accggcccca cttacattcg agtagcggat agcgagctgt 1500
acgcggactg gagttcggac tcagagggcg agcgcgacgg ttccctgtgg caggaccctc 1560
cggagagacc cgactcaccg tccacaaatg gatccggctt tgagatctta tccccaacgg 1620
cgccctctgt ataccccat agcgaagggc gtaaatcgcg ccgcccgctc accacctttg 1680
gttcaggaag cccgggacgt cgtcactccc aggcgtccta ttcttccgtc ttatggtaat 1740
gataataggc tggagcctcg gtggccatgc ttcttgcccc ttgggcctcc ccccagcccc 1800
tcctcccctt cctgcacccg tacccccgtg gtctttgaat aaagtctgag tgggcggc 1858

<210> SEQ ID NO 58
<211> LENGTH: 1330
<212> TYPE: DNA
<213> ORGANISM: Artificial Sequence
<220> FEATURE:
<223> OTHER INFORMATION: Synthetic Polynucleotide

<400> SEQUENCE: 58
tcaagctttt ggaccctcgt acagaagcta atacgactca ctatagggaa ataagagaga 60
aaagaagagt aagaagaaat ataagagcca ccatgcccgg ccgctcgctg cagggcctgg 120
cgatcctggg cctgtgggtc tgcgccaccg gcctggtcgt ccgcggcccc acggtcagtc 180
tggtctcaga ctcactcgtg gatgccgggg ccgtggggcc ccagggcttc gtggaagagg 240
acctgcgtgt tttcggggag cttcattttg tgggggccca ggtcccccac acaaactact 300
acgacggcat catcgagctg tttcactacc ccctggggaa ccactgcccc cgcgttgtac 360
acgtggtcac actgaccgca tgcccccgcc gcccccgccgt ggcgttcacc ttgtgtcgct 420
cgacgcacca cgcccacagc cccgcctatc cgaccctgga gctgggtctg gcgcggcagc 480
cgcttctgcg ggttcgaacg gcaacgcgcg actatgccgg tctgtatgtc ctgcgcgtat 540
gggtcggcag cgcgacgaac gccagcctgt ttgttttggg ggtggcgctc tctgccaacg 600
ggacgtttgt gtataacggc tcggactacg gctcctgcga tccggcgcag cttccctttt 660
cggccccgcg cctgggaccc tcgagcgtat acacccccgg agcctcccgg cccacccctc 720
cacggacaac gacatcaccg tcctccccac gagacccgac cccgcccccc ggggacacag 780
ggacgcctgc tcccgcgagc ggcgagagag ccccgcccaa ttccacgcga tcggccagcg 840
aatcgagaca caggctaacc gtagcccagg taatccagat cgccataccg gcgtccatca 900
tcgcctttgt gtttctgggc agctgtatct gcttcatcca tagatgccag cgccgataca 960
ggcgcccccg cggccagatt tacaaccccg ggggcgtttc ctgcgcggtc aacgaggcgg 1020
ccatggcccg cctcggagcc gagctgcgat cccacccaaa caccccccc aaaccccgac 1080 gccgttcgtc gtcgtccacg accatgcctt ccctaacgtc gatagctgag gaatcggagc 1140
caggtccagt cgtgctgctg tccgtcagtc ctcggccccg cagtggcccg acggcccccc 1200
aagaggtcta gtgataatag gctggagcct cggtggccat gcttcttgcc ccttgggcct 1260
ccccccagcc cctcctcccc ttcctgcacc cgtacccccg tggtctttga ataaagtctg 1320
agtgggcggc 1330

<210> SEQ ID NO 59
<211> LENGTH: 2515
<212> TYPE: DNA
<213> ORGANISM: Artificial Sequence
<220> FEATURE:
<223> OTHER INFORMATION: Synthetic Polynucleotide

<400> SEQUENCE: 59
tcaagctttt ggaccctcgt acagaagcta atacgactca ctatagggaa ataagagaga 60
aaagaagagt aagaagaaat ataagagcca ccatgcgcgg ggggggctta gtttgcgcgc 120
tggtcgtggg ggcgctcgta gccgcggtcg cgtcggcggc tccggctgcc ccacgcgctt 180
caggtggtgt cgctgcgacc gttgcggcga atggtggtcc cgccagccaa ccgcctcccg 240
tcccgagccc cgcgaccact aaggcccgga agcggaagac caagaagcca cccaagcggc 300
ccgaggcgac tccgccccca gacgccaacg cgaccgtcgc cgccggccac gccactctgc 360
gtgcgcacct gcgggaaatc aaggtcgaga acgcggacgc ccagttttac gtgtgcccgc 420
cgccgactgg cgccacggtg gtgcagtttg agcaacctag gcgctgcccg acgcgaccag 480
aggggcagaa ctacaccgag ggcatagcgg tggtctttaa ggaaaacatc gccccgtaca 540
aattcaaggc caccatgtac tacaaagacg tgaccgtgtc gcaggtgtgg ttcggccacc 600
gctactccca gtttatgggg atattcgagg accgcgcccc cgttcccttc gaagaggtga 660
ttgacaaaat taacgccaag gggtctgcc gcagtacggc gaagtacgtc cggaacaaca 720
tggagaccac tgccttccac cgggacgacc acgaaacaga catggagctc aaaccggcga 780
aagtcgccac gcgcacgagc cgggggtggc acaccaccga cctcaaatac aatccttcgc 840
gggtggaagc attccatcgg tatggcacga ccgtcaactg tatcgtagag gaggtggatg 900
cgcggtcggt gtacccctac gatgagttcg tgctggcaac gggcgatttt gtgtacatgt 960
ccccttttta cggctaccgg gaaggtagtc acaccgagca caccagttac gccgccgacc 1020
gctttaagca agtggacggc ttctacgcgc gcgacctcac cacaaaggcc cgggccacgt 1080
cgccgacgac ccgcaatttg ctgacgaccc ccaagtttac cgtggcctgg gactgggtgc 1140
ctaagcgacc ggcggtctgt accatgacaa agtggcagga ggtggacgaa atgctccgcg 1200
ctgaatacgg tggctctttc cgcttctctt ccgacgccat ctccaccacg ttcaccacca 1260
acctgaccca atactcgctc tcgagagtcg atctgggaga ctgcattggc cgggatgccc 1320
gcgaggcaat tgaccgcatg ttcgcgcgca agtacaacgc tacgcacata aaggttggcc 1380
aaccccagta ctacctagcc acgggggct tcctcatcgc ttatcaaccc ctcctcagca 1440
acacgctcgc cgagctgtac gtgcgggaat atatgcggga acaggaccgc aaaccccgaa 1500
acgccacgcc cgcgccgctg cgggaagcac cgagcgccaa cgcgtccgtg gagcgcatca 1560
agacgacatc ctcgattgag tttgctcgtc tgcagtttac gtataaccac atacagcgcc 1620
atgtaaacga catgctcggg cgcatcgccg tcgcgtggtg cgagctccaa aatcacgagc 1680

```
tcactctgtg gaacgaggca cgcaagctca atcccaacgc catcgcatcc gccaccgtag   1740

gccggcgggt gagcgctcgc atgctcgggg atgtcatggc cgtctccacg tgcgtgcccg   1800

tcgccccgga caacgtgatc gtgcaaaata gcatgcgcgt ttcttcgcgg ccggggacgt   1860

gctacagccg cccgctggtt agctttcggt acgaagacca aggcccgctg attgaggggc   1920

agctgggtga gaacaacgag ctgcgcctca cccgcgatgc gttagagccg tgtaccgtcg   1980

gccaccggcg ctacttcatc ttcggagggg gatacgtata cttcgaagaa tatgcgtact   2040

ctcaccaatt gagtcgcgcc gatgtcacca ctgttagcac cttcatcgac ctgaacatca   2100

ccatgctgga ggaccacgag ttcgtgcccc tggaggtcta cacacgccac gagatcaagg   2160

attccggcct actggactac accgaagtcc agagacgaaa tcagctgcac gatctccgct   2220

ttgctgacat cgatactgtt atccgcgccg acgccaacgc cgccatgttc gcaggtctgt   2280

gtgcgttttt cgagggtatg ggtgacttag ggcgcgcggt gggcaaggtc gtcatggggg   2340

tagtcggggg cgtggtgtcg gccgtctcgg gcgtctcctc ctttatgtct aacccctgat   2400

aataggctgg agcctcggtg gccatgcttc ttgccccttg ggcctccccc cagcccctcc   2460

tccccttcct gcacccgtac ccccgtggtc tttgaataaa gtctgagtgg gcggc        2515
```

<210> SEQ ID NO 60
<211> LENGTH: 1552
<212> TYPE: DNA
<213> ORGANISM: Artificial Sequence
<220> FEATURE:
<223> OTHER INFORMATION: Synthetic Polynucleotide

<400> SEQUENCE: 60

```
tcaagctttt ggaccctcgt acagaagcta atacgactca ctatagggaa ataagagaga     60

aaagaagagt aagaagaaat ataagagcca ccatggcact gggaagagtg ggattggccg    120

tcggactgtg ggactgctg tgggtgggag tcgtcgtcgt cctggctaac gcctcacccg    180

gtcggactat cactgtggga cccaggggga acgcctctaa cgccgcgccc tcagctagcc    240

ccaggaatgc cagcgctccc aggaccaccc cgactcctcc gcaaccccgc aaggcgacca    300

agtccaaggc gtccactgcc aagccagcgc ctccgcctaa gactggcccc cctaagacct    360

ccagcgaacc tgtgcggtgc aaccggcacg accctctggc acgctacgga tcgcgggtcc    420

aaatccggtg tcggttcccg aacagcactc ggaccgaatc gcggctccag atttggagat    480

acgcaactgc cactgatgcc gagatcggca ctgccccaag ccttgaggag gtcatggtca    540

acgtgtcagc tcctcctgga ggccagctgg tgtacgactc cgctccgaac cgaaccgacc    600

cgcacgtcat ctgggccgaa ggagccggtc ctggtgcatc gccgaggttg tactcggtag    660

tgggtcccct ggggagacag cggctgatca tcgaagaact gactctggag actcagggca    720

tgtactattg ggtgtggggc agaaccgata gaccatccgc atacggaacc tgggtgcgcg    780

tgagagtgtt cagacccccg tccttgacaa tccacccgca tgcggtgctc gaagggcagc    840

ccttcaaggc cacttgcact gcggccactt actaccctgg aaaccgggcc gaattcgtgt    900

ggttcgagga tggacggagg gtgttcgacc cggcgcagat tcatacgcag actcaggaaa    960

acccggacgg cttctccacc gtgtccactg tgacttcggc cgctgtggga ggacaaggac   1020

cgccacgcac cttcacctgt cagctgacct ggcaccgcga cagcgtgtcc tttagccggc   1080

ggaacgcatc aggcactgcc tccgtgttgc ctcgcccaac cattaccatg gagttcaccg   1140

gagatcacgc cgtgtgcact gctggctgcg tccccgaagg cgtgaccttc gcctggtttc   1200

tcggggacga ctcatccccg gcggaaaagg tggccgtggc ctctcagacc agctgcggta   1260
```

gaccgggaac cgccaccatc cgctccactc tgccggtgtc gtacgagcag accgagtaca 1320
tttgtcgcct ggccggatac ccggacggta tcccagtgct cgaacaccac ggcagccatc 1380
agcctccgcc gagagatcct accgagcgcc aggtcatccg ggccgtggaa ggatgataat 1440
aggctggagc ctcggtggcc atgcttcttg ccccttgggc ctccccccag cccctcctcc 1500
ccttcctgca cccgtacccc cgtggtcttt gaataaagtc tgagtgggcg gc 1552

<210> SEQ ID NO 61
<211> LENGTH: 1462
<212> TYPE: DNA
<213> ORGANISM: Artificial Sequence
<220> FEATURE:
<223> OTHER INFORMATION: Synthetic Polynucleotide

<400> SEQUENCE: 61
tcaagctttt ggaccctcgt acagaagcta atacgactca ctatagggaa ataagagaga 60
aaagaagagt aagaagaaat ataagagcca ccatggctcg cggggccggg ttggtgtttt 120
ttgttggagt ttgggtcgta tcgtgcctgg cggcagcacc cagaacgtcc tggaaacggg 180
ttacctcggg cgaggacgtg gtgttgcttc cggcgcccgc ggggccggag gaacgcacac 240
gggcccacaa actactgtgg gccgcggaac ccctggatgc ctgcggtccc ctgaggccgt 300
cgtgggtggc gctgtggccc ccgcgacggg tgctcgaaac ggtcgtggat gcggcgtgca 360
tgcgcgcccc ggaaccgctc gccatagcat acagtccccc gttccccgcg ggcgacgagg 420
gactgtattc ggagttggcg tggcgcgatc gcgtagccgt ggtcaacgag agtctggtca 480
tctacggggc cctggagacg gacagcggtc tgtacaccct gtccgtggtc ggcctaagcg 540
acgaggcgcg ccaagtggcg tcggtggttc tggtcgtgga gcccgcccct gtgccgaccc 600
cgacccccga cgactacgac gaagaagacg acgcgggcgt gagcgaacgc acgccggtca 660
gcgtaccccc cccgacccca ccccgtcgtc cccccgtcgc ccccccctacg caccctcgtg 720 ttatccccga ggtgtcccac gtgcgcgggg taacggtcca tatggagacc ccggaggcca 780
ttctgtttgc ccccggagag acgtttggga cgaacgtctc catccacgcc attgcccatg 840
acgacggtcc gtacgccatg gacgtcgtct ggatgcggtt tgacgtgccg tcctcgtgcg 900
ccgagatgcg gatctacgaa gcttgtctgt atcacccgca gcttccagaa tgtctatctc 960
cggccgacgc gccgtgcgct gtaagttcct gggcgtaccg cctggcggtc cgcagctacg 1020
ccggctgttc caggactacg cccccgccgc gatgttttgc cgaggctcgc atggaaccgg 1080
tcccggggtt ggcgtggtta gcctccaccg tcaacctgga attccagcac gcctcccctc 1140
agcacgccgg cctttacctg tgcgtggtgt acgtggacga tcatatccac gcctggggcc 1200
acatgaccat ctctaccgcg gcgcagtacc ggaacgcggt ggtggaacag cacttgcccc 1260
agcgccagcc tgaacccgtc gagcccaccc gcccgcacgt aagagcaccc cctcccgcgc 1320
cttccgcgcg cggcccgctg cgctgataat aggctggagc ctcggtggcc atgcttcttg 1380
ccccttgggc ctccccccag cccctcctcc ccttcctgca cccgtacccc cgtggtcttt 1440
gaataaagtc tgagtgggcg gc 1462

<210> SEQ ID NO 62
<211> LENGTH: 997
<212> TYPE: DNA
<213> ORGANISM: Artificial Sequence
<220> FEATURE:
<223> OTHER INFORMATION: Synthetic Polynucleotide

<400> SEQUENCE: 62
tcaagctttt ggaccctcgt acagaagcta atacgactca ctatagggaa ataagagaga 60
aaagaagagt aagaagaaat ataagagcca ccatgcccgg ccgctcgctg cagggcctgg 120
cgatcctggg cctgtgggtc tgcgccaccg gcctggtcgt ccgcggcccc acggtcagtc 180
tggtctcaga ctcactcgtg gatgccgggg ccgtggggcc ccagggcttc gtggaagagg 240
acctgcgtgt tttcggggag cttcattttg tgggggccca ggtcccccac acaaactact 300
acgacggcat catcgagctg tttcactacc ccctggggaa ccactgcccc cgcgttgtac 360
acgtggtcac actgaccgca tgcccccgcc gccccgccgt ggcgttcacc ttgtgtcgct 420
cgacgcacca cgcccacagc cccgcctatc cgaccctgga gctgggtctg gcgcggcagc 480
cgcttctgcg ggttcgaacg gcaacgcgcg actatgccgg tctgtatgtc ctgcgcgtat 540
gggtcggcag cgcgacgaac gccagcctgt ttgttttggg ggtggcgctc tctgccaacg 600
ggacgtttgt gtataacggc tcggactacg gctcctgcga tccggcgcag cttccctttt 660
cggccccgcg cctgggaccc tcgagcgtat acacccccgg agcctcccgg cccacccctc 720
cacggacaac gacatccccg tcctccccta gagacccgac cccgccccc ggggacacag 780 gaacgcctgc gcccgcgagc ggcgagagag ccccgcccaa ttccacgcga tcggccagcg 840
aatcgagaca caggctaacc gtagcccagg taatccagtg ataataggct ggagcctcgg 900
tggccatgct tcttgcccct tgggcctccc cccagcccct cctccccttc ctgcacccgt 960
acccccgtgg tctttgaata aagtctgagt gggcggc 997

<210> SEQ ID NO 63
<211> LENGTH: 1228
<212> TYPE: DNA
<213> ORGANISM: Artificial Sequence
<220> FEATURE:
<223> OTHER INFORMATION: Synthetic Polynucleotide

<400> SEQUENCE: 63
tcaagctttt ggaccctcgt acagaagcta atacgactca ctatagggaa ataagagaga 60
aaagaagagt aagaagaaat ataagagcca ccatggggcg tttgacctcc ggcgtcggga 120
cggcggccct gctagttgtc gcggtgggac tccgcgtcgt ctgcgccaaa tacgccttag 180
cagacccctc gcttaagatg gccgatccca atcgatttcg cgggaagaac cttccggttt 240
tggaccagct gaccgacccc cccggggtga agcgtgttta ccacattcag ccgagcctgg 300
aggacccgtt ccagcccccc agcatcccga tcactgtgta ctacgcagtg ctggaacgtg 360
cctgccgcag cgtgctccta catgccccat cggaggcccc ccagatcgtg cgcggggctt 420
cggacgaggc ccgaaagcac acgtacaacc tgaccatcgc ctggtatcgc atgggagaca 480
attgcgctat ccccatcacg gttatggaat acaccgagtg cccctacaac aagtcgttgg 540
gggtctgccc catccgaacg cagccccgct ggagctacta tgacagcttt agcgccgtca 600
gcgaggataa cctgggattc ctgatgcacg cccccgcctt cgagaccgcg ggtacgtacc 660
tgcggctagt gaagataaac gactggacgg agatcacaca atttatcctg gagcaccggg 720
cccgcgcctc ctgcaagtac gctctccccc tgcgcatccc cccggcagcg tgcctcacct 780
cgaaggccta ccaacagggc gtgacggtcg acagcatcgg gatgctaccc cgctttatcc 840
ccgaaaacca gcgcaccgtc gccctataca gcttaaaaat cgccgggtgg cacggcccca 900
agcccccgta caccagcacc ctgctgccgc cggagctgtc cgacaccacc aacgccacgc 960
aacccgaact cgttccggaa gaccccgagg actcggccct cttagaggat cccgccggga 1020
cggtgtcttc gcagatcccc ccaaactggc acatcccgtc gatccaggac gtcgcgccgc 1080
accacgcccc cgccgccccc agcaacccgt gataataggc tggagcctcg gtggccatgc 1140
ttcttgcccc ttgggcctcc ccccagcccc tcctcccctt cctgcacccg tacccccgtg 1200
gtctttgaat aaagtctgag tgggcggc 1228

<210> SEQ ID NO 64
<211> LENGTH: 2473
<212> TYPE: DNA
<213> ORGANISM: Artificial Sequence
<220> FEATURE:
<223> OTHER INFORMATION: Synthetic Polynucleotide

<400> SEQUENCE: 64
tcaagctttt ggaccctcgt acagaagcta atacgactca ctatagggaa ataagagaga 60
aaagaagagt aagaagaaat ataagagcca ccatggaacc gcggcctggt acttcatccc 120
gcgccgatcc tggaccggaa cggccacctc gccagacccc tggaacgcag cctgcagccc 180
ctcacgcctg gggatgctg aatgatatgc agtggctggc ctcaagcgac tccgaggaag 240
agacagaggt cggcatctcc gacgatgatc tccatcggga ttctacttcg gaagcgggct 300
ccaccgacac agagatgttc gaggccggcc tgatggatgc tgcgacccct cccgcaagac 360
cgcctgccga acgccaaggc tcgccgaccc ctgctgacgc ccagggttcg tgcggtggag 420
gccctgtggg ggaggaggaa gctgaagccg gaggcggtgg agatgtcaac accccggtgg 480
cctacctgat cgtgggcgtg actgccagcg gatccttctc gaccatcccc attgtcaacg 540
atccccgcac tcgggtcgaa gcggaggccg cagtgcgggc tggaactgcc gtggacttca 600
tttggactgg caatcccagg accgctcccc ggtcactgtc cctgggagga cacaccgtcc 660
gcgccctgtc accaactccc ccgtggcctg gaaccgatga cgaggacgac gacctggccg 720
atgtggacta cgtgcccccct gccccaagac gggctccacg gagaggaggc ggaggcgccg 780
gtgccaccag gggcaccagc caacccgctg ccacccggcc tgctcctcct ggggccccga 840
gatcctcctc atccggcggg gcacctctga gagcaggagt gggctcaggc tccggaggag 900
gacccgccgt ggcagctgtg gtcccgcgag tggcctcctt gcctccggcc gcaggaggcg 960
gccgggccca ggccagaagg gtgggggagg acgcggcagc cgccgaaggg cgcactcctc 1020
cagcgcgcca accaagagca gcgcaagagc ctccgatcgt gatctccgat agccccccac 1080
cgtcacctcg cagaccagcc ggacccgggc ctctgtcgtt cgtgagctcc agctcggccc 1140
aggtgtcgag cggacctggc ggtggtggac tccctcagag cagcggcaga gctgccagac 1200
ctcgcgccgc cgtggccccg agggtcaggt cgccgccgag agcagctgcc gccccagtgg 1260
tgtccgcctc agccgacgcc gccggtcccg cgcctcctgc tgtgccagtg gacgcccata 1320
gagcgccgcg gagcagaatg actcaggcac agactgacac ccaggcccag tcgctcggta 1380
gggctggagc caccgacgcc agaggatcgg gcggacccgg agccgaagga gggtccggtc 1440
ccgccgcttc ctcctccgcg tcctcatcag ccgctccgcg ctcaccgctc gcaccccagg 1500
gtgtcggagc aaagcgagca gctcctcgcc gggcccctga ctccgactca ggagatcggg 1560
gccacggacc actcgcgcct gccagcgctg gagcggctcc tccatcggct tccccatcct 1620
cgcaagcagc cgtggccgcc gcatcctcaa gctcggcgtc ctctagctca gcgagctcct 1680
ccagcgcctc gtcctcgtcc gcctccagca gctcagcctc ctcgtcctcg gcctcctcat 1740
cgtccgcctc ctcctccgct ggaggtgccg gaggatcggt cgcatccgct tccggcgcag 1800
gggagcgccg agaaacgtcc ctgggtccgc gggcagctgc tccgaggggt cctcgcaagt 1860
gcgcgcggaa aactcggcac gcggagggag gaccggaacc tggcgcgaga gatcctgcgc 1920
ctggactgac ccggtacctc cccattgccg gggtgtccag cgtggtggca cttgccccgt 1980
acgtcaacaa gaccgtgacc ggggactgtc tccccgtgct cgacatggag actggacaca 2040
ttggcgcgta tgtggtcctg gtggatcaga ccggtaatgt ggccgacctt ttgagagcag 2100
cggccccagc atggtcccgc agaaccctgc tgcctgagca cgccaggaat tgcgtgcggc 2160
cgccggacta cccgactccg cccgccagcg aatggaactc actgtggatg actcccgtgg 2220
gcaacatgct gttcgatcag gggaccctgg tcggagccct ggattttcac ggcctgcgct 2280
ccagacatcc gtggtctagg gaacagggtg ctcctgctcc cgcgggtgat gcccctgctg 2340
gccacggcga atagtgataa taggctggag cctcggtggc catgcttctt gccccttggg 2400
cctcccccca gcccctcctc cccttcctgc acccgtaccc ccgtggtctt tgaataaagt 2460
ctgagtgggc ggc 2473

<210> SEQ ID NO 65
<211> LENGTH: 4096
<212> TYPE: DNA
<213> ORGANISM: Artificial Sequence
<220> FEATURE:
<223> OTHER INFORMATION: Synthetic Polynucleotide

<400> SEQUENCE: 65
tcaagctttt ggaccctcgt acagaagcta atacgactca ctatagggaa ataagagaga 60
aaagaagagt aagaagaaat ataagagcca ccatgtcggc cgagcagcgc aagaagaaga 120
aaacgaccac cactacccag ggcagaggag ccgaagtcgc catggccgat gaagatggcg 180
ggaggctgcg ggccgccgct gaaaccaccg gaggaccggg atcccctgac cctgcggacg 240
gcccacctcc cacaccgaac ccggacagac ggcctgctgc aaggcccggt ttcggatggc 300
acgggggacc cgaagagaac gaggacgaag ccgatgacgc cgcggcggat gcagacgccg 360
acgaggcggc tcccgcttcg ggagaagcgg tggacgaacc ggccgccgat ggagtggtca 420
gcccccgcca gctcgcgctg ctcgcgtcca tggtggatga agccgtgaga actatcccct 480
cacctccgcc ggaacgggat ggagctcaag aggaagccgc cagaagcccg tcccctccga 540
gaactccatc catgcgggcc gactacggcg aagagaatga cgacgatgat gacgacgatg 600
atgacgatga ccgcgatgcc ggacggtggg tccgcggacc tgagactacc tccgccgtgc 660
gcggagccta ccctgatccg atggcctcac ttagcccccg gccacccgcc ccccgccgcc 720
accaccacca tcatcaccac cgcagaagaa gggctcccag gcgcagatca gcagcttccg 780
acagctcgaa gtccggctcc tcgtcctccg ccagcagcgc atcctcgtca gcgtcctcat 840
cgtccagcgc ctcggcgagc tcctccgacg atgacgacga cgacgatgcc gccagagctc 900
cggcatcagc cgcggaccat gccgccggag gaaccctcgg tgccgacgac gaggaggccg 960
gcgtgcctgc ccgcgctccg ggagctgctc ctaggccttc accaccccgg gcggagccag 1020
cccctgccag aacgccagca gccaccgctg ggcgattgga gaggcggaga gcccgggccg 1080
ccgtggccgg tcgggatgcc accggccgct tcactgccgg acgccctcgg cgcgtcgaac 1140
tggacgcaga cgccgcctcg ggcgcgttct acgcccgcta tcgggacggt tatgtgtccg 1200
gcgagccttg gcctggtgcc ggtcctcctc cgcctgggag agtgctctac gggggtctgg 1260
gtgattctcg gccagggttg tggggagccc ccgaggcgga ggaagccaga gcccgcttcg 1320
aagcatccgg agcaccggcc cctgtgtggg cgccggaact gggcgacgcc gcccaacaat 1380
acgccctgat cacacgcctg ctctacactc cggacgccga agccatgggc tggctgcaga 1440
acccgagagt ggccccgggt gatgtggccc tggaccaggc atgcttcagg attagcggag 1500
ccgcgagaaa ctcgagcagc tttatctcag gatctgtggc ccgagccgtg ccgcacctgg 1560
gctacgcgat ggccgccgga cgcttcggat gggggctggc ccatgtcgct gccgcggtgg 1620
cgatgtcccg gcggtacgac cgggctcaga agggtttcct cctcaccagc ctccggaggg 1680
catacgcccc gttgctggct cgggagaacg ccgctctgac tggcgcccgc actcctgatg 1740
acggtggcga cgccaaccgc cacgacggcg acgatgcacg gggaaagccc gcggccgccg 1800
ccgccccct tcctagcgca gccgcttcgc ctgccgacga acgggctgtc cctgccggat 1860
acggagccgc cggtgtgctg gcggcccttg ggagactgtc agccgcgcct gcttcagcgc 1920
cggccggagc cgacgatgac gacgacgacg atggagccgg aggaggggc ggcggtcgga 1980
gagcagaagc cggcagggtg gcagtcgaat gccttgctgc ctgtcgcggg atcctcgagg 2040
cgttggccga aggcttcgac ggcgacctgg cggcagtgcc tggcctggcc ggcgcccgcc 2100
ccgctgcccc tccacggccc ggtccggccg gggccgcagc ccctccgcat gctgacgcgc 2160
ctcgcctcag agcatggctg agagaattga gatttgtgcg ggatgcgctg gtccttatgc 2220
gcctgagggg ggatctgagg gtggccggag gttccgaggc ggccgtggct gctgtgcggg 2280
ccgtgtccct ggtggccggt gcgctgggtc ccgctctgcc gcggtcccct agattgcttt 2340
cctcagcggc cgccgccgca gccgatctgc tctttcagaa ccaaagcctc aggccgctgc 2400
tggccgacac tgtcgccgct gcggactccc tcgctgcccc agcctcggcc ccaagagagg 2460
ctgccgatgc ccctcgcccc gccgcggccc cgcctgccgg agcagcgccg cctgcacccc 2520
ctactccccc cccgcgaccg ccacgcccag ccgctcttac cagaaggcca gctgagggtc 2580
ctgacccgca gggcggctgg cgcagacagc ccccgggacc ttcccacact cccgccccat 2640
ctgcggctgc ccttgaagca tactgtgccc cgagagctgt ggcggagctg accgaccacc 2700
ctctgttccc tgcaccttgg cggcctgccc tgatgtttga cccgagagcg ttggcctccc 2760
tggcggccag atgtgcggcc ccgcctcccg gaggagcccc agctgcattc ggacctctgc 2820
gggcatccgg accactgcgg cgcgctgctg catggatgcg gcaagtgccg gaccctgagg 2880
acgttcgcgt ggtcattctt tactcccccc tgccgggaga agatctcgcc gccggccgcg 2940
cgggaggagg ccctccaccc gagtggtccg ctgaacgggg aggcctgtcc tgcctgctgg 3000
ctgccctggg aaaccgcctg tgcggaccag ctactgccgc ctgggctgga aactggaccg 3060
gcgcacccga tgtgtcagcc ctcggagcgc agggagtgct gctgctgtca actcgcgacc 3120
tggcattcgc cggagctgtg gagttcctgg gtctgcttgc cggcgcgtgc gaccggagat 3180
tgatcgtcgt gaacgctgtc agagcggccg cttggcctgc cgctgctccg gtggtcagcc 3240
ggcagcacgc atatctggcc tgcgaggtgc tgcccgccgt gcagtgtgcc gtgcggtggc 3300
cagcggccag agacttgcga cggaccgtgc tggcctccgg tagggtcttt ggccccggag 3360
tgttcgcccg cgtggaggcc gcccatgcca gactgtaccc cgacgcaccg cccctgagac 3420
tgtgccgggg agccaacgtg cggtacagag tccgcacccg cttcggaccc gatactctgg 3480
tgccaatgtc accgcgggaa tataggagag ccgtgctccc ggcactggac ggcagagccg 3540
ccgcatccgg tgctggggac gcgatggcac ccggagcccc cgacttttgc gaggatgaag 3600
cccacagcca tcgggcctgt gccagatggg gcctgggtgc ccctcttcgc cccgtgtacg 3660
tggccctggg gagagatgcc gtccgcggtg gaccagccga gctgagaggc ccacgccggg 3720

```
aattttgcgc tcgggccctg ctcgagcccg atggagatgc gcctcccctt gtgctgcgcg   3780

acgacgctga cgccggccca cctccgcaaa tccggtgggc cagcgccgcc ggtcgagcag   3840

gaacggtgtt ggcagcagcc ggaggaggag tcgaagtggt cggaaccgcg gctggactgg   3900

caaccccgcc aaggcgcgaa cctgtggata tggacgccga gctggaggat gacgacgatg   3960

gccttttcgg cgagtgatga taataggctg gagcctcggt ggccatgctt cttgcccctt   4020

gggcctcccc ccagcccctc ctccccttcc tgcacccgta cccccgtggt ctttgaataa   4080

agtctgagtg ggcggc                                                   4096
```

<210> SEQ ID NO 66
<211> LENGTH: 901
<212> TYPE: PRT
<213> ORGANISM: Artificial Sequence
<220> FEATURE:
<223> OTHER INFORMATION: Synthetic Polypeptide

<400> SEQUENCE: 66

```
Met Arg Gly Gly Gly Leu Val Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Gln Pro Pro
        35                  40                  45

Pro Val Pro Ser Pro Ala Thr Thr Lys Ala Arg Lys Arg Lys Thr Lys
    50                  55                  60

Lys Pro Pro Lys Arg Pro Glu Ala Thr Pro Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
    210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
```

```
    290                 295                 300

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
                325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

Arg Ala Glu Tyr Gly Gly Ser Phe Arg Phe Ser Ser Asp Ala Ile Ser
    370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
        435                 440                 445

Ser Asn Thr Leu Ala Glu Leu Tyr Val Arg Glu Tyr Met Arg Glu Gln
    450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
        515                 520                 525

Glu Leu Thr Leu Trp Asn Glu Ala Arg Lys Leu Asn Pro Asn Ala Ile
    530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
        595                 600                 605

Gly Gln Leu Gly Glu Asn Asn Glu Leu Arg Leu Thr Arg Asp Ala Leu
    610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
            660                 665                 670

Glu Asp His Glu Phe Val Pro Leu Glu Val Tyr Thr Arg His Glu Ile
        675                 680                 685

Lys Asp Ser Gly Leu Leu Asp Tyr Thr Glu Val Gln Arg Arg Asn Gln
    690                 695                 700

Leu His Asp Leu Arg Phe Ala Asp Ile Asp Thr Val Ile Arg Ala Asp
705                 710                 715                 720
```

Ala Asn Ala Ala Met Phe Ala Gly Leu Cys Ala Phe Phe Glu Gly Met
725 730 735

Gly Asp Leu Gly Arg Ala Val Gly Lys Val Val Met Gly Val Val Gly
740 745 750

Gly Val Val Ser Ala Val Ser Gly Val Ser Ser Phe Met Ser Asn Pro
755 760 765

Phe Gly Ala Leu Ala Val Gly Leu Leu Val Leu Ala Gly Leu Val Ala
770 775 780

Ala Phe Phe Ala Phe Arg Tyr Val Leu Gln Leu Gln Arg Asn Pro Met
785 790 795 800

Lys Ala Leu Tyr Pro Leu Thr Thr Lys Glu Leu Lys Thr Ser Asp Pro
805 810 815

Gly Gly Val Gly Gly Glu Gly Glu Glu Gly Ala Glu Gly Gly Gly Phe
820 825 830

Asp Glu Ala Lys Leu Ala Glu Ala Arg Glu Met Ile Arg Tyr Met Ala
835 840 845

Leu Val Ser Ala Met Glu Arg Thr Glu His Lys Ala Arg Lys Lys Gly
850 855 860

Thr Ser Ala Leu Leu Ser Ser Lys Val Thr Asn Met Val Leu Arg Lys
865 870 875 880

Arg Asn Lys Ala Arg Tyr Ser Pro Leu His Asn Glu Asp Glu Ala Gly
885 890 895

Asp Glu Asp Glu Leu
900

<210> SEQ ID NO 67
<211> LENGTH: 480
<212> TYPE: PRT
<213> ORGANISM: Artificial Sequence
<220> FEATURE:
<223> OTHER INFORMATION: Synthetic Polypeptide

<400> SEQUENCE: 67

Met Ala Leu Gly Arg Val Gly Leu Ala Val Gly Leu Trp Gly Leu Leu
1 5 10 15

Trp Val Gly Val Val Val Val Leu Ala Asn Ala Ser Pro Gly Arg Thr
20 25 30

Ile Thr Val Gly Pro Arg Gly Asn Ala Ser Asn Ala Ala Pro Ser Ala
35 40 45

Ser Pro Arg Asn Ala Ser Ala Pro Arg Thr Thr Pro Thr Pro Pro Gln
50 55 60

Pro Arg Lys Ala Thr Lys Ser Lys Ala Ser Thr Ala Lys Pro Ala Pro
65 70 75 80

Pro Pro Lys Thr Gly Pro Pro Lys Thr Ser Ser Glu Pro Val Arg Cys
85 90 95

Asn Arg His Asp Pro Leu Ala Arg Tyr Gly Ser Arg Val Gln Ile Arg
100 105 110

Cys Arg Phe Pro Asn Ser Thr Arg Thr Glu Ser Arg Leu Gln Ile Trp
115 120 125

Arg Tyr Ala Thr Ala Thr Asp Ala Glu Ile Gly Thr Ala Pro Ser Leu
130 135 140

Glu Glu Val Met Val Asn Val Ser Ala Pro Pro Gly Gly Gln Leu Val
145 150 155 160

Tyr Asp Ser Ala Pro Asn Arg Thr Asp Pro His Val Ile Trp Ala Glu
165 170 175

```
Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480
```

<210> SEQ ID NO 68
<211> LENGTH: 393
<212> TYPE: PRT
<213> ORGANISM: Artificial Sequence
<220> FEATURE:
<223> OTHER INFORMATION: Synthetic Polypeptide

<400> SEQUENCE: 68

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60
```

Ile Gln Pro Ser Leu Glu Asp Pro Phe Gln Pro Pro Ser Ile Pro Ile
65 70 75 80

Thr Val Tyr Tyr Ala Val Leu Glu Arg Ala Cys Arg Ser Val Leu Leu
85 90 95

His Ala Pro Ser Glu Ala Pro Gln Ile Val Arg Gly Ala Ser Asp Glu
100 105 110

Ala Arg Lys His Thr Tyr Asn Leu Thr Ile Ala Trp Tyr Arg Met Gly
115 120 125

Asp Asn Cys Ala Ile Pro Ile Thr Val Met Glu Tyr Thr Glu Cys Pro
130 135 140

Tyr Asn Lys Ser Leu Gly Val Cys Pro Ile Arg Thr Gln Pro Arg Trp
145 150 155 160

Ser Tyr Tyr Asp Ser Phe Ser Ala Val Ser Glu Asp Asn Leu Gly Phe
165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro Gly Leu Ile Ile Gly Ala Leu Ala Gly Ser Thr Leu Ala
340 345 350

Val Leu Val Ile Gly Gly Ile Ala Phe Trp Val Arg Arg Arg Ala Gln
355 360 365

Met Ala Pro Lys Arg Leu Arg Leu Pro His Ile Arg Asp Asp Asp Ala
370 375 380

Pro Pro Ser His Gln Pro Leu Phe Tyr
385 390

<210> SEQ ID NO 69
<211> LENGTH: 548
<212> TYPE: PRT
<213> ORGANISM: Artificial Sequence
<220> FEATURE:
<223> OTHER INFORMATION: Synthetic Polypeptide

<400> SEQUENCE: 69

Met Ala Arg Gly Ala Gly Leu Val Phe Phe Val Gly Val Trp Val Val
1 5 10 15

Ser Cys Leu Ala Ala Ala Pro Arg Thr Ser Trp Lys Arg Val Thr Ser
20 25 30

```
Gly Glu Asp Val Val Leu Leu Pro Ala Pro Ala Gly Pro Glu Glu Arg
        35                  40                  45

Thr Arg Ala His Lys Leu Leu Trp Ala Ala Glu Pro Leu Asp Ala Cys
    50                  55                  60

Gly Pro Leu Arg Pro Ser Trp Val Ala Leu Trp Pro Pro Arg Arg Val
65                  70                  75                  80

Leu Glu Thr Val Val Asp Ala Ala Cys Met Arg Ala Pro Glu Pro Leu
                85                  90                  95

Ala Ile Ala Tyr Ser Pro Pro Phe Pro Ala Gly Asp Glu Gly Leu Tyr
            100                 105                 110

Ser Glu Leu Ala Trp Arg Asp Arg Val Ala Val Val Asn Glu Ser Leu
        115                 120                 125

Val Ile Tyr Gly Ala Leu Glu Thr Asp Ser Gly Leu Tyr Thr Leu Ser
    130                 135                 140

Val Val Gly Leu Ser Asp Glu Ala Arg Gln Val Ala Ser Val Val Leu
145                 150                 155                 160

Val Val Glu Pro Ala Pro Val Pro Thr Pro Thr Pro Asp Asp Tyr Asp
                165                 170                 175

Glu Glu Asp Asp Ala Gly Val Ser Glu Arg Thr Pro Val Ser Val Pro
            180                 185                 190

Pro Pro Thr Pro Pro Arg Arg Pro Pro Val Ala Pro Pro Thr His Pro
        195                 200                 205

Arg Val Ile Pro Glu Val Ser His Val Arg Gly Val Thr Val His Met
    210                 215                 220

Glu Thr Pro Glu Ala Ile Leu Phe Ala Pro Gly Glu Thr Phe Gly Thr
225                 230                 235                 240

Asn Val Ser Ile His Ala Ile Ala His Asp Asp Gly Pro Tyr Ala Met
                245                 250                 255

Asp Val Val Trp Met Arg Phe Asp Val Pro Ser Ser Cys Ala Glu Met
            260                 265                 270

Arg Ile Tyr Glu Ala Cys Leu Tyr His Pro Gln Leu Pro Glu Cys Leu
        275                 280                 285

Ser Pro Ala Asp Ala Pro Cys Ala Val Ser Ser Trp Ala Tyr Arg Leu
    290                 295                 300

Ala Val Arg Ser Tyr Ala Gly Cys Ser Arg Thr Thr Pro Pro Pro Arg
305                 310                 315                 320

Cys Phe Ala Glu Ala Arg Met Glu Pro Val Pro Gly Leu Ala Trp Leu
                325                 330                 335

Ala Ser Thr Val Asn Leu Glu Phe Gln His Ala Ser Pro Gln His Ala
            340                 345                 350

Gly Leu Tyr Leu Cys Val Val Tyr Val Asp Asp His Ile His Ala Trp
        355                 360                 365

Gly His Met Thr Ile Ser Thr Ala Ala Gln Tyr Arg Asn Ala Val Val
    370                 375                 380

Glu Gln His Leu Pro Gln Arg Gln Pro Glu Pro Val Glu Pro Thr Arg
385                 390                 395                 400

Pro His Val Arg Ala Pro Pro Pro Ala Pro Ser Ala Arg Gly Pro Leu
                405                 410                 415

Arg Leu Gly Ala Val Leu Gly Ala Ala Leu Leu Leu Ala Ala Leu Gly
            420                 425                 430

Leu Ser Ala Trp Ala Cys Met Thr Cys Trp Arg Arg Arg Ser Trp Arg
        435                 440                 445
```

Ala Val Lys Ser Arg Ala Ser Ala Thr Gly Pro Thr Tyr Ile Arg Val
450 455 460

Ala Asp Ser Glu Leu Tyr Ala Asp Trp Ser Ser Asp Ser Glu Gly Glu
465 470 475 480

Arg Asp Gly Ser Leu Trp Gln Asp Pro Pro Glu Arg Pro Asp Ser Pro
485 490 495

Ser Thr Asn Gly Ser Gly Phe Glu Ile Leu Ser Pro Thr Ala Pro Ser
500 505 510

Val Tyr Pro His Ser Glu Gly Arg Lys Ser Arg Arg Pro Leu Thr Thr
515 520 525

Phe Gly Ser Gly Ser Pro Gly Arg Arg His Ser Gln Ala Ser Tyr Ser
530 535 540

Ser Val Leu Trp
545

<210> SEQ ID NO 70
<211> LENGTH: 372
<212> TYPE: PRT
<213> ORGANISM: Artificial Sequence
<220> FEATURE:
<223> OTHER INFORMATION: Synthetic Polypeptide

<400> SEQUENCE: 70

Met Pro Gly Arg Ser Leu Gln Gly Leu Ala Ile Leu Gly Leu Trp Val
1 5 10 15

Cys Ala Thr Gly Leu Val Val Arg Gly Pro Thr Val Ser Leu Val Ser
20 25 30

Asp Ser Leu Val Asp Ala Gly Ala Val Gly Pro Gln Gly Phe Val Glu
35 40 45

Glu Asp Leu Arg Val Phe Gly Glu Leu His Phe Val Gly Ala Gln Val
50 55 60

Pro His Thr Asn Tyr Tyr Asp Gly Ile Ile Glu Leu Phe His Tyr Pro
65 70 75 80

Leu Gly Asn His Cys Pro Arg Val Val His Val Val Thr Leu Thr Ala
85 90 95

Cys Pro Arg Arg Pro Ala Val Ala Phe Thr Leu Cys Arg Ser Thr His
100 105 110

His Ala His Ser Pro Ala Tyr Pro Thr Leu Glu Leu Gly Leu Ala Arg
115 120 125

Gln Pro Leu Leu Arg Val Arg Thr Ala Thr Arg Asp Tyr Ala Gly Leu
130 135 140

Tyr Val Leu Arg Val Trp Val Gly Ser Ala Thr Asn Ala Ser Leu Phe
145 150 155 160

Val Leu Gly Val Ala Leu Ser Ala Asn Gly Thr Phe Val Tyr Asn Gly
165 170 175

Ser Asp Tyr Gly Ser Cys Asp Pro Ala Gln Leu Pro Phe Ser Ala Pro
180 185 190

Arg Leu Gly Pro Ser Ser Val Tyr Thr Pro Gly Ala Ser Arg Pro Thr
195 200 205

Pro Pro Arg Thr Thr Thr Ser Pro Ser Ser Pro Arg Asp Pro Thr Pro
210 215 220

Ala Pro Gly Asp Thr Gly Thr Pro Ala Pro Ala Ser Gly Glu Arg Ala
225 230 235 240

Pro Pro Asn Ser Thr Arg Ser Ala Ser Glu Ser Arg His Arg Leu Thr
245 250 255

Val Ala Gln Val Ile Gln Ile Ala Ile Pro Ala Ser Ile Ile Ala Phe
260 265 270

Val Phe Leu Gly Ser Cys Ile Cys Phe Ile His Arg Cys Gln Arg Arg
275 280 285

Tyr Arg Arg Pro Arg Gly Gln Ile Tyr Asn Pro Gly Gly Val Ser Cys
290 295 300

Ala Val Asn Glu Ala Ala Met Ala Arg Leu Gly Ala Glu Leu Arg Ser
305 310 315 320

His Pro Asn Thr Pro Pro Lys Pro Arg Arg Arg Ser Ser Ser Ser Thr
325 330 335

Thr Met Pro Ser Leu Thr Ser Ile Ala Glu Glu Ser Glu Pro Gly Pro
340 345 350

Val Val Leu Leu Ser Val Ser Pro Arg Pro Arg Ser Gly Pro Thr Ala
355 360 365

Pro Gln Glu Val
370

<210> SEQ ID NO 71
<211> LENGTH: 768
<212> TYPE: PRT
<213> ORGANISM: Artificial Sequence
<220> FEATURE:
<223> OTHER INFORMATION: Synthetic Polypeptide

<400> SEQUENCE: 71

Met Arg Gly Gly Gly Leu Val Cys Ala Leu Val Val Gly Ala Leu Val
1 5 10 15

Ala Ala Val Ala Ser Ala Ala Pro Ala Ala Pro Arg Ala Ser Gly Gly
20 25 30

Val Ala Ala Thr Val Ala Ala Asn Gly Gly Pro Ala Ser Gln Pro Pro
35 40 45

Pro Val Pro Ser Pro Ala Thr Thr Lys Ala Arg Lys Arg Lys Thr Lys
50 55 60

Lys Pro Pro Lys Arg Pro Glu Ala Thr Pro Pro Pro Asp Ala Asn Ala
65 70 75 80

Thr Val Ala Ala Gly His Ala Thr Leu Arg Ala His Leu Arg Glu Ile
85 90 95

Lys Val Glu Asn Ala Asp Ala Gln Phe Tyr Val Cys Pro Pro Pro Thr
100 105 110

Gly Ala Thr Val Val Gln Phe Glu Gln Pro Arg Arg Cys Pro Thr Arg
115 120 125

Pro Glu Gly Gln Asn Tyr Thr Glu Gly Ile Ala Val Val Phe Lys Glu
130 135 140

Asn Ile Ala Pro Tyr Lys Phe Lys Ala Thr Met Tyr Tyr Lys Asp Val
145 150 155 160

Thr Val Ser Gln Val Trp Phe Gly His Arg Tyr Ser Gln Phe Met Gly
165 170 175

Ile Phe Glu Asp Arg Ala Pro Val Pro Phe Glu Glu Val Ile Asp Lys
180 185 190

Ile Asn Ala Lys Gly Val Cys Arg Ser Thr Ala Lys Tyr Val Arg Asn
195 200 205

Asn Met Glu Thr Thr Ala Phe His Arg Asp Asp His Glu Thr Asp Met
210 215 220

Glu Leu Lys Pro Ala Lys Val Ala Thr Arg Thr Ser Arg Gly Trp His
225 230 235 240

-continued

```
Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
    290                 295                 300

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
                325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

Arg Ala Glu Tyr Gly Gly Ser Phe Arg Phe Ser Ser Asp Ala Ile Ser
    370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
        435                 440                 445

Ser Asn Thr Leu Ala Glu Leu Tyr Val Arg Glu Tyr Met Arg Glu Gln
    450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
        515                 520                 525

Glu Leu Thr Leu Trp Asn Glu Ala Arg Lys Leu Asn Pro Asn Ala Ile
    530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
        595                 600                 605

Gly Gln Leu Gly Glu Asn Asn Glu Leu Arg Leu Thr Arg Asp Ala Leu
    610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
```

```
            660                 665                 670

Glu Asp His Glu Phe Val Pro Leu Glu Val Tyr Thr Arg His Glu Ile
        675                 680                 685

Lys Asp Ser Gly Leu Leu Asp Tyr Thr Glu Val Gln Arg Arg Asn Gln
    690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met
                725                 730                 735

Gly Asp Leu Gly Arg Ala Val Gly Lys Val Val Met Gly Val Val Gly
            740                 745                 750

Gly Val Val Ser Ala Val Ser Gly Val Ser Ser Phe Met Ser Asn Pro
        755                 760                 765
```

<210> SEQ ID NO 72
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 72

```
Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Ser Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
```

```
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly
        435                 440                 445


<210> SEQ ID NO 73
<211> LENGTH: 417
<212> TYPE: PRT
<213> ORGANISM: Artificial Sequence
<220> FEATURE:
<223> OTHER INFORMATION: Synthetic Polypeptide

<400> SEQUENCE: 73

Met Ala Arg Gly Ala Gly Leu Val Phe Phe Val Gly Val Trp Val Val
1               5                   10                  15

Ser Cys Leu Ala Ala Ala Pro Arg Thr Ser Trp Lys Arg Val Thr Ser
            20                  25                  30

Gly Glu Asp Val Val Leu Leu Pro Ala Pro Ala Gly Pro Glu Glu Arg
        35                  40                  45

Thr Arg Ala His Lys Leu Leu Trp Ala Ala Glu Pro Leu Asp Ala Cys
    50                  55                  60

Gly Pro Leu Arg Pro Ser Trp Val Ala Leu Trp Pro Pro Arg Arg Val
65                  70                  75                  80

Leu Glu Thr Val Val Asp Ala Ala Cys Met Arg Ala Pro Glu Pro Leu
                85                  90                  95

Ala Ile Ala Tyr Ser Pro Pro Phe Pro Ala Gly Asp Glu Gly Leu Tyr
            100                 105                 110

Ser Glu Leu Ala Trp Arg Asp Arg Val Ala Val Val Asn Glu Ser Leu
        115                 120                 125

Val Ile Tyr Gly Ala Leu Glu Thr Asp Ser Gly Leu Tyr Thr Leu Ser
    130                 135                 140

Val Val Gly Leu Ser Asp Glu Ala Arg Gln Val Ala Ser Val Val Leu
145                 150                 155                 160

Val Val Glu Pro Ala Pro Val Pro Thr Pro Thr Pro Asp Asp Tyr Asp
                165                 170                 175

Glu Glu Asp Asp Ala Gly Val Ser Glu Arg Thr Pro Val Ser Val Pro
```

180 185 190

Pro Pro Thr Pro Pro Arg Arg Pro Pro Val Ala Pro Pro Thr His Pro
195 200 205

Arg Val Ile Pro Glu Val Ser His Val Arg Gly Val Thr Val His Met
210 215 220

Glu Thr Pro Glu Ala Ile Leu Phe Ala Pro Gly Glu Thr Phe Gly Thr
225 230 235 240

Asn Val Ser Ile His Ala Ile Ala His Asp Asp Gly Pro Tyr Ala Met
245 250 255

Asp Val Val Trp Met Arg Phe Asp Val Pro Ser Ser Cys Ala Glu Met
260 265 270

Arg Ile Tyr Glu Ala Cys Leu Tyr His Pro Gln Leu Pro Glu Cys Leu
275 280 285

Ser Pro Ala Asp Ala Pro Cys Ala Val Ser Ser Trp Ala Tyr Arg Leu
290 295 300

Ala Val Arg Ser Tyr Ala Gly Cys Ser Arg Thr Thr Pro Pro Pro Arg
305 310 315 320

Cys Phe Ala Glu Ala Arg Met Glu Pro Val Pro Gly Leu Ala Trp Leu
325 330 335

Ala Ser Thr Val Asn Leu Glu Phe Gln His Ala Ser Pro Gln His Ala
340 345 350

Gly Leu Tyr Leu Cys Val Val Tyr Val Asp Asp His Ile His Ala Trp
355 360 365

Gly His Met Thr Ile Ser Thr Ala Ala Gln Tyr Arg Asn Ala Val Val
370 375 380

Glu Gln His Leu Pro Gln Arg Gln Pro Glu Pro Val Glu Pro Thr Arg
385 390 395 400

Pro His Val Arg Ala Pro Pro Pro Ala Pro Ser Ala Arg Gly Pro Leu
405 410 415

Arg

<210> SEQ ID NO 74
<211> LENGTH: 262
<212> TYPE: PRT
<213> ORGANISM: Artificial Sequence
<220> FEATURE:
<223> OTHER INFORMATION: Synthetic Polypeptide

<400> SEQUENCE: 74

Met Pro Gly Arg Ser Leu Gln Gly Leu Ala Ile Leu Gly Leu Trp Val
1 5 10 15

Cys Ala Thr Gly Leu Val Val Arg Gly Pro Thr Val Ser Leu Val Ser
20 25 30

Asp Ser Leu Val Asp Ala Gly Ala Val Gly Pro Gln Gly Phe Val Glu
35 40 45

Glu Asp Leu Arg Val Phe Gly Glu Leu His Phe Val Gly Ala Gln Val
50 55 60

Pro His Thr Asn Tyr Tyr Asp Gly Ile Ile Glu Leu Phe His Tyr Pro
65 70 75 80

Leu Gly Asn His Cys Pro Arg Val Val His Val Val Thr Leu Thr Ala
85 90 95

Cys Pro Arg Arg Pro Ala Val Ala Phe Thr Leu Cys Arg Ser Thr His
100 105 110

His Ala His Ser Pro Ala Tyr Pro Thr Leu Glu Leu Gly Leu Ala Arg
115 120 125

Gln Pro Leu Leu Arg Val Arg Thr Ala Thr Arg Asp Tyr Ala Gly Leu
130 135 140

Tyr Val Leu Arg Val Trp Val Gly Ser Ala Thr Asn Ala Ser Leu Phe
145 150 155 160

Val Leu Gly Val Ala Leu Ser Ala Asn Gly Thr Phe Val Tyr Asn Gly
165 170 175

Ser Asp Tyr Gly Ser Cys Asp Pro Ala Gln Leu Pro Phe Ser Ala Pro
180 185 190

Arg Leu Gly Pro Ser Ser Val Tyr Thr Pro Gly Ala Ser Arg Pro Thr
195 200 205

Pro Pro Arg Thr Thr Thr Ser Pro Ser Ser Pro Arg Asp Pro Thr Pro
210 215 220

Ala Pro Gly Asp Thr Gly Thr Pro Ala Pro Ala Ser Gly Glu Arg Ala
225 230 235 240

Pro Pro Asn Ser Thr Arg Ser Ala Ser Glu Ser Arg His Arg Leu Thr
245 250 255

Val Ala Gln Val Ile Gln
260

<210> SEQ ID NO 75
<211> LENGTH: 339
<212> TYPE: PRT
<213> ORGANISM: Artificial Sequence
<220> FEATURE:
<223> OTHER INFORMATION: Synthetic Polypeptide

<400> SEQUENCE: 75

Met Gly Arg Leu Thr Ser Gly Val Gly Thr Ala Ala Leu Leu Val Val
1 5 10 15

Ala Val Gly Leu Arg Val Val Cys Ala Lys Tyr Ala Leu Ala Asp Pro
20 25 30

Ser Leu Lys Met Ala Asp Pro Asn Arg Phe Arg Gly Lys Asn Leu Pro
35 40 45

Val Leu Asp Gln Leu Thr Asp Pro Pro Gly Val Lys Arg Val Tyr His
50 55 60

Ile Gln Pro Ser Leu Glu Asp Pro Phe Gln Pro Pro Ser Ile Pro Ile
65 70 75 80

Thr Val Tyr Tyr Ala Val Leu Glu Arg Ala Cys Arg Ser Val Leu Leu
85 90 95

His Ala Pro Ser Glu Ala Pro Gln Ile Val Arg Gly Ala Ser Asp Glu
100 105 110

Ala Arg Lys His Thr Tyr Asn Leu Thr Ile Ala Trp Tyr Arg Met Gly
115 120 125

Asp Asn Cys Ala Ile Pro Ile Thr Val Met Glu Tyr Thr Glu Cys Pro
130 135 140

Tyr Asn Lys Ser Leu Gly Val Cys Pro Ile Arg Thr Gln Pro Arg Trp
145 150 155 160

Ser Tyr Tyr Asp Ser Phe Ser Ala Val Ser Glu Asp Asn Leu Gly Phe
165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro

<210> SEQ ID NO 76
<211> LENGTH: 753
<212> TYPE: PRT
<213> ORGANISM: Artificial Sequence
<220> FEATURE:
<223> OTHER INFORMATION: Synthetic Polypeptide

<400> SEQUENCE: 76

Met Glu Pro Arg Pro Gly Thr Ser Ser Arg Ala Asp Pro Gly Pro Glu
1 5 10 15

Arg Pro Pro Arg Gln Thr Pro Gly Thr Gln Pro Ala Ala Pro His Ala
20 25 30

Trp Gly Met Leu Asn Asp Met Gln Trp Leu Ala Ser Ser Asp Ser Glu
35 40 45

Glu Glu Thr Glu Val Gly Ile Ser Asp Asp Asp Leu His Arg Asp Ser
50 55 60

Thr Ser Glu Ala Gly Ser Thr Asp Thr Glu Met Phe Glu Ala Gly Leu
65 70 75 80

Met Asp Ala Ala Thr Pro Pro Ala Arg Pro Pro Ala Glu Arg Gln Gly
85 90 95

Ser Pro Thr Pro Ala Asp Ala Gln Gly Ser Cys Gly Gly Gly Pro Val
100 105 110

Gly Glu Glu Glu Ala Glu Ala Gly Gly Gly Gly Asp Val Asn Thr Pro
115 120 125

Val Ala Tyr Leu Ile Val Gly Val Thr Ala Ser Gly Ser Phe Ser Thr
130 135 140

Ile Pro Ile Val Asn Asp Pro Arg Thr Arg Val Glu Ala Glu Ala Ala
145 150 155 160

Val Arg Ala Gly Thr Ala Val Asp Phe Ile Trp Thr Gly Asn Pro Arg
165 170 175

Thr Ala Pro Arg Ser Leu Ser Leu Gly Gly His Thr Val Arg Ala Leu
180 185 190

Ser Pro Thr Pro Pro Trp Pro Gly Thr Asp Asp Glu Asp Asp Asp Leu
195 200 205

Ala Asp Val Asp Tyr Val Pro Pro Ala Pro Arg Arg Ala Pro Arg Arg
210 215 220

Gly Gly Gly Gly Ala Gly Ala Thr Arg Gly Thr Ser Gln Pro Ala Ala
225 230 235 240

-continued

```
Thr Arg Pro Ala Pro Pro Gly Ala Pro Arg Ser Ser Ser Ser Gly Gly
                245                 250                 255

Ala Pro Leu Arg Ala Gly Val Gly Ser Gly Ser Gly Gly Gly Pro Ala
            260                 265                 270

Val Ala Ala Val Val Pro Arg Val Ala Ser Leu Pro Pro Ala Ala Gly
        275                 280                 285

Gly Gly Arg Ala Gln Ala Arg Arg Val Gly Glu Asp Ala Ala Ala Ala
    290                 295                 300

Glu Gly Arg Thr Pro Pro Ala Arg Gln Pro Arg Ala Ala Gln Glu Pro
305                 310                 315                 320

Pro Ile Val Ile Ser Asp Ser Pro Pro Pro Ser Pro Arg Arg Pro Ala
                325                 330                 335

Gly Pro Gly Pro Leu Ser Phe Val Ser Ser Ser Ser Ala Gln Val Ser
            340                 345                 350

Ser Gly Pro Gly Gly Gly Gly Leu Pro Gln Ser Ser Gly Arg Ala Ala
        355                 360                 365

Arg Pro Arg Ala Ala Val Ala Pro Arg Val Arg Ser Pro Pro Arg Ala
    370                 375                 380

Ala Ala Ala Pro Val Val Ser Ala Ser Ala Asp Ala Ala Gly Pro Ala
385                 390                 395                 400

Pro Pro Ala Val Pro Val Asp Ala His Arg Ala Pro Arg Ser Arg Met
                405                 410                 415

Thr Gln Ala Gln Thr Asp Thr Gln Ala Gln Ser Leu Gly Arg Ala Gly
            420                 425                 430

Ala Thr Asp Ala Arg Gly Ser Gly Gly Pro Gly Ala Glu Gly Gly Ser
        435                 440                 445

Gly Pro Ala Ala Ser Ser Ser Ala Ser Ser Ser Ala Ala Pro Arg Ser
    450                 455                 460

Pro Leu Ala Pro Gln Gly Val Gly Ala Lys Arg Ala Ala Pro Arg Arg
465                 470                 475                 480

Ala Pro Asp Ser Asp Ser Gly Asp Arg Gly His Gly Pro Leu Ala Pro
                485                 490                 495

Ala Ser Ala Gly Ala Ala Pro Pro Ser Ala Ser Pro Ser Ser Gln Ala
            500                 505                 510

Ala Val Ala Ala Ala Ser Ser Ser Ser Ala Ser Ser Ser Ser Ala Ser
        515                 520                 525

Ser Ser Ser Ala Ser Ser Ser Ser Ala Ser Ser Ser Ser Ala Ser Ser
    530                 535                 540

Ser Ser Ala Ser Ser Ser Ser Ala Ser Ser Ser Ala Gly Gly Ala Gly
545                 550                 555                 560

Gly Ser Val Ala Ser Ala Ser Gly Ala Gly Glu Arg Arg Glu Thr Ser
                565                 570                 575

Leu Gly Pro Arg Ala Ala Ala Pro Arg Gly Pro Arg Lys Cys Ala Arg
            580                 585                 590

Lys Thr Arg His Ala Glu Gly Gly Pro Glu Pro Gly Ala Arg Asp Pro
        595                 600                 605

Ala Pro Gly Leu Thr Arg Tyr Leu Pro Ile Ala Gly Val Ser Ser Val
    610                 615                 620

Val Ala Leu Ala Pro Tyr Val Asn Lys Thr Val Thr Gly Asp Cys Leu
625                 630                 635                 640

Pro Val Leu Asp Met Glu Thr Gly His Ile Gly Ala Tyr Val Val Leu
                645                 650                 655

Val Asp Gln Thr Gly Asn Val Ala Asp Leu Leu Arg Ala Ala Ala Pro
```

```
            660                 665                 670

Ala Trp Ser Arg Arg Thr Leu Leu Pro Glu His Ala Arg Asn Cys Val
        675                 680                 685

Arg Pro Pro Asp Tyr Pro Thr Pro Pro Ala Ser Glu Trp Asn Ser Leu
    690                 695                 700

Trp Met Thr Pro Val Gly Asn Met Leu Phe Asp Gln Gly Thr Leu Val
705                 710                 715                 720

Gly Ala Leu Asp Phe His Gly Leu Arg Ser Arg His Pro Trp Ser Arg
                725                 730                 735

Glu Gln Gly Ala Pro Ala Pro Ala Gly Asp Ala Pro Ala Gly His Gly
            740                 745                 750

Glu


<210> SEQ ID NO 77
<211> LENGTH: 1294
<212> TYPE: PRT
<213> ORGANISM: Artificial Sequence
<220> FEATURE:
<223> OTHER INFORMATION: Synthetic Polypeptide

<400> SEQUENCE: 77

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255

Ser Ser Asp Asp Asp Asp Asp Asp Asp Ala Ala Arg Ala Pro Ala Ser
            260                 265                 270
```

-continued

```
Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
                405                 410                 415

Pro Val Trp Ala Pro Glu Leu Gly Asp Ala Ala Gln Gln Tyr Ala Leu
            420                 425                 430

Ile Thr Arg Leu Leu Tyr Thr Pro Asp Ala Glu Ala Met Gly Trp Leu
        435                 440                 445

Gln Asn Pro Arg Val Ala Pro Gly Asp Val Ala Leu Asp Gln Ala Cys
    450                 455                 460

Phe Arg Ile Ser Gly Ala Ala Arg Asn Ser Ser Ser Phe Ile Ser Gly
465                 470                 475                 480

Ser Val Ala Arg Ala Val Pro His Leu Gly Tyr Ala Met Ala Ala Gly
                485                 490                 495

Arg Phe Gly Trp Gly Leu Ala His Val Ala Ala Ala Val Ala Met Ser
            500                 505                 510

Arg Arg Tyr Asp Arg Ala Gln Lys Gly Phe Leu Leu Thr Ser Leu Arg
        515                 520                 525

Arg Ala Tyr Ala Pro Leu Leu Ala Arg Glu Asn Ala Ala Leu Thr Gly
    530                 535                 540

Ala Arg Thr Pro Asp Asp Gly Gly Asp Ala Asn Arg His Asp Gly Asp
545                 550                 555                 560

Asp Ala Arg Gly Lys Pro Ala Ala Ala Ala Ala Pro Leu Pro Ser Ala
                565                 570                 575

Ala Ala Ser Pro Ala Asp Glu Arg Ala Val Pro Ala Gly Tyr Gly Ala
            580                 585                 590

Ala Gly Val Leu Ala Ala Leu Gly Arg Leu Ser Ala Ala Pro Ala Ser
        595                 600                 605

Ala Pro Ala Gly Ala Asp Asp Asp Asp Asp Asp Asp Gly Ala Gly Gly
    610                 615                 620

Gly Gly Gly Gly Arg Arg Ala Glu Ala Gly Arg Val Ala Val Glu Cys
625                 630                 635                 640

Leu Ala Ala Cys Arg Gly Ile Leu Glu Ala Leu Ala Glu Gly Phe Asp
                645                 650                 655

Gly Asp Leu Ala Ala Val Pro Gly Leu Ala Gly Ala Arg Pro Ala Ala
            660                 665                 670

Pro Pro Arg Pro Gly Pro Ala Gly Ala Ala Ala Pro Pro His Ala Asp
        675                 680                 685
```

```
Ala Pro Arg Leu Arg Ala Trp Leu Arg Glu Leu Arg Phe Val Arg Asp
    690                 695                 700

Ala Leu Val Leu Met Arg Leu Arg Gly Asp Leu Arg Val Ala Gly Gly
705                 710                 715                 720

Ser Glu Ala Ala Val Ala Ala Val Arg Ala Val Ser Leu Val Ala Gly
                725                 730                 735

Ala Leu Gly Pro Ala Leu Pro Arg Ser Pro Arg Leu Leu Ser Ser Ala
            740                 745                 750

Ala Ala Ala Ala Ala Asp Leu Leu Phe Gln Asn Gln Ser Leu Arg Pro
        755                 760                 765

Leu Leu Ala Asp Thr Val Ala Ala Ala Asp Ser Leu Ala Ala Pro Ala
    770                 775                 780

Ser Ala Pro Arg Glu Ala Ala Asp Ala Pro Arg Pro Ala Ala Ala Pro
785                 790                 795                 800

Pro Ala Gly Ala Ala Pro Pro Ala Pro Pro Thr Pro Pro Pro Arg Pro
                805                 810                 815

Pro Arg Pro Ala Ala Leu Thr Arg Arg Pro Ala Glu Gly Pro Asp Pro
            820                 825                 830

Gln Gly Gly Trp Arg Arg Gln Pro Pro Gly Pro Ser His Thr Pro Ala
        835                 840                 845

Pro Ser Ala Ala Ala Leu Glu Ala Tyr Cys Ala Pro Arg Ala Val Ala
    850                 855                 860

Glu Leu Thr Asp His Pro Leu Phe Pro Ala Pro Trp Arg Pro Ala Leu
865                 870                 875                 880

Met Phe Asp Pro Arg Ala Leu Ala Ser Leu Ala Ala Arg Cys Ala Ala
                885                 890                 895

Pro Pro Pro Gly Gly Ala Pro Ala Ala Phe Gly Pro Leu Arg Ala Ser
            900                 905                 910

Gly Pro Leu Arg Arg Ala Ala Ala Trp Met Arg Gln Val Pro Asp Pro
        915                 920                 925

Glu Asp Val Arg Val Val Ile Leu Tyr Ser Pro Leu Pro Gly Glu Asp
    930                 935                 940

Leu Ala Ala Gly Arg Ala Gly Gly Gly Pro Pro Pro Glu Trp Ser Ala
945                 950                 955                 960

Glu Arg Gly Gly Leu Ser Cys Leu Leu Ala Ala Leu Gly Asn Arg Leu
                965                 970                 975

Cys Gly Pro Ala Thr Ala Ala Trp Ala Gly Asn Trp Thr Gly Ala Pro
            980                 985                 990

Asp Val Ser Ala Leu Gly Ala Gln  Gly Val Leu Leu Leu  Ser Thr Arg
        995                 1000                 1005

Asp Leu  Ala Phe Ala Gly Ala  Val Glu Phe Leu Gly  Leu Leu Ala
    1010                 1015                 1020

Gly Ala  Cys Asp Arg Arg Leu  Ile Val Val Asn Ala  Val Arg Ala
    1025                 1030                 1035

Ala Ala  Trp Pro Ala Ala Ala  Pro Val Val Ser Arg  Gln His Ala
    1040                 1045                 1050

Tyr Leu  Ala Cys Glu Val Leu  Pro Ala Val Gln Cys  Ala Val Arg
    1055                 1060                 1065

Trp Pro  Ala Ala Arg Asp Leu  Arg Arg Thr Val Leu  Ala Ser Gly
    1070                 1075                 1080

Arg Val  Phe Gly Pro Gly Val  Phe Ala Arg Val Glu  Ala Ala His
    1085                 1090                 1095

Ala Arg  Leu Tyr Pro Asp Ala  Pro Pro Leu Arg Leu  Cys Arg Gly
```

1100 1105 1110

Ala Asn Val Arg Tyr Arg Val Arg Thr Arg Phe Gly Pro Asp Thr
1115 1120 1125

Leu Val Pro Met Ser Pro Arg Glu Tyr Arg Arg Ala Val Leu Pro
1130 1135 1140

Ala Leu Asp Gly Arg Ala Ala Ala Ser Gly Ala Gly Asp Ala Met
1145 1150 1155

Ala Pro Gly Ala Pro Asp Phe Cys Glu Asp Glu Ala His Ser His
1160 1165 1170

Arg Ala Cys Ala Arg Trp Gly Leu Gly Ala Pro Leu Arg Pro Val
1175 1180 1185

Tyr Val Ala Leu Gly Arg Asp Ala Val Arg Gly Gly Pro Ala Glu
1190 1195 1200

Leu Arg Gly Pro Arg Arg Glu Phe Cys Ala Arg Ala Leu Leu Glu
1205 1210 1215

Pro Asp Gly Asp Ala Pro Pro Leu Val Leu Arg Asp Asp Ala Asp
1220 1225 1230

Ala Gly Pro Pro Pro Gln Ile Arg Trp Ala Ser Ala Ala Gly Arg
1235 1240 1245

Ala Gly Thr Val Leu Ala Ala Ala Gly Gly Gly Val Glu Val Val
1250 1255 1260

Gly Thr Ala Ala Gly Leu Ala Thr Pro Pro Arg Arg Glu Pro Val
1265 1270 1275

Asp Met Asp Ala Glu Leu Glu Asp Asp Asp Asp Gly Leu Phe Gly
1280 1285 1290

Glu

<210> SEQ ID NO 78
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 78

Met Asp Trp Thr Trp Ile Leu Phe Leu Val Ala Ala Ala Thr Arg Val
1 5 10 15

His Ser

<210> SEQ ID NO 79
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 79

Met Glu Thr Pro Ala Gln Leu Leu Phe Leu Leu Leu Leu Trp Leu Pro
1 5 10 15

Asp Thr Thr Gly
20

<210> SEQ ID NO 80
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 80

Met Leu Gly Ser Asn Ser Gly Gln Arg Val Val Phe Thr Ile Leu Leu
1 5 10 15

Leu Leu Val Ala Pro Ala Tyr Ser
20

<210> SEQ ID NO 81
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 81

Met Lys Cys Leu Leu Tyr Leu Ala Phe Leu Phe Ile Gly Val Asn Cys
1 5 10 15

Ala

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

Met Trp Leu Val Ser Leu Ala Ile Val Thr Ala Cys Ala Gly Ala
1 5 10 15

<210> SEQ ID NO 83
<211> LENGTH: 1729
<212> TYPE: DNA
<213> ORGANISM: Artificial Sequence
<220> FEATURE:
<223> OTHER INFORMATION: Synthetic Polynucleotide

<400> SEQUENCE: 83
tcaagctttt ggaccctcgt acagaagcta atacgactca ctatagggaa ataagagaga 60
aaagaagagt aagaagaaat ataagagcca ccatggcaca agtcattaat acaaacagcc 120
tgtcgctgtt gacccagaat aacctgaaca aatcccagtc cgcactgggc actgctatcg 180
agcgtttgtc ttccggtctg cgtatcaaca gcgcgaaaga cgatgcggca ggacaggcga 240
ttgctaaccg ttttaccgcg aacatcaaag gtctgactca ggcttcccgt aacgctaacg 300
acggtatctc cattgcgcag accactgaag gcgcgctgaa cgaaatcaac aacaacctgc 360
agcgtgtgcg tgaactggcg gttcagtctg cgaatggtac taactcccag tctgacctcg 420
actccatcca ggctgaaatc acccagcgcc tgaacgaaat cgaccgtgta tccggccaga 480
ctcagttcaa cggcgtgaaa gtcctggcgc aggacaacac cctgaccatc caggttggtg 540
ccaacgacgg tgaaactatc gatattgatt taaaagaaat cagctctaaa acactgggac 600
ttgataagct taatgtccaa gatgcctaca ccccgaaaga aactgctgta accgttgata 660
aaactaccta taaaaatggt acagatccta ttacagccca gagcaatact gatatccaaa 720
ctgcaattgg cggtggtgca acgggggtta ctggggctga tatcaaattt aaagatggtc 780
aatactattt agatgttaaa ggcggtgctt ctgctggtgt ttataaagcc acttatgatg 840
aaactacaaa gaaagttaat attgatacga ctgataaaac tccgttggca actgcggaag 900
ctacagctat tcggggaacg gccactataa cccacaacca aattgctgaa gtaacaaaag 960
agggtgttga tacgaccaca gttgcggctc aacttgctgc agcaggggtt actggcgccg 1020
ataaggacaa tactagcctt gtaaaactat cgtttgagga taaaaacggt aaggttattg 1080
atggtggcta tgcagtgaaa atgggcgacg atttctatgc cgctacatat gatgagaaaa 1140
caggtgcaat tactgctaaa accactactt atacagatgg tactggcgtt gctcaaactg 1200
gagctgtgaa atttggtggc gcaaatggta aatctgaagt tgttactgct accgatggta 1260
agacttactt agcaagcgac cttgacaaac ataacttcag aacaggcggt gagcttaaag 1320
aggttaatac agataagact gaaaacccac tgcagaaaat tgatgctgcc ttggcacagg 1380
ttgatacact tcgttctgac ctgggtgcgg ttcagaaccg tttcaactcc gctatcacca 1440
acctgggcaa taccgtaaat aacctgtctt ctgcccgtag ccgtatcgaa gattccgact 1500
acgcaaccga agtctccaac atgtctcgcg cgcagattct gcagcaggcc ggtacctccg 1560
ttctggcgca ggcgaaccag gttccgcaaa acgtcctctc tttactgcgt tgataatagg 1620
ctggagcctc ggtggccatg cttcttgccc cttgggcctc cccccagccc ctcctcccct 1680
tcctgcaccc gtacccccgt ggtctttgaa taaagtctga gtgggcggc 1729

<210> SEQ ID NO 84
<211> LENGTH: 1518
<212> TYPE: DNA
<213> ORGANISM: Artificial Sequence
<220> FEATURE:
<223> OTHER INFORMATION: Synthetic Polynucleotide

<400> SEQUENCE: 84
atggcacaag tcattaatac aaacagcctg tcgctgttga cccagaataa cctgaacaaa 60
tcccagtccg cactgggcac tgctatcgag cgtttgtctt ccggtctgcg tatcaacagc 120
gcgaaagacg atgcggcagg acaggcgatt gctaaccgtt ttaccgcgaa catcaaaggt 180
ctgactcagg cttcccgtaa cgctaacgac ggtatctcca ttgcgcagac cactgaaggc 240
gcgctgaacg aaatcaacaa caacctgcag cgtgtgcgtg aactggcggt tcagtctgcg 300
aatggtacta actcccagtc tgacctcgac tccatccagg ctgaaatcac ccagcgcctg 360
aacgaaatcg accgtgtatc cggccagact cagttcaacg gcgtgaaagt cctggcgcag 420
gacaacaccc tgaccatcca ggttggtgcc aacgacggtg aaactatcga tattgattta 480
aaagaaatca gctctaaaac actgggactt gataagctta atgtccaaga tgcctacacc 540
ccgaaagaaa ctgctgtaac cgttgataaa actacctata aaaatggtac agatcctatt 600
acagcccaga gcaatactga tatccaaact gcaattggcg gtggtgcaac gggggttact 660
ggggctgata tcaaatttaa agatggtcaa tactatttag atgttaaagg cggtgcttct 720
gctggtgttt ataaagccac ttatgatgaa actacaaaga aagttaatat tgatacgact 780
gataaaactc cgttggcaac tgcggaagct acagctattc ggggaacggc cactataacc 840
cacaaccaaa ttgctgaagt aacaaaagag ggtgttgata cgaccacagt tgcggctcaa 900
cttgctgcag caggggttac tggcgccgat aaggacaata ctagccttgt aaaactatcg 960
tttgaggata aaaacggtaa ggttattgat ggtggctatg cagtgaaaat gggcgacgat 1020
ttctatgccg ctacatatga tgagaaaaca ggtgcaatta ctgctaaaac cactacttat 1080
acagatggta ctggcgttgc tcaaactgga gctgtgaaat ttggtggcgc aaatggtaaa 1140
tctgaagttg ttactgctac cgatggtaag acttacttag caagcgacct tgacaaacat 1200
aacttcagaa caggcggtga gcttaaagag gttaatacag ataagactga aaacccactg 1260
cagaaaattg atgctgcctt ggcacaggtt gatacacttc gttctgacct gggtgcggtt 1320
cagaaccgtt tcaactccgc tatcaccaac ctgggcaata ccgtaaataa cctgtcttct 1380
gcccgtagcc gtatcgaaga ttccgactac gcaaccgaag tctccaacat gtctcgcgcg 1440
cagattctgc agcaggccgg tacctccgtt ctggcgcagg cgaaccaggt tccgcaaaac 1500
gtcctctctt tactgcgt 1518

<210> SEQ ID NO 85
<211> LENGTH: 1790
<212> TYPE: RNA
<213> ORGANISM: Artificial Sequence
<220> FEATURE:
<223> OTHER INFORMATION: Synthetic Polynucleotide

<400> SEQUENCE: 85
ggggaaauaa gagagaaaag aagaguaaga agaaauauaa gagccaccau ggcacaaguc 60
auuaauacaa acagccuguc gcuguugacc cagaauaacc ugaacaaauc ccaguccgca 120
cugggcacug cuaucgagcg uuugucuucc ggucugcgua ucaacagcgc gaaagacgau 180
gcggcaggac aggcgauugc uaaccguuuu accgcgaaca ucaaaggucu gacucaggcu 240
ucccguaacg cuaacgacgg uaucuccauu gcgcagacca cugaaggcgc gcugaacgaa 300
aucaacaaca accugcagcg ugugcgugaa cuggcgguuc agucugcgaa ugguacuaac 360
ucccagucug accucgacuc cauccaggcu gaaaucaccc agcgccugaa cgaaaucgac 420
cguguauccg gccagacuca guucaacggc gugaaagucc uggcgcagga caacacccug 480
accauccagg uuggugccaa cgacggugaa acuaucgaua uugauuuaaa agaaaucagc 540
ucuaaaacac ugggacuuga uaagcuuaau guccaagaug ccuacacccc gaaagaaacu 600
gcuguaaccg uugauaaaac uaccuauaaa aaugguacag auccuauuac agcccagagc 660
aauacugaua uccaaacugc aauuggcggu ggugcaacgg ggguuacugg ggcugauauc 720
aaauuuaaag auggucaaua cuauuuagau guuaaaggcg gugcuucugc ugguguuuau 780
aaagccacuu augaugaaac uacaaagaaa guuaauauug auacgacuga uaaaacuccg 840
uuggcaacug cggaagcuac agcuauucgg ggaacggcca cuauaaccca caaccaaauu 900
gcugaaguaa caaaagaggg uguugauacg accacaguug cggcucaacu ugcugcagca 960
gggguuacug gcgccgauaa ggacaauacu agccuuguaa aacuaucguu ugaggauaaa 1020
aacgguaagg uuauugaugg uggcuaugca gugaaaaugg gcgacgauuu cuaugccgcu 1080
acauaugaug agaaaacagg ugcaauuacu gcuaaaacca cuacuuauac agaugguacu 1140
ggcguugcuc aaacuggagc ugugaaauuu gguggcgcaa augguaaauc ugaaguuguu 1200
acugcuaccg augguaagac uuacuuagca agcgaccuug acaaacauaa cuucagaaca 1260
ggcggugagc uuaaagaggu uaauacagau aagacugaaa acccacugca gaaaauugau 1320
gcugccuugg cacagguuga uacacuucgu ucugaccugg gugcgguuca gaaccguuuc 1380
aacuccgcua ucaccaaccu gggcaauacc guaaauaacc ugucuucugc ccguagccgu 1440
aucgaagauu ccgacuacgc aaccgaaguc uccaacaugu cucgcgcgca gauucugcag 1500
caggccggua ccuccguucu ggcgcaggcg aaccagguuc cgcaaaacgu ccucucuuua 1560
cugcguugau aauaggcugg agccucggug gccaugcuuc uugccccuug ggccuccccc 1620
cagccccucc uccccuuccu gcacccguac ccccgugguc uuugaauaaa gucugagugg 1680
gcggcaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaucuag 1790

<210> SEQ ID NO 86
<211> LENGTH: 1729
<212> TYPE: RNA
<213> ORGANISM: Artificial Sequence
<220> FEATURE:
<223> OTHER INFORMATION: Synthetic Polynucleotide

<400> SEQUENCE: 86
ucaagcuuuu ggacccucgu acagaagcua auacgacuca cuauagggaa auaagagaga 60
aaagaagagu aagaagaaau auaagagcca ccauggcaca agucauuaau acaaacagcc 120
ugucgcuguu gacccagaau aaccugaaca aaucccaguc cgcacugggc acugcuaucg 180
agcguuuguc uuccggucug cguaucaaca gcgcgaaaga cgaugcggca ggacaggcga 240
uugcuaaccg uuuuaccgcg aacaucaaag gucugacuca ggcuucccgu aacgcuaacg 300
acgguaucuc cauugcgcag accacugaag gcgcgcugaa cgaaaucaac aacaaccugc 360
agcgugugcg ugaacuggcg guucagucug cgaaugguac uaacucccag ucugaccucg 420
acuccaucca ggcugaaauc acccagcgcc ugaacgaaau cgaccgugua uccggccaga 480
cucaguucaa cggcgugaaa guccuggcgc aggacaacac ccugaccauc cagguuggug 540
ccaacgacgg ugaaacuauc gauauugauu uaaaagaaau cagcucuaaa acacugggac 600
uugauaagcu uaauguccaa gaugccuaca ccccgaaaga aacugcugua accguugaua 660
aaacuaccua uaaaaauggu acagauccua uuacagccca gagcaauacu gauauccaaa 720
cugcaauugg cgguggugca acgggggcua cuggggcuga uaucaaauuu aaagaugguc 780
aauacuauuu agauguuaaa ggcggugcuu cugcuggugu uuauaaagcc acuuaugaug 840
aaacuacaaa gaaaguuaau auugauacga cugauaaaac uccguuggca acugcggaag 900
cuacagcuau ucggggaacg gccacuauaa cccacaacca aauugcugaa guaacaaaag 960
agggguguga uacgaccaca guugcggcuc aacuugcugc agcaggggu acuggcgccg 1020 auaaggacaa uacuagccuu guaaaacuau cguuugagga uaaaaacggu aagguuauug 1080
augguggcua ugcagugaaa augggcgacg auuucuaugc cgcuacauau gaugagaaaa 1140
caggugcaau uacugcuaaa accacuacuu auacagaugg uacuggcguu gcucaaacug 1200
gagcugugaa auuugguggc gcaaauggua aaucugaagu uguuacugcu accgauggua 1260
agacuuacuu agcaagcgac cuugacaaac auaacuucag aacaggcggu gagcuuaaag 1320
agguuaauac agauaagacu gaaaacccac ugcagaaaau ugaugcugcc uuggcacagg 1380
uugauacacu ucguucugac cugggugcgg uucagaaccg uuucaacucc gcuaucacca 1440
accugggcaa uaccguaaau aaccugucuu cugcccguag ccguaucgaa gauuccgacu 1500
acgcaaccga agucuccaac augucucgcg cgcagauucu gcagcaggcc gguaccuccg 1560
uucuggcgca ggcgaaccag guuccgcaaa acguccucuc uuuacugcgu ugauaauagg 1620
cuggagccuc gguggccaug cuucuugccc cuugggccuc cccccagccc cuccuccccu 1680
uccugcaccc guacccccgu ggucuuugaa uaaagucuga gugggcggc 1729

<210> SEQ ID NO 87
<211> LENGTH: 1518
<212> TYPE: RNA
<213> ORGANISM: Artificial Sequence
<220> FEATURE:
<223> OTHER INFORMATION: Synthetic Polynucleotide

<400> SEQUENCE: 87
auggcacaag ucauuaauac aaacagccug ucgcuguuga cccagaauaa ccugaacaaa 60

```
ucccaguccg cacugggcac ugcuaucgag cguuugucuu ccggucugcg uaucaacagc    120

gcgaaagacg augcggcagg acaggcgauu gcuaaccguu uuaccgcgaa caucaaaggu    180

cugacucagg cuucccguaa cgcuaacgac gguaucucca uugcgcagac cacugaaggc    240

gcgcugaacg aaaucaacaa caaccugcag cgugugcgug aacuggcggu ucagucugcg    300

aaugguacua acucccaguc ugaccucgac uccauccagg cugaaaucac ccagcgccug    360

aacgaaaucg accguguauc cggccagacu caguucaacg gcgugaaagu ccuggcgcag    420

gacaacaccc ugaccaucca gguuggugcc aacgacggug aaacuaucga uauugauuua    480

aaagaaauca gcucuaaaac acugggacuu gauaagcuua auguccaaga ugccuacacc    540

ccgaaagaaa cugcuguaac cguugauaaa acuaccuaua aaaaugguac agauccuauu    600

acagcccaga gcaauacuga uauccaaacu gcaauuggcg gugguggcaac gggggguuacu    660

ggggcugaua ucaaauuuaa agauggucaa uacuauuuag auguuaaagg cggugcuucu    720

gcugguguuu auaaagccac uuaugaugaa acuacaaaga aaguuaauau ugauacgacu    780

gauaaaacuc cguuggcaac ugcggaagcu acagcuauuc ggggaacggc cacuauaacc    840

cacaaccaaa uugcugaagu aacaaaagag gguguugaua cgaccacagu ugcggcucaa    900

cuugcugcag caggggguuac uggcgccgau aaggacaaua cuagccuugu aaaacuaucg    960

uuugaggaua aaaacgguaa gguuauugau gguggcuaug cagugaaaau gggcgacgau   1020

uucuaugccg cuacauauga ugagaaaaca ggugcaauua cugcuaaaac cacuacuuau   1080

acagauggua cuggcguugc ucaaacugga gcugugaaau uugguggcgc aaaugguaaa   1140

ucugaaguug uuacugcuac cgaugguaag acuuacuuag caagcgaccu ugacaaacau   1200

aacuucagaa caggcgguga gcuuaaagag guuaauacag auaagacuga aaacccacug   1260

cagaaaauug augcugccuu ggcacagguu gauacacuuc guucugaccu gggugcgguu   1320

cagaaccguu ucaacuccgc uaucaccaac cugggcaaua ccguaaauaa ccugucuucu   1380

gcccguagcc guaucgaaga uuccgacuac gcaaccgaag ucuccaacau gucucgcgcg   1440

cagauucugc agcaggccgg uaccuccguu cuggcgcagg cgaaccaggu uccgcaaaac   1500

guccucucuu uacugcgu                                                 1518
```

<210> SEQ ID NO 88
<211> LENGTH: 1790
<212> TYPE: RNA
<213> ORGANISM: Artificial Sequence
<220> FEATURE:
<223> OTHER INFORMATION: Synthetic Polynucleotide

<400> SEQUENCE: 88

```
ggggaaauaa gagagaaaag aagaguaaga agaaauauaa gagccaccau ggcacaaguc     60

auuaauacaa acagccuguc gcuguugacc cagaauaacc ugaacaaauc ccaguccgca    120

cugggcacug cuaucgagcg uuugucuucc ggucugcgua ucaacagcgc gaaagacgau    180

gcggcaggac aggcgauugc uaaccguuuu accgcgaaca ucaaaggucu gacucaggcu    240

ucccguaacg cuaacgacgg uaucuccauu gcgcagacca cugaaggcgc gcugaacgaa    300

aucaacaaca accugcagcg ugugcgugaa cuggcgguuc agucugcgaa ugguacuaac    360

ucccagucug accucgacuc cauccaggcu gaaaucaccc agcgccugaa cgaaaucgac    420

cguguauccg gccagacuca guucaacggc gugaaagucc uggcgcagga caacacccug    480

accauccagg uuggugccaa cgacggugaa acuaucgaua uugauuuaaa agaaaucagc    540

ucuaaaacac ugggacuuga uaagcuuaau guccaagaug ccuacacccc gaaagaaacu    600
```

```
gcuguaaccg uugauaaaac uaccuauaaa aaugguacag auccuauuac agcccagagc    660

aauacugaua uccaaacugc aauuggcggu ggugcaacgg gguuacugg ggcugauauc    720

aaauuuaaag auggucaaua cuauuuagau guuaaaggcg gugcuucugc ugguguuuau    780

aaagccacuu augaugaaac uacaaagaaa guuaauauug auacgacuga uaaaacuccg    840

uuggcaacug cggaagcuac agcuauucgg ggaacggcca cuauaaccca caaccaaauu    900

gcugaaguaa caaaagaggg uguugauacg accacaguug cggcucaacu ugcugcagca    960

gggguuacug gcgccgauaa ggacaauacu agccuuguaa aacuaucguu ugaggauaaa   1020

aacgguaagg uuauugaugg uggcuaugca gugaaaaugg gcgacgauuu cuaugccgcu   1080

acauaugaug agaaaacagg ugcaauuacu gcuaaaacca cuacuuauac agaugguacu   1140

ggcguugcuc aaacuggagc ugugaaauuu gguggcgcaa augguaaauc ugaaguuguu   1200

acugcuaccg augguaagac uuacuuagca agcgaccuug acaaacauaa cuucagaaca   1260

ggcggugagc uuaaagaggu uaauacagau aagacugaaa acccacugca gaaaauugau   1320

gcugccuugg cacagguuga uacacuucgu ucugaccugg gugcgguuca gaaccguuuc   1380

aacuccgcua ucaccaaccu gggcaauacc guaaauaacc ugucuucugc ccguagccgu   1440

aucgaagauu ccgacuacgc aaccgaaguc uccaacaugu cucgcgcgca gauucugcag   1500

caggccggua ccuccguucu ggcgcaggcg aaccagguuc cgcaaaacgu ccucucuuua   1560

cugcguugau aauaggcugg agccucggug gccaugcuuc uugccccuug ggccuccccc   1620

cagccccucc uccccuuccu gcacccguac cccguggguc uuugaauaaa gucugagugg   1680

gcggcaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaucuag              1790
```

<210> SEQ ID NO 89
<211> LENGTH: 506
<212> TYPE: PRT
<213> ORGANISM: Artificial Sequence
<220> FEATURE:
<223> OTHER INFORMATION: Synthetic Polynucleotide

<400> SEQUENCE: 89

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
```

-continued

```
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Pro Ile Thr Ala Gln Ser Asn Thr Asp Ile
        195                 200                 205

Gln Thr Ala Ile Gly Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Thr Val Ala Ala Gln Leu Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Ala
            340                 345                 350

Ile Thr Ala Lys Thr Thr Thr Tyr Thr Asp Gly Thr Gly Val Ala Gln
        355                 360                 365

Thr Gly Ala Val Lys Phe Gly Gly Ala Asn Gly Lys Ser Glu Val Val
    370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Ser Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505
```

<210> SEQ ID NO 90
<211> LENGTH: 1961
<212> TYPE: RNA
<213> ORGANISM: Human herpesvirus 2

<400> SEQUENCE: 90

```
ucaagcuuuu ggacccucgu acagaagcua auacgacuca cuauagggaa auaagagaga      60

aaagaagagu aagaagaaau auaagagcca ccaugagagg ugguggcuua guuugcgcgc     120
```

```
ugguugucgg ggcgcucgua gccgccgugg cgucggccgc cccugcggcu ccucgcgcua    180

gcggaggcgu agccgcaaca guugcggcga acgggggucc agccucucag ccuccucccg    240

ucccgagccc ugcgaccacc aaggcuagaa agcggaagac caagaaaccg cccaagcgcc    300

ccgaggccac cccgcccccc gaugccaacg cgacugucgc cgcuggccau gcgacgcuuc    360

gcgcucaucu gagggagauc aagguugaaa augcugaugc ccaauuuuac gugugcccgc    420

ccccgacggg cgccacgguu gugcaguuug aacagccgcg gcgcuguccg acgcggccag    480

aaggccagaa cuauacggag ggcauagcgg uggucuuuaa ggaaaacauc gccccguaca    540

aauuuaaggc cacaauguac uacaaagacg ugacaguuuc gcaagugugg uuuggccaca    600

gauacucgca guuuauggga aucuucgaag auagagcccc uguucccuuc gaggaaguca    660

ucgacaagau uaaugccaaa gggguaugcc guuccacggc caaauacgug cgcaacaaua    720

uggagaccac cgccuuucac cgggaugauc acgagaccga cauggagcuu aagccggcga    780

aggucgccac gcguaccucc cgggguuggc acaccacaga ucuuaaguac aaucccucgc    840

gaguugaagc auuccaucgg uauggaacua ccguuaacug caucguugag gagguggaug    900

cgcggucggu guacccuuac gaugaguuug uguuagcgac cggcgauuuu guguacaugu    960

ccccguuuua cggcuaccgg gaggggucgc acaccgaaca uaccucguac gccgcugaca   1020

gguucaagca ggucgauggc uuuuacgcgc gcgaucucac cacgaaggcc cgggccacgu   1080

caccgacgac caggaacuug cucacgaccc ccaaguucac cgucgcuugg gauuuggucc   1140

caaagcgucc ggcggucugc acgaugacca aauggcagga gguggacgaa augcuccgcg   1200

cagaauacgg cggcuccuuc cgcuucucgu ccgacgccau cucgacaacc uucaccacca   1260

aucugaccca guacagucug ucgcgcguug auuuaggaga cugcauuggc cgggaugccc   1320

gggaggccau cgacagaaug uuugcgcgua aguacaaugc cacacauauu aaggugggcc   1380

agccgcaaua cuaccuugcc acgggcggcu uucucaucgc guaccagccc cuucucucaa   1440

auacgcucgc ugaacuguac gugcgggagu auaugaggga acaggaccgc aagccccgca   1500

augccacgcc ugcgccacua cgagaggcgc cuucagcuaa ugcgucggug gaacguauca   1560

agaccaccuc cucaauagag uucgcccggc ugcaauuuac guacaaccac auccagcgcc   1620

acgugaacga caugcugggc cgcaucgcug ucgccuggug cgagcugcag aaucacgagc   1680

ugacucuuug gaacgaggcc cgaaaacuca accccaacgc gaucgccucc gcaacagucg   1740

guagacgggu gagcgcucgc augcuaggag augucauggc uguguccacc ugcgugcccg   1800

ucgcuccgga caacgugauu gugcagaauu cgaugcgggu cuugauaaua ggcuggagcc   1860

ucgguggcca ugcuucuugc cccuugggcc uccccccagc cccuccuccc cuuccugcac   1920

ccguaccccc guggucuuug aauaaagucu gagugggcgg c                       1961
```

<210> SEQ ID NO 91
<211> LENGTH: 1654
<212> TYPE: RNA
<213> ORGANISM: Human herpesvirus 2

<400> SEQUENCE: 91

```
ucaagcuuuu ggacccucgu acagaagcua auacgacuca cuauagggaa auaagagaga     60

aaagaagagu aagaagaaau auaagagcca ccauggcccu uggacgggua ggccuagccg    120

ugggccugug gggccuacug ugggugggug uggucguggu gcuggccaau gccuccccccg   180

gacgcacgau aacggugggc ccgcgaggca acgcgagcaa ugcugccccc uccgcguccc    240
```

cgcggaacgc auccgccccc cgaaccacac ccacgccccc acaaccccgc aaagcgacga 300
aauccaaggc cuccaccgcc aaaccggcuc cgcccccaa gaccggaccc ccgaagacau 360
ccucggagcc cgugcgaugc aaccgccacg acccgcuggc ccgguacggc ucgcgggugc 420
aaauccgaug ccgguuuccc aacuccacga ggacugaguc ccgucuccag aucuggcguu 480
augccacggc gacggacgcc gaaaucggaa cagcgccuag cuuagaagag gugaugguga 540
acgugucggc cccgcccggg ggccaacugg uguaugacag ugcccccaac cgaacggacc 600
cgcauguaau cugggcggag ggcgccggcc cgggcgccag cccgcgccug uacucgguug 660
ucggcccgcu gggucggcag cggcucauca ucgaagaguu aacccuggag acacagggca 720
uguacuauug ggugugggc cggacggacc gcccguccgc cuacgggacc ugggucccgcg 780 uucgaguauu ucgcccuccg ucgcugacca uccaccccca cgcggugcug gagggccagc 840
cguuuaaggc gacgugcacg gccgcaaccu acuacccggg caaccgcgcg gaguucgucu 900
gguuugagga cggucgccgc guauucgauc cggcacagau acacacgcag acgcaggaga 960
accccgacgg cuuuuccacc gucuccaccg ugaccuccgc ggccgucggc gggcagggcc 1020
ccccucgcac cuucaccugc cagcugacgu ggcaccgcga cuccgugucg uucucucggc 1080
gcaacgccag cggcacggcc ucgguucugc cgcggccgac cauuaccaug gaguuuacag 1140
gcgaccaugc ggucugcacg gccggcugug ugcccgaggg ggucacguuu gcuugguucc 1200
ugggggauga cuccucgccg gcggaaaagg uggccgucgc gucccagaca ucgugcgggc 1260
gccccggcac cgccacgauc cgcuccaccc ugccggucuc guacgagcag accgaguaca 1320
ucuguagacu ggcgggauac ccggacggaa uuccggggucu agagcaccac ggaagccacc 1380
agcccccgcc gcgggaccca accgagcggc aggugauccg ggcgguggag ggggcgggga 1440
ucggaguggc uguccuuguc gcggugguuc uggccgggac cgcgguagug uaccugaccc 1500 augccucuc gguacgcuau cgucggcugc gguaaugaua auaggcugga gccucggugg 1560
ccaugcuucu ugccccuugg gccucccccc agccccuccu ccccuuccug cacccguacc 1620
cccguggucu uugaauaaag ucugaguggg cggc 1654

<210> SEQ ID NO 92
<211> LENGTH: 1393
<212> TYPE: RNA
<213> ORGANISM: Human herpesvirus 2

<400> SEQUENCE: 92
ucaagcuuuu ggacccucgu acagaagcua auacgacuca cuauagggaa auaagagaga 60
aaagaagagu aagaagaaau auaagagcca ccaugggggcg uuugaccucc ggcgucggga 120
cggcggcccu gcuaguuguc gcggugggac uccgcgucgu cugcgccaaa uacgccuuag 180
cagaccccuc gcuuaagaug gccgauccca aucgauuucg cgggaagaac cuuccgguuu 240
uggaccagcu gaccgacccc cccggggguga agcguguuua ccacauucag ccgagccugg 300
aggacccguu ccagcccccc agcaucccga ucacugugua cuacgcagug cuggaacgug 360
ccugccgcag cgugcuccua caugccccau cggaggcccc ccagaucgug cgcggggcuu 420
cggacgaggc ccgaaagcac acguacaacc ugaccaucgc cugguaucgc augggagaca 480
auugcgcuau ccccaucacg guuauggaau acaccgagug ccccuacaac aagucguugg 540
gggucugccc cauccgaacg cagccccgcu ggagcuacua ugacagcuuu agcgccguca 600
gcgaggauaa ccugggauuc cugaugcacg cccccgccuu cgagaccgcg gguacguacc 660
ugcggcuagu gaagauaaac gacuggacgg agaucacaca auuuauccug gagcaccggg 720

```
cccgcgccuc cugcaaguac gcucuccccc ugcgcauccc cccggcagcg ugccucaccu    780

cgaaggccua ccaacagggc gugacggucg acagcaucgg gaugcuaccc cgcuuuaucc    840

ccgaaaacca gcgcaccguc gcccuauaca gcuuaaaaau cgccgggugg cacggcccca    900

agcccccgua caccagcacc cugcugccgc cggagcuguc cgacaccacc aacgccacgc    960

aacccgaacu cguuccggaa gaccccgagg acucggcccu cuuagaggau cccgccggga   1020

cggugucuuc gcagaucccc ccaaacuggc acaucccguc gauccaggac gucgcaccgc   1080

accacgcccc cgccgccccc agcaacccgg gccugaucau cggcgcgcug gccggcagua   1140

cccuggcggu gcuggucauc ggcgguauug cguuuugggu acgccgccgc gcucagaugg   1200

cccccaagcg ccuacgucuc ccccacaucc gggaugacga cgcgcccccc ucgcaccagc   1260

cauuguuuua cuagugauaa uaggcuggag ccucggugge caugcuucuu gccccuuggg   1320

ccucccccca gccccuccuc cccuuccugc acccguaccc ccguggucuu ugaauaaagu   1380

cugagugggc ggc                                                       1393
```

```
<210> SEQ ID NO 93
<211> LENGTH: 1858
<212> TYPE: RNA
<213> ORGANISM: Human herpesvirus 2

<400> SEQUENCE: 93

ucaagcuuuu ggacccucgu acagaagcua auacgacuca cuauagggaa auaagagaga     60

aaagaagagu aagaagaaau auaagagcca ccauggcuag gggggccggg uugguuuuuu    120

uuguuggagu uugggucgua agcugccucg cggcagcgcc cagaacgucc uggaaacgcg    180

uaaccucggg cgaagacgug guguuacucc ccgcgccggc ggggccggaa gaacgcacuc    240

gggcccacaa acuacugugg gcagcggaac cgcuggaugc cugcggucce cugaggccgu    300

caugggugge acuguggccc ccccgacgag ugcuugagac gguugucgau gcggcgugca    360

ugcgcgcccc ggaaccgcuc gcuaucgcau acaguccccc guucccugcg ggcgacgagg    420

gacuuuauuc ggaguuggcg uggcgcgauc gcguagccgu ggucaacgag aguuuaguua    480

ucuacggggc ccuggagacg gacaguggue uguacacccu gucaguggug ggccuauccg    540

acgaggcccg ccaaguggcg uccgugguuc ucgucgucga gcccgccccu gugccuaccc    600

cgaccccega ugacuacgac gaggaggaug acgcgggcgu gagcgaacgc acgcccguca    660

gcguuccccc cccaacaccc ccccgacguc cccccgucgc ccccccgacg cacccucgug    720

uuaucccuga ggugagccac gugcgggggg ugacggucca cauggaaacc ccggaggcca    780

uucuguuugc gccaggggag acguuuggga cgaacgucuc cauccacgca auugcccacg    840

acgacggucc guacgccaug gacgucgucu ggaugcgauu ugaugucccg uccucgugcg    900

ccgagaugcg gaucuaugaa gcaugucugu aucacccgca gcugccugag ugucugucuc    960

cggccgaugc gccgugcgcc guaaguucgu gggcguaccg ccuggcgguc cgcagcuacg   1020

ccggcugcuc caggacuacg cccccaccuc gauguuuugc ugaagcucgc auggaaccgg   1080

uccccggguu ggcguggcuc gcaucaacug uuaaucugga auuccagcau gccucucccc   1140

aacacgccgg ccucuaucug uguguggugu auguggacga ccauauccau gccuggggcc   1200

acaugaccau cuccacagcg gcccaguacc ggaaugcggu gguggaacag caucuccccc   1260

agcgccagcc cgagcccgua gaacccaccc gaccgcaugu gagagccccc ccucccgcac   1320

ccuccgcgag aggcccguua cgcuuaggug cgguccuggg ggcggcccug uugcucgcgg   1380
```

-continued

```
cccucgggcu auccgccugg gcgugcauga ccugcuggcg caggcgcagu uggcgggcgg   1440

uuaaaagucg ggccucggcg accggcccca cuuacauucg aguagcggau agcgagcugu   1500

acgcggacug gaguucggac ucagagggcg agcgcgacgg uucccugugg caggacccuc   1560

cggagagacc cgacucaccg uccacaaaug gauccggcuu ugagaucuua uccccaacgg   1620

cgcccucugu auaccccau agcgaagggc guaaaucgcg ccgcccgcuc accaccuuug   1680

guucaggaag cccgggacgu cgucacuccc aggcguccua uucuuccguc uuaugguaau   1740

gauaauaggc uggagccucg guggccaugc uucuugcccc uugggccucc ccccagcccc   1800

uccucccccuu ccugcacccg uaccccgug gucuuugaau aaagucugag ugggcggc   1858
```

<210> SEQ ID NO 94
<211> LENGTH: 1330
<212> TYPE: RNA
<213> ORGANISM: Human herpesvirus 2

<400> SEQUENCE: 94

```
ucaagcuuuu ggacccucgu acagaagcua auacgacuca cuauagggaa auaagagaga     60

aaagaagagu aagaagaaau auaagagcca ccaugcccgg ccgcucgcug cagggccugg    120

cgauccuggg ccugugggucc ugcgccaccg gccuggucgu ccgcggcccc acggucaguc    180

uggucucaga cucacucgug gaugccgggg ccguggggcc ccagggcuuc guggaagagg    240

accugcgugu uuucggggag cuucauuuug ugggggccca gguccccac acaaacuacu    300

acgacggcau caucgagcug uuucacuacc cccuggggaa ccacugcccc cgcguuguac    360

acguggucac acugaccgca ugcccccgcc gccccgccgu ggcguucacc uugugucgcu    420

cgacgcacca cgcccacagc cccgccuauc cgacccugga gcugggucug gcgcggcagc    480

cgcuucugcg gguucgaacg gcaacgcgcg acuaugccgg ucuguauguc cugcgcguau    540

gggucggcag cgcgacgaac gccagccugu uuguuuuggg gguggcgcuc ucugccaacg    600

ggacguuugu guauaacggc ucggacuacg gcuccugcga uccggcgcag cuucccuuuu    660

cggccccgcg ccugggaccc ucgagcguau acacccccgg agccucccgg cccaccccuc    720

cacggacaac gacaucaccg uccuccccac gagacccgac ccccgccccc ggggacacag    780

ggacgccugc ucccgcgagc ggcgagagag ccccgcccaa uuccacgcga ucggccagcg    840

aaucgagaca caggcuaacc guagcccagg uaauccagau cgccauaccg gcguccauca    900

ucgccuuugu guuucugggc agcuguaucu gcuucaucca uagaugccag cgccgauaca    960

ggcgcccccg cggccagauu uacaaccccg ggggcguuuc cugcgcgguc aacgaggcgg   1020

ccauggcccg ccucggagcc gagcugcgau cccacccaaa caccccccccc aaaccccgac   1080

gccguucguc gucguccacg accaugccuu cccuaacguc gauagcugag gaaucggagc   1140

cagguccagu cgugcugcug uccgucaguc cucggccccg caguggcccg acggccccccc   1200

aagaggucua gugauaauag gcuggagccu cgguggccau gcuucuugcc ccuugggccu   1260

ccccccagcc ccuccucccc uuccugcacc cguaccccccg uggucuuuga auaaagucug   1320

agugggcggc                                                           1330
```

<210> SEQ ID NO 95
<211> LENGTH: 2515
<212> TYPE: RNA
<213> ORGANISM: Human herpesvirus 2

<400> SEQUENCE: 95

```
ucaagcuuuu ggacccucgu acagaagcua auacgacuca cuauagggaa auaagagaga     60
```

-continued

```
aaagaagagu aagaagaaau auaagagcca ccaugcgcgg ggggggcuua guuugcgcgc    120
uggucguggg ggcgcucgua gccgcggucg cgucggcggc uccggcugcc ccacgcgcuu    180
cagguggugu cgcugcgacc guugcggcga augguggucc cgccagccaa ccgccucccg    240
ucccgagccc cgcgaccacu aaggcccgga agcggaagac caagaagcca cccaagcggc    300
ccgaggcgac uccgcccccca gacgccaacg cgaccgucgc cgccggccac gccacucugc    360
gugcgcaccu gcgggaaauc aaggucgaga acgcggacgc ccaguuuuac gugugcccgc    420
cgccgacugg cgccacggug gugcaguuug agcaaccuag gcgcugcccg acgcgaccag    480
aggggcagaa cuacaccgag ggcauagcgg uggucuuuaa ggaaaacauc gccccguaca    540
aauucaaggc caccauguac uacaaagacg ugaccguguc gcaggugugg uucggccacc    600
gcuacuccca guuuaugggg auauucgagg accgcgcccc cguucccuuc gaagagguga    660
uugacaaaau uaacgccaag gggggucugcc gcaguacggc gaaguacguc cggaacaaca    720
uggagaccac ugccuuccac cgggacgacc acgaaacaga cauggagcuc aaaccggcga    780
aagucgccac gcgcacgagc cgggggguggc acaccaccga ccucaaauac aauccuucgc    840
ggguggaagc auuccaucgg uauggcacga ccgucaacug uaucguagag gagguggaug    900
cgcggucggu guaccccuac gaugaguucg ugcuggcaac gggcgauuuu guguacaugu    960
ccccuuuuua cggcuaccgg gaagguaguc acaccgagca caccaguuac gccgccgacc   1020
gcuuuaagca aguggacggc uucuacgcgc gcgaccucac cacaaaggcc cgggccacgu   1080
cgccgacgac ccgcaauuug cugacgaccc ccaaguuuac cguggccugg gacugggugc   1140
cuaagcgacc ggcggucugu accaugacaa aguggcagga gguggacgaa augcuccgcg   1200
cugaauacgg uggcucuuuc cgcuucucuu ccgacgccau cuccaccacg uucaccacca   1260
accugaccca auacucgcuc ucgagagucg aucugggaga cugcauuggc cgggaugccc   1320
gcgaggcaau ugaccgcaug uucgcgcgca aguacaacgc uacgcacaua aagguuggcc   1380
aaccccagua cuaccuagcc acgggggggcu uccucaucgc uuaucaaccc cuccucagca   1440
acacgcucgc cgagcuguac gugcgggaau auaugcggga acaggaccgc aaaccccgaa   1500
acgccacgcc cgcgccgcug cgggaagcac cgagcgccaa cgcguccgug gagcgcauca   1560
agacgacauc cucgauugag uuugcucguc ugcaguuuac guauaaccac auacagcgcc   1620
auguaaacga caugcucggg cgcaucgccg ucgcguggug cgagcuccaa aaucacgagc   1680
ucacucugug gaacgaggca cgcaagcuca aucccaacgc caucgcaucc gccaccguag   1740
gccggcgggu gagcgcucgc augcucgggg augucauggc cgucuccacg ugcgugcccg   1800
ucgccccgga caacgugauc gugcaaaaua gcaugcgcgu uucuucgcgg ccggggacgu   1860
gcuacagccg cccgcugguu agcuuucggu acgaagacca aggcccgcug auugaggggc   1920
agcuggguga gaacaacgag cugcgccuca cccgcgaugc guuagagccg uguaccgucg   1980
gccaccggcg cuacuucauc uucggagggg gauacguaua cuucgaagaa uaugcguacu   2040
cucaccaauu gagucgcgcc gaugucacca cuguuagcac cuucaucgac cugaacauca   2100
ccaugcugga ggaccacgag uucgugcccc uggaggucua cacacgccac gagaucaagg   2160
auuccggccu acuggacuac accgaagucc agagacgaaa ucagcugcac gaucuccgcu   2220
uugcugacau cgauacuguu auccgcgccg acgccaacgc cgccauguuc gcaggucugu   2280
gugcguuuuu cgaggguaug ggugacuuag ggcgcgcggu gggcaagguc gucaugggggg   2340
uagucggggg cguggugucg gccgucucgg gcgucuccuc cuuuaugucu aaccccugau   2400
```

-continued aauaggcugg agccucggug gccaugcuuc uugccccuug ggccuccccc cagccccucc 2460 ucccccuuccu gcacccguac ccccguggguc uuugaauaaa gucugagugg gcggc 2515

<210> SEQ ID NO 96
<211> LENGTH: 1552
<212> TYPE: RNA
<213> ORGANISM: Human herpesvirus 2

<400> SEQUENCE: 96
ucaagcuuuu ggacccucgu acagaagcua auacgacuca cuauagggaa auaagagaga 60
aaagaagagu aagaagaaau auaagagcca ccauggcccu uggacgggug ggccuagccg 120
ugggccugug gggccugcug ugggugggug uugucguggu gcuggccaau gccucccccug 180 gacgcacgau aacggugggc ccgcggggga acgcgagcaa ugccgcccca uccgcguccc 240
cgcggaacgc auccgccccc cgaaccacac ccacucccccc ccaaccccgc aaagcgacga 300
aaaguaaggc cuccaccgcc aaaccggccc cgcccccaa gaccgggccc ccgaagacau 360
cuucugagcc cgugcgcugc aaccgccacg acccgcuggc ccgguacggc ucgcgggugc 420
aaauccgaug ucgauuuccc aacuccacuc gcacggaauc ccgccuccag aucuggcguu 480
augccacggc gacggacgcc gagauuggaa cugcgccuag cuuagaggag gugaugguaa 540
acgugucggc cccgcccggg ggccaacugg uguaugauag cgcaccuaac cgaacggacc 600
cgcacgugau uugggcggag ggcgccggac cuggcgccuc accgcggcug uacucggucg 660
ucgggccgcu gggucggcag agacuuauca ucgaagagcu gacccucgag acacagggca 720
uguauuauug ggugugggc cggacggacc gcccguccgc guacgggacc ugggugcgcg 780
uucgcguguu ccgccccuccu ucgcugacca uccaccccca cgcggugcug gagggccagc 840
cguuuaaagc gacgugcacc gccgccaccu acuacccggg caaccgcgcg gaguucgucu 900
gguucgagga cggucgccgg guauucgauc cggcccagau acauacgcag acgcaggaaa 960
accccgacgg cuuuuccacc gucuccaccg ugaccuccgc ggccgucggc ggccagggcc 1020
ccccgcgcac cuucaccugu cagcugacgu ggcaccgcga cuccgugucg uucucucggc 1080
gcaaugccag cggcacggca ucggugcugc cacggccaac cauuaccaug gaguuuacgg 1140
gcgaccaugc ggucugcacg gccggcugug ugcccgaggg ggugacguuu gccugguucc 1200
ugggggacga cuccucgccg gccgagaagg uggccgucgc gucccagacc ucgugcgguc 1260
gccccggcac cgccacgauc cgcuccacac ugccggucuc guacgagcag accgaguaca 1320
ucugccggcu ggcgggauac ccggacggaa uuccggucccu agagcaccau ggcagccacc 1380 agccccgcc gcgggacccc accgaacggc aggugauucg ggcaguggaa gggugauaau 1440
aggcuggagc cucgguggcc augcuucuug ccccuugggc cuccccccag ccccuccucc 1500
ccuuccugca cccguacccc cguggucuuu gaauaaaguc ugagugggcg gc 1552

<210> SEQ ID NO 97
<211> LENGTH: 1462
<212> TYPE: RNA
<213> ORGANISM: Human herpesvirus 2

<400> SEQUENCE: 97
ucaagcuuuu ggacccucgu acagaagcua auacgacuca cuauagggaa auaagagaga 60
aaagaagagu aagaagaaau auaagagcca ccauggcucg cggggccggg uugguguuuu 120
uuguuggagu uugggucgua ucgugccugg cggcagcacc cagaacgucc uggaaacggg 180
uuaccucggg cgaggacgug guguugcuuc cggcgcccgc ggggccggag gaacgcacac 240

```
gggcccacaa acuacugugg gccgcggaac cccuggaugc cugcgguccc cugaggccgu    300
cgugggugggc gcuguggccc ccgcgacggg ugcucgaaac ggucguggau gcggcgugca    360
ugcgcgcccc ggaaccgcuc gccauagcau acaguccccc guuccccgcg ggcgacgagg    420
gacuguauuc ggaguuggcg uggcgcgauc gcguagccgu ggucaacgag agucugguca    480
ucuacggggc ccuggagacg gacagcgguc uguacacccu guccgugguc ggccuaagcg    540
acgaggcgcg ccaaguggcg ucgguggguuc uggucgugga gcccgccccu gugccgaccc    600
cgacccccga cgacuacgac gaagaagacg acgcgggcgu gagcgaacgc acgccgguca    660
gcguaccccc cccgacccca ccccgucguc cccccgucgc ccccccuacg cacccucgug    720
uuauccccga ggugucccac gugcgcgggg uaacggucca uauggagacc ccggaggcca    780
uucuguuugc ccccggagag acguuuggga cgaacgucuc cauccacgcc auugcccaug    840
acgacggucc guacgccaug gacgucgucu ggaugcgguu ugacgugccg uccucgugcg    900
ccgagaugcg gaucuacgaa gcuugucugu aucacccgca gcuuccagaa ugucuaucuc    960
cggccgacgc gccgugcgcu guaaguuccu gggcguaccg ccuggcgguc cgcagcuacg   1020
ccggcuguuc caggacuacg cccccgccgc gauguuuugc cgaggcucgc auggaaccgg   1080
ucccggggguu ggcgugguua gccuccaccg ucaaccugga auuccagcac gccuccccuc   1140
agcacgccgg ccuuuaccug ugcguggugu acguggacga ucauauccac gccuggggcc   1200
acaugaccau cucuaccgcg gcgcaguacc ggaacgcggu gguggaacag cacuugcccc   1260
agcgccagcc ugaacccguc gagcccaccc gcccgcacgu aagagcaccc ccucccgcgc   1320
cuuccgcgcg cggcccgcug cgcugauaau aggcuggagc cucgguggcc augcuucuug   1380
ccccuugggc cuccccccag ccccuccucc ccuuccugca cccguacccc cguggucuuu   1440
gaauaaaguc ugagugggcg gc                                             1462
```

<210> SEQ ID NO 98
<211> LENGTH: 4096
<212> TYPE: RNA
<213> ORGANISM: Human herpesvirus 2

<400> SEQUENCE: 98

```
ucaagcuuuu ggacccucgu acagaagcua auacgacuca cuauagggaa auaagagaga     60
aaagaagagu aagaagaaau auaagagcca ccaugucggc ggagcagcgg aagaagaaga    120
agacgacgac gacgacgcag ggccgcgggg ccgaggucgc gauggcggac gaggacgggg    180
gacgucuccg ggccgcggcg gagacgaccg gcggccccgg aucuccggau ccagccgacg    240
gaccgccgcc cacccccgaac ccggaccguc gccccgccgc gcggcccggg uucgggugggc    300
acggugggcc ggaggagaac gaagacgagg ccgacgacgc cgccgccgau gccgaugccg    360
acgaggcggc cccggcgucc ggggaggccg ucgacgagcc ugccgcggac ggcgucgucu    420
cgccgcggca gcuggcccug cuggccucga ugguggacga ggccguucgc acgaucccgu    480
cgcccccccc ggagcgcgac ggcgcgcaag aagaagcggc ccgcucgccu ucuccgccgc    540
ggacccccuc caugcgcgcc gauuauggcg aggagaacga cgacgacgac gacgacgacg    600
augacgacga ccgcgacgcg ggccgcuggg uccgcggacc ggagacgacg uccgcggucc    660
gcggggcgua cccggacccc auggccagcc ugucgccgcg acccccggcg ccccgccgac    720
accaccacca ccaccaccac cgccgccggc gcgcccccccg ccggcgcucg gccgccucug    780
acucaucaaa auccggaucc ucgucgucgg cguccuccgc cuccuccucc gccuccuccu    840
```

-continued

```
ccucgucugc auccgccucc ucgucugacg acgacgacga cgacgacgcc gcccgcgccc    900
ccgccagcgc cgcagaccac gccgcgggcg ggacccucgg cgcggacgac gaggaggcgg    960
gggugcccgc gagggccccg ggggcggcgc cccggccgag cccgcccagg gccgagcccg   1020
ccccggcccg gacccccgcg gcgaccgcgg gccgccugga gcgccgccgg gcccgcgcgg   1080
cgguggccgg ccgcgacgcc acgggccgcu ucacggccgg gcggccccgg cgggucgagc   1140
uggacgccga cgcggccucc ggcgccuucu acgcgcgcua ccgcgacggg uacgucagcg   1200
gggagccgug gcccggggcc ggcccccc gc ccccggggcg cgugcuguac ggcgggcugg   1260
gcgacagccg ccccggccuc uggggggcgc ccgaggcgga ggaggcgcgg gcccgguucg   1320
aggccucggg cgccccggcg cccgugug gg cgcccgagcu gggcgacgcg gcgcagcagu   1380
acgcccugau cacgcggcug cuguacacgc cggacgcgga ggcgaugggg uggcuccaga   1440
acccgcgcgu ggcgcccggg gacguggcgc uggaccaggc cugcuuccgg aucucgggcg   1500
cggcgcgcaa cagcagcucc uucaucuccg gcagcguggc gcgggccgug ccccaccugg   1560
gguacgccau ggcggcgggc cgcuucggcu ggggccuggc gcacguggcg gccgccgugg   1620
ccaugagccg ccgcuacgac cgcgcgcaga agggcuuccu gcugaccagc cugcgccgcg   1680
ccuacgcgcc ccugcuggcg cgcgagaacg cggcgcugac cggggcgcga acccccgacg   1740
acggcggcga cgccaaccgc cacgacggcg acgacgcccg cgggaagccc gccgccgccg   1800
ccgccccguu gccgucggcg gcggcgucgc cggccgacga gcgcgcggug cccgccggcu   1860
acggcgccgc gggggugcuc gccgcccugg ggcgccugag cgccgcgccc gccuccgcgc   1920
cggccggggc cgacgacgac gacgacgacg acggcgccgg cgguggu ggc ggcggccggc   1980
gcgcggaggc gggccgcgug gccguggagu gccuggccgc cugccgcggg auccuggagg   2040
cgcuggcgga gggcuucgac ggcgaccugg cggccgugcc ggggcuggcc ggagcccggc   2100
ccgccgcgcc cccgcgcccg gggcccgcgg gcgcggccgc cccgccgcac gccgacgcgc   2160
cccgccugcg cgccuggcug cgcgagcugc gguucgugcg cgacgcgcug gugcugaugc   2220
gccugcgcgg ggaccugcgc guggccggcg gcagcgaggc cgccguggcc gccgugcgcg   2280
ccgugagccu ggucgccggg gcccugggcc cggcgcugcc gcggagcccg cgccugcuga   2340
gcuccgccgc cgccgccgcc gcggaccugc ucuuccagaa ccagagccug cgcccccugc   2400
uggccgacac cgucgccgcg gccgacucgc ucgccgcgcc cgccuccgcg ccgcgggagg   2460
ccgcggacgc cccccgcccc gcggccgccc cucccgcggg ggccgcgccc cccgccccgc   2520
cgacgccgcc gccgcggccg ccgcgccccg cggcgcugac ccgccggccc gccgagggcc   2580
ccgacccgca gggcggcugg cgccgccagc cgccggggcc cagccacacg ccggcgcccu   2640
cggccgccgc ccuggaggcc uacugcgccc cgcgggccgu ggccgagcuc acggaccacc   2700
cgcucuuccc cgcgcc gugg cgcccggccc ucauguucga cccgcgcgcg cuggccucgc   2760
uggccgcgcg cugcgccgcc ccgccccccg gcggcgcgcc cgccgccuuc ggcccgcugc   2820
gcgccucggg cccgcugcgc cgcgcggcgg ccuggaugcg ccaggugccc gacccggagg   2880
acgugcgcgu ggugauccuc uacucgccgc ugccgggcga ggaccuggcc gcgggccgcg   2940
ccgggggcgg gcccccccg gagugguccg ccgagcgcgg cgggcugucc ugccugcugg   3000
cggcccuggg caaccggcuc ugcgggcccg ccacggccgc cugggcgggc aacuggaccg   3060
gcgcccccga cgucucggcg cugggcgcgc agggcgugcu gcugcugucc acgcgggacc   3120
uggccuucgc cggcgccgug gaguuccugg ggcugcuggc cggcgccugc gaccgccgcc   3180
ucaucgucgu caacgccgug cgcgccgcgg ccuggcccgc cgcugccccc guggucucgc   3240
```

-continued ggcagcacgc cuaccuggcc ugcgaggugc ugcccgccgu gcagugcgcc gugcgcuggc 3300
cggcggcgcg ggaccugcgc cgcaccgugc uggccuccgg ccgcguguuc gggccggggg 3360
ucuucgcgcg cguggaggcc gcgcacgcgc gccuguaccc cgacgcgccg ccgcugcgcc 3420
ucugccgcgg ggccaacgug cgguaccgcg ugcgcacgcg cuucggcccc gacacgcugg 3480
ugcccauguc cccgcgcgag uaccgccgcg ccgugcuccc ggcgcuggac ggccgggccg 3540
ccgccucggg cgcgggcgac gccauggcgc ccggcgcgcc ggacuucugc gaggacgagg 3600
cgcacucgca ccgcgccugc gcgcgcuggg gccugggcgc gccgcugcgg cccgucuacg 3660
uggcgcuggg gcgcgacgcc gugcgcggcg gcccggcgga gcugcgcggg ccgcggcggg 3720
aguucugcgc gcgggcgcug cucgagcccg acggcgacgc gcccccgcug gugcugcgcg 3780
acgacgcgga cgcgggcccg cccccgcaga uacgcugggc gucggccgcg ggccgcgcgg 3840
ggacggugcu ggccgcggcg ggcggcggcg uggagguggu ggggaccgcc gcggggcugg 3900
ccacgccgcc gaggcgcgag cccguggaca uggacgcgga gcuggaggac gacgacgacg 3960
gacuguuugg ggagugauga uaauaggcug gagccucggu ggccaugcuu cuugccccuu 4020
gggccucccc ccagccccuc cuccccuucc ugcacccgua cccccguggu cuuugaauaa 4080
agucugagug ggcggc 4096

<210> SEQ ID NO 99
<211> LENGTH: 997
<212> TYPE: RNA
<213> ORGANISM: Human herpesvirus 2

<400> SEQUENCE: 99
ucaagcuuuu ggacccucgu acagaagcua auacgacuca cuauagggaa auaagagaga 60
aaagaagagu aagaagaaau auaagagcca ccaugcccgg ccgcucgcug cagggccugg 120
cgauccuggg ccugugggguc ugcgccaccg gccuggucgu ccgcggcccc acggucaguc 180
uggucucaga cucacucgug gaugccgggg ccguggggcc ccagggcuuc guggaagagg 240
accugcgugu uuucggggag cuucauuuug ugggggccca gguccccac acaaacuacu 300 acgacggcau caucgagcug uuucacuacc cccuggggaa ccacugcccc cgcguuguac 360 acgugguicac acugaccgca ugcccccgcc gccccgccgu ggcguucacc uugugucgcu 420
cgacgcacca cgcccacagc cccgccuauc cgacccugga gcugggucug gcgcggcagc 480
cgcuucugcg gguucgaacg gcaacgcgcg acuaugccgg ucuguauguc cugcgcguau 540
gggucggcag cgcgacgaac gccagccugu uuguuuuggg gguggcgcuc ucugccaacg 600
ggacguuugu guauaacggc ucggacuacg gcuccugcga uccggcgcag cuucccuuuu 660
cggccccgcg ccugggaccc ucgagcguau acaccccccgg agccucccgg cccacccccuc 720 cacggacaac gacaucccccg uccuccccua gagacccgac ccccgccccc ggggacacag 780
gaacgccugc gcccgcgagc ggcgagagag ccccgcccaa uuccacgcga ucggccagcg 840
aaucgagaca caggcuaacc guagcccagg uaauccagug auaauaggcu ggagccucgg 900
uggccaugcu ucuugccccu ugggccuccc cccagccccu ccuccccuuc cugcacccgu 960
acccccgugg ucuuugaaua aagucugagu gggcggc 997

<210> SEQ ID NO 100
<211> LENGTH: 1228
<212> TYPE: RNA
<213> ORGANISM: Human herpesvirus 2

<400> SEQUENCE: 100
ucaagcuuuu ggacccucgu acagaagcua auacgacuca cuauagggaa auaagagaga 60
aaagaagagu aagaagaaau auaagagcca ccauggggcg uuugaccucc ggcgucggga 120
cggcggcccu gcuaguuguc gcggugggac uccgcgucgu cugcgccaaa uacgccuuag 180
cagaccccuc gcuuaagaug gccgauccca aucgauuucg cgggaagaac cuuccgguuu 240
uggaccagcu gaccgacccc cccgggguga agcguguuua ccacauucag ccgagccugg 300
aggacccguu ccagcccccc agcaucccga ucacugugua cuacgcagug cuggaacgug 360
ccugccgcag cgugcuccua caugccccau cggaggcccc ccagaucgug cgcggggcuu 420
cggacgaggc ccgaaagcac acguacaacc ugaccaucgc cugguaucgc augggagaca 480
auugcgcuau ccccaucacg guuauggaau acaccgagug ccccuacaac aagucguugg 540
gggucugccc cauccgaacg cagccccgcu ggagcuacua ugacagcuuu agcgccguca 600
gcgaggauaa ccugggauuc cugaugcacg cccccgccuu cgagaccgcg gguacguacc 660
ugcggcuagu gaagauaaac gacuggacgg agaucacaca auuuauccug gagcaccggg 720
cccgcgccuc cugcaaguac gcucuccccc ugcgcauccc cccggcagcg ugccucaccu 780
cgaaggccua ccaacagggc gugacggucg acagcaucgg gaugcuaccc cgcuuuaucc 840
ccgaaaacca gcgcaccguc gcccuauaca gcuuaaaaau cgccgggugg cacggcccca 900
agcccccgua caccagcacc cugcugccgc cggagcuguc cgacaccacc aacgccacgc 960
aacccgaacu cguuccggaa gaccccgagg acucggcccu cuuagaggau cccgccggga 1020
cggugucuuc gcagaucccc ccaaacuggc acaucccguc gauccaggac gucgcgccgc 1080
accacgcccc cgccgccccc agcaacccgu gauaauaggc uggagccucg guggccaugc 1140
uucuugcccc uugggccucc ccccagcccc uccuccccuu ccugcacccg uacccccgug 1200
gucuuugaau aaagucugag ugggcggc 1228

<210> SEQ ID NO 101
<211> LENGTH: 2706
<212> TYPE: RNA
<213> ORGANISM: Human herpesvirus 2

<400> SEQUENCE: 101
augcgcgggg ggggcuuggu uugcgcgcug gucguggggg cgcugguggc cgcgguggcg 60
ucggcggccc cggcggcccc ccgcgccucg ggcggcgugg ccgcgaccgu cgcggcgaac 120
gggggucccg ccucccagcc gcccccgcuc ccgagccccg cgaccaccaa ggcccggaag 180
cggaaaacca aaaagccgcc caagcggccc gaggcgaccc cgccccccga cgccaacgcg 240
accgucgccg ccggccacgc cacgcugcgc gcgcaccugc gggaaaucaa ggucgagaac 300
gccgaugccc aguuuuacgu gugcccgccc ccgacgggcg ccacggugu gcaguuugag 360 cagccgcgcc gcugcccgac gcgcccggag gggcagaacu acacggaggg caucgcggug 420
gucuucaagg agaacaucgc cccguacaaa uucaaggcca ccauguacua caaagacgug 480
accgugucgc aggugugguu cggccaccgc uacucccagu uuauggggau auucgaggac 540
cgcgcccccg uucccuucga ggaggugauc gacaagauua acgccaaggg ggucugccgc 600
uccacggcca aguacgugcg gaacaacaug gagaccaccg cguuucaccg ggacgaccac 660
gagaccgaca uggagcucaa gccggcgaag gucgccacgc gcacgagccg gggguggcac 720
accaccgacc ucaaguacaa ccccucgcgg guggaggcgu uccaucggua cggcacgacg 780
gucaacugca ucgucgagga gguggacgcg cggucggugu acccguacga ugaguuugug 840
cuggcgacgg gcgacuuugu guacaugucc ccguuuuacg gcuaccggga ggggucgcac 900
accgagcaca ccagcuacgc cgccgaccgc uucaagcagg ucgacggcuu cuacgcgcgc 960
gaccucacca cgaaggcccg ggccacgucg ccgacgaccc gcaacuugcu gacgaccccc 1020
aaguuuaccg uggccuggga cugggugccg aagcgaccgg cggucugcac caugaccaag 1080
uggcaggagg uggacgagau gcuccgcgcc gaguacggcg gcuccuuccg cuucuccucc 1140
gacgccaucu cgaccaccuu caccaccaac cugacccagu acucgcucuc gcgcgucgac 1200
cugggcgacu gcaucggccg ggaugcccgc gaggccaucg accgcauguu ugcgcgcaag 1260
uacaacgcca cgcacaucaa ggugggccag ccgcaguacu accuggccac gggggggcuuc 1320 cucaucgcgu accagccccu ccucagcaac acgcucgccg agcuguacgu gcgggaguac 1380
augcgggagc aggaccgcaa gccccggaau gccacgcccg cgccacugcg ggaggcgccc 1440
agcgccaacg cguccgugga gcgcaucaag accaccuccu cgaucgaguu cgcccggcug 1500
caguuuacgu auaaccacau acagcgccac gugaacgaca ugcuggggcg caucgccguc 1560
gcguggugcg agcugcagaa ccacgagcug acucucugga acgaggcccg caagcucaac 1620
cccaacgcca ucgccuccgc caccgucggc cggcggguga gcgcgcgcau gcucggagac 1680
gucauggccg ucuccacgug cgugcccguc gccccggaca acgugaucgu gcagaacucg 1740
augcgcguca gcucgcggcc ggggacgugc uacagccgcc cccuggucag cuuucgguac 1800
gaagaccagg gcccgcugau cgaggggcag cugggcgaga acaacgagcu gcgccucacc 1860
cgcgacgcgc ucgagccgug caccgugggc caccggcgcu acuucaucuu cggcgggggc 1920
uacguguacu ucgaggagua cgcguacucu caccagcuga gucgcgccga cgucaccacc 1980
gucagcaccu ucaucgaccu gaacaucacc augcuggagg accacgaguu ugugccccug 2040
gaggucuaca cgcgcgccacga gaucaaggac agcggccugc uggacuacac ggagguccag 2100
cgccgcaacc agcugcacga ccugcgcuuu gccgacaucg acacggucau ccgcgccgac 2160
gccaacgccg ccauguucgc ggggcugugc gcguucuucg aggggauggg ggacuugggg 2220
cgcgcggucg gcaaggucgu caugggagua gugggggggcg uggugucggc cgucucgggc 2280
guguccuccu uuauguccaa ccccuucggg gcgcuugccg uggggcugcu gguccuggcc 2340
ggccuggucg cggccuucuu cgccuuccgc uacguccugc aacugcaacg caaucccaug 2400
aaggcccugu auccgcucac caccaaggaa cucaagacuu ccgaccccgg gggcgugggc 2460
ggggaggggg aggaaggcgc ggaggggggc ggguuugacg aggccaaguu ggccgaggcc 2520
cgagaaauga uccgauauau ggcuuuggug ucggccaugg agcgcacgga acacaaggcc 2580
agaaagaagg gcacgagcgc ccugcucagc uccaagguca ccaacauggu ucugcgcaag 2640
cgcaacaaag ccagguacuc uccgcuccac aacgaggacg aggccggaga cgaagacgag 2700
cucuaa 2706

<210> SEQ ID NO 102
<211> LENGTH: 1443
<212> TYPE: RNA
<213> ORGANISM: Human herpesvirus 2

<400> SEQUENCE: 102
auggcccuug gacggguggg ccuagccgug ggccuguggg gccugcugug ggugggugug 60 gucgugguge uggccaaugc cucccccgga cgcacgauaa cggugggccc gcgggggaac 120
gcgagcaaug ccgcccccuc cgcguccccg cggaacgcau ccgcccccg aaccacaccc 180

-continued

```
acgccccccc aaccccgcaa ggcgacgaaa aguaaggccu ccaccgccaa accggccccg    240
cccccccaaga ccgggccccc gaagacaucc ucggagcccg ugcgaugcaa ccgccacgac    300
ccgcuggccc gguacggcuc gcgggugcaa auccgaugcc gguuucccaa cuccacccgc    360
acggaguccc gccuccagau cuggcguuau gccacggcga cggacgccga gaucggaacg    420
gcgccuagcu uagaggaggu gaugguaaac gugucggccc cgcccggggg ccaacuggug    480
uaugacagcg cccccaaccg aacggacccg cacgugaucu gggcggaggg cgccggcccg    540
ggcgccagcc cgcggcugua cucggucguc gggccgcugg gucggcagcg gcucaucauc    600
gaagagcuga cccuggagac ccagggcaug uacuacuggg uguggggccg gacggaccgc    660
ccguccgcgu acgggaccug ggugcgcguu cgcguguucc gcccuccguc gcugaccauc    720
caccccccacg cggugcugga gggccagccg uuuaaggcga cgugcacggc cgccaccuac    780
uacccgggca accgcgcgga guucgucugg uucgaggacg gucgccgggu auucgauccg    840
gcccagauac acacgcagac gcaggagaac cccgacggcu uuuccaccgu cuccaccgug    900
accuccgcgg ccgucggcgg ccagggcccc ccgcgcaccu ucaccugcca gcugacgugg    960
caccgcgacu ccgugucguu cucucggcgc aacgccagcg gcacggcauc ggugcugccg   1020
cggccaacca uuaccaugga guuuacgggc gaccaugcgg ucugcacggc cggcugugug   1080
cccgaggggg ugacguuugc cugguuccug ggggacgacu ccucgccggc ggagaaggug   1140
gccgucgcgu cccagacauc gugcgggcgc cccggcaccg ccacgauccg cuccacccug   1200
ccggucucgu acgagcagac cgaguacauc ugccggcugg cgggauaccc ggacggaauu   1260
ccgguccuag agcaccacgg cagccaccag cccccgccgc gggaccccac cgagcggcag   1320
gugauccggg cgguggaggg ggcggggauc ggaguggcug uccuugucgc ggugguucug   1380
gccgggaccg cgguagugua ccucacccac gccuccucgg ugcgcuaucg ucggcugcgg   1440
uaa                                                                 1443
```

<210> SEQ ID NO 103
<211> LENGTH: 1182
<212> TYPE: RNA
<213> ORGANISM: Human herpesvirus 2

<400> SEQUENCE: 103

```
auggggcguu ugaccuccgg cgucgggacg gcggcccugc uaguugucgc ggugggacuc     60
cgcgucgucu gcgccaaaua cgccuuagca gaccccucgc uuaagauggc cgaucccaau    120
cgauuucgcg ggaagaaccu uccgguuuug gaccagcuga ccgacccccc cggggugaag    180
cguguuuacc acauucagcc gagccuggag gacccguucc agcccccccag caucccgauc    240
acuguguacu acgcagugcu ggaacgugcc ugccgcagcg ugcuccuaca ugccccaucg    300
gaggcccccc agaucgugcg cggggcuucg gacgaggccc gaaagcacac guacaaccug    360
accaucgccu gguaucgcau gggagacaau ugcgcuaucc ccaucacggu uauggaauac    420
accgagugcc ccuacaacaa gucguugggg gucugcccca uccgaacgca gccccgcugg    480
agcuacuaug acagcuuuag cgccgucagc gaggauaacc ugggauuccu gaugcacgcc    540
cccgccuucg agaccgcggg uacguaccug cggcuaguga agauaaacga cuggacggag    600
aucacacaau uuauccugga gcaccgggcc cgcgccuccu gcaaguacgc ucuccccccug    660
cgcauccccc cggcagcgug ccucaccucg aaggccuacc aacagggcgu gacggucgac    720
agcaucggga ugcuaccccg cuuuaucccc gaaaaccagc gcaccgucgc ccuauacagc    780
uuaaaaaucg ccgggguggca cggccccaag cccccguaca ccagcacccu gcugccgccg    840
```

gagcuguccg acaccaccaa cgccacgcaa cccgaacucg uuccggaaga ccccgaggac 900
ucggcccucu uagaggaucc cgccgggacg gugucuucgc agaucccccc aaacuggcac 960
aucccgucga uccaggacgu cgcgccgcac cacgccccccg ccgcccccag caacccgggc 1020
cugaucaucg gcgcgcuggc cggcaguacc cuggcggugc uggucaucgg cgguauugcg 1080
uuuuggguac gccgccgcgc ucagauggcc cccaagcgcc uacgucuccc ccacauccgg 1140
gaugacgacg cgcccccuc gcaccagcca uuguuuuacu ag 1182

<210> SEQ ID NO 104
<211> LENGTH: 1647
<212> TYPE: RNA
<213> ORGANISM: Human herpesvirus 2

<400> SEQUENCE: 104
auggcucgcg gggccggguu gguguuuuuu guuggaguuu gggucguauc gugccuggcg 60
gcagcaccca gaacguccug gaaacgggua accucgggcg aggacguggu guugcuuccg 120
gcgcccgcgg ggccggagga acgcacccgg gcccacaaac uacugugggc cgcggaaccc 180
cuggaugccu gcgguccccu gcgcccgucg uggguggcgc uguggccccc ccgacgggug 240
cucgagacgg ucguggaugc ggcgugcaug cgcgccccgg aaccgcucgc cauagcauac 300
agucccccgu uccccgcggg cgacgaggga cuguauucgg aguuggcgug gcgcgaucgc 360
guagccgugg ucaacgagag ucuggucauc uacggggccc uggagacgga cagcggucug 420
uacacccugu ccguggucgg ccuaagcgac gaggcgcgcc aaguggcguc gguggguucug 480 gucguggagc ccgccccugu gccgaccccg acccccgacg acuacgacga agaagacgac 540
gcgggcguga gcgaacgcac gccggucagc guucccccc caacccccc ccgucguccc 600 cccgucgccc ccccgacgca cccucguguu auccccgagg ugucccacgu gcgcggggua 660
acgguccaua uggagacccc ggaggccauu cuguuugccc ccggggagac guuugggacg 720
aacgucucca uccacgccau ugcccacgac gacgguccgu acgccaugga cgucgucugg 780
augcgguuug acgugccguc cucgugcgcc gagaugcgga ucuacgaagc uugucuguau 840
cacccgcagc uuccagagug ucuaucuccg gccgacgcgc cgugcgccgu aaguuccugg 900
gcguaccgcc uggcgguccg cagcuacgcc ggcuguucca ggacuacgcc cccgccgcga 960
uguuuugccg aggcucgcau ggaaccgguc ccgggguugg cguggcuggc cuccaccguc 1020
aaucuggaau uccagcacgc cuccccccag cacgccggcc ucuaccugug cgugguguac 1080
guggacgauc auauccacgc cuggggccac augaccauca gcaccgcggc gcaguaccgg 1140
aacgcggugg uggaacagca ccucccccag cgccagcccg agcccgucga gcccacccgc 1200
ccgcacguga gagcccccc ucccgcgccc uccgcgcgcg gcccgcugcg ccucggggcg 1260
gugcuggggg cggcccuguu gcuggccgcc cucgggcugu ccgcgugggc gugcaugacc 1320
ugcuggcgca ggcgcuccug gcgggcgguu aaaagccggg ccucggcgac gggccccacu 1380
uacauucgcg uggcggacag cgagcuguac gcggacugga guucggacag cgagggggag 1440
cgcgacgggu cccuguggca ggacccuccg gagagacccg acucucccuc cacaaaugga 1500
uccggcuuug agaucuuauc accaacggcu ccgucuguau acccccauag cgaggggcgu 1560
aaaucucgcc gcccgcucac caccuuuggu ucgggaagcc cgggccgucg ucacucccag 1620
gccuccuauu cguccguccu cugguaa 1647

<210> SEQ ID NO 105

<211> LENGTH: 1119
<212> TYPE: RNA
<213> ORGANISM: Human herpesvirus 2

<400> SEQUENCE: 105
augcccggcc gcucgcugca gggccuggcg auccugggcc ugugggucug cgccaccggc 60
cuggucgucc gcggccccac ggucagucug gucucagacu cacucgugga ugccggggcc 120
guggggcccc agggcuucgu ggaagaggac cugcguguuu ucggggagcu ucauuuugug 180
ggggcccagg ucccccacac aaacuacuac gacggcauca ucgagcuguu ucacuacccc 240
cuggggaacc acugcccccg cguuguacac guggucacac ugaccgcaug cccccgccgc 300
cccgccgugg cguucaccuu gugucgcucg acgcaccacg cccacagccc cgccuauccg 360
acccuggagc ugggucuggc gcggcagccg cuucugcggg uucgaacggc aacgcgcgac 420
uaugccgguc uguaugccu gcgcguaugg gucggcagcg cgacgaacgc cagccuguuu 480
guuuuggggg uggcgcucuc ugccaacggg acguuugugu auaacggcuc ggacuacggc 540
uccugcgauc cggcgcagcu ucccuuuucg gccccgcgcc ugggacccuc gagcguauac 600
acccccggag ccucccggcc caccccucca cggacaacga cauccccguc cuccccccga 660
gacccgaccc ccgcccccgg ggacacaggg acgcccgcgc ccgcgagcgg cgagagagcc 720
ccgcccaauu ccacgcgauc ggccagcgaa ucgagacaca ggcuaaccgu agcccaggua 780
auccagaucg ccauaccggc guccaucauc gccuuugugu uucugggcag cuguaucugc 840
uucauccaua gaugccagcg ccgauacagg cgcccccgcg gccagauuua caaccccggg 900
ggcguuuccu gcgcggucaa cgaggcggcc auggcccgcc ucggagccga gcugcgaucc 960
cacccaaaca cccccccaa accccgacgc cguucgucgu cguccacgac caugccuucc 1020
cuaacgucga uagcugagga aucggagcca gguccagucg ugcugcuguc cgucaguccu 1080
cggccccgca guggcccgac ggcccccaa gaggucuag 1119

<210> SEQ ID NO 106
<211> LENGTH: 2262
<212> TYPE: RNA
<213> ORGANISM: Artificial Sequence
<220> FEATURE:
<223> OTHER INFORMATION: Synthetic Polynucleotide

<400> SEQUENCE: 106
auggaacccc ggcccggcac gagcucccgg gcggaccccg gccccgagcg gccgccgcgg 60
cagacccccg gcacgcagcc cgccgccccg cacgccuggg ggaugcucaa cgacaugcag 120
uggcucgcca gcagcgacuc ggaggaggag accgaggugg gaaucucuga cgacgaccuu 180
caccgcgacu ccaccuccga ggcgggcagc acggacacgg agauguucga ggcgggccug 240
auggacgcgg ccacgccccc ggcccggccc ccggccgagc gccagggcag ccccacgccc 300
gccgacgcgc agggauccug ugggggguggg cccgugggug aggaggaagc ggaagcggga 360 gggggggcg acgugaacac cccgguggcg uaccugauag ugggcgugac cgccagcggg 420
ucguucagca ccaucccgau agugaacgac ccccggaccc gcguggaggc cgaggcggcc 480
gugcgggccg gcacggccgu ggacuuuauc uggacgggca acccgcggac ggccccgcgc 540
ucccugucgc ugggggggaca cacgguccgc gcccugucgc ccaccccccc guggcccggc 600
acggacgacg aggacgauga ccuggccgac guggacuacg ucccgcccgc cccccgaaga 660
gcgccccggc gcgggggcgg cggugcgggg gcgacccgcg gaaccuccca gcccgccgcg 720
acccgaccgg cgcccccugg cgccccgcgg agcagcagca gcggcggcgc cccguugcgg 780

```
gcgggggugg gaucuggguc ugggggcggc ccugccgucg cggccgucgu gccgagagug    840

gccucucuuc ccccugcggc cggcgggggg cgcgcgcagg cgcggcgggu gggcgaagac    900

gccgcggcgg cggagggcag gacgcccccc gcgagacagc cccgcgcggc ccaggagccc    960

cccauaguca ucagcgacuc ucccccgccg ucuccgcgcc gccccgcggg ccccgggccg   1020

cucuccuuug ucuccuccuc cuccgcacag guguccucgg gccccggggg gggaggucug   1080

ccacagucgu cggggcgcgc cgcgcgcccc cgcgcggccg ucgccccgcg cguccggagu   1140

ccgccccgcg ccgccgccgc ccccguggug ucugcgagcg cggacgcggc cgggcccgcg   1200

ccgcccgccg ugccggugga cgcgcaccgc gcgccccggu cgcgcaugac ccaggcucag   1260

accgacaccc aagcacagag ucugggccgg gcaggcgcga ccgacgcgcg cgggucggga   1320

gggccgggcg cggagggagg aucgggcccc gcggccucgu ccuccgccuc uuccuccgcc   1380

gccccgcgcu cgccccucgc cccccagggg gugggggcca agagggcggc gccgcgccgg   1440

gccccggacu cggacucggg cgaccgcggc cacgggccgc ucgccccggc guccgcgggc   1500

gccgcgcccc cgucggcguc uccgucgucc caggccgcgg ucgccgccgc cuccuccucc   1560

uccgccuccu ccuccuccgc cuccuccucc uccgccuccu ccuccuccgc cuccuccucc   1620

uccgccuccu ccuccuccgc cuccuccucc uccgccucuu ccucugcggg cggggcuggu   1680

gggagcgucg cguccgcguc cggcgcuggg gagagacgag aaaccucccu cggcccccgc   1740

gcugcugcgc cgcgggggcc gaggaagugu gccaggaaga cgcgccacgc ggagggcggc   1800

cccgagcccg gggcccgcga cccggcgccc ggccucacgc gcuaccugcc caucgcgggg   1860

gucucgagcg ucguggcccu ggcgccuuac gugaacaaga cggucacggg ggacugccug   1920

cccguccugg acauggagac gggccacaua ggggccuacg ugguccucgu ggaccagacg   1980

gggaacgugg cggaccugcu gcgggccgcg gcccccgcgu ggagccgccg cacccugcuc   2040

cccgagcacg cgcgcaacug cgugaggccc cccgacuacc cgacgccccc cgcgucggag   2100

uggaacagcc ucuggaugac cccggugggc aacaugcucu uugaccaggg cacccuggug   2160

ggcgcgcugg acuuccacgg ccuccggucg cgccacccgu ggucucggga gcagggcgcg   2220

cccgcgccgg ccggcgacgc ccccgcgggc cacggggagu ag                      2262
```

<210> SEQ ID NO 107
<211> LENGTH: 2304
<212> TYPE: RNA
<213> ORGANISM: Human herpesvirus 2

<400> SEQUENCE: 107

```
augcgcgggg ggggcuuggu uugcgcgcug gucguggggg cgcugguggc cgcgguggcg     60

ucggcggccc cggcggcccc ccgcgccucg ggcggcgugg ccgcgaccgu cgcggcgaac    120

gggggucccg ccucccagcc gccccccguc ccgagccccg cgaccaccaa ggcccggaag    180

cggaaaacca aaaagccgcc caagcggccc gaggcgaccc cgccccccga cgccaacgcg    240

accgucgccg ccggccacgc cacgcugcgc gcgcaccugc gggaaaucaa ggucgagaac    300

gccgaugccc aguuuuacgu gugcccgccc ccgacgggcg ccacggugguu gcaguuugag    360

cagccgcgcc gcugcccgac gcgcccggag gggcagaacu acacggaggg caucgcggug    420

gucuucaagg agaacaucgc cccguacaaa uucaaggcca ccauguacua caaagacgug    480

accgugucgc aggugugguu cggccaccgc uacucccagu uuaugggau auucgaggac    540

cgcgcccccg uucccuucga ggaggugauc gacaagauua acgccaaggg ggucugccgc    600
```

uccacggcca aguacgugcg gaacaacaug gagaccaccg cguuucaccg ggacgaccac 660
gagaccgaca uggagcucaa gccggcgaag gucgccacgc gcacgagccg gggguggcac 720
accaccgacc ucaaguacaa ccccucgcgg guggaggcgu uccaucggua cggcacgacg 780
gucaacugca ucgucgagga gguggacgcg cggucggugu acccguacga ugaguuugug 840
cuggcgacgg gcgacuuugu guacaugucc ccguuuuacg gcuaccggga ggggucgcac 900
accgagcaca ccagcuacgc cgccgaccgc uucaagcagg ucgacggcuu cuacgcgcgc 960
gaccucacca cgaaggcccg ggccacgucg ccgacgaccc gcaacuugcu gacgaccccc 1020
aaguuuaccg uggccuggga cugggugccg aagcgaccgg cggucugcac caugaccaag 1080
uggcaggagg uggacgagau gcuccgcgcc gaguacggcg gcuccuuccg cuucuccucc 1140
gacgccaucu cgaccaccuu caccaccaac cugacccagu acucgcucuc gcgcgucgac 1200
cugggcgacu gcaucggccg ggaugcccgc gaggccaucg accgcauguu ugcgcgcaag 1260
uacaacgcca cgcacaucaa ggugggccag ccgcaguacu accuggccac gggggggcuuc 1320 cucaucgcgu accagccccu ccucagcaac acgcucgccg agcuguacgu gcgggaguac 1380
augcgggagc aggaccgcaa gccccggaau gccacgcccg cgccacugcg ggaggcgccc 1440
agcgccaacg cguccgugga gcgcaucaag accaccuccu cgaucgaguu cgcccggcug 1500
caguuuacgu auaaccacau acagcgccac gugaacgaca ugcuggggcg caucgccguc 1560
gcguggugcg agcugcagaa ccacgagcug acucucugga acgaggcccg caagcucaac 1620
cccaacgcca ucgccuccgc caccgucggc cggcggguga gcgcgcgcau gcucggagac 1680
gucauggccg ucuccacgug cgugcccguc gccccggaca acgugaucgu gcagaacucg 1740
augcgcguca gcucgcggcc ggggacgugc uacagccgcc cccuggucag cuuucgguac 1800
gaagaccagg gcccgcugau cgaggggcag cugggcgaga acaacgagcu gcgccucacc 1860
cgcgacgcgc ucgagccgug caccgugggc caccggcgcu acuucaucuu cggcgggggc 1920
uacguguacu ucgaggagua cgcguacucu caccagcuga gucgcgccga cgucaccacc 1980
gucagcaccu ucaucgaccu gaacaucacc augcuggagg accacgaguu ugugccccug 2040
gaggucuaca cgcgccacga gaucaaggac agcggccugc uggacuacac ggagguccag 2100
cgccgcaacc agcugcacga ccugcgcuuu gccgacaucg acacggucau ccgcgccgac 2160
gccaacgccg ccauguucgc ggggcugugc gcguucuucg aggggauggg ggacuugggg 2220
cgcgcggucg gcaaggucgu caugggagua guggggggcg uggugucggc cgucucgggc 2280
guguccuccu uuauguccaa cccc 2304

<210> SEQ ID NO 108
<211> LENGTH: 1341
<212> TYPE: RNA
<213> ORGANISM: Human herpesvirus 2

<400> SEQUENCE: 108
auggcccuug gacggguggg ccuagccgug ggccuguggg gccugcugug ggugggugug 60 gucgugguge uggccaaugc cucccccgga cgcacgauaa cggugggccc gcgggggaac 120
gcgagcaaug ccgcccccuc cgcguccccg cggaacgcau ccgccccccg aaccacaccc 180
acgccccccc aaccccgcaa ggcgacgaaa aguaaggccu ccaccgccaa accggccccg 240
ccccccaaga ccgggccccc gaagacaucc ucggagcccg ugcgaugcaa ccgccacgac 300
ccgcuggccc gguacggcuc gcgggugcaa auccgaugcc gguuucccaa cuccaccccgc 360 acggaguccc gccuccagau cuggcguuau gccacggcga cggacgccga gaucggaacg 420
gcgccuagcu uagaggaggu gaugguaaac gugucggccc cgcccggggg ccaacuggug 480
uaugacagcg cccccaaccg aacggacccg cacgugaucu gggcggaggg cgcccggcccg 540 ggcgccagcc cgcggcugua cucggucguc gggccgcugg gucggcagcg gcucaucauc 600
gaagagcuga cccuggagac ccagggcaug uacuacuggg uguggggccg gacggaccgc 660
ccguccgcgu acgggaccug ggugcgcguu cgcguguucc gcccuccguc gcugaccauc 720
cacccccacg cggugcugga gggccagccg uuuaaggcga cgugcacggc cgccaccuac 780
uacccgggca accgcgcgga guucgucugg uucgaggacg gucgccgggu auucgauccg 840
gcccagauac acacgcagac gcaggagaac cccgacggcu uuuccaccgu cuccaccgug 900
accuccgcgg ccgucggcgg ccagggcccc ccgcgcaccu ucaccugcca gcugacgugg 960
caccgcgacu ccgugucguu cucucggcgc aacgccagcg gcacggcauc ggugcugccg 1020
cggccaacca uuaccaugga guuuacgggc gaccaugcgg ucugcacggc cggcugugug 1080
cccgaggggg ugacguuugc cugguuccug ggggacgacu ccucgccggc ggagaaggug 1140
gccgucgcgu cccagacauc gugcgggcgc cccggcaccg ccacgauccg cuccacccug 1200
ccggucucgu acgagcagac cgaguacauc ugccggcugg cgggauaccc ggacggaauu 1260
ccgguccuag agcaccacgg cagccaccag cccccgccgc gggaccccac cgagcggcag 1320
gugauccggg cgguggaggg g 1341

<210> SEQ ID NO 109
<211> LENGTH: 1017
<212> TYPE: RNA
<213> ORGANISM: Human herpesvirus 2

<400> SEQUENCE: 109
auggggcguu ugaccuccgg cgucgggacg gcggcccugc uaguugucgc ggugggacuc 60
cgcgucgucu gcgccaaaua cgccuuagca gaccccucgc uuaagauggc cgaucccaau 120
cgauuucgcg ggaagaaccu uccgguuuug gaccagcuga ccgaccccc cggggugaag 180 cguguuuacc acauucagcc gagccuggag gacccguucc agcccccag cauccccgauc 240 acuguguacu acgcagugcu ggaacgugcc ugccgcagcg ugcuccuaca ugccccaucg 300
gaggcccccc agaucgugcg cggggcuucg gacgaggccc gaaagcacac guacaaccug 360
accaucgccu gguaucgcau gggagacaau ugcgcuaucc ccaucacggu uauggaauac 420
accgagugcc ccuacaacaa gucguugggg gucugcccca uccgaacgca gccccgcugg 480
agcuacuaug acagcuuuag cgccgucagc gaggauaacc ugggauuccu gaugcacgcc 540
cccgccuucg agaccgcggg uacguaccug cggcuaguga agauaaacga cuggacggag 600
aucacacaau uuauccugga gcaccgggcc cgcgccuccu gcaaguacgc ucuccccccug 660 cgcauccccc cggcagcgug ccucaccucg aaggccuacc aacagggcgu gacggucgac 720
agcaucggga ugcuaccccg cuuuaucccc gaaaaccagc gcaccgucgc ccuauacagc 780
uuaaaaaucg ccggguggca cggccccaag cccccguaca ccagcacccu gcugccgccg 840
gagcuguccg acaccaccaa cgccacgcaa ccccgaacucg uuccggaaga ccccgaggac 900
ucggcccucu uagaggaucc cgccgggacg gugucuucgc agaucccccc aaacuggcac 960
aucccgucga uccaggacgu cgcgccgcac cacgcccccg ccgcccccag caacccg 1017

<210> SEQ ID NO 110
<211> LENGTH: 1251
<212> TYPE: RNA

<213> ORGANISM: Human herpesvirus 2

<400> SEQUENCE: 110
auggcucgcg gggccggguu gguguuuuuu guuggaguuu gggucguauc gugccuggcg 60
gcagcaccca gaacguccug gaaacgggua accucgggcg aggacguggu guugcuuccg 120
gcgcccgcgg ggccggagga acgcacccgg gcccacaaac uacugugggc cgcggaaccc 180
cuggaugccu gcgguccccu gcgcccgucg ugggugggc ugugggcccc ccgacgggug 240
cucgagacgg ucguggaugc ggcgugcaug cgcgccccgg aaccgcucgc cauagcauac 300
agucccccgu uccccgcggg cgacgaggga cuguauucgg aguuggcgug gcgcgaucgc 360
guagccgugg ucaacgagag ucuggucauc uacggggccc uggagacgga cagcggucug 420
uacacccugu ccguggucgg ccuaagcgac gaggcgcgcc aaguggcguc ggugguucug 480
gucguggagc ccgccccugu gccgaccccg acccccgacg acuacgacga agaagacgac 540
gcgggcguga gcgaacgcac gccggucagc guuccccccc caaccccccc ccgucguccc 600
cccgucgccc ccccgacgca cccucguguu auccccgagg ugucccacgu gcgcggggua 660
acgguccaua uggagacccc ggaggccauu cuguuugccc ccggggagac guuugggacg 720
aacgucucca uccacgccau ugcccacgac gacgguccgu acgccaugga cgucgucugg 780
augcgguuug acgugccguc cucgugcgcc gagaugcgga ucuacgaagc uugucuguau 840
cacccgcagc uuccagagug ucuaucuccg gccgacgcgc cgugcgccgu aaguuccugg 900
gcguaccgcc uggcgguccg cagcuacgcc ggcuguucca ggacuacgcc cccgccgcga 960
uguuuugccg aggcucgcau ggaaccgguc ccgggguugg cguggcuggc cuccaccguc 1020
aaucuggaau uccagcacgc cuccccccag cacgccggcc ucuaccugug cgugguguac 1080
guggacgauc auauccacgc cuggggccac augaccauca gcaccgcggc gcaguaccgg 1140
aacgcggugg uggaacagca ccucccccag cgccagcccg agcccgucga gcccacccgc 1200
ccgcacguga gagccccccc ucccgcgccc uccgcgcgcg gcccgcugcg c 1251

<210> SEQ ID NO 111
<211> LENGTH: 786
<212> TYPE: RNA
<213> ORGANISM: Human herpesvirus 2

<400> SEQUENCE: 111
augcccggcc gcucgcugca gggccuggcg auccugggcc ugugggucug cgccaccggc 60
cuggucgucc gcggccccac ggucagucug gucucagacu cacucgugga ugccggggcc 120
guggggcccc agggcuucgu ggaagaggac cugcguguuu ucggggagcu ucauuuugug 180
ggggcccagg ucccccacac aaacuacuac gacggcauca ucgagcuguu ucacuacccc 240
cuggggaacc acugcccccg cguuguacac guggucacac ugaccgcaug cccccgccgc 300
cccgccgugg cguucaccuu gugucgcucg acgcaccacg cccacagccc cgccuauccg 360
acccuggagc ugggucuggc gcggcagccg cuucugcggg uucgaacggc aacgcgcgac 420
uaugccgguc uguaugucu gcgcguaugg gucggcagcg cgacgaacgc cagccuguuu 480
guuuuggggg uggcgcucuc ugccaacggg acguuugugu auaacggcuc ggacuacggc 540
uccugcgauc cggcgcagcu ucccuuuucg gccccgcgcc ugggacccuc gagcguauac 600
acccccggag ccucccggcc caccccucca cggacaacga cauccccguc cuccccccga 660
gacccgaccc ccgccccccgg ggacacaggg acgcccgcgc ccgcgagcgg cgagagagcc 720
ccgcccaauu ccacgcgauc ggccagcgaa ucgagacaca ggcuaaccgu agcccaggua 780
auccag 786

<210> SEQ ID NO 112
<211> LENGTH: 3885
<212> TYPE: RNA
<213> ORGANISM: Artificial Sequence
<220> FEATURE:
<223> OTHER INFORMATION: Synthetic Polynucleotide

<400> SEQUENCE: 112
augucggcgg agcagcggaa gaagaagaag acgacgacga cgacgcaggg ccgcggggcc 60
gaggucgcga uggcggacga ggacggggga cgucuccggg ccgcggcgga gacgaccggc 120
ggccccggau cuccggaucc agccgacgga ccgccgccca ccccgaaccc ggaccgucgc 180
cccgccgcgc ggcccggguu cggguggcac ggugggccgg aggagaacga agacgaggcc 240
gacgacgccg ccgccgaugc cgaugccgac gaggcggccc cggcguccgg ggaggccguc 300
gacgagccug ccgcggacgg cgucgucucg ccgcggcagc uggcccugcu ggccucgaug 360
guggacgagg ccguucgcac gaucccgucg ccccccccgg agcgcgacgg cgcgcaagaa 420
gaagcggccc gcucgccuuc uccgccgcgg acccccucca ugcgcgccga uuauggcgag 480
gagaacgacg acgacgacga cgacgacgau gacgacgacc gcgacgcggg ccgcuggguc 540
cgcggaccgg agacgacguc cgcgguccgc ggggcguacc cggaccccau ggccagccug 600
ucgccgcgac ccccggcgcc ccgccgacac caccaccacc accaccaccg ccgccggcgc 660 gcccccc gcc ggcgcucggc cgccucugac ucaucaaaau ccggauccuc gucgucggcg 720
uccuccgccu ccuccuccgc cuccuccucc ucgucugcau ccgccuccuc gucugacgac 780
gacgacgacg acgacgccgc ccgcgccccc gccagcgccg cagaccacgc cgcgggcggg 840
acccucggcg cggacgacga ggaggcgggg gugcccgcga gggccccggg ggcggcgccc 900
cggccgagcc cgcccagggc cgagcccgcc ccggcccgga cccccgcggc gaccgcgggc 960
cgccuggagc gccgccgggc ccgcgcggcg guggccggcc gcgacgccac gggccgcuuc 1020
acggccgggc ggccccggcg ggucgagcug gacgccgacg cggccuccgg cgccuucuac 1080
gcgcgcuacc gcgacgggua cgucagcggg gagccguggc ccggggccgg cccccgcccc 1140
ccggggcgcg ugcuguacgg cgggcugggc gacagccgcc ccggccucug gggggcgccc 1200
gaggcggagg aggcgcgggc ccgguucgag gccucgggcg ccccggcgcc cgugugggcg 1260
cccgagcugg gcgacgcggc gcagcaguac gcccugauca cgcggcugcu guacacgccg 1320
gacgcggagg cgauggggug gcuccagaac ccgcgcgugg cgcccgggga cguggcgcug 1380
gaccaggccu gcuuccggau cucgggcgcg gcgcgcaaca gcagcuccuu caucuccggc 1440
agcguggcgc gggccgugcc ccaccugggg uacgccaugg cggcgggccg cuucggcugg 1500
ggccuggcgc acguggcggc cgccguggcc augagccgcc gcuacgaccg cgcgcagaag 1560
ggcuuccugc ugaccagccu gcgccgcgcc uacgcgcccc ugcuggcgcg cgagaacgcg 1620
gcgcugaccg gggcgcgaac ccccgacgac ggcggcgacg ccaaccgcca cgacggcgac 1680
gacgcccgcg ggaagcccgc cgccgccgcc gccccguugc cgucggcggc ggcgucgccg 1740
gccgacgagc gcgcggugcc cgccggcuac ggcgccgcgg gggugcucgc cgcccugggg 1800
cgccugagcg ccgcgcccgc cuccgcgccg gccggggccg acgacgacga cgacgacgac 1860
ggcgccggcg gugguggcgg cggccggcgc gcggaggcgg gccgcguggc cguggagugc 1920
cuggccgccu gccgcgggau ccuggaggcg cuggcggagg gcuucgacgg cgaccuggcg 1980

-continued gccgugccgg ggcuggccgg agcccggccc gccgcgcccc cgcgcccggg gcccgcgggc 2040
gcggccgccc cgccgcacgc cgacgcgccc cgccugcgcg ccuggcugcg cgagcugcgg 2100
uucgugcgcg acgcgcuggu gcugaugcgc cugcgcgggg accugcgcgu ggccggcggc 2160
agcgaggccg ccguggccgc cgugcgcgcc gugagccugg ucgccggggc ccugggcccg 2220
gcgcugccgc ggagcccgcg ccugcugagc uccgccgccg ccgccgccgc ggaccugcuc 2280
uuccagaacc agagccugcg cccccugcug gccgacaccg ucgccgcggc cgacucgcuc 2340
gccgcgcccg ccuccgcgcc gcgggaggcc gcggacgccc cccgccccgc ggccgccccu 2400
cccgcggggg ccgcgccccc cgccccgccg acgccgccgc cgcggccgcc gcgccccgcg 2460
gcgcugaccc gccggcccgc cgagggcccc gacccgcagg gcggcuggcg ccgccagccg 2520
ccggggccca gccacacgcc ggcgcccucg gccgccgccc uggaggccua cugcgccccg 2580
cgggccgugg ccgagcucac ggaccacccg cucuuccccg cgccguggcg cccggcccuc 2640
auguucgacc cgcgcgcgcu ggccucgcug gccgcgcgcu gcgccgcccc gcccccccggc 2700 ggcgcgcccg ccgccuucgg cccgcugcgc gccucgggcc cgcugcgccg cgcggcggcc 2760
uggaugcgcc aggugcccga cccggaggac gugcgcgugg ugauccucua cucgccgcug 2820
ccgggcgagg accuggccgc gggccgcgcc gggggcgggc cccccccgga gugguccgcc 2880
gagcgcggcg ggcuguccug ccugcuggcg gcccugggca accggcucug cgggcccgcc 2940
acggccgccu gggcgggcaa cuggaccggc gcccccgacg ucucggcgcu gggcgcgcag 3000
ggcgugcugc ugcuguccac gcgggaccug gccuucgccg gcgccgugga guuccugggg 3060
cugcuggccg gcgccugcga ccgccgccuc aucgucguca acgccgugcg cgccgcggcc 3120
uggcccgccg cugcccccgu ggucucgcgg cagcacgccu accuggccug cgaggugcug 3180
cccgccgugc agugcgccgu gcgcuggccg gcggcgcggg accugcgccg caccgugcug 3240
gccuccggcc gcguguucgg gccggggguc uucgcgcgcg uggaggccgc gcacgcgcgc 3300
cuguaccccg acgcgccgcc gcugcgccuc ugccgcgggg ccaacgugcg guaccgcgug 3360
cgcacgcgcu ucggccccga cacgcuggug cccauguccc cgcgcgagua ccgccgcgcc 3420
gugcucccgg cgcuggacgg ccgggccgcc gccucgggcg cgggcgacgc cauggcgccc 3480
ggcgcgccgg acuucugcga ggacgaggcg cacucgcacc gcgccugcgc gcgcuggggc 3540
cugggcgcgc cgcugcggcc cgucuacgug gcgcuggggc gcgacgccgu gcgcggcggc 3600
ccggcggagc ugcgcgggcc gcggcgggag uucugcgcgc gggcgcugcu cgagcccgac 3660
ggcgacgcgc ccccgcuggu gcugcgcgac gacgcggacg cgggcccgcc cccgcagaua 3720
cgcugggcgu cggccgcggg ccgcgcgggg acggugcugg ccgcggcggg cggcggcgug 3780
gagguggugg ggaccgccgc ggggcuggcc acgccgccga ggcgcgagcc cguggacaug 3840
gacgcggagc uggaggacga cgacgacgga cuguuugggg aguga 3885

<210> SEQ ID NO 113
<211> LENGTH: 2917
<212> TYPE: RNA
<213> ORGANISM: Artificial Sequence
<220> FEATURE:
<223> OTHER INFORMATION: Synthetic Polynucleotide

<400> SEQUENCE: 113
ucaagcuuuu ggacccucgu acagaagcua auacgacuca cuauagggaa auaagagaga 60
aaagaagagu aagaagaaau auaagagcca ccaugagagg ugguggcuua guuugcgcgc 120
ugguugucgg ggcgcucgua gccgccgugg cgucggccgc cccugcggcu ccucgcgcua 180

-continued

```
gcggaggcgu agccgcaaca guugcggcga acgggggucc agccucucag ccuccucccg    240
ucccgagccc ugcgaccacc aaggcuagaa agcggaagac caagaaaccg cccaagcgcc    300
ccgaggccac cccgcccccc gaugccaacg cgacugucgc cgcuggccau gcgacgcuuc    360
gcgcucaucu gagggagauc aagguugaaa augcugaugc ccaauuuuac gugugcccgc    420
ccccgacggg cgccacgguu gugcaguuug aacagccgcg gcgcugnccg acgcggccag    480
aaggccagaa cuauacggag ggcauagcgg uggucuuuaa ggaaaacauc gccccguaca    540
aauuuaaggc cacaauguac uacaaagacg ugacaguuuc gcaagugugg uuuggccaca    600
gauacucgca guuuauggga aucuucgaag auagagcccc uguucccuuc gaggaaguca    660
ucgacaagau uaaugccaaa gggguaugcc guuccacggc caaauacgug cgcaacaaua    720
uggagaccac cgccuuucac cgggaugauc acgagaccga cauggagcuu aagccggcga    780
aggucgccac gcguaccucc cgggguuggc acaccacaga ucuuaaguac aaucccucgc    840
gaguugaagc auuccaucgg uauggaacua ccguuaacug caucguugag gagguggaug    900
cgcggucggu guacccuuac gaugaguuug uguuagcgac cggcgauuuu guguacaugu    960
ccccguuuua cggcuaccgg gaggggucgc acaccgaaca uaccucguac gccgcugaca   1020
gguucaagca ggucgauggc uuuuacgcgc gcgaucucac cacgaaggcc cgggccacgu   1080
caccgacgac caggaacuug cucacgaccc ccaaguucac cgucgcuugg gauugggucc   1140
caaagcgucc ggcggucugc acgaugacca aauggcagga gguggacgaa augcuccgcg   1200
cagaauacgg cggcuccuuc cgcuucucgu ccgacgccau cucgacaacc uucaccacca   1260
aucugaccca guacagucug ucgcgcguug auuuaggaga cugcauuggc cgggaugccc   1320
gggaggccau cgacagaaug uuugcgcgua aguacaaugc cacacauauu aaggugggcc   1380
agccgcaaua cuaccuugcc acgggcggcu uucucaucgc guaccagccc cuucucucaa   1440
auacgcucgc ugaacuguac gugcgggagu auaugaggga acaggaccgc aagccccgca   1500
augccacgcc ugcgccacua cgagaggcgc cuucagcuaa ugcgucggug gaacguauca   1560
agaccaccuc cucaauagag uucgcccggc ugcaauuuac guacaaccac auccagcgcc   1620
acgugaacga caugcugggc cgcaucgcug ucgccuggug cgagcugcag aaucacgagc   1680
ugacucuuug gaacgaggcc cgaaaacuca accccaacgc gaucgccucc gcaacagucg   1740
guagacgggu gagcgcucgc augcuaggag augucauggc uguguccacc ugcgugcccg   1800
ucgcuccgga caacgugauu gugcagaauu cgaugcgggu cucaucgcgg ccgggcaccu   1860
gcuacagcag gccccucguc agcuuccggu acgaagacca gggcccgcug auugaagggc   1920
aacugggaga gaacaaugag cugcgccuca cccgcgacgc gcucgaaccc ugcaccgucg   1980
gacaucggag auauuucauc uucggagggg gcuacgugua cuucgaagag uaugccuacu   2040
cucaccagcu gaguagagcc gacgucacua ccgucagcac cuuuauugac cugaauauca   2100
ccaugcugga ggaccacgag uuugugcccc uggaaguuua cacucgccac gaaaucaaag   2160
acuccggccu guuggauuac acggagguuc agaggcggaa ccagcugcau gaccugcgcu   2220
uugccgacau cgacaccguc auccgcgccg augccaacgc ugccauguuc gcggggcugu   2280
gcgcguucuu cgaggggaug ggugacuugg ggcgcgccgu cggcaagguc gucaugggag   2340
uaguggggggg cguugugagu gccgucagcg gcguguccuc cuucaugucc aauccauucg   2400
gagcgcuugc uguggggcug cugguccugg ccgggcuggu agccgccuuc uucgccuuuc   2460
gauauguucu gcaacugcaa cgcaauccca ugaaagcucu auauccgcuc accaccaagg   2520
```

agcuaaagac gucagaucca ggaggcgugg gcggggaagg ggaagagggc gcggagggcg 2580
gaggguuuga cgaagccaaa uuggccgagg cucgugaaau gauccgauau auggcacuag 2640
ugucggcgau ggaaaggacc gaacauaagg cccgaaagaa gggcacgucg gcgcugcucu 2700
cauccaaggu caccaacaug guacugcgca agcgcaacaa agccagguac ucuccgcucc 2760
auaacgagga cgaggcggga gaugaggaug agcucuaaug auaauaggcu ggagccucgg 2820
uggccaugcu ucuugccccu ugggccuccc cccagccccu ccucccuuc cugcacccgu 2880 acccccgugg ucuuugaaua aagucugagu gggcggc 2917

<210> SEQ ID NO 114
<211> LENGTH: 1654
<212> TYPE: RNA
<213> ORGANISM: Artificial Sequence
<220> FEATURE:
<223> OTHER INFORMATION: Synthetic Polynucleotide

<400> SEQUENCE: 114
ucaagcuuuu ggacccucgu acagaagcua auacgacuca cuauagggaa auaagagaga 60
aaagaagagu aagaagaaau auaagagcca ccauggcccu uggacgggua ggccuagccg 120
ugggccugug gggccuacug ugggugggug uggucguggu gcuggccaau gccuccccg 180 gacgcacgau aacggugggc ccgcgaggca acgcgagcaa ugcugccccc uccgcguccc 240
cgcggaacgc auccgccccc cgaaccacac ccacgccccc acaaccccgc aaagcgacga 300
aauccaaggc cuccaccgcc aaaccggcuc cgcccccaa gaccggaccc ccgaagacau 360
ccucggagcc cgugcgaugc aaccgccacg acccgcuggc ccgguacggc ucgcgggugc 420
aaauccgaug ccgguuuccc aacuccacga ggacugaguc ccgucuccag aucuggcguu 480
augccacggc gacggacgcc gaaaucggaa cagcgccuag cuuagaagag gugauggua 540 acgugucggc cccgcccggg ggccaacugg uguaugacag ugcccccaac cgaacggacc 600
cgcauguaau cugggcggag ggcgccggcc cgggcgccag cccgcgccug uacucgguug 660
ucggcccgcu gggucggcag cggcucauca ucgaagaguu aacccuggag acacagggca 720
uguacuauug gguguggggc cggacggacc gcccguccgc cuacgggacc ugguccgcg 780 uucgaguauu ucgcccuccg ucgcugacca uccaccccca cgcggugcug gagggccagc 840
cguuuaaggc gacgugcacg gccgcaaccu acuacccggg caaccgcgcg gaguucgucu 900
gguuugagga cggucgccgc guauucgauc cggcacagau acacacgcag acgcaggaga 960
accccgacgg cuuuuccacc gucuccaccg ugaccuccgc ggccgucggc gggcagggcc 1020
ccccucgcac cuucaccugc cagcugacgu ggcaccgcga cuccgugucg uucucucggc 1080
gcaacgccag cggcacggcc ucgguucugc cgcggccgac cauuaccaug gaguuuacag 1140
gcgaccaugc ggucugcacg gccggcugug ugcccgaggg ggucacguuu gcuugguucc 1200
ugggggauga cuccucgccg gcggaaaagg uggccgucgc gucccagaca ucgugcgggc 1260
gccccggcac cgccacgauc cgcuccaccc ugccggucuc guacgagcag accgaguaca 1320
ucuguagacu ggcgggauac ccggacggaa uuccggugcu agagcaccac ggaagccacc 1380 agccccgcc gcgggaccca accgagcggc aggugauccg ggcgguggag ggggcgggga 1440
ucggaguggc uguccuuguc gcgguguuc uggccgggac cgcgguagug uaccugaccc 1500
augccuccuc gguacgcuau cgucggcugc gguaaugaua auaggcugga gccucggugg 1560
ccaugcuucu ugccccuugg gccucccccc agccccuccu ccccuuccug cacccguacc 1620
cccguggucu uugaauaaag ucugaguggg cggc 1654

<210> SEQ ID NO 115
<211> LENGTH: 1393
<212> TYPE: RNA
<213> ORGANISM: Artificial Sequence
<220> FEATURE:
<223> OTHER INFORMATION: Synthetic Polynucleotide

<400> SEQUENCE: 115
ucaagcuuuu ggacccucgu acagaagcua auacgacuca cuauagggaa auaagagaga 60
aaagaagagu aagaagaaau auaagagcca ccauggggcg uuugaccucc ggcgucggga 120
cggcggcccu gcuaguuguc gcggugggac uccgcgucgu cugcgccaaa uacgccuuag 180
cagaccccuc gcuuaagaug gccgauccca aucgauuucg cgggaagaac cuuccgguuu 240
uggaccagcu gaccgacccc cccgggguga agcguguuua ccacauucag ccgagccugg 300
aggacccguu ccagccccccc agcaucccga ucacugugua cuacgcagug cuggaacgug 360
ccugccgcag cgugcuccua caugccccau cggaggcccc ccagaucgug cgcggggcuu 420
cggacgaggc ccgaaagcac acguacaacc ugaccaucgc cugguaucgc augggagaca 480
auugcgcuau ccccaucacg guuauggaau acaccgagug ccccuacaac aagucguugg 540
gggucugccc cauccgaacg cagccccgcu ggagcuacua ugacagcuuu agcgccguca 600
gcgaggauaa ccugggauuc cugaugcacg cccccgccuu cgagaccgcg gguacguacc 660
ugcggcuagu gaagauaaac gacuggacgg agaucacaca auuuauccug gagcaccggg 720
cccgcgccuc cugcaaguac gcucuccccc ugcgcauccc cccggcagcg ugccucaccu 780
cgaaggccua ccaacagggc gugacggucg acagcaucgg gaugcuaccc cgcuuuaucc 840
ccgaaaacca gcgcaccguc gcccuauaca gcuuaaaaau cgccgggugg cacggcccca 900
agcccccgua caccagcacc cugcugccgc cggagcuguc cgacaccacc aacgccacgc 960
aacccgaacu cguuccggaa gaccccgagg acucggcccu cuuagaggau cccgccggga 1020
cggugucuuc gcagaucccc ccaaacuggc acaucccguc gauccaggac gucgcaccgc 1080
accacgcccc cgccgccccc agcaacccgg gccugaucau cggcgcgcug gccggcagua 1140
cccuggcggu gcuggucauc ggcgguauug cguuuugggu acgccgccgc gcucagaugg 1200
cccccaagcg ccuacgucuc ccccacaucc gggaugacga cgcgcccccc ucgcaccagc 1260
cauuguuuua cuagugauaa uaggcuggag ccucgguggc caugcuucuu gccccuuggg 1320
ccucccccca gccccuccuc cccuuccugc acccguaccc ccguggucuu ugaauaaagu 1380
cugagugggc ggc 1393

<210> SEQ ID NO 116
<211> LENGTH: 1858
<212> TYPE: RNA
<213> ORGANISM: Artificial Sequence
<220> FEATURE:
<223> OTHER INFORMATION: Synthetic Polynucleotide

<400> SEQUENCE: 116
ucaagcuuuu ggacccucgu acagaagcua auacgacuca cuauagggaa auaagagaga 60
aaagaagagu aagaagaaau auaagagcca ccauggcuag gggggccggg uugguuuuuu 120
uuguuggagu uugggucgua agcugccucg cggcagcgcc cagaacgucc uggaaacgcg 180
uaaccucggg cgaagacgug guguuacucc ccgcgccggc ggggccggaa gaacgcacuc 240
gggcccacaa acuacugugg gcagcggaac cgcuggaugc cugcgguccc cugaggccgu 300

-continued caugggugge acuguggccc ccccgacgag ugcuugagac gguugucgau gcggcgugca 360
ugcgcgcccc ggaaccgcuc gcuaucgcau acaguccccc guucccugcg ggcgacgagg 420
gacuuuauuc ggaguuggcg uggcgcgauc gcguagccgu ggucaacgag aguuuaguua 480
ucuacggggc ccuggagacg gacagugguc uguacacccu gucaguggug ggccuauccg 540
acgaggcccg ccaaguggcg uccgugguuc ucgucgucga gcccgccccu gugccuaccc 600
cgacccccga ugacuacgac gaggaggaug acgcgggcgu gagcgaacgc acgcccguca 660
gcguuccccc cccaacaccc ccccgacguc cccccgucgc ccccccgacg cacccucgug 720
uuaucccuga ggugagccac gugcgggggg ugacggucca cauggaaacc ccggaggcca 780
uucuguuugc gccaggggag acguuuggga cgaacgucuc cauccacgca auugcccacg 840
acgacggucc guacgccaug gacgucgucu ggaugcgauu ugaugucccg uccucgugcg 900
ccgagaugcg gaucuaugaa gcaugucugu aucacccgca gcugccugag ugucugucuc 960
cggccgaugc gccgugcgcc guaaguucgu gggcguaccg ccuggcgguc cgcagcuacg 1020
ccggcugcuc caggacuacg cccccaccuc gauguuuugc ugaagcucgc auggaaccgg 1080
uccccggguu ggcguggcuc gcaucaacug uuaaucugga auuccagcau gccucucccc 1140
aacacgccgg ccucuaucug uguguggugu auguggacga ccauauccau gccuggggcc 1200
acaugaccau cuccacagcg gcccaguacc ggaaugcggu gguggaacag caucuccccc 1260
agcgccagcc cgagcccgua gaacccaccc gaccgcaugu gagagccccc ccucccgcac 1320
ccuccgcgag aggcccguua cgcuuaggug cgguccuggg ggcggcccug uugcucgcgg 1380
cccucgggcu auccgccugg gcgugcauga ccugcuggcg caggcgcagu uggcgggcgg 1440
uuaaaagucg ggccucggcg accggcccca cuuacauucg aguagcggau agcgagcugu 1500
acgcggacug gaguucggac ucagagggcg agcgcgacgg uucccugugg caggacccuc 1560
cggagagacc cgacucaccg uccacaaaug gauccggcuu ugagaucuua uccccaacgg 1620
cgcccucugu auacccccau agcgaagggc guaaaucgcg ccgccccgcuc accaccuuug 1680 guucaggaag cccgggacgu cgucacuccc aggcguccua uucuuccguc uuaugguaau 1740
gauaauaggc uggagccucg guggccaugc uucuugcccc uugggccucc ccccagcccc 1800
uccuccccuu ccugcacccg uacccccgug gucuuugaau aaagucugag ugggcggc 1858

<210> SEQ ID NO 117
<211> LENGTH: 1330
<212> TYPE: RNA
<213> ORGANISM: Artificial Sequence
<220> FEATURE:
<223> OTHER INFORMATION: Synthetic Polynucleotide

<400> SEQUENCE: 117
ucaagcuuuu ggacccucgu acagaagcua auacgacuca cuauagggaa auaagagaga 60
aaagaagagu aagaagaaau auaagagcca ccaugcccgg ccgcucgcug cagggccugg 120
cgauccuggg ccugugggggguc ugcgccaccg gccuggucgu ccgcggcccc acggucaguc 180
uggucucaga cucacucgug gaugccgggg ccgugggggcc ccagggcuuc guggaagagg 240
accugcgugu uuucggggag cuucauuuug ugggggccca ggucccccac acaaacuacu 300
acgacggcau caucgagcug uuucacuacc cccuggggaa ccacugcccc cgcguuguac 360 acgugguucac acugaccgca ugccccccgcc gccccgccgu ggcguucacc uugugucgcu 420
cgacgcacca cgcccacagc cccgccuauc cgacccugga gcugggucug gcgcggcagc 480
cgcuucugcg gguucgaacg gcaacgcgcg acuaugccgg ucuguauguc cugcgcguau 540

```
gggucggcag cgcgacgaac gccagccugu uuguuuuggg gguggcgcuc ucugccaacg    600

ggacguuugu guauaacggc ucggacuacg gcuccugcga uccggcgcag cuucccuuuu    660

cggccccgcg ccugggaccc ucgagcguau acaccccegg agccucccgg cccaccccuc    720

cacggacaac gacaucaccg uccuccccac gagacccgac ccccgccccc ggggacacag    780

ggacgccugc ucccgcgagc ggcgagagag ccccgcccaa uuccacgcga ucggccagcg    840

aaucgagaca caggcuaacc guagcccagg uaauccagau cgccauaccg gcguccauca    900

ucgccuuugu guuucugggc agcuguaucu gcuucaucca uagaugccag cgccgauaca    960

ggcgcccccg cggccagauu uacaaccccg ggggcguuuc cugcgcgguc aacgaggcgg   1020

ccauggcccg ccucggagcc gagcugcgau cccacccaaa caccccccccc aaaccccgac   1080

gccguucguc gucguccacg accaugccuu cccuaacguc gauagcugag gaaucggagc   1140

cagguccagu cgugcugcug uccgucaguc cucggccccg caguggcccg acggcccccc   1200

aagaggucua gugauaauag gcuggagccu cgguggccau gcuucuugcc ccuugggccu   1260

ccccccagcc ccuccucccc uuccugcacc cguaccccccg uggucuuuga auaaagucug   1320

agugggcggc                                                          1330
```

<210> SEQ ID NO 118
<211> LENGTH: 2515
<212> TYPE: RNA
<213> ORGANISM: Artificial Sequence
<220> FEATURE:
<223> OTHER INFORMATION: Synthetic Polynucleotide

<400> SEQUENCE: 118

```
ucaagcuuuu ggacccucgu acagaagcua auacgacuca cuauagggaa auaagagaga     60

aaagaagagu aagaagaaau auaagagcca ccaugcgcgg ggggggcuua guuugcgcgc    120

uggucguggg ggcgcucgua gccgcggucg cgucggcggc uccggcugcc ccacgcgcuu    180

cagguggugu cgcugcgacc guugcggcga augguggucc cgccagccaa ccgccucccg    240

ucccgagccc cgcgaccacu aaggcccgga agcggaagac caagaagcca cccaagcggc    300

ccgaggcgac uccgccccca gacgccaacg cgaccgucgc cgccggccac gccacucugc    360

gugcgcaccu gcgggaaauc aaggucgaga acgcggacgc ccaguuuuac gugugcccgc    420

cgccgacugg cgccacggug gugcaguuug agcaaccuag gcgcugcccg acgcgaccag    480

aggggcagaa cuacaccgag ggcauagcgg uggucuuuaa ggaaaacauc gccccguaca    540

aauucaaggc caccauguac uacaaagacg ugaccguguc gcaggugugg uucggccacc    600

gcuacuccca guuuaugggg auauucgagg accgcgcccc cguucccuuc gaagaggug a   660

uugacaaaau uaacgccaag ggggucugcc gcaguacggc gaaguacguc cggaacaaca    720

uggagaccac ugccuuccac cgggacgacc acgaaacaga cauggagcuc aaaccggcga    780

aagucgccac gcgcacgagc cgggggugge acaccaccga ccucaaauac aauccuucgc    840

gggugguaagc auuccaucgg uauggcacga ccgucaacug uaucguagag gagguggaug   900

cgcggucggu guaccccuac gaugaguucg ugcuggcaac gggcgauuuu guguacaugu    960

ccccuuuuua cggcuaccgg gaagguaguc acaccgagca caccaguuac gccgccgacc   1020

gcuuuaagca aguggacggc uucuacgcgc gcgaccucac cacaaaggcc cgggccacgu   1080

cgccgacgac ccgcaauuug cugacgaccc ccaaguuuac cguggccugg gacugggugc   1140

cuaagcgacc ggcggucugu accaugacaa aguggcagga gguggacgaa augcuccgcg   1200
```

cugaauacgg uggcucuuuc cgcuucucuu ccgacgccau cuccaccacg uucaccacca 1260
accugaccca auacucgcuc ucgagagucg aucugggaga cugcauuggc cgggaugccc 1320
gcgaggcaau ugaccgcaug uucgcgcgca aguacaacgc uacgcacaua aagguuggcc 1380
aaccccagua cuaccuagcc acgggggcu uccucaucgc uuaucaaccc cuccucagca 1440
acacgcucgc cgagcuguac gugcgggaau auaugcggga acaggaccgc aaaccccgaa 1500
acgccacgcc cgcgccgcug cgggaagcac cgagcgccaa cgcguccgug gagcgcauca 1560
agacgacauc cucgauugag uuugcucguc ugcaguuuac guauaaccac auacagcgcc 1620
auguaaacga caugcucggg cgcaucgccg ucgcguggug cgagcuccaa aaucacgagc 1680
ucacucugug gaacgaggca cgcaagcuca aucccaacgc caucgcaucc gccaccguag 1740
gccggcgggu gagcgcucgc augcucgggg augucauggc cgucuccacg ugcgugcccg 1800
ucgccccgga caacgugauc gugcaaaaua gcaugcgcgu uucuucgcgg ccggggacgu 1860
gcuacagccg cccgcugguu agcuuucggu acgaagacca aggcccgcug auugaggggc 1920
agcuggguga gaacaacgag cugcgccuca cccgcgaugc guuagagccg uguaccgucg 1980
gccaccggcg cuacuucauc uucggagggg gauacguaua cuucgaagaa uaugcguacu 2040
cucaccaauu gagucgcgcc gaugucacca cuguuagcac cuucaucgac cugaacauca 2100
ccaugcugga ggaccacgag uucgugcccc uggaggucua cacacgccac gagaucaagg 2160
auuccggccu acuggacuac accgaagucc agagacgaaa ucagcugcac gaucuccgcu 2220
uugcugacau cgauacuguu auccgcgccg acgccaacgc cgccauguuc gcaggucugu 2280
gugcguuuuu cgaggguaug ggugacuuag ggcgcgcggu gggcaagguc gucauggggg 2340
uagucggggg cguggugucg gccgucucgg gcgucuccuc cuuuaugucu aaccccugau 2400
aauaggcugg agccucggug gccaugcuuc uugccccuug ggccuccccc cagccccucc 2460
uccccuuccu gcacccguac ccccgugguc uuugaauaaa gucugagugg gcggc 2515

<210> SEQ ID NO 119
<211> LENGTH: 1552
<212> TYPE: RNA
<213> ORGANISM: Artificial Sequence
<220> FEATURE:
<223> OTHER INFORMATION: Synthetic Polynucleotide

<400> SEQUENCE: 119
ucaagcuuuu ggacccucgu acagaagcua auacgacuca cuauagggaa auaagagaga 60
aaagaagagu aagaagaaau auaagagcca ccauggcacu gggaagagug ggauuggccg 120
ucggacugug gggacugcug ugggugggag ucgucgucgu ccuggcuaac gccucacccg 180
gucggacuau cacuguggga cccaggggga acgccucuaa cgccgcgccc ucagcuagcc 240
ccaggaaugc cagcgcuccc aggaccaccc cgacuccucc gcaaccccgc aaggcgacca 300
aguccaaggc guccacugcc aagccagcgc cuccgccuaa gacuggcccc ccuaagaccu 360
ccagcgaacc ugugcggugc aaccggcacg acccucuggc acgcuacgga ucgcgggucc 420
aaauccggug ucgguucccg aacagcacuc ggaccgaauc gcggcuccag auuuggagau 480
acgcaacugc cacugaugcc gagaucggca cugccccaag ccuugaggag gucaugguca 540
acgugucagc uccuccugga ggccagcugg uguacgacuc cgcuccgaac cgaaccgacc 600
cgcacgucau cugggccgaa ggagccgguc cuggugcauc gccgagguug uacucgguag 660
uggguccccu ggggagacag cggcugauca ucgaagaacu gacucuggag acucagggca 720
uguacuauug ggugugggc agaaccgaua gaccauccgc auacggaacc ugggugcgcg 780

```
ugagagaguu cagaccccg uccuugacaa uccacccgca ugcggugcuc gaagggcagc    840

ccuucaaggc cacuugcacu gcggccacuu acuacccugg aaaccgggcc gaauucgugu    900

gguucgagga uggacggagg guguucgacc cggcgcagau ucauacgcag acucaggaaa    960

acccggacgg cuucuccacc guguccacug ugacuucggc cgcuguggga ggacaaggac   1020

cgccacgcac cuucaccugu cagcugaccu ggcaccgcga cagcgugucc uuuagccggc   1080

ggaacgcauc aggcacugcc uccguguugc cucgcccaac cauuaccaug gaguucaccg   1140

gagaucacgc cgugugcacu gcuggcugcg uccccgaagg cgugaccuuc gccugguuuc   1200

ucggggacga cucaucccg gcggaaaagg uggccguggc cucucagacc agcugcggua   1260

gaccgggaac cgccaccauc cgcuccacuc ugccggugc guacgagcag accgaguaca   1320

uuugucgccu ggccggauac ccggacggua ucccagugcu cgaacaccac ggcagccauc   1380

agccuccgcc gagagauccu accgagcgcc aggucauccg ggccguggaa ggaugauaau   1440

aggcuggagc cucgguggcc augcuucuug ccccuugggc cuccccccag ccccuccucc   1500

ccuuccugca cccguacccc cguggucuuu gaauaaaguc ugagugggcg gc           1552
```

<210> SEQ ID NO 120
<211> LENGTH: 1462
<212> TYPE: RNA
<213> ORGANISM: Artificial Sequence
<220> FEATURE:
<223> OTHER INFORMATION: Synthetic Polynucleotide

<400> SEQUENCE: 120

```
ucaagcuuuu ggacccucgu acagaagcua auacgacuca cuauagggaa auaagagaga     60

aaagaagagu aagaagaaau auaagagcca ccauggcucg cggggccggg uugguguuuu    120

uuguuggagu uugggucgua ucgugccugg cggcagcacc cagaacgucc uggaaacggg    180

uuaccucggg cgaggacgug guguugcuuc cggcgcccgc ggggccggag gaacgcacac    240

gggcccacaa acuacugugg gccgcggaac cccuggaugc cugcgguccc cugaggccgu    300

cgugggugc gcuguggccc ccgcgacggg ugcucgaaac ggucguggau gcggcgugca    360

ugcgcgcccc ggaaccgcuc gccauagcau acaguccccc guuccccgcg ggcgacgagg    420

gacuguauuc ggaguuggcg uggcgcgauc gcguagccgu ggucaacgag agucugguca    480

ucuacggggc ccuggagacg gacagcgguc uguacacccu guccguggc ggccuaagcg    540

acgaggcgcg ccaaguggcg ucgguggguuc uggucgugga gcccgccccu gugccgaccc    600

cgacccccga cgacuacgac gaagaagacg acgcgggcgu gagcgaacgc acgccgguca    660

gcguaccccc cccgacccca ccccgucguc cccccgucgc ccccccuacg cacccucgug    720

uuaucccga ggugucccac gugcgcgggg uaacggucca uauggagacc ccggaggcca    780

uucuguuugc ccccggagag acguuuggga cgaacgucuc cauccacgcc auugcccaug    840

acgacggucc guacgccaug gacgucgucu ggaugcgguu ugacgugccg uccucgugcg    900

ccgagaugcg gaucuacgaa gcuugucugu aucacccgca gcuuccagaa ugucuaucuc    960

cggccgacgc gccgugcgcu guaaguuccu gggcguaccg ccuggcgguc cgcagcuacg   1020

ccggcuguuc caggacuacg cccccgccgc gauguuuugc cgaggcucgc auggaaccgg   1080

ucccggggu ggcgugguua gccuccaccg ucaaccugga auccagcac gccuccccuc   1140

agcacgccgg ccuuuaccug ugcguggugu acguggacga ucauauccac gccuggggcc   1200

acaugaccau cucuaccgcg gcgcaguacc ggaacgcggu gguggaacag cacuugcccc   1260
```

agcgccagcc ugaacccguc gagcccaccc gcccgcacgu aagagcaccc ccucccgcgc 1320
cuuccgcgcg cggcccgcug cgcugauaau aggcuggagc cucgguggcc augcuucuug 1380
ccccuugggc cuccccccag ccccuccucc ccuuccugca cccguacccc cguggucuuu 1440
gaauaaaguc ugagugggcg gc 1462

<210> SEQ ID NO 121
<211> LENGTH: 997
<212> TYPE: RNA
<213> ORGANISM: Human herpesvirus 2

<400> SEQUENCE: 121
ucaagcuuuu ggacccucgu acagaagcua auacgacuca cuauagggaa auaagagaga 60
aaagaagagu aagaagaaau auaagagcca ccaugcccgg ccgcucgcug cagggccugg 120
cgauccuggg ccugugggguc ugcgccaccg gccuggucgu ccgcggcccc acggucaguc 180
uggucucaga cucacucgug gaugccgggg ccguggggcc ccagggcuuc guggaagagg 240
accugcgugu uuucggggag cuucauuuug uggggggccca gguccccccac acaaacuacu 300 acgacggcau caucgagcug uuucacuacc cccuggggaa ccacugcccc cgcguuguac 360
acguggucac acugaccgca ugcccccgcc gccccgccgu ggcguucacc uugugucgcu 420
cgacgcacca cgcccacagc cccgccuauc cgacccugga gcugggucug gcgcggcagc 480
cgcuucugcg gguucgaacg gcaacgcgcg acuaugccgg ucuguauguc cugcgcguau 540
gggucggcag cgcgacgaac gccagccugu uuguuuuggg gguggcgcuc ucugccaacg 600
ggacguuugu guauaacggc ucggacuacg gcuccugcga uccggcgcag cuucccuuuu 660
cggccccgcg ccugggaccc ucgagcguau acacccccgg agccucccgg cccacccc uc 720 cacggacaac gacauccccg uccuccccua gagacccgac ccccgccccc ggggacacag 780
gaacgccugc gcccgcgagc ggcgagagag ccccgcccaa uuccacgcga ucggccagcg 840
aaucgagaca caggcuaacc guagcccagg uaauccagug auaauaggcu ggagccucgg 900
uggccaugcu ucuugccccu ugggccuccc cccagccccu ccucccccuuc cugcacccgu 960 acccccgugg ucuuugaaua aagucugagu gggcggc 997

<210> SEQ ID NO 122
<211> LENGTH: 1228
<212> TYPE: RNA
<213> ORGANISM: Artificial Sequence
<220> FEATURE:
<223> OTHER INFORMATION: Synthetic Polynucleotide

<400> SEQUENCE: 122
ucaagcuuuu ggacccucgu acagaagcua auacgacuca cuauagggaa auaagagaga 60
aaagaagagu aagaagaaau auaagagcca ccaugggggcg uuugaccucc ggcgucggga 120
cggcggcccu gcuaguuguc gcggugggac uccgcgucgu cugcgccaaa uacgccuuag 180
cagaccccuc gcuuaagaug gccgauccca aucgauuucg cgggaagaac cuuccgguuu 240
uggaccagcu gaccgacccc cccgggguga agcguguuua ccacauucag ccgagccugg 300
aggacccguu ccagcccccc agcaucccga ucacugugua cuacgcagug cuggaacgug 360
ccugccgcag cgugcuccua caugccccau cggaggcccc ccagaucgug cgcggggcuu 420
cggacgaggc ccgaaagcac acguacaacc ugaccaucgc cugguaucgc augggagaca 480
auugcgcuau ccccaucacg guuauggaau acaccgagug ccccuacaac aagucguugg 540
gggucugccc cauccgaacg cagccccgcu ggagcuacua ugacagcuuu agcgccguca 600
gcgaggauaa ccugggauuc cugaugcacg cccccgccuu cgagaccgcg gguacguacc 660
ugcggcuagu gaagauaaac gacuggacgg agaucacaca auuuauccug gagcaccggg 720
cccgcgccuc cugcaaguac gcucuccccc ugcgcauccc cccggcagcg ugccucaccu 780
cgaaggccua ccaacagggc gugacggucg acagcaucgg gaugcuaccc cgcuuuaucc 840
ccgaaaacca gcgcaccguc gcccuauaca gcuuaaaaau cgccgggugg cacggcccca 900
agcccccgua caccagcacc cugcugccgc cggagcuguc cgacaccacc aacgccacgc 960
aacccgaacu cguuccggaa gaccccgagg acucggcccu cuuagaggau cccgccggga 1020
cggugucuuc gcagaucccc ccaaacuggc acaucccguc gauccaggac gucgcgccgc 1080
accacgcccc cgccgccccc agcaacccgu gauaauaggc uggagccucg guggccaugc 1140
uucuugcccc uugggccucc ccccagcccc uccuccccuu ccugcacccg uacccccgug 1200
gucuuugaau aaagucugag ugggcggc 1228

<210> SEQ ID NO 123
<211> LENGTH: 2473
<212> TYPE: RNA
<213> ORGANISM: Artificial Sequence
<220> FEATURE:
<223> OTHER INFORMATION: Synthetic Polynucleotide

<400> SEQUENCE: 123
ucaagcuuuu ggacccucgu acagaagcua auacgacuca cuauagggaa auaagagaga 60
aaagaagagu aagaagaaau auaagagcca ccauggaacc gcggccuggu acuucauccc 120
gcgccgaucc uggaccggaa cggccaccuc gccagacccc uggaacgcag ccugcagccc 180
cucacgccug ggggaugcug aaugauaugc aguggcuggc cucaagcgac uccgaggaag 240
agacagaggu cggcaucucc gacgaugauc uccaucggga uucuacuucg gaagcgggcu 300
ccaccgacac agagauguuc gaggccggcc ugauggaugc ugcgaccccu cccgcaagac 360
cgccugccga acgccaaggc ucgccgaccc cugcugacgc ccaggguucg ugcgguggag 420
gcccuguggg ggaggaggaa gcugaagccg gaggcggugg agaugucaac accccggugg 480
ccuaccugau cgugggcgug acugccagcg gauccuucuc gaccaucccc auugucaacg 540
auccccgcac ucgggucgaa gcggaggccg cagugcgggc uggaacugcc guggacuuca 600
uuuggacugg caaucccagg accgcucccc ggucacuguc ccugggagga cacaccgucc 660
gcgcccuguc accaacuccc ccguggccug gaaccgauga cgaggacgac gaccuggccg 720
auguggacua cgugcccccu gccccaagac gggcuccacg gagaggaggc ggaggcgccg 780
gugccaccag gggcaccagc caacccgcug ccacccggcc ugcuccuccu ggggccccga 840
gauccuccuc auccggcggg gcaccucuga gagcaggagu gggcucaggc uccggaggag 900
gacccgccgu ggcagcugug gucccgcgag uggccuccuu gccuccggcc gcaggaggcg 960
gccgggccca ggccagaagg gugggggagg acgcggcagc cgccgaaggg cgcacuccuc 1020
cagcgcgcca accaagagca gcgcaagagc cuccgaucgu gaucuccgau agccccccac 1080
cgucaccucg cagaccagcc ggacccgggc cucugucguu cgugagcucc agcucggccc 1140
aggugucgag cggaccuggc gguggugggac ucccucagag cagcggcaga gcugccagac 1200
cucgcgccgc cguggccccg agggucaggu cgccgccgag agcagcugcc gccccagugg 1260
uguccgccuc agccgacgcc gccggucccg cgccuccugc ugugccagug gacgcccaua 1320
gagcgccgcg gagcagaaug acucaggcac agacugacac ccaggcccag ucgcucggua 1380
gggcuggagc caccgacgcc agaggaucgg gcggacccgg agccgaagga ggguccgguc 1440
ccgccgcuuc cuccuccgcg uccucaucag ccgcuccgcg cucaccgcuc gcaccccagg 1500
gugucggagc aaagcgagca gcuccucgcc gggccccuga cuccgacuca ggagaucggg 1560
gccacggacc acucgcgccu gccagcgcug gagcggcucc uccaucggcu uccccauccu 1620
cgcaagcagc cguggccgcc gcauccucaa gcucggcguc cucuagcuca gcgagcuccu 1680
ccagcgccuc guccucgucc gccuccagca gcucagccuc cucguccucg gccuccucau 1740
cguccgccuc cuccuccgcu ggaggugccg gaggaucggu cgcauccgcu uccggcgcag 1800
gggagcgccg agaaacgucc cugggguccgc gggcagcugc uccgaggggu ccucgcaagu 1860
gcgcgcggaa aacucggcac gcggagggag gaccggaacc uggcgcgaga gauccugcgc 1920
cuggacugac ccgguaccuc cccauugccg ggguguccag cgugguggca cuugccccgu 1980
acgucaacaa gaccgugacc ggggacuguc uccccgugcu cgacauggag acuggacaca 2040
uuggcgcgua uguggguccug guggaucaga ccgguaaugu ggccgaccuu uugagagcag 2100
cggccccagc augguccccgc agaacccugc ugccugagca cgccaggaau ugcgugcggc 2160
cgccggacua cccgacuccg cccgccagcg aauggaacuc acuguggaug acucccgugg 2220
gcaacaugcu guucgaucag gggacccugg ucggagcccu ggauuuucac ggccugcgcu 2280
ccagacaucc guggucuagg gaacagggug cuccugcucc cgcgggugau gccccugcug 2340
gccacggcga auagugauaa uaggcuggag ccucggugggc caugcuucuu gccccuuggg 2400 ccuccccccca gccccuccuc cccuuccugc acccguaccc ccgugggucuu ugaauaaagu 2460 cugagugggc ggc 2473

<210> SEQ ID NO 124
<211> LENGTH: 4096
<212> TYPE: RNA
<213> ORGANISM: Human herpesvirus 2

<400> SEQUENCE: 124
ucaagcuuuu ggacccucgu acagaagcua auacgacuca cuauagggaa auaagagaga 60
aaagaagagu aagaagaaau auaagagcca ccaugucggc cgagcagcgc aagaagaaga 120
aaacgaccac cacuacccag ggcagaggag ccgaagucgc cauggccgau gaagauggcg 180
ggaggcugcg ggccgccgcu gaaaccaccg gaggaccggg auccccugac ccugcggacg 240
gcccaccucc cacaccgaac ccggacagac ggccugcugc aaggcccggu uucggauggc 300
acgggggacc cgaagagaac gaggacgaag ccgaugacgc cgcggcggau gcagacgccg 360
acgaggcggc ucccgcuucg ggagaagcgg uggacgaacc ggccgccgau ggagugguca 420
gcccccgcca gcucgcgcug cucgcgucca uggguggauga agccgugaga acuaucccu 480 caccuccgcc ggaacgggau ggagcucaag aggaagccgc cagaagcccg uccccuccga 540
gaacuccauc caugcgggcc gacuacggcg aagagaauga cgacgaugau gacgacgaug 600
augacgauga ccgcgaugcc ggacggugggg uccgcggacc ugagacuacc uccgccgugc 660
gcggagccua cccugauccg auggccucac uuagcccccg gccacccgcc ccccgccgcc 720
accaccacca ucaucaccac cgcagaagaa gggcucccag gcgcagauca gcagcuuccg 780
acagcucgaa guccggcucc ucguccuccg ccagcagcgc auccucguca gcguccucau 840
cguccagcgc cucggcgagc uccuccgacg augacgacga cgacgaugcc gccagagcuc 900
cggcaucagc cgcggaccau gccgccggag gaacccucgg ugccgacgac gaggaggccg 960
gcgugccugc ccgcgcuccg ggagcugcuc cuaggccuuc accaccccgg gcggagccag 1020

-continued

```
ccccugccag aacgccagca gccaccgcug ggcgauugga gaggcggaga gcccgggccg   1080
ccguggccgg ucgggaugcc accggccgcu ucacugccgg acgcccucgg cgcgucgaac   1140
uggacgcaga cgccgccucg ggcgcguucu acgcccgcua ucgggacggu uaugugcccg   1200
gcgagccuug gccuggugcc gguccuccuc cgccugggag agugcucuac gggggucugg   1260
gugauucucg gccaggguug uggggagccc ccgaggcgga ggaagccaga gcccgcuucg   1320
aagcauccgg agcaccggcc ccuguguggg cgccggaacu gggcgacgcc gcccaacaau   1380
acgcccugau cacacgccug cucuacacuc cggacgccga agccaugggc uggcugcaga   1440
acccgagagu ggcccccgggu gauguggccc uggaccaggc augcuucagg auuagcggag   1500
ccgcgagaaa cucgagcagc uuuaucucag gaucuguggc ccgagccgug ccgcaccugg   1560
gcuacgcgau ggccgccgga cgcuucggau gggggcuggc ccaugucgcu gccgcggugg   1620
cgauguccccg gcgguacgac cgggcucaga aggguuuccu ccucaccagc cuccggaggg   1680
cauacgcccc guugcuggcu cgggagaacg ccgcucugac uggcgcccgc acuccugaug   1740
acgguggcga cgccaaccgc cacgacggcg acgaugcacg gggaaagccc gcggccgccg   1800
ccgcccccccu uccuagcgca gccgcuucgc cugccgacga acgggcuguc ccugccggau   1860
acggagccgc cggugugcug gcggcccuug ggagacuguc agccgcgccu gcuucagcgc   1920
cggccggagc cgacgaugac gacgacgacg auggagccgg aggaggggc ggcggucgga   1980
gagcagaagc cggcagggug gcagucgaau gccuugcugc cugucgcggg auccucgagg   2040
cguuggccga aggcuucgac ggcgaccugg cggcagugcc uggccuggcc ggcgcccgcc   2100
ccgcugcccc uccacggccc gguccggccg gggccgcagc cccuccgcau gcugacgcgc   2160
cucgccucag agcauggcug agagaauuga gauuugugcg ggaugcgcug guccuuaugc   2220
gccugagggg ggaucugagg guggccggag guuccgaggc ggccguggcu gcugugcggg   2280
ccguguccccu gguggccggu gcgcugggguc ccgcucugcc gcgguccccu agauugcuuu   2340
ccucagcggc cgccgccgca gccgaucugc ucuuucagaa ccaaagccuc aggccgcugc   2400
uggccgacac ugucgccgcu gcggacuccc ucgcugcccc agccucggcc ccaagagagg   2460
cugccgaugc cccucgcccc gccgcggccc cgccugccgg agcagcgccg ccugcacccc   2520
cuacuccccc cccgcgaccg ccacgcccag ccgcucuuac cagaaggcca gcugagggguc   2580
cugacccgca gggcggcugg cgcagacagc ccccgggacc uucccacacu cccgccccau   2640
cugcggcugc ccuugaagca uacugugccc cgagagcugu ggcggagcug accgaccacc   2700
cucuguuccc ugcaccuugg cggccugccc ugauguuuga cccgagagcg uuggccuccc   2760
uggcggccag augugcggcc ccgccucccg gaggagcccc agcugcauuc ggaccucugc   2820
gggcauccgg accacugcgg cgcgcugcug cauggaugcg gcaagugccg gacccugagg   2880
acguucgcgu ggucauucuu uacucccccc ugccgggaga agaucucgcc gccggccgcg   2940
cgggaggagg cccuccaccc gaguggucg cugaacgggg aggccugucc ugccugcugg   3000
cugcccuggg aaaccgccug ugcggaccag cuacugccgc cugggcugga aacuggaccg   3060
gcgcacccga ugugucagcc cucggagcgc agggagugcu gcugcuguca acucgcgacc   3120
uggcauucgc cggagcugug gaguuccugg gucugcuugc cggcgcgugc gaccggagau   3180
ugaucgucgu gaacgcuguc agagcggccg cuuggccugc cgcugcuccg guggucagcc   3240
ggcagcacgc auaucuggcc ugcgaggugc ugcccgccgu gcagugugcc gugcgguggc   3300
cagcggccag agacuugcga cggaccgugc uggccuccgg uagggucuuu ggccccggag   3360
```

-continued uguucgcccg cguggaggcc gcccaugcca gacuguaccc cgacgcaccg ccccugagac 3420
ugugccgggg agccaacgug cgguacagag uccgcacccg cuucggaccc gauacucugg 3480
ugccaauguc accgcgggaa uauaggagag ccgugcuccc ggcacuggac ggcagagccg 3540
ccgcauccgg ugcuggggac gcgauggcac ccggagcccc cgacuuuugc gaggaugaag 3600
cccacagcca ucgggccugu gccagauggg gccugggugc cccucuucgc cccguguacg 3660
uggcccuggg gagagaugcc guccgcggug gaccagccga gcugagaggc ccacgccggg 3720
aauuuugcgc ucgggcccug cucgagcccg auggagaugc gccuccccuu gugcugcgcg 3780
acgacgcuga cgccggccca ccuccgcaaa uccggugggc cagcgccgcc ggucgagcag 3840 gaacggugugu ggcagcagcc ggaggaggag ucgaaguggu cggaaccgcg gcuggacugg 3900
caaccccgcc aaggcgcgaa ccuguggaua uggacgccga gcuggaggau gacgacgaug 3960
gccuuuucgg cgagugauga uaauaggcug gagccucggu ggccaugcuu cuugccccuu 4020
gggccucccc ccagccccuc cuccccuucc ugcacccgua cccccguggu cuuugaauaa 4080
agucugagug ggcggc 4096

<210> SEQ ID NO 125
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 125

Met Ala Gln Val Ile Asn Thr Asn Ser Leu Ser Leu Leu Thr Gln Asn
1 5 10 15

Asn Leu Asn Lys Ser Gln Ser Ala Leu Gly Thr Ala Ile Glu Arg Leu
20 25 30

Ser Ser Gly Leu Arg Ile Asn Ser Ala Lys Asp Asp Ala Ala Gly Gln
35 40 45

Ala Ile Ala Asn Arg Phe Thr Ala Asn Ile Lys Gly Leu Thr Gln Ala
50 55 60

Ser Arg Asn Ala Asn Asp Gly Ile Ser Ile Ala Gln Thr Thr Glu Gly
65 70 75 80

Ala Leu Asn Glu Ile Asn Asn Asn Leu Gln Arg Val Arg Glu Leu Ala
85 90 95

Val Gln Ser Ala Asn Ser Thr Asn Ser Gln Ser Asp Leu Asp Ser Ile
100 105 110

Gln Ala Glu Ile Thr Gln Arg Leu Asn Glu Ile Asp Arg Val Ser Gly
115 120 125

Gln Thr Gln Phe Asn Gly Val Lys Val Leu Ala Gln Asp Asn Thr Leu
130 135 140

Thr Ile Gln Val Gly Ala Asn Asp Gly Glu Thr Ile Asp Ile Asp Leu
145 150 155 160

Lys Gln Ile Asn Ser Gln Thr Leu Gly Leu Asp Thr Leu Asn Val Gln
165 170 175

Gln Lys Tyr Lys Val Ser Asp Thr Ala Ala Thr Val Thr Gly Tyr Ala
180 185 190

Asp Thr Thr Ile Ala Leu Asp Asn Ser Thr Phe Lys Ala Ser Ala Thr
195 200 205

Gly Leu Gly Gly Thr Asp Gln Lys Ile Asp Gly Asp Leu Lys Phe Asp
210 215 220

Asp Thr Thr Gly Lys Tyr Tyr Ala Lys Val Thr Val Thr Gly Gly Thr

```
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Gly
                485                 490                 495

Gly Gly Gly Ser Gly Gly Gly Gly Ser Met Met Ala Pro Asp Pro Asn
            500                 505                 510

Ala Asn Pro Asn Ala Asn Pro Asn Ala Asn Pro Asn Ala Asn Pro Asn
        515                 520                 525

Ala Asn Pro Asn Ala Asn Pro Asn Ala Asn Pro Asn Ala Asn Pro Asn
    530                 535                 540

Ala Asn Pro Asn Ala Asn Pro Asn Ala Asn Pro Asn Ala Asn Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Lys Asn Asn Gln
            580                 585                 590

Gly Asn Gly Gln Gly His Asn Met Pro Asn Asp Pro Asn Arg Asn Val
        595                 600                 605

Asp Glu Asn Ala Asn Ala Asn Asn Ala Val Lys Asn Asn Asn Asn Glu
    610                 615                 620

Glu Pro Ser Asp Lys His Ile Glu Gln Tyr Leu Lys Lys Ile Lys Asn
625                 630                 635                 640

Ser Ile Ser Thr Glu Trp Ser Pro Cys Ser Val Thr Cys Gly Asn Gly
                645                 650                 655
```

```
Ile Gln Val Arg Ile Lys Pro Gly Ser Ala Asn Lys Pro Lys Asp Glu
            660                 665                 670

Leu Asp Tyr Glu Asn Asp Ile Glu Lys Lys Ile Cys Lys Met Glu Lys
        675                 680                 685

Cys Ser Ser Val Phe Asn Val Val Asn Ser
    690                 695


<210> SEQ ID NO 126
<211> LENGTH: 692
<212> TYPE: PRT
<213> ORGANISM: Artificial Sequence
<220> FEATURE:
<223> OTHER INFORMATION: Synthetic Polypeptide

<400> SEQUENCE: 126

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Ala
65                  70                  75                  80

Asn Pro Asn Lys Asn Asn Gln Gly Asn Gly Gln Gly His Asn Met Pro
                85                  90                  95

Asn Asp Pro Asn Arg Asn Val Asp Glu Asn Ala Asn Ala Asn Asn Ala
            100                 105                 110

Val Lys Asn Asn Asn Asn Glu Glu Pro Ser Asp Lys His Ile Glu Gln
        115                 120                 125

Tyr Leu Lys Lys Ile Lys Asn Ser Ile Ser Thr Glu Trp Ser Pro Cys
    130                 135                 140

Ser Val Thr Cys Gly Asn Gly Ile Gln Val Arg Ile Lys Pro Gly Ser
145                 150                 155                 160

Ala Asn Lys Pro Lys Asp Glu Leu Asp Tyr Glu Asn Asp Ile Glu Lys
                165                 170                 175

Lys Ile Cys Lys Met Glu Lys Cys Ser Ser Val Phe Asn Val Val Asn
            180                 185                 190

Ser Arg Pro Val Thr Met Ala Gln Val Ile Asn Thr Asn Ser Leu Ser
        195                 200                 205

Leu Leu Thr Gln Asn Asn Leu Asn Lys Ser Gln Ser Ala Leu Gly Thr
    210                 215                 220

Ala Ile Glu Arg Leu Ser Ser Gly Leu Arg Ile Asn Ser Ala Lys Asp
225                 230                 235                 240

Asp Ala Ala Gly Gln Ala Ile Ala Asn Arg Phe Thr Ala Asn Ile Lys
                245                 250                 255

Gly Leu Thr Gln Ala Ser Arg Asn Ala Asn Asp Gly Ile Ser Ile Ala
            260                 265                 270

Gln Thr Thr Glu Gly Ala Leu Asn Glu Ile Asn Asn Asn Leu Gln Arg
        275                 280                 285

Val Arg Glu Leu Ala Val Gln Ser Ala Asn Ser Thr Asn Ser Gln Ser
    290                 295                 300

Asp Leu Asp Ser Ile Gln Ala Glu Ile Thr Gln Arg Leu Asn Glu Ile
305                 310                 315                 320
```

```
Asp Arg Val Ser Gly Gln Thr Gln Phe Asn Gly Val Lys Val Leu Ala
                325                 330                 335

Gln Asp Asn Thr Leu Thr Ile Gln Val Gly Ala Asn Asp Gly Glu Thr
            340                 345                 350

Ile Asp Ile Asp Leu Lys Gln Ile Asn Ser Gln Thr Leu Gly Leu Asp
        355                 360                 365

Thr Leu Asn Val Gln Gln Lys Tyr Lys Val Ser Asp Thr Ala Ala Thr
    370                 375                 380

Val Thr Gly Tyr Ala Asp Thr Thr Ile Ala Leu Asp Asn Ser Thr Phe
385                 390                 395                 400

Lys Ala Ser Ala Thr Gly Leu Gly Gly Thr Asp Gln Lys Ile Asp Gly
                405                 410                 415

Asp Leu Lys Phe Asp Asp Thr Thr Gly Lys Tyr Tyr Ala Lys Val Thr
            420                 425                 430

Val Thr Gly Gly Thr Gly Lys Asp Gly Tyr Tyr Glu Val Ser Val Asp
        435                 440                 445

Lys Thr Asn Gly Glu Val Thr Leu Ala Gly Gly Ala Thr Ser Pro Leu
    450                 455                 460

Thr Gly Gly Leu Pro Ala Thr Ala Thr Glu Asp Val Lys Asn Val Gln
465                 470                 475                 480

Val Ala Asn Ala Asp Leu Thr Glu Ala Lys Ala Ala Leu Thr Ala Ala
                485                 490                 495

Gly Val Thr Gly Thr Ala Ser Val Val Lys Met Ser Tyr Thr Asp Asn
            500                 505                 510

Asn Gly Lys Thr Ile Asp Gly Gly Leu Ala Val Lys Val Gly Asp Asp
        515                 520                 525

Tyr Tyr Ser Ala Thr Gln Asn Lys Asp Gly Ser Ile Ser Ile Asn Thr
    530                 535                 540

Thr Lys Tyr Thr Ala Asp Asp Gly Thr Ser Lys Thr Ala Leu Asn Lys
545                 550                 555                 560

Leu Gly Gly Ala Asp Gly Lys Thr Glu Val Val Ser Ile Gly Gly Lys
                565                 570                 575

Thr Tyr Ala Ala Ser Lys Ala Glu Gly His Asn Phe Lys Ala Gln Pro
            580                 585                 590

Asp Leu Ala Glu Ala Ala Ala Thr Thr Thr Glu Asn Pro Leu Gln Lys
        595                 600                 605

Ile Asp Ala Ala Leu Ala Gln Val Asp Thr Leu Arg Ser Asp Leu Gly
    610                 615                 620

Ala Val Gln Asn Arg Phe Asn Ser Ala Ile Thr Asn Leu Gly Asn Thr
625                 630                 635                 640

Val Asn Asn Leu Thr Ser Ala Arg Ser Arg Ile Glu Asp Ser Asp Tyr
                645                 650                 655

Ala Thr Glu Val Ser Asn Met Ser Arg Ala Gln Ile Leu Gln Gln Ala
            660                 665                 670

Gly Thr Ser Val Leu Ala Gln Ala Asn Gln Val Pro Gln Asn Val Leu
        675                 680                 685

Ser Leu Leu Arg
    690
```

<210> SEQ ID NO 127
<211> LENGTH: 13
<212> TYPE: PRT
<213> ORGANISM: Salmonella typhimurium -continued

```
<400> SEQUENCE: 127

Leu Gln Arg Val Arg Glu Leu Ala Val Gln Ser Ala Asn
1               5                   10
```